US012716072B2

(12) United States Patent
Khanna et al.

(10) Patent No.: US 12,716,072 B2
(45) Date of Patent: Aug. 25, 2026

(54) MANIPULATING PLANT SENSITIVITY TO LIGHT

(71) Applicants: Mendel Biotechnology, Inc., Hayward, CA (US); Monsanto Technology LLC, St. Louis, MO (US)

(72) Inventors: Rajnish Khanna, Livermore, CA (US); Brent A. Kronmiller, Corvallis, OR (US); Oliver J. Ratcliffe, Hayward, CA (US); T. Lynne Reuber, San Mateo, CA (US); Marie E. Petracek, Glendale, MO (US); Robert J. Meister, St. Peters, MO (US); Sasha Preuss, Webster Groves, MO (US); Amanda McClerren, St. Charles, MO (US); Qungang Qi, Chesterfield, MO (US)

(73) Assignees: Mendel Biotechnology, Inc., Hayward, CA (US); Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/465,595

(22) Filed: Sep. 12, 2023

(65) Prior Publication Data

US 2024/0124885 A1 Apr. 18, 2024

Related U.S. Application Data

(60) Continuation of application No. 17/404,842, filed on Aug. 17, 2021, now abandoned, which is a continuation of application No. 15/802,397, filed on Nov. 2, 2017, now abandoned, which is a division of application No. 14/118,491, filed as application No. PCT/US2012/038719 on May 18, 2012, now abandoned.

(60) Provisional application No. 61/488,592, filed on May 20, 2011.

(51) Int. Cl.

*C12N 15/82* (2006.01)
*C07K 14/415* (2006.01)

(52) U.S. Cl.

CPC ........ *C12N 15/8261* (2013.01); *C07K 14/415* (2013.01); *C12N 15/8223* (2013.01); *C12N 15/8225* (2013.01); *C12N 15/8229* (2013.01); *C12N 15/8241* (2013.01); *C12N 15/8243* (2013.01); *C12N 15/8245* (2013.01); *C12N 15/8246* (2013.01); *C12N 15/8271* (2013.01); *C12N 15/8273* (2013.01); *Y02A 40/146* (2018.01)

(58) Field of Classification Search

CPC ........................................................ C12N 15/82
See application file for complete search history.

(56) References Cited

U.S. PATENT DOCUMENTS

| | | | | |
|---|---|---|---|---|
| 2008/0010703 | A1 * | 1/2008 | Creelman .......... | C12N 15/8261 800/278 |
| 2019/0002907 | A1 | 1/2019 | Cole et al. | |
| 2019/0002908 | A1 | 1/2019 | Cole et al. | |
| 2020/0354738 | A1 | 11/2020 | Cole et al. | |

FOREIGN PATENT DOCUMENTS

| | | | | |
|---|---|---|---|---|
| WO | WO-2009117448 A1 * | 9/2009 | ......... | C12N 15/8218 |

OTHER PUBLICATIONS

Talar et al. ("Beyond *Arabidopsis*: BBX regulators in crop plants." International Journal of Molecular Sciences 22.6 (2021): 2906). (Year: 2021).*

* cited by examiner

*Primary Examiner* — Charles Logsdon
*Assistant Examiner* — Jessica Nicole Stockdale
(74) *Attorney, Agent, or Firm* — Dentons US LLP; David Lanzotti

(57) ABSTRACT

The present disclosure identifies new genes which have the potential to increase broad acre yield in crops. This disclosure is based upon our fundamental knowledge of light signal transduction and our understanding of the roles these genes play in regulating plant growth and development in response to light. Transgenic plants with gain- or loss-of-function of one of these genes, or in combination, are expected to show significant improvements in broad acre yield and stress tolerance.

7 Claims, 50 Drawing Sheets

Figure 1:
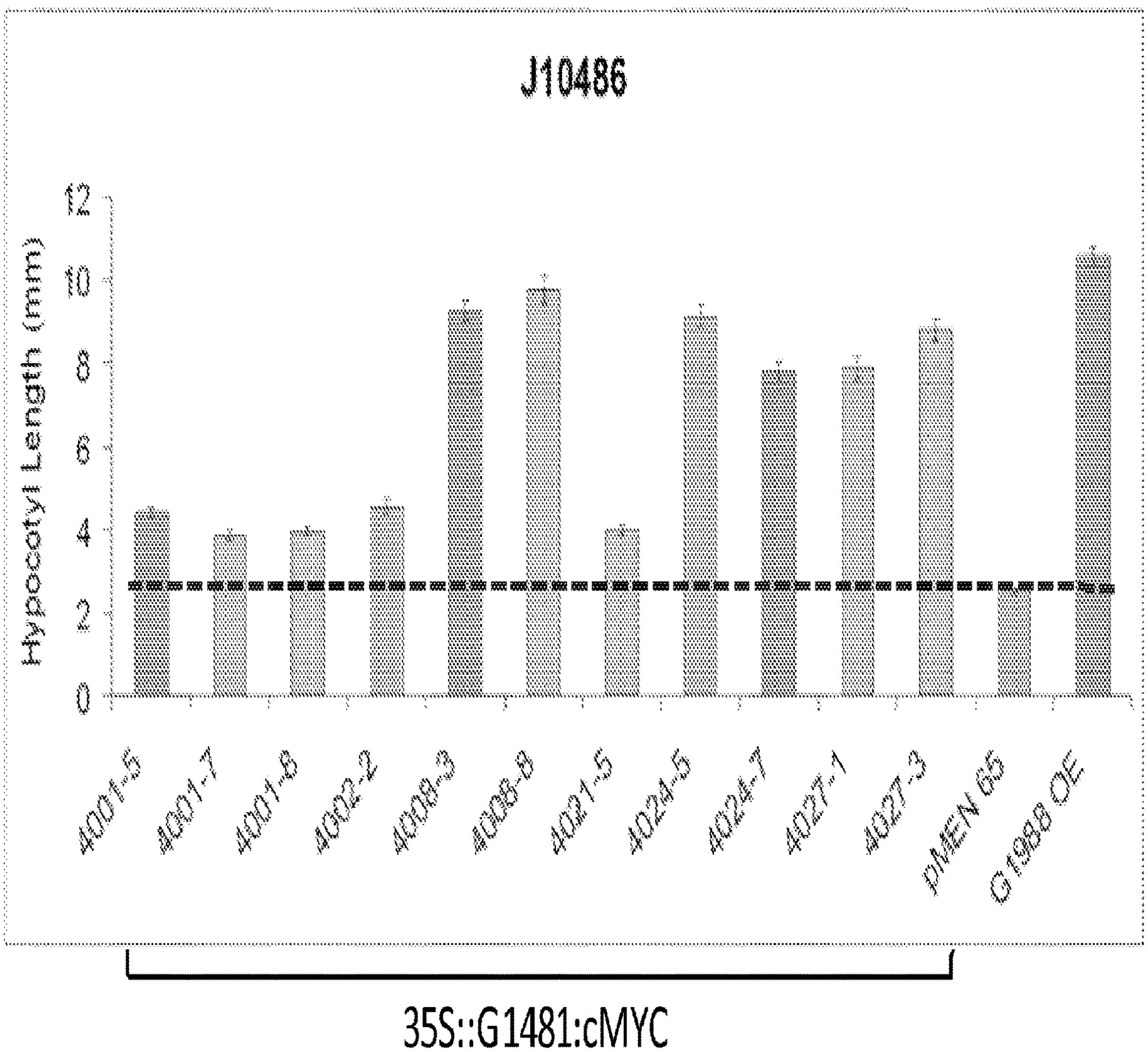

Specification includes a Sequence Listing.

```
                              <------- 1st B-box type ZF domain ------->                     <--
Os04g41560.2        (182) MRIQCDACEAAAATVVCCADEAALCARCDVEIHAANKLASKHQRLPLDAALPAALPRCDV
Os04g41560.4        (184) MRIQCDACEAAAATVVCCADEAALCARCDVEIHAANKLASKHQRLPLDAALPAALPRCDV
Os02g39360.1        (180) MKIQCDACESAAAAVVCCADEAALCAACDVEVHAANKLAGKHQRLPLE-ALSARLPRCDV
ACF84591.1          (156) MKIQCDACEGAAATVVCCADEAALCARCDVEIHAANKLASKHQRLPLE-ALSAKLPRCDV
ACF86823.1          (158) MKIQCDACEGAAATVVCCADEAALCARCDVEIHAANKLASKHQRLPLE-ALSASLPRCDV
ACG28309.1          (160) MKIQCDACEGAAATVVCCADEAALCARCDVEIHAANKLASKHQRLPLE-ALSASLPRCDV
NP_001141667.1      (174) MKIQCDACEGAAATVVCCADEAALCARCDVEIHAANKLASKHQRLPLE-ALSASLPRCDV
CAW36812.1          (162) MKIQCDACEGAAATVVCCADEAALCARCDVEIHAANKLASKHQRLPLE-ALSASLPRCDV
CAW39068.1          (164) MKIQCDACEGAAATVVCCADEAALCARCDVEIHAANKLASKHQRLPLE-ALSASLPRCDV
CAW54445.1          (166) MKIQCDACEGAAATVVCCADEAALCARCDVEIHAANKLASKHQRLPLE-ALSASLPRCDV
CAW74336.1          (168) MKIQCDACEGAAATVVCCADEAALCARCDVEIHAANKLASKHQRLPLE-ALSASLPRCDV
CAW80388.1          (170) MKIQCDACEGAAATVVCCADEAALCARCDVEIHAANKLASKHQRLPLE-ALSASLPRCDV
CAW82896.1          (172) MKIQCDACEGAAATVVCCADEAALCARCDVEIHAANKLASKHQRLPLE-ALSASLPRCDV
G1894 AT2G31380.1  (154) MKIQCDVCEKAPATLICCADEAALCAKCDVEVHAANKLASKHQRLFLD-SLSTKFPPCDI
G329 AT1G06040.1    (152) MKIQCDVCEKAPATVICCADEAALCPQCDIEIHAANKLASKHQRLHLN-SLSTKFPRCDI
AAS67368.1          (198) MKIQCDVCEKAQATVICCADEAALCAKCDIEVHAANKLASKHQRLHLQ-CLSNKLPPCDI
Pt_216458           (176) MKIQCDVCEKAPATVICCADEAALCEKCDIEVHAANKLASKHQRLLLQ-CLSNKLPPCDI
Pt_827145           (178) MKIQCDVCEKAPATVICCADEAALCAKCDIEVHAANKLASKHQRLLLQ-CLSNKLPPCDI
Glyma11g13570.1     (186) MKIQCDVCEKAPATVICCADEAALCAKCDVEVHAANKLASKHQRLLLQ-CLSNKLPRCDI
Glyma12g05570.1     (188) MKIQCDVCEKAPATVICCADEAALCAKCDVEVHAANKLASKHQRLLLQ-SLSNKLPRCDI
Glyma13g41980.2     (192) ----------------------------MDIVISFLEVL------LILF------FPFSYI
Glyma13g41980.3     (194) ----------------------------MDIVISFLEVL------LILF------FPFSYI
Glyma13g41980.1     (190) MKIQCDVCERAPATVICCADEAALCAKCDVEVHAANKLASKHQRLLLQ-CLSSKLPRCDI
Glyma15g03400.1     (196) MKIQCDVCERAPATVICCADEAALCAKCDVEVHAANKLASKHQRLLLQ-CLSSKLPTCDI
                                                  *: :   : *    * *       :*. :
```

FIG. 5A

```
                          ---- 2nd B-box type ZF domain ---->
Os04g41560.2       (182) CQ-EKAAFIFCVEDRALFCRDCDEPIHVPGTLSGNHQRYLTTGIRVGFSSV-------CS
Os04g41560.4       (184) CQ-EKAAFIFCVEDRALFCRDCDEPIHVPGTLSGNHQRYLTTGIRVGFSSV-------CS
Os02g39360.1       (180) CQ-EKAAFIFCVEDRALFCRDCDEPIHVPGTLSGNHQRYLATGIRVGFASASP-----CD
ACF84591.1         (156) CQ-EKAAFIFCVEDRALFCQDCDEPIHVPGTLSGNHQRYLATGIRVGLASA-SACSDACD
ACF86823.1         (158) CQ-EKAAFIFCVEDRALFCRDCDEPIHVPGTLSGNHQRYLATDIRVGFASASSACSDACD
ACG28309.1         (160) CQ-EKAAFIFCVEDRALFCRDCDEPIHVPGTLSGNHQRYLATDIRVGFASASSACSDACD
NP_001141667.1     (174) CQ-EKAAFIFCVEDRALFCRDCDEPIHVPGTLSGNHQRYLATDIRVGFASASSACSDACD
CAW36812.1         (162) CQ-EKAAFIFCVEDRALFCRDCDEPIHVPGTLSGNHQRYLATGIRVGFASASSACSDACD
CAW39068.1         (164) CQ-EKAAFIFCVEDRALFCRDCDEPIHVPGTLSGNHQRYLATGIRVGFASASSACSDACD
CAW54445.1         (166) CQ-EKAAFIFCVEDRALFCRDCDEPIHVPGTLSGNHQRYLATGIRVGFASASSACSDACD
CAW74336.1         (168) CQ-EKAAFIFCVEDRALFCRDCDEPIHVPGTLSGNHQRYLATGIRVGFASASSACSDACD
CAW80388.1         (170) CQ-EKAAFIFCVEDRALFCRDCDEPIHVPGTLSGNHQRYLATGIRVGFASASSACSDACD
CAW82896.1         (172) CQ-EKAAFIFCVEDRALFCRDCDEPIHVPGTLSGNHQRYLATGIRVGFASASSACSDACD
G1894 AT2G31380.1 (154) CL-EKAAFIFCVEDRALLCRDCDEATHAPNTRSANHQRFLATGIRVALSSTS------CN
G329 AT1G06040.1  (152) CQ-EKAAFIFCVEDRALLCRDCDESIHVANSRSANHQRFLATGIKVALTSTI------CS
AAS67368.1         (198) CQ-DKAAFIFCVEDRALFCKDCDEAIHSASSLAKNHQRFLATGIRVALSSS-------CN
Pt_216458          (176) CQ-EKAAFIFCVEDRALFCRDCDEPIHSAGSLSANHQRFLATGIRVALSSS-------CS
Pt_827145          (178) CQ-EKAAFIFCVEDRALFCRDCDEPIHSAGSLSANHQRFLATGIRVALSSS-------CS
Glyma11g13570.1    (186) CQ-DKPAFIFCVEDRALFCKDCDEPIHLASSLSANHQRFLATGIRVALGSN-------CT
Glyma12g05570.1    (188) CQ-DKPAFIFCVEDRALFCKDCDEPIHLASSLSANHQRFLATGIRVALGSN-------CT
Glyma13g41980.2    (192) YQQDKPAFIFCVEDRALFCQDCDEPIHSAGSLSANHQRFLATGIRVASSSN-------CT
Glyma13g41980.3    (194) YQQDKPAFIFCVEDRALFCQDCDEPIHSAGSLSANHQRFLATGIRVASSSN-------CT
Glyma13g41980.1    (190) CQ-DKPAFIFCVEDRALFCQDCDEPIHSAGSLSANHQRFLATGIRVASSSN-------CT
Glyma15g03400.1    (196) CQ-DKPAFIFCVEDRALFCQDCDEPIHSAGSLSANHQRFLATGIRVASSSN-------CT
                            :*.************:*.****.  *  ..: :  ****:*:*.*.*.   *       *
```

FIG. 5B

```
Os04g41560.2       (182) ANADHLPPPAPKGNSK--PPASGIAAAAAPKPAVSAAAQEVPSSPFLPPSGWAVEDLLQL
Os04g41560.4       (184) ANADHLPPPAPKGNSK--PPASGIAAAAAPKPAVSAAAQEVPSSPFLPPSGWAVEDLLQL
Os02g39360.1       (180) GGSD----AHDSDHHA--PPMGSSEHHHHHQQPAPTVAVDTPS-PQFLPQGWAVDELLQF
ACF84591.1         (156) AH-D-------SDHHA--PPKATIE---PPHAAVSAAVQQVPSPPQFLPQGWAVDELLQF
ACF86823.1         (158) AHDD-------SDHHA--PPKAA----------VSSAAQQVPSPPQFLPQGWAVDELLQF
ACG28309.1         (160) AHDD-------SDHHA--PPKAA----------VSSAAQQVPSPPQFLPQGWAVDELLQF
NP_001141667.1     (174) AHDD-------SDHHA--PPKAA----------VSSAAQQVPSPPQFLPQGWAVDELLQF
CAW36812.1         (162) AHDD-------SDHHA--PPKAA----------VSSAAQQVPSPPQFLPQGWAVDELLQF
CAW39068.1         (164) AHDD-------SDHHA--PPKAA----------VSSAAQQVPSPPQFLPQGWAVDELLQF
CAW54445.1         (166) AHDD-------SDHHA--PPKAA----------VSSAAQQVPSPPQFLPQGWAVDELLQF
CAW74336.1         (168) AHDD-------SDHHA--PPKAA----------VSSAAQQVPSPPQFLPQGWAVDELLQF
CAW80388.1         (170) AHDD-------SDHHA--PPKAA----------VSSAAQQVPSPPQFLPQGWAVDELLQF
CAW82896.1         (172) AHDD-------SDHHA--PPKAA----------VSSAAQQVPSPPQFLPQGWAVDELLQF
G1894 AT2G31380.1(154) QEVE-------KNHFD--PSNQQ---------SLSKPPTQQPA---APSPLWATDEFFSY
G329 AT1G06040.1 (152) KEIE-------KNQPE--PSNNQ---QKANQIPAKSTSQQQQQPSSATPLPWAVDDFFHF
AAS67368.1         (198) KESV-------KNQLQPQPPQQN-----SQQVGLKMPPQQLSC---ITSPSWPVDDLLGF
Pt_216458          (176) KDTQ-------KSSLE--PPNQS------EQQTSKLPWQHASS---FGSS-WAVDDFLQF
Pt_827145          (178) KDTQ-------TNSSG--PPNQS-----AQQTPMKIPAQQTSS---FATS-WAVDDLLQF
Glyma11g13570.1    (186) KGHE-------KGNME--PSNPN-----AQEVPVKTPSQQVPS---FTSS-WAVDDLLEL
Glyma12g05570.1    (188) KGNE-------KGHVE--PSKPK-----AQEVPAKIPSQQVPS---FTSS-WAVDDLLEL
Glyma13g41980.2    (192) KDNE-------KSHLE--PPTRN-----AQQVSAKIPPQQVPS---FTSS-WAVDDLLEL
Glyma13g41980.3    (194) KDNE-------KSHLE--PPTRN-----AQQVSAKIPPQQVPS---FTSS-WAVDDLLEL
Glyma13g41980.1    (190) KDNE-------KSHLE--PPTRN-----AQQVSAKIPPQQVPS---FTSS-WAVDDLLEL
Glyma15g03400.1    (196) KDNE-------KSHSE--PPNRS-----AQQVSAKIPPQQVPS---FTSS-WAVDDLLEL
                                    ..      *.                         .   *..::::
```

FIG. 5C

```
Os04g41560.2       (182) SDYE-SSDKKGS----PIGFKDLEWLDDIDLFHVQSPA---KGGSTAAEVPELFASPQPA
Os04g41560.4       (184) SDYE-SSDK---------------------------------------------------
Os02g39360.1       (180) SDYE-TGDKLQKESSPPLGFQELEWFADIDLFHNQAPKGGAAAGRTTAEVPELFAS-QAA
ACF84591.1         (156) SDYE-SSDKLHKE--PTLGFKELEWFADIDLFHEQAPK----ASRTLAEVPELFGY-QAA
ACF86823.1         (158) SDCE-SSDKLHKE--SPLGFKELEWFTDIDLFHEQTPK----AGRRLAEVPELSGT-QAA
ACG28309.1         (160) SDCE-SSDKLHKE--SPLGFKELEWFTDIDLFHEQTPK----AGRRLAEVPELSGT-QAA
NP_001141667.1     (174) SDCE-SSDKLHKE--SPLGFKELEWFTDIDLFHEQTPK----AGRRLAEVPELSGT-QAA
CAW36812.1         (162) SDCE-SSDKLHKE--SPLGFKELEWFTDIDLFHEQTPK----AGRRLAEVPELSGT-QAA
CAW39068.1         (164) SDCE-SSDKLHKE--SPLGFKELEWFTDIDLFHEQTPK----AGRRLAEVPELSGT-QAA
CAW54445.1         (166) SDCE-SSDKLHKE--SPLGFKELEWFTDIDLFHEQTPK----AGRRLAEVPELSGT-QAA
CAW74336.1         (168) SDCE-SSDKLHKE--SPLGFKELEWFTDIDLFHEQTPK----AGRRLAEVPELSGT-QAA
CAW80388.1         (170) SDCE-SSDKLHKE--SPLGFKELEWFTDIDLFHEQTPK----AGRRLAEVPELSGT-QAA
CAW82896.1         (172) SDCE-SSDKLHKE--SPLGFKELEWFTDIDLFHEQTPK----AGRRLAEVPELSGT-QAA
G1894 AT2G31380.1(154) SDLD-CSNK-EKE---QLDLGELDWLAEMGLFGDQPDQ----EALPVAEVPELSFS-HLA
G329 AT1G06040.1 (152) SDIE-STDKKGQL---DLGAGELDWFSDMGFFGDQIND----KALPAAEVPELSVS-H-L
AAS67368.1         (198) PDYE-SSDK--KD---LLELGEFEWLGGIDLFGEQ----------TAAEVPELSVP-Q-S
Pt_216458          (176) SDIEESTDK-------------------------------------------VI----
Pt_827145          (178) SEFESSTDK--KE---QLELGEFEWLADMGLFGEQLPQ----EALAAAEVPQLPIS-P-P
Glyma11g13570.1    (186) TDFE-SPDK--KQ---SLEFGELEWLADAGLFSEQFPH----EALVAAEVPQLPVP-H-T
Glyma12g05570.1    (188) TDFE-SPDKVQKQ---SLEFGELEWLADVGLFGEQFPH----EALAAAEVPQLPMT----
Glyma13g41980.2    (192) TAFE-SPEK--KE---SLQFGELEWLTDVGIFGEQFAQ----EALAAAEVPQLPVT-HNS
Glyma13g41980.3    (194) TAFE-SPEK---E---SLQFGELEWLTDVGIFGEQFAQ----EALAAAEVPQLPVT-HNS
Glyma13g41980.1    (190) TAFE-SPEK--KE---SLQFGELEWLTDVGIFGEQFAQ----EALAAAEVPQLPVT-HNS
Glyma15g03400.1    (196) TGFE-SPEK--KE---SLQFGELEWLTDVGIFGEQFAQ----EALAAAEVPQLPET-HNS
                         .  :   :*
```

FIG. 5D

```
Os04g41560.2      (182) SNMGLYKA------------SGARQSKKPRVEIP--DDDEDFFIVPDLG
Os04g41560.4      (184) -----ART-----------------------------------------
Os02g39360.1      (180) NDVAYYRPPTRTAAAAFTAATGFRQSKKARVELP--DDEEDYLIVPDLG
ACF84591.1        (156) NDAAYYRP----AKAAAGGGAGVRQSKKARIEV---TDDEDYLIVPDLG
ACF86823.1        (158) NDAAYYRP----AKATATAGAGVRQSKKARTEV---TDDEDHLIVPDLG
ACG28309.1        (160) NDAAYYRP----AKATATAGAGVRQSKKARTEV---TDDEDHLIVPDLG
NP_001141667.1    (174) NDAAYYRP----AKATATAGAGVRQSKKARTEV---TDDEDHLIVPDLG
CAW36812.1        (162) NDAAYYRP----AKATATAVAGVRQSKKGRTEV---TDDEDHLIVPDLV
CAW39068.1        (164) NDAAYYRP----AKATATAVAGVRQSKKGRTEV---TDDEDHLIVPDLV
CAW54445.1        (166) NDAAYYRP----AKATATAVAGVRQSKKGRTEV---TDDEDHLIVPDLV
CAW74336.1        (168) NDAAYYRP----AKATATAVAGVRQSKKGRTEV---TDDEDHLIVPDLV
CAW80388.1        (170) NDAAYYRP----AKATATAVAGVRQSKKGRTEV---TDDEDHLIVPDLV
CAW82896.1        (172) NDAAYYRP----AKATATAVAGVRQSKKGRTEV---TDDEDHLIVPDLV
G1894 AT2G31380.1(154) HAHSYNRP-----------MKSNVPNKKQRLEYRY-DDEEEHFLVPDLG
G329 AT1G06040.1  (152) GHVHSYKP-----------MKSNVSHKKPRFETRYDDDDEEHFIVPDLG
AAS67368.1        (198) SNTNIYRT-----------TKYQMPYKKSRIEI---PDDDEYFTVPDLG
Pt_216458         (176) -------------------------------------------------
Pt_827145         (178) TNVNSCRP-----------TKSSMPHKKPRIEIS--DDDDEYLTVPDLG
Glyma11g13570.1   (186) SSVASHKA-----------PKSLVSYKKPRIEVLD-EDDDEHCTVPDLG
Glyma12g05570.1   (188) SSVGSHKA-----------PKSLLSYKKPRIEVLD-EDDDEHFTVPDLG
Glyma13g41980.2   (192) SSVASYRT-----------SKSYMSHKKPRIEVLN-DDDDEYFTVPDLG
Glyma13g41980.3   (194) SSVASYRT-----------SKSYMSHKKPRIEVLN-DDDDEYFTVPDLG
Glyma13g41980.1   (190) SSVASYRT-----------SKSYMSHKKPRIEVLN-DDDDEYFTVPDLG
Glyma15g03400.1   (196) SSVASYKT-----------SKSYMSHKKPRIEVLNDDDDDEYFTVPDLG
```

FIG. 5E

```
                             ←— 1st B-box type ZF domain —→                ←--
Os09g35880.1     (220) MRTICDVCESAPAVLFCVADEAALCRSCDEKVHMCNKLARRHVRVGLADPNKVQRCDICE
ACF85933.1       (204) MRTICDVCESAPAVLFCAADEAALCRPCDEKVHMCNKLASRHVRVGLADPNKLVRCDICE
ACG27957.1       (206) MRTICDVCESAPAVLFCAADEAALCRPCDEKVHMCNKLASRHVRVGLADPNKLVRCDICE
NP_001141274.1   (210) MRTICDVCESAPAVLFCAADEAALCRPCDEKVHMCNKLASRHVRVGLADPNKLVRCDICE
ACL52378.1       (208) MRTICDVCESAPAVLFCAADEAALCRPCDEKVHMCNKLASRHVRVGLADPNKLARCDICE
G1881 AT2G21320.1(202) MRILCDACESAAAIVFCAADEAALCCSCDEKVHKCNKLASRHLRVGLADPSNAPSCDICE
G902 AT4G38960.1 (200) MRILCDACENAAAIIFCAADEAALCRPCDEKVHMCNKLASRHVRVGLAEPSNAPCCDICE
Pt_648693        (212) MRMLCDVCESAAAILFCAADEAALCRSCDEKVHMCNKLASRHVRVGLADPSDVPQCDICE
Pt_721866        (214) MRTICDVCESAAAILFCAADEAALCRSCDEKVHLCNKLASRHVRVGLADPSAVPQCDICE
Glyma01g37370.1  (222) MRTLCDACESAAAIVFCAADEAALCRACDEKVHMCNKLASRHVRVGLASPSDVPRCDICE
Glyma11g07930.1  (224) MRTLCDACESAAAIVFCAADEAALCRACDEKVHMCNKLASRHVRVGLASPSDVPRCDICE
Glyma11g07930.4  (230) MRTLCDACESAAAIVFCAADEAALCRACDEKVHMCNKLASRHVRVGLASPSDVPRCDICE
Glyma11g07930.2  (226) MRTLCDACESAAAIVFCAADEAALCRACDEKVHMCNKLASRHVRVGLASPSDVPRCDICE
Glyma11g07930.3  (228) MRTLCDACESAAAIVFCAADEAALCRACDEKVHMCNKLASRHVRVGLASPSDVPRCDICE
Glyma11g11850.1  (232) MRTLCDVCESAAAILFCAADEAALCSACDHKIHMCNKLASRHVRVGLADPTDVPRCDICE
Glyma12g04130.1  (234) MRTLCDVCESAAAIVFCAADEAALCSACDHKIHMCNKLASRHVRVGLADPTDVPRCDICE
Pt_741179        (216) MRTLCDACESAFAIVFCAADEAALCLACDKKVHMCNKLASRHVRVGLANPSEVPRCDICE
Pt_820080        (218) MRTLCDACESAAAIVFCAADEAALCLACDEKVHMCNKLASRHVRVGLANPSDVPRCDICE
                                                         ***** **:*****.*.    *****
```

FIG. 6A

```
                              --- 2nd B-box type ZF domain --->
Os09g35880.1        (220) NAPAFFYCEIDGTSLCLSCDMTVHVGGKRTHGRYLLLRQRVEFPGDKPGHMDDVAMQQKD
ACF85933.1          (204) NSPAFFYCEIDGTSLCLSCDMTVHVGGKRTHGRYLLLRQRVEFPGDKPGHMDDVPMEIQD
ACG27957.1          (206) NSPAFFYCEIDGTSLCLSCDMTVHVGGKRTHGRYLLLRQRVEFPGDKPGHMDDVPMEIQD
NP_001141274.1      (210) NSPAFFYCEIDGTSLCLSCDMTVHVGGKRTHGRYLLLRQRVEFPGDKPGHMDDVPMEIQD
ACL52378.1          (208) NSPAFFYCEIDGTSLCLSCDMTVHVGGKRTHGRYLLLRQRVEFPGDKPGHMDDVPMEIKD
G1881 AT2G21320.1   (202) NAPAFFYCEIDGSSLCLQCDMVVHVGGKRTHRRFLLLRQRIEFPGDKPNHADQLGLRC--
G902 AT4G38960.1    (200) NAPAFFYCEIDGSSLCLQCDMVVHVGGKRTHGRFLLLRQRIEFPGDKPKENNT-------
Pt_648693           (212) KAPAFFYCEIDGSSLCLQCDMIVHVGGKRTHGRYLLLRQRVEFPGDKPGCTEEQGQQPLD
Pt_721866           (214) NAPAFFYCEIDGSSLCLQCDMIVHVGGKRTHGRYLLLRQRVEFPGDKPGRMEEQGQQPLD
Glyma01g37370.1     (222) NAPAFFYCETDGSSLCLQCDMIVHVGGKRTHGRYLLFRQRVEFPGDKSSHAENPASQPLE
Glyma11g07930.1     (224) NAPAFFYCETDGSSLCLQCDMIVHVGGKRTHGRYLLFRQRVEFPGDKSSHAENPASQALE
Glyma11g07930.4     (230) NAPAFFYCETDGSSLCLQCDMIVHVGGKRTHGRYLLFRQRVEFPGDKSSHAENPASQALE
Glyma11g07930.2     (226) NAPAFFYCETDGSSLCLQCDMIVHVGGKRTHGRYLLFRQRVEFPGDKSSHAENPASQALE
Glyma11g07930.3     (228) NAPAFFYCETDGSSLCLQCDMIVHVGGKRTHGRYLLFRQRVEFPGDKSSHAENPASQALE
Glyma11g11850.1     (232) NAPAFFYCEIDGSSLCLQCDMIVHVGGKRTHGRYLLLRQRAQFPGDKPAQMEELELQPMD
Glyma12g04130.1     (234) NAPAFFYCEIDGSSLCLQCDMIVHVGGKRTHGRYLLLRQRVQFP----------------
Pt_741179           (216) NAPAFFYCETDGSSLCLQCDMTVHVGGKRTHGRYLLLRQKIEFPGDQP-QPEDPAPQPMY
Pt_820080           (218) NAPAFFYCETDGSSLCLQCDMTVHVGGKRTHGRYLLLRQRVEFPGDKP-QPDDLHSQPMH
                          ::******* **:****.*** ********* *:**:**. :**
```

FIG. 6B

```
Os09g35880.1      (220) P-ENRTDQKKAPHSVTKEQMANHHNVSDDPASDGNCDDQGNIDSKMIDLNMRPVRT-HGQ
ACF85933.1        (204) P-ENQRDQKKPPK----EQTANHH-NGDDPATDGNCDDQGNIDSKMIDLNMRPVRT-HGQ
ACG27957.1        (206) P-ENQRDQKKPPK----EQTANHH-NGDDPATDGNCDDQGNIDSKMIDLNMRPVRT-HGQ
NP_001141274.1    (210) P-ENQRDQKKPPK----EQTANHH-NGDDPATDGNCDDQGNIDSKMIDLNMRPVRT-HGQ
ACL52378.1        (208) P-ENQREQNT-PK----EQMANHH-NVNDPVSDGNCDGQGNIDSKMIDLNMRPART-HGQ
G1881 AT2G21320.1(202) ----------------------QK---ASSGRGQESNGNGDHDHNMIDLNSNPQRV-HEP
G902 AT4G38960.1 (200) ----------------RDNLQNQR-VS----TNGNGEANGKIDDEMIDLNANPQRV-HEP
Pt_648693         (212) DNETRRDQNQPPKLTARENQQNHR-ASPVPMVENNTDSDGKMDNKLIDLNARPQRV-HGK
Pt_721866         (214) HNETRRDQNQPLKLTARENKQNHR-ASPVPMVENNTDSDGKMDNNLIDLNARPQRI-HGQ
Glyma01g37370.1   (222) PGEAKRGQNPLPKLKMGEKQQNHK-MPMVPTPGPDADGHAKMESKMIDLNMKPNRI-HEQ
Glyma11g07930.1   (224) PGEAKRGQNPLPKLKMGEKQQNHR-MPMVPTPGPDADGQTKMETKMIDLNMKPNRI-HEQ
Glyma11g07930.4   (230) PGEAKRGQNPLPKLKMGEKQQNHR-MPMVPTPGPDADGQTKMETKMIDLNMKPNRI-HEQ
Glyma11g07930.2   (226) PGEAKRGQNPLPKLKMGEKQQNHR-MPMVPTPGPDADGQTKMETKMIDLNMKPNRI-HEQ
Glyma11g07930.3   (228) PGEAKRGQNPLPKLKMGEKQQNHR-MPMVPTPGPDADGQTKMETKMIDLNMKPNRI-HEQ
Glyma11g11850.1   (232) QNESRRDESQSLKLKTRDSQQNHS-VSPFPRQENNIDGHGKMDKKLIDLNTRPLRL-NGS
Glyma12g04130.1   (234) -----------------YSQQNHS-VSPVPRQENNIDGHGKMDKKLIDLNTRPLRL-NGA
Pt_741179         (216) PGETRRGQNRPQKATSGENRQNRQ-ASPVLMSVTNSDGHDKVDKNMIDLNMKPHRI-HEH
Pt_820080         (218) PGETRKGQNQPPKATAEEKRQNRQ-VSPAPMSLSNSDGHDKVDKKMIDLNMKPQRTDHEQ
                                              .           : :   . : ::**** .* *  :
```

FIG. 6C

```
Os09g35880.1      (220) GSNSQTQGVDV-SVNNHDSPGVVPTCNFEREANK
ACF85933.1        (204) ESNSQTQGVGL-SVNNHDSPGVVPTSNSERDTSK
ACG27957.1        (206) ESNSQTQGVGL-SVNNHDSPGVVPTSNSERDTSK
NP_001141274.1    (210) ESNSQTQGVGL-SVNNHDSPGVVPTSNSERDTSK
ACL52378.1        (208) GSNSQTQGVDL-SVNNHDSPGVVPTSNSERDAIK
G1881 AT2G21320.1(202) GSHNQEEGIDVNNANNHEHE--------------
G902 AT4G38960.1 (200) SSNNN--GIDVNNENNHEPAGLVPVGPFKRESEK
Pt_648693         (212) NPTNQE---------NHESSSLAPFGFFKGEPQK
Pt_721866         (214) NSTNQE---------NHESSSAVPVGSFKREPQK
Glyma01g37370.1   (222) ASNNQP----------------------------
Glyma11g07930.1   (224) ASNNQCSWMKV-------------------EPFP
Glyma11g07930.4   (230) ASNNQVRVHGK-----------------------
Glyma11g07930.2   (226) ASNNQP----------------------------
Glyma11g07930.3   (228) ASNNQP----------------------------
Glyma11g11850.1   (232) APNNQEQCMDILRGNNHESASVPPVESFKQESEK
Glyma12g04130.1   (234) APNNQERGMDILRGNNHKSASVPPVESFKQESEK
Pt_741179         (216) ASNNQEQ---------------------------
Pt_820080         (218) ASNNQEL---------------------------
                         .  .:
```

FIG. 6D

```
                                                      ←—— B-box type ZF domain ——
G1478 AT4G15248.1 (40) MCRGFEKEEERRSDNGGCQRLCTESHKAPVSCELCGENATVYCEADAAFLCRKCDRWVHS
Glyma12g32230.1   (48) MCKG--AEGEKQHGFCSSFLHKESATRSAICCELCGLQASLYCQADDAYLCKKCDKRVHE
Glyma13g38240.1   (50) MCKG--AEGEKQHGFCSSYLHKECATRSATCCELCGLQASLYCQADDAYLCRKCDKRVHE
Pt_562313         (44) MCRGIHQERNNQGGSCGEEVVSSKATSRLVCCELCGSRASLYCQADDAFLCQKCDKWVHG
Pt_594447         (46) MCRG-NQERSNQGSSCNKEAVSPNATSRFVCCELCGSRATLYCQADHAFLCQKCDGWVHG
                       **.*   * ... .  .       :     .***** .*::**:** *:**.*** .**

                       --——→
G1478 AT4G15248.1 (40) ANFLARRHLRRVICTTCRKLTRRCLVGDNFNVVLPEI--------RMIARIEEHSSD-HK
Glyma12g32230.1   (48) ANFLALRHIRCFLCNTCQNLTRRYLIGASLEVVLPANINWTIRNLLNNRGIYRKCSRMHN
Glyma13g38240.1   (50) ANFLALRHIRCFLCNTCQNLTRRYLIGASIEVVLPANINWTIGNLPSNRGIHRKCSRMHN
Pt_562313         (44) ANFLAQRHVRCMLCNTCQNLTQRYLIGASTELLLPTIVSWRERR-QCNSNLEKKSSGSLK
Pt_594447         (46) ANFLALRHVRNMLCNTCQNLTQRCLIGASTEVMLSTIVSWRERR-DRNSNLEKKCSGSLK
                       ***** **:* .:*.**.:**.* *:* . :::*.               :  :.*   :

G1478 AT4G15248.1 (40) IPFVFL
Glyma12g32230.1   (48) SPSLFL
Glyma13g38240.1   (50) NLSLLL
Pt_562313         (44) MPFLFL
Pt_594447         (46) KPFSFL
                           :*
```

FIG. 7

```
                                                                      <-- B-box type ZF domain -->
ACN33981.1           (6) MSAAAAAEVGKEKGAATPGPGPGPGGA CELCGAAARVYCGADEATLCWGCDAQVHGANFL
Os08g08120.2        (18) ----MSVAAEGKEKGVGGGGGGAGAGA CELCGAAARVYCGADEATLCWGCDAQVHGANFL
Os08g08120.1        (16) ----MSVAAEGKEKGVGGGGGGAGAGA CELCGAAARVYCGADEATLCWGCDAQVHGANFL
Os08g08120.3        (20) ----MSVAAEGKEKGVGGGGGGAGAGA CELCGAAARVYCGADEATLCWGCDAQVHGANFL
Pt_758524           (14) ------------------------MKK CELCDSFAQMHCESDQAILCSACDAYVHSANFL
Glyma13g32160.1     (34) ------------------------MRK CELCNSPAKLFCESDQASLCWKCDAKVHSANFL
Glyma15g07140.1     (38) ------------------------MRK CELCNSPAKLFCESDQASLCWECDAKVHSANFL
G1481 AT4G27310.1    (2) -----------------------MGKK CDLCNGVARMYCESDQASLCWDCDGKVHGANFL
G900 AT5G54470.1     (4) ----------------------MGKKK CELCCGVARMYCESDQASLCWDCDGKVHGANFL
Glyma12g32470.1     (32) ------------------------MKN CELCKLPARTFCESDQASLCWDCDAKVHGANFL
Glyma13g37970.1     (36) ------------------------MKN CELCKLPARTFCESDQASLCWDCDAKVHGANFL
Pt_568988            (8) ------------------------MKG CELCGSSARMFCESDEASLCWDCDEKVHSANFL
Pt_571834           (10) ------------------------MKK CELCKNPARTYCESDEANLCWNCDTKVHGANFL
Glyma06g45620.1     (24) ------------------------MNK CELCKVPARIFCESDQASLCWDCDAKVHSANFL
Glyma12g11230.1     (30) ------------------------MKK CELCKVPARIFCESDQASLCWDCDAKVHSANFL
Pt_582065           (12) ------------------------MKG CELCGSSARMFCESDQASLCWDCDEKVHSANFL
Glyma06g39810.1     (22) --------------------MEESSTT CVLCEKRAMMLCDSDQAKLCWECDEKVHSANFL
Glyma09g35960.1     (28) ----------------------MGEYS CALCKKRAMMLCDSDQAKLCWECDEKVHSANFL
                                                    * **   *   * :*.* **  **  **.****
```

FIG. 8A

```
ACN33981.1          (6)  VARHARSLLCRGCARPTPWRAAGPRLGPTVSLCVRCVRRGP-------------------
Os08g08120.2        (18) VARHARALLCRGCARPTPWRAAGPRLGPTASLCERCVRRGGGGRGGGGGGGAAG------
Os08g08120.1        (16) VARHARALLCRGCARPTPWRAAGPRLGPTASLCERCVRRGGGGRGGGGGGGAAG------
Os08g08120.3        (20) VARHARALLCRGCARPTPWRAAGPRLGPTASLCERCVRRGGGGRGGGGGGGAAG------
Pt_758524           (14) AAKHSRTLLCHVCQSHTPWIGTGPLLGATLSVCNSCINNSS-------------------
Glyma13g32160.1     (34) VTKHPRILLCHVCQSLTAWHGTGPKFVPTMSVCNTCVNNNS-------------------
Glyma15g07140.1     (38) VTKHPRILLCHVCQSLTAWHGTGPKFVPTMSVCNTCVNNNS-------------------
G1481 AT4G27310.1   (2)  VAKHTRCLLCSACQSLTPWKATGLRLGPTFSVCESCVALKNAGGGRGNRVLSENRGQEEV
AT5G54470.1         (4)  VAKHMRCLLCSACQSHTPWKASGLNLGPTVSICESCLARKK-------------------
Glyma12g32470.1     (32) VARHTRTLLCHACQSLTPWKASGSALGNTVSLCQSCAGGTT-------------------
Glyma13g37970.1     (36) VERHTRTLLCHACQSPTPWKASGAALGNTVSLCERCAGGTT-------------------
Pt_568988           (8)  VAKHCRTLLCQVCQSPTPWKASVSKFAPTVSICESCFTIPN-------------------
Pt_571834           (10) VARHARALLCQSCQSLTPWKASGSQLGHTVSVCERCGAMVT-------------------
Glyma06g45620.1     (24) VARHARTLLCRTCRSPTPWKASGASLASAVSVCDRCAASEE-------------------
Glyma12g11230.1     (30) VARHVRTLLCRTCRSPTPWKASGASLAHAASVCDRCAAAEE-------------------
Pt_582065           (12) VAKHCRTLLCQVCQSPTPWKSSGSKLAPTVSVCESCFAVHK-------------------
Glyma06g39810.1     (22) VAKHSRVLLCRLCHSPTPWKASGMKLTPTVSFCNRCVAERNARWNRLVNNENEHQQQQ--
Glyma09g35960.1     (28) VAKHSRVLLCRLCHSPTPWKASGTKLMLTVSFCQRCVAHRH-------------------
                         . .* * ***  *   :.   :          * *  *
```

FIG. 8B

```
ACN33981.1          (6) ------AGAVGVGGDEEMGGAGDGDAEDDDDE---DDDSEEEEEE---------------
Os08g08120.2       (18) ------GGGRGGGGDEEMGGEGDEEEEDEDEEVVVEEEEDEDDED---------------
Os08g08120.1       (16) ------GGGRGGGGDEEMGGEGDEEEEDEDEEVVVEEEEDEDDED---------------
Os08g08120.3       (20) ------GGGRGGGGDEEMGGEGDEEEEDEDEEVVVEEEEDEDDED---------------
Pt_758524          (14) --------------------------CTDGKGSENDQIANNDD----------------
Glyma13g32160.1    (34) ------TETCSQQNHEDDDDDGTGEDHAENDDGGVAEDDDDDDDE---------------
Glyma15g07140.1    (38) ---------------ETCSQQNHVEDHDDNHDDGTGEDHVENHDG---------------
G1481 AT4G27310.1 (2) NSFESEEDRIREDHGDGDDAESYDDDEEEDEDEEYSDDEDEDDDE---------------
AT5G54470.1         (4) ------NNNSSLAGRDQNLNQEEEIIGCNDGAESYDE----ESDE---------------
Glyma12g32470.1    (32) -----------EQGPESQGGNDDDDIDTDDEDDYDDDGESEENEV---------------
Glyma13g37970.1    (36) -----------EQGQESQGGNDDDIDTDIDTDDEDDYDESEDEV----------------
Pt_568988           (8) ---KTKETEERMKGCELCGSSARMYCESDQASLCWDCDEKVHTANFLVAKHCRTLLCQVC
Pt_571834          (10) ------------------------------------------------------------
Glyma06g45620.1    (24) ---------------------------PEESEAGNDDEPDTEDD---------------
Glyma12g11230.1    (30) ---------------------------TEESEAGNDDEPDTEDD---------------
Pt_582065          (12) NNKKQLQDLNVMASDQESREAGNDYDESENDREFDDDDTDDDSDE---------------
Glyma06g39810.1    (22) -----QQQQQSDFVVDDGREYGSDHVFDDDDGDYSDDSGEEEEED---------------
Glyma09g35960.1    (28) ------------------------------------------------------------
```

FIG. 8C

```
ACN33981.1          (6)  --------EEEEGEGENQVVPWTEDAE-----ATPPPVGSSTSSSSREAPANGAERAA--
Os08g08120.2        (18) --------EEGEGEGENQVVPWAEEAE-----ATPPPVASSTSSSSREAAANGANAADRV
Os08g08120.1        (16) --------EEGEGEGENQVVPWAEEAE-----ATPPPVASSTSSSSREAAANGANAADRV
Os08g08120.3        (20) --------EEGEGEGENQVVPWAEEAE-----ATPPPVASSTSSSSREAAANGANAADRV
Pt_758524           (14) -----------------EIIANM--MK-----TMMVVKTAMKTMKKIKCVYGLVKQGKDR
Glyma13g32160.1     (34) ---------------ENQVVPWT---------STPPPPASTSSNSVTTSSTRF-------
Glyma15g07140.1     (38) --------GVSEDDEENQVVPWT---------STPPPPASTSSNSVTTSSTRFSNV----
G1481 AT4G27310.1   (2)  --------DGDDEEAENQVVPWS--AA-----AQVPPVMSSSSSDGGSGGSVTKRTRARE
AT5G54470.1         (4)  --------DEEEEEVENQVVPAA--VE-----QELPVVSSSSSVSSGEGDQVVKRTRLDL
Glyma12g32470.1     (32) --------AADEEDGDNQVVPWS--SE-----PPPPSPSSSSSEESISRCNNVDEVSTTL
Glyma13g37970.1     (36) --------AADEEDGDNQVVPWS--SE-----PPPPAPSSSSSEESVSRCNNVDEVSTTL
Pt_568988           (8)  QSPTPWKASGSKFAPTVSVVPWSGPTASSSPSPVPPVASSSSEEETSCAGRNGFLKRMRE
Pt_571834           (10) ----------------------------------------NNTTSTAICKLFLFLYQF
Glyma06g45620.1     (24) --------DNDDEDGDNQVVPWS--SS-----PPPPPPSSSSGSEWSECKNDDASISASE
Glyma12g11230.1     (30) --------D----DVDNQVVPWS--ST-----PPPPPPSSSSGSECSECKNNVASFSASE
Pt_582065           (12) --------YDEEEDGDNQ------------------------------------------
Glyma06g39810.1     (22) --------EDDEEENENQVVPMSSGSA-----TSPPKVACLALKRLRNNSFSVDSS----
Glyma09g35960.1     (28) ------------------------------------------------------------
```

FIG. 8D

```
ACN33981.1          (6) -------KENAPCSTSQPGLCHHASSARHGG--RSDEATSSR----SGGRVLASRHRKRS
Os08g08120.2       (18) -------KEDQPCSTSQPSLCRYASSAHHGGGGRSDEATSSRNGGGVGGRFLASRHRKRS
Os08g08120.1       (16) -------KEDQPCSTSQPSLCRYASSAHHGGGGRSDEATSSRNGGGVGGRFLASRHRKRS
Os08g08120.3       (20) -------KEDQPCSTSQPSLCRYASSAHHGGGGRSDEATSSRNGGGVGGRFLASRHRKRS
Pt_758524          (14) -------QEVSTRQMLF-------------------------------------------
Glyma13g32160.1    (34) --------------------------------SDVEEGGSD------------------
Glyma15g07140.1    (38) -----------------------------------EEGGSD------------------
G1481 AT4G27310.1   (2) -------NSDLLC--------------------SDDEIGSSS---AQGSNYSRPLKRSAF
AT5G54470.1         (4) -------DLNLSDEENQSRPLKR----------LSRDEGLSRSTVVMNSSIVKLHGGRRK
Glyma12g32470.1    (32) -------KRRRENDDFQGS--------------NSNNWKCERSEVDRGCWLARLRRRTAD
Glyma13g37970.1    (36) -------KRRRQEDNDFQGW-------------NSNNWGCERSEVERGGWLVRLRRRTAD
Pt_568988           (8) SNVDLDSDDEIGCS-------------------SSHNIGGRILSNDGGNSLSSMRPWKQA
Pt_571834          (10) ------------------------------------------------------------
Glyma06g45620.1    (24) -------QETTTCSLKRQRE-------------DDDDASSDR--------DPRVLRRVGR
Glyma12g11230.1    (30) -------QETTTSSLKRQRE-------------DDDDASSDP--------DPRVLRRVGR
Pt_582065          (12) ------------------------------------------------------------
Glyma06g39810.1    (22) -------HDETACS-------------------SSEMLSSTLPSGDESTSLSSVLKRHRV
Glyma09g35960.1    (28) ------------------------------------------------------------
```

FIG. 8E

```
ACN33981.1          (6) PSDFFSSDGSPQPGNGTPAARNCSDAGIARNDFT
Os08g08120.2       (18) PSDFRRSGLAQSVSGVQGRNCSNAVVGRNDFS--
Os08g08120.1       (16) PSDFRRSGLAQSVSGVQGRNCSNAVVGRNDASMM
Os08g08120.3       (20) PSDFRRSGLAQSVSGVQGRNCSNAVVGRNE----
Pt_758524          (14) ----------------------------------
Glyma13g32160.1    (34) ----------------------------------
Glyma15g07140.1    (38) ----------------------------------
G1481 AT4G27310.1  (2) KSTVVV----------------------------
AT5G54470.1         (4) AEGCDTSSSSSFY---------------------
Glyma12g32470.1    (32) DVAVERRRARAAFPYGCCDDRASEDV--------
Glyma13g37970.1    (36) DVAVEQRSARAASPDGCCGDRASEDV--------
Pt_568988           (8) RTSVNVEEDG------------------------
Pt_571834          (10) ----------------------------------
Glyma06g45620.1    (24) LNGGCV----------------------------
Glyma12g11230.1    (30) LNGGCV----------------------------
Pt_582065          (12) ----------------------------------
Glyma06g39810.1    (22) D---------------------------------
Glyma09g35960.1    (28) ----------------------------------
```

FIG. 8F

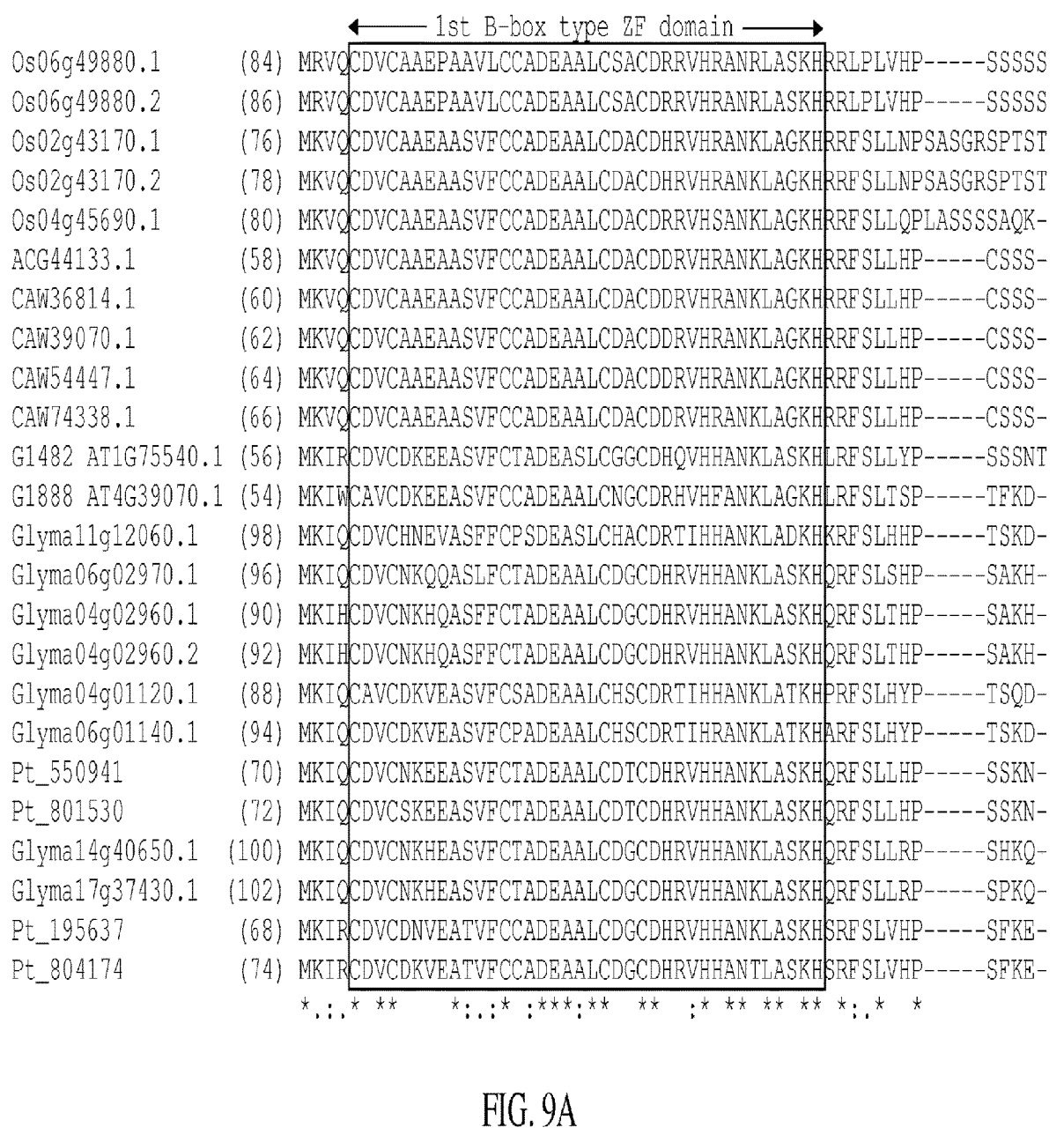

```
                                       ←—— 1st B-box type ZF domain ——→
Os06g49880.1         (84)  MRVQCDVCAAEPAAVLCCADEAALCSACDRRVHRANRLASKHRRLPLVHP-----SSSSS
Os06g49880.2         (86)  MRVQCDVCAAEPAAVLCCADEAALCSACDRRVHRANRLASKHRRLPLVHP-----SSSSS
Os02g43170.1         (76)  MKVQCDVCAAEAASVFCCADEAALCDACDHRVHRANKLAGKHRRFSLLNPSASGRSPTST
Os02g43170.2         (78)  MKVQCDVCAAEAASVFCCADEAALCDACDHRVHRANKLAGKHRRFSLLNPSASGRSPTST
Os04g45690.1         (80)  MKVQCDVCAAEAASVFCCADEAALCDACDRRVHSANKLAGKHRRFSLLQPLASSSSAQK-
ACG44133.1           (58)  MKVQCDVCAAEAASVFCCADEAALCDACDDRVHRANKLAGKHRRFSLLHP-----CSSS-
CAW36814.1           (60)  MKVQCDVCAAEAASVFCCADEAALCDACDDRVHRANKLAGKHRRFSLLHP-----CSSS-
CAW39070.1           (62)  MKVQCDVCAAEAASVFCCADEAALCDACDDRVHRANKLAGKHRRFSLLHP-----CSSS-
CAW54447.1           (64)  MKVQCDVCAAEAASVFCCADEAALCDACDDRVHRANKLAGKHRRFSLLHP-----CSSS-
CAW74338.1           (66)  MKVQCDVCAAEAASVFCCADEAALCDACDDRVHRANKLAGKHRRFSLLHP-----CSSS-
G1482 AT1G75540.1    (56)  MKIRCDVCDKEEASVFCTADEASLCGGCDHQVHHANKLASKHLRFSLLYP-----SSSNT
G1888 AT4G39070.1    (54)  MKIWCAVCDKEEASVFCCADEAALCNGCDRHVHFANKLAGKHLRFSLTSP-----TFKD-
Glyma11g12060.1      (98)  MKIQCDVCHNEVASFFCPSDEASLCHACDRTIHHANKLADKHKRFSLHHP-----TSKD-
Glyma06g02970.1      (96)  MKIQCDVCNKQQASLFCTADEAALCDGCDHRVHHANKLASKHQRFSLSHP-----SAKH-
Glyma04g02960.1      (90)  MKIHCDVCNKHQASFFCTADEAALCDGCDHRVHHANKLASKHQRFSLTHP-----SAKH-
Glyma04g02960.2      (92)  MKIHCDVCNKHQASFFCTADEAALCDGCDHRVHHANKLASKHQRFSLTHP-----SAKH-
Glyma04g01120.1      (88)  MKIQCAVCDKVEASVFCSADEAALCHSCDRTIHHANKLATKHPRFSLHYP-----TSQD-
Glyma06g01140.1      (94)  MKIQCDVCDKVEASVFCPADEAALCHSCDRTIHRANKLATKHARFSLHYP-----TSKD-
Pt_550941            (70)  MKIQCDVCNKEEASVFCTADEAALCDTCDHRVHHANKLASKHQRFSLLHP-----SSKN-
Pt_801530            (72)  MKIQCDVCSKEEASVFCTADEAALCDTCDHRVHHANKLASKHQRFSLLHP-----SSKN-
Glyma14g40650.1     (100)  MKIQCDVCNKHEASVFCTADEAALCDGCDHRVHHANKLASKHQRFSLLRP-----SHKQ-
Glyma17g37430.1     (102)  MKIQCDVCNKHEASVFCTADEAALCDGCDHRVHHANKLASKHQRFSLLRP-----SPKQ-
Pt_195637            (68)  MKIRCDVCDNVEATVFCCADEAALCDGCDHRVHHANKLASKHSRFSLVHP-----SFKE-
Pt_804174            (74)  MKIRCDVCDKVEATVFCCADEAALCDGCDHRVHHANTLASKHSRFSLVHP-----SFKE-
                           *.:.* **    *:.:* :***:**  **  :* ** ** ** *:.*  *
```

FIG. 9A

```
                                       <---- 2nd B-box type ZF domain ---->
Os06g49880.1        (84) GDGGAAAAPLCDVCREKRGLVFCVEDRAILCADCDEPIHSANDLTAKHTRFLLVGAKL--
Os06g49880.2        (86) GDGGAAAAPLCDVCREKRGLVFCVEDRAILCADCDEPIHSANDLTAKHTRFLLVGAKL--
Os02g43170.1        (76) ------TAPLCDICQEKRGFLFCKEDRAILCRECDVPVHTASELTMRHSRYLLTGVRL--
Os02g43170.2        (78) ------TAPLCDICQEKRGFLFCKEDRAILCRECDVPVHTASELTMRHSRYLLTGVRL--
Os04g45690.1        (80) -------PPLCDICQEKRGFLFCKEDRAILCRECDVTVHTTSELTRRHGRFLLTGVRL--
ACG44133.1          (58) ----AQKPPLCDICQERRGFLFCKEDRAILCRECDAPVHSANDMTRRHSRFLLTGVRL--
CAW36814.1          (60) ----AHKPPLCDICQERRGFLFCKEDRAILCRECDAPVHSANDMTRRHSRFLLTGVRL--
CAW39070.1          (62) ----AHKPPLCDICQERRGFLFCKEDRAILCRECDAPVHSANDMTRRHSRFLLTGVRL--
CAW54447.1          (64) ----AHKPPLCDICQERRGFLFCKEDRAILCRECDAPVHSANDMTRRHSRFLLTGVRL--
CAW74338.1          (66) ----AHKPPLCDICQERRGFLFCKEDRAILCRECDAPVHSANDMTRRHSRFLLTGVRL--
G1482 AT1G75540.1   (56) ------SSPLCDICQDKKALLFCQQDRAILCKDCDSSIHAANEHTKKHDRFLLTGVKL--
G1888 AT4G39070.1   (54) -------APLCDICGERRALLFCQEDRAILCRECDIPIHQANEHTKKHNRFLLTGVKI--
Glyma11g12060.1     (98) -------SPLCDICHERRAYLFCKEDRAILCRECDLSIHGVNEHTKKHNRFLLTGVKI--
Glyma06g02970.1     (96) -------FPLCDVCQERRAFVFCQQDRAILCKECDVPVHSANDLTKNHNRFLLTGIKF--
Glyma04g02960.1     (90) -------FPLCDVCQERRAFVFCQQDRAILCKECDVPIHSANDLTKNHSRFLLTGIKFSA
Glyma04g02960.2     (92) -------FPLCDVCQERRAFVFCQQDRAILCKECDVPIHSANDLTKNHSRFLLTGIKFSA
Glyma04g01120.1     (88) -------FPLCDICQERRAYLFCQEDRALLCRECDVPIHRANEHTQKHNRFLLTGVKL--
Glyma06g01140.1     (94) -------FPLCDICQERRAYLFCQEDRALLCRECDVPIHRANEHTQKHNRFLLTGVKL--
Pt_550941           (70) -------FPICDICQEKRAFLFCQQDRAILCRECDGPIHTANEHTQKHNRFLLTGVKL--
Pt_801530           (72) -------FPICDICQDKRAFLFCQQDRAILCRDCDGPIHTANEHTQKHNRFLLTGVKL--
Glyma14g40650.1    (100) -------HPLCDICQERRAFTFCQQDRAILCKECDVSIHSANEHTLKHDRFLLTGVKL--
Glyma17g37430.1    102) -------HPLCDICQERRAFTFCQQDRAILCKECDVSIHSANEHTLKHDRFLLTGVKL--
Pt_195637           (68) -------SPLCDICQERRALLFCQEDRAILCRECDLPIHKANEHTQKHNRFLLTGVKL--
Pt_804174           (74) -------SPLCDICQERRAVLFCQEDRAILCRECDLPIHKVNEHTQKHNRFLLTGVKL--
                                *:**:* :...  ** :***:** :** .:* ..: * .* *:**.* .:
```

FIG. 9B

```
Os06g49880.1        (84)  SPAALAEQPLPSSDCSSDDDAAAAATEE--------------------EYHSSAASTGAA
Os06g49880.2        (86)  SPAALAEQPLPSSDCSSDDDAAAAATEE--------------------EYHSSAASTGAA
Os02g43170.1        (76)  SSEPAASPAPPSEEENS-------------------------------SSFCCSADDAVP
Os02g43170.2        (78)  SSEPAASPAPPSEEENS-------------------------------SSFCCSADDAVP
Os04g45690.1        (80)  SSAPMDSPAPSEEEEE--------------------------------------EAGED
ACG44133.1          (58)  SSAPVDSADPSEGEEE--------------------------------EEQENSSRPGNG
CAW36814.1          (60)  SSAPVDSADPSEGEEE--------------------------------EEQENSSRPGNG
CAW39070.1          (62)  SSAPVDSADPSEGEEE--------------------------------EEQENSSRPGNG
CAW54447.1          (64)  SSAPVDSADPSEGEEE--------------------------------EEQENSSRPGNG
CAW74338.1          (66)  SSAPVDSADPSEGEEE--------------------------------EEQENSSRPGNG
G1482 AT1G75540.1   (56)  SATSSVYKPTSKSSSSSSSNQDFSVPG---------------------SSISNPPPLKKP
G1888 AT4G39070.1   (54)  SASPSAYPRASNSNSAAAFGRAKTRPKS----------VSSEVPSSASNEVFTSSSSTTT
Glyma11g12060.1     (98)  GADASDPTSLSSNDTAIEERTTSSSKIN--------------------RPISSLSNENIS
Glyma06g02970.1     (96)  ------------------------------------------------SALDSPSTPPKP
Glyma04g02960.1     (90)  SATPYDYSSPPPPPPPPPPKRN--------------------------PVLDSPSTPSPP
Glyma04g02960.2     (92)  SATPYDYSSPPPPPPPPPPKRN--------------------------PVLDSPSTPSPP
Glyma04g01120.1     (88)  SGTSLDPAASSTNCTHGSEGRNNARSRM-------------------NRPRSSVSNEENA
Glyma06g01140.1     (94)  SGTCLDPASSSTNYTNNNRVTGSEGRND--------------ARSRMNRPRSSVSNEENA
Pt_550941           (70)  SATSAVYISSSSVTNSGGDLVPDSKSQQQQQQQQSIKKPVFDAPVNSNPPTVPSTLSTNT
Pt_801530           (72)  SATSAVYMSSSSSVTMNSN-----------------------------PPAVPSTLSANT
Glyma14g40650.1    (100)  AASAMLRSSQTTSDSNSTPSLLNVSHQT--------------------TPLPSSTTTTTT
Glyma17g37430.1    (102)  SASAMLRSSETTSDSNSNPSLLNFSHQ---------------------TTLLPPSSTTTT
Pt_195637           (68)  SASSSLHTASSTSTNNFDSNINTTSNRN-----------HQPYLKNSNEILSSPSVETAS
Pt_804174           (74)  CGPSLYATSSSASNCDANINTTRNRNHQ---------HYLKKPISASNEIFSSPSVATAS
```

FIG. 9C

```
Os06g49880.1       (84) VSAPLDASSN----GAGGGGGV-----GGSSISDYLTTICPGWRVEDLLPDDDAFAAAAA
Os06g49880.2       (86) VSAPLDASSN----GAGGGGGV-----GGSSISDYLTTICPGWRVEDLLPDDDAFAAAAA
Os02g43170.1       (76) APAAP---------ATSHGGSS-----GSSSISEYLT-TLPGWHVEDFLVDDATAEAAAA
Os02g43170.2       (78) APAAP---------ATSHGGSS-----GSSSISEYLT-TLPGWHVEDFLVDDATAEAAAA
Os04g45690.1       (80) YSCSPSSVA-----GTAAGSAS-----DGSSISEYLTKTLPGWHVEDFLVDEATAASS--
ACG44133.1         (58) ESCSGGAGA-----GATTATAS-----DGSSISEYLTKTLPGWHVEDFLVDDAYASDVGA
CAW36814.1         (60) ESCSGGA-------GATTATAS-----DGSSISEYLTKTLPGWHVEDFLVDDAYASDVGA
CAW39070.1         (62) ESCSGGA-------GATTATAS-----DGSSISEYLTKTLPGWHVEDFLVDDAYASDVGA
CAW54447.1         (64) ESCSGGA-------GATTATAS-----DGSSISEYLTKTLPGWHVEDFLVDDAYASDVGA
CAW74338.1         (66) ESCSGGA-------GATTATAS-----DGSSISEYLTKTLPGWHVEDFLVDDAYASDVGA
G1482 AT1G75540.1  (56) LSAPPQSNKIQPFSKINGGDASVNQWGSTSTISEYLMDTLPGWHVEDFL--DSSLPTYGF
G1888 AT4G39070.1  (54) SNCYYGIEENYHHVSDSGSGSG-----CTGSISEYLMETLPGWRVEDLL-EHPSCVSYED
Glyma11g12060.1    (98) SSPTVGDN------MACDTGSV-----STSSISEYLIQTIPGYCMEDLL--DASFASNGL
Glyma06g02970.1    (96) AGGNSLTNQ-----QPQQQTGF-----TGSSISEYLINTIPGMEFEDFL--DSHSLPFA-
Glyma04g02960.1    (90) KPGGNSL-------TNEEEPGF-----TGSSISEYLINSIPGMKFEDFL--DSHSLPFA-
Glyma04g02960.2    (92) KPGGNSL-------TNEEEPGF-----TGSSISEYLINSIPGMKFEDFL--DSHSLPFA-
Glyma04g01120.1    (88) SNSSCKVEDN----VASDTGSV-----STSSISEYLIETIPGYCFEDLL--DASFAPNGF
Glyma06g01140.1    (94) SNSSCKVEDN----VASDTGSI-----STSSISEYLIETIPGYCFEDLL--DASFAPNGF
Pt_550941          (70) EVNKGGDNLV----TNEGFGST-----TSSTISEYLMETLPGWHVEDFL--DSSTTPFGF
Pt_801530          (72) VINKDGDNLV----TSEGFGST-----TSSTISEYLMETLPGWHVEEFL-DSSSTTPFGF
Glyma14g40650.1   (100) NNNNNKV-------AVEGTGST-----SASSISEYLIETLPGWQVEDFL--DSYFVPFGF
Glyma17g37430.1   (102) TTSNNNNNKV----AVEGTGST-----SASSISEYLIETLPGWQVEDFL--DSYSVPFGF
Pt_195637          (68) ATTAYNFEEN----HVSDNGSI-----STSSISEYL-ETVPGWRIDDFL--D--------
Pt_804174          (74) PPTAYSYDDN----HVSGGGSV-----STSSISEYLETVVPGWRVDDFL--DPSFTSNN-
                                            .        .:**:**    **  .:::*
```

FIG. 9D

```
Os06g49880.1        (84)  QA---GKEKDERVPFLDAD--------------LFDVVAGRPEKKGGAWAPHVPHLPAWC
Os06g49880.2        (86)  A----GKEKDERVPFLDAD--------------LFDVVAGRPEKKGGAWAPHVPHLPAWC
Os02g43170.1        (76)  AAAT-SSGISANGPCQG----------------VTRIGGLQESAGYPAWMAQQQLCCDGL
Os02g43170.2        (78)  -----AAAT------------------------SSGISANGPCQVGATDRP---------
Os04g45690.1        (80)  -----SSDGLFQGG-------------------LLAQIGGVPDG-YAAWAGREQLHSGVA
ACG44133.1          (58)  -----CSDGLYQG--------------------QDGQISGVLQEAYMPWTGRELVPSDVA
CAW36814.1          (60)  -----CSSDG-----------------------LYQVSSVLPCE----WNCKLSLRRS--
CAW39070.1          (62)  -----CSSDG-----------------------LYQVSSVLPCE----WNCKLSLRRS--
CAW54447.1          (64)  -----CSSDG-----------------------LYQVSSVLPCE----WNCKLSLRRS--
CAW74338.1          (66)  -----CSSDG-----------------------LYQVSSVLPCE----WNCKLSLRRS--
G1482 AT1G75540.1   (56)  SK---SGDDDGVLPYMEPEDDNNTKRNNNNNNNNNNNTVSLPSKNLGIWVPQIPQTLPSS
G1888 AT4G39070.1   (54)  NI---ITNNNNSESYR-----------------VYDGSSQFHHQ--GFWDHKPFS-----
Glyma11g12060.1     (98)  -----SKDYEHQSAFQ-----------------NQDVQVSMCSFPLQSWVPQSQAGSPQL
Glyma06g02970.1     (96)  -----CSKNSDDMMLS-----------------MFGEGNMVSFSAGGIWVPQAPSSVQMD
Glyma04g02960.1     (90)  -----CSKNSDDMLS------------------LFGEGNMVSFSPGGFWVPQAPPSSVQM
Glyma04g02960.2     (92)  -----CSKQLIIV-----------------------------------------------
Glyma04g01120.1     (88)  -----CKNQNYDRHRRFRTKIFKLLGRVWFELRRFQNLNAIDDQLFVKICWKISSFVFVI
Glyma06g01140.1     (94)  LTCFSSQKQNFDHPWA-----------------FQDQKRTSGDTMAVPFLKLVIH-----
Pt_550941           (70)  -----CKIDDGLLPFMDAHD-------------LESNMSSFSSESLGLWVPQAPSTPYTS
Pt_801530           (72)  -----SKIDDGLLPYMDTHD-------------LERNMSSFSSESLGLWVPQAPTPPLCT
Glyma14g40650.1    (100)  -----CKNDE-VLPRLDAD--------------VEGHMGSFSTENMGIWVPQAPPPLVCS
Glyma17g37430.1    (102)  -----CK-DDEVLPRFDGE--------------MEGHLSSFSTENMGIWVPQAPPTLMCS
Pt_195637           (68)  ------------------------------------------------------------
Pt_804174           (74)  -----SFSKGWNAPYI--------------------------------------------
```

FIG. 9E

```
Os06g49880.1       (84)  -------------LDEVPVVVAASAAPAATPVKAKQGHVRDSHWSDSDAFAVPEFSPPPP
Os06g49880.2       (86)  -------------LDEVPVVVAASAAPAATPVKAKQGHVRDSHWSDSDAFAVPEFSPPPP
Os02g43170.1       (76)  -------------------------------VAGDASPASRERWVPQMYADQLAAGSKRS
Os02g43170.2       (78)  ------------------------------------------------------------
Os04g45690.1       (80)  --------------------------------VAADERASRERWVPQMNAEWGAGSKRP-
ACG44133.1         (58)  -----------------------------------DERDNWERWVPQMHAEFAGDSKRPR
CAW36814.1         (60)  ------------------------------------------------------------
CAW39070.1         (62)  ------------------------------------------------------------
CAW54447.1         (64)  ------------------------------------------------------------
CAW74338.1         (66)  ------------------------------------------------------------
G1482 AT1G75540.1   (56)  YPNQYFSQDNNIQFGMYNKETSPEVVSFAPIQNMKQQGQNNKRWYDDGGFTVPQITPPPL
G1888 AT4G39070.1   (54)  ------------------------------------------------------------
Glyma11g12060.1    (98)  ---------ISTTSNLHPQINSLVGVMEMPKAKASEGYSNCIYNYDYSAYKVPSICPPLI
Glyma06g02970.1    (96)  ----------------------------QQSGYKDTWETSIRSSFGDDSLLVPQMTPPSN
Glyma04g02960.1    (90)  ---------------------------DRQSGYRETREGSIRSSFGDDNFIVPQMSPPSN
Glyma04g02960.2    (92)  ------------------------------------------------------------
Glyma04g01120.1    (88)  CISFWAPCCILYDFFFILYSRPLFRPLILVFFSIFIGLINNIFWGGVHAFIDMNMNSLNN
Glyma06g01140.1    (94)  ------------------------------------------------------------
Pt_550941          (70)  ----------------QQYYYPQLVGQSGFKEIKETTNMKANRRLADDVFTVPQISLPAN
Pt_801530          (72)  ---------------SQQYYYPQLVGQSGFKETKESTNMKANRRLTDDAFTVPQISPPSN
Glyma14g40650.1   (100)  -----------------------SQMDRVIVQSETNIKGSSISRLKDDTFTVPQISPPS-
Glyma17g37430.1   (102)  -----------------------SQMDRVIVHGETNIKGSSRSRLKDDNFTVPQISPPS-
Pt_195637          (68)  ------------------------------------------------------------
Pt_804174          (74)  ------------------------------------------------------------
```

FIG. 9F

```
Os06g49880.1       (84) PAKRARPSSQFWCF
Os06g49880.2       (86) PAKRARPSSQFWCF
Os02g43170.1       (76) RTSTASSYSYW---
Os02g43170.2       (78) --------------
Os04g45690.1       (80) --RASPPCLYW---
ACG44133.1         (58) A-SPSPPCSYW---
CAW36814.1         (60) --------------
CAW39070.1         (62) --------------
CAW54447.1         (64) --------------
CAW74338.1         (66) --------------
G1482 AT1G75540.1  (56) S-SNKKFRSFW---
G1888 AT4G39070.1  (54) --------------
Glyma11g12060.1    (98) K-KCKRSR------
Glyma06g02970.1    (96) VFNNKRSRLLW---
Glyma04g02960.1    (90) V-SNKRSRLLW---
Glyma04g02960.2    (92) --------------
Glyma04g01120.1    (88) ATEYYVPLS-----
Glyma06g01140.1    (94) --------------
Pt_550941          (70) I-SSKRSRPLW---
Pt_801530          (72) I-GSKRSRPLW---
Glyma14g40650.1   (100) --NSKRARFLW---
Glyma17g37430.1   (102) --NSKRARFLW---
Pt_195637          (68) --------------
Pt_804174          (74) --------------
```

FIG. 9G

| | | |
|---|---|---|
| ACF80403.1 | (108) | ------------------------------------------------------------ |
| ACG44361.1 | (112) | ------------------------------------------------------------ |
| NP_001131822.1 | (116) | ------------------------------------------------------------ |
| ACN25813.1 | (114) | ------------------------------------------------------------ |
| Os02g49230.5 | (132) | ------------------------------------------------------------ |
| Os02g49230.1 | (124) | ------------------------------------------------------------ |
| Os02g49230.3 | (128) | ------------------------------------------------------------ |
| Os02g49230.4 | (130) | ------------------------------------------------------------ |
| Os02g49230.6 | (134) | ------------------------------------------------------------ |
| Os02g49230.2 | (126) | MLISHPMLSNSSGSFHGLYQYTYISPTLTKEWKQTHHYPGRIPLNSTVEQKARKVAVLVA |
| ACG34885.1 | (110) | ------------------------------------------------------------ |
| NP_001149294.1 | (118) | ------------------------------------------------------------ |
| Os06g19444.1 | (136) | ------------------------------------------------------------ |
| Os06g19444.2 | (138) | ------------------------------------------------------------ |
| Pt_247140 | (120) | ------------------------------------------------------------ |
| Pt_409151 | (122) | ------------------------------------------------------------ |
| Glyma02g38870.1 | (140) | ------------------------------------------------------------ |
| Glyma14g36930.1 | (144) | ------------------------------------------------------------ |
| Glyma14g36930.2 | (146) | ------------------------------------------------------------ |
| Glyma13g11590.1 | (142) | ------------------------------------------------------------ |
| Glyma20g07050.1 | (148) | ------------------------------------------------------------ |
| Glyma20g07050.2 | (150) | ------------------------------------------------------------ |
| G2440 AT3G07650.1 | (104) | ------------------------------------------------------------ |
| G1479 AT5G48250.1 | (106) | ------------------------------------------------------------ |

FIG. 10A

```
                                              ←— 1st B-box type ZF domain —→
ACF80403.1         (108) -------------MVPLCGFCGKQRSMIYCRSDAASLCLSCDRSVHSANALSRRHRRTLL
ACG44361.1         (112) -------------MVPLCGFCGKQRSMIYCRSDAASLCLSCDRSVHSANALSRRHRRTLL
NP_001131822.1     (116) -------------MVPLCGFCGKQRSMIYCRSDAASLCLSCDRSVHSANALSRRHRRTLL
ACN25813.1         (114) -------------MASLCDFCGKQRSMIYCRSDAASLCLSCDRNVHSANALSRRHTRTLL
Os02g49230.5       (132) -------------MDALCDFCREQRSMVYCRSDAASLCLSCDRNVHSANALSRRHTRTLL
Os02g49230.1       (124) -------------MDALCDFCREQRSMVYCRSDAASLCLSCDRNVHSANALSRRHTRTLL
Os02g49230.3       (128) -------------MDALCDFCREQRSMVYCRSDAASLCLSCDRNVHSANALSRRHTRTLL
Os02g49230.4       (130) -------------MDALCDFCREQRSMVYCRSDAASLCLSCDRNVHSANALSRRHTRTLL
Os02g49230.6       (134) -------------MDALCDFCREQRSMVYCRSDAASLCLSCDRNVHSANALSRRHTRTLL
Os02g49230.2       (126) LSASGSAPVLYRTMDALCDFCREQRSMVYCRSDAASLCLSCDRNVHSANALSRRHTRTLL
ACG34885.1         (110) -------------MGALCDFCGEQRSMVYCRSDAASLCLSCDRNVHSANALSRRHTRTLL
NP_001149294.1     (118) -------------MGALCDFCGEQRSMVYCRSDAASLCLSCDRNVHSANALSRRHTRTLL
Os06g19444.1       (136) -------------MGALCDFCGEQRSMVYCRSDAASLCLSCDRNVHSANALSRRHTRTLL
Os06g19444.2       (138) -------------MGALCDFCGEQRSMVYCRSDAASLCLSCDRNVHSANALSRRHTRTLL
Pt_247140          (120) -------------MGYVCDFCGEQRSMVYCRSDAASLCLSCDRNVHSANALSKRHSRTLL
Pt_409151          (122) -------------MGYICDFCGEQRSMVYCRSDAACLCLSCDQIVHSANALSKRHSRTLL
Glyma02g38870.1    (140) -------------MGYLCDFCGDQRSLVYCRSDSACLCLSCDRNVHSANALSRRHSRTLV
Glyma14g36930.1    (144) -------------MGYLCDFCGDQRSLVYCRSDAACLCLSCDRNVHSANALSRRHSRTLV
Glyma14g36930.2    (146) -------------MGYLCDFCGDQRSLVYCRSDAACLCLSCDRNVHSANALSRRHSRTLV
Glyma13g11590.1    (142) -------------M-----------------------------------------SIN
Glyma20g07050.1    (148) -------------M-----------------------------------------SIN
Glyma20g07050.2    (150) -------------M-----------------------------------------SIN
G2440 AT3G07650.1 (104) -------------MGYMCDFCGEQRSMVYCRSDAACLCLSCDRSVHSANALSKRHSRTLV
G1479 AT5G48250.1 (106) -------------MGYMCDFCGEQRSMVYCRSDAACLCLSCDRNVHSANALSKRHSRTLV
                                      *                                              ::
```

FIG. 10B

```
                              2nd B-box type ZF domain
ACN25813.1          (114) CDRCGSQPASVRCLEDNASLCQNCDWNGHD---------AESGASGHKRQAINCYSGCPS
Os02g49230.5        (132) CDRCVGQPAAVRCLEENTSLCQNCDWNGHG---------AASSAAGHKRQTINCYSGCPS
Os02g49230.1        (124) CDRCVGQPAAVRCLEENTSLCQNCDWNGHG---------AASSAAGHKRQTINCYSGCPS
Os02g49230.3        (128) CDRCVGQPAAVRCLEENTSLCQNCDWNGHG---------AASSAAGHKRQTINCYSGCPS
Os02g49230.4        (130) CDRCVGQPAAVRCLEENTSLCQNCDWNGHG---------AASSAAGHKRQTINCYSGCPS
Os02g49230.6        (134) CDRCVGQPAAVRCLEENTSLCQNCDWNGHG---------AASSAAGHKRQTINCYSGCPS
Os02g49230.2        (126) CDRCVGQPAAVRCLEENTSLCQNCDWNGHG---------AASSAAGHKRQTINCYSGCPS
ACG34885.1          (110) CDRCASQPAMVRCLAENASLCQNCDWNGHI---------AGSSSAGHKRQTINCYSGCPS
NP_001149294.1      (118) CDRCASQPAMVRCLAENASLCQNCDWNGHI---------AGSSSAGHKRQTINCYSGCPS
Os06g19444.1        (136) CDRCASQPAMVRCLVENASLCQNCDWNGHS---------AGSSAAGHKRQTINCYSGCPS
Os06g19444.2        (138) CDRCASQPAMVRCLVENASLCQNCDWNGHS---------AGSSAAGHKRQTINCYSGCPS
Pt_247140           (120) CERCNSQPALVRCAEERISLCQNCDWIGHG---------TSTSASTHRRQTINSYSGCPS
Pt_409151           (122) CERCNSQPALVRRVEERISLCQNCDWMGYG---------SSTSASTHKRQTINCYFGCPS
Glyma02g38870.1     (140) CERCNSQPAFVRSVEEKISLCQNCDWLGHG---------TSPSSSMHKRQSINCYSGCPS
Glyma14g36930.1     (144) CERCNSQPAFVRCVDEKISLCQNCDWLGHG---------TSPSSSTHKRQSINCYSGCPS
Glyma14g36930.2     (146) CERCNSQPAFVRCVDEKISLCQNCDWLGHG---------TSPSSSTHKRQSINCYSGCPS
Glyma13g11590.1     (142) ENKSVGVP-----------------------------------------------------
Glyma20g07050.1     (148) ENKCVGVP-----------------------------------------------------
Glyma20g07050.2     (150) ENKCVGVP-----------------------------------------------------
G2440 AT3G07650.1   (104) CERCNAQPATVRCVEERVSLCQNCDWSGHNNSNNNNSSSSSTSPQQHKRQTISCYSGCPS
G1479 AT5G48250.1   (106) CERCNAQPASVRCSDERVSLCQNCDWSGHD-------GKNSTTTSHHKRQTINCYSGCPS
                           :..    *
```

FIG. 10C

```
ACF80403.1        (108) SAELSRIWSFIIDIP-TVAAEPNCEDGLSMMTIDDSDVTNHHGASDDKRLLEIANTALMS
ACG44361.1        (112) SAELSRIWSFIIDIP-TVAAEPNCEDGLSMMTIDDSDVTNHHGASDDKRLLEIANTALMS
NP_001131822.1    (116) SAELSRIWSFIIDIP-TVAAEPNCEDGLSMMTIDDSDVTNHHGASDDKRLLEIANTALMS
ACN25813.1        (114) SAELSRIWSFITDIP-TVAAEPDYEDGLSMMTIDGSDVTNRHDTSDDKRLLEIANTTLMS
Os02g49230.5      (132) SAELSRIWSFSMDIP-TVAAEPNCEEGINMMSINDNDVNNHCGAPEDGRLLDIASTALMS
Os02g49230.1      (124) SAELSRIWSFSMDIP-TVAAEPNCEEGINMMSINDNDVNNHCGAPEDGRLLDIASTALMS
Os02g49230.3      (128) SAELSRIWSFSMDIP-TVAAEPNCEEGINMMSINDNDVNNHCGAPEDGRLLDIASTALMS
Os02g49230.4      (130) SAELSRIWSFSMDIP-TVAAEPNCEEGINMMSINDNDVNNHCGAPEDGRLLDIASTALMS
Os02g49230.6      (134) SAELSRIWSFSMDIP-TVAAEPNCEEGINMMSINDNDVNNHCGAPEDGRLLDIASTALMS
Os02g49230.2      (126) SAELSRIWSFSMDIP-TVAAEPNCEEGINMMSINDNDVNNHCGAPEDGRLLDIASTALMS
ACG34885.1        (110) SAELSRIWSFVSDIP-NVAPEPNCEQGISMMSISDSGVSNQDNAAGDSILLDIASATLVS
NP_001149294.1    (118) SAELSRIWSFVSDIP-NVAPEPNCEQGISMMSISDSGVSNQDNAAGDSILLDIASATLVS
Os06g19444.1      (136) SSELSKIWTFVSDIP-NVAPEPNCEQGISMMSISDSGVSNQDNAAGDSSLLDIASATLMS
Os06g19444.2      (138) SSELSKIWTFVSDIP-NVAPEPNCEQGISMMSISDSGVSNQDNAAGDSSLLDIASATLMS
Pt_247140         (120) ASELSSIWSFVLDFP-S-RGESTCEQELGLMSIAENSTTDSWGPTENTIGQNASGVVEVN
Pt_409151         (122) VSELSSKWPFILDSP-S-GGGSTCEQELGLMSIAENSTKNTWGPTENTICHNASG-----
Glyma02g38870.1   (140) AAEFSSIWSFFLDIP---SLGEACEQELGLMSINENI------PPEGQ---NVSGSTEVT
Glyma14g36930.1   (144) AAEFSSIWSFFLDIP---SMGEACEQELGLMSINENSNKNAWASPEGQ---NVSGSAEVT
Glyma14g36930.2   (146) AAEFSSIWSFFLDIP---SMGEACEQELGLMSINENSNKNAWASPEGQ---NVSGSAEVT
Glyma13g11590.1   (142) -------------------------------------------PEGQ---NVSGSDEVT
Glyma20g07050.1   (148) -------------------------------------------PEDQ---NVSGSDEVT
Glyma20g07050.2   (150) -------------------------------------------PEDQ---NVSGSDEVT
G2440 AT3G07650.1(104) SSELASIWSFCLDL----AGQSICEQELGMMNIDDDG-------PTDK---KTCNE----
G1479 AT5G48250.1(106) SAELSSIWSFCMDLNISSAEESACEQGMGLMTIDEDGTGEKSGVQKINVEQPETSS----
```

FIG. 10D

```
ACF80403.1        (108) DPPSPDKLKPLIGSSSGDGFDVLPLATDQP--AGPVSAT-PKVPYARDD--NKFNDG-MY
ACG44361.1        (112) DPPSPDKLKPLIGSSSGDGFDVLPLATDQP--AGPVSAT-PKVPYARDD--NKFNDG-MY
NP_001131822.1    (116) DPPSPDKLKPLIGSSSGDGFDVLPLATDQP--AGPVSAT-PKVPYARDD--NKFNDG-MY
ACN25813.1        (114) DPPSADKLKSPTGSSSGDGFDVMTLATDQP--AGPVSAT-PKVPNARDD--DKFNDG-MY
Os02g49230.5      (132) DLPTGDKFKPLIGSSSGDGMNLLPLNSDQP--AEPVSTT-PKAPCVTDK--DMFNDGSVY
Os02g49230.1      (124) DLPTGDKFKPLIGSSSGDGMNLLPLNSDQP--AEPVSTT-PKAPCVTDK--DMFNDGSVY
Os02g49230.3      (128) DLPTGDKFKPLIGSSSGDGMNLLPLNSDQP--AEPVSTT-PKAPCVTDK--DMFNDGSVY
Os02g49230.4      (130) DLPTGDKFKPLIGSSSGDGMNLLPLNSDQP--AEPVSTT-PKAPCVTDK--DMFNDGSVY
Os02g49230.6      (134) DLPTGDKFKPLIGSSSGDGMNLLPLNSDQP--AEPVSTT-PKAPCVTDK--DMFNDGSVY
Os02g49230.2      (126) DLPTGDKFKPLIGSSSGDGMNLLPLNSDQP--AEPVSTT-PKAPCVTDK--DMFNDGSVY
ACG34885.1        (110) DIGTCDKL--LVGSSSGAGVNLLPLVTGQTETAGSVDSTPDKVPYTPDK--DMFSKDSIY
NP_001149294.1    (118) DIGTCDKL--LVGSSSGAGVNLLPLVTGQTETAGSVDSTPDKVPYTPDK--DMFSKDSIY
Os06g19444.1      (136) DLGTAGKPKSLIGSSSEAGVNLLPLATDQM--AGSVDSTSAKVPYTADQ--DMFSKDSIY
Os06g19444.2      (138) DLGTAGKPKSLIGSSSEAGVNLLPLATDQM--AGSVDSTSAKVPYTADQ--DMFSKDSIY
Pt_247140         (120) DRREIAKSGVWLGSSSIPESSSVPNNLDQT--TRSANTSLPK------------------
Pt_409151         (122) ----------IVGASSVPESSSVPKNLDQP--TRSPNSSLPKVC-----------DADLY
Glyma02g38870.1   (140) DLPSKGKS--WAGTPSIPESSSEPRILDQP--PGPANECVPKLYCPGKKASGICEDDDLY
Glyma14g36930.1   (144) DLPSKGKS--WAGTSSVPESSSEPRILDQP--PGPANECMPKLYCPGKKVSGIYEDDDLY
Glyma14g36930.2   (146) DLPSKGKS--WAGTSSVPESSSEPRILDQP--PGPANECMPKLYCPGKKVSGIYEDDDLY
Glyma13g11590.1   (142) DQPALDKS--LVGTSSMPESSSKPRILDQP--ARPANECLSKLYCPATKFPALCENDNLY
Glyma20g07050.1   (148) DLPALNKS--LVGASLMPESSSEPCILDQP--AGPTNECLPKLYCPATKCPALSEDDNLY
Glyma20g07050.2   (150) DLPALNKS--LVGASLMPESSSEPCILDQP--AGPTNECLPKLYCPATKCPALSEDDNLY
G2440 AT3G07650.1(104) -----DKKDVLVGSSSIPETSSVPQGKSSS--AKDVGMC----------------EDDFY
G1479 AT5G48250.1(106) -------------AAQGMDHSSVPENSSM---AKELGVC----------------EDDFN
                                     :.        .  .   .    .    .
```

FIG. 10E

```
ACF80403.1       (108) EDLCVDDADLTFENYEELFGTSHIRIEELFDDAGIDSYFEMKETP--------------P
ACG44361.1       (112) EDLCVDDADLTFENYEELFGTSHIRIEELFDDAGIDSYFEMKETP--------------P
NP_001131822.1   (116) EDLCVDDADLTFENYEELFGTSHIRIEELFDDAGIDSYFEMKETP--------------P
ACN25813.1       (114) EDLCVDDADLTFEDYEELFGTSHIRTEELFDDAGIDGYFELKETP--------------P
Os02g49230.5     (132) GDFCVDDADLTFENYEELFGTSHVQTEQLFDDAGIDSYFEMKDVP--------------A
Os02g49230.1     (124) GDFCVDDADLTFENYEELFGTSHVQTEQLFDDAGIDSYFEMKDVP--------------A
Os02g49230.3     (128) GDFCVDDADLTFENYEELFGTSHVQTEQLFDDAGIDSYFEMKDVP--------------A
Os02g49230.4     (130) GDFCVDDADLTFENYEELFGTSHVQTEQLFDDAGIDSYFEMKDVP--------------A
Os02g49230.6     (134) GDFCVDDADLTFENYEELFGTSHVQTEQLFDDAGIDSYFEMKDVP--------------A
Os02g49230.2     (126) GDFCVDDADLTFENYEELFGTSHVQTEQLFDDAGIDSYFEMKDVP--------------A
ACG34885.1       (110) EDFCVDDADLAFENYEELFGTSHIQTEQLFDDAGIDIYFEMKEAP--------------A
NP_001149294.1   (118) EDFCVDDADLAFENYEELFGTSHIQTEQLFDDAGIDIYFEMKEAP--------------A
Os06g19444.1     (136) EDFCVDDVDLSFENYEELFGTSHIQTEQLFDDAGIDSYFESKEIP--------------S
Os06g19444.2     (138) EDFCVDDVDLSFENYEELFGTSHIQTEQLFDDAGIDSYFESKEIP--------------S
Pt_247140        (120) -DFNMDEMDLSLENYEELFGVTLNNSEELLENGGIDSLFGTKDMS---------------
Pt_409151        (122) EDFNMAEMDLNLENYEELFGVTLNNSEELFENGGIDSLFGTKDMP-------------IV
Glyma02g38870.1  (140) DDFIMDEVDLELENYEELFGMALSHSEELFENGGINSLFEAKDMSASAGDSHCQGAVAAE
Glyma14g36930.1  (144) DDFIMDEVDLQLENYEELFGMALSHSEELFENGGINSLFETKDMSASAGDSHCQGAVAAE
Glyma14g36930.2  (146) DDFIMDEVDLQLENYEELFGMALSHSEELFENGGINSLFETKDMSASAGDSHCQGAVAAE
Glyma13g11590.1  (142) DDFNMDEVDLNLENYEELFGMALSHSEELFENGGIDSLFGTKDMS--AGDFSCEDAI--A
Glyma20g07050.1  (148) DDFNMDEVDLDLENYEELFGMALSHSEELFENGGIDSLFGTKGMS--AGDSNCQEAIAAE
Glyma20g07050.2  (150) DDFNMDEVDLDLENYEELFGMALSHSEELFENGGIDSLFGTKGMS--AGDSNCQEAIAAE
G2440 AT3G07650.1(104) GNLGMDEVDMALENYEELFGTAFNPSEELFGHGGIDSLFHKHQTA---------------
G1479 AT5G48250.1(106) GNLISDEVDLALENYEELFGSAFNSSRYLFEHGGIGSLFEKDEAH---------------
                        ::   : *: :*:****** :      *:  .**.  *
```

FIG. 10F

```
ACF80403.1         (108) FDFNEQPKIVQLQCSDVVPADCAMSNTGERADSSLCIPVRQVRSSISHPLSGLTGESSAG
ACG44361.1         (112) FDFNEQPKIVQLQCSDVVPADCAMSNTGERADSSLCIPVRQVRSSISHPLSGLTGESSAG
NP_001131822.1     (116) FDFNEQPKIVQLQCSDVVPADCAMSNTGERADSSLCIPVRQVRSSISHPLSGLTGESSAG
ACN25813.1         (114) FYFNEQPKAMQIECGNVVSADCAMSNPGARADSSLCIPVRQVRSSISHSLSGLTGESSAG
Os02g49230.5       (132) DESNE-PKPVQPECSNVASVDSGMSNPAARADSSHCIPGRQAISNISLSFSGLTGESSAG
Os02g49230.1       (124) DESNEQPKPVQPECSNVASVDSGMSNPAARADSSHCIPGRQAISNISLSFSGLTGESSAG
Os02g49230.3       (128) DESNEQPKPVQPECSNVASVDSGMSNPAARADSSHCIPGRQAISNISLSFSGLTGESSAG
Os02g49230.4       (130) DESNEQPKPVQPECSNVASVDSGMSNPAARADSSHCIPGRQAISNISLSFSGLTGESSAG
Os02g49230.6       (134) DESNEQPKPVQPECSNVASVDSGMSNPAARADSSHCIPGRQAISNISLSFSGLTGESSAG
Os02g49230.2       (126) DESNEQPKPVQPECSNVASVDSGMSNPAARADSSHCIPGRQAISNISLSFSGLTGESSAG
ACG34885.1         (110) GNSTE-SKLKQPANSNAVSADSGMSNPGVKGDSSVCTPLRQARSSLSLSFAGLTGESSAG
NP_001149294.1     (118) GNSTE-SKLKQPANSNAVSADSGMSNPGVKGDSSVCTPLRQARSSLSLSFAGLTGESSAG
Os06g19444.1       (136) GNSDEQPKLMQPVTSNAVSADSGMSIPGAKGDSSLCIPVRQARSSISLSFSGLTGESSAG
Os06g19444.2       (138) GNSDE-PKLMQPVTSNAVSADSGMSIPGAKGDSSLCIPVRQARSSISLSFSGLTGESSAG
Pt_247140          (120) -----VVNAVQPASSNAASADSMMSN---KTEPILCFTEKQGHSSLS--FSGLNVESSAA
Pt_409151          (122) DSNFGLVNTIQPTCSNAPSTDSMISS---KTEPILCFTAKQGHSSLS--FSGLTGESNAG
Glyma02g38870.1    (140) GSSAGLVNPIQPACSNAASADSVMST---KTEPIVCFTARQSQSNIS--FSGVTKDS-AG
Glyma14g36930.1    (144) GSSAELVNAIQPACSNAASADSMMST---KTEPIVCFTARQSLSNIS--FSGVTKDS-VG
Glyma14g36930.2    (146) GSSAELVNAIQPACSNAASADSMMST---KTEPIVCFTARQSLSNIS--FSGVTKDS-VG
Glyma13g11590.1    (142) AEASQIPTMLAPQPHNAASADSILST---KTEPILCFTGRQAQSNLS--FSGVTGDSSAG
Glyma20g07050.1    (148) GSSVGQVNAMQPACSNAASADSILST---KTEPILCFTGRQTQSNLS--FSGVTGESSAG
Glyma20g07050.2    (150) GSSVGQVNAMQPACSNAASADSILST---KTEPILCFTGRQTQSNLS--FSGVTGESSAG
G2440 AT3G07650.1(104) ---PEGGNSVQPAGSN----DSFMSS---KTEPIICFASKPAHSNIS--FSGVTGESSAG
G1479 AT5G48250.1(106) -----EGSMQQPALSNNASADSFMTC---RTEPIICYSSKPAHSNIS--FSGITGESNAG
                                    .        :    *. ::    . :.  *  . .   *.:*  ::*:. :* ..
```

FIG. 10G

```
ACF80403.1        (108) DHQDCGVSPIL-LMGEP-PWYSPG-PEGSL---AGGSRDSALTRYKEKKKKRMFDKKIRY
ACG44361.1        (112) DHQDCGVSPIL-LMGEP-PWYSPG-PEGSL---AGGSRDSALTRYKEKKKKRMFDKKIRY
NP_001131822.1    (116) DHQDCGVSPIL-LMGEP-PWYSPG-PEGSL---AGGSRDSALTRYKEKKKKRMFDKKIRY
ACN25813.1        (114) DHHDCGVSPML-LMGEP-PWHSPGGPEGSV---AGGSRDSALTRYKEKKKRRKFDKKIRY
Os02g49230.5      (132) YFQDCGVSSMI-LMGEP-PWHPPG-PESSS---AGGSRDNALTRYKEKKKRRKFDKKIRY
Os02g49230.1      (124) YFQDCGVSSMI-LMGEP-PWHPPG-PESSS---AGGSRDNALTRYKEKKKRRKFDKKIRY
Os02g49230.3      (128) YFQDCGVSSMI-LMGEP-PWHPPG-PESSS---AGGSRDNALTRYKEKKKRRKFDKKIRY
Os02g49230.4      (130) YFQDCGVSSMI-LMGEP-PWHPPG-PESSS---AGGSRDNALTRYKEKKKRRKFDKKIRY
Os02g49230.6      (134) YFQDCGVSSMI-LMGEP-PWHPPG-PESSS---AGGSRDNALTRYKEKKKRRKFDKKIRY
Os02g49230.2      (126) YFQDCGVSSMI-LMGEP-PWHPPG-PESSS---AGGSRDNALTRYKEKKKRRKFDKKIRY
ACG34885.1        (110) DNQDCVVSSLL-LMGEP-PWQPPG-PEGSI---AGGSRDSALTRYKEKKMRRKFDKKIRY
NP_001149294.1    (118) DNQDCVVSSLL-LMGEP-PWQPPG-PEGSI---AGGSRDSALTRYKEKKMRRKFDKKIRY
Os06g19444.1      (136) DYQDCGVSPVL-LMGEP-PWHPPG-PEGSF---AGATRDDAITRYKEKKKRRKFDKKIRY
Os06g19444.2      (138) DYQDCGVSPVL-LMGEP-PWHPPG-PEGSF---AGATRDDAITRYKEKKKRRKFDKKIRY
Pt_247140         (120) DYQDCGASSML-LMGEP-PWCPPC-PESPF---SSANRSDAVMRYKEKKKTRMFEKKVRY
Pt_409151         (122) DYQDCGASSML-LMGEP-SWCPPC-LESPL---PSANRSDAVKRYMEKKKTRKFEKKVRY
Glyma02g38870.1   (140) DYQDCGASSML-LMGEP-PWCPPC-PESSL---HSANRSNAVMRYKEKKKTRKFEKKVRY
Glyma14g36930.1   (144) DYQDCGASSML-LMGEP-PWCPPC-PESSL---HSANRSNAVMRYKEKKKTRKFEKKVRY
Glyma14g36930.2   (146) DYQDCGASSML-LMGEP-PWCPPC-PESSL---HSANRSNAVMRYKEKKKTRKFEKKVRY
Glyma13g11590.1   (142) DYQDCGASSML-LMGEP-PWFAPC-PENSL---QSANRSNAVMRYKEKKKTRMFDKKVRY
Glyma20g07050.1   (148) DYQDCGASSML-LMGEP-PWFAPC-PENSL---QSANRSNAVMRYKEKKKTRMFDKKVRY
Glyma20g07050.2   (150) DYQDCGASSML-LMGEP-PWFAPC-PENSL---QSANRSNAVMRYKEKKKTRMFDKKVRY
G2440 AT3G07650.1(104) DFQECGASSSIQLSGEP-PWYPPT-LQDNNACSHSVTRNNAVMRYKEKKKARKFDKRVRY
G1479 AT5G48250.1(106) DFQDCGASSMKQLSREPQPWCHPT-AQDIIASSHATTRNNAVMRYKEKKKARKFDKRVRY
                          ::* .*.    *   ** .*  *    :.        . .*..*: ** ***  * *:*.:**
```

FIG. 10H

```
ACF80403.1          (108) ASRKARADVRKRVKGRFIKAGEAYDYDPLSQTRSY
ACG44361.1          (112) ASRKARADVRKRVKGRFIKAGEAYDYDPLSQTRSY
NP_001131822.1      (116) ASRKARADVRKRVKGRFIKAGEAYDYDPLSQTRSY
ACN25813.1          (114) ASRKARADVRKRVKGRFIKAGEAYDYDPLSQTRSY
Os02g49230.5        (132) ASRKARADVRKRVKGRFVKAGEAYDYDPLSQTRSY
Os02g49230.1        (124) ASRKARADVRKRVKGRFVKAGEAYDYDPLSQTRSY
Os02g49230.3        (128) ASRKARADVRKRVKGRFVKAGEAYDYDPLSQTRSY
Os02g49230.4        (130) ASRKARADVRKRVKGRFVKAGEAYDYDPLSQTRSY
Os02g49230.6        (134) ASRKARADVRKRVKGRFVKAGEAYDYDPLSQTRSY
Os02g49230.2        (126) ASRKARADVRKRVKGRFVKAGEAYDYDPLSQTRSY
ACG34885.1          (110) ASRKARADVRKRVKGRFVKAGEAYDYDPLCQTRSY
NP_001149294.1      (118) ASRKARADVRKRVKGRFVKAGEAYDYDPLCQTRSY
Os06g19444.1        (136) ASRKARADVRKRVKGRFVKAGEAYDYDPLCETRSY
Os06g19444.2        (138) ASRKARADVRKRVKGRFVKAGEAYDYDPLCETRSY
Pt_247140           (120) ASRKARADVRRRVKGRFVKAGEAYDYDPLSQTRSF
Pt_409151           (122) ASRKARADVRRRVKGRFVKAGDAYDYDPLGQTRSF
Glyma02g38870.1     (140) ASRKARADVRKRVKGRFVKAGDVYDYDPLNQTRSY
Glyma14g36930.1     (144) ASRKARADVRKRVKGRFVKAGDVYDYDPLNQTRSC
Glyma14g36930.2     (146) ASRKARADVRKRVKGRFVKAGDVYDYDPLNQTRSC
Glyma13g11590.1     (142) ASRKARADVRRRVKGRFVKAGDVYDYDPLSTTRSF
Glyma20g07050.1     (148) ASRKARADVRRRVKGRFVKAGDVYDYDPLSTTRSC
Glyma20g07050.2     (150) ASRKARADVRRRVKGRFVKAGDVYDYDPLSTTRSC
G2440 AT3G07650.1   (104) ASRKARADVRRRVKGRFVKAGEAYDYDPLTPTRSY
G1479 AT5G48250.1   (106) VSRKERADVRRRVKGRFVKSGEAYDYDPMSPTRSY
                          .*** *****.******:*:*:.*****:  ***
```

FIG. 10I

SEQUENCE LISTING

```
Sequence total quantity: 550
SEQ ID NO: 1            moltype = DNA  length = 669
FEATURE                 Location/Qualifiers
misc_feature            1..669
                        note = AtBBX28 (G1481), AT4G27310.1, paralog of AtBBX29
                         (G900)
source                  1..669
                        mol_type = unassigned DNA
                        organism = Arabidopsis thaliana
SEQUENCE: 1
atggggaaga agtgtgattt atgtaacggt gttgcaagaa tgtattgcga gtcagatcaa  60
gctagtttat gttgggattg cgacggtaaa gttcacggcg ctaatttctt ggtagctaaa  120
cacacgcgtt gtcttctctg tagcgcttgt cagtctctta cgccgtggaa agctactggg  180
cttcgtcttg gcccaacttt ctccgtctgc gagtcatgcg tcgctcttaa aaacgccggc  240
ggtggccgtg gaaacagagt tttatcggag aatcgtggtc aggaggaggt taatagtttc  300
gagtccgaag aagatcggat tagagaagat cacggtgacg gtgacgacgc ggagtcttac  360
gatgatgatg aggaagaaga tgaggatgaa gagtacagcg acgatgagga tgaggatgat  420
gatgaggatg gtgatgatga ggaagcggag aatcaagttg tgccgtggtc tgcggcggcg  480
caagttcctc cggtgatgag ttcttcatct tctgacggag gaagcggagg ttcagtgacg  540
aagaggacga gggctagaga gaattcagat cttctctgct ccgatgatga gatcggaagc  600
tcttcagctc aagggtcaaa ctattctcgg ccgttgaagc gatcggcgtt taaatcaacg  660
gttgttgtt                                                         669

SEQ ID NO: 2            moltype = AA  length = 223
FEATURE                 Location/Qualifiers
REGION                  1..223
                        note = AtBBX28 (G1481), AT4G27310.1, domain coordinates
                         5-41, paralog of AtBBX29 (G900)
source                  1..223
                        mol_type = protein
                        organism = Arabidopsis thaliana
SEQUENCE: 2
MGKKCDLCNG VARMYCESDQ ASLCWDCDGK VHGANFLVAK HTRCLLCSAC QSLTPWKATG  60
LRLGPTFSVC ESCVALKNAG GGRGNRVLSE NRGQEEVNSF ESEEDRIRED HGDGDDAESY  120
DDDEEEDEDE EYSDDEDEDD DEDGDDEEAE NQVVPWSAAA QVPPVMSSSS SDGGSGGSVT  180
KRTRARENSD LLCSDDEIGS SSAQGSNYSR PLKRSAFKST VVV                  223

SEQ ID NO: 3            moltype = DNA  length = 645
FEATURE                 Location/Qualifiers
misc_feature            1..645
                        note = AtBBX29 (G900), AT5G54470.1 paralog of AtBBX28
                         (G1481)
source                  1..645
                        mol_type = unassigned DNA
                        organism = Arabidopsis thaliana
SEQUENCE: 3
atggggaaga agaagtgcga gttatgttgt ggtgtagcga gaatgtattg tgagtcagat  60
caagcgagtt tatgttggga ttgtgacggt aaagttcacg gagctaattt tctggtggcg  120
aaacacatgc gttgtcttct atgtagcgcg tgtcagtcac acacgccttg gaaagcttct  180
gggctgaatc ttggcccaac tgtttctatc tgtgagtctt gtttagctcg taagaagaat  240
aacaacagct ccctcgccgg gagggatcag aatcttaacc aagaagaaga gatcattggt  300
tgtaacgacg gagctgagtc ttatgatgag gaaagcgatg aggatgaaga agaagaagaa  360
gtggagaatc aggttgttcc ggctgcggtg gagcaagaac ttccggtggt gagttcgtcg  420
tcttcggtta gtagtggtga aggagatcag gtggtgaaaa ggacgagact tgatttggat  480
cttaacctct ccgatgagga gaaccaatct agaccattga aaagattatc gagagacgaa  540
ggtttgtcaa gatcaactgt tgtgatgaat agctcaatcg tgaaattaca cggagggagg  600
agaaaagcag agggatgtga tacatcatcg tcgtcttcgt tttat                645

SEQ ID NO: 4            moltype = AA  length = 215
FEATURE                 Location/Qualifiers
REGION                  1..215
                        note = AtBBX29 (G900), AT5G54470.1, domain coordinates
                         11-42, paralog of AtBBX28 (G1481)
source                  1..215
                        mol_type = protein
                        organism = Arabidopsis thaliana
SEQUENCE: 4
MGKKKCELCC GVARMYCESD QASLCWDCDG KVHGANFLVA KHMRCLLCSA CQSHTPWKAS  60
GLNLGPTVSI CESCLARKKN NNSSLAGRDQ NLNQEEEIIG CNDGAESYDE ESDEDEEEEE  120
VENQVVPAAV EQELPVVSSS SSVSSGEGDQ VVKRTRLDLD LNLSDEENQS RPLKRLSRDE  180
GLSRSTVVMN SSIVKLHGGR RKAEGCDTSS SSSFY                            215

SEQ ID NO: 5            moltype = DNA  length = 789
FEATURE                 Location/Qualifiers
misc_feature            1..789
                        note = ACN33981.1, ortholog of AtBBX28 (G1481), AtBBX29
                         (G900)
source                  1..789
```

```
                        mol_type = unassigned DNA
                        organism = Zea mays
SEQUENCE: 5
atgtcggcgg ctgcggcagc ggaagtgggg aaggagaagg gcgccgccac ccccggcccc  60
ggccccggcc ccggtggcgc gtgcgagctg tgcggcgccg cggccagggt gtactgcggc  120
gccgacgagg ccacgctctg ctggggctgc gacgcgcagg tgcacggcgc caacttcctg  180
gtggcgcgcc acgcgcgctc gctgctgtgc cggggctgcg cgcgccccac gccgtggcgc  240
gccgcgggcc cgcgcctcgg ccccaccgtc tccctctgcg tccgctgcgt ccgccgcggc  300
ccggcggggg ccgtgggcgt cggcggcgat gaggagatgg ggggagcggg cgacggagac  360
gccgaggatg acgacgacga ggacgacgac tccgaggagg aggaggagga ggaggaggag  420
gaaggggagg gggagaacca ggtcgtgccg tggacggagg acgccgaggc cacgccgccg  480
cccgtcggga gctccacgtc cagcagcagc cgggaggccc ccgccaacgg cgcagagcgc  540
gcagcgaagg aaaacgcccc gtgctccacc tcgcagccag gcctgtgcca ccacgcgtcg  600
tccgcgcgcc acggcggccg gagcgacgag gccacctcgt cccggagcgg cggccgggtc  660
ctcgcctccc gccacaggaa gagatcgccc tcggatttct tcagctctga tgggtcgccg  720
cagcccggga atggcacacc ggcggcgagg aattgctccg acgccggcat tgccaggaat  780
gactttacc                                                          789

SEQ ID NO: 6            moltype = AA  length = 263
FEATURE                 Location/Qualifiers
REGION                  1..263
                        note = ACN33981.1, domain coordinates 32-64, ortholog of
                         AtBBX28 (G1481), AtBBX29 (G900)
source                  1..263
                        mol_type = protein
                        organism = Zea mays
SEQUENCE: 6
MSAAAAAEVG KEKGAATPGP GPGPGGACEL CGAAARVYCG ADEATLCWGC DAQVHGANFL  60
VARHARSLLC RGCARPTPWR AAGPRLGPTV SLCVRCVRRG PAGAVGVGGD EEMGGAGDGD  120
AEDDDDEDDD SEEEEEEEEE EGEGENQVVP WTEDAEATPP PVGSSTSSSS REAPANGAER  180
AAKENAPCST SQPGLCHHAS SARHGGRSDE ATSSRSGGRV LASRHRKRSP SDFFSSDGSP  240
QPGNGTPAAR NCSDAGIARN DFT                                          263

SEQ ID NO: 7            moltype = DNA  length = 735
FEATURE                 Location/Qualifiers
misc_feature            1..735
                        note = Pt_568988, ortholog of AtBBX28 (G1481), AtBBX29
                         (G900)
source                  1..735
                        mol_type = unassigned DNA
                        organism = Populus trichocarpa
SEQUENCE: 7
atgaaagggt gtgagctttg tgggagttca gcaagaatgt tctgtgaatc agacgaagct  60
agtttatgtt gggattgtga tgagaaagta cactctgcca actttcttgt agctaaacac  120
tgtagaaccc ttctttgtca agtctgtcaa tctccaactc cttggaaagc ctcggtgtct  180
aaatttgctc ctactgtttc catatgtgaa tcttgtttta ctatccctaa caaaacaaaa  240
gaaacagaag agagaatgaa agggtgcgag ctttgtggga gttcagcaag gatgtattgt  300
gaatcagacc aagctagttt atgttgggat tgtgatgaga aagtgcacac tgccaacttt  360
cttgttgcta aacattgtag aacccttctt tgtcaagtct gtcaatctcc aactccttgg  420
aaagcctcgg ggtctaaatt tgctcctact gtttccgtgg tgccatggtc aggtcctact  480
gcgtcgtcgt cgccatcacc tgtgccacct gtggctagtt ctagtagtga agaggagact  540
tcttgtgctg gtagaaatgg attcttgaaa cggatgcgag agagtaatgt tgatcttgat  600
tctgatgatg aaattggatg ttcctcttct cataatatag gaggtcgaat attgagcaat  660
gatggaggga attctttgag ttcaatgagg ccatggaagc aagcaagaac aagtgttaat  720
gttgaagaag atggt                                                   735

SEQ ID NO: 8            moltype = AA  length = 245
FEATURE                 Location/Qualifiers
REGION                  1..245
                        note = Pt_568988, domain coordinates 4-40, 89-125, ortholog
                         of AtBBX28 (G1481), AtBBX29 (G900)
source                  1..245
                        mol_type = protein
                        organism = Populus trichocarpa
SEQUENCE: 8
MKGCELCGSS ARMFCESDEA SLCWDCDEKV HSANFLVAKH CRTLLCQVCQ SPTPWKASVS  60
KFAPTVSICE SCFTIPNKTK ETEERMKGCE LCGSSARMYC ESDQASLCWD CDEKVHTANF  120
LVAKHCRTLL CQVCQSPTPW KASGSKFAPT VSVVPWSGPT ASSSPSPVPP VASSSSEEET  180
SCAGRNGFLK RMRESNVDLD SDDEIGCSSS HNIGGRILSN DGGNSLSSMR PWKQARTSVN  240
VEEDG                                                              245

SEQ ID NO: 9            moltype = DNA  length = 285
FEATURE                 Location/Qualifiers
misc_feature            1..285
                        note = Pt_571834, ortholog of AtBBX28 (G1481), AtBBX29
                         (G900)
source                  1..285
                        mol_type = unassigned DNA
                        organism = Populus trichocarpa
```

```
SEQUENCE: 9
atgaagaagt gtgagctatg caagaaccca gcaagaacat actgtgaatc agacgaagca  60
aatctttgtt ggaactgtga tacaaaagtc catggagcca actttcttgt tgctagacat  120
gctcgtgctc ttctttgtca gtcttgtcaa tcgctaactc cctggaaagc ctctgggtct  180
caactagggc acactgtgtc tgtatgtgag agatgtggtg ccatggtcac caacaacacc  240
acctccaccg ccatctgcaa gctcttcttg ttcttgtacc agttc                  285

SEQ ID NO: 10          moltype = AA  length = 95
FEATURE                Location/Qualifiers
REGION                 1..95
                       note = Pt_571834, domain coordinates 4-40, ortholog of
                        AtBBX28 (G1481), AtBBX29 (G900)
source                 1..95
                       mol_type = protein
                       organism = Populus trichocarpa
SEQUENCE: 10
MKKCELCKNP ARTYCESDEA NLCWNCDTKV HGANFLVARH ARALLCQSCQ SLTPWKASGS  60
QLGHTVSVCE RCGAMVTNNT TSTAICKLFL FLYQF                             95

SEQ ID NO: 11          moltype = DNA  length = 1121
FEATURE                Location/Qualifiers
misc_feature           1..1121
                       note = Pt_582065, ortholog of AtBBX28 (G1481), AtBBX29
                        (G900)
source                 1..1121
                       mol_type = unassigned DNA
                       organism = Populus trichocarpa
SEQUENCE: 11
atgaaagggt gtgagctatg tgggagttca gcaagaatgt tctgtgaatc agaccaagct  60
agtttatgtt gggattgtga tgagaaagta cactctgcca acttccttgt tgcaaagcat  120
tgtagaaccc ttctttgtca agtgtgtcaa tctccaactc cttggaaatc ctcagggtct  180
aaacttgccc ctaccgtttc tgtatgtgaa tcatgttttg ctgtccataa aaataataaa  240
aaacaactcc aagatctgaa cgtcatggct agtgatcaag aaagccgaga agccggaaat  300
gattatgacg agtctgaaaa tgatcgagaa ttcgacgacg acgacactga tgatgatagt  360
gatgaatatg acgaggagga agatggagac aaccagtgaa gaggagattt cctgtgctgg  420
tggaaatggg ttcttgaaac ggatgcgaga cagtaatgtt gatcttgatt ctgatgtaag  480
tctctttttc tttttctttc atttctttgc cattttttt atattagttt ttagagggca  540
cattttaata attgaatttg tggatcttag gaaatattgg gtcttcttcc tcttcctttt  600
taggttacaa actttgggtt tggtgaatac atttaatgtt ggataaatgc aggatgaaac  660
tggatgttcc tcttcgcata atttaagagg tggaagcatg agcaccgagg aagggaattc  720
tttgagttca tcaaggccat ggaagcaagc aagaacaagc gttcatgtag aagaagatgg  780
tcatgatggt caagcaatgt caagatcatc ggctatcata gactccctga agagactgca  840
gaaagacttg gtcgcgaatg gagaaaacgc gtctgctgct attcttggga tctgcaaatt  900
gagcagagat cagagccttt gatttctgcc cccccccccc cccctaactt tttttatatg  960
attaattagt aaccatctag tttttgaacc ataactattt agtatttcat tttattttga  1020
agcttgtttt agtagctggt tgtgtttgtc ttcatggttt tgtacatgag atggtatttg  1080
gttcaatggt taatgcaata tattacctta tgctatttgt t                      1121

SEQ ID NO: 12          moltype = AA  length = 132
FEATURE                Location/Qualifiers
REGION                 1..132
                       note = Pt_582065, domain coordinates 4-40, ortholog of
                        AtBBX28 (G1481), AtBBX29 (G900)
source                 1..132
                       mol_type = protein
                       organism = Populus trichocarpa
SEQUENCE: 12
MKGCELCGSS ARMFCESDQA SLCWDCDEKV HSANFLVAKH CRTLLCQVCQ SPTPWKSSGS  60
KLAPTVSVCE SCFAVHKNNK KQLQDLNVMA SDQESREAGN DYDESENDRE FDDDDTDDDS  120
DEYDEEEDGD NQ                                                      132

SEQ ID NO: 13          moltype = DNA  length = 420
FEATURE                Location/Qualifiers
misc_feature           1..420
                       note = Pt_758524, ortholog of AtBBX28 (G1481), AtBBX29
                        (G900)
source                 1..420
                       mol_type = unassigned DNA
                       organism = Populus trichocarpa
SEQUENCE: 13
atgaaaaagt gtgagctctg tgattctttt gcacaaatgc actgtgaatc ggatcaagct  60
atcctgtgtt cagcctgtga tgcatatgtt cacagtgcaa attttcttgc tgcaaaacat  120
tcaagaacgc ttctttgcca tgtttgtcaa tctcacacgc cctggattgg caccggaccc  180
ctgttaggtg ctactctttc ggtttgcaac agctgcataa acaactcgag ttgtactgat  240
ggaaaaggca gtgagaatga tcaaatcgcc aataatgatg atgagataat tgcgaacatg  300
atgaaaacga tgatggtggt taagacggcg atgaagacga tgaagaaaat caaatgtgtt  360
tatggattag ttaaacaagg caaagatcgt caagaagtct ctacgcgtca aatgctattt  420

SEQ ID NO: 14          moltype = AA  length = 140
```

```
FEATURE                Location/Qualifiers
REGION                 1..140
                       note = Pt_758524, domain coordinates 4-40, ortholog of
                        AtBBX28 (G1481), AtBBX29 (G900)
source                 1..140
                       mol_type = protein
                       organism = Populus trichocarpa
SEQUENCE: 14
MKKCELCDSF AQMHCESDQA ILCSACDAYV HSANFLAAKH SRTLLCHVCQ SHTPWIGTGP  60
LLGATLSVCN SCINNSSCTD GKGSENDQIA NNDDEIIANM MKTMMVVKTA MKTMKKIKCV  120
YGLVKQGKDR QEVSTRQMLF                                              140

SEQ ID NO: 15          moltype = DNA  length = 849
FEATURE                Location/Qualifiers
misc_feature           1..849
                       note = Os08g08120.1, ortholog of AtBBX28 (G1481), AtBBX29
                        (G900)
source                 1..849
                       mol_type = unassigned DNA
                       organism = Oryza sativa
SEQUENCE: 15
atgtcggtgg cggcggaggg gaaggagaag ggggttggtg gtgggggtgg tggtgcgggt  60
gcgggggcgt gcgagctgtg cggggcggcg gcgagggtgt actgcggggc ggacgaggcg  120
acgctgtgct gggggtgcga cgcgcaggtg cacggggcca acttcctggt ggcgcggcac  180
gcgcgggcgc tgctgtgccg cgggtgcgcg aggcccacgc cgtggcgcgc cgcggggccc  240
aggctgggcc ccaccgcgtc gctctgcgag cgctgcgtcc gccgcggcgg tggtggccgt  300
ggtggtggag gaggtggagg cgctgctggt ggtggaggcc gtggtggtgg gggagacgag  360
gagatgggcg gcgagggcga tgaggaggag gaggacgagg acgaggaggt ggtcgtcgag  420
gaggaggagg acgaggatga tgaagacgag gagggggagg gggaggggga gaaccaggtg  480
gtgccgtggg cggaggaggc ggaggccacg ccgccgcccg tcgcgagctc cacgtcgagc  540
agcagccggg aggccgccgc caacggcgcg aacgccgccg accgcgtcaa ggaggaccag  600
ccgtgctcga cgtcgcagcc gagcttgtgc cggtacgcgt cctcggctca ccatggcggt  660
ggtggccgga gcgacgaggc cacctcctcc cggaacggcg gtggcgtcgg cggccgattc  720
cttgcctccc ggcataggaa gagatcgccc tcggatttcc gccggtcggg gttggcgcag  780
tcggtgagcg gcgtgcaggg gaggaattgc tccaatgcgg tcgttggtcg aaatgatgca  840
agcatgatg                                                          849

SEQ ID NO: 16          moltype = AA  length = 283
FEATURE                Location/Qualifiers
REGION                 1..283
                       note = Os08g08120.1, domain coordinates 28-60, ortholog of
                        AtBBX28 (G1481), AtBBX29 (G900)
source                 1..283
                       mol_type = protein
                       organism = Oryza sativa
SEQUENCE: 16
MSVAAEGKEK GVGGGGGGAG AGACELCGAA ARVYCGADEA TLCWGCDAQV HGANFLVARH  60
ARALLCRGCA RPTPWRAAGP RLGPTASLCE RCVRRGGGGR GGGGGGGAAG GGGRGGGGDE  120
EMGGEGDEEE EDEDEEVVVE EEEDEDDEDE EGEGEGENQV VPWAEEAEAT PPPVASSTSS  180
SSREAAANGA NAADRVKEDQ PCSTSQPSLC RYASSAHHGG GGRSDEATSS RNGGGVGGRF  240
LASRHRKRSP SDFRRSGLAQ SVSGVQGRNC SNAVVGRNDA SMM                    283

SEQ ID NO: 17          moltype = DNA  length = 843
FEATURE                Location/Qualifiers
misc_feature           1..843
                       note = Os08g08120.2, ortholog of AtBBX28 (G1481), AtBBX29
                        (G900)
source                 1..843
                       mol_type = unassigned DNA
                       organism = Oryza sativa
SEQUENCE: 17
atgtcggtgg cggcggaggg gaaggagaag ggggttggtg gtgggggtgg tggtgcgggt  60
gcgggggcgt gcgagctgtg cggggcggcg gcgagggtgt actgcggggc ggacgaggcg  120
acgctgtgct gggggtgcga cgcgcaggtg cacggggcca acttcctggt ggcgcggcac  180
gcgcgggcgc tgctgtgccg cgggtgcgcg aggcccacgc cgtggcgcgc cgcggggccc  240
aggctgggcc ccaccgcgtc gctctgcgag cgctgcgtcc gccgcggcgg tggtggccgt  300
ggtggtggag gaggtggagg cgctgctggt ggtggaggcc gtggtggtgg gggagacgag  360
gagatgggcg gcgagggcga tgaggaggag gaggacgagg acgaggaggt ggtcgtcgag  420
gaggaggagg acgaggatga tgaagacgag gagggggagg gggaggggga gaaccaggtg  480
gtgccgtggg cggaggaggc ggaggccacg ccgccgcccg tcgcgagctc cacgtcgagc  540
agcagccggg aggccgccgc caacggcgcg aacgccgccg accgcgtcaa ggaggaccag  600
ccgtgctcga cgtcgcagcc gagcttgtgc cggtacgcgt cctcggctca ccatggcggt  660
ggtggccgga gcgacgaggc cacctcctcc cggaacggcg gtggcgtcgg cggccgattc  720
cttgcctccc ggcataggaa gagatcgccc tcggatttcc gccggtcggg gttggcgcag  780
tcggtgagcg gcgtgcaggg gaggaattgc tccaatgcgg tcgttggtcg aaatgacttt  840
tcc                                                                843

SEQ ID NO: 18          moltype = AA  length = 281
FEATURE                Location/Qualifiers
```

```
REGION                  1..281
                        note = Os08g08120.2, domain coordinates 28-60, ortholog of
                         AtBBX28 (G1481), AtBBX29 (G900)
source                  1..281
                        mol_type = protein
                        organism = Oryza sativa
SEQUENCE: 18
MSVAAEGKEK GVGGGGGGAG AGACELCGAA ARVYCGADEA TLCWGCDAQV HGANFLVARH  60
ARALLCRGCA RPTPWRAAGP RLGPTASLCE RCVRRGGGGR GGGGGGGAAG GGGRGGGGDE  120
EMGGEGDEEE EDEDEEVVVE EEEDEDDEDE EGEGEGENQV VPWAEEAEAT PPPVASSTSS  180
SSREAAANGA NAADRVKEDQ PCSTSQPSLC RYASSAHHGG GGRSDEATSS RNGGGVGGRF  240
LASRHRKRSP SDFRRSGLAQ SVSGVQGRNC SNAVVGRNDF S                      281

SEQ ID NO: 19           moltype = DNA  length = 837
FEATURE                 Location/Qualifiers
misc_feature            1..837
                        note = Os08g08120.3, ortholog of AtBBX28 (G1481), AtBBX29
                         (G900)
source                  1..837
                        mol_type = unassigned DNA
                        organism = Oryza sativa
SEQUENCE: 19
atgtcggtgg cggcggaggg gaaggagaag ggggttggtg gtgggggtgg tggtgcgggt  60
gcgggggcgt gcgagctgtg cggggcggcg gcgagggtgt actgcggggc ggacgaggcg  120
acgctgtgct gggggtgcga cgcgcaggtg cacggggcca acttcctggt ggcgcggcac  180
gcgcgggcgc tgctgtgccg cgggtgcgcg aggcccacgc cgtggcgcgc cgcggggccc  240
aggctgggcc ccaccgcgtc gctctgcgag cgctgcgtcc gccgcggcgg tggtggccgt  300
ggtggtggag gaggtggagg cgctgctggt ggtggaggcc gtggtggtgg gggagacgag  360
gagatgggcg gcgagggcga tgaggaggag gaggacgagg acgaggaggt ggtcgtcgag  420
gaggaggagg acgaggatga tgaagacgag gagggggagg gggaggggga gaaccaggtg  480
gtgccgtggg cggaggaggc ggaggccacg ccgccgcccg tcgcgagctc cacgtcgagc  540
agcagccggg aggccgccgc caacggcgcg aacgccgccg accgcgtcaa ggaggaccag  600
ccgtgctcga cgtcgcagcc gagcttgtgc cggtacgcgt cctcggctca ccatggcggt  660
ggtggccgga gcgacgaggc cacctcctcc cggaacggcg gtggcgtcgg cggccgattc  720
cttgcctccc ggcataggaa gagatcgccc tcggatttcc gccggtcggg gttggcgcag  780
tcggtgagcg gcgtgcaggg gaggaattgc tccaatgcgg tcgttggtcg aaatgag     837

SEQ ID NO: 20           moltype = AA  length = 279
FEATURE                 Location/Qualifiers
REGION                  1..279
                        note = Os08g08120.3, domain coordinates 28-60, ortholog of
                         AtBBX28 (G1481), AtBBX29 (G900)
source                  1..279
                        mol_type = protein
                        organism = Oryza sativa
SEQUENCE: 20
MSVAAEGKEK GVGGGGGGAG AGACELCGAA ARVYCGADEA TLCWGCDAQV HGANFLVARH  60
ARALLCRGCA RPTPWRAAGP RLGPTASLCE RCVRRGGGGR GGGGGGGAAG GGGRGGGGDE  120
EMGGEGDEEE EDEDEEVVVE EEEDEDDEDE EGEGEGENQV VPWAEEAEAT PPPVASSTSS  180
SSREAAANGA NAADRVKEDQ PCSTSQPSLC RYASSAHHGG GGRSDEATSS RNGGGVGGRF  240
LASRHRKRSP SDFRRSGLAQ SVSGVQGRNC SNAVVGRNE                         279

SEQ ID NO: 21           moltype = DNA  length = 648
FEATURE                 Location/Qualifiers
misc_feature            1..648
                        note = Glyma06g39810.1, ortholog of AtBBX28 (G1481),
                         AtBBX29 (G900)
source                  1..648
                        mol_type = unassigned DNA
                        organism = Glycine max
SEQUENCE: 21
atggaggaat catcaacaac atgcgtgttg tgcgagaaga gggcaatgat gctctgcgac  60
tcggaccagg ctaagctatg ctgggaatgc gacgagaaag tccacagcgc caatttcttg  120
gtcgcgaaac attctagggt tcttttatgt cgtttgtgtc actccccgac tccgtggaag  180
gcttcgggga tgaaactcac gcccactgtg tcgttttgta accgctgcgt tgcggaacgg  240
aacgcgaggt ggaaccgatt ggtgaataat gaaaatgaac atcaacaaca gcaacaacaa  300
caacaacaga gtgattttgt ggtggatgat ggtagggaat atggttctga tcatgttttt  360
gatgatgacg atggtgatta tagtgatgat agtggtgaag aagaagaaga ggacgaggat  420
gatgaagagg agaatgagaa tcaagtggtt ccaatgtctt ctggttctgc cacgtcacca  480
cctaaggttg cctgtttagc gttgaagcga ttgagaaaca actctttttc tgtcgattct  540
tcacatgatg agacagcgtg ctcttcatct gagatgctta gttctacatt gcctagtggt  600
gatgaatcaa cctctttgag tagtgtatta aagaggcatc gggttgat               648

SEQ ID NO: 22           moltype = AA  length = 216
FEATURE                 Location/Qualifiers
REGION                  1..216
                        note = Glyma06g39810.1, domain coordinates 15-44, ortholog
                         of AtBBX28 (G1481), AtBBX29 (G900)
source                  1..216
```

-continued

```
                        mol_type = protein
                        organism = Glycine max
SEQUENCE: 22
MEESSTTCVL CEKRAMMLCD SDQAKLCWEC DEKVHSANFL VAKHSRVLLC RLCHSPTPWK  60
ASGMKLTPTV SFCNRCVAER NARWNRLVNN ENEHQQQQQQ QQQSDFVVDD GREYGSDHVF  120
DDDDGDYSDD SGEEEEEDED DEEENENQVV PMSSGSATSP PKVACLALKR LRNNSFSVDS  180
SHDETACSSS EMLSSTLPSG DESTSLSSVL KRHRVD                          216

SEQ ID NO: 23           moltype = DNA  length = 531
FEATURE                 Location/Qualifiers
misc_feature            1..531
                        note = Glyma06g45620.1, ortholog of AtBBX28 (G1481),
                         AtBBX29 (G900)
source                  1..531
                        mol_type = unassigned DNA
                        organism = Glycine max
SEQUENCE: 23
atgaacaagt gcgaactgtg caaagttccg gcgaggatct tctgcgagtc ggaccaggcg  60
agcttatgct gggactgcga cgctaaggtt cacagcgcca acttcttggt cgcgagacac  120
gcgcgaacct tactctgccg cacgtgccgc tctcccacgc cgtggaaggc ctccggcgcc  180
tcactcgcca gcgccgtctc cgtctgcgac cgctgcgccg cctccgaaga accggaagag  240
agtgaagccg gcaatgacga cgaaccagac acggaggacg acgacaacga cgacgaggac  300
ggcgacaatc aggtcgtgcc gtggtcctcc tccccgccgc cgcctccgcc gtcgagctcc  360
tccggcagcg aatggtcgga gtgcaaaaac gacgacgctt ctatttccgc ctcggaacag  420
gaaacgacaa catgctcgtt gaaacgacag cgcgaggacg atgatgatgc ttcttccgat  480
cgtgatccca gggtgttgag aagggttggg cgtctcaacg gaggttgcgt g          531

SEQ ID NO: 24           moltype = AA  length = 177
FEATURE                 Location/Qualifiers
REGION                  1..177
                        note = Glyma06g45620.1, domain coordinates 4-40, ortholog
                         of AtBBX28 (G1481), AtBBX29 (G900)
source                  1..177
                        mol_type = protein
                        organism = Glycine max
SEQUENCE: 24
MNKCELCKVP ARIFCESDQA SLCWDCDAKV HSANFLVARH ARTLLCRTCR SPTPWKASGA  60
SLASAVSVCD RCAASEEPEE SEAGNDDEPD TEDDDNDDED GDNQVVPWSS SPPPPPPSSS  120
SGSEWSECKN DDASISASEQ ETTTCSLKRQ REDDDDASSD RDPRVLRRVG RLNGGCV     177

SEQ ID NO: 25           moltype = DNA  length = 1236
FEATURE                 Location/Qualifiers
misc_feature            1..1236
                        note = G4015, ortholog of AtBBX28 (G1481), AtBBX29 (G900)
source                  1..1236
                        mol_type = unassigned DNA
                        organism = Glycine max
SEQUENCE: 25
atggaggaat catcaacaac atgcgtgttg tgcgagaaga gggcaatgat gctctgcgac  60
tcggaccagg ctaagctatg ctgggaatgc gacgagaaag tccacagcgc caatttcttg  120
gtcgcgaaac attctagggt tcttttatgt cgtttgtgtc actccccgac tccgtggaag  180
gcttcgggga tgaaactcac gcccactgtg tcgttttgta accgctgcgt tgcggaacgg  240
aacgcgaggt ggaaccgatt ggtgaataat gaaaatgaac atcaacaaca gcaacaacaa  300
caacaacaga gtgattttgt ggtggatgat gggagggaat atggttctga tcatgttttt  360
gatgatgacg atggtgatta tagtgatgat agtggtgaag aagaagaaga ggacgaggat  420
gatgaagagg agaatgagaa tcaagtggtt ccaatgtctt ctggttctgc cacgtcacca  480
cctaaggttg cctgtttagc gttgaagcga ttgagaaaca actcttttct gtcgattctt  540
cacatgatga gacagcgtgc tcttcatctg agatgcttag ttctacattg cctagtggtg  600
atgaatcacc ctctttgaat ggaggaatca tcaacaacat gcgtgttgtg cgagaagagg  660
gcaatgatgc tctgcgactc ggaccaggct aagctatgct gggaatgcga cgagaaagtc  720
cacagcgcca atttcttggt cgcgaaacat tctagggttc ttttatgtcg tttgtgtcac  780
tccccgactc cgtggaaggc ttcggggatg aaactcacgc ccactgtgtc gttttgtaac  840
cgctgcgttg cggaacggaa cgcgaggtgg aaccgattgg tgaataatga aaatgaacat  900
caacaacagc aacaacaaca acaacagagt gattttgtgg tggatgatgg gagggaatat  960
ggttctgatc atgtttttga tgatgacgat ggtgattata gtgatgatag tggtgaagaa  1020
gaagaagagg acgaggatga tgaagaggag aatgagaatc aagtggttcc aatgtcttct  1080
ggttctgcca cgtcaccacc taaggttgcc tgtttagcgt tgaagcgatt gagaaacaac  1140
tcttttctgt cgattcttca catgatgaga cagcgtgctc ttcatctgag atgcttagtt  1200
ctacattgcc tagtggtgat gaatcaccct ctttga                          1236

SEQ ID NO: 26           moltype = AA  length = 205
FEATURE                 Location/Qualifiers
REGION                  1..205
                        note = G4015, domain coordinates 8-44, ortholog of AtBBX28
                         (G1481), AtBBX29 (G900)
source                  1..205
                        mol_type = protein
                        organism = Glycine max
SEQUENCE: 26
```

```
MEESSTTCVL CEKRAMMLCD SDQAKLCWEC DEKVHSANFL VAKHSRVLLC RLCHSPTPWK  60
ASGMKLTPTV SFCNRCVAER NARWNRLVNN ENEHQQQQQQ QQQSDFVVDD GREYGSDHVF  120
DDDDGDYSDD SGEEEEEDED DEEENENQVV PMSSGSATSP PKVACLALKR LRNNSFLSIL  180
HMMRQRALHL RCLVLHCLVV MNHPL                                        205

SEQ ID NO: 27          moltype = DNA  length = 237
FEATURE                Location/Qualifiers
misc_feature           1..237
                       note = Glyma09g35960.1, ortholog of AtBBX28 (G1481),
                        AtBBX29 (G900)
source                 1..237
                       mol_type = unassigned DNA
                       organism = Glycine max
SEQUENCE: 27
atgggggaat attcatgcgc gttgtgcaag aagagggcga tgatgctgtg cgactcggac  60
caggctaagc tatgctggga gtgcgacgag aaagttcaca gcgcgaattt cttggtggct  120
aagcattcgc gtgtgcttct ctgtcgttta tgccattccc cgactccgtg gaaggcctcc  180
ggcaccaaac tcatgctcac ggtgtcgttt tgtcagcgtt gcgtcgcgca tcgacac     237

SEQ ID NO: 28          moltype = AA  length = 79
FEATURE                Location/Qualifiers
REGION                 1..79
                       note = Glyma09g35960.1, domain coordinates 13-42, ortholog
                        of AtBBX28 (G1481), AtBBX29 (G900)
source                 1..79
                       mol_type = protein
                       organism = Glycine max
SEQUENCE: 28
MGEYSCALCK KRAMMLCDSD QAKLCWECDE KVHSANFLVA KHSRVLLCRL CHSPTPWKAS  60
GTKLMLTVSF CQRCVAHRH                                               79

SEQ ID NO: 29          moltype = DNA  length = 519
FEATURE                Location/Qualifiers
misc_feature           1..519
                       note = Glyma12g11230.1, ortholog of AtBBX28 (G1481),
                        AtBBX29 (G900)
source                 1..519
                       mol_type = unassigned DNA
                       organism = Glycine max
SEQUENCE: 29
atgaagaagt gcgaactgtg taaagttccg gcgaggatct tctgcgagtc ggaccaggct  60
agcttatgct gggactgcga cgctaaggtt cacagcgcca acttcttggt cgcgaggcac  120
gtgcgaaccc tactctgccg cacgtgtcgt tctcccacgc cctggaaggc ctccggcgcc  180
tcactcgccc acgccgcctc cgtctgcgac cgctgcgccg ccgcggaaga gacggaagag  240
agcgaagccg gcaatgacga cgaaccagac accgaggacg acgacgatgt cgacaaccag  300
gtcgtgccgt ggtcctccac gccgccgccg ccgccgccgt cgagctcctc cggcagcgaa  360
tgctcggagt gcaaaaacaa cgttgcttct ttttccgcct cggaacagga aacgacaaca  420
tcctcgttga aacgacagcg cgaggacgac gacgatgctt cttccgatcc tgatcccagg  480
gtgttgagaa gggttgggcg tctcaacgga ggttgcgtg                         519

SEQ ID NO: 30          moltype = AA  length = 173
FEATURE                Location/Qualifiers
REGION                 1..173
                       note = Glyma12g11230.1, domain coordinates 4-40, ortholog
                        of AtBBX28 (G1481), AtBBX29 (G900)
source                 1..173
                       mol_type = protein
                       organism = Glycine max
SEQUENCE: 30
MKKCELCKVP ARIFCESDQA SLCWDCDAKV HSANFLVARH VRTLLCRTCR SPTPWKASGA  60
SLAHAASVCD RCAAAEETEE SEAGNDDEPD TEDDDDVDNQ VVPWSSTPPP PPPSSSSGSE  120
CSECKNNVAS FSASEQETTT SSLKRQREDD DDASSDPDPR VLRRVGRLNG GCV         173

SEQ ID NO: 31          moltype = DNA  length = 663
FEATURE                Location/Qualifiers
misc_feature           1..663
                       note = Glyma12g32470.1, ortholog of AtBBX28 (G1481),
                        AtBBX29 (G900)
source                 1..663
                       mol_type = unassigned DNA
                       organism = Glycine max
SEQUENCE: 31
atgaagaact gcgagctatg caagcttcca gctaggacct tctgcgagtc ggaccaggct  60
agcttatgct gggactgcga cgccaaggtc cacggagcga acttcctcgt cgcgagacac  120
acgcgcacgc tcctctgcca cgcgtgccag tcactcacgc cgtggaaggc ctccggctct  180
gccctcggca acaccgtctc gctgtgccag agttgcgccg gcggaaccac cgaacagggc  240
ccagagagcc aaggagggaa tgacgacgac gacatagaca ccgacgatga ggatgactac  300
gatgacgatg gtgagagcga ggagaacgag gttgcagccg acgaggagga cggagacaac  360
caggttgtcc cttggtcctc cgagccgccg ccaccgtccc caagctcttc cagcagcgaa  420
```

```
gagtcgatta gccggtgcaa caacgtggac gaggtttcga ccacattgaa acgacgtcgc  480
gagaacgacg attttcaggg ttcgaattcg aataattgga aatgtgaacg gagcgaagtg  540
gacagaggat gttggttggc tcggttgcgg cggagaaccg ccgatgatgt ggcggttgag  600
cgacggaggg ctagagcggc gtttccgtac ggttgttgtg atgatagagc atctgaagac  660
gtt                                                               663

SEQ ID NO: 32           moltype = AA  length = 221
FEATURE                 Location/Qualifiers
REGION                  1..221
                        note = Glyma12g32470.1, domain coordinates 10-40, ortholog
                         of AtBBX28 (G1481), AtBBX29 (G900)
source                  1..221
                        mol_type = protein
                        organism = Glycine max
SEQUENCE: 32
MKNCELCKLP ARTFCESDQA SLCWDCDAKV HGANFLVARH TRTLLCHACQ SLTPWKASGS  60
ALGNTVSLCQ SCAGGTTEQG PESQGGNDDD DIDTDDEDDY DDDGESEENE VAADEEDGDN  120
QVVPWSSEPP PPSPSSSSSE ESISRCNNVD EVSTTLKRRR ENDDFQGSNS NNWKCERSEV  180
DRGCWLARLR RRTADDVAVE RRRARAAFPY GCCDDRASED V                     221

SEQ ID NO: 33           moltype = DNA  length = 462
FEATURE                 Location/Qualifiers
misc_feature            1..462
                        note = G4014, Glyma13g32160.1, ortholog of AtBBX28 (G1481),
                         AtBBX29 (G900)
source                  1..462
                        mol_type = unassigned DNA
                        organism = Glycine max
SEQUENCE: 33
atgaggaagt gtgagctctg taacagtccc gcgaagttgt tctgcgaatc agatcaagcc  60
agcctctgtt ggaaatgcga tgctaaggtt cacagtgcaa acttcctcgt caccaaacat  120
cccaggattc ttctctgcca tgtttgtcaa tcactaacag cgtggcacgg cacaggaccc  180
aagtttgtac ccaccatgtc agtttgcaac acttgtgtca acaacaatag tactgagacc  240
tgcagccaac agaatcatga agacgatgat gatgatggta cgggagagga tcatgcagaa  300
aacgacgatg gtggtgtggc tgaagatgat gatgatgatg atgatgaaga aaatcaagtg  360
gttccatgga catctacacc accaccccca gcttccactt cttcaaatag tgttacaact  420
agttctacca ggttctctga tgttgaagaa ggtggctccg at                    462

SEQ ID NO: 34           moltype = AA  length = 154
FEATURE                 Location/Qualifiers
REGION                  1..154
                        note = G4014, Glyma13g32160.1, domain coordinates 4-40,
                         ortholog of AtBBX28 (G1481), AtBBX29 (G900)
source                  1..154
                        mol_type = protein
                        organism = Glycine max
SEQUENCE: 34
MRKCELCNSP AKLFCESDQA SLCWKCDAKV HSANFLVTKH PRILLCHVCQ SLTAWHGTGP  60
KFVPTMSVCN TCVNNNSTET CSQQNHEDDD DDGTGEDHAE NDDGGVAEDD DDDDDEENQV  120
VPWTSTPPPP ASTSSNSVTT SSTRFSDVEE GGSD                              154

SEQ ID NO: 35           moltype = DNA  length = 663
FEATURE                 Location/Qualifiers
misc_feature            1..663
                        note = G4016, Glyma13g37970.1, ortholog of AtBBX28 (G1481),
                         AtBBX29 (G900)
source                  1..663
                        mol_type = unassigned DNA
                        organism = Glycine max
SEQUENCE: 35
atgaagaact gcgagttgtg caagcttccg gctcggactt tctgcgagtc ggaccaggct  60
agcttatgct gggactgcga cgccaaggtt catggagcca acttcctcgt ggaaagacac  120
acgcgcacgc tcctctgcca cgcgtgccag tcgcccacgc cgtggaaggc ctccggcgcc  180
gccctcggaa acaccgtctc gctgtgcgag agatgcgccg gcggaaccac cgaacaaggt  240
caagagagcc aaggaggcaa tgacgacgac atagacaccg acatagacac cgacgatgag  300
gatgactacg atgagagcga ggacgaggtt gccgccgacg aggaggacgg agacaaccag  360
gttgtccctt ggtcctccga gccgccgcca ccagccccga gctcttccag cagcgaagaa  420
tcggttagcc ggtgcaacaa cgtggacgag gtttcgacca cattgaaacg ccgtcgccag  480
gaggacaatg attttcaggg ttggaattcg aataattggg gatgtgaacg gagcgaagtg  540
gagagaggag gttggttggt tcggttgcgg cggagaaccg ccgatgatgt ggcggttgag  600
caacggagtg ctagagcggc gtctccagac ggttgctgtg gtgatagagc atctgaagac  660
gtt                                                               663

SEQ ID NO: 36           moltype = AA  length = 221
FEATURE                 Location/Qualifiers
REGION                  1..221
                        note = G4016, Glyma13g37970.1, domain coordinates 10-40,
                         ortholog of AtBBX28 (G1481), AtBBX29 (G900)
source                  1..221
```

-continued

```
                        mol_type = protein
                        organism = Glycine max
SEQUENCE: 36
MKNCELCKLP ARTFCESDQA SLCWDCDAKV HGANFLVERH TRTLLCHACQ SPTPWKASGA  60
ALGNTVSLCE RCAGGTTEQG QESQGGNDDD IDTDIDTDDE DDYDESEDEV AADEEDGDNQ  120
VVPWSSEPPP PAPSSSSSEE SVSRCNNVDE VSTTLKRRRQ EDNDFQGWNS NNWGCERSEV  180
ERGGWLVRLR RRTADDVAVE QRSARAASPD GCCGDRASED V                     221

SEQ ID NO: 37           moltype = DNA  length = 456
FEATURE                 Location/Qualifiers
misc_feature            1..456
                        note = Glyma15g07140.1, ortholog of AtBBX28 (G1481),
                         AtBBX29 (G900)
source                  1..456
                        mol_type = unassigned DNA
                        organism = Glycine max
SEQUENCE: 37
atgaggaagt gtgaactctg taatagtccc gcaaagttgt tctgtgaatc agatcaagcc  60
agcctctgtt gggaatgcga tgctaaggtt cacagtgcaa acttcctcgt caccaaacat  120
cccaggattc ttctctgcca tgtttgtcaa tcactaacgg cctggcacgg cacgggaccc  180
aagtttgtac ccaccatgtc cgtttgcaac acttgtgtca acaacaatag tgagacctgc  240
agccaacaga atcatgttga ggaccacgac gacaatcatg atgatggcac gggagaggat  300
catgtagaaa accatgatgg tggtgtgtct gaagatgatg aagaaaatca agttgttcca  360
tggacatcta caccaccacc cccagcttcc acttcttcaa atagtgttac aactagttct  420
accaggttct ctaatgttga agaaggtggc tccgat                           456

SEQ ID NO: 38           moltype = AA  length = 152
FEATURE                 Location/Qualifiers
REGION                  1..152
                        note = Glyma15g07140.1, domain coordinates 4-40, ortholog
                         of AtBBX28 (G1481), AtBBX29 (G900)
source                  1..152
                        mol_type = protein
                        organism = Glycine max
SEQUENCE: 38
MRKCELCNSP AKLFCESDQA SLCWECDAKV HSANFLVTKH PRILLCHVCQ SLTAWHGTGP  60
KFVPTMSVCN TCVNNNSETC SQQNHVEDHD DNHDDGTGED HVENHDGGVS EDDEENQVVP  120
WTSTPPPPAS TSSNSVTTSS TRFSNVEEGG SD                               152

SEQ ID NO: 39           moltype = DNA  length = 351
FEATURE                 Location/Qualifiers
misc_feature            1..351
                        note = AtBBX30 (G1478), AT4G15248.1, paralog of AtBBX31
                         (G1929)
source                  1..351
                        mol_type = unassigned DNA
                        organism = Arabidopsis thaliana
SEQUENCE: 39
atgtgtagag ggtttgagaa agaagaagag agaagaagcg acaatggagg atgccaaaga  60
ctatgcacgg agagtcacaa agctccggta agctgtgagc tttgcggcga gaacgccacc  120
gtgtattgtg aggcagacgc agctttcctt tgtaggaaat gcgatcgatg ggtccattct  180
gctaattttc tagctcggag acatctccgg cgcgtgatct gcacgacctg tcggaagcta  240
actcgtcgat gtcttgtcgg tgataatttt aatgttgttt taccggagat aaggatgata  300
gcaaggattg aagaacatag tagtgatcac aaaattccct ttgtgtttct c          351

SEQ ID NO: 40           moltype = AA  length = 117
FEATURE                 Location/Qualifiers
REGION                  1..117
                        note = AtBBX30 (G1478), AT4G15248.1, domain coordinates
                         39-68, paralog of AtBBX31 (G1929)
source                  1..117
                        mol_type = protein
                        organism = Arabidopsis thaliana
SEQUENCE: 40
MCRGFEKEEE RRSDNGGCQR LCTESHKAPV SCELCGENAT VYCEADAAFL CRKCDRWVHS  60
ANFLARRHLR RVICTTCRKL TRRCLVGDNF NVVLPEIRMI ARIEEHSSDH KIPFVFL     117

SEQ ID NO: 41           moltype = DNA  length = 366
FEATURE                 Location/Qualifiers
misc_feature            1..366
                        note = AtBBX31 (G1929), paralog of AtBBX30 (G1478)
source                  1..366
                        mol_type = unassigned DNA
                        organism = Arabidopsis thaliana
SEQUENCE: 41
atgtgtagag gcttgaataa tgaagagagc agaagaagtg acggaggagg ttgccggagt  60
ctctgcacga gaccgagtgt tccggtaagg tgtgagcttt gcgacggaga cgcctccgtg  120
ttctgtgaag cggactcggc gttcctctgt agaaaatgtg accggtgggt tcatggagcg  180
aattttctag cttggagaca cgtaaggcgc gtgctatgca cttcttgtca gaaactcacg  240
```

```
cgccggtgcc tcgtcggaga tcatgacttc cacgttgttt taccgtcggt gacgacggtc  300
ggagaaacca ccgtggagaa tagaagtgaa caagataatc atgaggttcc gtttgttttt  360
ctctga                                                             366

SEQ ID NO: 42          moltype = AA  length = 121
FEATURE                Location/Qualifiers
REGION                 1..121
                       note = AtBBX31 (G1929), paralog of AtBBX30 (G1478)
source                 1..121
                       mol_type = protein
                       organism = Arabidopsis thaliana
SEQUENCE: 42
MCRGLNNEES RRSDGGGCRS LCTRPSVPVR CELCDGDASV FCEADSAFLC RKCDRWVHGA  60
NFLAWRHVRR VLCTSCQKLT RRCLVGDHDF HVVLPSVTTV GETTVENRSE QDNHEVPFVF  120
L                                                                  121

SEQ ID NO: 43          moltype = DNA  length = 878
FEATURE                Location/Qualifiers
misc_feature           1..878
                       note = Pt_562313, ortholog of AtBBX30 (G1478), AtBBX31
                        (G1929)
source                 1..878
                       mol_type = unassigned DNA
                       organism = Populus trichocarpa
SEQUENCE: 43
atgtgtaggg gtattcatca ggagagaaat aaccaaggcg gttcttgtgg cgaagaggtg  60
gtttcatcta aggcaacctc aagattggtt tgttgtgagc tgtgtggatc aagggcatca  120
ttatattgtc aagcagatga tgcattttta tgtcaaaaat gtgacaaatg ggtgcatgga  180
gcaaatttcc tagctcaaag gcatgttaga tgcatgctat gcaacacatg ccaaaatctt  240
acacaaagat atctcatagg ggcttcaact gagttgttgc ttccaactat tgtgagttgg  300
agagaaagaa ggcagtgcaa ttctaatctt gaaaagaaga gctctggatc acttaaaatg  360
ccctttttgt ttctttgatt ctgcttctct ctttcacctt ttctgtccct tttttcttcc  420
ctttttttta gttttctggt gctgttcaag gattttttt cttgagattt attgatggag  480
agaacacaaa actgtcactt gaagggtttt gggtgcatat gagaattgtt gcaagtgggt  540
gataaaattg atcagtcaat ttttctgtta tatgcaccac catatatatc caagaaaata  600
cagagaccat agcagctgct tggaatcctg gaaaaggaag agaggagaaa aacacagaca  660
gaaagatggg tgatgaaata gaggataccc tggaatcatt gtctccatga aatcctctga  720
aagagatcaa attaaatcag aaaatgtatt tttttttct ctggaaattt tctaatttta  780
tcacctcttt tttgtccaaa gtaatgtttt tctggtgtgt gtacttttct ttttggttat  840
aaatagtgtg taatcattta gatcaaaagg taagggaa                          878

SEQ ID NO: 44          moltype = AA  length = 125
FEATURE                Location/Qualifiers
REGION                 1..125
                       note = Pt_562313, domain coordinates 32-68, ortholog of
                        AtBBX30 (G1478), AtBBX31 (G1929)
source                 1..125
                       mol_type = protein
                       organism = Populus trichocarpa
SEQUENCE: 44
MCRGIHQERN NQGGSCGEEV VSSKATSRLV CCELCGSRAS LYCQADDAFL CQKCDKWVHG  60
ANFLAQRHVR CMLCNTCQNL TQRYLIGAST ELLLPTIVSW RERRQCNSNL EKKSSGSLKM  120
PFLFL                                                              125

SEQ ID NO: 45          moltype = DNA  length = 372
FEATURE                Location/Qualifiers
misc_feature           1..372
                       note = Pt_594447, ortholog of AtBBX30 (G1478), AtBBX31
                        (G1929)
source                 1..372
                       mol_type = unassigned DNA
                       organism = Populus trichocarpa
SEQUENCE: 45
atgtgtagag gtaatcagga gagaagtaac caaggcagtt cttgtaacaa ggaggctgtt  60
tcacctaatg caacctcaag attcgtttgt tgtgagctat gtggctcgag ggcaacattg  120
tattgtcaag cagatcatgc atttctatgt caaaaatgtg acggatgggt gcatggagct  180
aatttcttag ccctcaggca tgttagaaac atgttatgca acacatgcca aaatcttaca  240
cagagatgtc tcattggggc ttcaactgag gtgatgcttt caactattgt gagttggaga  300
gaaagaaggg atcgtaattc taatcttgaa aagaagtgct ctggatcact taaaaagccc  360
ttttcgtttc tt                                                      372

SEQ ID NO: 46          moltype = AA  length = 124
FEATURE                Location/Qualifiers
REGION                 1..124
                       note = Pt_594447, domain coordinates 31-67, ortholog of
                        AtBBX30 (G1478), AtBBX31 (G1929)
source                 1..124
                       mol_type = protein
                       organism = Populus trichocarpa
```

```
SEQUENCE: 46
MCRGNQERSN QGSSCNKEAV SPNATSRFVC CELCGSRATL YCQADHAFLC QKCDGWVHGA  60
NFLALRHVRN MLCNTCQNLT QRCLIGASTE VMLSTIVSWR ERRDRNSNLE KKCSGSLKKP  120
FSFL                                                               124

SEQ ID NO: 47          moltype = DNA  length = 372
FEATURE                Location/Qualifiers
misc_feature           1..372
                       note = Glyma12g32230.1, ortholog of AtBBX30 (G1478),
                        AtBBX31 (G1929)
source                 1..372
                       mol_type = unassigned DNA
                       organism = Glycine max
SEQUENCE: 47
atgtgcaaag gtgcagaagg agaaaagcaa catggtttct gcagcagctt tctacataaa  60
gagagtgcaa ccagaagtgc tatatgttgt gagctatgtg ggttacaggc ttcattgtat  120
tgccaagctg atgatgccta cttgtgtaaa aaatgcgata aacgggttca tgaagctaat  180
tttttggccc ttaggcacat taggtgcttt ctgtgcaaca catgtcagaa ccttacgcga  240
agatatctca ttggagcatc actagaggtg gttcttccgg ccaatataaa ctggaccatt  300
agaaatctcc ttaacaacag aggaatctac agaaagtgtt caagaatgca taacagccct  360
tccctctttt ta                                                      372

SEQ ID NO: 48          moltype = AA  length = 124
FEATURE                Location/Qualifiers
REGION                 1..124
                       note = Glyma12g32230.1, domain coordinates 30-66, ortholog
                        of AtBBX30 (G1478), AtBBX31 (G1929)
source                 1..124
                       mol_type = protein
                       organism = Glycine max
SEQUENCE: 48
MCKGAEGEKQ HGFCSSFLHK ESATRSAICC ELCGLQASLY CQADDAYLCK KCDKRVHEAN  60
FLALRHIRCF LCNTCQNLTR RYLIGASLEV VLPANINWTI RNLLNNRGIY RKCSRMHNSP  120
SLFL                                                               124

SEQ ID NO: 49          moltype = DNA  length = 372
FEATURE                Location/Qualifiers
misc_feature           1..372
                       note = G4019, Glyma13g38240.1, ortholog of AtBBX30 (G1478),
                        AtBBX31 (G1929)
source                 1..372
                       mol_type = unassigned DNA
                       organism = Glycine max
SEQUENCE: 49
atgtgcaaag gtgcagaagg agaaaagcaa catggtttct gcagcagcta tctacataaa  60
gaatgtgcaa ccagaagtgc tacatgttgt gagctatgtg ggttacaggc ttcattgtat  120
tgtcaagctg atgatgcata cttgtgtaga aaatgtgata aaagggttca tgaagctaat  180
tttttggccc ttaggcacat taggtgcttt ctgtgcaaca catgtcaaaa ccttacgcga  240
agatatctca ttggagcatc aatagaggtg gttcttccag ccaacattaa ctggaccatt  300
ggaaatctcc ctagcaacag aggaatccac agaaagtgct caagaatgca taacaacctt  360
tccctcttgt ta                                                      372

SEQ ID NO: 50          moltype = AA  length = 124
FEATURE                Location/Qualifiers
REGION                 1..124
                       note = G4019, Glyma13g38240.1, domain coordinates 30-66,
                        ortholog of AtBBX30 (G1478), AtBBX31 (G1929)
source                 1..124
                       mol_type = protein
                       organism = Glycine max
SEQUENCE: 50
MCKGAEGEKQ HGFCSSYLHK ECATRSATCC ELCGLQASLY CQADDAYLCR KCDKRVHEAN  60
FLALRHIRCF LCNTCQNLTR RYLIGASIEV VLPANINWTI GNLPSNRGIH RKCSRMHNNL  120
SLLL                                                               124

SEQ ID NO: 51          moltype = DNA  length = 753
FEATURE                Location/Qualifiers
misc_feature           1..753
                       note = AtBBX26 (G1486), AT1G60250.1, ortholog of AtBBX26
                        (G1486)
source                 1..753
                       mol_type = unassigned DNA
                       organism = Arabidopsis thaliana
SEQUENCE: 51
atggctcaag tttgtcacac atgtagacat gtaacagccg tgatccattg tgttacagaa  60
gctcttaact tctgccttac atgtgacaac cttcgccatc ataataacat acatgcagaa  120
cacgtacgtt accaactttg cgataactgc tcgatgtatc cgtctatact tttctgttat  180
gaggacggga tggttctttg tcaatcatgt tattcgcacc attacaattg tgccactaat  240
ggccatcaaa ctcaagtcgt cttcgctaac atgaataatc aacaccatga tcatgcacat  300
```

-continued

```
atgcctcatg tggttcacca taacaataac aataatcatc agcagcagca tgtgggtggt  360
caccaaagaa gagcagagat gtttgagagg agctgccacg gggataacaa ttgcgagaga  420
tggatgtttg caatgagatg tgagttatgc gtagcttcga attcaaatgc tgttgtttat  480
tgtcctacac acaaccagat tctatgcgat agttgcgacc ggatgattca cagtcacgag  540
gacgcggtgc cgccgcattc gaggtgtaag ctttgcgtaa tctgcaagag accttctcgc  600
cgttttctca ttggcggcta tcagtttaat ttcccaccgg ttcatcctcc tgcggcagag  660
gggattccag ttacgccccc aacagaacta cctcaacaag atattaatta tgattatcta  720
gatgatgttg atgatttttc ttggtttggt agg                                753

SEQ ID NO: 52          moltype = AA  length = 251
FEATURE                Location/Qualifiers
REGION                 1..251
                       note = AtBBX26 (G1486), AT1G60250.1, domain coordinates
                        5-36, 47-77
source                 1..251
                       mol_type = protein
                       organism = Arabidopsis thaliana
SEQUENCE: 52
MAQVCHTCRH VTAVIHCVTE ALNFCLTCDN LRHHNNIHAE HVRYQLCDNC SMYPSILFCY  60
EDGMVLCQSC YSHHYNCATN GHQTQVVFAN MNNQHHDHAH MPHVVHHNNN NNHQQQHVGG  120
HQRRAEMFER SCHGDNNCER WMFAMRCELC VASNSNAVVY CPTHNQILCD SCDRMIHSHE  180
DAVPPHSRCK LCVICKRPSR RFLIGGYQFN FPPVHPPAAE GIPVTPPTEL PQQDINYDYL  240
DDVDDFSWFG R                                                        251

SEQ ID NO: 53          moltype = DNA  length = 726
FEATURE                Location/Qualifiers
misc_feature           1..726
                       note = AtBBX20 (G1888), AT4G39070.1, paralog of AtBBX21
                        (G1482)
source                 1..726
                       mol_type = unassigned DNA
                       organism = Arabidopsis thaliana
SEQUENCE: 53
atgaagattt ggtgtgctgt ttgtgataaa gaagaagctt cggtgttttg ttgtgcggat  60
gaagcagctc tttgtaatgg ttgcgatcgc catgttcatt tcgccaataa actagccggg  120
aaacatctcc ggttctctct cacttctcct actttcaaag atgctcctct ttgtgatatt  180
tgcggggaga ggcgtgcatt attattttgc caagaagaca gagcaatact atgcagagaa  240
tgtgacattc caatacatca agctaatgag cacactaaga aacacaatag attcctcctt  300
accggcgtta agatctctgc ctccccgtca gcctacccaa gagcctccaa ttccaactct  360
gctgctgcat ttggtcgagc caaaacccga ccaaaatcag tatcgagcga ggtcccgagc  420
tcggcctcca atgaggtatt tacgagctct tcttcgacga ccacgagcaa ttgctattat  480
gggatagaag aaaactacca tcacgtgagc gattcggggt cgggatcggg ttgtacaggt  540
agtatatccg agtatttgat ggagacatta ccgggttgga gagtggagga tttgcttgaa  600
cacccttctt gtgtctccta tgaggataac attattacta ataacaataa cagtgagtct  660
tatagggttt atgatggttc ttcacaattc catcatcaag ggttttggga tcacaaaccc  720
ttctct                                                              726

SEQ ID NO: 54          moltype = AA  length = 242
FEATURE                Location/Qualifiers
REGION                 1..242
                       note = AtBBX20 (G1888), AT4G39070.1, domain coordinates
                        5-42, 58-95, paralog of AtBBX21 (G1482)
source                 1..242
                       mol_type = protein
                       organism = Arabidopsis thaliana
SEQUENCE: 54
MKIWCAVCDK EEASVFCCAD EAALCNGCDR HVHFANKLAG KHLRFSLTSP TFKDAPLCDI  60
CGERRALLFC QEDRAILCRE CDIPIHQANE HTKKHNRFLL TGVKISASPS AYPRASNSNS  120
AAAFGRAKTR PKSVSSEVPS SASNEVFTSS SSTTTSNCYY GIEENYHHVS DSGSGSGCTG  180
SISEYLMETL PGWRVEDLLE HPSCVSYEDN IITNNNNSES YRVYDGSSQF HHQGFWDHKP  240
FS                                                                  242

SEQ ID NO: 55          moltype = DNA  length = 993
FEATURE                Location/Qualifiers
misc_feature           1..993
                       note = AtBBX21 (G1482), AT1G75540.1, paralog of AtBBX20
                        (G1888)
source                 1..993
                       mol_type = unassigned DNA
                       organism = Arabidopsis thaliana
SEQUENCE: 55
atgaagatca ggtgcgacgt ctgcgataaa gaagaagcgt cggtgttttg cacggccgac  60
gaagcatctc tctgcggcgg ctgcgaccac caagtccacc acgctaacaa actcgcctct  120
aaacatctcc gtttctctct cctttatcct tcttcttcca acacctcctc tcctctctgc  180
gacatctgtc aggataaaaa agctctgttg ttctgtcaac aagatagagc tattttatgc  240
aaagattgcg attcatcgat ccacgctgcg aacgaacaca caaagaaaca cgataggttt  300
cttcttacag gggttaagct ctctgcaaca tcgtctgttt acaaacctac ttcgaaatct  360
tcttcttctt cttcaagcaa ccaagatttc tctgtccctg gatcatcaat ctctaatcct  420
cctcctctca agaaacctct ctcagctcct cctcagagca acaagatcca acccttttcg  480
```

```
aagatcaacg gcggtgatgc gtcggtgaat cagtggggat ccacaagcac gatttctgag  540
tatttgatgg atacgttacc tggttggcac gttgaggatt tcctcgattc ctctcttcct  600
acttatggtt tctctaagag tggtgatgat gatggagtgt taccatatat ggaaccagaa  660
gatgacaaca acactaagag aaacaacaac aacaacaaca acaacaacaa caatacagtg  720
tcacttccat ctaagaattt aggatttgg gtccctcaga ttccacaaac tcttccttct  780
tcatacccaa atcaatactt ttctcaagac aacaacatac agtttgggat gtacaacaaa  840
gaaacatcac cagaagtagt gtcttttgct ccaatacaaa acatgaaaca acaaggacag  900
aacaacaaga gatggtatga tgatggtggc ttcactgtcc cacagatcac tcctcctcct  960
ctttcttcta ataaaaagtt tagatctttc tgg                                993

SEQ ID NO: 56           moltype = AA  length = 331
FEATURE                 Location/Qualifiers
REGION                  1..331
                        note = AtBBX21 (G1482), AT1G75540.1, domain coordinates
                         5-42, 60-97, paralog of AtBBX20 (G1888)
source                  1..331
                        mol_type = protein
                        organism = Arabidopsis thaliana
SEQUENCE: 56
MKIRCDVCDK EEASVFCTAD EASLCGGCDH QVHHANKLAS KHLRFSLLYP SSSNTSSPLC  60
DICQDKKALL FCQQDRAILC KDCDSSIHAA NEHTKKHDRF LLTGVKLSAT SSVYKPTSKS  120
SSSSSSNQDF SVPGSSISNP PPLKKPLSAP PQSNKIQPFS KINGGDASVN QWGSTSTISE  180
YLMDTLPGWH VEDFLDSSLP TYGFSKSGDD DGVLPYMEPE DDNNTKRNNN NNNNNNNNTV  240
SLPSKNLGIW VPQIPQTLPS SYPNQYFSQD NNIQFGMYNK ETSPEVVSFA PIQNMKQQGQ  300
NNKRWYDDGG FTVPQITPPP LSSNKKFRSF W                                  331

SEQ ID NO: 57           moltype = DNA  length = 768
FEATURE                 Location/Qualifiers
misc_feature            1..768
                        note = ACG44133.1, ortholog of AtBBX20 (G1888), AtBBX21
                         (G1482), AtBBX21 (G1482)
source                  1..768
                        mol_type = unassigned DNA
                        organism = Zea mays
SEQUENCE: 57
atgaaggtgc agtgcgacgt gtgcgcggcc gaggcggcct ccgtcttctg ctgcgccgac  60
gaggccgcgc tgtgcgacgc gtgcgacgac cgcgtccacc gcgccaacaa gctcgcgggg  120
aagcaccgcc gcttctccct cctccacccc tgttcgtcct ctgcgcagaa gccgccgctc  180
tgcgacatct gccaggagcg gagaggcttc ttgttctgca aggaggacag ggcgatcctg  240
tgccgggagt gcgacgcgcc ggtgcacagc gcgaacgaca tgacgaggcg gcacagccgg  300
ttcctgctca ccggcgtgcg cctctcgtca gcgccggtgg actctgctga cccatcagaa  360
ggggaggagg aggaggagca ggagaacagc agcaggcccg gcaacggcga gtcctgcagc  420
ggcggcgccg gcgccggcgc gaccacggcg accgccagcg acgggagcag catctccgag  480
tacctgacca agaccctgcc cgggtggcac gtcgaggact tcctcgttga cgacgcgtac  540
gccagcgacg tcggcgcctg ctcagacggc ctttatcagg gacaagatgg acagatcagc  600
ggggtgctgc aagaagctta catgccgtgg acggggcggg agctggtgcc ctctgacgtc  660
gcagacgagc gggacaactg ggagcggtgg gtgccgcaga tgcacgcgga gttcgccggc  720
gacagcaagc ggcccagagc gtcgccttcg cctccctgtt cgtactgg                768

SEQ ID NO: 58           moltype = AA  length = 256
FEATURE                 Location/Qualifiers
REGION                  1..256
                        note = ACG44133.1, domain coordinates 5-42, 61-98, ortholog
                         of AtBBX20 (G1888), AtBBX21 (G1482), AtBBX21 (G1482)
source                  1..256
                        mol_type = protein
                        organism = Zea mays
SEQUENCE: 58
MKVQCDVCAA EAASVFCCAD EAALCDACDD RVHRANKLAG KHRRFSLLHP CSSSAQKPPL  60
CDICQERRGF LFCKEDRAIL CRECDAPVHS ANDMTRRHSR FLLTGVRLSS APVDSADPSE  120
GEEEEEQENS SRPGNGESCS GGAGAGATTA TASDGSSISE YLTKTLPGWH VEDFLVDDAY  180
ASDVGACSDG LYQGQDGQIS GVLQEAYMPW TGRELVPSDV ADERDNWERW VPQMHAEFAG  240
DSKRPRASPS PPCSYW                                                   256

SEQ ID NO: 59           moltype = DNA  length = 630
FEATURE                 Location/Qualifiers
misc_feature            1..630
                        note = CAW36814.1, ortholog of AtBBX20 (G1888), AtBBX21
                         (G1482), AtBBX21 (G1482)
source                  1..630
                        mol_type = unassigned DNA
                        organism = Zea mays
SEQUENCE: 59
atgaaggtgc agtgcgacgt gtgcgcggcc gaggcggcct ccgtcttctg ctgtgccgac  60
gaggccgcgc tgtgcgacgc gtgcgacgac cgcgtccacc gcgccaacaa gctcgcgggg  120
aagcaccgcc gcttctccct cctccacccc tgttcgtcct ctgcgcacaa gccgccgctc  180
tgcgacatct gccaggagcg gagaggcttc ttgttctgca aggaggacag ggcgatcctg  240
tgccgggagt gcgacgcgcc ggtgcacagc gcgaacgaca tgacgaggcg gcacagccgg  300
ttcctgctca ccggcgtgcg cctctcgtcg gcgccggtgg actctgctga cccatcagaa  360
```

```
ggggaggagg aggaggagca ggagaacagc agcaggcccg gcaacggtga gtcctgcagc  420
ggcggcgccg gcgctaccac ggcgaccgct agcgacggga gcagcatctc cgagtacctg  480
accaagaccc tgcccgggtg gcacgtcgag gatttcctcg ttgacgacgc gtacgccagc  540
gacgtcggcg cctgctcatc agacgggctt tatcaggtca gttcagttct tccatgcgaa  600
tggaactgca agctttcact gaggcgttcc                                   630

SEQ ID NO: 60           moltype = AA  length = 210
FEATURE                 Location/Qualifiers
REGION                  1..210
                        note = CAW36814.1, domain coordinates 5-42, 61-98, ortholog
                         of AtBBX20 (G1888), AtBBX21 (G1482), AtBBX21 (G1482)
source                  1..210
                        mol_type = protein
                        organism = Zea mays
SEQUENCE: 60
MKVQCDVCAA EAASVFCCAD EAALCDACDD RVHRANKLAG KHRRFSLLHP CSSSAHKPPL  60
CDICQERRGF LFCKEDRAIL CRECDAPVHS ANDMTRRHSR FLLTGVRLSS APVDSADPSE  120
GEEEEEQENS SRPGNGESCS GGAGATTATA SDGSSISEYL TKTLPGWHVE DFLVDDAYAS  180
DVGACSSDGL YQVSSVLPCE WNCKLSLRRS                                   210

SEQ ID NO: 61           moltype = DNA  length = 630
FEATURE                 Location/Qualifiers
misc_feature            1..630
                        note = CAW39070.1, ortholog of AtBBX20 (G1888), AtBBX21
                         (G1482)
source                  1..630
                        mol_type = unassigned DNA
                        organism = Zea mays
SEQUENCE: 61
atgaaggtgc agtgcgacgt gtgcgcggcc gaggcggcct ccgtcttctg ctgtgccgac  60
gaggccgcgc tgtgcgacgc gtgcgacgac cgcgtccacc gcgccaacaa gctcgcgggg  120
aagcaccgcc gcttctccct cctccacccc tgttcgtcct ctgcgcacaa gccgccgctc  180
tgcgacatct gccaggagcg gagaggcttc ttgttctgca aggaggacag ggcgatcctg  240
tgccgggagt gcgacgcgcc ggtgcacagc gcgaacgaca tgacgaggcg gcacagccgg  300
ttcctgctca ccggcgtgcg cctctcgtcg gcgccggtgg actctgctga cccatcagaa  360
ggggaggagg aggaggagca ggagaacagc agcaggcccg gcaacggtga gtcctgcagc  420
ggcggcgccg gcgctaccac ggcgaccgct agcgacggga gcagcatctc cgagtacctg  480
accaagaccc tgcccgggtg gcacgtcgag gatttcctcg ttgacgacgc gtacgccagc  540
gacgtcggcg cctgctcatc agacgggctt tatcaggtca gttcagttct tccatgcgaa  600
tggaactgca agctttcact gaggcgttcc                                   630

SEQ ID NO: 62           moltype = AA  length = 210
FEATURE                 Location/Qualifiers
REGION                  1..210
                        note = CAW39070.1, domain coordinates 5-42, 61-98, ortholog
                         of AtBBX20 (G1888), AtBBX21 (G1482)
source                  1..210
                        mol_type = protein
                        organism = Zea mays
SEQUENCE: 62
MKVQCDVCAA EAASVFCCAD EAALCDACDD RVHRANKLAG KHRRFSLLHP CSSSAHKPPL  60
CDICQERRGF LFCKEDRAIL CRECDAPVHS ANDMTRRHSR FLLTGVRLSS APVDSADPSE  120
GEEEEEQENS SRPGNGESCS GGAGATTATA SDGSSISEYL TKTLPGWHVE DFLVDDAYAS  180
DVGACSSDGL YQVSSVLPCE WNCKLSLRRS                                   210

SEQ ID NO: 63           moltype = DNA  length = 630
FEATURE                 Location/Qualifiers
misc_feature            1..630
                        note = CAW54447.1, ortholog of AtBBX20 (G1888), AtBBX21
                         (G1482)
source                  1..630
                        mol_type = unassigned DNA
                        organism = Zea mays
SEQUENCE: 63
atgaaggtgc agtgcgacgt gtgcgcggcc gaggcggcct ccgtcttctg ctgtgccgac  60
gaggccgcgc tgtgcgacgc gtgcgacgac cgcgtccacc gcgccaacaa gctcgcgggg  120
aagcaccgcc gcttctccct cctccacccc tgttcgtcct ctgcgcacaa gccgccgctc  180
tgcgacatct gccaggagcg gagaggcttc ttgttctgca aggaggacag ggcgatcctg  240
tgccgggagt gcgacgcgcc ggtgcacagc gcgaacgaca tgacgaggcg gcacagccgg  300
ttcctgctca ccggcgtgcg cctctcgtcg gcgccggtgg actctgctga cccatcagaa  360
ggggaggagg aggaggagca ggagaacagc agcaggcccg gcaacggtga gtcctgcagc  420
ggcggcgccg gcgctaccac ggcgaccgct agcgacggga gcagcatctc cgagtacctg  480
accaagaccc tgcccgggtg gcacgtcgag gatttcctcg ttgacgacgc gtacgccagc  540
gacgtcggcg cctgctcatc agacgggctt tatcaggtca gttcagttct tccatgcgaa  600
tggaactgca agctttcact gaggcgttcc                                   630

SEQ ID NO: 64           moltype = AA  length = 210
FEATURE                 Location/Qualifiers
REGION                  1..210
```

```
                        note = CAW54447.1, domain coordinates 5-42, 61-98, ortholog
                         of AtBBX20 (G1888), AtBBX21 (G1482)
source                  1..210
                        mol_type = protein
                        organism = Zea mays
SEQUENCE: 64
MKVQCDVCAA EAASVFCCAD EAALCDACDD RVHRANKLAG KHRRFSLLHP CSSSAHKPPL  60
CDICQERRGF LFCKEDRAIL CRECDAPVHS ANDMTRRHSR FLLTGVRLSS APVDSADPSE  120
GEEEEEQENS SRPGNGESCS GGAGATTATA SDGSSISEYL TKTLPGWHVE DFLVDDAYAS  180
DVGACSSDGL YQVSSVLPCE WNCKLSLRRS                                  210

SEQ ID NO: 65           moltype = DNA  length = 630
FEATURE                 Location/Qualifiers
misc_feature            1..630
                        note = CAW74338.1, ortholog of AtBBX20 (G1888), AtBBX21
                         (G1482)
source                  1..630
                        mol_type = unassigned DNA
                        organism = Zea mays
SEQUENCE: 65
atgaaggtgc agtgcgacgt gtgcgcggcc gaggcggcct ccgtcttctg ctgtgccgac  60
gaggccgcgc tgtgcgacgc gtgcgacgac cgcgtccacc gcgccaacaa gctcgcgggg  120
aagcaccgcc gcttctccct cctccacccc tgttcgtcct ctgcgcacaa gccgccgctc  180
tgcgacatct gccaggagcg gagaggcttc ttgttctgca aggaggacag ggcgatcctg  240
tgccgggagt gcgacgcgcc ggtgcacagc gcgaacgaca tgacgaggcg gcacagccgg  300
ttcctgctca ccggcgtgcg cctctcgtcg gcgccggtgg actctgctga cccatcagaa  360
ggggaggagg aggaggagca ggagaacagc agcaggcccg gcaacggtga gtcctgcagc  420
ggcggcgccg gcgctaccac ggcgaccgct agcgacggga gcagcatctc cgagtacctg  480
accaagaccc tgcccgggtg gcacgtcgag gatttcctcg ttgacgacgc gtacgccagc  540
gacgtcggcg cctgctcatc agacgggctt tatcaggtca gttcagttct tccatgcgaa  600
tggaactgca agctttcact gaggcgttcc                                  630

SEQ ID NO: 66           moltype = AA  length = 210
FEATURE                 Location/Qualifiers
REGION                  1..210
                        note = CAW74338.1, domain coordinates 5-42, 61-98, ortholog
                         of AtBBX20 (G1888), AtBBX21 (G1482)
source                  1..210
                        mol_type = protein
                        organism = Zea mays
SEQUENCE: 66
MKVQCDVCAA EAASVFCCAD EAALCDACDD RVHRANKLAG KHRRFSLLHP CSSSAHKPPL  60
CDICQERRGF LFCKEDRAIL CRECDAPVHS ANDMTRRHSR FLLTGVRLSS APVDSADPSE  120
GEEEEEQENS SRPGNGESCS GGAGATTATA SDGSSISEYL TKTLPGWHVE DFLVDDAYAS  180
DVGACSSDGL YQVSSVLPCE WNCKLSLRRS                                  210

SEQ ID NO: 67           moltype = DNA  length = 582
FEATURE                 Location/Qualifiers
misc_feature            1..582
                        note = Pt_195637, ortholog of AtBBX20 (G1888), AtBBX21
                         (G1482)
source                  1..582
                        mol_type = unassigned DNA
                        organism = Populus trichocarpa
SEQUENCE: 67
atgaagatcc ggtgtgatgt gtgtgacaat gtagaggcga cagttttctg ttgtgcggat  60
gaagctgctc tctgcgatgg atgtgatcac agagttcacc atgcaaacaa gttagcaagc  120
aaacactcga ggttctcttt agtccatcct tctttcaaag aatcccctct ctgtgatatc  180
tgtcaggaga ggagagccct tctgttttgt caagaggata gggcaattct atgcagagaa  240
tgtgaccttc caattcacaa agctaatgaa catactcaga aacacaacag gtttcttctc  300
acaggtgtaa agctctctgc ttcttcttct ctgcacacag catcatcgac ctccactaat  360
aactttgact caaacattaa cactactagc aatagaaacc atcagccata cctaaagaat  420
tccaacgaaa tcctcagctc tccttcagtt gagacagcat cagcaacaac ggcatataat  480
ttcgaagaaa atcatgttag tgacaatggt tcaatttcaa caagtagcat atctgagtat  540
ttagagacag taccaggctg gcgcatcgat gatttttcttg at                   582

SEQ ID NO: 68           moltype = AA  length = 194
FEATURE                 Location/Qualifiers
REGION                  1..194
                        note = Pt_195637, domain coordinates 5-42, 58-95, ortholog
                         of AtBBX20 (G1888), AtBBX21 (G1482)
source                  1..194
                        mol_type = protein
                        organism = Populus trichocarpa
SEQUENCE: 68
MKIRCDVCDN VEATVFCCAD EAALCDGCDH RVHHANKLAS KHSRFSLVHP SFKESPLCDI  60
CQERRALLFC QEDRAILCRE CDLPIHKANE HTQKHNRFLL TGVKLSASSS LHTASSTSTN  120
NFDSNINTTS NRNHQPYLKN SNEILSSPSV ETASATTAYN FEENHVSDNG SISTSSISEY  180
LETVPGWRID DFLD                                                   194
```

```
SEQ ID NO: 69           moltype = DNA  length = 930
FEATURE                 Location/Qualifiers
misc_feature            1..930
                        note = Pt_550941, ortholog of AtBBX20 (G1888), AtBBX21
                         (G1482)
source                  1..930
                        mol_type = unassigned DNA
                        organism = Populus trichocarpa
SEQUENCE: 69
atgaagatcc agtgcgatgt gtgtaacaaa gaagaggcat cggtgttttg caccgctgac  60
gaggcagctc tttgcgacac ctgtgaccac cgtgttcacc atgccaacaa gcttgcttca  120
aagcaccaac gtttttccct tctccatcct tcctcaaaaa acttccccat ctgtgatatc  180
tgccaggaga aacgggcttt cttgttctgt caacaagaca gggcgatttt atgtagagag  240
tgtgatggtc caatacacac agcaaacgag catacccaga agcacaacag gtttcttctc  300
acaggagtca agctctctgc tacatctgct gtttatatat cttcttcctc tgtcaccaac  360
agtggtggtg atctcgttcc tgattcaaag tctcaacagc agcagcagca gcagcaatca  420
atcaagaaac ctgtgtttga tgctccagtg aattccaatc cacctacagt tcccagtacc  480
ttatctacaa acacagaagt aaacaagggt ggggataatt tggtaacaaa tgaagggttt  540
ggttcaacaa caagtagtac tatatcagag tacttgatgg agactcttcc tggctggcat  600
gttgaagact ttcttgattc ctctactact ccctttggtt tctgtaagat tgatgatggt  660
ctattgccgt ttatggatgc tcatgatctt gagagcaaca tgagttcttt ctcatcagaa  720
agtttggggc tttgggtccc tcaagcacca tctactccat acacatctca acagtattat  780
tatccacagt tggtagggca aagtgggttc aaggagataa aagagaccac aaacatgaaa  840
gctaacagaa ggttggcaga tgatgtcttc actgttccac agatcagcct cccggccaat  900
ataagctcta agagatctag gcccttatgg                                   930

SEQ ID NO: 70           moltype = AA  length = 310
FEATURE                 Location/Qualifiers
REGION                  1..310
                        note = Pt_550941, domain coordinates 5-42, 58-95, ortholog
                         of AtBBX20 (G1888), AtBBX21 (G1482)
source                  1..310
                        mol_type = protein
                        organism = Populus trichocarpa
SEQUENCE: 70
MKIQCDVCNK EEASVFCTAD EAALCDTCDH RVHHANKLAS KHQRFSLLHP SSKNFPICDI  60
CQEKRAFLFC QQDRAILCRE CDGPIHTANE HTQKHNRFLL TGVKLSATSA VYISSSSVTN  120
SGGDLVPDSK SQQQQQQQS IKKPVFDAPV NSNPPTVPST LSTNTEVNKG GDNLVTNEGF  180
GSTTSSTISE YLMETLPGWH VEDFLDSSTT PFGFCKIDDG LLPFMDAHDL ESNMSSFSSE  240
SLGLWVPQAP STPYTSQQYY YPQLVGQSGF KEIKETTNMK ANRRLADDVF TVPQISLPAN  300
ISSKRSRPLW                                                         310

SEQ ID NO: 71           moltype = DNA  length = 849
FEATURE                 Location/Qualifiers
misc_feature            1..849
                        note = Pt_801530, ortholog of AtBBX20 (G1888), AtBBX21
                         (G1482)
source                  1..849
                        mol_type = unassigned DNA
                        organism = Populus trichocarpa
SEQUENCE: 71
atgaagatcc agtgtgacgt ttgtagcaaa gaagaggcct cggtgttttg caccgctgac  60
gaggcagccc tttgtgacac ttgtgaccac cgtgtccatc atgccaacaa gcttgcttca  120
aagcatcagc gtttttccct tctccatcct tcctcaaaaa acttccccat ctgtgatatc  180
tgccaggaca aacgggcttt cttgttctgt caacaagaca gggcgatttt atgcagagat  240
tgtgacggtc caatacacac agcaaacgag catacccaga agcataatag gtttcttctc  300
acaggagtca agctctctgc tacatctgct gtttatatgt cttcctcttc ctccgttacc  360
atgaattcca atccacctgc agttcccagt accttgtcag caaacacagt aataaacaag  420
gacggggata atttggtaac aagtgaaggg tttggttcga caacaagtag tactatatca  480
gagtacttga tggagactct tcctggctgg catgttgaag aatttcttga ttcctcttcc  540
accactccat ttggtttcag taagattgat gatggtctct tgccgtatat ggacactcat  600
gatcttgaac gcaatatgag ttctttctcg tcagaaagtt tggggctttg ggtcccccaa  660
gcaccaactc ctcctctatg cacatctcaa caatattact atccacaatt ggtagggcag  720
agtggattca aggagacaaa agagagcaca aacatgaaag ctaacagaag gttaacagat  780
gatgccttca ctgttccaca gataagccct ccatcaaata ttggctccaa gagatctagg  840
cccttgtgg                                                          849

SEQ ID NO: 72           moltype = AA  length = 283
FEATURE                 Location/Qualifiers
REGION                  1..283
                        note = Pt_801530, domain coordinates 5-42, 58-95, ortholog
                         of AtBBX20 (G1888), AtBBX21 (G1482)
source                  1..283
                        mol_type = protein
                        organism = Populus trichocarpa
SEQUENCE: 72
MKIQCDVCSK EEASVFCTAD EAALCDTCDH RVHHANKLAS KHQRFSLLHP SSKNFPICDI  60
CQDKRAFLFC QQDRAILCRD CDGPIHTANE HTQKHNRFLL TGVKLSATSA VYMSSSSSVT  120
```

-continued

```
MNSNPPAVPS TLSANTVINK DGDNLVTSEG FGSTTSSTIS EYLMETLPGW HVEEFLDSSS  180
TTPFGFSKID DGLLPYMDTH DLERNMSSFS SESLGLWVPQ APTPPLCTSQ QYYYPQLVGQ  240
SGFKETKEST NMKANRRLTD DAFTVPQISP PSNIGSKRSR PLW                    283

SEQ ID NO: 73          moltype = DNA  length = 645
FEATURE                Location/Qualifiers
misc_feature           1..645
                       note = Pt_804174, ortholog of AtBBX20 (G1888), AtBBX21
                        (G1482)
source                 1..645
                       mol_type = unassigned DNA
                       organism = Populus trichocarpa
SEQUENCE: 73
atgaagatcc ggtgtgatgt gtgtgacaag gtagaggcca cagttttttg ttgtgcagat  60
gaagctgctc tctgtgatgg atgtgatcac agagttcacc atgcaaacac gctagcaagc  120
aaacactcaa ggttctcttt agtccatcct tccttcaaag aatcccctct ttgtgatatc  180
tgccaggaga ggagagccgt tctgttttgt caagaggata gagcaattct atgcagagaa  240
tgtgaccttc caattcacaa agttaatgaa catacccaga aacacaatag gtttcttctc  300
acaggtgtaa agctctgtgg tccttctctg tacgcaacat catcctccgc tagtaactgt  360
gatgcaaaca ttaacactac tagaaataga aaccatcagc actacctgaa gaaaccgatt  420
tcagcttcca atgaaatctt cagttctcct tcagtagcga cagcgtcgcc accaacagca  480
tatagttatg acgataatca tgttagtggc ggtggttcag tttcaacaag tagcatatct  540
gagtatttag agacggtagt accagggtgg cgcgtggatg atttcttgga tccttcattc  600
actagcaata atagtttcag caagggttgg aatgcaccct atata                  645

SEQ ID NO: 74          moltype = AA  length = 215
FEATURE                Location/Qualifiers
REGION                 1..215
                       note = Pt_804174, domain coordinates 5-42, 58-95, ortholog
                        of AtBBX20 (G1888), AtBBX21 (G1482)
source                 1..215
                       mol_type = protein
                       organism = Populus trichocarpa
SEQUENCE: 74
MKIRCDVCDK VEATVFCCAD EAALCDGCDH RVHHANTLAS KHSRFSLVHP SFKESPLCDI  60
CQERRAVLFC QEDRAILCRE CDLPIHKVNE HTQKHNRFLL TGVKLCGPSL YATSSSASNC  120
DANINTTRNR NHQHYLKKPI SASNEIFSSP SVATASPPTA YSYDDNHVSG GGSVSTSSIS  180
EYLETVVPGW RVDDFLDPSF TSNNSFSKGW NAPYI                             215

SEQ ID NO: 75          moltype = DNA  length = 807
FEATURE                Location/Qualifiers
misc_feature           1..807
                       note = Os02g43170.1, ortholog of AtBBX20 (G1888), AtBBX21
                        (G1482)
source                 1..807
                       mol_type = unassigned DNA
                       organism = Oryza sativa
SEQUENCE: 75
atgaaggtgc agtgcgacgt gtgcgcggcc gaggcggcgt cggtgttctg ctgcgccgac  60
gaggccgcgc tgtgcgacgc gtgcgaccac cgggtgcacc gggccaacaa gctcgccggg  120
aagcaccgcc ggttctcgct gctcaacccc tcggcgtccg gccgctcgcc gacatcgacg  180
acggcgccgc tctgcgacat ctgccaggag aagaggggtt tcctgttctg caaggaggac  240
cgggcgatcc tgtgccgcga gtgcgacgtg ccggtgcaca cggcgagcga gctcaccatg  300
cgccacagcc ggtacctcct caccggcgtg cggctctcct cggagcctgc cgcgtccccg  360
gcgccgccgt cggaggagga gaacagcagc agcttctgct gcagcgccga cgacgccgtg  420
ccggccccgg cggcgcccgc cacgagccac ggcgggagca gcggcagcag cagcatctcc  480
gagtacctca ccacgctgcc cgggtggcac gtcgaggact tcctcgtcga cgacgccact  540
gccgaggccg ccgccgccgc cgccgccacc tcttccggca tctccgcgaa cgggccgtgt  600
caggggggtaa cacggatcgg agggctgcaa gaatccgccg gctaccctgc gtggatggcg  660
cagcagcagc tgtgctgcga cggcctcgtc gccggcgacg cgtcgccggc tagccgggag  720
cggtgggtgc cgcagatgta cgcggatcag cttgccgccg gcagcaagag atccaggacg  780
tccactgctt cttcctactc ctactgg                                      807

SEQ ID NO: 76          moltype = AA  length = 269
FEATURE                Location/Qualifiers
REGION                 1..269
                       note = Os02g43170.1, domain coordinates 5-42, 65-102,
                        ortholog of AtBBX20 (G1888), AtBBX21 (G1482)
source                 1..269
                       mol_type = protein
                       organism = Oryza sativa
SEQUENCE: 76
MKVQCDVCAA EAASVFCCAD EAALCDACDH RVHRANKLAG KHRRFSLLNP SASGRSPTST  60
TAPLCDICQE KRGFLFCKED RAILCRECDV PVHTASELTM RHSRYLLTGV RLSSEPAASP  120
APPSEEENSS SFCCSADDAV PAPAAPATSH GGSSGSSSIS EYLTTLPGWH VEDFLVDDAT  180
AEAAAAAAAT SSGISANGPC QGVTRIGGLQ ESAGYPAWMA QQQLCCDGLV AGDASPASRE  240
RWVPQMYADQ LAAGSKRSRT STASSYSYW                                    269

SEQ ID NO: 77          moltype = DNA  length = 624
```

```
FEATURE                Location/Qualifiers
misc_feature           1..624
                       note = Os02g43170.2, ortholog of AtBBX20 (G1888), AtBBX21
                        (G1482)
source                 1..624
                       mol_type = unassigned DNA
                       organism = Oryza sativa
SEQUENCE: 77
atgaaggtgc agtgcgacgt gtgcgcggcc gaggcggcgt cggtgttctg ctgcgccgac  60
gaggccgcgc tgtgcgacgc gtgcgaccac cgggtgcacc gggccaacaa gctcgccggg  120
aagcaccgcc ggttctcgct gctcaacccc tcggcgtccg gccgctcgcc gacatcgacg  180
acggcgccgc tctgcgacat ctgccaggag aagaggggtt tcctgttctg caaggaggac  240
cgggcgatcc tgtgccgcga gtgcgacgtg ccggtgcaca cggcgagcga gctcaccatg  300
cgccacagcc ggtacctcct caccggcgtg cggctctcct cggagcctgc cgcgtccccg  360
gcgccgccgt cggaggagga gaacagcagc agcttctgct gcagcgccga cgacgccgtg  420
ccggccccgg cggcgcccgc cacgagccac ggcgggagca gcggcagcag cagcatctcc  480
gagtacctca ccacgctgcc cgggtggcac gtcgaggact tcctcgtcga cgacgccact  540
gccgaggccg ccgccgccgc cgccgccacc tcttccggca tctccgcgaa cgggccgtgt  600
caggttggtg ccactgatcg acca                                         624

SEQ ID NO: 78          moltype = AA  length = 208
FEATURE                Location/Qualifiers
REGION                 1..208
                       note = Os02g43170.2, domain coordinates 5-42, 65-102,
                       ortholog of AtBBX20 (G1888), AtBBX21 (G1482)
source                 1..208
                       mol_type = protein
                       organism = Oryza sativa
SEQUENCE: 78
MKVQCDVCAA EAASVFCCAD EAALCDACDH RVHRANKLAG KHRRFSLLNP SASGRSPTST  60
TAPLCDICQE KRGFLFCKED RAILCRECDV PVHTASELTM RHSRYLLTGV RLSSEPAASP  120
APPSEEENSS SFCCSADDAV PAPAAPATSH GGSSGSSSIS EYLTTLPGWH VEDFLVDDAT  180
AEAAAAAAAT SSGISANGPC QVGATDRP                                     208

SEQ ID NO: 79          moltype = DNA  length = 750
FEATURE                Location/Qualifiers
misc_feature           1..750
                       note = Os04g45690.1, ortholog of AtBBX20 (G1888), AtBBX21
                        (G1482)
source                 1..750
                       mol_type = unassigned DNA
                       organism = Oryza sativa
SEQUENCE: 79
atgaaggtgc agtgcgacgt gtgcgcggcc gaggccgcct cggtcttctg ctgcgccgac  60
gaggccgcgc tgtgcgacgc gtgcgaccgc cgcgtccaca gcgcgaacaa gctcgccggg  120
aagcaccgcc gattctccct cctccaaccg ttggcgtcgt cgtcgtccgc ccagaagcca  180
ccgctctgcg acatctgtca ggagaagagg gggttcttgt tctgcaagga ggacagggcg  240
atcctgtgcc gggagtgcga cgtcacggtg cacaccacga gcgagctgac gaggcggcac  300
ggccggttcc tcctcaccgg cgtgcgcctc tcgtcggcgc cgatggactc ccccgcgccg  360
tcggaggaag aggaggagga agcaggggag gactacagct gcagccccag cagcgtcgcc  420
ggcaccgccg cggggagcgc gagcgacggg agcagcatct ccgagtacct caccaagacg  480
ctgcccggtt ggcacgtcga ggacttcctc gtcgacgagg ccaccgccgc ctcctcctcc  540
tcagacgggc tatttcaggg tgggctgctg gctcagatcg gtggggtgcc ggacggttac  600
gcggcgtggg ccggcgcgga gcagctgcac agtggcgtcg ctgtcgccgc cgacgagcgg  660
gccagccgcg agcggtgggt gccgcagatg aacgcggagt ggggcgccgg cagcaagcga  720
cccagggcgt cgcctccctg cttgtactgg                                   750

SEQ ID NO: 80          moltype = AA  length = 250
FEATURE                Location/Qualifiers
REGION                 1..250
                       note = Os04g45690.1, domain coordinates 5-42, 63-100,
                       ortholog of AtBBX20 (G1888), AtBBX21 (G1482)
source                 1..250
                       mol_type = protein
                       organism = Oryza sativa
SEQUENCE: 80
MKVQCDVCAA EAASVFCCAD EAALCDACDR RVHSANKLAG KHRRFSLLQP LASSSSAQKP  60
PLCDICQEKR GFLFCKEDRA ILCRECDVTV HTTSELTRRH GRFLLTGVRL SSAPMDSPAP  120
SEEEEEEAGE DYSCSPSSVA GTAAGSASDG SSISEYLTKT LPGWHVEDFL VDEATAASSS  180
SDGLFQGGLL AQIGGVPDGY AAWAGREQLH SGVAVAADER ASRERWVPQM NAEWGAGSKR  240
PRASPPCLYW                                                         250

SEQ ID NO: 81          moltype = DNA  length = 753
FEATURE                Location/Qualifiers
misc_feature           1..753
                       note = G5159,, ortholog of AtBBX20 (G1888), AtBBX21 (G1482)
source                 1..753
                       mol_type = unassigned DNA
                       organism = Oryza sativa
```

```
SEQUENCE: 81
atgaaggtgc agtgcgacgt gtgcgcggcc gaggccgcct cggtcttctg ctgcgccgac  60
gaggccgcgc tgtgcgacgc gtgcgaccgc cgcgtccaca gcgcgaacaa gctcgccggg  120
aagcaccgcc gattctccct cctccaaccg ttggcgtcgt cgtcgtccgc ccagaagcca  180
ccgctctgcg acatctgtca ggagaagagg gggttcttgt tctgcaagga ggacagggcg  240
atcctgtgcc gggagtgcga cgtcacggtg cacaccacga gcgagctgac gaggcggcac  300
ggccggttcc tcctcaccgg cgtgcgcctc tcgtcggcgc cgatggactc ccccgcgccg  360
tcggaggaag aggaggagga agcaggggag gactacagct gcagccccag cagcgtcgcc  420
ggcaccgccg cggggagcgc gagcgacggg agcagcatct ccgagtacct caccaagacg  480
ctgcccggtt ggcacgtcga ggacttcctc gtcgacgagg ccaccgccgg cttctcctcc  540
tcagacgggc tatttcaggg tgggctgctg gctcagatcg gtggggtgcc ggacggttac  600
gcggcgtggg ccggccggga gcagctgcac agtggcgtcg ctgtcgccgc cgacgagcgg  660
gccagccgcg agcggtgggt gccgcagatg aacgcggagt ggggcgccgg cagcaagcga  720
cccagggcgt cgcctccctg cttgtactgg tga                               753

SEQ ID NO: 82          moltype = AA  length = 250
FEATURE                Location/Qualifiers
REGION                 1..250
                       note = G5159, domain coordinates 5-42, 63-100, ortholog of
                        AtBBX20 (G1888), AtBBX21 (G1482)
source                 1..250
                       mol_type = protein
                       organism = Oryza sativa
SEQUENCE: 82
MKVQCDVCAA EAASVFCCAD EAALCDACDR RVHSANKLAG KHRRFSLLQP LASSSSAQKP  60
PLCDICQEKR GFLFCKEDRA ILCRECDVTV HTTSELTRRH GRFLLTGVRL SSAPMDSPAP  120
SEEEEEEAGE DYSCSPSSVA GTAAGSASDG SSISEYLTKT LPGWHVEDFL VDEATAGFSS  180
SDGLFQGGLL AQIGGVPDGY AAWAGREQLH SGVAVAADER ASRERWVPQM NAEWGAGSKR  240
PRASPPCLYW                                                         250

SEQ ID NO: 83          moltype = DNA  length = 924
FEATURE                Location/Qualifiers
misc_feature           1..924
                       note = Os06g49880.1, ortholog of AtBBX20 (G1888), AtBBX21
                        (G1482)
source                 1..924
                       mol_type = unassigned DNA
                       organism = Oryza sativa
SEQUENCE: 83
atgcgggtgc agtgcgacgt ctgcgccgcc gagccggccg cggtgctctg ctgcgccgac  60
gaggccgcgc tctgctccgc ctgcgaccgc cgcgtccacc gcgccaaccg cctcgccagc  120
aagcaccgcc gcctcccgct cgtccacccg tcctcctcct cctccggcga cggtggcgcc  180
gccgccgcgc cgctgtgcga cgtgtgcagg gagaagaggg gcctcgtgtt ctgcgtcgag  240
gaccgcgcca tcctgtgcgc cgactgcgac gagcccatcc actccgccaa cgacctcacc  300
gccaagcaca cccgcttcct cctcgtcggc gccaagctct cccccgccgc gctcgccgaa  360
cagccgctcc cgtcctccga ctgcagctcc gacgacgacg ccgccgccgc cgccaccgag  420
gaggagtacc actcctccgc cgcatccacc ggcgccgcag tgagcgcgcc tcttgacgcc  480
tccagcaacg gcgccggtgg cggaggagga gtaggaggga gcagcatctc cgactacctc  540
accaccatct gccccggctg gcgcgtcgag gacctcctcc ccgacgacga cgccttcgcc  600
gccgccgccg cgcaggcggg gaaagagaag gacgagcgcg tgccgttcct cgacgccgac  660
ctgttcgacg tggtcgccgg ccggccggag aagaagggcg gcgcgtgggc gccgcacgtg  720
ccgcacctgc cggcgtggtg cctcgacgag gtgccggtcg tcgtcgccgc gtcggcggcg  780
ccagcggcga cacctgtaaa ggcgaagcag ggacacgtgc gggacagcca ctggagcgac  840
agcgacgcgt tcgccgtgcc ggagttctcg ccgccgccgc cgccggccaa gagggcgcgg  900
cccagctcgc agttctggtg cttc                                         924

SEQ ID NO: 84          moltype = AA  length = 308
FEATURE                Location/Qualifiers
REGION                 1..308
                       note = Os06g49880.1, domain coordinates 5-42, 66-103,
                        ortholog of AtBBX20 (G1888), AtBBX21 (G1482)
source                 1..308
                       mol_type = protein
                       organism = Oryza sativa
SEQUENCE: 84
MRVQCDVCAA EPAAVLCCAD EAALCSACDR RVHRANRLAS KHRRLPLVHP SSSSSGDGGA  60
AAAPLCDVCR EKRGLVFCVE DRAILCADCD EPIHSANDLT AKHTRFLLVG AKLSPAALAE  120
QPLPSSDCSS DDDAAAAATE EEYHSSAAST GAAVSAPLDA SSNGAGGGGG VGGSSISDYL  180
TTICPGWRVE DLLPDDDAFA AAAAQAGKEK DERVPFLDAD LFDVVAGRPE KKGGAWAPHV  240
PHLPAWCLDE VPVVVAASAA PAATPVKAKQ GHVRDSHWSD SDAFAVPEFS PPPPPAKRAR  300
PSSQFWCF                                                           308

SEQ ID NO: 85          moltype = DNA  length = 921
FEATURE                Location/Qualifiers
misc_feature           1..921
                       note = Os06g49880.2, ortholog of AtBBX20 (G1888), AtBBX21
                        (G1482)
source                 1..921
                       mol_type = unassigned DNA
```

```
                         organism = Oryza sativa
SEQUENCE: 85
atgcgggtgc agtgcgacgt ctgcgccgcc gagccggccg cggtgctctg ctgcgccgac  60
gaggccgcgc tctgctccgc ctgcgaccgc cgcgtccacc gcgccaaccg cctcgccagc  120
aagcaccgcc gcctcccgct cgtccacccg tcctcctcct cctccggcga cggtggcgcc  180
gccgccgcgc cgctgtgcga cgtgtgcagg gagaagaggg gcctcgtgtt ctgcgtcgag  240
gaccgcgcca tcctgtgcgc cgactgcgac gagcccatcc actccgccaa cgacctcacc  300
gccaagcaca cccgcttcct cctcgtcggc gccaagctct cccccgccgc gctcgccgaa  360
cagccgctcc cgtcctccga ctgcagctcc gacgacgacg ccgccgccgc cgccaccgag  420
gaggagtacc actcctccgc cgcatccacc ggcgccgcag tgagcgcgcc tcttgacgcc  480
tccagcaacg gcgccggtgg cggaggagga gtaggaggga gcagcatctc cgactacctc  540
accaccatct gccccggctg gcgcgtcgag gacctcctcc ccgacgacga cgccttcgcc  600
gccgccgccg cggcggggaa agagaaggac gagcgcgtgc cgttcctcga cgccgacctg  660
ttcgacgtgg tcgccggccg gccggagaag aagggcggcg cgtgggcgcc gcacgtgccg  720
cacctgccgg cgtggtgcct cgacgaggtg ccggtcgtcg tcgccgcgtc ggcggcgcca  780
gcggcgacac ctgtaaaggc gaagcaggga cacgtgcggg acagccactg gagcgacagc  840
gacgcgttcg ccgtgccgga gttctcgccg ccgccgccgc cggccaagag ggcgcggccc  900
agctcgcagt tctggtgctt c                                            921

SEQ ID NO: 86            moltype = AA  length = 307
FEATURE                  Location/Qualifiers
REGION                   1..307
                         note = Os06g49880.2, domain coordinates 5-42, 66-103,
                          ortholog of AtBBX20 (G1888), AtBBX21 (G1482)
source                   1..307
                         mol_type = protein
                         organism = Oryza sativa
SEQUENCE: 86
MRVQCDVCAA EPAAVLCCAD EAALCSACDR RVHRANRLAS KHRRLPLVHP SSSSSGDGGA  60
AAAPLCDVCR EKRGLVFCVE DRAILCADCD EPIHSANDLT AKHTRFLLVG AKLSPAALAE  120
QPLPSSDCSS DDDAAAAATE EEYHSSAAST GAAVSAPLDA SSNGAGGGGG VGGSSISDYL  180
TTICPGWRVE DLLPDDDAFA AAAAAGKEKD ERVPFLDADL FDVVAGRPEK KGGAWAPHVP  240
HLPAWCLDEV PVVVAASAAP AATPVKAKQG HVRDSHWSDS DAFAVPEFSP PPPPAKRARP  300
SSQFWCF                                                            307

SEQ ID NO: 87            moltype = DNA  length = 957
FEATURE                  Location/Qualifiers
misc_feature             1..957
                         note = Glyma04g01120.1, ortholog of AtBBX20 (G1888),
                          AtBBX21 (G1482)
source                   1..957
                         mol_type = unassigned DNA
                         organism = Glycine max
SEQUENCE: 87
atgaagatcc agtgtgctgt gtgtgacaaa gtggaagcct ccgtcttctg ctctgcagat  60
gaagctgctc tttgccatag ttgtgaccgc accattcacc acgccaacaa gcttgcaacc  120
aaacacccac gcttctctct ccattacccc acctcccaag acttccctct ttgtgatatt  180
tgccaagaga ggcgtgcata tctattttgc caagaagaca gggcattgct atgcagggag  240
tgtgacgttc ctatccacag ggcgaatgag catacccaga agcataacag gtttcttctc  300
accggagtga agctctctgg tacttctttg gatcctgctg cgtcctccac caattgcacc  360
catggctctg aaggaagaaa caacgctcga tctagaatga acagacccag atcatcagtt  420
tccaatgaag aaaatgcaag taattcttct tgcaaggttg aagacaacgt ggctagtgac  480
actggttcgg tttcaactag cagcatttct gagtacttga tcgaaacaat acccggttac  540
tgttttgaag accttcttga tgcttcattt gcacctaatg gtttctgtaa gaaccagaac  600
tatgatcgtc ataggcgttt caggaccaag atcttcaagt tattaggacg tgtttggttt  660
gagttaagga gattccaaaa tcttaacgct atcgatgatc aactgtttgt aaaaatctgt  720
tggaaaatat cttcttttgt ttttgttatt tgcatttctt tttgggctcc ctgctgcatt  780
ctttatgatt ttttttcat tctctattcc cgaccactgt ttcggcctct tattttagta  840
ttttttcaa ttttcattgg gttaattaat aatattttt ggggggggt ccatgctttt  900
attgacatga acatgaattc attgaataac gcaactgaat attatgtgcc actttct     957

SEQ ID NO: 88            moltype = AA  length = 319
FEATURE                  Location/Qualifiers
REGION                   1..319
                         note = Glyma04g01120.1, domain coordinates 5-42, 58-95,
                          ortholog of AtBBX20 (G1888), AtBBX21 (G1482)
source                   1..319
                         mol_type = protein
                         organism = Glycine max
SEQUENCE: 88
MKIQCAVCDK VEASVFCSAD EAALCHSCDR TIHHANKLAT KHPRFSLHYP TSQDFPLCDI  60
CQERRAYLFC QEDRALLCRE CDVPIHRANE HTQKHNRFLL TGVKLSGTSL DPAASSTNCT  120
HGSEGRNNAR SRMNRPRSSV SNEENASNSS CKVEDNVASD TGSVSTSSIS EYLIETIPGY  180
CFEDLLDASF APNGFCKNQN YDRHRRFRTK IFKLLGRVWF ELRRFQNLNA IDDQLFVKIC  240
WKISSFVFVI CISFWAPCCI LYDFFFILYS RPLFRPLILV FFSIFIGLIN NIFWGGVHAF  300
IDMNMNSLNN ATEYYVPLS                                               319

SEQ ID NO: 89            moltype = DNA  length = 798
FEATURE                  Location/Qualifiers
```

```
misc_feature           1..798
                       note = G5365, Glyma04g02960.1, ortholog of AtBBX20 (G1888),
                        AtBBX21 (G1482)
source                 1..798
                       mol_type = unassigned DNA
                       organism = Glycine max
SEQUENCE: 89
atgaagatcc actgcgacgt gtgtaacaag caccaggcct ctttcttctg caccgccgac  60
gaagctgccc tatgcgacgg ctgcgaccac cgcgtccacc acgccaacaa gctcgcctcc  120
aaacaccaac gcttctccct cacccacccc tctgcgaaac attttcccct ctgcgatgtt  180
tgccaggaga gaagagcctt cgtgttttgt cagcaagata gagcgattct gtgcaaagag  240
tgtgacgtgc ccattcattc tgccaacgac ctcaccaaga accatagcag gtttcttctc  300
actgggatta agttctctgc ttctgccacg ccttatgatt attcatcacc accaccacca  360
ccaccaccac caccacccaa gagaaaccct gttctcgatt ctccttcaac accgtcaccg  420
cctaagcctg gggaaactc gctaacaaac gaagaagaac ctggtttcac aggtagcagc  480
atttcagagt acttgataaa ctctatccca ggcatgaagt tcgaagattt cctcgattca  540
cattctcttc cctttgcttg ctccaagaat agtgatgaca tgttgtcgct gtttggtgag  600
ggaaacatgg tttctttctc acccggtggg ttctgggttc ctcaagcacc accatcttca  660
gtacaaatgg atcggcagag tggtacaga gagacaaggg aaggtagcat tagatcaagt  720
tttggagatg ataatttcat agttccacag atgagtcctc ccagcaatgt gtctaataag  780
agatccaggc ttctctgg                                                798

SEQ ID NO: 90          moltype = AA  length = 266
FEATURE                Location/Qualifiers
REGION                 1..266
                       note = G5365, Glyma04g02960.1, domain coordinates 5-42,
                        58-95, ortholog of AtBBX20 (G1888), AtBBX21 (G1482)
source                 1..266
                       mol_type = protein
                       organism = Glycine max
SEQUENCE: 90
MKIHCDVCNK HQASFFCTAD EAALCDGCDH RVHHANKLAS KHQRFSLTHP SAKHFPLCDV  60
CQERRAFVFC QQDRAILCKE CDVPIHSAND LTKNHSRFLL TGIKFSASAT PYDYSSPPPP  120
PPPPPPKRNP VLDSPSTPSP PKPGGNSLTN EEEPGFTGSS ISEYLINSIP GMKFEDFLDS  180
HSLPFACSKN SDDMLSLFGE GNMVSFSPGG FWVPQAPPSS VQMDRQSGYR ETREGSIRSS  240
FGDDNFIVPQ MSPPSNVSNK RSRLLW                                        266

SEQ ID NO: 91          moltype = DNA  length = 582
FEATURE                Location/Qualifiers
misc_feature           1..582
                       note = Glyma04g02960.2, ortholog of AtBBX20 (G1888),
                        AtBBX21 (G1482)
source                 1..582
                       mol_type = unassigned DNA
                       organism = Glycine max
SEQUENCE: 91
atgaagatcc actgcgacgt gtgtaacaag caccaggcct ctttcttctg caccgccgac  60
gaagctgccc tatgcgacgg ctgcgaccac cgcgtccacc acgccaacaa gctcgcctcc  120
aaacaccaac gcttctccct cacccacccc tctgcgaaac attttcccct ctgcgatgtt  180
tgccaggaga gaagagcctt cgtgttttgt cagcaagata gagcgattct gtgcaaagag  240
tgtgacgtgc ccattcattc tgccaacgac ctcaccaaga accatagcag gtttcttctc  300
actgggatta agttctctgc ttctgccacg ccttatgatt attcatcacc accaccacca  360
ccaccaccac caccacccaa gagaaaccct gttctcgatt ctccttcaac accgtcaccg  420
cctaagcctg gggaaactc gctaacaaac gaagaagaac ctggtttcac aggtagcagc  480
atttcagagt acttgataaa ctctatccca ggcatgaagt tcgaagattt cctcgattca  540
cattctcttc cctttgcttg ctccaagcaa ttgatcatag tt                      582

SEQ ID NO: 92          moltype = AA  length = 194
FEATURE                Location/Qualifiers
REGION                 1..194
                       note = Glyma04g02960.2, domain coordinates 5-42, 58-95,
                        ortholog of AtBBX20 (G1888), AtBBX21 (G1482)
source                 1..194
                       mol_type = protein
                       organism = Glycine max
SEQUENCE: 92
MKIHCDVCNK HQASFFCTAD EAALCDGCDH RVHHANKLAS KHQRFSLTHP SAKHFPLCDV  60
CQERRAFVFC QQDRAILCKE CDVPIHSAND LTKNHSRFLL TGIKFSASAT PYDYSSPPPP  120
PPPPPPKRNP VLDSPSTPSP PKPGGNSLTN EEEPGFTGSS ISEYLINSIP GMKFEDFLDS  180
HSLPFACSKQ LIIV                                                    194

SEQ ID NO: 93          moltype = DNA  length = 714
FEATURE                Location/Qualifiers
misc_feature           1..714
                       note = Glyma06g01140.1, ortholog of AtBBX20 (G1888),
                        AtBBX21 (G1482)
source                 1..714
                       mol_type = unassigned DNA
                       organism = Glycine max
```

-continued

```
SEQUENCE: 93
atgaagatcc agtgtgatgt gtgtgacaaa gtggaagcct ccgtcttctg tcctgcagat  60
gaagctgctc tttgccatag ctgtgatcgc accattcacc gcgccaacaa gcttgcaacc  120
aaacacgccc gtttctctct ccactacccc acctccaaag acttccctct ttgtgatata  180
tgccaagaga ggcgtgcata tctattttgc caagaagaca gggcgttgtt atgcagggaa  240
tgcgacgttc ctatccacag agccaatgag catacccaaa agcataacag gtttcttctc  300
acgggtgtga agctctctgg tacttgttta gatcctgctt cgtcctccac caattacacc  360
aataataata gagtcactgg ctctgaagga agaaacgacg ctcgatctag aatgaacaga  420
cccagatcat cagtttccaa tgaagaaaat gcaagtaatt cttcttgcaa ggttgaagac  480
aacgtggcta gtgacactgg ttcgatttca actagcagca tttctgagta cttgattgaa  540
acaataccog gttactgttt tgaagacctc cttgatgctt cgtttgcacc taatggtttc  600
ttaacttgtt tttcttctca gaagcagaac tttgatcatc cctgggcgtt tcaggaccaa  660
aagcgaacaa gtggagacac tatggccgtg ccgttcctga aactagtcat ccat        714

SEQ ID NO: 94           moltype = AA  length = 238
FEATURE                 Location/Qualifiers
REGION                  1..238
                        note = Glyma06g01140.1, domain coordinates 5-42, 58-95,
                         ortholog of AtBBX20 (G1888), AtBBX21 (G1482)
source                  1..238
                        mol_type = protein
                        organism = Glycine max
SEQUENCE: 94
MKIQCDVCDK VEASVFCPAD EAALCHSCDR TIHRANKLAT KHARFSLHYP TSKDFPLCDI  60
CQERRAYLFC QEDRALLCRE CDVPIHRANE HTQKHNRFLL TGVKLSGTCL DPASSSTNYT  120
NNNRVTGSEG RNDARSRMNR PRSSVSNEEN ASNSSCKVED NVASDTGSIS TSSISEYLIE  180
TIPGYCFEDL LDASFAPNGF LTCFSSQKQN FDHPWAFQDQ KRTSGDTMAV PFLKLVIH    238

SEQ ID NO: 95           moltype = DNA  length = 735
FEATURE                 Location/Qualifiers
misc_feature            1..735
                        note = G5367. Glyma06g02970.1, ortholog of AtBBX20 (G1888),
                         AtBBX21 (G1482)
source                  1..735
                        mol_type = unassigned DNA
                        organism = Glycine max
SEQUENCE: 95
atgaagatcc agtgcgacgt gtgtaacaaa cagcaggcat cgttgttctg caccgccgac  60
gaagccgccc tatgcgacgg ctgcgaccac cgcgtccacc acgccaacaa gctcgcctcc  120
aaacaccaac gcttctccct cagccacccc tctgcaaaac atttcctctc ctgcgatgtt  180
tgccaggaga gaagagcctt tgtgttttgt cagcaagata gagcgattct gtgcaaagag  240
tgtgacgtgc ccgttcattc tgccaacgac ctcaccaaga accataacag gtttcttctc  300
actgggatta agtttctgc cctcgattct ccttcaacac ctcctaagcc tgcaggtgga  360
aactccctaa caaatcaaca accacaacaa caaactggtt tcacaggtag cagcatatca  420
gaatacttga taaacactat cccaggcatg gagttcgaag atttcctcga ttcacattct  480
cttccctttg cttgctccaa gaatagtgat gacatgatgt tgtcgatgtt tggtgaggga  540
aacatggttt cgttctcagc cggagggatc tgggttcctc aagcaccatc ttcagtacaa  600
atggatcagc agagtgggta caaagacaca tgggaaacta gcattagatc aagttttggg  660
gatgatagtt tattagttcc acagatgact cctcccagca atgtgtttaa taataagaga  720
tccaggcttc tatgg                                                   735

SEQ ID NO: 96           moltype = AA  length = 245
FEATURE                 Location/Qualifiers
REGION                  1..245
                        note = G5367, Glyma06g02970.1, domain coordinates 5-42,
                         58-95, ortholog of AtBBX20 (G1888), AtBBX21 (G1482)
source                  1..245
                        mol_type = protein
                        organism = Glycine max
SEQUENCE: 96
MKIQCDVCNK QQASLFCTAD EAALCDGCDH RVHHANKLAS KHQRFSLSHP SAKHFPLCDV  60
CQERRAFVFC QQDRAILCKE CDVPVHSAND LTKNHNRFLL TGIKFSALDS PSTPPKPAGG  120
NSLTNQQPQQ QTGFTGSSIS EYLINTIPGM EFEDFLDSHS LPFACSKNSD DMMLSMFGEG  180
NMVSFSAGGI WVPQAPSSVQ MDQQSGYKDT WETSIRSSFG DDSLLVPQMT PPSNVFNNKR  240
SRLLW                                                              245

SEQ ID NO: 97           moltype = DNA  length = 864
FEATURE                 Location/Qualifiers
misc_feature            1..864
                        note = Glyma11g12060.1, ortholog of AtBBX20 (G1888),
                         AtBBX21 (G1482)
source                  1..864
                        mol_type = unassigned DNA
                        organism = Glycine max
SEQUENCE: 97
atgaagatcc agtgtgatgt gtgtcacaat gaagttgctt ccttttctg cccctctgat  60
gaagcctctc tctgccatgc ttgtgatcgc accatccacc atgccaacaa gctcgcagac  120
aaacacaaac gcttctccct tcaccacccc acttccaaag actcccctct ttgtgatatc  180
tgtcatgaga ggcgtgcata tcttttttgc aaagaggaca gagcaatact atgtagagaa  240
```

```
tgtgatcttt ctattcatgg ggtcaacgaa cataccaaga aacacaacag gtttcttctc  300
actggcgtaa agatcggtgc tgatgcttca gacccaacat cactttcctc aaatgacact  360
gccattgaag aaagaacaac ctctagttct aaaataaaca gaccaataag ttctttgtca  420
aatgagaata tcagttcttc tcccacggtt ggagacaaca tggcttgtga cacgggttcg  480
gtttcaacta gcagcatttc tgagtacttg attcagacca ttcccggtta ctgcatggaa  540
gatcttttag atgcttcatt tgcatctaat ggtttatcta aggattatga gcaccaatca  600
gcgtttcaga accaagatgt tcaagtcagc atgtgttcgt ttccactgca aagttgggta  660
ccacaatctc aagctggatc ccctcaacta attagcacta cctcgaatct tcatccccag  720
attaattctt tagttggagt aatggaaatg cctaaagcca aagctagtga aggatactcc  780
aattgcatat ataattatga ctactcagct tacaaagttc cttcaatttg tcctccattg  840
atcaaaaaat gtaaacgctc tcgt                                        864
```

```
SEQ ID NO: 98          moltype = AA  length = 288
FEATURE                Location/Qualifiers
REGION                 1..288
                       note = Glyma11g12060.1, domain coordinates 5-42, 58-95,
                        ortholog of AtBBX20 (G1888), AtBBX21 (G1482)
source                 1..288
                       mol_type = protein
                       organism = Glycine max
SEQUENCE: 98
MKIQCDVCHN EVASFFCPSD EASLCHACDR TIHHANKLAD KHKRFSLHHP TSKDSPLCDI  60
CHERRAYLFC KEDRAILCRE CDLSIHGVNE HTKKHNRFLL TGVKIGADAS DPTSLSSNDT  120
AIEERTTSSS KINRPISSLS NENISSSPTV GDNMACDTGS VSTSSISEYL IQTIPGYCME  180
DLLDASFASN GLSKDYEHQS AFQNQDVQVS MCSFPLQSWV PQSQAGSPQL ISTTSNLHPQ  240
INSLVGVMEM PKAKASEGYS NCIYNYDYSA YKVPSICPPL IKKCKRSR                288
```

```
SEQ ID NO: 99          moltype = DNA  length = 828
FEATURE                Location/Qualifiers
misc_feature           1..828
                       note = G5396 Glyma14g40650.1, ortholog of AtBBX20 (G1888),
                        AtBBX21 (G1482)
source                 1..828
                       mol_type = unassigned DNA
                       organism = Glycine max
SEQUENCE: 99
atgaagatcc agtgcgacgt gtgcaacaaa cacgaggcct ccgtcttctg cacagccgac  60
gaagccgccc tctgcgacgg ctgcgaccac cgtgtccacc atgccaacaa actcgcctcc  120
aaacaccaac gcttctctct tctccgccct tctcataaac aacaccctct ctgcgatatt  180
tgccaggaga gaagagcctt cacgttctgt cagcaagaca gagcgattct ctgcaaagag  240
tgtgacgtgt caattcactc tgccaacgaa cacaccctta agcacgatag gttccttctc  300
actggtgtta aactcgcagc ttctgccatg cttcgttcat cacaaactac ctctgattca  360
aactcaaccc cttctcttct taacgtttca catcaaacta ctccacttcc atcttccacc  420
accaccacca ccaccaacaa caacaacaac aaggttgctg ttgaaggaac tggttcaacg  480
agtgctagca gcatatcaga gtatttgata gagactcttc ctgggtggca agttgaggac  540
tttctcgatt catattttgt tccctttggt ttctgtaaga atgatgaagt gttgccacgg  600
ttggatgctg acgtggaggg gcatatgggt tcgttttcaa ccgagaacat ggggatctgg  660
gttcctcaag cgccaccacc tcttgtgtgt tcttcacaaa tggatcgggt gatagttcaa  720
agtgagacca acatcaaagg tagcagcata tcgaggttga aggatgatac tttcactgtt  780
ccacagatta gtcctccctc caattccaag agagccagat ttctatgg                828
```

```
SEQ ID NO: 100         moltype = AA  length = 276
FEATURE                Location/Qualifiers
REGION                 1..276
                       note = G5396 Glyma14g40650.1, domain coordinates 5-42,
                        58-95, ortholog of AtBBX20 (G1888), AtBBX21 (G1482)
source                 1..276
                       mol_type = protein
                       organism = Glycine max
SEQUENCE: 100
MKIQCDVCNK HEASVFCTAD EAALCDGCDH RVHHANKLAS KHQRFSLLRP SHKQHPLCDI  60
CQERRAFTFC QQDRAILCKE CDVSIHSANE HTLKHDRFLL TGVKLAASAM LRSSQTTSDS  120
NSTPSLLNVS HQTTPLPSST TTTTNNNNN KVAVEGTGST SASSISEYLI ETLPGWQVED  180
FLDSYFVPFG FCKNDEVLPR LDADVEGHMG SFSTENMGIW VPQAPPPLVC SSQMDRVIVQ  240
SETNIKGSSI SRLKDDTFTV PQISPPSNSK RARFLW                            276
```

```
SEQ ID NO: 101         moltype = DNA  length = 834
FEATURE                Location/Qualifiers
misc_feature           1..834
                       note = G5400 Glyma17g37430.1, ortholog of AtBBX20 (G1888),
                        AtBBX21 (G1482)
source                 1..834
                       mol_type = unassigned DNA
                       organism = Glycine max
SEQUENCE: 101
atgaagatcc agtgcgacgt ttgcaacaaa cacgaggcct ccgtcttctg caccgccgat  60
gaagccgccc tctgcgacgg ctgcgaccac cgtgtccacc atgccaacaa actcgcctcc  120
aaacaccaac gcttctctct tctccgccct tctcctaaac aacaccctct ctgcgatatt  180
tgccaggaga gaagagcctt tacattctgt cagcaagaca gagcgattct ctgcaaagag  240
```

```
tgtgacgtgt caattcactc tgccaacgaa cacaccctta agcacgatag gttccttctc  300
accggtgtta aactttctgc ttctgctatg cttcgttcgt cagaaactac ctctgattca  360
aactcaaacc cttctcttct taacttttca caccaaacaa cattactacc tccatcttcc  420
accaccacca ccaccaccag caacaacaac aacaacaagg ttgctgttga aggaactggt  480
tcaactagtg ctagcagcat atcggagtat ttgatagaga ctcttcctgg gtggcaagtt  540
gaagactttc ttgattcata ttctgttccc tttggtttct gtaaggatga tgaagtgttg  600
ccacggtttg atggtgaaat ggaggggcat ctgagttctt tctcaaccga gaacatgggg  660
atctgggttc ctcaagcgcc accaactctt atgtgttctt cacaaatgga tcgggtgata  720
gttcacggtg agaccaatat caaaggtagc agcagatcaa ggttgaagga tgataatttc  780
actgttccac agattagtcc tccttccaat tccaagagag ccagatttct gtgg        834

SEQ ID NO: 102         moltype = AA  length = 278
FEATURE                Location/Qualifiers
REGION                 1..278
                       note = G5400 Glyma17g37430.1, domain coordinates 5-42,
                        58-95, ortholog of AtBBX20 (G1888), AtBBX21 (G1482)
source                 1..278
                       mol_type = protein
                       organism = Glycine max
SEQUENCE: 102
MKIQCDVCNK HEASVFCTAD EAALCDGCDH RVHHANKLAS KHQRFSLLRP SPKQHPLCDI  60
CQERRAFTFC QQDRAILCKE CDVSIHSANE HTLKHDRFLL TGVKLSASAM LRSSETTSDS  120
NSNPSLLNFS HQTTLLPPSS TTTTTTSNNN NNKVAVEGTG STSASSISEY LIETLPGWQV  180
EDFLDSYSVP FGFCKDDEVL PRFDGEMEGH LSSFSTENMG IWVPQAPPTL MCSSQMDRVI  240
VHGETNIKGS SRSRLKDDNF TVPQISPPSN SKRARFLW                          278

SEQ ID NO: 103         moltype = DNA  length = 1116
FEATURE                Location/Qualifiers
misc_feature           1..1116
                       note = AtBBX7 (G2440), AT3G07650.1, paralog of AtBBX8
                        (G1479)
source                 1..1116
                       mol_type = unassigned DNA
                       organism = Arabidopsis thaliana
SEQUENCE: 103
atgggttaca tgtgtgactt ctgtggtgaa caaagatcta tggtgtactg tcgatccgat  60
gcagcttgtt tgtgtctctc ctgtgaccgg agtgttcatt ccgctaatgc attgtccaaa  120
cgacattctc ggacacttgt ctgcgagaga tgcaatgctc agcctgctac tgtcaggtgt  180
gttgaagaaa gggtttcact ctgtcaaaac tgtgactggt ctggccacaa caacagcaac  240
aacaacaatt cttcgtcttc ttctacttcg ccgcagcagc ataagaggca aaccataagt  300
tgctattcgg gttgcccttc cagctcagaa ctcgcttcca tttggtcttt ctgtttggac  360
ttagctggac aatctatttg tgaacaagaa ctgggtatga tgaatataga cgatgatggt  420
cctaccgaca agaaaacttg taatgaggat aagaaagatg tcttggttgg atcctcttca  480
attcctgaaa ccagttctgt accacaagga aaatcatctt ctgctaagga tgttggaatg  540
tgtgaagatg acttctacgg gaaccttggt atggatgaag ttgacatggc acttgagaac  600
tatgaagaac tctttggtac cgcctttaac ccctctgaag agctattcgg gcatggtgga  660
atcgatagcc ttttccataa gcaccaaaca gctccagagg gagggaattc ggtgcagcca  720
gcaggcagta atgattcgtt catgagttcg aaaactgagc caataatttg cttcgcatcg  780
aagccagcac attcgaacat atccttctct ggagtcactg gagaaagtag tgctggagat  840
ttccaagaat gtggtgcatc atcttccata cagctctcgg gggagccacc atggtatcct  900
ccaacattac aggataacaa tgcctgctca cattcagtaa cccgtaataa cgcagttatg  960
cgttacaagg agaagaagaa ggctcgcaag tttgataaga gagtgaggta tgcttcccgc  1020
aaagcaagag ctgatgtgag acggcgtgta aaggggcgat ttgtcaaagc tggtgaagct  1080
tatgattacg accctctcac cccaaccaga agttat                            1116

SEQ ID NO: 104         moltype = AA  length = 372
FEATURE                Location/Qualifiers
REGION                 1..372
                       note = AtBBX7 (G2440), AT3G07650.1, domain coordinates
                        5-42, 48-76, 315-356, paralog of AtBBX8 (G1479)
source                 1..372
                       mol_type = protein
                       organism = Arabidopsis thaliana
SEQUENCE: 104
MGYMCDFCGE QRSMVYCRSD AACLCLSCDR SVHSANALSK RHSRTLVCER CNAQPATVRC  60
VEERVSLCQN CDWSGHNNSN NNNSSSSSTS PQQHKRQTIS CYSGCPSSSE LASIWSFCLD  120
LAGQSICEQE LGMMNIDDDG PTDKKTCNED KKDVLVGSSS IPETSSVPQG KSSSAKDVGM  180
CEDDFYGNLG MDEVDMALEN YEELFGTAFN PSEELFGHGG IDSLFHKHQT APEGGNSVQP  240
AGSNDSFMSS KTEPIICFAS KPAHSNISFS GVTGESSAGD FQECGASSSI QLSGEPPWYP  300
PTLQDNNACS HSVTRNNAVM RYKEKKKARK FDKRVRYASR KARADVRRRV KGRFVKAGEA  360
YDYDPLTPTR SY                                                      372

SEQ ID NO: 105         moltype = DNA  length = 1119
FEATURE                Location/Qualifiers
misc_feature           1..1119
                       note = AtBBX8 (G1479), AT5G48250.1, paralog of AtBBX7
                        (G2440)
source                 1..1119
                       mol_type = unassigned DNA
```

```
                         organism = Arabidopsis thaliana
SEQUENCE: 105
atgggttata tgtgtgattt ctgtggtgaa caaagatcaa tggtgtattg tcgatctgat  60
gcagcgtgtt tgtgtctttc gtgtgaccgt aatgttcatt ctgctaatgc tctatcgaaa  120
cgtcattcgc ggactttggt atgtgagagg tgtaatgcac agccagcttc tgtccggtgt  180
agtgatgaga gggtttctct atgtcaaaac tgtgattggt caggccatga cggcaagaat  240
tctactacta cttcacatca taaaaggcaa accatcaatt gttattctgg ttgtccctcg  300
agtgccgaat tatcctcgat atggtctttc tgtatggatt tgaatatctc ttctgctgaa  360
gaatccgctt gtgagcaagg aatgggtttg atgactatag atgaagatgg cacaggagaa  420
aaatctggtg tccaaaaaat taatgtagaa cagcctgaaa ccagttcggc tgcacaaggt  480
atggatcact ctagtgttcc agaaaattca tcaatggcta aggagcttgg agtatgtgag  540
gatgacttca atggaaatct catttcagat gaagtagact tggctcttga gaactatgaa  600
gaactctttg gttcagcctt caactcatca agatatctct tcgagcacgg tggaattgga  660
agtcttttcg agaaagatga agctcatgag ggctcaatgc agcagccagc attaagcaat  720
aatgcatctg cagattcgtt catgacttgt agaaccgagc caataatttg ctattcatca  780
aagccagcac attcgaatat ctccttctct ggcatcactg gagaaagtaa tgctggagat  840
ttccaagatt gtggggcgtc atcgatgaag cagctttcaa gggagccaca accatggtgc  900
catccaacag cacaggacat tattgcttcc tcacatgcaa caacacgtaa taacgctgtt  960
atgcgttaca aggaaaagaa gaaggctcgc aagtttgaca agcgagtaag gtatgtctct  1020
aggaaagaaa gggctgatgt gagacggcgt gtgaaaggac ggtttgtcaa gtccggtgaa  1080
gcttatgatt acgacccgat gagcccaaca agaagctac                         1119

SEQ ID NO: 106           moltype = AA  length = 373
FEATURE                  Location/Qualifiers
REGION                   1..373
                         note = AtBBX8 (G1479), AT5G48250.1, domain coordinates
                          5-42, 48-76, 316-357, paralog of AtBBX7 (G2440)
source                   1..373
                         mol_type = protein
                         organism = Arabidopsis thaliana
SEQUENCE: 106
MGYMCDFCGE QRSMVYCRSD AACLCLSCDR NVHSANALSK RHSRTLVCER CNAQPASVRC  60
SDERVSLCQN CDWSGHDGKN STTTSHHKRQ TINCYSGCPS SAELSSIWSF CMDLNISSAE  120
ESACEQGMGL MTIDEDGTGE KSGVQKINVE QPETSSAAQG MDHSSVPENS SMAKELGVCE  180
DDFNGNLISD EVDLALENYE ELFGSAFNSS RYLFEHGGIG SLFEKDEAHE GSMQQPALSN  240
NASADSFMTC RTEPIICYSS KPAHSNISFS GITGESNAGD FQDCGASSMK QLSREPQPWC  300
HPTAQDIIAS SHATTRNNAV MRYKEKKKAR KFDKRVRYVS RKERADVRRR VKGRFVKSGE  360
AYDYDPMSPT RSY                                                     373

SEQ ID NO: 107           moltype = DNA  length = 1218
FEATURE                  Location/Qualifiers
misc_feature             1..1218
                         note = ACF80403.1, ortholog of AtBBX7 (G2440), AtBBX8
                          (G1479)
source                   1..1218
                         mol_type = unassigned DNA
                         organism = Zea mays
SEQUENCE: 107
atggttcctc tctgtggttt ctgtgggaaa caaaggtcaa tgatctactg cagatcggat  60
gcggcatcat tgtgcttatc atgcgaccgt agcgttcatt cagctaatgc actgtctcgg  120
cgtcatagaa ggacccttct ttgtgatcgt tgtggtttac agcctgcatc agtccgatgt  180
cttgaggaca acacatcact ttgccaaaac tgtgattgga atgggcatga tgcagcatca  240
ggggcttctg ggcataaaag gcaggccata aactgttact cagggtgccc atcatcagca  300
gagctttcga gaatctggtc atttattatc gatatcccga ctgtagctgc tgagcccaac  360
tgtgaggatg ggctaagcat gatgacaatt gatgacagtg atgtgactaa tcatcacggt  420
gcttcagatg ataaacgatt gttggaaata gctaacacag cactcatgag tgatccacct  480
tcacctgaca agcttaaacc tctgataggc tcttcttctg gagatgggtt tgatgttctg  540
cctctagcca cagatcagcc tgctggacca gtttcagcga cacctaaggt accttatgcc  600
agagatgaca ataagttcaa tgatggcatg tatgaagact tatgtgtgga tgatgctgac  660
ctgacattcg agaattatga agagctattc ggtacctctc acattcgaat agaggaactc  720
tttgatgacg ccggaattga cagttacttt gaaatgaagg aaacaccgcc ttttgatttc  780
aatgagcagc ccaaaattgt gcagctacaa tgtagcgatg tggtaccagc tgattgtgcg  840
atgtcaaaca caggggaaag ggctgattcc agcctttgta ttcctgttag gcaggtcaga  900
tctagtatat cccatccctt atctggtttg actggtgaga gcagcgctgg agatcaccaa  960
gactgtgggg tgtcaccaat tctcctcatg ggcgagccac cctggtattc tcctggtcca  1020
gaaggctcat tagctggagg aagcagagat agtgctctca cacgatacaa ggagaagaag  1080
aagaaaagaa tgtttgacaa gaagatcaga tatgcttctc gcaaggctag ggcagacgtg  1140
aggaagaggg tcaagggacg gtttataaag gctggcgaag cgtatgacta tgatccacta  1200
agtcaaacta gaagctac                                                1218

SEQ ID NO: 108           moltype = AA  length = 406
FEATURE                  Location/Qualifiers
REGION                   1..406
                         note = ACF80403.1, domain coordinates 5-42, 48-85, 349-390,
                          ortholog of AtBBX7 (G2440), AtBBX8 (G1479)
source                   1..406
                         mol_type = protein
                         organism = Zea mays
SEQUENCE: 108
```

```
MVPLCGFCGK QRSMIYCRSD AASLCLSCDR SVHSANALSR RHRRTLLCDR CGLQPASVRC  60
LEDNTSLCQN CDWNGHDAAS GASGHKRQAI NCYSGCPSSA ELSRIWSFII DIPTVAAEPN  120
CEDGLSMMTI DDSDVTNHHG ASDDKRLLEI ANTALMSDPP SPDKLKPLIG SSSGDGFDVL  180
PLATDQPAGP VSATPKVPYA RDDNKFNDGM YEDLCVDDAD LTFENYEELF GTSHIRIEEL  240
FDDAGIDSYF EMKETPPFDF NEQPKIVQLQ CSDVVPADCA MSNTGERADS SLCIPVRQVR  300
SSISHPLSGL TGESSAGDHQ DCGVSPILLM GEPPWYSPGP EGSLAGGSRD SALTRYKEKK  360
KKRMFDKKIR YASRKARADV RKRVKGRFIK AGEAYDYDPL SQTRSY                406

SEQ ID NO: 109          moltype = DNA  length = 1221
FEATURE                 Location/Qualifiers
misc_feature            1..1221
                        note = ACG34885.1, ortholog of AtBBX7 (G2440), AtBBX8
                         (G1479)
source                  1..1221
                        mol_type = unassigned DNA
                        organism = Zea mays
SEQUENCE: 109
atgggcgctc tctgtgattt ctgtggggag cagaggtcta tggtttactg ccgatcagat  60
gcagcatcct tgtgtttatc atgtgaccgt aatgtgcatt cagctaatgc tctttctcgg  120
cgtcatacaa ggacactttt atgtgaccgg tgtgcttcac agcctgctat ggtccgctgt  180
ctagcagaaa atgcctcgct ttgccaaaat tgtgattgga atggccacat tgcaggatcc  240
tcatctgccg gacacaaaag gcagactata aattgctatt caggatgtcc atcgtctgca  300
gaactttcta gaatatggtc cttcgtttca gatattccta atgtagcacc tgagccaaac  360
tgtgagcaag gaataagcat gatgagcatc agcgacagtg gtgtcagtaa tcaagataat  420
gctgcagggg acagtatttt gttagatata gctagtgcaa cacttgtaag tgatattggt  480
acttgtgaca agcttttggt aggttcctct tcaggagctg gagtgaacct acttccactg  540
gttactggtc aaacagaaac agctggatct gtggattcca caccagataa ggttccctat  600
acgccagata aagatatgtt cagtaaggac agcatatatg aagatttttg tgtggatgac  660
gctgaccttg ctttcgaaaa ttatgaagaa ctctttggta cctctcatat tcaaacagaa  720
caactctttg atgatgctgg aatagacatt tactttgaaa tgaaggaagc acctgctggg  780
aattccactg agtccaagct gaagcaacct gcaaatagca atgcggtatc tgccgactct  840
gggatgtcga accctggagt gaaaggtgat tccagtgttt gtaccccttt gaggcaggct  900
aggtctagtc tgtctctttc ctttgctggt ttgactggtg agagtagtgc gggagacaac  960
caagattgtg tggtatcatc attgcttctt atgggtgagc ctccttggca gcctcctggc  1020
cccgagggct caattgctgg aggtagtaga gacagtgcac tcacacgata caaggagaag  1080
aaaatgagaa gaaagttcga caagaaaatc aggtacgctt ctcgtaaggc tagagcagat  1140
gtgcgaaaga gggtaaaggg tcggtttgtt aaggctggtg aagcatatga ctatgatcct  1200
ctctgccaaa cgaggagtta c                                           1221

SEQ ID NO: 110          moltype = AA  length = 407
FEATURE                 Location/Qualifiers
REGION                  1..407
                        note = ACG34885.1, domain coordinates 5-42, 48-85, 350-391,
                        ortholog of AtBBX7 (G2440), AtBBX8 (G1479)
source                  1..407
                        mol_type = protein
                        organism = Zea mays
SEQUENCE: 110
MGALCDFCGE QRSMVYCRSD AASLCLSCDR NVHSANALSR RHTRTLLCDR CASQPAMVRC  60
LAENASLCQN CDWNGHIAGS SSAGHKRQTI NCYSGCPSSA ELSRIWSFVS DIPNVAPEPN  120
CEQGISMMSI SDSGVSNQDN AAGDSILLDI ASATLVSDIG TCDKLLVGSS SGAGVNLLPL  180
VTGQTETAGS VDSTPDKVPY TPDKDMFSKD SIYEDFCVDD ADLAFENYEE LFGTSHIQTE  240
QLFDDAGIDI YFEMKEAPAG NSTESKLKQP ANSNAVSADS GMSNPGVKGD SSVCTPLRQA  300
RSSLSLSFAG LTGESSAGDN QDCVVSSLLL MGEPPWQPPG PEGSIAGGSR DSALTRYKEK  360
KMRRKFDKKI RYASRKARAD VRKRVKGRFV KAGEAYDYDP LCQTRSY               407

SEQ ID NO: 111          moltype = DNA  length = 1218
FEATURE                 Location/Qualifiers
misc_feature            1..1218
                        note = ACG44361.1, ortholog of AtBBX7 (G2440), AtBBX8
                         (G1479)
source                  1..1218
                        mol_type = unassigned DNA
                        organism = Zea mays
SEQUENCE: 111
atggttcctc tctgtggttt ctgtgggaaa caaaggtcaa tgatctactg cagatcggat  60
gcggcatcat tgtgcttatc atgcgaccgt agcgttcatt cagctaatgc actgtctcgg  120
cgtcatagaa ggacccttct ttgtgatcgt tgtggtttac agcctgcatc agtccgatgt  180
cttgaggaca acacatcact ttgccaaaac tgtgattgga atgggcatga tgcagcatca  240
ggggcttctg ggcataaaag gcaggccata aactgttact cagggtgccc atcatcagca  300
gagctttcga gaatctggtc atttattatc gatatcccga ctgtagctgc tgagcccaac  360
tgtgaggatg ggctaagcat gatgacaatt gatgacagtg atgtgactaa tcatcacggt  420
gcttcagatg ataaacgatt gttggaaata gctaacacag cactcatgag tgatccacct  480
tcacctgaca agcttaaacc tctgataggc tcttcttctg gagatgggtt tgatgttctg  540
cctctagcca cagatcagcc tgctggacca gtttcagcga cacctaaggt accttatgcc  600
agagatgaca ataagttcaa tgatggcatg tatgaagact tatgtgtgga tgatgctgac  660
ctgacattcg agaattatga agagctattc ggtacctctc acattcgaat agaggaactc  720
tttgatgacg ccggaattga cagttacttt gaaatgaagg aaacaccgcc ttttgatttc  780
aatgagcagc ccaaaattgt gcagctacaa tgtagcgatg tggtaccagc tgattgtgcg  840
```

```
atgtcaaaca caggggaaag ggctgattcc agcctttgta ttcctgttag gcaggtcaga  900
tctagtatat cccatccctt atctggtttg actggtgaga gcagcgctgg agatcaccaa  960
gactgtgggg tgtcaccaat tctcctcatg ggcgagccac cctggtattc tcctggtcca  1020
gaaggctcat tagctggagg aagcagagat agtgctctca cacgatacaa ggagaagaag  1080
aagaaaagaa tgtttgacaa gaagatcaga tatgcttctc gcaaggctag ggcagacgtg  1140
aggaagaggg tcaagggacg gtttataaag gctggcgaag cgtatgacta tgatccacta  1200
agtcaaacta gaagctac                                                1218

SEQ ID NO: 112          moltype = AA  length = 406
FEATURE                 Location/Qualifiers
REGION                  1..406
                        note = ACG44361.1, domain coordinates 5-42, 48-85, 349-390,
                         ortholog of AtBBX7 (G2440), AtBBX8 (G1479)
source                  1..406
                        mol_type = protein
                        organism = Zea mays
SEQUENCE: 112
MVPLCGFCGK QRSMIYCRSD AASLCLSCDR SVHSANALSR RHRRTLLCDR CGLQPASVRC  60
LEDNTSLCQN CDWNGHDAAS GASGHKRQAI NCYSGCPSSA ELSRIWSFII DIPTVAAEPN  120
CEDGLSMMTI DDSDVTNHHG ASDDKRLLEI ANTALMSDPP SPDKLKPLIG SSSGDGFDVL  180
PLATDQPAGP VSATPKVPYA RDDNKFNDGM YEDLCVDDAD LTFENYEELF GTSHIRIEEL  240
FDDAGIDSYF EMKETPPFDF NEQPKIVQLQ CSDVVPADCA MSNTGERADS SLCIPVRQVR  300
SSISHPLSGL TGESSAGDHQ DCGVSPILLM GEPPWYSPGP EGSLAGGSRD SALTRYKEKK  360
KKRMFDKKIR YASRKARADV RKRVKGRFIK AGEAYDYDPL SQTRSY                 406

SEQ ID NO: 113          moltype = DNA  length = 1221
FEATURE                 Location/Qualifiers
misc_feature            1..1221
                        note = ACN25813.1, ortholog of AtBBX7 (G2440), AtBBX8
                         (G1479)
source                  1..1221
                        mol_type = unassigned DNA
                        organism = Zea mays
SEQUENCE: 113
atggcttctc tctgtgattt ctgtgggaaa caaaggtcaa tgatctactg cagatcagat  60
gcggcatcat tgtgcttatc atgcgaccgt aatgttcatt cagctaatgc actgtctcga  120
cgtcatacaa ggacccttct ttgtgatcgt tgtggttcac agcctgcatc agtccgatgt  180
cttgaggaca acgcatcact ttgccaaaac tgtgactgga atgggcatga tgcagaatca  240
ggggcttctg gacataaaag gcaagccata aactgctact cagggtgccc atcatctgca  300
gagctttcga gaatctggtc atttattact gatatcccga ctgtagcagc tgagcccgac  360
tatgaggatg gactaagcat gatgacaatt gatggcagtg atgttactaa tcgtcacgat  420
acttcagatg ataaaagatt gttggaaata gctaacacaa cactcatgag cgatccacct  480
tcagccgaca agcttaaatc tccgacaggc tcttcttctg gagatgggtt tgatgttatg  540
actctagcca cagatcagcc tgctggacca gtttcagcaa cgcctaaggt acctaatgcc  600
agagatgatg ataagttcaa tgatggcatg tacgaagact tgtgtgtaga tgatgctgac  660
cttacattcg aggattatga agagctattt ggtacctctc acattcgaac agaggaactc  720
tttgatgacg ctggaattga cggttacttc gaattgaaag agacaccacc tttttatttc  780
aacgagcagc ccaaagctat gcagatagaa tgtggcaacg tggtatcagc tgattgtgcg  840
atgtcaaacc caggggcaag ggctgattcc agcctttgta ttcccgtcag gcaggtcaga  900
tctagtatat cccactcctt atctggtctg actggtgaga gcagcgctgg agatcaccac  960
gactgtgggg tgtcaccgat gctcctcatg ggtgagccac cctggcattc tcctggtggt  1020
ccagaaggct cagtcgctgg aggcagcaga gatagcgctc tcacacggta caaggagaag  1080
aagaagagga gaaagtttga caagaagatc agatatgctt ctcgcaaggc tagggcggac  1140
gtgaggaagc gggtcaaggg acggttcata aaggccggtg aagcgtacga ctatgatccg  1200
ctaagccaga ctagaagcta c                                            1221

SEQ ID NO: 114          moltype = AA  length = 407
FEATURE                 Location/Qualifiers
REGION                  1..407
                        note = ACN25813.1, domain coordinates 5-42, 48-85, 350-391,
                         ortholog of AtBBX7 (G2440), AtBBX8 (G1479)
source                  1..407
                        mol_type = protein
                        organism = Zea mays
SEQUENCE: 114
MASLCDFCGK QRSMIYCRSD AASLCLSCDR NVHSANALSR RHTRTLLCDR CGSQPASVRC  60
LEDNASLCQN CDWNGHDAES GASGHKRQAI NCYSGCPSSA ELSRIWSFIT DIPTVAAEPD  120
YEDGLSMMTI DGSDVTNRHD TSDDKRLLEI ANTTLMSDPP SADKLKSPTG SSSGDGFDVM  180
TLATDQPAGP VSATPKVPNA RDDDKFNDGM YEDLCVDDAD LTFEDYEELF GTSHIRTEEL  240
FDDAGIDGYF ELKETPPFYF NEQPKAMQIE CGNVVSADCA MSNPGARADS SLCIPVRQVR  300
SSISHSLSGL TGESSAGDHH DCGVSPMLLM GEPPWHSPGG PEGSVAGGSR DSALTRYKEK  360
KKRRKFDKKI RYASRKARAD VRKRVKGRFI KAGEAYDYDP LSQTRSY                407

SEQ ID NO: 115          moltype = DNA  length = 1218
FEATURE                 Location/Qualifiers
misc_feature            1..1218
                        note = NP_001131822.1, ortholog of AtBBX7 (G2440), AtBBX8
                         (G1479)
source                  1..1218
```

```
                        mol_type = unassigned DNA
                        organism = Zea mays
SEQUENCE: 115
atggttcctc tctgtggttt ctgtgggaaa caaaggtcaa tgatctactg cagatcggat  60
gcggcatcat tgtgcttatc atgcgaccgt agcgttcatt cagctaatgc actgtctcgg  120
cgtcatagaa ggacccttct ttgtgatcgt tgtggtttac agcctgcatc agtccgatgt  180
cttgaggaca acacatcact ttgccaaaac tgtgattgga atgggcatga tgcagcatca  240
ggggcttctg ggcataaaag gcaggccata aactgttact cagggtgccc atcatcagca  300
gagctttcga gaatctggtc atttattatc gatatcccga ctgtagctgc tgagcccaac  360
tgtgaggatg ggctaagcat gatgacaatt gatgacagtg atgtgactaa tcatcacggt  420
gcttcagatg ataaacgatt gttggaaata gctaacacag cactcatgag tgatccacct  480
tcacctgaca agcttaaacc tctgataggc tcttcttctg gagatgggtt tgatgttctg  540
cctctagcca cagatcagcc tgctggacca gtttcagcga cacctaaggt accttatgcc  600
agagatgaca ataagttcaa tgatggcatg tatgaagact tatgtgtgga tgatgctgac  660
ctgacattcg agaattatga agagctattc ggtacctctc acattcgaat agaggaactc  720
tttgatgacg ccggaattga cagttacttt gaaatgaagg aaacaccgcc ttttgatttc  780
aatgagcagc ccaaaattgt gcagctacaa tgtagcgatg tggtaccagc tgattgtgcg  840
atgtcaaaca caggggaaag ggctgattcc agcctttgta ttcctgttag gcaggtcaga  900
tctagtatat cccatccctt atctggtttg actggtgaga gcagcgctgg agatcaccaa  960
gactgtgggg tgtcaccaat tctcctcatg ggcgagccac cctggtattc tcctggtcca  1020
gaaggctcat tagctggagg aagcagagat agtgctctca cacgatacaa ggagaagaag  1080
aagaaaagaa tgtttgacaa gaagatcaga tatgcttctc gcaaggctag ggcagacgtg  1140
aggaagaggg tcaagggacg gtttataaag gctggcgaag cgtatgacta tgatccacta  1200
agtcaaacta gaagctac                                                 1218

SEQ ID NO: 116          moltype = AA  length = 406
FEATURE                 Location/Qualifiers
REGION                  1..406
                        note = NP_001131822.1, domain coordinates 5-42, 48-85,
                         349-390, ortholog of AtBBX7 (G2440), AtBBX8 (G1479)
source                  1..406
                        mol_type = protein
                        organism = Zea mays
SEQUENCE: 116
MVPLCGFCGK QRSMIYCRSD AASLCLSCDR SVHSANALSR RHRRTLLCDR CGLQPASVRC  60
LEDNTSLCQN CDWNGHDAAS GASGHKRQAI NCYSGCPSSA ELSRIWSFII DIPTVAAEPN  120
CEDGLSMMTI DDSDVTNHHG ASDDKRLLEI ANTALMSDPP SPDKLKPLIG SSSGDGFDVL  180
PLATDQPAGP VSATPKVPYA RDDNKFNDGM YEDLCVDDAD LTFENYEELF GTSHIRIEEL  240
FDDAGIDSYF EMKETPPFDF NEQPKIVQLQ CSDVVPADCA MSNTGERADS SLCIPVRQVR  300
SSISHPLSGL TGESSAGDHQ DCGVSPILLM GEPPWYSPGP EGSLAGGSRD SALTRYKEKK  360
KKRMFDKKIR YASRKARADV RKRVKGRFIK AGEAYDYDPL SQTRSY                  406

SEQ ID NO: 117          moltype = DNA  length = 1221
FEATURE                 Location/Qualifiers
misc_feature            1..1221
                        note = NP_001149294.1, ortholog of AtBBX7 (G2440), AtBBX8
                         (G1479)
source                  1..1221
                        mol_type = unassigned DNA
                        organism = Zea mays
SEQUENCE: 117
atgggcgctc tctgtgattt ctgtggggag cagaggtcta tggtttactg ccgatcagat  60
gcagcatcct tgtgtttatc atgtgaccgt aatgtgcatt cagctaatgc tctttctcgg  120
cgtcatacaa ggacactttt atgtgaccgg tgtgcttcac agcctgctat ggtccgctgt  180
ctagcagaaa atgcctcgct ttgccaaaat tgtgattgga atggccacat tgcaggatcc  240
tcatctgccg gacacaaaag gcagactata aattgctatt caggatgtcc atcgtctgca  300
gaactttcta gaatatggtc cttcgtttca gatattccta atgtagcacc tgagccaaac  360
tgtgagcaag gaataagcat gatgagcatc agcgacagtg gtgtcagtaa tcaagataat  420
gctgcagggg acagtatttt gttagatata gctagtgcaa cacttgtaag tgatattggt  480
acttgtgaca agcttttggt aggttcctct tcaggagctg gagtgaacct acttccactg  540
gttactggtc aaacagaaac agctggatct gtggattcca caccagataa ggttccctat  600
acgccagata aagatatgtt cagtaaggac agcatatatg aagatttttg tgtggatgac  660
gctgaccttg ctttcgaaaa ttatgaagaa ctctttggta cctctcatat tcaaacagaa  720
caactctttg atgatgctgg aatagacatt tactttgaaa tgaaggaagc acctgctggg  780
aattccactg agtccaagct gaagcaacct gcaaatagca atgcggtatc tgccgactct  840
gggatgtcga accctggagt gaaaggtgat tccagtgttt gtacccettt gaggcaggct  900
aggtctagtc tgtctctttc ctttgctggt ttgactggtg agagtagtgc gggagacaac  960
caagattgtg tggtatcatc attgcttctt atgggtgagc ctccttggca gcctcctggc  1020
cccgagggct caattgctgg aggtagtaga gacagtgcac tcacacgata caaggagaag  1080
aaaatgagaa gaaagttcga caagaaaatc aggtacgctt ctcgtaaggc tagagcagat  1140
gtgcgaaaga gggtaaaggg tcggtttgtt aaggctggtg aagcatatga ctatgatcct  1200
ctctgccaaa cgaggagtta c                                             1221

SEQ ID NO: 118          moltype = AA  length = 407
FEATURE                 Location/Qualifiers
REGION                  1..407
                        note = NP_001149294.1, domain coordinates 5-42, 48-85,
                         350-391, ortholog of AtBBX7 (G2440), AtBBX8 (G1479)
source                  1..407
```

```
                         mol_type = protein
                         organism = Zea mays
SEQUENCE: 118
MGALCDFCGE QRSMVYCRSD AASLCLSCDR NVHSANALSR RHTRTLLCDR CASQPAMVRC  60
LAENASLCQN CDWNGHIAGS SSAGHKRQTI NCYSGCPSSA ELSRIWSFVS DIPNVAPEPN  120
CEQGISMMSI SDSGVSNQDN AAGDSILLDI ASATLVSDIG TCDKLLVGSS SGAGVNLLPL  180
VTGQTETAGS VDSTPDKVPY TPDKDMFSKD SIYEDFCVDD ADLAFENYEE LFGTSHIQTE  240
QLFDDAGIDI YFEMKEAPAG NSTESKLKQP ANSNAVSADS GMSNPGVKGD SSVCTPLRQA  300
RSSLSLSFAG LTGESSAGDN QDCVVSSLLL MGEPPWQPPG PEGSIAGGSR DSALTRYKEK  360
KMRRKFDKKI RYASRKARAD VRKRVKGRFV KAGEAYDYDP LCQTRSY                407

SEQ ID NO: 119           moltype = DNA  length = 1137
FEATURE                  Location/Qualifiers
misc_feature             1..1137
                         note = Pt_247140, ortholog of AtBBX7 (G2440), AtBBX8 (G1479)
source                   1..1137
                         mol_type = unassigned DNA
                         organism = Populus trichocarpa
SEQUENCE: 119
atgggttacg tttgtgattt ttgtggggaa caaaggtcca tggtttattg ccggtcagat  60
gctgcaagct tatgtttatc atgcgatcga aatgttcatt ctgctaatgc tttgtccaag  120
cgtcattcac ggaccctctt atgtgaaaga tgcaattcac aaccagcgtt agttagatgt  180
gctgaagaaa gaatctctct atgtcaaaat tgtgattgga ttggccatgg cacctcgaca  240
tcagcttcca cacatagaag gcaaacgatc aattcttact ctggctgtcc atcagcttct  300
gagctttctt caatatggtc atttgtttta gacttccctt ccagaggtga atctacttgt  360
gagcaggagt tgggtttgat gagcattgct gaaaatagca ccacagactc ctggggtcct  420
acagagaata ctattggcca aaatgcatct ggagttgttg aagttaatga caggcgtgaa  480
atagctaaat caggtgtttg gcttgggtct tcttcgatac ctgaatcgag ctctgtgcca  540
aacaatctag accagacaac cagatccgca aatacatctt tgcctaagga cttcaatatg  600
gatgaaatgg atttgagtct cgaaaactat gaagaactct ttggtgttac cctcaataat  660
tcagaagagc ttcttgagaa tggtggcatt gatagcttat ttgggacaaa ggacatgtct  720
gtggtcaacg ccgtacagcc agcaagcagc aacgcagcat ctgctgattc tatgatgagc  780
aataagactg aaccaatcct ttgttttacg gaaaagcaag gccattccag cctctcattt  840
tctggcctta atgtagagag tagtgctgca gattatcaag attgtggagc atcttcaatg  900
cttcttatgg gagagcctcc ctggtgcccc ccatgccccg agagtccctt ctcatcagct  960
aaccggagtg atgctgtaat gcgttacaag gaaaagaaga agacacggat gtttgaaaag  1020
aaagtgaggt atgcatctcg caaagcaagg gcagatgtaa gaaggcgtgt gaagggtcgt  1080
tttgtcaaag ctggtgaagc ttatgattac gacccactta gccaaacgag aagtttc     1137

SEQ ID NO: 120           moltype = AA  length = 379
FEATURE                  Location/Qualifiers
REGION                   1..379
                         note = Pt_247140, domain coordinates 5-42, 48-85, 322-363,
                          ortholog of AtBBX7 (G2440), AtBBX8 (G1479)
source                   1..379
                         mol_type = protein
                         organism = Populus trichocarpa
SEQUENCE: 120
MGYVCDFCGE QRSMVYCRSD AASLCLSCDR NVHSANALSK RHSRTLLCER CNSQPALVRC  60
AEERISLCQN CDWIGHGTST SASTHRRQTI NSYSGCPSAS ELSSIWSFVL DFPSRGESTC  120
EQELGLMSIA ENSTTDSWGP TENTIGQNAS GVVEVNDRRE IAKSGVWLGS SSIPESSSVP  180
NNLDQTTRSA NTSLPKDFNM DEMDLSLENY EELFGVTLNN SEELLENGGI DSLFGTKDMS  240
VVNAVQPASS NAASADSMMS NKTEPILCFT EKQGHSSLSF SGLNVESSAA DYQDCGASSM  300
LLMGEPPWCP PCPESPFSSA NRSDAVMRYK EKKKTRMFEK KVRYASRKAR ADVRRRVKGR  360
FVKAGEAYDY DPLSQTRSF                                               379

SEQ ID NO: 121           moltype = DNA  length = 1137
FEATURE                  Location/Qualifiers
misc_feature             1..1137
                         note = Pt_409151, ortholog of AtBBX7 (G2440), AtBBX8 (G1479)
source                   1..1137
                         mol_type = unassigned DNA
                         organism = Populus trichocarpa
SEQUENCE: 121
atgggttata tttgtgattt ttgtggggag caaaggtcca tggtttattg ccggtcagat  60
gctgcgtgct tatgcttatc atgcgatcaa attgttcatt ctgctaatgc cttgtccaag  120
cgtcactcac ggaccctctt atgtgaaaga tgcaattcac aacctgcatt agttagacgc  180
gtggaagaaa gaatctctct ttgtcagaat tgtgattgga tgggctatgg ctcctcaaca  240
tcagcttcca cacataaaag gcaaacgatc aattgttact ttggctgtcc atcagtttct  300
gagctttctt caaaatggcc attcatttta gactcccctt ctgggggtgg atctacttgt  360
gagcaggagt tgggtttaat gagcattgct gaaaatagca ccaaaaacac ctggggtccg  420
acagagaata ctatttgcca taatgcatct ggaattgttg ggcttcttc agtacctgaa  480
tcaagctctg tgccaaaaaa tttagaccag ccaaccagat ctccaaattc atctttgcca  540
aaggtatgtg atgctgatct ttatgaggac ttcaatatgg ctgaaatgga tttgaatctt  600
gaaaactatg aagaactatt tggtgttacc ctcaataatt cagaagagct ttttgagaat  660
ggtggcattg atagcttatt tgggacaaag gacatgccca ttgttgattc caattttgga  720
ctggtcaaca caatacagcc aacatgcagc aacgcaccat ctactgattc tatgattagt  780
agtaagactg aaccaatcct ttgttttacg gcaaagcaag gccattccag cctatcattt  840
tctggcctta ctggagagag taatgctgga gattatcaag actgtggagc atcttcaatg  900
```

```
cttctcatgg gagagccttc atggtgtccc ccgtgccttg agagtccttt accttcagct  960
aaccgaagtg atgcggtaaa gcgttacatg gaaaagaaaa agacacgcaa gtttgaaaag  1020
aaagtgaggt atgcgtctcg caaagcaagg gcagatgtaa gaaggcgtgt gaagggtcgt  1080
tttgtcaaag ctggtgatgc ttatgattat gacccactgg gccaaacaag aagtttc     1137

SEQ ID NO: 122         moltype = AA  length = 379
FEATURE                Location/Qualifiers
REGION                 1..379
                       note = Pt_409151, domain coordinates 5-42, 48-85, 322-363,
                        ortholog of AtBBX7 (G2440), AtBBX8 (G1479)
source                 1..379
                       mol_type = protein
                       organism = Populus trichocarpa
SEQUENCE: 122
MGYICDFCGE QRSMVYCRSD AACLCLSCDQ IVHSANALSK RHSRTLLCER CNSQPALVRR  60
VEERISLCQN CDWMGYGSST SASTHKRQTI NCYFGCPSVS ELSSKWPFIL DSPSGGGSTC  120
EQELGLMSIA ENSTKNTWGP TENTICHNAS GIVGASSVPE SSSVPKNLDQ PTRSPNSSLP  180
KVCDADLYED FNMAEMDLNL ENYEELFGVT LNNSEELFEN GGIDSLFGTK DMPIVDSNFG  240
LVNTIQPTCS NAPSTDSMIS SKTEPILCFT AKQGHSSLSF SGLTGESNAG DYQDCGASSM  300
LLMGEPSWCP PCLESPLPSA NRSDAVKRYM EKKKTRKFEK KVRYASRKAR ADVRRRVKGR  360
FVKAGDAYDY DPLGQTRSF                                               379

SEQ ID NO: 123         moltype = DNA  length = 1221
FEATURE                Location/Qualifiers
misc_feature           1..1221
                       note = Os02g49230.1, ortholog of AtBBX7 (G2440), AtBBX8
                        (G1479)
source                 1..1221
                       mol_type = unassigned DNA
                       organism = Oryza sativa
SEQUENCE: 123
atggatgctc tttgtgattt ctgcagggag caaaggtcaa tggtctattg ccgatcagat  60
gcagcatcct tgtgcttgtc gtgtgatcgt aatgtgcatt cagccaatgc cctttcccga  120
cgccatacaa gaacccttct ttgtgatcgt tgtgttggac agcctgcagc agtccgttgt  180
cttgaagaga acacctcact ttgccaaaac tgtgactgga atggacatgg ggcagcatcc  240
tcagctgctg ggcataaaag gcagaccata aactgttact cggggtgccc atcgtcggca  300
gagctctcga gaatctggtc ctttagtatg gatatcccaa ctgtagctgc ggagccaaac  360
tgtgaggaag gaataaacat gatgagcatt aatgacaatg acgtcaataa ccattgtggt  420
gctccagaag atggccgctt gttggatata gctagcacag cactcatgag tgatttacct  480
acaggagaca agttcaaacc tttaataggt tcttcttcag gagatgggat gaatcttctg  540
ccacttaatt cagatcagcc agctgagcca gtttcaacga cgcctaaggc accctgtgtc  600
acagacaaag atatgttcaa tgatgggagc gtatatggag acttctgtgt ggatgatgct  660
gacctaacat ttgagaatta tgaagaatta ttcggtacct ctcacgttca aacagaacaa  720
ctctttgatg atgctggaat tgacagttat tttgaaatga aggatgtgcc agcagatgaa  780
tctaatgagc agcccaaacc tgtgcagcca gaatgtagca atgtcgcatc tgttgattct  840
gggatgtcaa acccagctgc aagggctgat tccagccatt gtattcctgg taggcaggct  900
atatccaaca tatccctttc cttctctggt ttgactggtg aaagcagtgc tggatatttt  960
caagattgtg gggtatcgtc aatgatcctt atgggtgagc caccctggca tcctcctggt  1020
cctgaaagtt catctgctgg aggcagcaga gataatgctc ttacacggta caaggagaag  1080
aagaagagaa gaaaatttga caagaagata aggtatgctt ctcgtaaggc tagggcagat  1140
gtgagaaaaa gggtcaaagg acggtttgta aaggctggcg aagcatatga ctacgatccg  1200
ctgagccaaa caagaagcta c                                            1221

SEQ ID NO: 124         moltype = AA  length = 407
FEATURE                Location/Qualifiers
REGION                 1..407
                       note = Os02g49230.1, domain coordinates 5-42, 48-85,
                        350-391, ortholog of AtBBX7 (G2440), AtBBX8 (G1479)
source                 1..407
                       mol_type = protein
                       organism = Oryza sativa
SEQUENCE: 124
MDALCDFCRE QRSMVYCRSD AASLCLSCDR NVHSANALSR RHTRTLLCDR CVGQPAAVRC  60
LEENTSLCQN CDWNGHGAAS SAAGHKRQTI NCYSGCPSSA ELSRIWSFSM DIPTVAAEPN  120
CEEGINMMSI NDNDVNNHCG APEDGRLLDI ASTALMSDLP TGDKFKPLIG SSSGDGMNLL  180
PLNSDQPAEP VSTTPKAPCV TDKDMFNDGS VYGDFCVDDA DLTFENYEEL FGTSHVQTEQ  240
LFDDAGIDSY FEMKDVPADE SNEQPKPVQP ECSNVASVDS GMSNPAARAD SSHCIPGRQA  300
ISNISLSFSG LTGESSAGYF QDCGVSSMIL MGEPPWHPPG PESSSAGGSR DNALTRYKEK  360
KKRRKFDKKI RYASRKARAD VRKRVKGRFV KAGEAYDYDP LSQTRSY                407

SEQ ID NO: 125         moltype = DNA  length = 1440
FEATURE                Location/Qualifiers
misc_feature           1..1440
                       note = Os02g49230.2, ortholog of AtBBX7 (G2440), AtBBX8
                        (G1479)
source                 1..1440
                       mol_type = unassigned DNA
                       organism = Oryza sativa
SEQUENCE: 125
```

```
atgctaataa gccatcccat gctgagcaat tcaagtggtt catttcatgg cctgtatcaa  60
tatacttata tatctccaac acttaccaag gaatggaaac aaactcatca ttatcctggt  120
aggatcccac tgaattcaac tgttgaacaa aaagccagga aggtggctgt tcttgtggca  180
ctcagtgcta gtggaagtgc tccagtactg tacaggacca tggatgctct ttgtgatttc  240
tgcagggagc aaaggtcaat ggtctattgc cgatcagatg cagcatcctt gtgcttgtcg  300
tgtgatcgta atgtgcattc agccaatgcc ctttcccgac gccatacaag aacccttctt  360
tgtgatcgtt gtgttggaca gcctgcagca gtccgttgtc ttgaagagaa cacctcactt  420
tgccaaaact gtgactggaa tggacatggg gcagcatcct cagctgctgg gcataaaagg  480
cagaccataa actgttactc ggggtgccca tcgtcggcag agctctcgag aatctggtcc  540
tttagtatgg atatcccaac tgtagctgcg gagccaaact gtgaggaagg aataaacatg  600
atgagcatta atgacaatga cgtcaataac cattgtggtg ctccagaaga tggccgcttg  660
ttggatatag ctagcacagc actcatgagt gatttaccta caggagacaa gttcaaacct  720
ttaataggtt cttcttcagg agatgggatg aatcttctgc cacttaattc agatcagcca  780
gctgagccag tttcaacgac gcctaaggca ccctgtgtca cagacaaaga tatgttcaat  840
gatgggagcg tatatggaga cttctgtgtg gatgatgctg acctaacatt tgagaattat  900
gaagaattat tcggtacctc tcacgttcaa acagaacaac tctttgatga tgctggaatt  960
gacagttatt ttgaaatgaa ggatgtgcca gcagatgaat ctaatgagca gcccaaacct  1020
gtgcagccag aatgtagcaa tgtcgcatct gttgattctg ggatgtcaaa cccagctgca  1080
agggctgatt ccagccattg tattcctggt aggcaggcta tatccaacat atccctttcc  1140
ttctctggtt tgactggtga aagcagtgct ggatattttc aagattgtgg ggtatcgtca  1200
atgatcctta tgggtgagcc accctggcat cctcctggtc ctgaaagttc atctgctgga  1260
ggcagcagag ataatgctct tacacggtac aaggagaaga agaagagaag aaaatttgac  1320
aagaagataa ggtatgcttc tcgtaaggct agggcagatg tgagaaaaag ggtcaaagga  1380
cggtttgtaa aggctggcga agcatatgac tacgatccgc tgagccaaac aagaagctac  1440
```

```
SEQ ID NO: 126          moltype = AA  length = 480
FEATURE                 Location/Qualifiers
REGION                  1..480
                        note = Os02g49230.2, domain coordinates 78-115, 121-158,
                         423-464, ortholog of AtBBX7 (G2440), AtBBX8 (G1479)
source                  1..480
                        mol_type = protein
                        organism = Oryza sativa
SEQUENCE: 126
MLISHPMLSN SSGSFHGLYQ YTYISPTLTK EWKQTHHYPG RIPLNSTVEQ KARKVAVLVA  60
LSASGSAPVL YRTMDALCDF CREQRSMVYC RSDAASLCLS CDRNVHSANA LSRRHTRTLL  120
CDRCVGQPAA VRCLEENTSL CQNCDWNGHG AASSAAGHKR QTINCYSGCP SSAELSRIWS  180
FSMDIPTVAA EPNCEEGINM MSINDNDVNN HCGAPEDGRL LDIASTALMS DLPTGDKFKP  240
LIGSSSGDGM NLLPLNSDQP AEPVSTTPKA PCVTDKDMFN DGSVYGDFCV DDADLTFENY  300
EELFGTSHVQ TEQLFDDAGI DSYFEMKDVP ADESNEQPKP VQPECSNVAS VDSGMSNPAA  360
RADSSHCIPG RQAISNISLS FSGLTGESSA GYFQDCGVSS MILMGEPPWH PPGPESSSAG  420
GSRDNALTRY KEKKKRRKFD KKIRYASRKA RADVRKRVKG RFVKAGEAYD YDPLSQTRSY  480
```

```
SEQ ID NO: 127          moltype = DNA  length = 1221
FEATURE                 Location/Qualifiers
misc_feature            1..1221
                        note = Os02g49230.3, ortholog of AtBBX7 (G2440), AtBBX8
                         (G1479)
source                  1..1221
                        mol_type = unassigned DNA
                        organism = Oryza sativa
SEQUENCE: 127
atggatgctc tttgtgattt ctgcagggag caaaggtcaa tggtctattg ccgatcagat  60
gcagcatcct tgtgcttgtc gtgtgatcgt aatgtgcatt cagccaatgc cctttcccga  120
cgccatacaa gaacccttct ttgtgatcgt tgtgttggac agcctgcagc agtccgttgt  180
cttgaagaga acacctcact ttgccaaaac tgtgactgga atggacatgg ggcagcatcc  240
tcagctgctg ggcataaaag gcagaccata aactgttact cggggtgccc atcgtcggca  300
gagctctcga gaatctggtc ctttagtatg gatatcccaa ctgtagctgc ggagccaaac  360
tgtgaggaag gaataaacat gatgagcatt aatgacaatg acgtcaataa ccattgtggt  420
gctccagaag atggccgctt gttggatata gctagcacag cactcatgag tgatttacct  480
acaggagaca agttcaaacc tttaataggt tcttcttcag gagatgggat gaatcttctg  540
ccacttaatt cagatcagcc agctgagcca gtttcaacga cgcctaaggc accctgtgtc  600
acagacaaag atatgttcaa tgatgggagc gtatatggag acttctgtgt ggatgatgct  660
gacctaacat ttgagaatta tgaagaatta ttcggtacct ctcacgttca aacagaacaa  720
ctctttgatg atgctggaat tgacagttat tttgaaatga aggatgtgcc agcagatgaa  780
tctaatgagc agcccaaacc tgtgcagcca gaatgtagca atgtcgcatc tgttgattct  840
gggatgtcaa acccagctgc aagggctgat tccagccatt gtattcctgg taggcaggct  900
atatccaaca tatccctttc cttctctggt ttgactggtg aaagcagtgc tggatatttt  960
caagattgtg gggtatcgtc aatgatcctt atgggtgagc caccctggca tcctcctggt  1020
cctgaaagtt catctgctgg aggcagcaga gataatgctc ttacacggta caaggagaag  1080
aagaagagaa gaaaatttga caagaagata aggtatgctt ctcgtaaggc tagggcagat  1140
gtgagaaaaa gggtcaaagg acggtttgta aaggctggcg aagcatatga ctacgatccg  1200
ctgagccaaa caagaagcta c                                           1221
```

```
SEQ ID NO: 128          moltype = AA  length = 407
FEATURE                 Location/Qualifiers
REGION                  1..407
                        note = Os02g49230.3, domain coordinates 5-42, 48-85,
                         350-391, ortholog of AtBBX7 (G2440), AtBBX8 (G1479)
```

-continued

```
source                1..407
                      mol_type = protein
                      organism = Oryza sativa
SEQUENCE: 128
MDALCDFCRE QRSMVYCRSD AASLCLSCDR NVHSANALSR RHTRTLLCDR CVGQPAAVRC  60
LEENTSLCQN CDWNGHGAAS SAAGHKRQTI NCYSGCPSSA ELSRIWSFSM DIPTVAAEPN  120
CEEGINMMSI NDNDVNNHCG APEDGRLLDI ASTALMSDLP TGDKFKPLIG SSSGDGMNLL  180
PLNSDQPAEP VSTTPKAPCV TDKDMFNDGS VYGDFCVDDA DLTFENYEEL FGTSHVQTEQ  240
LFDDAGIDSY FEMKDVPADE SNEQPKPVQP ECSNVASVDS GMSNPAARAD SSHCIPGRQA  300
ISNISLSFSG LTGESSAGYF QDCGVSSMIL MGEPPWHPPG PESSSAGGSR DNALTRYKEK  360
KKRRKFDKKI RYASRKARAD VRKRVKGRFV KAGEAYDYDP LSQTRSY                407

SEQ ID NO: 129        moltype = DNA  length = 1221
FEATURE               Location/Qualifiers
misc_feature          1..1221
                      note = Os02g49230.4, ortholog of AtBBX7 (G2440), AtBBX8
                       (G1479)
source                1..1221
                      mol_type = unassigned DNA
                      organism = Oryza sativa
SEQUENCE: 129
atggatgctc tttgtgattt ctgcagggag caaaggtcaa tggtctattg ccgatcagat  60
gcagcatcct tgtgcttgtc gtgtgatcgt aatgtgcatt cagccaatgc cctttcccga  120
cgccatacaa gaacccttct ttgtgatcgt tgtgttggac agcctgcagc agtccgttgt  180
cttgaagaga acacctcact ttgccaaaac tgtgactgga atggacatgg ggcagcatcc  240
tcagctgctg ggcataaaag gcagaccata aactgttact cggggtgccc atcgtcggca  300
gagctctcga gaatctggtc ctttagtatg gatatcccaa ctgtagctgc ggagccaaac  360
tgtgaggaag gaataaacat gatgagcatt aatgacaatg acgtcaataa ccattgtggt  420
gctccagaag atggccgctt gttggatata gctagcacag cactcatgag tgatttacct  480
acaggagaca agttcaaacc tttaataggt tcttcttcag gagatgggat gaatcttctg  540
ccacttaatt cagatcagcc agctgagcca gtttcaacga cgcctaaggc accctgtgtc  600
acagacaaag atatgttcaa tgatgggagc gtatatggag acttctgtgt ggatgatgct  660
gacctaacat ttgagaatta tgaagaatta ttcggtacct ctcacgttca aacagaacaa  720
ctctttgatg atgctggaat tgacagttat tttgaaatga aggatgtgcc agcagatgaa  780
tctaatgagc agcccaaacc tgtgcagcca gaatgtagca atgtcgcatc tgttgattct  840
gggatgtcaa acccagctgc aagggctgat tccagccatt gtattcctgg taggcaggct  900
atatccaaca tatccctttc cttctctggt ttgactggtg aaagcagtgc tggatatttt  960
caagattgtg ggtatcgtc aatgatcctt atgggtgagc caccctggca tcctcctggt  1020
cctgaaagtt catctgctgg aggcagcaga gataatgctc ttacacggta caaggagaag  1080
aagaagagaa gaaaatttga caagaagata aggtatgctt ctcgtaaggc tagggcagat  1140
gtgagaaaaa gggtcaaagg acggtttgta aaggctggcg aagcatatga ctacgatccg  1200
ctgagccaaa caagaagcta c                                            1221

SEQ ID NO: 130        moltype = AA  length = 407
FEATURE               Location/Qualifiers
REGION                1..407
                      note = Os02g49230.4, domain coordinates 5-42, 48-85,
                       350-391, ortholog of AtBBX7 (G2440), AtBBX8 (G1479)
source                1..407
                      mol_type = protein
                      organism = Oryza sativa
SEQUENCE: 130
MDALCDFCRE QRSMVYCRSD AASLCLSCDR NVHSANALSR RHTRTLLCDR CVGQPAAVRC  60
LEENTSLCQN CDWNGHGAAS SAAGHKRQTI NCYSGCPSSA ELSRIWSFSM DIPTVAAEPN  120
CEEGINMMSI NDNDVNNHCG APEDGRLLDI ASTALMSDLP TGDKFKPLIG SSSGDGMNLL  180
PLNSDQPAEP VSTTPKAPCV TDKDMFNDGS VYGDFCVDDA DLTFENYEEL FGTSHVQTEQ  240
LFDDAGIDSY FEMKDVPADE SNEQPKPVQP ECSNVASVDS GMSNPAARAD SSHCIPGRQA  300
ISNISLSFSG LTGESSAGYF QDCGVSSMIL MGEPPWHPPG PESSSAGGSR DNALTRYKEK  360
KKRRKFDKKI RYASRKARAD VRKRVKGRFV KAGEAYDYDP LSQTRSY                407

SEQ ID NO: 131        moltype = DNA  length = 1218
FEATURE               Location/Qualifiers
misc_feature          1..1218
                      note = Os02g49230.5, ortholog of AtBBX7 (G2440), AtBBX8
                       (G1479)
source                1..1218
                      mol_type = unassigned DNA
                      organism = Oryza sativa
SEQUENCE: 131
atggatgctc tttgtgattt ctgcagggag caaaggtcaa tggtctattg ccgatcagat  60
gcagcatcct tgtgcttgtc gtgtgatcgt aatgtgcatt cagccaatgc cctttcccga  120
cgccatacaa gaacccttct ttgtgatcgt tgtgttggac agcctgcagc agtccgttgt  180
cttgaagaga acacctcact ttgccaaaac tgtgactgga atggacatgg ggcagcatcc  240
tcagctgctg ggcataaaag gcagaccata aactgttact cggggtgccc atcgtcggca  300
gagctctcga gaatctggtc ctttagtatg gatatcccaa ctgtagctgc ggagccaaac  360
tgtgaggaag gaataaacat gatgagcatt aatgacaatg acgtcaataa ccattgtggt  420
gctccagaag atggccgctt gttggatata gctagcacag cactcatgag tgatttacct  480
acaggagaca agttcaaacc tttaataggt tcttcttcag gagatgggat gaatcttctg  540
ccacttaatt cagatcagcc agctgagcca gtttcaacga cgcctaaggc accctgtgtc  600
```

```
acagacaaag atatgttcaa tgatgggagc gtatatggag acttctgtgt ggatgatgct  660
gacctaacat ttgagaatta tgaagaatta ttcggtacct ctcacgttca aacagaacaa  720
ctctttgatg atgctggaat tgacagttat tttgaaatga aggatgtgcc agcagatgaa  780
tctaatgagc ccaaacctgt gcagccagaa tgtagcaatg tcgcatctgt tgattctggg  840
atgtcaaacc cagctgcaag ggctgattcc agccattgta ttcctggtag gcaggctata  900
tccaacatat ccctttcctt ctctggtttg actggtgaaa gcagtgctgg atattttcaa  960
gattgtgggg tatcgtcaat gatccttatg ggtgagccac cctggcatcc tcctggtcct  1020
gaaagttcat ctgctggagg cagcagagat aatgctctta cacggtacaa ggagaagaag  1080
aagagaagaa aatttgacaa gaagataagg tatgcttctc gtaaggctag ggcagatgtg  1140
agaaaaaggg tcaaaggacg gtttgtaaag gctggcgaag catatgacta cgatccgctg  1200
agccaaacaa gaagctac                                                1218

SEQ ID NO: 132         moltype = AA  length = 406
FEATURE                Location/Qualifiers
REGION                 1..406
                       note = Os02g49230.5, domain coordinates 5-42, 48-85,
                        349-390, ortholog of AtBBX7 (G2440), AtBBX8 (G1479)
source                 1..406
                       mol_type = protein
                       organism = Oryza sativa
SEQUENCE: 132
MDALCDFCRE QRSMVYCRSD AASLCLSCDR NVHSANALSR RHTRTLLCDR CVGQPAAVRC  60
LEENTSLCQN CDWNGHGAAS SAAGHKRQTI NCYSGCPSSA ELSRIWSFSM DIPTVAAEPN  120
CEEGINMMSI NDNDVNNHCG APEDGRLLDI ASTALMSDLP TGDKFKPLIG SSSGDGMNLL  180
PLNSDQPAEP VSTTPKAPCV TDKDMFNDGS VYGDFCVDDA DLTFENYEEL FGTSHVQTEQ  240
LFDDAGIDSY FEMKDVPADE SNEPKPVQPE CSNVASVDSG MSNPAARADS SHCIPGRQAI  300
SNISLSFSGL TGESSAGYFQ DCGVSSMILM GEPPWHPPGP ESSSAGGSRD NALTRYKEKK  360
KRRKFDKKIR YASRKARADV RKRVKGRFVK AGEAYDYDPL SQTRSY                  406

SEQ ID NO: 133         moltype = DNA  length = 1221
FEATURE                Location/Qualifiers
misc_feature           1..1221
                       note = Os02g49230.6, ortholog of AtBBX7 (G2440), AtBBX8
                        (G1479)
source                 1..1221
                       mol_type = unassigned DNA
                       organism = Oryza sativa
SEQUENCE: 133
atggatgctc tttgtgattt ctgcagggag caaaggtcaa tggtctattg ccgatcagat  60
gcagcatcct tgtgcttgtc gtgtgatcgt aatgtgcatt cagccaatgc cctttcccga  120
cgccatacaa gaacccttct ttgtgatcgt tgtgttggac agcctgcagc agtccgttgt  180
cttgaagaga acacctcact ttgccaaaac tgtgactgga atggacatgg ggcagcatcc  240
tcagctgctg ggcataaaag gcagaccata aactgttact cggggtgccc atcgtcggca  300
gagctctcga gaatctggtc ctttagtatg gatatcccaa ctgtagctgc ggagccaaac  360
tgtgaggaag gaataaacat gatgagcatt aatgacaatg acgtcaataa ccattgtggt  420
gctccagaag atggccgctt gttggatata gctagcacag cactcatgag tgatttacct  480
acaggagaca agttcaaacc tttaataggt tcttcttcag gagatgggat gaatcttctg  540
ccacttaatt cagatcagcc agctgagcca gtttcaacga cgcctaaggc accctgtgtc  600
acagacaaag atatgttcaa tgatgggagc gtatatggag acttctgtgt ggatgatgct  660
gacctaacat ttgagaatta tgaagaatta ttcggtacct ctcacgttca aacagaacaa  720
ctctttgatg atgctggaat tgacagttat tttgaaatga aggatgtgcc agcagatgaa  780
tctaatgagc agcccaaacc tgtgcagcca gaatgtagca atgtcgcatc tgttgattct  840
gggatgtcaa acccagctgc aagggctgat tccagccatt gtattcctgg taggcaggct  900
atatccaaca tatccctttc cttctctggt ttgactggtg aaagcagtgc tggatatttt  960
caagattgtg gggtatcgtc aatgatcctt atgggtgagc caccctggca tcctcctggt  1020
cctgaaagtt catctgctgg aggcagcaga gataatgctc ttacacggta caaggagaag  1080
aagaagagaa gaaaatttga caagaagata aggtatgctt ctcgtaaggc tagggcagat  1140
gtgagaaaaa gggtcaaagg acggtttgta aaggctggcg aagcatatga ctacgatccg  1200
ctgagccaaa caagaagcta c                                            1221

SEQ ID NO: 134         moltype = AA  length = 407
FEATURE                Location/Qualifiers
REGION                 1..407
                       note = Os02g49230.6, domain coordinates 5-42, 48-85,
                        350-391, ortholog of AtBBX7 (G2440), AtBBX8 (G1479)
source                 1..407
                       mol_type = protein
                       organism = Oryza sativa
SEQUENCE: 134
MDALCDFCRE QRSMVYCRSD AASLCLSCDR NVHSANALSR RHTRTLLCDR CVGQPAAVRC  60
LEENTSLCQN CDWNGHGAAS SAAGHKRQTI NCYSGCPSSA ELSRIWSFSM DIPTVAAEPN  120
CEEGINMMSI NDNDVNNHCG APEDGRLLDI ASTALMSDLP TGDKFKPLIG SSSGDGMNLL  180
PLNSDQPAEP VSTTPKAPCV TDKDMFNDGS VYGDFCVDDA DLTFENYEEL FGTSHVQTEQ  240
LFDDAGIDSY FEMKDVPADE SNEQPKPVQP ECSNVASVDS GMSNPAARAD SSHCIPGRQA  300
ISNISLSFSG LTGESSAGYF QDCGVSSMIL MGEPPWHPPG PESSSAGGSR DNALTRYKEK  360
KKRRKFDKKI RYASRKARAD VRKRVKGRFV KAGEAYDYDP LSQTRSY                 407

SEQ ID NO: 135         moltype = DNA  length = 1224
FEATURE                Location/Qualifiers
```

```
misc_feature            1..1224
                        note = Os06g19444.1, ortholog of AtBBX7 (G2440), AtBBX8
                         (G1479)
source                  1..1224
                        mol_type = unassigned DNA
                        organism = Oryza sativa
SEQUENCE: 135
atgggcgctc tttgtgattt ctgcggggag cagaggtcta tggtttattg ccgatcagat  60
gcagcatcct tgtgcttatc gtgtgaccgt aatgtgcatt cagctaatgc tctttctcgg  120
cgccatacaa ggacacttct gtgtgataga tgtgcttcac agcctgccat ggtccgctgc  180
cttgtagaaa atgcctcgct ttgccaaaat tgtgattgga atgggcatag tgctgggtct  240
tcagctgctg gtcataagag gcagaccata aactgctact cagggtgccc atcatcttca  300
gaactttcaa aaatctggac atttgtttcg gatattccta atgtagctcc tgagccgaat  360
tgcgagcaag ggataagcat gatgagcatc agcgacagtg gtgtcagtaa tcaagacaat  420
gctgcagggg acagcagttt gttagatatt gctagtgcaa cccttatgag tgatcttggc  480
actgctggca agccaaagtc tttgataggc tcctcatctg aagctggcgt gaaccttctt  540
ccacttgcta ctgatcagat ggctggatcc gtggattcga catcagctaa ggtgccctat  600
acggcagacc aagatatgtt cagcaaagac agtatatatg aagatttctg tgtggacgat  660
gttgatctta gtttcgaaaa ttatgaggaa ctatttggca cctcccatat tcaaacagag  720
caactgtttg atgatgctgg gatcgacagt tactttgaat cgaaggaaat accttctgga  780
aactctgatg agcagcccaa gctgatgcag ccagtgacca gcaatgcagt atctgctgat  840
tcagggatgt cgatcccagg agccaaaggt gattccagtc tttgtatacc tgtgaggcaa  900
gctaggtcca gtatctctct ttcattttct ggtttgactg gtgagagcag tgctggagat  960
taccaagatt gtggggtatc accagtgctc cttatgggtg agcctccttg gcatcctcct  1020
ggccctgagg ggtcatttgc tggagctacc agagacgatg ctatcacacg atacaaggag  1080
aagaagaaga gaagaaaatt tgacaagaaa atcaggtatg catctcgcaa ggctagggca  1140
gatgtgagaa aaagagtcaa gggccggttt gttaaggctg gtgaagcata cgactacgat  1200
ccactctgtg aaacgaggag ctac                                        1224

SEQ ID NO: 136          moltype = AA  length = 408
FEATURE                 Location/Qualifiers
REGION                  1..408
                        note = Os06g19444.1, domain coordinates 5-42, 48-85,
                         351-392, ortholog of AtBBX7 (G2440), AtBBX8 (G1479)
source                  1..408
                        mol_type = protein
                        organism = Oryza sativa
SEQUENCE: 136
MGALCDFCGE QRSMVYCRSD AASLCLSCDR NVHSANALSR RHTRTLLCDR CASQPAMVRC  60
LVENASLCQN CDWNGHSAGS SAAGHKRQTI NCYSGCPSSS ELSKIWTFVS DIPNVAPEPN  120
CEQGISMMSI SDSGVSNQDN AAGDSSLLDI ASATLMSDLG TAGKPKSLIG SSSEAGVNLL  180
PLATDQMAGS VDSTSAKVPY TADQDMFSKD SIYEDFCVDD VDLSFENYEE LFGTSHIQTE  240
QLFDDAGIDS YFESKEIPSG NSDEQPKLMQ PVTSNAVSAD SGMSIPGAKG DSSLCIPVRQ  300
ARSSISLSFS GLTGESSAGD YQDCGVSPVL LMGEPPWHPP GPEGSFAGAT RDDAITRYKE  360
KKKRRKFDKK IRYASRKARA DVRKRVKGRF VKAGEAYDYD PLCETRSY                408

SEQ ID NO: 137          moltype = DNA  length = 1221
FEATURE                 Location/Qualifiers
misc_feature            1..1221
                        note = Os06g19444.2, ortholog of AtBBX7 (G2440), AtBBX8
                         (G1479)
source                  1..1221
                        mol_type = unassigned DNA
                        organism = Oryza sativa
SEQUENCE: 137
atgggcgctc tttgtgattt ctgcggggag cagaggtcta tggtttattg ccgatcagat  60
gcagcatcct tgtgcttatc gtgtgaccgt aatgtgcatt cagctaatgc tctttctcgg  120
cgccatacaa ggacacttct gtgtgataga tgtgcttcac agcctgccat ggtccgctgc  180
cttgtagaaa atgcctcgct ttgccaaaat tgtgattgga atgggcatag tgctgggtct  240
tcagctgctg gtcataagag gcagaccata aactgctact cagggtgccc atcatcttca  300
gaactttcaa aaatctggac atttgtttcg gatattccta atgtagctcc tgagccgaat  360
tgcgagcaag ggataagcat gatgagcatc agcgacagtg gtgtcagtaa tcaagacaat  420
gctgcagggg acagcagttt gttagatatt gctagtgcaa cccttatgag tgatcttggc  480
actgctggca agccaaagtc tttgataggc tcctcatctg aagctggcgt gaaccttctt  540
ccacttgcta ctgatcagat ggctggatcc gtggattcga catcagctaa ggtgccctat  600
acggcagacc aagatatgtt cagcaaagac agtatatatg aagatttctg tgtggacgat  660
gttgatctta gtttcgaaaa ttatgaggaa ctatttggca cctcccatat tcaaacagag  720
caactgtttg atgatgctgg gatcgacagt tactttgaat cgaaggaaat accttctgga  780
aactctgatg agcccaagct gatgcagcca gtgaccagca atgcagtatc tgctgattca  840
gggatgtcga tcccaggagc caaaggtgat tccagtcttt gtatacctgt gaggcaagct  900
aggtccagta tctctctttc attttctggt ttgactggtg agagcagtgc tggagattac  960
caagattgtg gggtatcacc agtgctcctt atgggtgagc ctccttggca tcctcctggc  1020
cctgaggggt catttgctgg agctaccaga gacgatgcta tcacacgata caaggagaag  1080
aagaagagaa gaaaatttga caagaaaatc aggtatgcat ctcgcaaggc tagggcagat  1140
gtgagaaaaa gagtcaaggg ccggtttgtt aaggctggtg aagcatacga ctacgatcca  1200
ctctgtgaaa cgaggagcta c                                           1221

SEQ ID NO: 138          moltype = AA  length = 407
FEATURE                 Location/Qualifiers
```

```
REGION                1..407
                      note = Os06g19444.2, domain coordinates 5-42, 48-85,
                       350-391, ortholog of AtBBX7 (G2440), AtBBX8 (G1479)
source                1..407
                      mol_type = protein
                      organism = Oryza sativa
SEQUENCE: 138
MGALCDFCGE QRSMVYCRSD AASLCLSCDR NVHSANALSR RHTRTLLCDR CASQPAMVRC  60
LVENASLCQN CDWNGHSAGS SAAGHKRQTI NCYSGCPSSS ELSKIWTFVS DIPNVAPEPN  120
CEQGISMMSI SDSGVSNQDN AAGDSSLLDI ASATLMSDLG TAGKPKSLIG SSSEAGVNLL  180
PLATDQMAGS VDSTSAKVPY TADQDMFSKD SIYEDFCVDD VDLSFENYEE LFGTSHIQTE  240
QLFDDAGIDS YFESKEIPSG NSDEPKLMQP VTSNAVSADS GMSIPGAKGD SSLCIPVRQA  300
RSSISLSFSG LTGESSAGDY QDCGVSPVLL MGEPPWHPPG PEGSFAGATR DDAITRYKEK  360
KKRRKFDKKI RYASRKARAD VRKRVKGRFV KAGEAYDYDP LCETRSY             407

SEQ ID NO: 139        moltype = DNA  length = 1215
FEATURE               Location/Qualifiers
misc_feature          1..1215
                      note = Glyma02g38870.1, ortholog of AtBBX7 (G2440), AtBBX8
                       (G1479)
source                1..1215
                      mol_type = unassigned DNA
                      organism = Glycine max
SEQUENCE: 139
atgggttact tatgtgattt ttgtggagac cagaggtcct tggtgtactg ccgctctgat  60
tccgcgtgct tatgtttgtc atgcgatcga aatgttcatt ctgccaatgc actttctagg  120
cgtcattcga gaacccttgt atgcgagaga tgcaattcac aacctgcatt tgtgaggtct  180
gttgaagaga aaatttcact ttgtcagaac tgtgattggt tgggtcatgg tacctcaccg  240
tcttcttcga tgcacaagag gcaatcaatc aattgctact ctggctgccc ttcagcggca  300
gaattttctt caatatggtc ctttttctta gacatccctt ctttgggtga agcatgtgag  360
caggaactag gtttgatgag cattaatgag aacattcctc cagaagggca gaatgtgtct  420
ggttcaactg aagtgactga tctacccagc aagggtaaat cttgggctgg cacaccttca  480
atacctgagt caagctcaga acctcgtatt ctggaccagc cgcctggacc tgccaatgaa  540
tgtgtgccca agttgtactg tcctgggaag aaagcttctg gaatatgtga agatgatgat  600
ctatatgatg atttcatcat ggatgaagtt gatctagaac ttgagaacta tgaggaactt  660
tttgggatgg ctctcagtca ctctgaagag ctttttgaaa atggtggaat taatagctta  720
tttgaggcaa aggacatgtc tgctagtgct ggtgattccc attgtcaggg tgctgttgct  780
gctgagggat cgtctgctgg gttggtcaat cctatccaac cagcatgcag caatgcagca  840
tctgcagatt cagtgatgag tacaaaaact gaaccaattg tttgttttac ggcaaggcaa  900
tctcaatcaa acatttcctt ttctggtgtt accaaagata gtgctggtga ctatcaagac  960
tgtggtgctt cttcaatgct tctcatggga gaacctccct ggtgtcctcc ttgccctgag  1020
agttctctgc attctgctaa ccgaagcaat gctgtcatgc gctacaagga aaaaaagaag  1080
acccggaagt tcgagaagaa agtaagatat gcctctcgca aggctagggc tgatgtcaga  1140
aagcgtgtga agggccgatt tgtcaaagct ggtgatgtct atgactatga ccctttgaac  1200
caaaccagaa gctac                                                 1215

SEQ ID NO: 140        moltype = AA  length = 405
FEATURE               Location/Qualifiers
REGION                1..405
                      note = Glyma02g38870.1, domain coordinates 5-42, 48-85,
                       348-389, ortholog of AtBBX7 (G2440), AtBBX8 (G1479)
source                1..405
                      mol_type = protein
                      organism = Glycine max
SEQUENCE: 140
MGYLCDFCGD QRSLVYCRSD SACLCLSCDR NVHSANALSR RHSRTLVCER CNSQPAFVRS  60
VEEKISLCQN CDWLGHGTSP SSSMHKRQSI NCYSGCPSAA EFSSIWSFFL DIPSLGEACE  120
QELGLMSINE NIPPEGQNVS GSTEVTDLPS KGKSWAGTPS IPESSSEPRI LDQPPGPANE  180
CVPKLYCPGK KASGICEDDD LYDDFIMDEV DLELENYEEL FGMALSHSEE LFENGGINSL  240
FEAKDMSASA GDSHCQGAVA AEGSSAGLVN PIQPACSNAA SADSVMSTKT EPIVCFTARQ  300
SQSNISFSGV TKDSAGDYQD CGASSMLLMG EPPWCPPCPE SSLHSANRSN AVMRYKEKKK  360
TRKFEKKVRY ASRKARADVR KRVKGRFVKA GDVYDYDPLN QTRSY               405

SEQ ID NO: 141        moltype = DNA  length = 843
FEATURE               Location/Qualifiers
misc_feature          1..843
                      note = Glyma13g11590.1, ortholog of AtBBX7 (G2440), AtBBX8
                       (G1479)
source                1..843
                      mol_type = unassigned DNA
                      organism = Glycine max
SEQUENCE: 141
atgagtatta atgagaacaa gagtgttggg gttcctccag agggccagaa tgtgtctggt  60
tcagatgaag ttactgatca acctgctttg gacaagtctt tggttggtac atcttcaatg  120
cctgaatcaa gctccaaacc tcgtattctg gaccagccag ctagacctgc caatgaatgt  180
ctttcaaagt tatactgtcc tgctacaaaa ttccccgcat tatgtgaaaa tgataatctg  240
tatgatgatt tcaacatgga tgaagtggat ctaaatcttg agaactatga agaacttttt  300
ggtatggccc tcagtcattc tgaagagcta tttgaaaatg gtggaattga tagcttgttt  360
gggacaaaag acatgtctgc tggagatttc agttgtgagg atgctattgc tgctgaggca  420
```

```
tcacaaattc caactatgtt ggcacctcag cctcacaatg cagcatctgc agattccatt  480
ttgagtacta aaactgaacc aattctttgt tttacgggaa ggcaagctca atcaaacctt  540
tctttttctg gcgttaccgg agacagtagt gctggagact atcaagactg tggggcttct  600
tcaatgcttc tcatgggaga acctccttgg tttgctcctt gtcctgagaa ttccctacaa  660
tcagccaacc gtagtaatgc tgtcatgcgg tacaaggaaa agaagaagac acggatgttt  720
gacaaaaaag tgaggtatgc ctctcgcaag gcaagggctg atgtcagaag gcgcgtgaaa  780
ggccggtttg tcaaagctgg tgacgtctac gattatgatc ctttgagcac aaccagaagc  840
ttc                                                                843

SEQ ID NO: 142         moltype = AA  length = 281
FEATURE                Location/Qualifiers
REGION                 1..281
                       note = Glyma13g11590.1, domain coordinates 224-265,
                        ortholog of AtBBX7 (G2440), AtBBX8 (G1479)
source                 1..281
                       mol_type = protein
                       organism = Glycine max
SEQUENCE: 142
MSINENKSVG VPPEGQNVSG SDEVTDQPAL DKSLVGTSSM PESSSKPRIL DQPARPANEC  60
LSKLYCPATK FPALCENDNL YDDFNMDEVD LNLENYEELF GMALSHSEEL FENGGIDSLF  120
GTKDMSAGDF SCEDAIAAEA SQIPTMLAPQ PHNAASADSI LSTKTEPILC FTGRQAQSNL  180
SFSGVTGDSS AGDYQDCGAS SMLLMGEPPW FAPCPENSLQ SANRSNAVMR YKEKKKTRMF  240
DKKVRYASRK ARADVRRRVK GRFVKAGDVY DYDPLSTTRS F                      281

SEQ ID NO: 143         moltype = DNA  length = 1233
FEATURE                Location/Qualifiers
misc_feature           1..1233
                       note = Glyma14g36930.1, ortholog of AtBBX7 (G2440), AtBBX8
                        (G1479)
source                 1..1233
                       mol_type = unassigned DNA
                       organism = Glycine max
SEQUENCE: 143
atgggttact tatgtgattt ttgtggagac cagaggtccc tggtgtactg ccgctctgat  60
gctgcgtgct tatgtttgtc gtgtgatcga aatgttcatt ctgctaatgc cctttctagg  120
cgtcattcga gaacccttgt atgcgagaga tgcaattcgc aacctgcatt tgtgaggtgt  180
gttgatgaga agatttcact ttgtcagaac tgtgattggt tgggtcatgg tacctcacca  240
tcttcttcga cacacaagag gcaatcaatc aattgctact ctggctgccc ttcagctgca  300
gaatttttctt caatatggtc ctttttctta gacatccctt ctatgggtga agcatgtgag  360
caggaactag gtttgatgag cattaatgag aacagcaata agaatgcttg ggcttctcca  420
gaagggcaga atgtgtctgg ttcagctgaa gtgactgatc tacccagcaa gggtaaatct  480
tgggctggca catcttcagt acctgagtca agctcagaac ctcgtattct agaccagccg  540
cctggacctg ccaatgaatg tatgcccaag ttgtactgtc ctgggaagaa agtttctgga  600
atatatgaag atgatgatct atatgatgat ttcatcatgg atgaagtgga tctacaactt  660
gagaactacg aggaactttt tgggatggct ctcagtcact ctgaagagct ttttgaaaat  720
ggtggaatta atagcttatt tgagacaaag gacatgtctg ctagtgctgg tgattcccat  780
tgtcagggtg ctgttgctgc tgagggatcg tctgctgagt tggtcaatgc tatccaacca  840
gcatgcagca atgcagcatc tgcagactca atgatgagta caaaaactga accaattgtt  900
tgttttacgg caaggcaatc tctatcaaac atttctttct ctggtgttac caaagatagt  960
gttggtgact atcaagattg tggtgcttct tcaatgcttc tcatgggaga gcctccctgg  1020
tgtcctcctt gccctgagag ttctctgcat tctgctaacc gcagcaatgc tgtcatgcgc  1080
tataaggaaa agaagaagac ccggaagttc gagaagaaag taaggtatgc ctctcgcaag  1140
gctagggctg atgtcagaaa gcgtgtgaag ggtcgatttg tcaaagccgg tgatgtctat  1200
gactatgacc ctttgaacca aaccagaagc tgc                               1233

SEQ ID NO: 144         moltype = AA  length = 411
FEATURE                Location/Qualifiers
REGION                 1..411
                       note = Glyma14g36930.1, domain coordinates 5-42, 48-85,
                        354-395, ortholog of AtBBX7 (G2440), AtBBX8 (G1479)
source                 1..411
                       mol_type = protein
                       organism = Glycine max
SEQUENCE: 144
MGYLCDFCGD QRSLVYCRSD AACLCLSCDR NVHSANALSR RHSRTLVCER CNSQPAFVRC  60
VDEKISLCQN CDWLGHGTSP SSSTHKRQSI NCYSGCPSAA EFSSIWSFFL DIPSMGEACE  120
QELGLMSINE NSNKNAWASP EGQNVSGSAE VTDLPSKGKS WAGTSSVPES SSEPRILDQP  180
PGPANECMPK LYCPGKKVSG IYEDDDLYDD FIMDEVDLQL ENYEELFGMA LSHSEELFEN  240
GGINSLFETK DMSASAGDSH CQGAVAAEGS SAELVNAIQP ACSNAASADS MMSTKTEPIV  300
CFTARQSLSN ISFSGVTKDS VGDYQDCGAS SMLLMGEPPW CPPCPESSLH SANRSNAVMR  360
YKEKKKTRKF EKKVRYASRK ARADVRKRVK GRFVKAGDVY DYDPLNQTRS C            411

SEQ ID NO: 145         moltype = DNA  length = 1233
FEATURE                Location/Qualifiers
misc_feature           1..1233
                       note = Glyma14g36930.2, ortholog of AtBBX7 (G2440), AtBBX8
                        (G1479)
source                 1..1233
                       mol_type = unassigned DNA
```

```
                         organism = Glycine max
SEQUENCE: 145
atgggttact tatgtgattt ttgtggagac cagaggtccc tggtgtactg ccgctctgat  60
gctgcgtgct tatgtttgtc gtgtgatcga aatgttcatt ctgctaatgc cctttctagg  120
cgtcattcga gaacccttgt atgcgagaga tgcaattcgc aacctgcatt tgtgaggtgt  180
gttgatgaga agatttcact ttgtcagaac tgtgattggt tgggtcatgg tacctcacca  240
tcttcttcga cacacaagag gcaatcaatc aattgctact ctggctgccc ttcagctgca  300
gaattttctt caatatggtc ctttttctta gacatccctt ctatgggtga agcatgtgag  360
caggaactag gtttgatgag cattaatgag aacagcaata agaatgcttg ggcttctcca  420
gaagggcaga atgtgtctgg ttcagctgaa gtgactgatc tacccagcaa gggtaaatct  480
tgggctggca catcttcagt acctgagtca agctcagaac ctcgtattct agaccagccg  540
cctggacctg ccaatgaatg tatgcccaag ttgtactgtc ctgggaagaa agtttctgga  600
atatatgaag atgatgatct atatgatgat ttcatcatgg atgaagtgga tctacaactt  660
gagaactacg aggaactttt tgggatggct ctcagtcact ctgaagagct tttgaaaat  720
ggtggaatta atagcttatt tgagacaaag gacatgtctg ctagtgctgg tgattcccat  780
tgtcagggtg ctgttgctgc tgagggatcg tctgctgagt tggtcaatgc tatccaacca  840
gcatgcagca atgcagcatc tgcagactca atgatgagta caaaaactga accaattgtt  900
tgttttacgg caaggcaatc tctatcaaac atttctttct ctggtgttac caaagatagt  960
gttggtgact atcaagattg tggtgcttct tcaatgcttc tcatgggaga gcctccctgg  1020
tgtcctcctt gccctgagag ttctctgcat tctgctaacc gcagcaatgc tgtcatgcgc  1080
tataaggaaa agaagaagac ccggaagttc gagaagaaag taaggtatgc ctctcgcaag  1140
gctagggctg atgtcagaaa gcgtgtgaag ggtcgatttg tcaaagccgg tgatgtctat  1200
gactatgacc ctttgaacca aaccagaagc tgc                              1233

SEQ ID NO: 146          moltype = AA  length = 411
FEATURE                 Location/Qualifiers
REGION                  1..411
                        note = Glyma14g36930.2, domain coordinates 5-42, 48-85,
                         354-395, ortholog of AtBBX7 (G2440), AtBBX8 (G1479)
source                  1..411
                        mol_type = protein
                        organism = Glycine max
SEQUENCE: 146
MGYLCDFCGD QRSLVYCRSD AACLCLSCDR NVHSANALSR RHSRTLVCER CNSQPAFVRC  60
VDEKISLCQN CDWLGHGTSP SSSTHKRQSI NCYSGCPSAA EFSSIWSFFL DIPSMGEACE  120
QELGLMSINE NSNKNAWASP EGQNVSGSAE VTDLPSKGKS WAGTSSVPES SSEPRILDQP  180
PGPANECMPK LYCPGKKVSG IYEDDDLYDD FIMDEVDLQL ENYEELFGMA LSHSEELFEN  240
GGINSLFETK DMSASAGDSH CQGAVAAEGS SAELVNAIQP ACSNAASADS MMSTKTEPIV  300
CFTARQSLSN ISFSGVTKDS VGDYQDCGAS SMLLMGEPPW CPPCPESSLH SANRSNAVMR  360
YKEKKKTRKF EKKVRYASRK ARADVRKRVK GRFVKAGDVY DYDPLNQTRS C           411

SEQ ID NO: 147          moltype = DNA  length = 849
FEATURE                 Location/Qualifiers
misc_feature            1..849
                        note = Glyma20g07050.1, ortholog of AtBBX7 (G2440), AtBBX8
                         (G1479)
source                  1..849
                        mol_type = unassigned DNA
                        organism = Glycine max
SEQUENCE: 147
atgagtatta atgagaacaa gtgtgttggt gttcctccgg aagaccagaa tgtgtctggt  60
tcagatgaag ttaccgatct acctgctttg aacaagtctt tggttggtgc atctttgatg  120
cctgaatcaa gctccgaacc ttgtattctg gaccagccag ctggacctac caatgaatgt  180
ctgccaaagt tatactgtcc tgctacaaaa tgccctgcct tatctgaaga tgataatctg  240
tatgatgatt tcaacatgga tgaagtggat ctagatcttg agaactatga agaacttttt  300
ggtatggccc tcagtcattc tgaggagctt tttgaaaatg gtggaattga tagcttgttt  360
gggacaaaag gcatgtctgc tggagattcc aattgtcagg aagctattgc tgctgagggg  420
tcgtcggttg gacaggtcaa tgcaatgcaa ccagcttgca gcaatgcagc gtctgcagat  480
tccattttga gtactaaaac tgaaccaatt ctttgtttta ctggaaggca aactcaatca  540
aacctttctt tttctggtgt tactggagag agtagtgctg gagactatca agactgtggg  600
gcttcttcaa tgcttctcat gggagaacct ccttggtttg ctccttgtcc ggagaattcc  660
ctacaatccg ccaaccgtag taatgctgtc atgcggtaca aggaaaagaa gaagacacgg  720
atgtttgaca aaaaagttag gtatgcctct cgcaaggcaa gggctgatgt cagaaggcgt  780
gtgaaagggc ggtttgtcaa agccggtgac gtctatgatt atgacccttt gagcacaacc  840
agaagctgc                                                         849

SEQ ID NO: 148          moltype = AA  length = 283
FEATURE                 Location/Qualifiers
REGION                  1..283
                        note = Glyma20g07050.1, domain coordinates 226-267,
                         ortholog of AtBBX7 (G2440), AtBBX8 (G1479)
source                  1..283
                        mol_type = protein
                        organism = Glycine max
SEQUENCE: 148
MSINENKCVG VPPEDQNVSG SDEVTDLPAL NKSLVGASLM PESSSEPCIL DQPAGPTNEC  60
LPKLYCPATK CPALSEDDNL YDDFNMDEVD LDLENYEELF GMALSHSEEL FENGGIDSLF  120
GTKGMSAGDS NCQEAIAAEG SSVGQVNAMQ PACSNAASAD SILSTKTEPI LCFTGRQTQS  180
NLSFSGVTGE SSAGDYQDCG ASSMLLMGEP PWFAPCPENS LQSANRSNAV MRYKEKKKTR  240
```

```
MFDKKVRYAS RKARADVRRR VKGRFVKAGD VYDYDPLSTT RSC                283

SEQ ID NO: 149          moltype = DNA  length = 849
FEATURE                 Location/Qualifiers
misc_feature            1..849
                        note = Glyma20g07050.2, ortholog of AtBBX7 (G2440), AtBBX8
                         (G1479)
source                  1..849
                        mol_type = unassigned DNA
                        organism = Glycine max
SEQUENCE: 149
atgagtatta atgagaacaa gtgtgttggt gttcctccgg aagaccagaa tgtgtctggt  60
tcagatgaag ttaccgatct acctgctttg aacaagtctt tggttggtgc atctttgatg  120
cctgaatcaa gctccgaacc ttgtattctg gaccagccag ctggacctac caatgaatgt  180
ctgccaaagt tatactgtcc tgctacaaaa tgccctgcct tatctgaaga tgataatctg  240
tatgatgatt tcaacatgga tgaagtggat ctagatcttg agaactatga agaacttttt  300
ggtatggccc tcagtcattc tgaggagctt tttgaaaatg gtggaattga tagcttgttt  360
gggacaaaag gcatgtctgc tggagattcc aattgtcagg aagctattgc tgctgagggg  420
tcgtcggttg gacaggtcaa tgcaatgcaa ccagcttgca gcaatgcagc gtctgcagat  480
tccattttga gtactaaaac tgaaccaatt ctttgtttta ctggaaggca aactcaatca  540
aacctttctt tttctggtgt tactggagag agtagtgctg gagactatca agactgtggg  600
gcttcttcaa tgcttctcat gggagaacct ccttggtttg ctccttgtcc ggagaattcc  660
ctacaatccg ccaaccgtag taatgctgtc atgcggtaca aggaaaagaa gaagacacgg  720
atgtttgaca aaaaagttag gtatgcctct cgcaaggcaa gggctgatgt cagaaggcgt  780
gtgaaagggc ggtttgtcaa agccggtgac gtctatgatt atgacccttt gagcacaacc  840
agaagctgc                                                      849

SEQ ID NO: 150          moltype = AA  length = 283
FEATURE                 Location/Qualifiers
REGION                  1..283
                        note = Glyma20g07050.2, domain coordinates 226-267,
                         ortholog of AtBBX7 (G2440), AtBBX8 (G1479)
source                  1..283
                        mol_type = protein
                        organism = Glycine max
SEQUENCE: 150
MSINENKCVG VPPEDQNVSG SDEVTDLPAL NKSLVGASLM PESSSEPCIL DQPAGPTNEC  60
LPKLYCPATK CPALSEDDNL YDDFNMDEVD LDLENYEELF GMALSHSEEL FENGGIDSLF  120
GTKGMSAGDS NCQEAIAAEG SSVGQVNAMQ PACSNAASAD SILSTKTEPI LCFTGRQTQS  180
NLSFSGVTGE SSAGDYQDCG ASSMLLMGEP PWFAPCPENS LQSANRSNAV MRYKEKKKTR  240
MFDKKVRYAS RKARADVRRR VKGRFVKAGD VYDYDPLSTT RSC                283

SEQ ID NO: 151          moltype = DNA  length = 744
FEATURE                 Location/Qualifiers
misc_feature            1..744
                        note = AtBBX24 (G329), AT1G06040.1, paralog of AtBBX25
                         (G1894)
source                  1..744
                        mol_type = unassigned DNA
                        organism = Arabidopsis thaliana
SEQUENCE: 151
atgaagatac agtgtgatgt gtgtgagaaa gctccggcga cggtgatttg ttgcgccgac  60
gaagctgctc tctgtcctca atgcgacatc gagattcacg ccgctaacaa actcgctagc  120
aagcaccaac gtcttcatct taattccctc tccaccaaat tccctcgttg cgatatctgc  180
caagagaagg cagctttcat ttctgtgta gaggatagag ctctgctttg cagggactgc  240
gatgaatcca tccacgtggc taattctcga tctgctaatc accagaggtt cttagccact  300
gggatcaaag tagctctgac ctcaactata tgtagtaaag aaattgagaa gaatcaacct  360
gagccttcca acaaccaaca gaaggctaat cagattcctg ctaaatccac aagccagcag  420
caacaacaac cttcttctgc tactccactt ccctgggctg ttgacgattt ctttcacttc  480
tctgatattg aatccaccga caagaaagga cagcttgatc ttggggcagg ggagttggat  540
tggttttcag acatgggatt cttcggtgat cagattaatg acaaggctct tcctgcagct  600
gaagttcctg agctttctgt ttcgcattta ggtcatgttc attcatacaa acctatgaag  660
tcaaatgttt cacacaagaa gccgaggttt gagaccagat atgatgatga tgatgaggaa  720
cacttcattg tccctgatct tggc                                     744

SEQ ID NO: 152          moltype = AA  length = 248
FEATURE                 Location/Qualifiers
REGION                  1..248
                        note = AtBBX24 (G329), AT1G06040.1, domain coordinates
                         5-42, 57-94, paralog of AtBBX25 (G1894)
source                  1..248
                        mol_type = protein
                        organism = Arabidopsis thaliana
SEQUENCE: 152
MKIQCDVCEK APATVICCAD EAALCPQCDI EIHAANKLAS KHQRLHLNSL STKFPRCDIC  60
QEKAAFIFCV EDRALLCRDC DESIHVANSR SANHQRFLAT GIKVALTSTI CSKEIEKNQP  120
EPSNNQQKAN QIPAKSTSQQ QQQPSSATPL PWAVDDFFHF SDIESTDKKG QLDLGAGELD  180
WFSDMGFFGD QINDKALPAA EVPELSVSHL GHVHSYKPMK SNVSHKKPRF ETRYDDDDEE  240
HFIVPDLG                                                       248
```

```
SEQ ID NO: 153         moltype = DNA  length = 714
FEATURE                Location/Qualifiers
misc_feature           1..714
                       note = AtBBX25 (G1894), AT2G31380.1, paralog of AtBBX24
                        (G329)
source                 1..714
                       mol_type = unassigned DNA
                       organism = Arabidopsis thaliana
SEQUENCE: 153
atgaagatac aatgtgatgt gtgtgagaaa gctccggcca cgcttatatg ttgtgctgat  60
gaagctgctc tctgcgctaa atgtgacgtt gaggttcatg ctgctaataa actcgctagc  120
aaacaccaac gccttttttct tgactctctc tcaactaaat tccctccctg cgacatctgc  180
cttgagaagg cagctttcat attctgtgta gaggataggg ctctgctctg cagagattgc  240
gatgaggcga cccatgcgcc aaatactcgc tctgctaatc accagaggtt cttagccact  300
ggaatccgag ttgctcttag ttccactagt tgcaatcaag aagtggaaaa gaatcacttt  360
gacccatcta atcagcagag tctctctaaa ccgccaactc agcaacccgc tgctccatct  420
cctttgtggg ctaccgatga attcttcagc tactctgatc ttgactgcag taataaggag  480
aaagagcaac tcgatctcgg ggagctggat tggcttgcag agatgggtct gtttggtgac  540
cagcctgatc aagaggctct accggtagcc gaagttcccg agctttcctt ttcacatttg  600
gctcatgctc attcctacaa cagacctatg aagtccaatg tacccaacaa gaagcagagg  660
cttgagtacc ggtatgatga tgaagaagag cacttcctag tccccgacct aggc        714

SEQ ID NO: 154         moltype = AA  length = 238
FEATURE                Location/Qualifiers
REGION                 1..238
                       note = AtBBX25 (G1894), AT2G31380.1, domain coordinates
                        5-42, 57-94, paralog of AtBBX24 (G329)
source                 1..238
                       mol_type = protein
                       organism = Arabidopsis thaliana
SEQUENCE: 154
MKIQCDVCEK APATLICCAD EAALCAKCDV EVHAANKLAS KHQRLFLDSL STKFPPCDIC  60
LEKAAFIFCV EDRALLCRDC DEATHAPNTR SANHQRFLAT GIRVALSSTS CNQEVEKNHF  120
DPSNQQSLSK PPTQQPAAPS PLWATDEFFS YSDLDCSNKE KEQLDLGELD WLAEMGLFGD  180
QPDQEALPVA EVPELSFSHL AHAHSYNRPM KSNVPNKKQR LEYRYDDEEE HFLVPDLG    238

SEQ ID NO: 155         moltype = DNA  length = 774
FEATURE                Location/Qualifiers
misc_feature           1..774
                       note = ACF84591.1, ortholog of AtBBX24 (G329), AtBBX25
                        (G1894)
source                 1..774
                       mol_type = unassigned DNA
                       organism = Zea mays
SEQUENCE: 155
atgaagatcc agtgcgacgc gtgcgagggc gcggctgcca cggtggtgtg ctgcgccgac  60
gaggccgcgc tgtgcgcgcg ctgcgacgtc gagatccacg ccgccaacaa gctcgcgagc  120
aagcaccagc gcctcccgct cgaggcgctc tccgccaagc tcccgcgctg cgacgtctgc  180
caggagaaag cggcgttcat cttctgcgtg gaggaccggg cgctcttctg ccaggactgc  240
gacgagccca tccacgtccc gggcacgctc tccgggaacc accagcgcta cctggccacc  300
ggcatccgcg tcggcctcgc ctcggcttcc gcctgcagcg acgcctgcga cgcccacgac  360
tccgaccacc acgccccgcc caaggccacc atcgagccac cgcacgccgc cgtctccgcc  420
gcggtgcagc aggtgccctc gccgccgcag ttcctgccgc agggctgggc cgtcgacgag  480
ctcctgcagt tctccgacta cgagtccagc gacaagctgc acaaggagcc gacgctcggg  540
ttcaaggagc tggagtggtt cgccgacatc gacctcttcc acgagcaggc gcccaaagcc  600
agcaggacgt tggcggaggt gccggagctt ttcggatacc aggcggcgaa cgacgcggcg  660
tactacaggc cggccaaagc cgccgccggc ggcggcgctg gggttcgcca gagcaagaag  720
gcccggatcg aggtcaccga cgacgaggat tacctcatag tccctgatct tggt        774

SEQ ID NO: 156         moltype = AA  length = 258
FEATURE                Location/Qualifiers
REGION                 1..258
                       note = ACF84591.1, domain coordinates 5-42, 57-94, ortholog
                        of AtBBX24 (G329), AtBBX25 (G1894)
source                 1..258
                       mol_type = protein
                       organism = Zea mays
SEQUENCE: 156
MKIQCDACEG AAATVVCCAD EAALCARCDV EIHAANKLAS KHQRLPLEAL SAKLPRCDVC  60
QEKAAFIFCV EDRALFCQDC DEPIHVPGTL SGNHQRYLAT GIRVGLASAS ACSDACDAHD  120
SDHHAPPKAT IEPPHAAVSA AVQQVPSPPQ FLPQGWAVDE LLQFSDYESS DKLHKEPTLG  180
FKELEWFADI DLFHEQAPKA SRTLAEVPEL FGYQAANDAA YYRPAKAAAG GGAGVRQSKK  240
ARIEVTDDED YLIVPDLG                                                258

SEQ ID NO: 157         moltype = DNA  length = 759
FEATURE                Location/Qualifiers
misc_feature           1..759
                       note = ACF86823.1, ortholog of AtBBX24 (G329), AtBBX25
```

```
                          (G1894)
source                   1..759
                         mol_type = unassigned DNA
                         organism = Zea mays
SEQUENCE: 157
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
gacatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggct  600
gaggtaccgg agctttccgg aacccaggcc gcgaacgacg cggcgtacta caggccagcc  660
aaagccactg ccactgccgg cgccggggtg cgccagagca agaaggcccg gaccgaggtc  720
accgacgacg aggaccacct catcgtccct gatctcggc                         759

SEQ ID NO: 158           moltype = AA  length = 253
FEATURE                  Location/Qualifiers
REGION                   1..253
                         note = ACF86823.1, domain coordinates 5-42, 57-94, ortholog
                          of AtBBX24 (G329), AtBBX25 (G1894)
source                   1..253
                         mol_type = protein
                         organism = Zea mays
SEQUENCE: 158
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT DIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAGAGV RQSKKARTEV  240
TDDEDHLIVP DLG                                                     253

SEQ ID NO: 159           moltype = DNA  length = 759
FEATURE                  Location/Qualifiers
misc_feature             1..759
                         note = ACG28309.1, ortholog of AtBBX24 (G329), AtBBX25
                          (G1894)
source                   1..759
                         mol_type = unassigned DNA
                         organism = Zea mays
SEQUENCE: 159
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
gacatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggct  600
gaggtaccgg agctttccgg aacccaggcc gcgaacgacg cggcgtacta caggccagcc  660
aaagccactg ccactgccgg cgccggggtg cgccagagca agaaggcccg gaccgaggtc  720
accgacgacg aggaccacct catcgtccct gatctcggc                         759

SEQ ID NO: 160           moltype = AA  length = 253
FEATURE                  Location/Qualifiers
REGION                   1..253
                         note = ACG28309.1, domain coordinates 5-42, 57-94, ortholog
                          of AtBBX24 (G329), AtBBX25 (G1894)
source                   1..253
                         mol_type = protein
                         organism = Zea mays
SEQUENCE: 160
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT DIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAGAGV RQSKKARTEV  240
TDDEDHLIVP DLG                                                     253

SEQ ID NO: 161           moltype = DNA  length = 759
FEATURE                  Location/Qualifiers
misc_feature             1..759
                         note = CAW36812.1, ortholog of AtBBX24 (G329), AtBBX25
                          (G1894)
source                   1..759
                         mol_type = unassigned DNA
```

```
                        organism = Zea mays
SEQUENCE: 161
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                        759

SEQ ID NO: 162          moltype = AA  length = 253
FEATURE                 Location/Qualifiers
REGION                  1..253
                        note = CAW36812.1, domain coordinates 5-42, 57-94, ortholog
                         of AtBBX24 (G329), AtBBX25 (G1894)
source                  1..253
                        mol_type = protein
                        organism = Zea mays
SEQUENCE: 162
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                    253

SEQ ID NO: 163          moltype = DNA  length = 759
FEATURE                 Location/Qualifiers
misc_feature            1..759
                        note = CAW39068.1, ortholog of AtBBX24 (G329), AtBBX25
                         (G1894)
source                  1..759
                        mol_type = unassigned DNA
                        organism = Zea mays
SEQUENCE: 163
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                        759

SEQ ID NO: 164          moltype = AA  length = 253
FEATURE                 Location/Qualifiers
REGION                  1..253
                        note = CAW39068.1, domain coordinates 5-42, 57-94, ortholog
                         of AtBBX24 (G329), AtBBX25 (G1894)
source                  1..253
                        mol_type = protein
                        organism = Zea mays
SEQUENCE: 164
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                    253

SEQ ID NO: 165          moltype = DNA  length = 759
FEATURE                 Location/Qualifiers
misc_feature            1..759
                        note = CAW54445.1, ortholog of AtBBX24 (G329), AtBBX25
                         (G1894)
source                  1..759
                        mol_type = unassigned DNA
                        organism = Zea mays
SEQUENCE: 165
atgaagatcc agtgcgacgc gtgcgagggc gcggctgcca ccgtggtgtg ctgcgccgac  60
```

```
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                        759

SEQ ID NO: 166          moltype = AA  length = 253
FEATURE                 Location/Qualifiers
REGION                  1..253
                        note = CAW54445.1, domain coordinates 5-42, 57-94, ortholog
                         of AtBBX24 (G329), AtBBX25 (G1894)
source                  1..253
                        mol_type = protein
                        organism = Zea mays
SEQUENCE: 166
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                    253

SEQ ID NO: 167          moltype = DNA  length = 759
FEATURE                 Location/Qualifiers
misc_feature            1..759
                        note = CAW74336.1, ortholog of AtBBX24 (G329), AtBBX25
                         (G1894)
source                  1..759
                        mol_type = unassigned DNA
                        organism = Zea mays
SEQUENCE: 167
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                        759

SEQ ID NO: 168          moltype = AA  length = 253
FEATURE                 Location/Qualifiers
REGION                  1..253
                        note = CAW74336.1, domain coordinates 5-42, 57-94, ortholog
                         of AtBBX24 (G329), AtBBX25 (G1894)
source                  1..253
                        mol_type = protein
                        organism = Zea mays
SEQUENCE: 168
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                    253

SEQ ID NO: 169          moltype = DNA  length = 759
FEATURE                 Location/Qualifiers
misc_feature            1..759
                        note = CAW80388.1, ortholog of AtBBX24 (G329), AtBBX25
                         (G1894)
source                  1..759
                        mol_type = unassigned DNA
                        organism = Zea mays
SEQUENCE: 169
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
```

```
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                         759

SEQ ID NO: 170          moltype = AA  length = 253
FEATURE                 Location/Qualifiers
REGION                  1..253
                        note = CAW80388.1, domain coordinates 5-42, 57-94, ortholog
                         of AtBBX24 (G329), AtBBX25 (G1894)
source                  1..253
                        mol_type = protein
                        organism = Zea mays
SEQUENCE: 170
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                     253

SEQ ID NO: 171          moltype = DNA  length = 759
FEATURE                 Location/Qualifiers
misc_feature            1..759
                        note = CAW82896.1, ortholog of AtBBX24 (G329), AtBBX25
                         (G1894)
source                  1..759
                        mol_type = unassigned DNA
                        organism = Zea mays
SEQUENCE: 171
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
ggcatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggcc  600
gaggtaccgg agctttccgg aacccaggcc gcgaacgacg cggcgtacta caggccagcc  660
aaagccactg ccactgccgt cgccggggtg cgccagagca agaagggccg gaccgaggtc  720
accgacgacg aggaccacct catcgtccct gatctcgtt                         759

SEQ ID NO: 172          moltype = AA  length = 253
FEATURE                 Location/Qualifiers
REGION                  1..253
                        note = CAW82896.1, domain coordinates 5-42, 57-94, ortholog
                         of AtBBX24 (G329), AtBBX25 (G1894)
source                  1..253
                        mol_type = protein
                        organism = Zea mays
SEQUENCE: 172
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT GIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAVAGV RQSKKGRTEV  240
TDDEDHLIVP DLV                                                     253

SEQ ID NO: 173          moltype = DNA  length = 759
FEATURE                 Location/Qualifiers
misc_feature            1..759
                        note = NP_001141667.1, ortholog of AtBBX24 (G329), AtBBX25
                         (G1894)
source                  1..759
                        mol_type = unassigned DNA
                        organism = Zea mays
SEQUENCE: 173
atgaagatcc agtgcgacgc gtgcgagggc gcggctgcca ccgtggtgtg ctgcgccgac  60
gaggccgcgc tgtgcgcgcg ctgcgacgtc gagatccacg ccgccaacaa gctcgccagc  120
aagcaccagc gcctcccgct cgaggctctc tccgccagcc tcccgcgctg cgacgtctgc  180
caggagaaag cggcgttcat cttctgcgtg gaggaccggg cgctcttctg ccgggactgc  240
gacgagccca tccacgtccc gggcacgctc tccgggaacc accagcgcta cctcgccacc  300
gacatccgcg tcggcttcgc ctccgcttcg tcagcgtgca gtgacgcctg cgacgcccac  360
gacgactccg accaccacgc cccgcccaag gccgccgtct cctccgcggc gcagcaggtg  420
```

```
ccctcgccgc cgcagttcct gccacagggc tgggccgtcg acgagctcct gcagttctcc  480
gactgcgagt ccagcgacaa gctgcacaag gagtccccgc tcgggttcaa ggagctggag  540
tggttcaccg acatcgacct cttccacgag cagacgccga aagccggcag gagattggct  600
gaggtaccgg agctttccgg aacccaggcc gcgaacgacg cggcgtacta caggccagcc  660
aaagccactg ccactgccgg cgccggggtg cgccagagca agaaggcccg gaccgaggtc  720
accgacgacg aggaccacct catcgtccct gatctcggc                         759

SEQ ID NO: 174         moltype = AA  length = 253
FEATURE                Location/Qualifiers
REGION                 1..253
                       note = NP_001141667.1, domain coordinates 5-42, 57-94,
                        ortholog of AtBBX24 (G329), AtBBX25 (G1894)
source                 1..253
                       mol_type = protein
                       organism = Zea mays
SEQUENCE: 174
MKIQCDACEG AAATVVCCAD EAALCARCDV EIHAANKLAS KHQRLPLEAL SASLPRCDVC  60
QEKAAFIFCV EDRALFCRDC DEPIHVPGTL SGNHQRYLAT DIRVGFASAS SACSDACDAH  120
DDSDHHAPPK AAVSSAAQQV PSPPQFLPQG WAVDELLQFS DCESSDKLHK ESPLGFKELE  180
WFTDIDLFHE QTPKAGRRLA EVPELSGTQA ANDAAYYRPA KATATAGAGV RQSKKARTEV  240
TDDEDHLIVP DLG                                                     253

SEQ ID NO: 175         moltype = DNA  length = 489
FEATURE                Location/Qualifiers
misc_feature           1..489
                       note = Pt_216458, ortholog of AtBBX24 (G329), AtBBX25
                        (G1894)
source                 1..489
                       mol_type = unassigned DNA
                       organism = Populus trichocarpa
SEQUENCE: 175
atgaaaattc agtgtgatgt gtgtgagaaa gcaccagcca cagtgatttg ttgtgctgat  60
gaggctgccc tttgtgaaaa atgtgacata gaagttcatg cagcaaacaa gcttgctagc  120
aaacaccaaa gacttcttct ccagtgcctc tccaacaagc tgcctccatg cgatatatgc  180
caagaaaagg ctgctttcat tttctgtgtt gaagacagag ccctcttttg ccgggattgt  240
gatgaaccaa tccattcagc tggtagcctt tcagcaaatc accagcggtt tctggccact  300
ggaatccgag tggctttaag ctctagttgc tccaaggaca ctcagaagag ttctttagag  360
ccaccaaatc agagtgaaca acaaacttcc aagttgcctt ggcagcatgc atcgagtttt  420
ggctcttctt gggctgttga tgatttttcta cagttctctg acattgaaga atccactgac  480
aaggtaata                                                          489

SEQ ID NO: 176         moltype = AA  length = 163
FEATURE                Location/Qualifiers
REGION                 1..163
                       note = Pt_216458, domain coordinates 5-42, 57-94, ortholog
                        of AtBBX24 (G329), AtBBX25 (G1894)
source                 1..163
                       mol_type = protein
                       organism = Populus trichocarpa
SEQUENCE: 176
MKIQCDVCEK APATVICCAD EAALCEKCDI EVHAANKLAS KHQRLLLQCL SNKLPPCDIC  60
QEKAAFIFCV EDRALFCRDC DEPIHSAGSL SANHQRFLAT GIRVALSSSC SKDTQKSSLE  120
PPNQSEQQTS KLPWQHASSF GSSWAVDDFL QFSDIEESTD KVI                    163

SEQ ID NO: 177         moltype = DNA  length = 1475
FEATURE                Location/Qualifiers
misc_feature           1..1475
                       note = Pt_827145, ortholog of AtBBX24 (G329), AtBBX25
                        (G1894)
source                 1..1475
                       mol_type = unassigned DNA
                       organism = Populus trichocarpa
SEQUENCE: 177
ctctgagcct tatctgcaca cactcagctt cttggtttct ccaccaaaca ctcctctttc  60
tgtatcttcc acagattctt gcttgcatta tacagtactt cacaaagctc ccatctccca  120
tttctattat tatacttctct catagttttt cctctcttct tctgttcttt ccttttcttt  180
cgtggccaaa ctctttcttt ctcttgttgt ttcgccagta gtttcttggg gaaaagatta  240
ttatcatttc aggctgtttt ttgagctact ttgaaacata tgtttcactg tctcatttac  300
tgtatgctga gttcacttaa aaggtagaga gaaactggag aaggtgtaac caagtgggga  360
tctgctaaaa gagaggagga ggtttggtct gttttaagca agatgaagat tcagtgtgat  420
gtgtgtgaga aagcacccgc cacagtgatt tgttgtgctg atgaggctgc actttgtgct  480
aaatgtgaca tagaagttca tgcagcaaac aagcttgcta gcaagcacca aaggcttctt  540
ctccagtgcc tctccaacaa gctgcctcca tgtgatatat gccaagagaa ggcagctttc  600
attttctgtg ttgaagacag ggccctcttt tgccgggatt gtgatgaacc aatccattca  660
gctggtagcc tttctgcgaa tcaccagcgg tttctggcca ctggaatccg agtggcttta  720
agctcgagtt gctccaagga cacgcagacg aattcttcag ggccaccaaa tcagagcgca  780
cagcaaactc ccatgaaaat ccctgcacag caaacatcga gcttcgccac ttcatgggca  840
gttgatgact tgctacagtt ttccgagttt gaatcatcca ctgacaagaa agagcaactt  900
gagttaggag agtttgagtg gctagctgac atgggtcttt tcggtgagca acttcctcaa  960
```

-continued

```
gaagctctag cagcagctga agttcctcaa ctgccaatct caccaccaac caatgtgaac  1020
tcatgcagac ccaccaaatc cagcatgccc cataagaagc ctagaattga aatctcagac  1080
gatgacgacg agtacttaac tgtgcctgat cttggctgaa cttggggtgt tgaactcagc  1140
acttttgagt tcaactttta aggaactata catgctttct ctaagttccc gtaggcattg  1200
atgtatgtat atactatata gtatgtattt gcatacacgg gcatgaaact ctgcatttta  1260
aggactagag agtagcatca cagtcagctc tggggattca ttttccatgt tatcctatat  1320
attgttattt ttgttagttc ttttttccat ttgaaagagc aatcacatca atcagtgctc  1380
ttgattgtaa tagctcaatg tatgattctc agctattgca tgtatatctg tgtgccagga  1440
tattactagc tgcaagtata tggattgttt ctcgc                             1475

SEQ ID NO: 178         moltype = AA  length = 238
FEATURE                Location/Qualifiers
REGION                 1..238
                       note = Pt_827145, domain coordinates 5-42, 57-94, ortholog
                        of AtBBX24 (G329), AtBBX25 (G1894)
source                 1..238
                       mol_type = protein
                       organism = Populus trichocarpa
SEQUENCE: 178
MKIQCDVCEK APATVICCAD EAALCAKCDI EVHAANKLAS KHQRLLLQCL SNKLPPCDIC  60
QEKAAFIFCV EDRALFCRDC DEPIHSAGSL SANHQRFLAT GIRVALSSSC SKDTQTNSSG  120
PPNQSAQQTP MKIPAQQTSS FATSWAVDDL LQFSEFESST DKKEQLELGE FEWLADMGLF  180
GEQLPQEALA AAEVPQLPIS PPTNVNSCRP TKSSMPHKKP RIEISDDDDE YLTVPDLG    238

SEQ ID NO: 179         moltype = DNA  length = 813
FEATURE                Location/Qualifiers
misc_feature           1..813
                       note = Os02g39360.1, ortholog of AtBBX24 (G329), AtBBX25
                        (G1894)
source                 1..813
                       mol_type = unassigned DNA
                       organism = Oryza sativa
SEQUENCE: 179
atgaagatcc agtgcgacgc gtgcgagagc gcggcggcgg cggtggtgtg ctgcgcggac  60
gaggcggcgc tgtgcgcggc gtgcgacgtg gaggtgcacg cggcgaacaa gctggccggg  120
aagcaccagc ggctgccgct ggaggcgctc tcggcgaggc tcccgcgctg cgacgtgtgc  180
caggagaagg cggcgttcat cttctgcgtg gaggaccgcg cgctcttctg ccgcgactgc  240
gacgagccca tccacgtccc cggcacgctc tccggcaacc accagcgcta cctcgccacc  300
ggcatccgcg tcggcttcgc ctccgcctcg ccctgcgacg gcggcagcga cgcccatgac  360
tccgaccacc acgccccgcc catgggctcc tccgagcatc atcaccatca tcagcagccg  420
gccccgaccg tcgccgtcga cacgccctcg ccgcagttcc tgccgcaggg ctgggccgtc  480
gacgagctcc tccagttctc cgactacgag accggcgaca agctgcagaa ggagtcgtcg  540
ccgccgctcg ggttccagga gctggagtgg ttcgccgaca tcgacctgtt ccacaaccag  600
gcgcccaagg gcggcgccgc cgccggccgg acgacggcgg aggtccccga gctcttcgct  660
tcgcaggcgg ccaacgacgt ggcgtactac aggccgccga ccaggaccgc cgccgccgcc  720
ttcaccgcgg ccaccggctt ccgccagagc aagaaggccc gcgtcgagct ccccgacgac  780
gaggaggatt acctcatcgt ccctgatctt ggt                               813

SEQ ID NO: 180         moltype = AA  length = 271
FEATURE                Location/Qualifiers
REGION                 1..271
                       note = Os02g39360.1, domain coordinates 5-42, 57-94,
                        ortholog of AtBBX24 (G329), AtBBX25 (G1894)
source                 1..271
                       mol_type = protein
                       organism = Oryza sativa
SEQUENCE: 180
MKIQCDACES AAAAVVCCAD EAALCAACDV EVHAANKLAG KHQRLPLEAL SARLPRCDVC  60
QEKAAFIFCV EDRALFCRDC DEPIHVPGTL SGNHQRYLAT GIRVGFASAS PCDGGSDAHD  120
SDHHAPPMGS SEHHHHHQQP APTVAVDTPS PQFLPQGWAV DELLQFSDYE TGDKLQKESS  180
PPLGFQELEW FADIDLFHNQ APKGGAAAGR TTAEVPELFA SQAANDVAYY RPPTRTAAAA  240
FTAATGFRQS KKARVELPDD EEDYLIVPDL G                                 271

SEQ ID NO: 181         moltype = DNA  length = 771
FEATURE                Location/Qualifiers
misc_feature           1..771
                       note = Os04g41560.2, ortholog of AtBBX24 (G329), AtBBX25
                        (G1894)
source                 1..771
                       mol_type = unassigned DNA
                       organism = Oryza sativa
SEQUENCE: 181
atgaggatcc agtgcgacgc gtgcgaggcc gcggcggcca cggtggtgtg ctgcgcggac  60
gaggcggcgc tgtgcgcgcg ctgcgacgtc gagatccacg ccgccaacaa gctcgccagc  120
aagcaccagc gcctcccgct cgacgccgcg ctccccgccg ccctcccgcg ctgcgacgtc  180
tgccaggaga aggcggcgtt catcttctgc gtggaggaca gggcgctctt ctgccgggac  240
tgcgacgagc ccatccacgt cccggggacg ctctccggca accaccagcg ctacctcacc  300
accggcatcc gcgtcgggtt cagctccgtc tgtagcgcca acgccgacca cctcccgccg  360
ccagcgccca aggggaactc caagccgccg gcaagcggca tcgctgctgc tgctgctccc  420
```

```
aagccggccg tgtccgcggc ggcgcaggag gtgccgtcgt caccgttctt gccgccgtcg  480
ggctgggccg tcgaggatct cctgcagctc tccgactacg agtccagcga caagaagggc  540
tctcctattg ggttcaagga tctggagtgg ctcgatgaca tcgacctgtt ccatgtccag  600
tcgccggcca agggaggcag cacggcggcg gaggtgcctg agctcttcgc ctcgccgcag  660
ccagcgagca acatggggct ctacaaggcg agcggtgcac gccaaagcaa gaagccacgg  720
gtggagatac ccgatgacga cgaggacttc ttcatcgttc ctgatcttgg a           771

SEQ ID NO: 182          moltype = AA  length = 257
FEATURE                 Location/Qualifiers
REGION                  1..257
                        note = Os04g41560.2, domain coordinates 5-42, 58-95,
                         ortholog of AtBBX24 (G329), AtBBX25 (G1894)
source                  1..257
                        mol_type = protein
                        organism = Oryza sativa
SEQUENCE: 182
MRIQCDACEA AAATVVCCAD EAALCARCDV EIHAANKLAS KHQRLPLDAA LPAALPRCDV  60
CQEKAAFIFC VEDRALFCRD CDEPIHVPGT LSGNHQRYLT TGIRVGFSSV CSANADHLPP  120
PAPKGNSKPP ASGIAAAAAP KPAVSAAAQE VPSSPFLPPS GWAVEDLLQL SDYESSDKKG  180
SPIGFKDLEW LDDIDLFHVQ SPAKGGSTAA EVPELFASPQ PASNMGLYKA SGARQSKKPR  240
VEIPDDDEDF FIVPDLG                                                 257

SEQ ID NO: 183          moltype = DNA  length = 543
FEATURE                 Location/Qualifiers
misc_feature            1..543
                        note = Os04g41560.4, ortholog of AtBBX24 (G329), AtBBX25
                         (G1894)
source                  1..543
                        mol_type = unassigned DNA
                        organism = Oryza sativa
SEQUENCE: 183
atgaggatcc agtgcgacgc gtgcgaggcc gcggcggcca cggtggtgtg ctgcgcggac  60
gaggcggcgc tgtgcgcgcg ctgcgacgtc gagatccacg ccgccaacaa gctcgccagc  120
aagcaccagc gcctcccgct cgacgccgcg ctccccgccg ccctcccgcg ctgcgacgtc  180
tgccaggaga aggcggcgtt catcttctgc gtggaggaca gggcgctctt ctgccgggac  240
tgcgacgagc ccatccacgt cccggggacg ctctccggca accaccagcg ctacctcacc  300
accggcatcc gcgtcgggtt cagctccgtc tgtagcgcca acgccgacca cctcccgccg  360
ccagcgccca aggggaactc caagccgccg gcaagcggca tcgctgctgc tgctgctccc  420
aagccggccg tgtccgcggc ggcgcaggag gtgccgtcgt caccgttctt gccgccgtcg  480
ggctgggccg tcgaggatct cctgcagctc tccgactacg agtccagcga caaggcaagg  540
acc                                                                543

SEQ ID NO: 184          moltype = AA  length = 181
FEATURE                 Location/Qualifiers
REGION                  1..181
                        note = Os04g41560.4, domain coordinates 5-42, 58-95,
                         ortholog of AtBBX24 (G329), AtBBX25 (G1894)
source                  1..181
                        mol_type = protein
                        organism = Oryza sativa
SEQUENCE: 184
MRIQCDACEA AAATVVCCAD EAALCARCDV EIHAANKLAS KHQRLPLDAA LPAALPRCDV  60
CQEKAAFIFC VEDRALFCRD CDEPIHVPGT LSGNHQRYLT TGIRVGFSSV CSANADHLPP  120
PAPKGNSKPP ASGIAAAAAP KPAVSAAAQE VPSSPFLPPS GWAVEDLLQL SDYESSDKAR  180
T                                                                  181

SEQ ID NO: 185          moltype = DNA  length = 714
FEATURE                 Location/Qualifiers
misc_feature            1..714
                        note = Glyma11g13570.1, ortholog of AtBBX24 (G329), AtBBX25
                         (G1894)
source                  1..714
                        mol_type = unassigned DNA
                        organism = Glycine max
SEQUENCE: 185
atgaagattc agtgtgatgt gtgtgagaaa gcccctgcaa ccgtgatttg ttgcgcagat  60
gaggcagctt tgtgtgccaa atgtgacgtt gaagttcatg ctgcaaacaa gcttgcaagc  120
aagcaccaga ggcttctcct tcaatgtcta tcaaacaagc ttcccagatg tgacatatgc  180
caagataagc cagctttcat attttgtgtt gaggacagag cactcttctg taaagactgt  240
gatgagccaa ttcatttagc cagtagcctt tctgcaaacc accagcgctt cctcgctact  300
ggtatcaggg tggctttggg ttctaattgc accaaaggcc atgaaaaagg taacatggaa  360
ccatctaatc caaatgcaca agaagttcct gtgaaaactc cttctcagca agtgcctagc  420
ttcacatcct cttgggcagt tgatgacttg ttggaattaa cagactttga atcgccagac  480
aaaaagcaat ccctggaatt tggagaactt gaatggctag cagatgcagg cctttcagt  540
gaacagtttc ctcatgaagc tttagtcgca gctgaagttc ctcagcttcc agtgccacac  600
actagcagtg ttgcctcaca taaagccccc aaatccttgg tgtcttacaa aaagcctagg  660
attgaagtcc tggatgaaga tgatgatgaa cactgcactg tcccggatct cgga        714

SEQ ID NO: 186          moltype = AA  length = 238
```

```
FEATURE                Location/Qualifiers
REGION                 1..238
                       note = Glyma11g13570.1, domain coordinates 5-42, 57-94,
                        ortholog of AtBBX24 (G329), AtBBX25 (G1894)
source                 1..238
                       mol_type = protein
                       organism = Glycine max
SEQUENCE: 186
MKIQCDVCEK APATVICCAD EAALCAKCDV EVHAANKLAS KHQRLLLQCL SNKLPRCDIC  60
QDKPAFIFCV EDRALFCKDC DEPIHLASSL SANHQRFLAT GIRVALGSNC TKGHEKGNME  120
PSNPNAQEVP VKTPSQQVPS FTSSWAVDDL LELTDFESPD KKQSLEFGEL EWLADAGLFS  180
EQFPHEALVA AEVPQLPVPH TSSVASHKAP KSLVSYKKPR IEVLDEDDDE HCTVPDLG    238

SEQ ID NO: 187         moltype = DNA  length = 714
FEATURE                Location/Qualifiers
misc_feature           1..714
                       note = Glyma12g05570.1, ortholog of AtBBX24 (G329), AtBBX25
                        (G1894)
source                 1..714
                       mol_type = unassigned DNA
                       organism = Glycine max
SEQUENCE: 187
atgaaaattc agtgcgatgt gtgtgagaaa gccccggcaa ccgtgatttg ctgcgcagat  60
gaggcagctt tgtgtgccaa atgtgacgtt gaagttcatg ctgcaaacaa gcttgcaagc  120
aagcaccaga ggcttctcct tcaatcttta tctaacaagc ttcccagatg tgacatatgt  180
caagataagc cagctttcat attttgtgtt gaggacagag cactcttctg taaagactgt  240
gatgaaccta ttcatttagc cagtagcctt tctgcaaacc accagcgctt ccttgctact  300
ggtatccggg tggctttggg ttctaattgc accaaaggca atgaaaaagg tcacgtggaa  360
ccatctaaac caaaagcaca agaagttcct gcgaaaattc cttctcagca agtgcctagc  420
ttcacatcct cttgggcagt tgatgacttg ttggaattaa cagactttga atcaccagac  480
aaagttcaga agcaatccct tgagtttgga gaacttgaat ggctagcaga tgtaggcctt  540
tttggtgaac agtttcctca tgaagcttta gcggcggctg aagttcctca gcttccaatg  600
actagcagtg ttggctcaca caaagccccc aaatccttgt tgtcttacaa aaagcctagg  660
attgaagtcc tagatgaaga tgatgatgag cacttcaccg taccagatct cgga        714

SEQ ID NO: 188         moltype = AA  length = 238
FEATURE                Location/Qualifiers
REGION                 1..238
                       note = Glyma12g05570.1, domain coordinates 5-42, 57-94,
                        ortholog of AtBBX24 (G329), AtBBX25 (G1894)
source                 1..238
                       mol_type = protein
                       organism = Glycine max
SEQUENCE: 188
MKIQCDVCEK APATVICCAD EAALCAKCDV EVHAANKLAS KHQRLLLQSL SNKLPRCDIC  60
QDKPAFIFCV EDRALFCKDC DEPIHLASSL SANHQRFLAT GIRVALGSNC TKGNEKGHVE  120
PSKPKAQEVP AKIPSQQVPS FTSSWAVDDL LELTDFESPD KVQKQSLEFG ELEWLADVGL  180
FGEQFPHEAL AAAEVPQLPM TSSVGSHKAP KSLLSYKKPR IEVLDEDDDE HFTVPDLG    238

SEQ ID NO: 189         moltype = DNA  length = 717
FEATURE                Location/Qualifiers
misc_feature           1..717
                       note = Glyma13g41980.1, ortholog of AtBBX24 (G329), AtBBX25
                        (G1894)
source                 1..717
                       mol_type = unassigned DNA
                       organism = Glycine max
SEQUENCE: 189
atgaaaattc agtgtgatgt gtgtgagaga gctccggcaa cagtgatttg ttgtgcggat  60
gaggcagctt tgtgtgccaa atgtgacgtt gaagttcatg ctgcaaacaa gcttgcaagc  120
aagcaccaaa ggcttcttct tcaatgtcta tcaagcaagc ttccaagatg tgacatttgc  180
caagacaagc cagcattcat attttgtgtt gaagacagag cactcttctg tcaggattgt  240
gatgaaccaa ttcattcagc cggaagcctt tctgcgaacc accagcgctt ccttgctact  300
ggtatccgag tggcatcgag ttctaattgc accaaggaca atgaaaaaag tcacttggag  360
cctcctacta ggaatgcaca acaagtttct gcgaaaattc ctcctcagca agtgcctagc  420
ttcacttcct cttgggctgt tgatgactta ttggaactaa cagcctttga atcacctgag  480
aaaaaggaat ctctgcagtt tggagagctg gaatggctta cagatgtggg tatttttggt  540
gaacaatttg ctcaggaagc cttggctgca gctgaagtac ctcagcttcc agtaactcat  600
aacagtagca gtgttgcttc atacagaact tccaaatcct acatgtccca caaaaagcct  660
aggattgaag tcctaaatga tgatgatgat gagtatttta ctgtgcctga tcttggc     717

SEQ ID NO: 190         moltype = AA  length = 239
FEATURE                Location/Qualifiers
REGION                 1..239
                       note = Glyma13g41980.1, domain coordinates 5-42, 57-94,
                        ortholog of AtBBX24 (G329), AtBBX25 (G1894)
source                 1..239
                       mol_type = protein
                       organism = Glycine max
```

```
SEQUENCE: 190
MKIQCDVCER APATVICCAD EAALCAKCDV EVHAANKLAS KHQRLLLQCL SSKLPRCDIC  60
QDKPAFIFCV EDRALFCQDC DEPIHSAGSL SANHQRFLAT GIRVASSSNC TKDNEKSHLE  120
PPTRNAQQVS AKIPPQQVPS FTSSWAVDDL LELTAFESPE KKESLQFGEL EWLTDVGIFG  180
EQFAQEALAA AEVPQLPVTH NSSSVASYRT SKSYMSHKKP RIEVLNDDDD EYFTVPDLG   239

SEQ ID NO: 191         moltype = DNA  length = 606
FEATURE                Location/Qualifiers
misc_feature           1..606
                       note = Glyma13g41980.2, ortholog of AtBBX24 (G329), AtBBX25
                        (G1894)
source                 1..606
                       mol_type = unassigned DNA
                       organism = Glycine max
SEQUENCE: 191
atggatattg taataagttt cttagaagta ttgctcattt tgttctttcc tttctcctac  60
atataccaac aggacaagcc agcattcata ttttgtgttg aagacagagc actcttctgt  120
caggattgtg atgaaccaat tcattcagcc ggaagccttt ctgcgaacca ccagcgcttc  180
cttgctactg gtatccgagt ggcatcgagt tctaattgca ccaaggacaa tgaaaaaagt  240
cacttggagc ctcctactag gaatgcacaa caagtttctg cgaaaattcc tcctcagcaa  300
gtgcctagct tcacttcctc ttgggctgtt gatgacttat tggaactaac agcctttgaa  360
tcacctgaga aaaaggaatc tctgcagttt ggagagctgg aatggcttac agatgtgggt  420
atttttggtg aacaatttgc tcaggaagcc ttggctgcag ctgaagtacc tcagcttcca  480
gtaactcata acagtagcag tgttgcttca tacagaactt ccaaatccta catgtcccac  540
aaaaagccta ggattgaagt cctaaatgat gatgatgatg agtattttac tgtgcctgat  600
cttggc                                                             606

SEQ ID NO: 192         moltype = AA  length = 202
FEATURE                Location/Qualifiers
REGION                 1..202
                       note = Glyma13g41980.2, domain coordinates 24-57, ortholog
                        of AtBBX24 (G329), AtBBX25 (G1894)
source                 1..202
                       mol_type = protein
                       organism = Glycine max
SEQUENCE: 192
MDIVISFLEV LLILFFPFSY IYQQDKPAFI FCVEDRALFC QDCDEPIHSA GSLSANHQRF  60
LATGIRVASS SNCTKDNEKS HLEPPTRNAQ QVSAKIPPQQ VPSFTSSWAV DDLLELTAFE  120
SPEKKESLQF GELEWLTDVG IFGEQFAQEA LAAAEVPQLP VTHNSSSVAS YRTSKSYMSH  180
KKPRIEVLND DDDEYFTVPD LG                                           202

SEQ ID NO: 193         moltype = DNA  length = 603
FEATURE                Location/Qualifiers
misc_feature           1..603
                       note = Glyma13g41980.3, ortholog of AtBBX24 (G329), AtBBX25
                        (G1894)
source                 1..603
                       mol_type = unassigned DNA
                       organism = Glycine max
SEQUENCE: 193
atggatattg taataagttt cttagaagta ttgctcattt tgttctttcc tttctcctac  60
atataccaac aggacaagcc agcattcata ttttgtgttg aagacagagc actcttctgt  120
caggattgtg atgaaccaat tcattcagcc ggaagccttt ctgcgaacca ccagcgcttc  180
cttgctactg gtatccgagt ggcatcgagt tctaattgca ccaaggacaa tgaaaaaagt  240
cacttggagc ctcctactag gaatgcacaa caagtttctg cgaaaattcc tcctcagcaa  300
gtgcctagct tcacttcctc ttgggctgtt gatgacttat tggaactaac agcctttgaa  360
tcacctgaga aagaatctct gcagtttgga gagctggaat ggcttacaga tgtgggtatt  420
tttggtgaac aatttgctca ggaagccttg gctgcagctg aagtacctca gcttccagta  480
actcataaca gtagcagtgt tgcttcatac agaacttcca aatcctacat gtcccacaaa  540
aagcctagga ttgaagtcct aaatgatgat gatgatgagt attttactgt gcctgatctt  600
ggc                                                                603

SEQ ID NO: 194         moltype = AA  length = 201
FEATURE                Location/Qualifiers
REGION                 1..201
                       note = Glyma13g41980.3, domain coordinates 24-57, ortholog
                        of AtBBX24 (G329), AtBBX25 (G1894)
source                 1..201
                       mol_type = protein
                       organism = Glycine max
SEQUENCE: 194
MDIVISFLEV LLILFFPFSY IYQQDKPAFI FCVEDRALFC QDCDEPIHSA GSLSANHQRF  60
LATGIRVASS SNCTKDNEKS HLEPPTRNAQ QVSAKIPPQQ VPSFTSSWAV DDLLELTAFE  120
SPEKESLQFG ELEWLTDVGI FGEQFAQEAL AAAEVPQLPV THNSSSVASY RTSKSYMSHK  180
KPRIEVLNDD DDEYFTVPDL G                                            201

SEQ ID NO: 195         moltype = DNA  length = 720
FEATURE                Location/Qualifiers
misc_feature           1..720
```

```
                        note = Glyma15g03400.1, ortholog of AtBBX24 (G329), AtBBX25
                         (G1894)
source                  1..720
                        mol_type = unassigned DNA
                        organism = Glycine max
SEQUENCE: 195
atgaaaattc agtgtgacgt gtgtgagaga gctccagcaa cagtgatttg ttgcgcggat  60
gaggctgctt tgtgtgccaa atgtgacgtt gaagttcatg ctgcaaacaa gcttgcaagc  120
aagcaccaaa gacttcttct tcaatgtcta tcaagcaagc ttcccacatg tgacatttgc  180
caagacaagc cagcattcat atttgtgttt gaagacagag cactcttctg tcaggattgt  240
gatgaaccaa ttcattcagc cggaagcctt tccgcgaacc accagcgctt ccttgctact  300
ggtatccgag tggcctcgag ttctaattgc accaaagaca atgaaaaaag tcactcggag  360
cctcctaata ggagtgcaca acaagtttct gcgaaaattc ctcctcagca agtgcctagc  420
ttcacatcct cttgggctgt tgatgactta ttggaactaa caggctttga atcacctgag  480
aaaaaggaat ctctgcagtt tggagagctg gaatggctta cagatgtggg tattttcggc  540
gaacaatttg ctcaggaagc cttggctgca gctgaagtac ctcagcttcc cgaaactcat  600
aacagtagca gtgttgcttc atacaaaacc tccaaatcct acatgtccca caaaaagcct  660
aggattgaag tcctaaatga tgatgatgat gatgagtatt ttactgtgcc cgatctcggc  720

SEQ ID NO: 196          moltype = AA  length = 240
FEATURE                 Location/Qualifiers
REGION                  1..240
                        note = Glyma15g03400.1, domain coordinates 5-42, 57-94,
                         ortholog of AtBBX24 (G329), AtBBX25 (G1894)
source                  1..240
                        mol_type = protein
                        organism = Glycine max
SEQUENCE: 196
MKIQCDVCER APATVICCAD EAALCAKCDV EVHAANKLAS KHQRLLLQCL SSKLPTCDIC  60
QDKPAFIFCV EDRALFCQDC DEPIHSAGSL SANHQRFLAT GIRVASSSNC TKDNEKSHSE  120
PPNRSAQQVS AKIPPQQVPS FTSSWAVDDL LELTGFESPE KKESLQFGEL EWLTDVGIFG  180
EQFAQEALAA AEVPQLPETH NSSSVASYKT SKSYMSHKKP RIEVLNDDDD DEYFTVPDLG  240

SEQ ID NO: 197          moltype = DNA  length = 699
FEATURE                 Location/Qualifiers
misc_feature            1..699
                        note = AAS67368.1, ortholog of AtBBX24 (G329), AtBBX25
                         (G1894)
source                  1..699
                        mol_type = unassigned DNA
                        organism = Solanum lycopersicum
SEQUENCE: 197
atgaagatac agtgtgatgt gtgtgagaaa gctcaagcta ctgtgatttg ctgtgctgat  60
gaggctgctc tgtgtgcaaa atgtgatatt gaagttcatg ctgctaataa attagcaagc  120
aagcaccaaa ggcttcatct tcagtgccta tctaacaagc ttcctccttg tgatatttgc  180
caagataaag cagccttcat cttctgtgtt gaggatagag ctctcttttg caaggactgt  240
gacgaagcaa ttcattcagc cagcagcctc gctaagaacc accaacgctt cttagccact  300
ggaatccgtg tagccttgag ctcaagctgt aataaggaat cagtaaaaaa ccaactgcag  360
ccacaaccac ctcagcagaa ttcccaacaa gttggcttga aaatgcctcc acagcagttg  420
tcctgtataa catcaccatc ttggcctgtc gatgatttac taggatttcc agattatgag  480
tcgagtgaca agaaggatct acttgagctt ggtgaatttg agtggttagg gggcattgat  540
ctctttggtg aacaaacagc agctgaagtg cccgagctat cagtacctca gtcgagcaat  600
acaaatattt acaggacaac caaatatcaa atgccttaca agaagtccag aattgaaatc  660
ccagatgatg atgagtattt tactgtcccc gatcttggt                        699

SEQ ID NO: 198          moltype = AA  length = 233
FEATURE                 Location/Qualifiers
REGION                  1..233
                        note = AAS67368.1, domain coordinates 5-42, 57-94, ortholog
                         of AtBBX24 (G329), AtBBX25 (G1894)
source                  1..233
                        mol_type = protein
                        organism = Solanum lycopersicum
SEQUENCE: 198
MKIQCDVCEK AQATVICCAD EAALCAKCDI EVHAANKLAS KHQRLHLQCL SNKLPPCDIC  60
QDKAAFIFCV EDRALFCKDC DEAIHSASSL AKNHQRFLAT GIRVALSSSC NKESVKNQLQ  120
PQPPQQNSQQ VGLKMPPQQL SCITSPSWPV DDLLGFPDYE SSDKKDLLEL GEFEWLGGID  180
LFGEQTAAEV PELSVPQSSN TNIYRTTKYQ MPYKKSRIEI PDDDEYFTVP DLG         233

SEQ ID NO: 199          moltype = DNA  length = 549
FEATURE                 Location/Qualifiers
misc_feature            1..549
                        note = AtBBX19 (G902), AT4G38960.1, paralog of AtBBX18
                         (G1881)
source                  1..549
                        mol_type = unassigned DNA
                        organism = Arabidopsis thaliana
SEQUENCE: 199
atgcggattt tgtgcgatgc ttgcgagaac gcagccgcaa tcatcttttg cgccgccgat  60
```

```
gaagctgccc tttgtcgccc ctgcgatgaa aaagttcata tgtgcaacaa gctagctagt  120
cggcatgtac gtgttggttt agctgaacca agcaatgccc catgctgtga tatatgcgaa  180
aatgcacctg ccttctttta ctgtgagata gacggtagtt ctctttgtct gcaatgtgac  240
atggtagtac atgttggtgg caagagaaca cacggtcggt ttcttttgct gagacagaga  300
atcgagtttc caggggataa gcctaaagaa aacaatacga gggacaattt gcagaaccaa  360
agagtctcta caaatggaaa tggtgaagcc aatgggaaga ttgatgacga aatgattgat  420
ctaaatgcta atccacaaag agtacatgag ccatcatcaa ataacaacgg gattgatgta  480
aataacgaga acaatcacga gcctgcaggc cttgtaccag ttggaccctt taaacgagag  540
tctgagaag                                                          549

SEQ ID NO: 200         moltype = AA  length = 183
FEATURE                Location/Qualifiers
REGION                 1..183
                       note = AtBBX19 (G902), AT4G38960.1, domain coordinates
                        5-42, 56-84, paralog of AtBBX18 (G1881)
source                 1..183
                       mol_type = protein
                       organism = Arabidopsis thaliana
SEQUENCE: 200
MRILCDACEN AAAIIFCAAD EAALCRPCDE KVHMCNKLAS RHVRVGLAEP SNAPCCDICE  60
NAPAFFYCEI DGSSLCLQCD MVVHVGGKRT HGRFLLLRQR IEFPGDKPKE NNTRDNLQNQ  120
RVSTNGNGEA NGKIDDEMID LNANPQRVHE PSSNNNGIDV NNENNHEPAG LVPVGPFKRE  180
SEK                                                                183

SEQ ID NO: 201         moltype = DNA  length = 516
FEATURE                Location/Qualifiers
misc_feature           1..516
                       note = AtBBX18 (G1881), AT2G21320.1, paralog of AtBBX19
                        (G902)
source                 1..516
                       mol_type = unassigned DNA
                       organism = Arabidopsis thaliana
SEQUENCE: 201
atgcgaattt tgtgtgatgc ttgtgagagc gccgccgcta tcgtcttttg cgccgccgac  60
gaagctgccc tctgttgctc ctgcgacgaa aaagttcata agtgcaacaa gctggctagt  120
cggcatcttc gtgtaggctt agctgatccg agtaatgcac caagctgtga catatgcgaa  180
aatgcacccg cattctttta ctgtgagata gatggtagtt ccctttgtct acaatgtgat  240
atggtggtac atgttggtgg gaagagaaca cataggcggt ttctattact gagacagaga  300
attgagtttc caggcgataa gcctaatcat gctgaccaac tgggactacg gtgtcaaaag  360
gcttcctctg gtcgtggtca agaatcaaat gggaatggtg atcatgatca taatatgatc  420
gatcttaact ccaatcctca aagagtacac gagcctggat cacataacca agaggagggt  480
attgatgtaa ataacgcaaa caatcacgag catgaa                            516

SEQ ID NO: 202         moltype = AA  length = 172
FEATURE                Location/Qualifiers
REGION                 1..172
                       note = AtBBX18 (G1881), AT2G21320.1, domain coordinates
                        5-42, 56-92, paralog of AtBBX19 (G902)
source                 1..172
                       mol_type = protein
                       organism = Arabidopsis thaliana
SEQUENCE: 202
MRILCDACES AAAIVFCAAD EAALCCSCDE KVHKCNKLAS RHLRVGLADP SNAPSCDICE  60
NAPAFFYCEI DGSSLCLQCD MVVHVGGKRT HRRFLLLRQR IEFPGDKPNH ADQLGLRCQK  120
ASSGRGQESN GNGDHDHNMI DLNSNPQRVH EPGSHNQEEG IDVNNANNHE HE          172

SEQ ID NO: 203         moltype = DNA  length = 618
FEATURE                Location/Qualifiers
misc_feature           1..618
                       note = ACF85933.1, ortholog of AtBBX19 (G902), AtBBX18
                        (G1881)
source                 1..618
                       mol_type = unassigned DNA
                       organism = Zea mays
SEQUENCE: 203
atgcggacga tctgcgatgt gtgcgagagc gcaccggcgg tgctcttctg tgcggccgac  60
gaggcagcgc tttgccggcc ctgcgacgag aaggtacaca tgtgtaacaa gcttgctagt  120
cggcatgtga gagttggact tgcagaccct aataaacttg tccggtgtga tatatgtgaa  180
aattcacccg ctttcttcta ctgtgagata gacggcacct cactttgcct gagctgtgat  240
atgactgttc atgttggtgg caagcgaacc catggaagat acctgctcct aaggcaaagg  300
gttgaatttc caggagataa accgggccat atggatgacg tgcctatgga aatccaagat  360
cctgaaaacc agagagacca gaaaaagcca cccaaggagc aaacggcaaa ccaccataac  420
ggcgatgatc cggccactga tggcaactgt gatgaccagg gtaacattga ttcaaaaatg  480
atcgatctta atatgcgccc ggttcgtact catgggcaag aatcaaattc ccagactcag  540
ggggtaggtc ttagtgtgaa caaccatgac tctccagggg tggtgccaac aagcaattcc  600
gaaagagaca ccagcaag                                                618

SEQ ID NO: 204         moltype = AA  length = 206
FEATURE                Location/Qualifiers
```

```
REGION                  1..206
                        note = ACF85933.1, domain coordinates 5-42, 56-84, ortholog
                         of AtBBX19 (G902), AtBBX18 (G1881)
source                  1..206
                        mol_type = protein
                        organism = Zea mays
SEQUENCE: 204
MRTICDVCES APAVLFCAAD EAALCRPCDE KVHMCNKLAS RHVRVGLADP NKLVRCDICE  60
NSPAFFYCEI DGTSLCLSCD MTVHVGGKRT HGRYLLLRQR VEFPGDKPGH MDDVPMEIQD  120
PENQRDQKKP PKEQTANHHN GDDPATDGNC DDQGNIDSKM IDLNMRPVRT HGQESNSQTQ  180
GVGLSVNNHD SPGVVPTSNS ERDTSK                                       206

SEQ ID NO: 205          moltype = DNA  length = 618
FEATURE                 Location/Qualifiers
misc_feature            1..618
                        note = ACG27957.1, ortholog of AtBBX19 (G902), AtBBX18
                         (G1881)
source                  1..618
                        mol_type = unassigned DNA
                        organism = Zea mays
SEQUENCE: 205
atgcggacga tctgcgatgt gtgcgagagc gcaccggcgg tgctcttctg tgcggccgac  60
gaggcagcgc tttgccggcc ctgcgacgag aaggtacaca tgtgtaacaa gcttgctagt  120
cggcatgtga gagttggact tgcagaccct aataaacttg tccggtgtga tatatgtgaa  180
aattcacccg ctttcttcta ctgtgagata gacggcacct cactttgcct gagctgtgat  240
atgactgttc atgttggtgg caagcgaacc catggaagat acctgctcct aaggcaaagg  300
gttgaatttc caggagataa accgggccat atggatgacg tgcctatgga aatccaagat  360
cctgaaaacc agagagacca gaaaaagcca cccaaggagc aaacggcaaa ccaccataac  420
ggcgatgatc cggccactga tggcaactgt gatgaccagg gtaacattga ttcaaaaatg  480
atcgatctta atatgcgccc ggttcgtact catgggcaag aatcaaattc ccagactcag  540
ggggtaggtc ttagtgtgaa caaccatgac tctccagggg tggtgccaac aagcaattcc  600
gaaagagaca ccagcaag                                                618

SEQ ID NO: 206          moltype = AA  length = 206
FEATURE                 Location/Qualifiers
REGION                  1..206
                        note = ACG27957.1, domain coordinates 5-42, 56-84, ortholog
                         of AtBBX19 (G902), AtBBX18 (G1881)
source                  1..206
                        mol_type = protein
                        organism = Zea mays
SEQUENCE: 206
MRTICDVCES APAVLFCAAD EAALCRPCDE KVHMCNKLAS RHVRVGLADP NKLVRCDICE  60
NSPAFFYCEI DGTSLCLSCD MTVHVGGKRT HGRYLLLRQR VEFPGDKPGH MDDVPMEIQD  120
PENQRDQKKP PKEQTANHHN GDDPATDGNC DDQGNIDSKM IDLNMRPVRT HGQESNSQTQ  180
GVGLSVNNHD SPGVVPTSNS ERDTSK                                       206

SEQ ID NO: 207          moltype = DNA  length = 615
FEATURE                 Location/Qualifiers
misc_feature            1..615
                        note = ACL52378.1, ortholog of AtBBX19 (G902), AtBBX18
                         (G1881)
source                  1..615
                        mol_type = unassigned DNA
                        organism = Zea mays
SEQUENCE: 207
atgcggacga tctgcgatgt gtgcgagagc gcaccggcgg tgctcttctg tgcggccgac  60
gaggctgcgc tttgccggcc ttgcgacgag aaggtacaca tgtgcaacaa gcttgctagt  120
cggcatgtga gagttgggct tgcagaccct aataaactgg cacgttgtga tatatgcgag  180
aattcacctg ctttcttcta ctgtgagata gatggcacct cactttgcct gagctgtgat  240
atgactgttc atgttggtgg caaaagaacc catggtagat acctgctcct aaggcaaagg  300
gttgaatttc caggagataa accgggccat atggatgacg tgcctatgga gatcaaagat  360
cctgaaaacc agagagagca aaacacgccc aaggagcaaa tggcaaacca ccataacgtc  420
aatgatccag tctctgatgg caattgcgat ggccagggta acattgattc gaaaatgatc  480
gatcttaata tgcgcccggc tcgtactcat gggcaaggat caaattccca gactcagggg  540
gtggatctta gtgtgaacaa ccatgactct ccaggggtgg tgccaacaag taattccgaa  600
agagacgcca tcaag                                                   615

SEQ ID NO: 208          moltype = AA  length = 205
FEATURE                 Location/Qualifiers
REGION                  1..205
                        note = ACL52378.1, domain coordinates 5-42, 56-88, ortholog
                         of AtBBX19 (G902), AtBBX18 (G1881)
source                  1..205
                        mol_type = protein
                        organism = Zea mays
SEQUENCE: 208
MRTICDVCES APAVLFCAAD EAALCRPCDE KVHMCNKLAS RHVRVGLADP NKLARCDICE  60
NSPAFFYCEI DGTSLCLSCD MTVHVGGKRT HGRYLLLRQR VEFPGDKPGH MDDVPMEIKD  120
```

-continued

```
PENQREQNTP KEQMANHHNV NDPVSDGNCD GQGNIDSKMI DLNMRPARTH GQGSNSQTQG  180
VDLSVNNHDS PGVVPTSNSE RDAIK                                        205

SEQ ID NO: 209          moltype = DNA  length = 618
FEATURE                 Location/Qualifiers
misc_feature            1..618
                        note = NP_001141274.1, ortholog of AtBBX19 (G902), AtBBX18
                         (G1881)
source                  1..618
                        mol_type = unassigned DNA
                        organism = Zea mays
SEQUENCE: 209
atgcggacga tctgcgatgt gtgcgagagc gcaccggcgg tgctcttctg tgcggccgac  60
gaggcagcgc tttgccggcc ctgcgacgag aaggtacaca tgtgtaacaa gcttgctagt  120
cggcatgtga gagttggact tgcagaccct aataaacttg tccggtgtga tatatgtgaa  180
aattcacccg ctttcttcta ctgtgagata gacggcacct cactttgcct gagctgtgat  240
atgactgttc atgttggtgg caagcgaacc catggaagat acctgctcct aaggcaaagg  300
gttgaatttc caggagataa accgggccat atggatgacg tgcctatgga aatccaagat  360
cctgaaaacc agagagacca gaaaaagcca cccaaggagc aaacggcaaa ccaccataac  420
ggcgatgatc cggccactga tggcaactgt gatgaccagg gtaacattga ttcaaaaatg  480
atcgatctta atatgcgccc ggttcgtact catgggcaag aatcaaattc ccagactcag  540
ggggtaggtc ttagtgtgaa caaccatgac tctccagggg tggtgccaac aagcaattcc  600
gaaagagaca ccagcaag                                                618

SEQ ID NO: 210          moltype = AA  length = 206
FEATURE                 Location/Qualifiers
REGION                  1..206
                        note = NP_001141274.1, domain coordinates 5-42, 56-84,
                         ortholog of AtBBX19 (G902), AtBBX18 (G1881)
source                  1..206
                        mol_type = protein
                        organism = Zea mays
SEQUENCE: 210
MRTICDVCES APAVLFCAAD EAALCRPCDE KVHMCNKLAS RHVRVGLADP NKLVRCDICE  60
NSPAFFYCEI DGTSLCLSCD MTVHVGGKRT HGRYLLLRQR VEFPGDKPGH MDDVPMEIQD  120
PENQRDQKKP PKEQTANHHN GDDPATDGNC DDQGNIDSKM IDLNMRPVRT HGQESNSQTQ  180
GVGLSVNNHD SPGVVPTSNS ERDTSK                                       206

SEQ ID NO: 211          moltype = DNA  length = 1346
FEATURE                 Location/Qualifiers
misc_feature            1..1346
                        note = Pt_648693, ortholog of AtBBX19 (G902), AtBBX18
                         (G1881)
source                  1..1346
                        mol_type = unassigned DNA
                        organism = Populus trichocarpa
SEQUENCE: 211
aacagaaggc aggcaaagca agcgacgaat atcactccat tttcctttct tcttcatcgt  60
ccccagtttc ttagactcat aaacaagtcc tgttgtatgc tctcatcccc tctcctctcc  120
tctcctctcc ttttcaccat ttaaatctcc ctctccagtc tgtttgtcat tgactgttta  180
acttaataat aatcttaatc tcatgaaata ttgacaaatg gtgatgagaa ggagaaagga  240
gaaataatag aaagtagaga ttgaaaggtg acaggacagt gacaataata aagaaagaac  300
caaaactgat tctaaaaaac ggaaatgcga atgctttgtg atgtgtgtga aagcgcagct  360
gcgattcttt tctgtgctgc tgatgaagcc gcgctttgcc gctcctgcga cgagaaggtt  420
catatgtgta acaagctagc tagtcggcat gtacgagtag gacttgcaga tcctagtgat  480
gttccacagt gtgacatatg tgaaaaggca ccagctttct tttactgcga gatagatggc  540
agttcgctct gcttgcaatg tgatatgata gtgcatgttg gtggtaaaag gacccatggg  600
agatatctcc tgttgaggca gagagttgag tttccagggg ataaacctgg ctgtacagag  660
gaacaaggac agcaaccgct tgatgataat gaaacaagaa gggaccaaaa tcagccgcct  720
aagctcacag ctagagaaaa tcaacagaac cacagggcct ctccagttcc aatggtagag  780
aataacactg atagtgacgg gaaaatggac aacaaattga ttgatcttaa tgccaggcct  840
cagcgtgtac atgggaaaaa tccaactaac caggaaaacc atgaatcctc tagtttggct  900
ccttttggat tcttttaaagg ggagccacaa aagtaagcaa ggtatgatct gcatttagta  960
agcctaactc gtgttttctt ttctccattt attgtttcat aaagttgaca ttatggatgg  1020
ttgtgcggga agcttcaagt ttccattgaa gtcgattttc ttaaaccagc tcttggatga  1080
cttctacatg caaatatgca taggactcta aattccgctg cttgtaagat ggtgaatgta  1140
atcttctttt attcaaactg tggtttaaat atgtagctat atggatctgc aatgaagata  1200
aacaaatgtt gttatggcct tttaccgtgt tccatgtttg taagggcata acaaactgtg  1260
gtttaaatat atagctatat ggattctcaa aagaacaaaa agggcacatc tgttattgag  1320
atggagccta gctgaaattt actata                                       1346

SEQ ID NO: 212          moltype = AA  length = 203
FEATURE                 Location/Qualifiers
REGION                  1..203
                        note = Pt_648693, domain coordinates 5-42, 56-88, ortholog
                         of AtBBX19 (G902), AtBBX18 (G1881)
source                  1..203
                        mol_type = protein
                        organism = Populus trichocarpa
```

```
SEQUENCE: 212
MRMLCDVCES AAAILFCAAD EAALCRSCDE KVHMCNKLAS RHVRVGLADP SDVPQCDICE  60
KAPAFFYCEI DGSSLCLQCD MIVHVGGKRT HGRYLLLRQR VEFPGDKPGC TEEQGQQPLD  120
DNETRRDQNQ PPKLTARENQ QNHRASPVPM VENNTDSDGK MDNKLIDLNA RPQRVHGKNP  180
TNQENHESSS LAPFGFFKGE PQK                                         203

SEQ ID NO: 213          moltype = DNA  length = 996
FEATURE                 Location/Qualifiers
misc_feature            1..996
                        note = Pt_721866, ortholog of AtBBX19 (G902), AtBBX18
                         (G1881)
source                  1..996
                        mol_type = unassigned DNA
                        organism = Populus trichocarpa
SEQUENCE: 213
atgcgaacga tttgtgacgt gtgtgagagc gcagccgcga ttcttttttg tgcagctgat  60
gaagccgctc tttgccgttc ctgtgacgag aaggttcatt tgtgcaacaa gctagctagt  120
cggcacgtgc gagtaggact tgcagatcct agcgctgttc cacagtgtga catatgtgaa  180
aatgcaccag ctttctttta ctgtgagata gatggtagtt cgctctgctt gcaatgcgat  240
atgatagtac atgttggtgg taaaagaacc catggtagat atctcctgtt gaggcagagg  300
gttgagtttc caggggataa acctggccgg atggaggagc aaggacaaca acctcttgat  360
cataatgaaa caaggaggga ccaaaaccag ccacttaaac tcacagctag agaaaataaa  420
caaaaccaca gagcctctcc agttccaatg gtagagaata acacagatag cgacggaaaa  480
atggacaaca atttgattga tcttaatgcc aggcctcagc ggatacatgg acaaaattca  540
actaaccagg aaaatcacga atcttctagt gcggttcctg ttggatcctt caaaagagag  600
cctcaaaagt aagcaaggtg atttcggatg catgttgaga tattcagtac tgcaaccagc  660
cttgtctgct cttgcacttg cagcatttct tgtggttagg ctttccttcc tagcgcgaag  720
ttggtgaggt gatttttagt cttttgtatc aaatatcaat agagatatag cttgtgtgaa  780
agaaataaca agactctttg ttggttagca tttggctcat gtgctggctt gagttcacca  840
tcaccttcag gtcctgagat ttataattta ataaagcacg attcattcta aagatgatga  900
tgtgaagcga ccttcggaca ggagaaagtg gcttctgtcg tcgttattat tttgtttttt  960
tggtcagaaa tataaaaaaa atccactttt aaaaaa                           996

SEQ ID NO: 214          moltype = AA  length = 203
FEATURE                 Location/Qualifiers
REGION                  1..203
                        note = Pt_721866, domain coordinates 5-42, 56-88, ortholog
                        of AtBBX19 (G902), AtBBX18 (G1881)
source                  1..203
                        mol_type = protein
                        organism = Populus trichocarpa
SEQUENCE: 214
MRTICDVCES AAAILFCAAD EAALCRSCDE KVHLCNKLAS RHVRVGLADP SAVPQCDICE  60
NAPAFFYCEI DGSSLCLQCD MIVHVGGKRT HGRYLLLRQR VEFPGDKPGR MEEQGQQPLD  120
HNETRRDQNQ PLKLTARENK QNHRASPVPM VENNTDSDGK MDNNLIDLNA RPQRIHGQNS  180
TNQENHESSS AVPVGSFKRE PQK                                         203

SEQ ID NO: 215          moltype = DNA  length = 1073
FEATURE                 Location/Qualifiers
misc_feature            1..1073
                        note = Pt_741179, ortholog of AtBBX19 (G902), AtBBX18
                         (G1881)
source                  1..1073
                        mol_type = unassigned DNA
                        organism = Populus trichocarpa
SEQUENCE: 215
ttatgtccct ctctttctat caccaccaac aacaaaaaca ttaacatttg atagacagcg  60
taaaaatcaa atagtgaagc tgtgtcttgt tgtggtgttt gttatcttta ttaaaagaaa  120
ctgtacgtaa atatttttc tattttcttg attttggaga aatgagagtg agagataatt  180
aattatgcgt accctttgtg acgcttgtga aagtgctttt gctattgttt tctgtgctgc  240
tgatgaggcc gcactttgcc ttgcctgcga taagaaggtt catatgtgca acaaacttgc  300
gagcaggcat gttcgagtgg gtctggcgaa tcccagtgaa gttcctcgtt gtgatatatg  360
tgaaaatgca cctgctttct tctactgtga gacagatgga agttcccttt gcttgcaatg  420
tgatatgact gttcatgttg gaggtaaaag aacacacggg agatatcttc tgttgagaca  480
aaaaattgag tttccagggg atcaacctca gcctgaggac ccagcaccgc aacctatgta  540
tccaggggag acaagaagag gacagaatcg accacaaaag gcaacatcag gagagaacag  600
acagaatcgc caagcttctc cagttctgat gtcggtcact aattctgatg ggcatgacaa  660
ggtggataag aatatgattg atttgaatat gaagcctcat cgaattcatg aacatgcttc  720
aaataatcag gaacaataat atttttatat taacggagcg gccgcgaagc tgaaagcagg  780
gttcctatgt tgcctggaaa gctggagaag agcagggttt tttctatgct tctcttatca  840
agtagttggc atttcatgtt tcaatatttc attttcttct cccctgtttt cctttgatat  900
ggatgatgtg ctttaagtct tgcagatgga tttttaccaa taatgtagtt tagttgctag  960
acaagctttg gacggtatac acatctattg tgaaaaaaca tgcagcaatt atagatggat  1020
attgtaatag aagagaaact agaaataact gaagatttaa tatagttcga aaa         1073

SEQ ID NO: 216          moltype = AA  length = 184
FEATURE                 Location/Qualifiers
REGION                  1..184
                        note = Pt_741179, domain coordinates 5-42, 56-88, ortholog
```

-continued

```
                          of AtBBX19 (G902), AtBBX18 (G1881)
source                   1..184
                         mol_type = protein
                         organism = Populus trichocarpa
SEQUENCE: 216
MRTLCDACES AFAIVFCAAD EAALCLACDK KVHMCNKLAS RHVRVGLANP SEVPRCDICE  60
NAPAFFYCET DGSSLCLQCD MTVHVGGKRT HGRYLLLRQK IEFPGDQPQP EDPAPQPMYP  120
GETRRGQNRP QKATSGENRQ NRQASPVLMS VTNSDGHDKV DKNMIDLNMK PHRIHEHASN  180
NQEQ                                                              184

SEQ ID NO: 217           moltype = DNA  length = 1347
FEATURE                  Location/Qualifiers
misc_feature             1..1347
                         note = Pt_820080, ortholog of AtBBX19 (G902), AtBBX18
                          (G1881)
source                   1..1347
                         mol_type = unassigned DNA
                         organism = Populus trichocarpa
SEQUENCE: 217
gctgtgcctt gttgcgatgt ttgatatctt tattaaagga aactgtactt gaatcctttt  60
tcttgttgct tgattttgga gaaatgagag tgagagaaaa ttatgcgtac cctttgcgac  120
gcctgtgaga gtgctgctgc tattgtcttc tgtgctgctg atgaggctgc actttgcctt  180
gcctgcgatg agaaggttca tatgtgcaac aaacttgcta gcaggcatgt gcgagtgggt  240
ctggcaaatc ccagtgacgt tccacgctgt gacatatgtg aaaatgcacc tgctttcttt  300
tattgtgaga cagatggaag ttccctttgc ttgcaatgtg atatgactgt tcatgttgga  360
ggtaaaagga cacatgggag atatcttttg ttgagacaaa gagttgagtt tccaggggat  420
aaacctcagc ctgatgacct acattcgcaa cctatgcatc caggggagac aaggaaagga  480
cagaatcagc caccaaaggc aacagcagaa gagaagcgac agaatcgcca ggtttctcca  540
gctccaatgt cactctctaa ttctgatgga catgacaaag tggataaaaa gatgattgat  600
ttgaatatga agcctcaacg aactgatcac gaacaagctt ctaataatca ggaactgtga  660
cattattatg ttaatggagc gatcgcaaag ctgaaagcac ggttcctatg ccctcagaga  720
gctggacagg agcagggttt cttctatgct tctcttacgt agtacgtagt tagcatgtca  780
tgtgtcaata tttcatgttc ttctcccctg tttttcttc gacatggatg atgtgcttct  840
aaggcttggg gaatgtgttt tcacgaataa tgtagcttag ttgtttagac tagcagtgga  900
cagtatccac atcttcaatt gcaaagaaaa ggtatagaat caagtgcaat tggttgcttt  960
gtggttgtgt tcgagatatt tttcttccca tgcatccctt atttccaagt gtctgatatt  1020
cgcagaagtg gcattgtaag aaatttcttt ggagtctaga gaattcggta tactatttca  1080
gattactgca agagcaagtt tccagctgtt ctttgtcttg atttcggatg gcgaacgttg  1140
tttttgaaag cagacttctg atacatgtca caacgcttcc aacgcaaatc gatagaatcg  1200
ttacatttgc atgcatgggc catggatcta agctcgctgg atttcaagac cagtggcatt  1260
tcccattttt ctgtgaacgc aacttggaca cctcctgtct tctgtgtatg tgttgaagaa  1320
caataatcag tttattaacc atggttt                                     1347

SEQ ID NO: 218           moltype = AA  length = 185
FEATURE                  Location/Qualifiers
REGION                   1..185
                         note = Pt_820080, domain coordinates 5-42, 56-88, ortholog
                          of AtBBX19 (G902), AtBBX18 (G1881)
source                   1..185
                         mol_type = protein
                         organism = Populus trichocarpa
SEQUENCE: 218
MRTLCDACES AAAIVFCAAD EAALCLACDE KVHMCNKLAS RHVRVGLANP SDVPRCDICE  60
NAPAFFYCET DGSSLCLQCD MTVHVGGKRT HGRYLLLRQR VEFPGDKPQP DDLHSQPMHP  120
GETRKGQNQP PKATAEEKRQ NRQVSPAPMS LSNSDGHDKV DKKMIDLNMK PQRTDHEQAS  180
NNQEL                                                             185

SEQ ID NO: 219           moltype = DNA  length = 633
FEATURE                  Location/Qualifiers
misc_feature             1..633
                         note = Os09g35880.1, ortholog of AtBBX19 (G902), AtBBX18
                          (G1881)
source                   1..633
                         mol_type = unassigned DNA
                         organism = Oryza sativa
SEQUENCE: 219
atgcggacga tctgcgacgt gtgcgagagc gcgccggcgg tgctcttctg cgtggccgac  60
gaggccgcgc tctgccggtc ctgcgacgag aaggtgcata tgtgtaacaa gcttgctagg  120
cggcacgtga gagttgggct tgcagaccct aataaagttc aacgctgtga tatatgtgaa  180
aatgcccccg ccttcttcta ttgcgagata gatggtacat cactttgcct tagttgtgat  240
atgactgttc atgttggtgg gaaacgaacc catggaagat acctgctcct aaggcaacgg  300
gttgaatttc caggagataa accaggtcat atggatgatg ttgctatgca acagaaagat  360
cctgaaaacc ggacggatca aaagaaggcc cctcactcag taacaaagga gcaaatggca  420
aaccatcata atgtgtctga tgatccagcc tcagatggca actgcgatga ccagggtaac  480
atcgattcca aaatgattga tcttaatatg agacccgtcc gtactcatgg acaaggttca  540
aactcacaga ctcagggcgt ggatgttagc gtcaacaatc atgattctcc aggagtggtg  600
ccaacatgta atttcgaacg agaagccaac aaa                              633

SEQ ID NO: 220           moltype = AA  length = 211
```

```
FEATURE                 Location/Qualifiers
REGION                  1..211
                        note = Os09g35880.1, domain coordinates 5-42, 56-88,
                         ortholog of AtBBX19 (G902), AtBBX18 (G1881)
source                  1..211
                        mol_type = protein
                        organism = Oryza sativa
SEQUENCE: 220
MRTICDVCES APAVLFCVAD EAALCRSCDE KVHMCNKLAR RHVRVGLADP NKVQRCDICE  60
NAPAFFYCEI DGTSLCLSCD MTVHVGGKRT HGRYLLLRQR VEFPGDKPGH MDDVAMQQKD  120
PENRTDQKKA PHSVTKEQMA NHHNVSDDPA SDGNCDDQGN IDSKMIDLNM RPVRTHGQGS  180
NSQTQGVDVS VNNHDSPGVV PTCNFEREAN K                                211

SEQ ID NO: 221          moltype = DNA  length = 552
FEATURE                 Location/Qualifiers
misc_feature            1..552
                        note = Glyma01g37370.1, ortholog of AtBBX19 (G902), AtBBX18
                         (G1881)
source                  1..552
                        mol_type = unassigned DNA
                        organism = Glycine max
SEQUENCE: 221
atgcgaacgc tttgtgatgc ttgtgagagc gccgcggcta tagttttctg cgccgctgat  60
gaggctgcac tttgtcgtgc ctgtgatgag aaggttcaca tgtgcaacaa gctagctagt  120
aggcatgtga gggttggtct tgctagtcca agtgatgtac cacggtgtga catatgtgag  180
aatgcacctg ctttcttcta ttgcgagaca gatggaagtt ccctttgttt gcagtgtgat  240
atgattgttc atgttggagg taaaagaacg catggaagat atcttctgtt caggcaaaga  300
gttgagtttc caggagataa atctagtcat gctgaaaatc cggcttcaca accattggaa  360
ccaggtgagg ctaaaagagg acaaaatcca cttcccaaac taaaaatggg agagaagcaa  420
caaaatcaca agatgcctat ggttccaacg ccaggacctg atgctgatgg gcatgccaag  480
atggaaagta aaatgattga tttgaacatg aagcctaata gaatacatga acaagcatca  540
aataatcagc ca                                                     552

SEQ ID NO: 222          moltype = AA  length = 184
FEATURE                 Location/Qualifiers
REGION                  1..184
                        note = Glyma01g37370.1, domain coordinates 5-42, 56-88,
                         ortholog of AtBBX19 (G902), AtBBX18 (G1881)
source                  1..184
                        mol_type = protein
                        organism = Glycine max
SEQUENCE: 222
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQPLE  120
PGEAKRGQNP LPKLKMGEKQ QNHKMPMVPT PGPDADGHAK MESKMIDLNM KPNRIHEQAS  180
NNQP                                                              184

SEQ ID NO: 223          moltype = DNA  length = 579
FEATURE                 Location/Qualifiers
misc_feature            1..579
                        note = Glyma11g07930.1, ortholog of AtBBX19 (G902), AtBBX18
                         (G1881)
source                  1..579
                        mol_type = unassigned DNA
                        organism = Glycine max
SEQUENCE: 223
atgcgaacgc tttgtgatgc ttgtgagagt gcggcggcta tagttttctg cgccgctgat  60
gaggctgcac tttgtcgtgc ctgtgatgag aaggttcaca tgtgcaataa gctagctagt  120
aggcatgtga gggttggtct tgcaagtcca agtgatgtgc cacggtgtga catatgtgag  180
aatgcaccag ctttcttcta ttgcgagaca gatggaagtt ccctttgttt gcagtgtgat  240
atgattgttc atgttggtgg taaaagaacg catggaagat atcttctgtt caggcaaaga  300
gttgagtttc caggagataa atctagtcat gctgaaaatc cggcttcaca agcattggaa  360
ccaggtgagg ctaaaagagg acaaaatcca cttcccaagc taaaaatggg agagaaacaa  420
caaaatcaca ggatgcctat ggttccaaca ccaggacctg atgctgatgg gcaaaccaag  480
atggaaacta aaatgattga tttgaacatg aagcctaata gaatacatga acaagcatca  540
aataaccagt gcagttggat gaaagtagaa ccctttcca                        579

SEQ ID NO: 224          moltype = AA  length = 193
FEATURE                 Location/Qualifiers
REGION                  1..193
                        note = Glyma11g07930.1, domain coordinates 5-42, 56-88,
                         ortholog of AtBBX19 (G902), AtBBX18 (G1881)
source                  1..193
                        mol_type = protein
                        organism = Glycine max
SEQUENCE: 224
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQALE  120
PGEAKRGQNP LPKLKMGEKQ QNHRMPMVPT PGPDADGQTK METKMIDLNM KPNRIHEQAS  180
```

```
NNQCSWMKVE PFP                                                  193

SEQ ID NO: 225         moltype = DNA  length = 552
FEATURE                Location/Qualifiers
misc_feature           1..552
                       note = Glyma11g07930.2, ortholog of AtBBX19 (G902), AtBBX18
                        (G1881)
source                 1..552
                       mol_type = unassigned DNA
                       organism = Glycine max
SEQUENCE: 225
atgcgaacgc tttgtgatgc ttgtgagagt gcggcggcta tagttttctg cgccgctgat  60
gaggctgcac tttgtcgtgc ctgtgatgag aaggttcaca tgtgcaataa gctagctagt  120
aggcatgtga gggttggtct tgcaagtcca agtgatgtgc cacggtgtga catatgtgag  180
aatgcaccag ctttcttcta ttgcgagaca gatggaagtt ccctttgttt gcagtgtgat  240
atgattgttc atgttggtgg taaaagaacg catggaagat atcttctgtt caggcaaaga  300
gttgagtttc caggagataa atctagtcat gctgaaaatc cggcttcaca agcattggaa  360
ccaggtgagg ctaaaagagg acaaaatcca cttcccaagc taaaaatggg agagaaacaa  420
caaaatcaca ggatgcctat ggttccaaca ccaggacctg atgctgatgg gcaaaccaag  480
atggaaacta aaatgattga tttgaacatg aagcctaata gaatacatga acaagcatca  540
aataaccagc ca                                                   552

SEQ ID NO: 226         moltype = AA  length = 184
FEATURE                Location/Qualifiers
REGION                 1..184
                       note = Glyma11g07930.2, domain coordinates 5-42, 56-88,
                        ortholog of AtBBX19 (G902), AtBBX18 (G1881)
source                 1..184
                       mol_type = protein
                       organism = Glycine max
SEQUENCE: 226
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQALE  120
PGEAKRGQNP LPKLKMGEKQ QNHRMPMVPT PGPDADGQTK METKMIDLNM KPNRIHEQAS  180
NNQP                                                            184

SEQ ID NO: 227         moltype = DNA  length = 552
FEATURE                Location/Qualifiers
misc_feature           1..552
                       note = Glyma11g07930.3, ortholog of AtBBX19 (G902), AtBBX18
                        (G1881)
source                 1..552
                       mol_type = unassigned DNA
                       organism = Glycine max
SEQUENCE: 227
atgcgaacgc tttgtgatgc ttgtgagagt gcggcggcta tagttttctg cgccgctgat  60
gaggctgcac tttgtcgtgc ctgtgatgag aaggttcaca tgtgcaataa gctagctagt  120
aggcatgtga gggttggtct tgcaagtcca agtgatgtgc cacggtgtga catatgtgag  180
aatgcaccag ctttcttcta ttgcgagaca gatggaagtt ccctttgttt gcagtgtgat  240
atgattgttc atgttggtgg taaaagaacg catggaagat atcttctgtt caggcaaaga  300
gttgagtttc caggagataa atctagtcat gctgaaaatc cggcttcaca agcattggaa  360
ccaggtgagg ctaaaagagg acaaaatcca cttcccaagc taaaaatggg agagaaacaa  420
caaaatcaca ggatgcctat ggttccaaca ccaggacctg atgctgatgg gcaaaccaag  480
atggaaacta aaatgattga tttgaacatg aagcctaata gaatacatga acaagcatca  540
aataaccagc ca                                                   552

SEQ ID NO: 228         moltype = AA  length = 184
FEATURE                Location/Qualifiers
REGION                 1..184
                       note = Glyma11g07930.3, domain coordinates 5-42, 56-88,
                        ortholog of AtBBX19 (G902), AtBBX18 (G1881)
source                 1..184
                       mol_type = protein
                       organism = Glycine max
SEQUENCE: 228
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQALE  120
PGEAKRGQNP LPKLKMGEKQ QNHRMPMVPT PGPDADGQTK METKMIDLNM KPNRIHEQAS  180
NNQP                                                            184

SEQ ID NO: 229         moltype = DNA  length = 567
FEATURE                Location/Qualifiers
misc_feature           1..567
                       note = Glyma11g07930.4, ortholog of AtBBX19 (G902), AtBBX18
                        (G1881)
source                 1..567
                       mol_type = unassigned DNA
                       organism = Glycine max
SEQUENCE: 229
```

```
atgcgaacgc tttgtgatgc ttgtgagagt gcggcggcta tagttttctg cgccgctgat  60
gaggctgcac tttgtcgtgc ctgtgatgag aaggttcaca tgtgcaataa gctagctagt  120
aggcatgtga gggttggtct tgcaagtcca agtgatgtgc cacggtgtga catatgtgag  180
aatgcaccag ctttcttcta ttgcgagaca gatggaagtt ccctttgttt gcagtgtgat  240
atgattgttc atgttggtgg taaaagaacg catggaagat atcttctgtt caggcaaaga  300
gttgagtttc caggagataa atctagtcat gctgaaaatc cggcttcaca agcattggaa  360
ccaggtgagg ctaaaagagg acaaaatcca cttcccaagc taaaaatggg agagaaacaa  420
caaaatcaca ggatgcctat ggttccaaca ccaggacctg atgctgatgg gcaaaccaag  480
atggaaacta aaatgattga tttgaacatg aagcctaata gaatacatga acaagcatca  540
aataaccagg ttagagttca tgggaag                                      567

SEQ ID NO: 230         moltype = AA  length = 189
FEATURE                Location/Qualifiers
REGION                 1..189
                       note = Glyma11g07930.4, domain coordinates 5-42, 56-88,
                        ortholog of AtBBX19 (G902), AtBBX18 (G1881)
source                 1..189
                       mol_type = protein
                       organism = Glycine max
SEQUENCE: 230
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQALE  120
PGEAKRGQNP LPKLKMGEKQ QNHRMPMVPT PGPDADGQTK METKMIDLNM KPNRIHEQAS  180
NNQVRVHGK                                                          189

SEQ ID NO: 231         moltype = DNA  length = 636
FEATURE                Location/Qualifiers
misc_feature           1..636
                       note = Glyma11g11850.1, ortholog of AtBBX19 (G902), AtBBX18
                        (G1881)
source                 1..636
                       mol_type = unassigned DNA
                       organism = Glycine max
SEQUENCE: 231
atgcgaaccc tttgcgacgt atgcgagagc gccgctgcca ttctcttctg cgccgctgat  60
gaggccgctc tctgctccgc ttgtgaccac aagatccata tgtgtaacaa acttgctagt  120
aggcatgttc gagttggcct tgctgacccc actgatgttc cacgctgtga catatgtgaa  180
aatgcacctg ctttctttta ctgtgagata gatggtagtt cgctgtgtct gcaatgtgat  240
atgattgtgc atgttggtgg taaaagaacc catggaagat atcttctatt gaggcaaaga  300
gctcagtttc caggtgataa acctgcccaa atggaagaac tagagctgca acctatggat  360
caaaatgaat cgagaaggga tgaaagtcag tcactcaagc taaaaacaag agatagtcag  420
cagaatcaca gtgtctcacc ttttccaagg caagaaaata atattgatgg tcatggaaaa  480
atggataaaa agttaattga tcttaatacc aggccactgc ggttaaatgg atcagcacca  540
aacaaccagg aacaatgcat ggatatttta agaggcaata atcatgaatc tgccagtgtg  600
ccaccagtag aatccttcaa acaagagtct gagaag                            636

SEQ ID NO: 232         moltype = AA  length = 212
FEATURE                Location/Qualifiers
REGION                 1..212
                       note = Glyma11g11850.1, domain coordinates 5-42, 56-88,
                        ortholog of AtBBX19 (G902), AtBBX18 (G1881)
source                 1..212
                       mol_type = protein
                       organism = Glycine max
SEQUENCE: 232
MRTLCDVCES AAAILFCAAD EAALCSACDH KIHMCNKLAS RHVRVGLADP TDVPRCDICE  60
NAPAFFYCEI DGSSLCLQCD MIVHVGGKRT HGRYLLLRQR AQFPGDKPAQ MEELELQPMD  120
QNESRRDESQ SLKLKTRDSQ QNHSVSPFPR QENNIDGHGK MDKKLIDLNT RPLRLNGSAP  180
NNQEQCMDIL RGNNHESASV PPVESFKQES EK                                 212

SEQ ID NO: 233         moltype = DNA  length = 537
FEATURE                Location/Qualifiers
misc_feature           1..537
                       note = Glyma12g04130.1, ortholog of AtBBX19 (G902), AtBBX18
                        (G1881)
source                 1..537
                       mol_type = unassigned DNA
                       organism = Glycine max
SEQUENCE: 233
atgcgaaccc tttgcgacgt atgcgagagc gccgctgcca ttgtcttctg cgccgctgat  60
gaggctgctc tctgctccgc ttgtgaccac aagatccata tgtgtaacaa acttgctagt  120
agacacgttc gggttggcct tgctgacccc actgatgttc cacgctgtga catatgtgaa  180
aacgcacctg ctttctttta ctgtgagata gatggtagtt cgctgtgtct gcaatgtgat  240
atgattgtgc atgttggtgg taaaagaact catggaagat atcttctatt gaggcaaaga  300
gttcagtttc catatagtca gcagaatcac agtgtctcac ctgttccaag acaagaaaat  360
aatattgatg gtcatggaaa aatggataaa aagttaattg atcttaatac gaggccactg  420
cggttaaatg gagcagcacc aaacaaccag gaacgaggta tggatatttt aagaggcaat  480
aatcataaat ctgcgagtgt gccaccagta gaatccttca aacaagagtc tgagaag     537
```

```
SEQ ID NO: 234          moltype = AA  length = 179
FEATURE                 Location/Qualifiers
REGION                  1..179
                        note = Glyma12g04130.1, domain coordinates 5-42, 56-88,
                         ortholog of AtBBX19 (G902), AtBBX18 (G1881)
source                  1..179
                        mol_type = protein
                        organism = Glycine max
SEQUENCE: 234
MRTLCDVCES AAAIVFCAAD EAALCSACDH KIHMCNKLAS RHVRVGLADP TDVPRCDICE  60
NAPAFFYCEI DGSSLCLQCD MIVHVGGKRT HGRYLLLRQR VQFPYSQQNH SVSPVPRQEN  120
NIDGHGKMDK KLIDLNTRPL RLNGAAPNNQ ERGMDILRGN NHKSASVPPV ESFKQESEK   179

SEQ ID NO: 235          moltype = AA  length = 37
FEATURE                 Location/Qualifiers
REGION                  1..37
                        note = conserved domain of AtBBX28 (G1481)
source                  1..37
                        mol_type = protein
                        organism = Arabidopsis thaliana
SEQUENCE: 235
CDLCNGVARM YCESDQASLC WDCDGKVHGA NFLVAKH                           37

SEQ ID NO: 236          moltype = AA  length = 37
FEATURE                 Location/Qualifiers
REGION                  1..37
                        note = conserved domain of AtBBX29 (G900)
source                  1..37
                        mol_type = protein
                        organism = Arabidopsis thaliana
SEQUENCE: 236
CELCCGVARM YCESDQASLC WDCDGKVHGA NFLVAKH                           37

SEQ ID NO: 237          moltype = AA  length = 37
FEATURE                 Location/Qualifiers
REGION                  1..37
                        note = conserved domain of ACN33981.1
source                  1..37
                        mol_type = protein
                        organism = Zea mays
SEQUENCE: 237
CELCGAAARV YCGADEATLC WGCDAQVHGA NFLVARH                           37

SEQ ID NO: 238          moltype = AA  length = 37
FEATURE                 Location/Qualifiers
REGION                  1..37
                        note = conserved domain of Pt_568988
source                  1..37
                        mol_type = protein
                        organism = Populus trichocarpa
SEQUENCE: 238
CELCGSSARM YCESDQASLC WDCDEKVHTA NFLVAKH                           37

SEQ ID NO: 239          moltype = AA  length = 37
FEATURE                 Location/Qualifiers
REGION                  1..37
                        note = conserved domain of Pt_571834
source                  1..37
                        mol_type = protein
                        organism = Populus trichocarpa
SEQUENCE: 239
CELCKNPART YCESDEANLC WNCDTKVHGA NFLVARH                           37

SEQ ID NO: 240          moltype = AA  length = 37
FEATURE                 Location/Qualifiers
REGION                  1..37
                        note = conserved domain of Pt_582065
source                  1..37
                        mol_type = protein
                        organism = Populus trichocarpa
SEQUENCE: 240
CELCGSSARM FCESDQASLC WDCDEKVHSA NFLVAKH                           37

SEQ ID NO: 241          moltype = AA  length = 37
FEATURE                 Location/Qualifiers
REGION                  1..37
                        note = conserved domain of Pt_758524
source                  1..37
                        mol_type = protein
```

```
                         organism = Populus trichocarpa
SEQUENCE: 241
CELCDSFAQM HCESDQAILC SACDAYVHSA NFLAAKH                         37

SEQ ID NO: 242           moltype = AA  length = 37
FEATURE                  Location/Qualifiers
REGION                   1..37
                         note = conserved domain of Os08g08120.1
source                   1..37
                         mol_type = protein
                         organism = Oryza sativa
SEQUENCE: 242
CELCGAAARV YCGADEATLC WGCDAQVHGA NFLVARH                         37

SEQ ID NO: 243           moltype = AA  length = 37
FEATURE                  Location/Qualifiers
REGION                   1..37
                         note = conserved domain of Os08g08120.2
source                   1..37
                         mol_type = protein
                         organism = Oryza sativa
SEQUENCE: 243
CELCGAAARV YCGADEATLC WGCDAQVHGA NFLVARH                         37

SEQ ID NO: 244           moltype = AA  length = 37
FEATURE                  Location/Qualifiers
REGION                   1..37
                         note = conserved domain of Os08g08120.3
source                   1..37
                         mol_type = protein
                         organism = Oryza sativa
SEQUENCE: 244
CELCGAAARV YCGADEATLC WGCDAQVHGA NFLVARH                         37

SEQ ID NO: 245           moltype = AA  length = 37
FEATURE                  Location/Qualifiers
REGION                   1..37
                         note = conserved domain of Glyma06g39810.1
source                   1..37
                         mol_type = protein
                         organism = Glycine max
SEQUENCE: 245
CVLCEKRAMM LCDSDQAKLC WECDEKVHSA NFLVAKH                         37

SEQ ID NO: 246           moltype = AA  length = 37
FEATURE                  Location/Qualifiers
REGION                   1..37
                         note = conserved domain of Glyma06g45620.1
source                   1..37
                         mol_type = protein
                         organism = Glycine max
SEQUENCE: 246
CELCKVPARI FCESDQASLC WDCDAKVHSA NFLVARH                         37

SEQ ID NO: 247           moltype = AA  length = 37
FEATURE                  Location/Qualifiers
REGION                   1..37
                         note = conserved domain of G4015
source                   1..37
                         mol_type = protein
                         organism = Glycine max
SEQUENCE: 247
CELCHQLASL YCPSDSAFLC FHCDAAVHAA NFLVARH                         37

SEQ ID NO: 248           moltype = AA  length = 37
FEATURE                  Location/Qualifiers
REGION                   1..37
                         note = conserved domain of Glyma09g35960.1
source                   1..37
                         mol_type = protein
                         organism = Glycine max
SEQUENCE: 248
CALCKKRAMM LCDSDQAKLC WECDEKVHSA NFLVAKH                         37

SEQ ID NO: 249           moltype = AA  length = 37
FEATURE                  Location/Qualifiers
REGION                   1..37
                         note = conserved domain of Glyma12g11230.1
source                   1..37
```

```
                        mol_type = protein
                        organism = Glycine max
SEQUENCE: 249
CELCKVPARI FCESDQASLC WDCDAKVHSA NFLVARH                            37

SEQ ID NO: 250          moltype = AA  length = 37
FEATURE                 Location/Qualifiers
REGION                  1..37
                        note = conserved domain of Glyma12g32470.1
source                  1..37
                        mol_type = protein
                        organism = Glycine max
SEQUENCE: 250
CELCKLPART FCESDQASLC WDCDAKVHGA NFLVARH                            37

SEQ ID NO: 251          moltype = AA  length = 37
FEATURE                 Location/Qualifiers
REGION                  1..37
                        note = conserved domain of G4014
source                  1..37
                        mol_type = protein
                        organism = Glycine max
SEQUENCE: 251
CELCNSPAKL FCESDQASLC WKCDAKVHSA NFLVTKH                            37

SEQ ID NO: 252          moltype = AA  length = 37
FEATURE                 Location/Qualifiers
REGION                  1..37
                        note = conserved domain of G4016
source                  1..37
                        mol_type = protein
                        organism = Glycine max
SEQUENCE: 252
CELCKLPART FCESDQASLC WDCDAKVHGA NFLVERH                            37

SEQ ID NO: 253          moltype = AA  length = 37
FEATURE                 Location/Qualifiers
REGION                  1..37
                        note = conserved domain of Glyma15g07140.1
source                  1..37
                        mol_type = protein
                        organism = Glycine max
SEQUENCE: 253
CELCNSPAKL FCESDQASLC WECDAKVHSA NFLVTKH                            37

SEQ ID NO: 254          moltype = AA  length = 38
FEATURE                 Location/Qualifiers
REGION                  1..38
                        note = conserved domain of AtBBX24 (G329)
source                  1..38
                        mol_type = protein
                        organism = Arabidopsis thaliana
SEQUENCE: 254
CDVCEKAPAT VICCADEAAL CPQCDIEIHA ANKLASKH                           38

SEQ ID NO: 255          moltype = AA  length = 38
FEATURE                 Location/Qualifiers
REGION                  1..38
                        note = conserved domain of AtBBX24 (G329)
source                  1..38
                        mol_type = protein
                        organism = Arabidopsis thaliana
SEQUENCE: 255
CDICQEKAAF IFCVEDRALL CRDCDESIHV ANSRSANH                           38

SEQ ID NO: 256          moltype = AA  length = 38
FEATURE                 Location/Qualifiers
REGION                  1..38
                        note = conserved domain of AtBBX25 (G1894)
source                  1..38
                        mol_type = protein
                        organism = Arabidopsis thaliana
SEQUENCE: 256
CDVCEKAPAT LICCADEAAL CAKCDVEVHA ANKLASKH                           38

SEQ ID NO: 257          moltype = AA  length = 38
FEATURE                 Location/Qualifiers
REGION                  1..38
                        note = conserved domain of AtBBX25 (G1894)
```

```
source                  1..38
                        mol_type = protein
                        organism = Arabidopsis thaliana
SEQUENCE: 257
CDICLEKAAF IFCVEDRALL CRDCDEATHA PNTRSANH                          38

SEQ ID NO: 258          moltype = AA  length = 38
FEATURE                 Location/Qualifiers
REGION                  1..38
                        note = conserved domain of ACF84591.1
source                  1..38
                        mol_type = protein
                        organism = Zea mays
SEQUENCE: 258
CDACEGAAAT VVCCADEAAL CARCDVEIHA ANKLASKH                          38

SEQ ID NO: 259          moltype = AA  length = 38
FEATURE                 Location/Qualifiers
REGION                  1..38
                        note = conserved domain of ACF84591.1
source                  1..38
                        mol_type = protein
                        organism = Zea mays
SEQUENCE: 259
CDVCQEKAAF IFCVEDRALF CQDCDEPIHV PGTLSGNH                          38

SEQ ID NO: 260          moltype = AA  length = 38
FEATURE                 Location/Qualifiers
REGION                  1..38
                        note = conserved domain of ACF86823.1
source                  1..38
                        mol_type = protein
                        organism = Zea mays
SEQUENCE: 260
CDACEGAAAT VVCCADEAAL CARCDVEIHA ANKLASKH                          38

SEQ ID NO: 261          moltype = AA  length = 38
FEATURE                 Location/Qualifiers
REGION                  1..38
                        note = conserved domain of ACF86823.1
source                  1..38
                        mol_type = protein
                        organism = Zea mays
SEQUENCE: 261
CDVCQEKAAF IFCVEDRALF CRDCDEPIHV PGTLSGNH                          38

SEQ ID NO: 262          moltype = AA  length = 38
FEATURE                 Location/Qualifiers
REGION                  1..38
                        note = conserved domain of CAW36812.1
source                  1..38
                        mol_type = protein
                        organism = Zea mays
SEQUENCE: 262
CDACEGAAAT VVCCADEAAL CARCDVEIHA ANKLASKH                          38

SEQ ID NO: 263          moltype = AA  length = 38
FEATURE                 Location/Qualifiers
REGION                  1..38
                        note = conserved domain of CAW36812.1
source                  1..38
                        mol_type = protein
                        organism = Zea mays
SEQUENCE: 263
CDVCQEKAAF IFCVEDRALF CRDCDEPIHV PGTLSGNH                          38

SEQ ID NO: 264          moltype = AA  length = 38
FEATURE                 Location/Qualifiers
REGION                  1..38
                        note = conserved domain of Pt_216458
source                  1..38
                        mol_type = protein
                        organism = Populus trichocarpa
SEQUENCE: 264
CDVCEKAPAT VICCADEAAL CEKCDIEVHA ANKLASKH                          38

SEQ ID NO: 265          moltype = AA  length = 38
FEATURE                 Location/Qualifiers
REGION                  1..38
```

```
                         note = conserved domain of Pt_216458
source                   1..38
                         mol_type = protein
                         organism = Populus trichocarpa
SEQUENCE: 265
CDICQEKAAF IFCVEDRALF CRDCDEPIHS AGSLSANH                         38

SEQ ID NO: 266           moltype = AA  length = 38
FEATURE                  Location/Qualifiers
REGION                   1..38
                         note = conserved domain of Pt_827145
source                   1..38
                         mol_type = protein
                         organism = Populus trichocarpa
SEQUENCE: 266
CDVCEKAPAT VICCADEAAL CAKCDIEVHA ANKLASKH                         38

SEQ ID NO: 267           moltype = AA  length = 38
FEATURE                  Location/Qualifiers
REGION                   1..38
                         note = conserved domain of Pt_827145
source                   1..38
                         mol_type = protein
                         organism = Populus trichocarpa
SEQUENCE: 267
CDICQEKAAF IFCVEDRALF CRDCDEPIHS AGSLSANH                         38

SEQ ID NO: 268           moltype = AA  length = 38
FEATURE                  Location/Qualifiers
REGION                   1..38
                         note = conserved domain of Os02g39360.1
source                   1..38
                         mol_type = protein
                         organism = Oryza sativa
SEQUENCE: 268
CDACESAAAA VVCCADEAAL CAACDVEVHA ANKLAGKH                         38

SEQ ID NO: 269           moltype = AA  length = 38
FEATURE                  Location/Qualifiers
REGION                   1..38
                         note = conserved domain of Os02g39360.1
source                   1..38
                         mol_type = protein
                         organism = Oryza sativa
SEQUENCE: 269
CDVCQEKAAF IFCVEDRALF CRDCDEPIHV PGTLSGNH                         38

SEQ ID NO: 270           moltype = AA  length = 38
FEATURE                  Location/Qualifiers
REGION                   1..38
                         note = conserved domain of Os04g41560.2
source                   1..38
                         mol_type = protein
                         organism = Oryza sativa
SEQUENCE: 270
CDACEAAAAT VVCCADEAAL CARCDVEIHA ANKLASKH                         38

SEQ ID NO: 271           moltype = AA  length = 38
FEATURE                  Location/Qualifiers
REGION                   1..38
                         note = conserved domain of Os04g41560.2
source                   1..38
                         mol_type = protein
                         organism = Oryza sativa
SEQUENCE: 271
CDVCQEKAAF IFCVEDRALF CRDCDEPIHV PGTLSGNH                         38

SEQ ID NO: 272           moltype = AA  length = 38
FEATURE                  Location/Qualifiers
REGION                   1..38
                         note = conserved domain of Os04g41560.4
source                   1..38
                         mol_type = protein
                         organism = Oryza sativa
SEQUENCE: 272
CDACEAAAAT VVCCADEAAL CARCDVEIHA ANKLASKH                         38

SEQ ID NO: 273           moltype = AA  length = 38
FEATURE                  Location/Qualifiers
```

```
REGION                 1..38
                       note = conserved domain of Os04g41560.4
source                 1..38
                       mol_type = protein
                       organism = Oryza sativa
SEQUENCE: 273
CDVCQEKAAF IFCVEDRALF CRDCDEPIHV PGTLSGNH                         38

SEQ ID NO: 274         moltype = AA  length = 38
FEATURE                Location/Qualifiers
REGION                 1..38
                       note = conserved domain of Glyma11g13570
source                 1..38
                       mol_type = protein
                       organism = Glycine max
SEQUENCE: 274
CDVCEKAPAT VICCADEAAL CAKCDVEVHA ANKLASKH                         38

SEQ ID NO: 275         moltype = AA  length = 38
FEATURE                Location/Qualifiers
REGION                 1..38
                       note = conserved domain of Glyma11g13570.1
source                 1..38
                       mol_type = protein
                       organism = Glycine max
SEQUENCE: 275
CDICQDKPAF IFCVEDRALF CKDCDEPIHL ASSLSANH                         38

SEQ ID NO: 276         moltype = AA  length = 38
FEATURE                Location/Qualifiers
REGION                 1..38
                       note = conserved domain of Glyma12g05570.1
source                 1..38
                       mol_type = protein
                       organism = Glycine max
SEQUENCE: 276
CDVCEKAPAT VICCADEAAL CAKCDVEVHA ANKLASKH                         38

SEQ ID NO: 277         moltype = AA  length = 38
FEATURE                Location/Qualifiers
REGION                 1..38
                       note = conserved domain of Glyma12g05570.1
source                 1..38
                       mol_type = protein
                       organism = Glycine max
SEQUENCE: 277
CDICQDKPAF IFCVEDRALF CKDCDEPIHL ASSLSANH                         38

SEQ ID NO: 278         moltype = AA  length = 38
FEATURE                Location/Qualifiers
REGION                 1..38
                       note = conserved domain of Glyma13g41980.1
source                 1..38
                       mol_type = protein
                       organism = Glycine max
SEQUENCE: 278
CDVCERAPAT VICCADEAAL CAKCDVEVHA ANKLASKH                         38

SEQ ID NO: 279         moltype = AA  length = 38
FEATURE                Location/Qualifiers
REGION                 1..38
                       note = conserved domain of Glyma13g41980.1
source                 1..38
                       mol_type = protein
                       organism = Glycine max
SEQUENCE: 279
CDICQDKPAF IFCVEDRALF CQDCDEPIHS AGSLSANH                         38

SEQ ID NO: 280         moltype = AA  length = 34
FEATURE                Location/Qualifiers
REGION                 1..34
                       note = conserved domain of Glyma13g41980.2
source                 1..34
                       mol_type = protein
                       organism = Glycine max
SEQUENCE: 280
QDKPAFIFCV EDRALFCQDC DEPIHSAGSL SANH                             34

SEQ ID NO: 281         moltype = AA  length = 33
```

```
FEATURE                Location/Qualifiers
REGION                 1..33
                       note = conserved domain of Glyma13g41980.2
source                 1..33
                       mol_type = protein
                       organism = Glycine max
SEQUENCE: 281
DKPAFIFCVE DRALFCQDCD EPIHSAGSLS ANH                             33

SEQ ID NO: 282         moltype = AA  length = 34
FEATURE                Location/Qualifiers
REGION                 1..34
                       note = conserved domain of Glyma13g41980.3
source                 1..34
                       mol_type = protein
                       organism = Glycine max
SEQUENCE: 282
QDKPAFIFCV EDRALFCQDC DEPIHSAGSL SANH                            34

SEQ ID NO: 283         moltype = AA  length = 33
FEATURE                Location/Qualifiers
REGION                 1..33
                       note = conserved domain of Glyma13g41980.3
source                 1..33
                       mol_type = protein
                       organism = Glycine max
SEQUENCE: 283
DKPAFIFCVE DRALFCQDCD EPIHSAGSLS ANH                             33

SEQ ID NO: 284         moltype = AA  length = 38
FEATURE                Location/Qualifiers
REGION                 1..38
                       note = conserved domain of Glyma15g03400.1
source                 1..38
                       mol_type = protein
                       organism = Glycine max
SEQUENCE: 284
CDVCERAPAT VICCADEAAL CAKCDVEVHA ANKLASKH                        38

SEQ ID NO: 285         moltype = AA  length = 38
FEATURE                Location/Qualifiers
REGION                 1..38
                       note = conserved domain of Glyma15g03400.1
source                 1..38
                       mol_type = protein
                       organism = Glycine max
SEQUENCE: 285
CDICQDKPAF IFCVEDRALF CQDCDEPIHS AGSLSANH                        38

SEQ ID NO: 286         moltype = AA  length = 38
FEATURE                Location/Qualifiers
REGION                 1..38
                       note = conserved domain of AAS67368
source                 1..38
                       mol_type = protein
                       organism = Solanum lycopersicum
SEQUENCE: 286
CDVCEKAQAT VICCADEAAL CAKCDIEVHA ANKLASKH                        38

SEQ ID NO: 287         moltype = AA  length = 38
FEATURE                Location/Qualifiers
REGION                 1..38
                       note = conserved domain of AAS67368
source                 1..38
                       mol_type = protein
                       organism = Solanum lycopersicum
SEQUENCE: 287
CDICQDKAAF IFCVEDRALF CKDCDEAIHS ASSLAKNH                        38

SEQ ID NO: 288         moltype = AA  length = 38
FEATURE                Location/Qualifiers
REGION                 1..38
                       note = conserved domain of AtBBX20 (G1888)
source                 1..38
                       mol_type = protein
                       organism = Arabidopsis thaliana
SEQUENCE: 288
CAVCDKEEAS VFCCADEAAL CNGCDRHVHF ANKLAGKH                        38
```

-continued

```
SEQ ID NO: 289          moltype = AA  length = 38
FEATURE                 Location/Qualifiers
REGION                  1..38
                        note = conserved domain of AtBBX20 (G1888)
source                  1..38
                        mol_type = protein
                        organism = Arabidopsis thaliana
SEQUENCE: 289
CDICGERRAL LFCQEDRAIL CRECDIPIHQ ANEHTKKH                          38

SEQ ID NO: 290          moltype = AA  length = 38
FEATURE                 Location/Qualifiers
REGION                  1..38
                        note = conserved domain of AtBBX21 (G1482)
source                  1..38
                        mol_type = protein
                        organism = Arabidopsis thaliana
SEQUENCE: 290
CDVCDKEEAS VFCTADEASL CGGCDHQVHH ANKLASKH                          38

SEQ ID NO: 291          moltype = AA  length = 38
FEATURE                 Location/Qualifiers
REGION                  1..38
                        note = conserved domain of AtBBX21 (G1482)
source                  1..38
                        mol_type = protein
                        organism = Arabidopsis thaliana
SEQUENCE: 291
CDICQDKKAL LFCQQDRAIL CKDCDSSIHA ANEHTKKH                          38

SEQ ID NO: 292          moltype = AA  length = 38
FEATURE                 Location/Qualifiers
REGION                  1..38
                        note = conserved domain of ACG44133.1
source                  1..38
                        mol_type = protein
                        organism = Zea mays
SEQUENCE: 292
CDVCAAEAAS VFCCADEAAL CDACDDRVHR ANKLAGKH                          38

SEQ ID NO: 293          moltype = AA  length = 38
FEATURE                 Location/Qualifiers
REGION                  1..38
                        note = conserved domain of ACG44133.1
source                  1..38
                        mol_type = protein
                        organism = Zea mays
SEQUENCE: 293
CDICQERRGF LFCKEDRAIL CRECDAPVHS ANDMTRRH                          38

SEQ ID NO: 294          moltype = AA  length = 38
FEATURE                 Location/Qualifiers
REGION                  1..38
                        note = conserved domain of CAW36814.1
source                  1..38
                        mol_type = protein
                        organism = Zea mays
SEQUENCE: 294
CDVCAAEAAS VFCCADEAAL CDACDDRVHR ANKLAGKH                          38

SEQ ID NO: 295          moltype = AA  length = 38
FEATURE                 Location/Qualifiers
REGION                  1..38
                        note = conserved domain of CAW36814.1
source                  1..38
                        mol_type = protein
                        organism = Zea mays
SEQUENCE: 295
CDICQERRGF LFCKEDRAIL CRECDAPVHS ANDMTRRH                          38

SEQ ID NO: 296          moltype = AA  length = 38
FEATURE                 Location/Qualifiers
REGION                  1..38
                        note = conserved domain of Pt_195637
source                  1..38
                        mol_type = protein
                        organism = Populus trichocarpa
SEQUENCE: 296
CDVCDNVEAT VFCCADEAAL CDGCDHRVHH ANKLASKH                          38
```

```
SEQ ID NO: 297          moltype = AA  length = 38
FEATURE                 Location/Qualifiers
REGION                  1..38
                        note = conserved domain of Pt_195637
source                  1..38
                        mol_type = protein
                        organism = Populus trichocarpa
SEQUENCE: 297
CDICQERRAL LFCQEDRAIL CRECDLPIHK ANEHTQKH                           38

SEQ ID NO: 298          moltype = AA  length = 38
FEATURE                 Location/Qualifiers
REGION                  1..38
                        note = conserved domain of Pt_550941
source                  1..38
                        mol_type = protein
                        organism = Populus trichocarpa
SEQUENCE: 298
CDVCNKEEAS VFCTADEAAL CDTCDHRVHH ANKLASKH                           38

SEQ ID NO: 299          moltype = AA  length = 38
FEATURE                 Location/Qualifiers
REGION                  1..38
                        note = conserved domain of Pt_550941
source                  1..38
                        mol_type = protein
                        organism = Populus trichocarpa
SEQUENCE: 299
CDICQEKRAF LFCQQDRAIL CRECDGPIHT ANEHTQKH                           38

SEQ ID NO: 300          moltype = AA  length = 38
FEATURE                 Location/Qualifiers
REGION                  1..38
                        note = conserved domain of Pt_801530
source                  1..38
                        mol_type = protein
                        organism = Populus trichocarpa
SEQUENCE: 300
CDVCSKEEAS VFCTADEAAL CDTCDHRVHH ANKLASKH                           38

SEQ ID NO: 301          moltype = AA  length = 38
FEATURE                 Location/Qualifiers
REGION                  1..38
                        note = conserved domain of Pt_801530
source                  1..38
                        mol_type = protein
                        organism = Populus trichocarpa
SEQUENCE: 301
CDICQDKRAF LFCQQDRAIL CRDCDGPIHT ANEHTQKH                           38

SEQ ID NO: 302          moltype = AA  length = 38
FEATURE                 Location/Qualifiers
REGION                  1..38
                        note = conserved domain of Pt_804174
source                  1..38
                        mol_type = protein
                        organism = Populus trichocarpa
SEQUENCE: 302
CDVCDKVEAT VFCCADEAAL CDGCDHRVHH ANTLASKH                           38

SEQ ID NO: 303          moltype = AA  length = 38
FEATURE                 Location/Qualifiers
REGION                  1..38
                        note = conserved domain of Pt_804174
source                  1..38
                        mol_type = protein
                        organism = Populus trichocarpa
SEQUENCE: 303
CDICQERRAV LFCQEDRAIL CRECDLPIHK VNEHTQKH                           38

SEQ ID NO: 304          moltype = AA  length = 38
FEATURE                 Location/Qualifiers
REGION                  1..38
                        note = conserved domain of Os02g43170.1
source                  1..38
                        mol_type = protein
                        organism = Oryza sativa
SEQUENCE: 304
```

-continued

```
CDVCAAEAAS VFCCADEAAL CDACDHRVHR ANKLAGKH                    38

SEQ ID NO: 305          moltype = AA  length = 38
FEATURE                 Location/Qualifiers
REGION                  1..38
                        note = conserved domain of Os02g43170.1
source                  1..38
                        mol_type = protein
                        organism = Oryza sativa
SEQUENCE: 305
CDICQEKRGF LFCKEDRAIL CRECDVPVHT ASELTMRH                    38

SEQ ID NO: 306          moltype = AA  length = 38
FEATURE                 Location/Qualifiers
REGION                  1..38
                        note = conserved domain of Os02g43170.2
source                  1..38
                        mol_type = protein
                        organism = Oryza sativa
SEQUENCE: 306
CDVCAAEAAS VFCCADEAAL CDACDHRVHR ANKLAGKH                    38

SEQ ID NO: 307          moltype = AA  length = 38
FEATURE                 Location/Qualifiers
REGION                  1..38
                        note = conserved domain of Os02g43170.2
source                  1..38
                        mol_type = protein
                        organism = Oryza sativa
SEQUENCE: 307
CDICQEKRGF LFCKEDRAIL CRECDVPVHT ASELTMRH                    38

SEQ ID NO: 308          moltype = AA  length = 38
FEATURE                 Location/Qualifiers
REGION                  1..38
                        note = conserved domain of Os04g45690.1
source                  1..38
                        mol_type = protein
                        organism = Oryza sativa
SEQUENCE: 308
CDVCAAEAAS VFCCADEAAL CDACDRRVHS ANKLAGKH                    38

SEQ ID NO: 309          moltype = AA  length = 38
FEATURE                 Location/Qualifiers
REGION                  1..38
                        note = conserved domain of Os04g45690.1
source                  1..38
                        mol_type = protein
                        organism = Oryza sativa
SEQUENCE: 309
CDICQEKRGF LFCKEDRAIL CRECDVTVHT TSELTRRH                    38

SEQ ID NO: 310          moltype = AA  length = 38
FEATURE                 Location/Qualifiers
REGION                  1..38
                        note = conserved domain of G5159
source                  1..38
                        mol_type = protein
                        organism = Oryza sativa
SEQUENCE: 310
CDVCAAEAAS VFCCADEAAL CDACDRRVHS ANKLAGKH                    38

SEQ ID NO: 311          moltype = AA  length = 38
FEATURE                 Location/Qualifiers
REGION                  1..38
                        note = conserved domain of G5159
source                  1..38
                        mol_type = protein
                        organism = Oryza sativa
SEQUENCE: 311
CDICQEKRGF LFCKEDRAIL CRECDVTVHT TSELTRRH                    38

SEQ ID NO: 312          moltype = AA  length = 38
FEATURE                 Location/Qualifiers
REGION                  1..38
                        note = conserved domain of Os06g49880.1
source                  1..38
                        mol_type = protein
                        organism = Oryza sativa
```

```
SEQUENCE: 312
CDVCAAEPAA VLCCADEAAL CSACDRRVHR ANRLASKH                          38

SEQ ID NO: 313          moltype = AA  length = 38
FEATURE                 Location/Qualifiers
REGION                  1..38
                        note = conserved domain of Os06g49880.1
source                  1..38
                        mol_type = protein
                        organism = Oryza sativa
SEQUENCE: 313
CDVCREKRGL VFCVEDRAIL CADCDEPIHS ANDLTAKH                          38

SEQ ID NO: 314          moltype = AA  length = 38
FEATURE                 Location/Qualifiers
REGION                  1..38
                        note = conserved domain of Os06g49880.2
source                  1..38
                        mol_type = protein
                        organism = Oryza sativa
SEQUENCE: 314
CDVCAAEPAA VLCCADEAAL CSACDRRVHR ANRLASKH                          38

SEQ ID NO: 315          moltype = AA  length = 38
FEATURE                 Location/Qualifiers
REGION                  1..38
                        note = conserved domain of Os06g49880.2
source                  1..38
                        mol_type = protein
                        organism = Oryza sativa
SEQUENCE: 315
CDVCREKRGL VFCVEDRAIL CADCDEPIHS ANDLTAKH                          38

SEQ ID NO: 316          moltype = AA  length = 38
FEATURE                 Location/Qualifiers
REGION                  1..38
                        note = conserved domain of Glyma04g01120.1
source                  1..38
                        mol_type = protein
                        organism = Glycine max
SEQUENCE: 316
CAVCDKVEAS VFCSADEAAL CHSCDRTIHH ANKLATKH                          38

SEQ ID NO: 317          moltype = AA  length = 38
FEATURE                 Location/Qualifiers
REGION                  1..38
                        note = conserved domain of Glyma04g01120.1
source                  1..38
                        mol_type = protein
                        organism = Glycine max
SEQUENCE: 317
CDICQERRAY LFCQEDRALL CRECDVPIHR ANEHTQKH                          38

SEQ ID NO: 318          moltype = AA  length = 38
FEATURE                 Location/Qualifiers
REGION                  1..38
                        note = conserved domain of G5365
source                  1..38
                        mol_type = protein
                        organism = Glycine max
SEQUENCE: 318
CDVCNKHQAS FFCTADEAAL CDGCDHRVHH ANKLASKH                          38

SEQ ID NO: 319          moltype = AA  length = 38
FEATURE                 Location/Qualifiers
REGION                  1..38
                        note = conserved domain of G5365
source                  1..38
                        mol_type = protein
                        organism = Glycine max
SEQUENCE: 319
CDVCQERRAF VFCQQDRAIL CKECDVPIHS ANDLTKNH                          38

SEQ ID NO: 320          moltype = AA  length = 38
FEATURE                 Location/Qualifiers
REGION                  1..38
                        note = conserved domain of Glyma04g02960.2
source                  1..38
                        mol_type = protein
```

```
                         organism = Glycine max
SEQUENCE: 320
CDVCNKHQAS FFCTADEAAL CDGCDHRVHH ANKLASKH                              38

SEQ ID NO: 321           moltype = AA  length = 38
FEATURE                  Location/Qualifiers
REGION                   1..38
                         note = conserved domain of Glyma04g02960.2
source                   1..38
                         mol_type = protein
                         organism = Glycine max
SEQUENCE: 321
CDVCQERRAF VFCQQDRAIL CKECDVPIHS ANDLTKNH                              38

SEQ ID NO: 322           moltype = AA  length = 38
FEATURE                  Location/Qualifiers
REGION                   1..38
                         note = conserved domain of Glyma06g01140.1
source                   1..38
                         mol_type = protein
                         organism = Glycine max
SEQUENCE: 322
CDVCDKVEAS VFCPADEAAL CHSCDRTIHR ANKLATKH                              38

SEQ ID NO: 323           moltype = AA  length = 38
FEATURE                  Location/Qualifiers
REGION                   1..38
                         note = conserved domain of Glyma06g01140.1
source                   1..38
                         mol_type = protein
                         organism = Glycine max
SEQUENCE: 323
CDICQERRAY LFCQEDRALL CRECDVPIHR ANEHTQKH                              38

SEQ ID NO: 324           moltype = AA  length = 38
FEATURE                  Location/Qualifiers
REGION                   1..38
                         note = conserved domain of G5367
source                   1..38
                         mol_type = protein
                         organism = Glycine max
SEQUENCE: 324
CDVCNKQQAS LFCTADEAAL CDGCDHRVHH ANKLASKH                              38

SEQ ID NO: 325           moltype = AA  length = 38
FEATURE                  Location/Qualifiers
REGION                   1..38
                         note = conserved domain of G5367
source                   1..38
                         mol_type = protein
                         organism = Glycine max
SEQUENCE: 325
CDVCQERRAF VFCQQDRAIL CKECDVPVHS ANDLTKNH                              38

SEQ ID NO: 326           moltype = AA  length = 38
FEATURE                  Location/Qualifiers
REGION                   1..38
                         note = conserved domain of Glyma11g12060.1
source                   1..38
                         mol_type = protein
                         organism = Glycine max
SEQUENCE: 326
CDVCHNEVAS FFCPSDEASL CHACDRTIHH ANKLADKH                              38

SEQ ID NO: 327           moltype = AA  length = 38
FEATURE                  Location/Qualifiers
REGION                   1..38
                         note = conserved domain of Glyma11g12060.1
source                   1..38
                         mol_type = protein
                         organism = Glycine max
SEQUENCE: 327
CDICHERRAY LFCKEDRAIL CRECDLSIHG VNEHTKKH                              38

SEQ ID NO: 328           moltype = AA  length = 38
FEATURE                  Location/Qualifiers
REGION                   1..38
                         note = conserved domain of G5396
source                   1..38
```

```
                       mol_type = protein
                       organism = Glycine max
SEQUENCE: 328
CDVCNKHEAS VFCTADEAAL CDGCDHRVHH ANKLASKH                          38

SEQ ID NO: 329         moltype = AA  length = 38
FEATURE                Location/Qualifiers
REGION                 1..38
                       note = conserved domain of G5396
source                 1..38
                       mol_type = protein
                       organism = Glycine max
SEQUENCE: 329
CDICQERRAF TFCQQDRAIL CKECDVSIHS ANEHTLKH                          38

SEQ ID NO: 330         moltype = AA  length = 38
FEATURE                Location/Qualifiers
REGION                 1..38
                       note = conserved domain of G5400
source                 1..38
                       mol_type = protein
                       organism = Glycine max
SEQUENCE: 330
CDVCNKHEAS VFCTADEAAL CDGCDHRVHH ANKLASKH                          38

SEQ ID NO: 331         moltype = AA  length = 38
FEATURE                Location/Qualifiers
REGION                 1..38
                       note = conserved domain of G5400
source                 1..38
                       mol_type = protein
                       organism = Glycine max
SEQUENCE: 331
CDICQERRAF TFCQQDRAIL CKECDVSIHS ANEHTLKH                          38

SEQ ID NO: 332         moltype = AA  length = 37
FEATURE                Location/Qualifiers
REGION                 1..37
                       note = conserved domain of AtBBX26 (G1486)
source                 1..37
                       mol_type = protein
                       organism = Arabidopsis thaliana
SEQUENCE: 332
CHTCRHVTAV IHCVTEALNF CLTCDNLRHH NNIHAEH                           37

SEQ ID NO: 333         moltype = AA  length = 37
FEATURE                Location/Qualifiers
REGION                 1..37
                       note = conserved domain of AtBBX30 (G1478)
source                 1..37
                       mol_type = protein
                       organism = Arabidopsis thaliana
SEQUENCE: 333
CELCGENATV YCEADAAFLC RKCDRWVHSA NFLARRH                           37

SEQ ID NO: 334         moltype = AA  length = 37
FEATURE                Location/Qualifiers
REGION                 1..37
                       note = conserved domain of AtBBX31 (G1929)
source                 1..37
                       mol_type = protein
                       organism = Arabidopsis thaliana
SEQUENCE: 334
CELCDGDASV FCEADSAFLC RKCDRWVHGA NFLAWRH                           37

SEQ ID NO: 335         moltype = AA  length = 37
FEATURE                Location/Qualifiers
REGION                 1..37
                       note = conserved domain of Pt_562313
source                 1..37
                       mol_type = protein
                       organism = Populus trichocarpa
SEQUENCE: 335
CELCGSRASL YCQADDAFLC QKCDKWVHGA NFLAQRH                           37

SEQ ID NO: 336         moltype = AA  length = 37
FEATURE                Location/Qualifiers
REGION                 1..37
                       note = conserved domain of Pt_594447
```

```
source                  1..37
                        mol_type = protein
                        organism = Populus trichocarpa
SEQUENCE: 336
CELCGSRATL YCQADHAFLC QKCDGWVHGA NFLALRH                        37

SEQ ID NO: 337          moltype = AA  length = 37
FEATURE                 Location/Qualifiers
REGION                  1..37
                        note = conserved domain of Glyma12g32230.1
source                  1..37
                        mol_type = protein
                        organism = Glycine max
SEQUENCE: 337
CELCGLQASL YCQADDAYLC KKCDKRVHEA NFLALRH                        37

SEQ ID NO: 338          moltype = AA  length = 37
FEATURE                 Location/Qualifiers
REGION                  1..37
                        note = conserved domain of G4019
source                  1..37
                        mol_type = protein
                        organism = Glycine max
SEQUENCE: 338
CELCGLQASL YCQADDAYLC RKCDKRVHEA NFLALRH                        37

SEQ ID NO: 339          moltype = AA  length = 38
FEATURE                 Location/Qualifiers
REGION                  1..38
                        note = conserved domain of AtBBX7 (G2440)
source                  1..38
                        mol_type = protein
                        organism = Arabidopsis thaliana
SEQUENCE: 339
CDFCGEQRSM VYCRSDAACL CLSCDRSVHS ANALSKRH                       38

SEQ ID NO: 340          moltype = AA  length = 47
FEATURE                 Location/Qualifiers
REGION                  1..47
                        note = conserved domain of AtBBX7 (G2440)
source                  1..47
                        mol_type = protein
                        organism = Arabidopsis thaliana
SEQUENCE: 340
CERCNAQPAT VRCVEERVSL CQNCDWSGHN NSNNNNSSSS STSPQQH             47

SEQ ID NO: 341          moltype = AA  length = 42
FEATURE                 Location/Qualifiers
REGION                  1..42
                        note = conserved domain of AtBBX7 (G2440)
source                  1..42
                        mol_type = protein
                        organism = Arabidopsis thaliana
SEQUENCE: 341
RNNAVMRYKE KKKARKFDKR VRYASRKARA DVRRRVKGRF VK                  42

SEQ ID NO: 342          moltype = AA  length = 38
FEATURE                 Location/Qualifiers
REGION                  1..38
                        note = conserved domain of AtBBX8 (G1479)
source                  1..38
                        mol_type = protein
                        organism = Arabidopsis thaliana
SEQUENCE: 342
CDFCGEQRSM VYCRSDAACL CLSCDRNVHS ANALSKRH                       38

SEQ ID NO: 343          moltype = AA  length = 40
FEATURE                 Location/Qualifiers
REGION                  1..40
                        note = conserved domain of AtBBX8 (G1479)
source                  1..40
                        mol_type = protein
                        organism = Arabidopsis thaliana
SEQUENCE: 343
CERCNAQPAS VRCSDERVSL CQNCDWSGHD GKNSTTTSHH                     40

SEQ ID NO: 344          moltype = AA  length = 42
FEATURE                 Location/Qualifiers
REGION                  1..42
```

```
                         note = conserved domain of AtBBX8 (G1479)
source                   1..42
                         mol_type = protein
                         organism = Arabidopsis thaliana
SEQUENCE: 344
RNNAVMRYKE KKKARKFDKR VRYVSRKERA DVRRRVKGRF VK                        42

SEQ ID NO: 345           moltype = AA  length = 38
FEATURE                  Location/Qualifiers
REGION                   1..38
                         note = conserved domain of ACF80403.1
source                   1..38
                         mol_type = protein
                         organism = Zea mays
SEQUENCE: 345
CGFCGKQRSM IYCRSDAASL CLSCDRSVHS ANALSRRH                             38

SEQ ID NO: 346           moltype = AA  length = 38
FEATURE                  Location/Qualifiers
REGION                   1..38
                         note = conserved domain of ACF80403.1
source                   1..38
                         mol_type = protein
                         organism = Zea mays
SEQUENCE: 346
CDRCGLQPAS VRCLEDNTSL CQNCDWNGHD AASGASGH                             38

SEQ ID NO: 347           moltype = AA  length = 42
FEATURE                  Location/Qualifiers
REGION                   1..42
                         note = conserved domain of ACF80403.1
source                   1..42
                         mol_type = protein
                         organism = Zea mays
SEQUENCE: 347
RDSALTRYKE KKKKRMFDKK IRYASRKARA DVRKRVKGRF IK                        42

SEQ ID NO: 348           moltype = AA  length = 38
FEATURE                  Location/Qualifiers
REGION                   1..38
                         note = conserved domain of ACG34885.1
source                   1..38
                         mol_type = protein
                         organism = Zea mays
SEQUENCE: 348
CDFCGEQRSM VYCRSDAASL CLSCDRNVHS ANALSRRH                             38

SEQ ID NO: 349           moltype = AA  length = 38
FEATURE                  Location/Qualifiers
REGION                   1..38
                         note = conserved domain of ACG34885.1
source                   1..38
                         mol_type = protein
                         organism = Zea mays
SEQUENCE: 349
CDRCASQPAM VRCLAENASL CQNCDWNGHI AGSSSAGH                             38

SEQ ID NO: 350           moltype = AA  length = 42
FEATURE                  Location/Qualifiers
REGION                   1..42
                         note = conserved domain of ACG34885.1
source                   1..42
                         mol_type = protein
                         organism = Zea mays
SEQUENCE: 350
RDSALTRYKE KKMRRKFDKK IRYASRKARA DVRKRVKGRF VK                        42

SEQ ID NO: 351           moltype = AA  length = 38
FEATURE                  Location/Qualifiers
REGION                   1..38
                         note = conserved domain of ACN25813.1
source                   1..38
                         mol_type = protein
                         organism = Zea mays
SEQUENCE: 351
CDFCGKQRSM IYCRSDAASL CLSCDRNVHS ANALSRRH                             38

SEQ ID NO: 352           moltype = AA  length = 38
FEATURE                  Location/Qualifiers
```

```
REGION                 1..38
                       note = conserved domain of ACN25813.1
source                 1..38
                       mol_type = protein
                       organism = Zea mays
SEQUENCE: 352
CDRCGSQPAS VRCLEDNASL CQNCDWNGHD AESGASGH                          38

SEQ ID NO: 353         moltype = AA  length = 20
FEATURE                Location/Qualifiers
REGION                 1..20
                       note = conserved domain of ACN25813.1
source                 1..20
                       mol_type = protein
                       organism = Zea mays
SEQUENCE: 353
YASRKARADV RKRVKGRFIK                                              20

SEQ ID NO: 354         moltype = AA  length = 38
FEATURE                Location/Qualifiers
REGION                 1..38
                       note = conserved domain of Pt_247140
source                 1..38
                       mol_type = protein
                       organism = Populus trichocarpa
SEQUENCE: 354
CDFCGEQRSM VYCRSDAASL CLSCDRNVHS ANALSKRH                          38

SEQ ID NO: 355         moltype = AA  length = 38
FEATURE                Location/Qualifiers
REGION                 1..38
                       note = conserved domain of Pt_247140
source                 1..38
                       mol_type = protein
                       organism = Populus trichocarpa
SEQUENCE: 355
CERCNSQPAL VRCAEERISL CQNCDWIGHG TSTSASTH                          38

SEQ ID NO: 356         moltype = AA  length = 42
FEATURE                Location/Qualifiers
REGION                 1..42
                       note = conserved domain of Pt_247140
source                 1..42
                       mol_type = protein
                       organism = Populus trichocarpa
SEQUENCE: 356
RSDAVMRYKE KKKTRMFEKK VRYASRKARA DVRRRVKGRF VK                     42

SEQ ID NO: 357         moltype = AA  length = 38
FEATURE                Location/Qualifiers
REGION                 1..38
                       note = conserved domain of Pt_409151
source                 1..38
                       mol_type = protein
                       organism = Populus trichocarpa
SEQUENCE: 357
CDFCGEQRSM VYCRSDAACL CLSCDQIVHS ANALSKRH                          38

SEQ ID NO: 358         moltype = AA  length = 38
FEATURE                Location/Qualifiers
REGION                 1..38
                       note = conserved domain of Pt_409151
source                 1..38
                       mol_type = protein
                       organism = Populus trichocarpa
SEQUENCE: 358
CERCNSQPAL VRRVEERISL CQNCDWMGYG SSTSASTH                          38

SEQ ID NO: 359         moltype = AA  length = 42
FEATURE                Location/Qualifiers
REGION                 1..42
                       note = conserved domain of Pt_409151
source                 1..42
                       mol_type = protein
                       organism = Populus trichocarpa
SEQUENCE: 359
RSDAVKRYME KKKTRKFEKK VRYASRKARA DVRRRVKGRF VK                     42

SEQ ID NO: 360         moltype = AA  length = 38
```

-continued

```
FEATURE                 Location/Qualifiers
REGION                  1..38
                        note = conserved domain of Os02g49230.1
source                  1..38
                        mol_type = protein
                        organism = Oryza sativa
SEQUENCE: 360
CDFCREQRSM VYCRSDAASL CLSCDRNVHS ANALSRRH                           38

SEQ ID NO: 361          moltype = AA  length = 38
FEATURE                 Location/Qualifiers
REGION                  1..38
                        note = conserved domain of Os02g49230.1
source                  1..38
                        mol_type = protein
                        organism = Oryza sativa
SEQUENCE: 361
CDRCVGQPAA VRCLEENTSL CQNCDWNGHG AASSAAGH                           38

SEQ ID NO: 362          moltype = AA  length = 42
FEATURE                 Location/Qualifiers
REGION                  1..42
                        note = conserved domain of Os02g49230.1
source                  1..42
                        mol_type = protein
                        organism = Oryza sativa
SEQUENCE: 362
RDNALTRYKE KKKRRKFDKK IRYASRKARA DVRKRVKGRF VK                      42

SEQ ID NO: 363          moltype = AA  length = 38
FEATURE                 Location/Qualifiers
REGION                  1..38
                        note = conserved domain of Os02g49230.2
source                  1..38
                        mol_type = protein
                        organism = Oryza sativa
SEQUENCE: 363
CDFCREQRSM VYCRSDAASL CLSCDRNVHS ANALSRRH                           38

SEQ ID NO: 364          moltype = AA  length = 38
FEATURE                 Location/Qualifiers
REGION                  1..38
                        note = conserved domain of Os02g49230.2
source                  1..38
                        mol_type = protein
                        organism = Oryza sativa
SEQUENCE: 364
CDRCVGQPAA VRCLEENTSL CQNCDWNGHG AASSAAGH                           38

SEQ ID NO: 365          moltype = AA  length = 42
FEATURE                 Location/Qualifiers
REGION                  1..42
                        note = conserved domain of Os02g49230.2
source                  1..42
                        mol_type = protein
                        organism = Oryza sativa
SEQUENCE: 365
RDNALTRYKE KKKRRKFDKK IRYASRKARA DVRKRVKGRF VK                      42

SEQ ID NO: 366          moltype = AA  length = 38
FEATURE                 Location/Qualifiers
REGION                  1..38
                        note = conserved domain of Os02g49230.3
source                  1..38
                        mol_type = protein
                        organism = Oryza sativa
SEQUENCE: 366
CDFCREQRSM VYCRSDAASL CLSCDRNVHS ANALSRRH                           38

SEQ ID NO: 367          moltype = AA  length = 38
FEATURE                 Location/Qualifiers
REGION                  1..38
                        note = conserved domain of Os02g49230.3
source                  1..38
                        mol_type = protein
                        organism = Oryza sativa
SEQUENCE: 367
CDRCVGQPAA VRCLEENTSL CQNCDWNGHG AASSAAGH                           38
```

-continued

```
SEQ ID NO: 368          moltype = AA  length = 42
FEATURE                 Location/Qualifiers
REGION                  1..42
                        note = conserved domain of Os02g49230.3
source                  1..42
                        mol_type = protein
                        organism = Oryza sativa
SEQUENCE: 368
RDNALTRYKE KKKRRKFDKK IRYASRKARA DVRKRVKGRF VK                      42

SEQ ID NO: 369          moltype = AA  length = 38
FEATURE                 Location/Qualifiers
REGION                  1..38
                        note = conserved domain of Os02g49230.4
source                  1..38
                        mol_type = protein
                        organism = Oryza sativa
SEQUENCE: 369
CDFCREQRSM VYCRSDAASL CLSCDRNVHS ANALSRRH                           38

SEQ ID NO: 370          moltype = AA  length = 38
FEATURE                 Location/Qualifiers
REGION                  1..38
                        note = conserved domain of Os02g49230.4
source                  1..38
                        mol_type = protein
                        organism = Oryza sativa
SEQUENCE: 370
CDRCVGQPAA VRCLEENTSL CQNCDWNGHG AASSAAGH                           38

SEQ ID NO: 371          moltype = AA  length = 42
FEATURE                 Location/Qualifiers
REGION                  1..42
                        note = conserved domain of Os02g49230.4
source                  1..42
                        mol_type = protein
                        organism = Oryza sativa
SEQUENCE: 371
RDNALTRYKE KKKRRKFDKK IRYASRKARA DVRKRVKGRF VK                      42

SEQ ID NO: 372          moltype = AA  length = 38
FEATURE                 Location/Qualifiers
REGION                  1..38
                        note = conserved domain of Os02g49230.5
source                  1..38
                        mol_type = protein
                        organism = Oryza sativa
SEQUENCE: 372
CDFCREQRSM VYCRSDAASL CLSCDRNVHS ANALSRRH                           38

SEQ ID NO: 373          moltype = AA  length = 38
FEATURE                 Location/Qualifiers
REGION                  1..38
                        note = conserved domain of Os02g49230.5
source                  1..38
                        mol_type = protein
                        organism = Oryza sativa
SEQUENCE: 373
CDRCVGQPAA VRCLEENTSL CQNCDWNGHG AASSAAGH                           38

SEQ ID NO: 374          moltype = AA  length = 42
FEATURE                 Location/Qualifiers
REGION                  1..42
                        note = conserved domain of Os02g49230.5
source                  1..42
                        mol_type = protein
                        organism = Oryza sativa
SEQUENCE: 374
RDNALTRYKE KKKRRKFDKK IRYASRKARA DVRKRVKGRF VK                      42

SEQ ID NO: 375          moltype = AA  length = 38
FEATURE                 Location/Qualifiers
REGION                  1..38
                        note = conserved domain of Os02g49230.6
source                  1..38
                        mol_type = protein
                        organism = Oryza sativa
SEQUENCE: 375
CDFCREQRSM VYCRSDAASL CLSCDRNVHS ANALSRRH                           38
```

```
SEQ ID NO: 376          moltype = AA  length = 38
FEATURE                 Location/Qualifiers
REGION                  1..38
                        note = conserved domain of Os02g49230.6
source                  1..38
                        mol_type = protein
                        organism = Oryza sativa
SEQUENCE: 376
CDRCVGQPAA VRCLEENTSL CQNCDWNGHG AASSAAGH                          38

SEQ ID NO: 377          moltype = AA  length = 42
FEATURE                 Location/Qualifiers
REGION                  1..42
                        note = conserved domain of Os02g49230.6
source                  1..42
                        mol_type = protein
                        organism = Oryza sativa
SEQUENCE: 377
RDNALTRYKE KKKRRKFDKK IRYASRKARA DVRKRVKGRF VK                     42

SEQ ID NO: 378          moltype = AA  length = 38
FEATURE                 Location/Qualifiers
REGION                  1..38
                        note = conserved domain of Os06g19444.1
source                  1..38
                        mol_type = protein
                        organism = Oryza sativa
SEQUENCE: 378
CDFCGEQRSM VYCRSDAASL CLSCDRNVHS ANALSRRH                          38

SEQ ID NO: 379          moltype = AA  length = 38
FEATURE                 Location/Qualifiers
REGION                  1..38
                        note = conserved domain of Os06g19444.1
source                  1..38
                        mol_type = protein
                        organism = Oryza sativa
SEQUENCE: 379
CDRCASQPAM VRCLVENASL CQNCDWNGHS AGSSAAGH                          38

SEQ ID NO: 380          moltype = AA  length = 20
FEATURE                 Location/Qualifiers
REGION                  1..20
                        note = conserved domain of Os06g19444.1
source                  1..20
                        mol_type = protein
                        organism = Oryza sativa
SEQUENCE: 380
YASRKARADV RKRVKGRFVK                                              20

SEQ ID NO: 381          moltype = AA  length = 38
FEATURE                 Location/Qualifiers
REGION                  1..38
                        note = conserved domain of Os06g19444.2
source                  1..38
                        mol_type = protein
                        organism = Oryza sativa
SEQUENCE: 381
CDFCGEQRSM VYCRSDAASL CLSCDRNVHS ANALSRRH                          38

SEQ ID NO: 382          moltype = AA  length = 38
FEATURE                 Location/Qualifiers
REGION                  1..38
                        note = conserved domain of Os06g19444.2
source                  1..38
                        mol_type = protein
                        organism = Oryza sativa
SEQUENCE: 382
CDRCASQPAM VRCLVENASL CQNCDWNGHS AGSSAAGH                          38

SEQ ID NO: 383          moltype = AA  length = 20
FEATURE                 Location/Qualifiers
REGION                  1..20
                        note = conserved domain of Os06g19444.2
source                  1..20
                        mol_type = protein
                        organism = Oryza sativa
SEQUENCE: 383
```

-continued

```
YASRKARADV RKRVKGRFVK                                              20

SEQ ID NO: 384          moltype = AA  length = 38
FEATURE                 Location/Qualifiers
REGION                  1..38
                        note = conserved domain of Glyma02g38870.1
source                  1..38
                        mol_type = protein
                        organism = Glycine max
SEQUENCE: 384
CDFCGDQRSL VYCRSDSACL CLSCDRNVHS ANALSRRH                          38

SEQ ID NO: 385          moltype = AA  length = 38
FEATURE                 Location/Qualifiers
REGION                  1..38
                        note = conserved domain of Glyma02g38870.1
source                  1..38
                        mol_type = protein
                        organism = Glycine max
SEQUENCE: 385
CERCNSQPAF VRSVEEKISL CQNCDWLGHG TSPSSSMH                          38

SEQ ID NO: 386          moltype = AA  length = 42
FEATURE                 Location/Qualifiers
REGION                  1..42
                        note = conserved domain of Glyma02g38870.1
source                  1..42
                        mol_type = protein
                        organism = Glycine max
SEQUENCE: 386
RSNAVMRYKE KKKTRKFEKK VRYASRKARA DVRKRVKGRF VK                     42

SEQ ID NO: 387          moltype = AA  length = 42
FEATURE                 Location/Qualifiers
REGION                  1..42
                        note = conserved domain of Glyma13g11590.1
source                  1..42
                        mol_type = protein
                        organism = Glycine max
SEQUENCE: 387
RSNAVMRYKE KKKTRMFDKK VRYASRKARA DVRRRVKGRF VK                     42

SEQ ID NO: 388          moltype = AA  length = 38
FEATURE                 Location/Qualifiers
REGION                  1..38
                        note = conserved domain of Glyma14g36930.1
source                  1..38
                        mol_type = protein
                        organism = Glycine max
SEQUENCE: 388
CDFCGDQRSL VYCRSDAACL CLSCDRNVHS ANALSRRH                          38

SEQ ID NO: 389          moltype = AA  length = 38
FEATURE                 Location/Qualifiers
REGION                  1..38
                        note = conserved domain of Glyma14g36930.1
source                  1..38
                        mol_type = protein
                        organism = Glycine max
SEQUENCE: 389
CERCNSQPAF VRCVDEKISL CQNCDWLGHG TSPSSSTH                          38

SEQ ID NO: 390          moltype = AA  length = 42
FEATURE                 Location/Qualifiers
REGION                  1..42
                        note = conserved domain of Glyma14g36930.1
source                  1..42
                        mol_type = protein
                        organism = Glycine max
SEQUENCE: 390
RSNAVMRYKE KKKTRKFEKK VRYASRKARA DVRKRVKGRF VK                     42

SEQ ID NO: 391          moltype = AA  length = 38
FEATURE                 Location/Qualifiers
REGION                  1..38
                        note = conserved domain of Glyma14g36930.2
source                  1..38
                        mol_type = protein
                        organism = Glycine max
```

```
SEQUENCE: 391
CDFCGDQRSL VYCRSDAACL CLSCDRNVHS ANALSRRH                            38

SEQ ID NO: 392          moltype = AA  length = 38
FEATURE                 Location/Qualifiers
REGION                  1..38
                        note = conserved domain of Glyma14g36930.2
source                  1..38
                        mol_type = protein
                        organism = Glycine max
SEQUENCE: 392
CERCNSQPAF VRCVDEKISL CQNCDWLGHG TSPSSSTH                            38

SEQ ID NO: 393          moltype = AA  length = 42
FEATURE                 Location/Qualifiers
REGION                  1..42
                        note = conserved domain of Glyma14g36930.2
source                  1..42
                        mol_type = protein
                        organism = Glycine max
SEQUENCE: 393
RSNAVMRYKE KKKTRKFEKK VRYASRKARA DVRKRVKGRF VK                       42

SEQ ID NO: 394          moltype = AA  length = 42
FEATURE                 Location/Qualifiers
REGION                  1..42
                        note = conserved domain of Glyma20g07050.1
source                  1..42
                        mol_type = protein
                        organism = Glycine max
SEQUENCE: 394
RSNAVMRYKE KKKTRMFDKK VRYASRKARA DVRRRVKGRF VK                       42

SEQ ID NO: 395          moltype = AA  length = 42
FEATURE                 Location/Qualifiers
REGION                  1..42
                        note = conserved domain of Glyma20g07050.2
source                  1..42
                        mol_type = protein
                        organism = Glycine max
SEQUENCE: 395
RSNAVMRYKE KKKTRMFDKK VRYASRKARA DVRRRVKGRF VK                       42

SEQ ID NO: 396          moltype = AA  length = 38
FEATURE                 Location/Qualifiers
REGION                  1..38
                        note = conserved domain of AtBBX19 (G902)
source                  1..38
                        mol_type = protein
                        organism = Arabidopsis thaliana
SEQUENCE: 396
CDACENAAAI IFCAADEAAL CRPCDEKVHM CNKLASRH                            38

SEQ ID NO: 397          moltype = AA  length = 36
FEATURE                 Location/Qualifiers
REGION                  1..36
                        note = conserved domain of AtBBX19 (G902)
source                  1..36
                        mol_type = protein
                        organism = Arabidopsis thaliana
SEQUENCE: 397
CDICENAPAF FYCEIDGSSL CLQCDMVVHV GGKRTH                              36

SEQ ID NO: 398          moltype = AA  length = 38
FEATURE                 Location/Qualifiers
REGION                  1..38
                        note = conserved domain of AtBBX18 (G1881)
source                  1..38
                        mol_type = protein
                        organism = Arabidopsis thaliana
SEQUENCE: 398
CDACESAAAI VFCAADEAAL CCSCDEKVHK CNKLASRH                            38

SEQ ID NO: 399          moltype = AA  length = 36
FEATURE                 Location/Qualifiers
REGION                  1..36
                        note = conserved domain of AtBBX18 (G1881)
source                  1..36
                        mol_type = protein
```

```
                          organism = Arabidopsis thaliana
SEQUENCE: 399
CDICENAPAF FYCEIDGSSL CLQCDMVVHV GGKRTH                                  36

SEQ ID NO: 400            moltype = AA  length = 38
FEATURE                   Location/Qualifiers
REGION                    1..38
                          note = conserved domain of ACF85933.1
source                    1..38
                          mol_type = protein
                          organism = Zea mays
SEQUENCE: 400
CDVCESAPAV LFCAADEAAL CRPCDEKVHM CNKLASRH                                38

SEQ ID NO: 401            moltype = AA  length = 36
FEATURE                   Location/Qualifiers
REGION                    1..36
                          note = conserved domain of ACF85933.1
source                    1..36
                          mol_type = protein
                          organism = Zea mays
SEQUENCE: 401
CDICENSPAF FYCEIDGTSL CLSCDMTVHV GGKRTH                                  36

SEQ ID NO: 402            moltype = AA  length = 38
FEATURE                   Location/Qualifiers
REGION                    1..38
                          note = conserved domain of ACL52378.1
source                    1..38
                          mol_type = protein
                          organism = Zea mays
SEQUENCE: 402
CDVCESAPAV LFCAADEAAL CRPCDEKVHM CNKLASRH                                38

SEQ ID NO: 403            moltype = AA  length = 36
FEATURE                   Location/Qualifiers
REGION                    1..36
                          note = conserved domain of ACL52378.1
source                    1..36
                          mol_type = protein
                          organism = Zea mays
SEQUENCE: 403
CDICENSPAF FYCEIDGTSL CLSCDMTVHV GGKRTH                                  36

SEQ ID NO: 404            moltype = AA  length = 38
FEATURE                   Location/Qualifiers
REGION                    1..38
                          note = conserved domain of Pt_648693
source                    1..38
                          mol_type = protein
                          organism = Populus trichocarpa
SEQUENCE: 404
CDVCESAAAI LFCAADEAAL CRSCDEKVHM CNKLASRH                                38

SEQ ID NO: 405            moltype = AA  length = 36
FEATURE                   Location/Qualifiers
REGION                    1..36
                          note = conserved domain of Pt_648693
source                    1..36
                          mol_type = protein
                          organism = Populus trichocarpa
SEQUENCE: 405
CDICEKAPAF FYCEIDGSSL CLQCDMIVHV GGKRTH                                  36

SEQ ID NO: 406            moltype = AA  length = 38
FEATURE                   Location/Qualifiers
REGION                    1..38
                          note = conserved domain of Pt_721866
source                    1..38
                          mol_type = protein
                          organism = Populus trichocarpa
SEQUENCE: 406
CDVCESAAAI LFCAADEAAL CRSCDEKVHL CNKLASRH                                38

SEQ ID NO: 407            moltype = AA  length = 36
FEATURE                   Location/Qualifiers
REGION                    1..36
                          note = conserved domain of Pt_721866
source                    1..36
```

```
                        mol_type = protein
                        organism = Populus trichocarpa
SEQUENCE: 407
CDICENAPAF FYCEIDGSSL CLQCDMIVHV GGKRTH                               36

SEQ ID NO: 408          moltype = AA  length = 38
FEATURE                 Location/Qualifiers
REGION                  1..38
                        note = conserved domain of Pt_741179
source                  1..38
                        mol_type = protein
                        organism = Populus trichocarpa
SEQUENCE: 408
CDACESAFAI VFCAADEAAL CLACDKKVHM CNKLASRH                             38

SEQ ID NO: 409          moltype = AA  length = 36
FEATURE                 Location/Qualifiers
REGION                  1..36
                        note = conserved domain of Pt_741179
source                  1..36
                        mol_type = protein
                        organism = Populus trichocarpa
SEQUENCE: 409
CDICENAPAF FYCETDGSSL CLQCDMTVHV GGKRTH                               36

SEQ ID NO: 410          moltype = AA  length = 38
FEATURE                 Location/Qualifiers
REGION                  1..38
                        note = conserved domain of Pt_820080
source                  1..38
                        mol_type = protein
                        organism = Populus trichocarpa
SEQUENCE: 410
CDACESAAAI VFCAADEAAL CLACDEKVHM CNKLASRH                             38

SEQ ID NO: 411          moltype = AA  length = 36
FEATURE                 Location/Qualifiers
REGION                  1..36
                        note = conserved domain of Pt_820080
source                  1..36
                        mol_type = protein
                        organism = Populus trichocarpa
SEQUENCE: 411
CDICENAPAF FYCETDGSSL CLQCDMTVHV GGKRTH                               36

SEQ ID NO: 412          moltype = AA  length = 38
FEATURE                 Location/Qualifiers
REGION                  1..38
                        note = conserved domain of Os09g35880.1
source                  1..38
                        mol_type = protein
                        organism = Oryza sativa
SEQUENCE: 412
CDVCESAPAV LFCVADEAAL CRSCDEKVHM CNKLARRH                             38

SEQ ID NO: 413          moltype = AA  length = 36
FEATURE                 Location/Qualifiers
REGION                  1..36
                        note = conserved domain of Os09g35880.1
source                  1..36
                        mol_type = protein
                        organism = Oryza sativa
SEQUENCE: 413
CDICENAPAF FYCEIDGTSL CLSCDMTVHV GGKRTH                               36

SEQ ID NO: 414          moltype = AA  length = 38
FEATURE                 Location/Qualifiers
REGION                  1..38
                        note = conserved domain of Glyma01g37370.1
source                  1..38
                        mol_type = protein
                        organism = Glycine max
SEQUENCE: 414
CDACESAAAI VFCAADEAAL CRACDEKVHM CNKLASRH                             38

SEQ ID NO: 415          moltype = AA  length = 36
FEATURE                 Location/Qualifiers
REGION                  1..36
                        note = conserved domain of Glyma01g37370.1
```

```
source                  1..36
                        mol_type = protein
                        organism = Glycine max
SEQUENCE: 415
CDICENAPAF FYCETDGSSL CLQCDMIVHV GGKRTH                                 36

SEQ ID NO: 416          moltype = AA  length = 38
FEATURE                 Location/Qualifiers
REGION                  1..38
                        note = conserved domain of Glyma11g07930.1
source                  1..38
                        mol_type = protein
                        organism = Glycine max
SEQUENCE: 416
CDACESAAAI VFCAADEAAL CRACDEKVHM CNKLASRH                               38

SEQ ID NO: 417          moltype = AA  length = 36
FEATURE                 Location/Qualifiers
REGION                  1..36
                        note = conserved domain of Glyma11g07930.1
source                  1..36
                        mol_type = protein
                        organism = Glycine max
SEQUENCE: 417
CDICENAPAF FYCETDGSSL CLQCDMIVHV GGKRTH                                 36

SEQ ID NO: 418          moltype = AA  length = 38
FEATURE                 Location/Qualifiers
REGION                  1..38
                        note = conserved domain of Glyma11g07930.2
source                  1..38
                        mol_type = protein
                        organism = Glycine max
SEQUENCE: 418
CDACESAAAI VFCAADEAAL CRACDEKVHM CNKLASRH                               38

SEQ ID NO: 419          moltype = AA  length = 36
FEATURE                 Location/Qualifiers
REGION                  1..36
                        note = conserved domain of Glyma11g07930.2
source                  1..36
                        mol_type = protein
                        organism = Glycine max
SEQUENCE: 419
CDICENAPAF FYCETDGSSL CLQCDMIVHV GGKRTH                                 36

SEQ ID NO: 420          moltype = AA  length = 38
FEATURE                 Location/Qualifiers
REGION                  1..38
                        note = conserved domain of Glyma11g07930.3
source                  1..38
                        mol_type = protein
                        organism = Glycine max
SEQUENCE: 420
CDACESAAAI VFCAADEAAL CRACDEKVHM CNKLASRH                               38

SEQ ID NO: 421          moltype = AA  length = 36
FEATURE                 Location/Qualifiers
REGION                  1..36
                        note = conserved domain of Glyma11g07930.3
source                  1..36
                        mol_type = protein
                        organism = Glycine max
SEQUENCE: 421
CDICENAPAF FYCETDGSSL CLQCDMIVHV GGKRTH                                 36

SEQ ID NO: 422          moltype = AA  length = 38
FEATURE                 Location/Qualifiers
REGION                  1..38
                        note = conserved domain of Glyma11g07930.4
source                  1..38
                        mol_type = protein
                        organism = Glycine max
SEQUENCE: 422
CDACESAAAI VFCAADEAAL CRACDEKVHM CNKLASRH                               38

SEQ ID NO: 423          moltype = AA  length = 36
FEATURE                 Location/Qualifiers
REGION                  1..36
```

```
                         note = conserved domain of Glyma11g07930.4
source                   1..36
                         mol_type = protein
                         organism = Glycine max
SEQUENCE: 423
CDICENAPAF FYCETDGSSL CLQCDMIVHV GGKRTH                          36

SEQ ID NO: 424           moltype = AA  length = 38
FEATURE                  Location/Qualifiers
REGION                   1..38
                         note = conserved domain of Glyma11g11850.1
source                   1..38
                         mol_type = protein
                         organism = Glycine max
SEQUENCE: 424
CDVCESAAAI LFCAADEAAL CSACDHKIHM CNKLASRH                        38

SEQ ID NO: 425           moltype = AA  length = 36
FEATURE                  Location/Qualifiers
REGION                   1..36
                         note = conserved domain of Glyma11g11850.1
source                   1..36
                         mol_type = protein
                         organism = Glycine max
SEQUENCE: 425
CDICENAPAF FYCEIDGSSL CLQCDMIVHV GGKRTH                          36

SEQ ID NO: 426           moltype = AA  length = 38
FEATURE                  Location/Qualifiers
REGION                   1..38
                         note = conserved domain of Glyma12g04130.1
source                   1..38
                         mol_type = protein
                         organism = Glycine max
SEQUENCE: 426
CDVCESAAAI VFCAADEAAL CSACDHKIHM CNKLASRH                        38

SEQ ID NO: 427           moltype = AA  length = 36
FEATURE                  Location/Qualifiers
REGION                   1..36
                         note = conserved domain of Glyma12g04130.1
source                   1..36
                         mol_type = protein
                         organism = Glycine max
SEQUENCE: 427
CDICENAPAF FYCEIDGSSL CLQCDMIVHV GGKRTH                          36

SEQ ID NO: 428           moltype = DNA  length = 3157
FEATURE                  Location/Qualifiers
misc_feature             1..3157
                         note = pMEN65 vector (35S::MCS::E9)
source                   1..3157
                         mol_type = other DNA
                         organism = synthetic construct
SEQUENCE: 428
aagcttnnnn ctgcagnnnn nnnnnnnnnn nnnnnnnnnn nnnnnnnnnn nntcggattc  60
cattgcccag ctatctgtca ctttattgtg aagatagtga aaaagaaggt ggctcctaca  120
aatgccatca ttgcgataaa ggaaaggcca tcgttgaaga tgcctctgcc gacagtggtc  180
ccaaagatgg acccccaccc acgaggagca tcgtggaaaa agaagacgtt ccaaccacgt  240
cttcaaagca agtggattga tgtgatggtc cgattgagac ttttcaacaa agggtaatat  300
ccggaaacct cctcggattc cattgcccag ctatctgtca ctttattgtg aagatagtgg  360
aaaaggaagg tggctcctac aaatgccatc attgcgataa aggaaaggcc atcgttgaag  420
atgcctctgc cgacagtggt cccaaagatg gacccccacc cacgaggagc atcgtggaaa  480
aagaagacgt tccaaccacg tcttcaaagc aagtggattg atgtgatatc tccactgacg  540
taagggatga cgcacaatcc cactatcctt cgcaagaccc ttcctctata taaggaagtt  600
catttcattt ggagaggaca cgctgacaag ctgactctag cagatctggt accgtcgacg  660
gtgagctccg cggccgctct agacaggcct cgtaccggat cctctagcta gagctttcgt  720
tcgtatcatc ggtttcgaca acgttcgtca agttcaatgc atcagtttca ttgcgcacac  780
accagaatcc tactgagttt gagtattatg gcattgggaa aactgttttt cttgtaccat  840
ttgttgtgct tgtaatttac tgtgtttttt attcggtttt cgctatcgaa ctgtgaaatg  900
gaaatggatg gagaagagtt aatgaatgat atggtccttt tgttcattct caaattaata  960
ttatttgttt tttctcttat ttgttgtgtg ttgaatttga aattataaga gatatgcaaa  1020
cattttgttt tgagtaaaaa tgtgtcaaat cgtggcctct aatgaccgaa gttaatatga  1080
ggagtaaaac acttgtagtt gtaccattat gcttattcac taggcaacaa atatattttc  1140
agacctagaa aagctgcaaa tgttactgaa tacaagtatg tcctcttgtg ttttagacat  1200
ttatgaactt tcctttatgt aattttccag aatccttgtc agattctaat cattgcttta  1260
taattatagt tatactcatg gatttgtagt tgagtatgaa aatatttttt aatgcatttt  1320
atgacttgcc aattgattga caacatgcat caatcgacct gcagccactc gaagcggccg  1380
gccgccactc gagatcatga gcggagaatt aagggagtca cgttatgacc cccgccgatg  1440
```

```
acgcgggaca agccgtttta cgtttggaac tgacagaacc gcaacgttga aggagccact  1500
cagccgcggg tttctggagt ttaatgagct aagcacatac gtcagaaacc attattgcgc  1560
gttcaaaagt cgcctaaggt cactatcagc tagcaaatat ttcttgtcaa aaatgctcca  1620
ctgacgttcc ataaattccc ctcggtatcc aattagagtc tcatattcac tctcaatcca  1680
aataatctgc accggatctg gatcgtttcg catgattgaa caagatggat tgcacgcagg  1740
ttctccggcc gcttgggtgg agaggctatt cggctatgac tgggcacaac agacaatcgg  1800
ctgctctgat gccgccgtgt tccggctgtc agcgcagggg cgcccggttc tttttgtcaa  1860
gaccgacctg tccggtgccc tgaatgaact gcaggacgag gcagcgcggc tatcgtggct  1920
ggccacgacg ggcgttcctt gcgcagctgt gctcgacgtt gtcactgaag cgggaaggga  1980
ctggctgcta ttgggcgaag tgccggggca ggatctcctg tcatctcacc ttgctcctgc  2040
cgagaaagta tccatcatgg ctgatgcaat gcggcggctg catacgcttg atccggctac  2100
ctgcccattc gaccaccaag cgaaacatcg catcgagcga gcacgtactc ggatggaagc  2160
cggtcttgtc gatcaggatg atctggacga agagcatcag gggctcgcgc cagccgaact  2220
gttcgccagg ctcaaggcgc gcatgcccga cggcgaggat ctcgtcgtga cccatggcga  2280
tgcctgcttg ccgaatatca tggtggaaaa tggccgcttt tctggattca tcgactgtgg  2340
ccggctgggt gtggcggacc gctatcagga catagcgttg gctacccgtg atattgctga  2400
agagcttggc ggcgaatggg ctgaccgctt cctcgtgctt tacggtatcg ccgctcccga  2460
ttcgcagcgc atcgccttct atcgccttct tgacgagttc ttctgagcgg gactctgggg  2520
ttcgaaatga ccgaccaagc gacgcccaac ctgccatcac gagatttcga ttccaccgcc  2580
gccttctatg aaaggttggg cttcggaatc gttttccggg acgccggctg gatgatcctc  2640
cagcgcgggg atctcatgct ggagttcttc gcccacggga tctctgcgga acaggcggtc  2700
gaaggtgccg atatcattac gacagcaacg gccgacaagc acaacgccac gatcctgagc  2760
gacaatatga tcgggcccgg cgtccacatc aacggcgtcg gcggcgactg cccaggcaag  2820
accgagatgc accgcgatat cttgctgcgt tcggatattt tcgtggagtt cccgccacag  2880
acccggatga tccccgatcg ttcaaacatt tggcaataaa gtttcttaag attgaatcct  2940
gttgccggtc ttgcgatgat tatcatataa tttctgttga attacgttaa gcatgtaata  3000
attaacatgt aatgcatgac gttatttatg agatgggttt ttatgattag agtcccgcaa  3060
ttatacattt aatacgcgat agaaaacaaa atatagcgcg caaactagga taaattatcg  3120
cgcgcggtgt catctatgtt actagatcgg gctcgag                           3157
```

```
SEQ ID NO: 429         moltype = DNA  length = 906
FEATURE                Location/Qualifiers
misc_feature           1..906
                       note = BBX32 (G1988)
source                 1..906
                       mol_type = unassigned DNA
                       organism = Arabidopsis thaliana
SEQUENCE: 429
tgctactctc atcaaccatg aaccataaaa actccaccgc tctttctctc cctcaatcat  60
ttacatctct tccttaaatc tctcttccca ccatcatcat tccaaaccaa ttctctctca  120
cttctttctg gtgatcagag agatcgactc aatggtgagc ttttgcgagc tttgtggtgc  180
cgaagctgat ctccattgtg ccgcggactc tgccttcctc tgccgttctt gtgacgctaa  240
gttccatgcc tcaaatttc tcttcgctcg tcatttccgg cgtgtcatct gcccaaattg  300
caaatctctt actcaaaatt tcgtttctgg tcctcttctt ccttggcctc cacgaacaac  360
atgttgttca gaatcgtcgt cttcttcttg ctgctcgtct cttgactgtg tctcaagctc  420
cgagctatcg tcaacgacgc gtgacgtaaa cagagcgcga gggagggaaa acagagtgaa  480
tgccaaggcc gttgcggtta cggtggcgga tggcattttt gtaaattggt gtggtaagtt  540
aggactaaac agggatttaa caaacgctgt cgtttcatat gcgtctttgg ctttggctgt  600
ggagacgagg ccaagagcga cgaagagagt gttcttagcg gcggcgtttt ggttcggcgt  660
taagaacacg acgacgtggc agaatttaaa gaaagtagaa gatgtgactg gagtttcagc  720
tgggatgatt cgagcggttg aaagcaaatt ggcgcgtgca atgacgcagc agcttagacg  780
gtggcgcgtg gattcggagg aaggatgggc tgaaaacgac aacgtttgag aaatattatt  840
gacatgggtc ccgcattatg caaattagga catttagtgt ttagtgcatt aattatagtt  900
tgtgtc                                                            906
```

```
SEQ ID NO: 430         moltype = AA  length = 225
FEATURE                Location/Qualifiers
REGION                 1..225
                       note = G1988 polypeptide (BBX32, domain in aa coordinates:
                        5-50)
source                 1..225
                       mol_type = protein
                       organism = Arabidopsis thaliana
SEQUENCE: 430
MVSFCELCGA EADLHCAADS AFLCRSCDAK FHASNFLFAR HFRRVICPNC KSLTQNFVSG  60
PLLPWPPRTT CCSESSSSSC CSSLDCVSSS ELSSTTRDVN RARGRENRVN AKAVAVTVAD  120
GIFVNWCGKL GLNRDLTNAV VSYASLALAV ETRPRATKRV FLAAAFWFGV KNTTTWQNLK  180
KVEDVTGVSA GMIRAVESKL ARAMTQQLRR WRVDSEEGWA ENDNV                 225
```

```
SEQ ID NO: 431         moltype = DNA  length = 732
FEATURE                Location/Qualifiers
misc_feature           1..732
                       note = G4004
source                 1..732
                       mol_type = unassigned DNA
                       organism = Glycine max
SEQUENCE: 431
atgaagccca agacttgcga gctttgtcat caactagctt ctctctattg tccctccgat  60
tccgcatttc tctgcttcca ctgcgacgcc gccgtccacg ccgccaactt cctcgtagct  120
```

```
cgccacctcc gccgcctcct ctgctccaaa tgcaaccgtt tcgccgcaat tcacatctcc  180
ggtgctatat cccgccacct ctcctccacc tgcacctctt gctccctgga gattccttcc  240
gccgactccg attctctccc ttcctcttct acctgcgtct ccagttccga gtcttgctct  300
acgaatcaga ttaaggcgga gaagaagagg aggaggagga ggaggagttt ctcgagttcc  360
tccgtgaccg acgacgcatc tccggcggcg aagaagcggc ggagaaatgg cggatcggtg  420
gcggaggtgt ttgagaaatg gagcagagag atagggttag ggttaggggt gaacggaaat  480
cgcgtggcgt cgaacgctct gagtgtgtgc ctcggaaagt ggaggtcgct tccgttcagg  540
gtggctgctg cgacgtcgtt ttggttgggg ctgagatttt gtggggacag aggcctcgcc  600
acgtgtcaga atctggcgag gttggaggca atatctggag tgccagcaaa gctgattctg  660
ggcgcacatg ccaacctcgc acgtgtcttc acgcaccgcc gcgaattgca ggaaggatgg  720
ggcgagtcct ag                                                    732

SEQ ID NO: 432          moltype = AA  length = 243
FEATURE                 Location/Qualifiers
REGION                  1..243
                        note = G4004 polypeptide
source                  1..243
                        mol_type = protein
                        organism = Glycine max
SEQUENCE: 432
MKPKTCELCH QLASLYCPSD SAFLCFHCDA AVHAANFLVA RHLRRLLCSK CNRFAAIHIS  60
GAISRHLSST CTSCSLEIPS ADSDSLPSSS TCVSSSESCS TNQIKAEKKR RRRRRSFSSS  120
SVTDDASPAA KKRRRNGGSV AEVFEKWSRE IGLGLGVNGN RVASNALSVC LGKWRSLPFR  180
VAAATSFWLG LRFCGDRGLA TCQNLARLEA ISGVPAKLIL GAHANLARVF THRRELQEGW  240
GES                                                              243

SEQ ID NO: 433          moltype = DNA  length = 726
FEATURE                 Location/Qualifiers
misc_feature            1..726
                        note = G4005
source                  1..726
                        mol_type = unassigned DNA
                        organism = Glycine max
SEQUENCE: 433
atgaagggta agacttgcga gctttgtgat caacaagctt ctctctattg tccctccgat  60
tccgcatttc tctgctccga ctgcgacgcc gccgtgcacg ccgccaactt tctcgtagct  120
cgtcacctcc gtcgcctcct ctgctccaaa tgcaaccgtt tcgccggatt tcacatctcc  180
tccggcgcta tatcccgcca cctctcgtcc acctgcagct cttgctcccc ggagaatcct  240
tccgctgact actccgattc tctcccttcc tcttctacct gcgtctccag ttccgagtct  300
tgctccacga agcagattaa ggcggagaag aagaggagtt ggtcgggttc ctccgtgacc  360
gacgacgcat ctccggcggc gaagaagcgg cagaggagtg gaggatcgga ggaggtgttt  420
gagaaatgga gcagagagat agggttaggg ttagggttag ggtaaacgg aaatcgcgtg  480
gcgtcgaacg ctctgagtgt gtgcctggga aagtggaggt ggcttccgtt cagggtggct  540
gctgcgacgt cgttttggtt ggggctgaga ttttgtgggg acagagggct ggcctcgtgt  600
cagaatctgg cgaggttgga ggcaatatcc ggagtgccag ttaagctgat tctggccgca  660
catggcgacc tggcacgtgt cttcacgcac cgccgcgaat tgcaggaagg atggggcgag  720
tcctag                                                           726

SEQ ID NO: 434          moltype = AA  length = 241
FEATURE                 Location/Qualifiers
REGION                  1..241
                        note = G4005 polypeptide
source                  1..241
                        mol_type = protein
                        organism = Glycine max
SEQUENCE: 434
MKGKTCELCD QQASLYCPSD SAFLCSDCDA AVHAANFLVA RHLRRLLCSK CNRFAGFHIS  60
SGAISRHLSS TCSSCSPENP SADYSDSLPS SSTCVSSSES CSTKQIKAEK KRSWSGSSVT  120
DDASPAAKKR QRSGGSEEVF EKWSREIGLG LGLGVNGNRV ASNALSVCLG KWRWLPFRVA  180
AATSFWLGLR FCGDRGLASC QNLARLEAIS GVPVKLILAA HGDLARVFTH RRELQEGWGE  240
S                                                                241

SEQ ID NO: 435          moltype = DNA  length = 1047
FEATURE                 Location/Qualifiers
misc_feature            1..1047
                        note = GmBBX1
source                  1..1047
                        mol_type = unassigned DNA
                        organism = Glycine max
SEQUENCE: 435
atgttggatg gagaagcaac aatgggcacg tgggctcgca tgtgcgacac gtgccgttcg  60
gccccctcct ccgtgttctg ccgcgcccac accgccttcc tctgcgccac gtgcgacgcg  120
cgcctccacg cctcgctgac gtggcacgag cgcgtgtggg tgtgcgaggc ctgcgagcgc  180
gcccctgcgg ccttcctctg caaggctgac gccgcctccc tctgcgcctc ctgcgacgcc  240
gacatccacg ccgccaaccc cctcgccagc cgccaccacc gtgtccccat cctccccatc  300
gccgccgccc ccggcaacaa cgacaacgac aacgtcgacg atgctgactt ggacgacgat  360
gacgaaaccg cttcatggct cttgctcaac cctgtcaaaa gcgctagtgt ccctaacaac  420
aataacacta ataatgggtt ctcgtataat ggtgaggttg atgagtattt ggaccttgtt  480
gatgactgcg acaaccacca ctttgcttct gttgctacta ctacggacca ttactctcat  540
```

```
cagcaccaac atttcggtgt tgtttctcac aagagttatg ctggggacag tgttgttccg  600
gttcagcacc accagcattt tcagcttggc ttggagtttg acaactccaa agctgccttc  660
agttacaatg cttctgttaa tcaaagtgtt tcagtttcat caatggatat tggtgttgta  720
cctgaatcac cgatgaggga tgtctcaatt ggccatacaa gaaccccca agggacaatt  780
gacctatttt ctggacctcc cattcaggtg ccttcccatt tttctccaat ggacagggag  840
gccagagtcc taaggtacag ggagaaaaag aagacaagaa aatttgagaa gacaatcagg  900
tatgcctcaa ggaaggccta tgcagagact agaccccgta taaaaggtcg atttgccaag  960
agaacagatg tagaagctga agtggatcag atgttctcca caacactaat tacagaagtt  1020
ggatatggca ttgttccctc tttctga                                    1047

SEQ ID NO: 436         moltype = AA  length = 348
FEATURE                Location/Qualifiers
REGION                 1..348
                       note = GmBBX1 soybean B-box polypeptide
source                 1..348
                       mol_type = protein
                       organism = Glycine max
SEQUENCE: 436
MLDGEATMGT WARMCDTCRS APSSVFCRAH TAFLCATCDA RLHASLTWHE RVWVCEACER  60
APAAFLCKAD AASLCASCDA DIHAANPLAS RHHRVPILPI AAAPGNNDND NVDDADLDDD  120
DETASWLLLN PVKSASVPNN NNTNNGFSYN GEVDEYLDLV DDCDNHHFAS VATTTDHYSH  180
QHQHFGVVSH KSYAGDSVVP VQHHQHFQLG LEFDNSKAAF SYNASVNQSV SVSSMDIGVV  240
PESPMRDVSI GHTRTPKGTI DLFSGPPIQV PSHFSPMDRE ARVLRYREKK KTRKFEKTIR  300
YASRKAYAET RPRIKGRFAK RTDVEAEVDQ MFSTTLITEV GYGIVPSF          348

SEQ ID NO: 437         moltype = DNA  length = 1059
FEATURE                Location/Qualifiers
misc_feature           1..1059
                       note = GmBBX2
source                 1..1059
                       mol_type = unassigned DNA
                       organism = Glycine max
SEQUENCE: 437
atgttggagg gccaagcaac aacgcccacg tggccgcgca tgtgcgacac gtgccgctcc  60
gtcccctcca ccgtcttctg ccgctcccac accgcctttc tctgcgccac gtgcgacact  120
cgcctccacg tctctctcac gtggcacgag cgcgtgtggg tgtgcgaggc gtgcgagcgc  180
gccccggcgg cgttcctctg caaggccgac gccgcctccc tctgcgcctc ctgcgacgcc  240
gacatccacg ccgccaaccc cctcgccagc cgccaccacc gcgtccccat cctccccatc  300
gccgccgcca acaacaacaa caacgacgac gacgacgttg ctgacgttga cgacgaagac  360
gaaaccgctt catggctctt gctcaaccct atcaagagtg ctactgtccc taacaccaat  420
aacaataaca ataataacgg gttcttgtat aacggtgagg ttgatgagta tttggacctt  480
gttgataatt gtaactcttg tggtgataat aatcacttcg cttcagctgc tgctactact  540
gatcattacg ctcagcacca acatttcgct ggtgtttctc agaagagtta tgctggggac  600
agtgttgttc cggttcagca acaccagcat tttcagcttg ggttggagtt tgacaactcc  660
aaacctgcct tcagttacaa tggttctgtt agtcaaagtg tttcagtttc atcaatggat  720
attggtgttg tacctgaatc accaatgagg gatgtctcaa ttgcccatac aagacccccc  780
aaagggacaa ttgacctatt ttctggacct ccaattcagg tgccttccca tttttctcca  840
atggacaggg aggccagagt cctaaggtac agggagaaaa agaagatgag aaaatttgag  900
aagacaatca ggtatgcctc aaggaaggcc tatgcagaga ctagacctcg tataaaaggt  960
cgatttgcca agagaacaga tgtagaagct gaagtggatc agatgttctc gacaacacta  1020
attacagaag ttggatatgg aattgttccc tctttctga                       1059

SEQ ID NO: 438         moltype = AA  length = 352
FEATURE                Location/Qualifiers
REGION                 1..352
                       note = GmBBX2 soybean B-box polypeptide
source                 1..352
                       mol_type = protein
                       organism = Glycine max
SEQUENCE: 438
MLEGQATTPT WPRMCDTCRS VPSTVFCRSH TAFLCATCDT RLHVSLTWHE RVWVCEACER  60
APAAFLCKAD AASLCASCDA DIHAANPLAS RHHRVPILPI AAANNNNNDD DDVADVDDED  120
ETASWLLLNP IKSATVPNTN NNNNNNGFLY NGEVDEYLDL VDNCNSCGDN NHFASAAATT  180
DHYAQHQHFA GVSQKSYAGD SVVPVQQHQH FQLGLEFDNS KPAFSYNGSV SQSVSVSSMD  240
IGVVPESPMR DVSIAHTRPP KGTIDLFSGP PIQVPSHFSP MDREARVLRY REKKKMRKFE  300
KTIRYASRKA YAETRPRIKG RFAKRTDVEA EVDQMFSTTL ITEVGYGIVP SF        352

SEQ ID NO: 439         moltype = DNA  length = 1086
FEATURE                Location/Qualifiers
misc_feature           1..1086
                       note = GmBBX3
source                 1..1086
                       mol_type = unassigned DNA
                       organism = Glycine max
SEQUENCE: 439
atgttgaagg aaggcaccaa caacgttggt ggcagcaccg gcacctggtc acatgtctgc  60
gacacgtgcc ggtcagcgcc atgcgtactg tactgccatg cagactcagc atacctttgc  120
tcatcctgcg atgctcgtgt ccatgcggct aaccgtgtgg cctcaagaca cgagcgtgtg  180
tgggtgtgcg aagcgtgtga acgtgctccc gcagcgtttc tatgcaaagc cgacgcagct  240
```

```
tctctttgtt cttcctgtga tgctgacatt cactcagcaa accctctcgc tagccgccac  300
caccgcgtgc ccattctccc gatctctggt tccctcttcg gggaaccaga gcatgaacgc  360
gtgtacgcgt tcgtgaatga agtggaagcg gaggaggaag aggaagaggt tttgatgag   420
tatgatgagg ttgaagcagc ttcgtggttg ttgccacatc ctatgaaaaa tgataaaatt  480
gacgagaatg gtggtgataa gggtttttg tttggtgatg agtatttcga caaccttgtt   540
gattgtaact catgtggtca caataacaac cagtttagca acgtttatga tcagcaccag  600
cagaattaca gcaacactgt ccctcagaac tatgcagtgg ttccagttca ggtgccgcag  660
cattttcaac cgggtttgga ctttgactca tcaaaagctg ggttcagtta cgatggttct  720
cttagtcaaa gtgtttcggt ttcatcgatg gatgttggtg ttgtactcga atcaacaata  780
agtgacatct caatgtccca ctcaaagtcg ccaataggga caactgacct atttcctccc  840
cttcccatgc cttcacatct cacaccaatg gacagagagg caagagtcct aagatacagg  900
gagaaaaaga agacaagaaa atttgagaag aaaataaggt atgcctcaag gaaggcctat  960
gcagagacta gaccccgcat aaagggtcgt tttgcaaaga gaaccgatgt agaagctgaa  1020
gtggaccaga tgttctccac aacactattc actgaagttg gaggtagcat tttcccact   1080
ttctag                                                             1086

SEQ ID NO: 440         moltype = AA  length = 361
FEATURE                Location/Qualifiers
REGION                 1..361
                       note = GmBBX3 soybean B-box polypeptide
source                 1..361
                       mol_type = protein
                       organism = Glycine max
SEQUENCE: 440
MLKEGTNNVG GSTGTWSHVC DTCRSAPCVL YCHADSAYLC SSCDARVHAA NRVASRHERV  60
WVCEACERAP AAFLCKADAA SLCSSCDADI HSANPLASRH HRVPILPISG SLFGEPEHER  120
VYAFVNEVEA EEEEEEVFDE YDEVEAASWL LPHPMKNDKI DENGGDKGFL FGDEYFDNLV  180
DCNSCGHNNN QFSNVYDQHQ QNYSNTVPQN YAVVPVQVPQ HFQPGLDFDS SKAGFSYDGS  240
LSQSVSVSSM DVGVVLESTI SDISMSHSKS PIGTTDLFPP LPMPSHLTPM DREARVLRYR  300
EKKKTRKFEK KIRYASRKAY AETRPRIKGR FAKRTDVEAE VDQMFSTTLF TEVGGSIFPT  360
F                                                                  361

SEQ ID NO: 441         moltype = DNA  length = 1101
FEATURE                Location/Qualifiers
misc_feature           1..1101
                       note = GmBBX4
source                 1..1101
                       mol_type = unassigned DNA
                       organism = Glycine max
SEQUENCE: 441
atgttgaagg aaggcaccaa caacgttggt ggcagcaaca ctggcaccac ctggtcacgt  60
gtctgtgaca cgtgcctgtc tgcgccatgc gtgctgtact gccatgcaga ctcagcatat  120
ctttgctctt cctgtgatgc tcgtgtgcat gcagctaacc gtgtggcctc gagacacaag  180
cgtgtgtggg tgtgcgaagc gtgtgagcgt gctccggcgg cgtttctatg caaagctgac  240
gcagcttctc tttgttcttc ctgtgatgct gacattcact cagcaaaccc tctcgctagc  300
cgccacaacc gtgttcccat tctcccgatc tcaggttccc tcttcaggga accagagcac  360
aatcacaaac gcgtggaaca cgcgttcgtg aatgaggttg aggaggaaga ggaaggggtt  420
tttgatgagt atgaagacga ggttgaagct gcttcgtggt tgttgccaca tcctatgaaa  480
aataatgatg aaattgagga gaatgattgt ggtgacgagg gtttttttgtt tgttgatgag  540
tatttggaca atcttgttga ttgttgtaac tcatgtggtc acaatgacaa ccagtttagc  600
aacgtttatc agcaccagca gaattacaac actgtccctc agaactatgt agtggttcca  660
gttcaggtgc cgcagcattt tcaacccggt ttggactttg actcatcaaa agctgggttc  720
agttacgatg gttctcttag tcaaagtgtt tcggtttcat caatggatgt tggagttgta  780
cccgaatcaa cagtaagtgg catctcaatg tcccactcaa agtcaccaat agggacaaat  840
gacctatttc ctccccttct catgccttca catctcacac caatggacag agaggcaaga  900
gtcctaagat atagggagaa aaagaagaca agaaagttcg agaagaaaat aagatatgcc  960
tcaaggaagg cctatgcaga gactagaccc cgcataaagg gtcgttttgc aaagagaact  1020
gatgtagaag ctgaagtgga tcagatgttc tccacaaaac tattcaatga agttggaggt  1080
agcatttttc ccactttcta g                                            1101

SEQ ID NO: 442         moltype = AA  length = 366
FEATURE                Location/Qualifiers
REGION                 1..366
                       note = GmBBX4 soybean B-box polypeptide
source                 1..366
                       mol_type = protein
                       organism = Glycine max
SEQUENCE: 442
MLKEGTNNVG GSNTGTTWSR VCDTCLSAPC VLYCHADSAY LCSSCDARVH AANRVASRHK  60
RVWVCEACER APAAFLCKAD AASLCSSCDA DIHSANPLAS RHNRVPILPI SGSLFREPEH  120
NHKRVEHAFV NEVEEEEEGV FDEYEDEVEA ASWLLPHPMK NNDEIEENDC GDEGFLFVDE  180
YLDNLVDCCN SCGHNDNQFS NVYQHQQNYN TVPQNYVVVP VQVPQHFQPG LDFDSSKAGF  240
SYDGSLSQSV SVSSMDVGVV PESTVSGISM SHSKSPIGTN DLFPPLLMPS HLTPMDREAR  300
VLRYREKKKT RKFEKKIRYA SRKAYAETRP RIKGRFAKRT DVEAEVDQMF STKLFNEVGG  360
SIFPTF                                                             366

SEQ ID NO: 443         moltype = DNA  length = 1098
FEATURE                Location/Qualifiers
misc_feature           1..1098
```

-continued

```
                         note = GmBBX5
source                   1..1098
                         mol_type = unassigned DNA
                         organism = Glycine max
SEQUENCE: 443
atgggaattg aaagaggagg cttgaaggga ttcaggagcg gctggagtgt gccgccgaag  60
aagccatgcg actcctgtaa gctggcttcg gcggcgcttt tctgccacct cgattccgcg  120
tttctctgca tcgcgtgcga ttccaagatt cactgcgcga ataaactcgc gtcgcgccac  180
gagcgcgtgt ggatgtgtga ggtgtgcgag caggcacccg cttctgtcac gtgcaaggct  240
gacgcggccg ccctttgcgt cacgtgcgac tccgacatcc actccgccaa cccactcgcg  300
caacgccacg agcgcgttcc cgtggagccc ttcttcgatt ccgcggaatc catcgtcaaa  360
gcctccgcca ccgcctcttt cgggttcgtc gtcccctccg acgatggcgc tgcctccgac  420
gtcttcgccc ccgacgactc cgactccgcc gcctggctca tcccgaaccc caatttcggg  480
tccaaactca tggacgcccc cgaaatcaag tccaaggaga tattcttctc tgaaatggac  540
cccttcctcg attttgatta ctcaaactcc ttccaaaacc acaacagcgc cgtaaacgac  600
agtgtcgttc cagttcaaac caaaccctct ctcgcccctc cccccatcaa caatcaccag  660
caccaccacc aatctgagac ttgcttcgac atcgattttt gccgctcgaa gctctcctcc  720
tttaactacc catcccagtc tcttagccaa agcgtttctt cgtcgtcgct tgatgtcgga  780
gtggtgccgg acgggaacac agtgtcggac atgtcgtatt cgagtgggat tgtggtgtcg  840
ggtggacaag gcgcgacgca gttgtgtggg atggatcggg aagcgagggt gctgcgatac  900
agagagaaaa ggaagaaccg aaaatttgag aagacgattc gatacgcatc gcgaaaggct  960
tatgcggaaa cccggcccag gataaaaggc cggttcgcga aacgaaccga aattgactcg  1020
gatgtggagc gtctctatag ccctggcgct gcggcgctca tgctggacac tccatacggt  1080
gtcgtaccaa cgttttag                                               1098

SEQ ID NO: 444           moltype = AA  length = 365
FEATURE                  Location/Qualifiers
REGION                   1..365
                         note = GmBBX5 soybean B-box polypeptide
source                   1..365
                         mol_type = protein
                         organism = Glycine max
SEQUENCE: 444
MGIERGGLKG FRSGWSVPPK KPCDSCKLAS AALFCHLDSA FLCIACDSKI HCANKLASRH  60
ERVWMCEVCE QAPASVTCKA DAALCVTCD SDIHSANPLA QRHERVPVEP FFDSAESIVK  120
ASATASFGFV VPSDDGAASD VFAPDDSDSA AWLIPNPNFG SKLMDAPEIK SKEIFFSEMD  180
PFLDFDYSNS FQNHNSAVND SVVPVQTKPS LAPPPINNHQ HHHQSETCFD IDFCRSKLSS  240
FNYPSQSLSQ SVSSSSLDVG VVPDGNTVSD MSYSSGIVVS GGQGATQLCG MDREARVLRY  300
REKRKNRKFE KTIRYASRKA YAETRPRIKG RFAKRTEIDS DVERLYSPGA AALMLDTPYG  360
VVPTF                                                              365

SEQ ID NO: 445           moltype = DNA  length = 1125
FEATURE                  Location/Qualifiers
misc_feature             1..1125
                         note = GmBBX6
source                   1..1125
                         mol_type = unassigned DNA
                         organism = Glycine max
SEQUENCE: 445
atgggaattg aaagaggagg cttcaaggga ttcaggagcg cctggagcgt gccgcccaag  60
ccgtgcgatt cctgcaagct ggcctcggcg gcgcttttct gccgccccga ttccgcgttt  120
ctctgcatcg cctgcgattc caacattcac tgctcgaaca aactcgcgtc gcgccacgag  180
cgcgtgtgga tgtgtgaggt gtgcgagcag gcacccgctg ctgtcacgtg caaggccgac  240
gccgccgccc tctgcgtcac gtgtgactcc gacatccact ccgcgaaccc cctcgcgcaa  300
cgccacgagc gcgtccccgt ggaacctttc tttgactccg ctgagtccat agtgaaagcc  360
tctgctgccg ccaccttcgg gttcattgtc ccatccgacg acggcggcgc ctccgacgct  420
ttcgcccccg atgactccga cgccgccgcg tggctcatcc cgaaccctaa tttcgggtcc  480
aagctcatgg acgcccccga aatcaagtcc aaggagatat tcttctctga aatggacccc  540
ttcctcgatt ttgattactc aaactccttc caaaacaaca acagcgccgg aaacgacagc  600
gtcgttccag ttcaaaaacc ctctctcgcc cctcccctaa tcaataatca ccaccaccac  660
caatcagaaa cttgcttcga cgtcgatttt tgtcgctcga agctctcctc ctttaactac  720
ccttccaatt ctcttagcca aagcgtttcg tcgtcgtcgc ttgatgttgg agtggtgccg  780
gacgggaaca cggtgtcaga catgtcgtat tcttttggtc ggaacagttc ggattcgagt  840
gggattgttg ttgtgtcagg aaatagtgtg gggcaaggtg cgacgcagtt gtgtggaatg  900
gatcgggaag cgagggtact gcgatacaga gagaaaagga agaaccgaaa attcgagaag  960
acaattcgat acgcatcgcg aaaagcatat gcggaaaccc ggcccaggat aaaaggccgc  1020
ttcgccaaac gaacagaaat tgactcggat gtggagcgtc tctatagccc tggccctgcg  1080
gtgctcatgc tggacactcc atacggcgtc gtaccatcgt tttag                  1125

SEQ ID NO: 446           moltype = AA  length = 89
FEATURE                  Location/Qualifiers
REGION                   1..89
                         note = GmBBX6 soybean B-box polypeptide
source                   1..89
                         mol_type = protein
                         organism = Glycine max
SEQUENCE: 446
MGIERGGFKG FRSAWSVPPK PCDSCKLASA ALFCRPDSAF LCIACDSNIH CSNKLASRHE  60
RVWMCEVCEQ APAAVTCKAD AAALCVTCD                                    89
```

```
SEQ ID NO: 447          moltype = DNA  length = 684
FEATURE                 Location/Qualifiers
misc_feature            1..684
                        note = GmBBX7
source                  1..684
                        mol_type = unassigned DNA
                        organism = Glycine max
SEQUENCE: 447
atggtcaatc aactcttcga ctcatgcaaa tcagccactg ctaccttgta ctgccgcatc  60
gacacgacgt tcctctgcgg cacctgtgac tctaaggttc atgccgccaa caagctcgtg  120
tcgcgccacc cgcgcgttgc actctgcgag gtgtgcaagc aggcgtcaac gcatgtgacc  180
tgcaaggccg gcgctgccgc tctctgcctc acctgtgact ctgagatcca ctccaccaac  240
cccctcgcca gccgccacga gcgcatcccc atcacgctgt tcttcgagta cgtacactca  300
gtcaaggcct cttcatcgat caacttccac cactgcttct tctccgacac cgacgctgat  360
gtcagcacca aggaggccga ggtcgcgtcc tggctactaa ataatctgaa gacatatcta  420
aattcgtctc agtacttgtt ctcagaaaag ttccgccatc gccgatggcg tcattccagt  480
gtagagcaac ttcaagccgt tcacctacga gcaccaaaca tctttcttca cagctacttc  540
tctcgatcta gaaccttcgg agtaattaat tattacatac taactggagt tagatccaac  600
ataaatgact tctctctcaa cttacaaaat caagttaaaa atattattaa gtctaaaatt  660
gctctcaata attttttcca ataa                                          684

SEQ ID NO: 448          moltype = AA  length = 227
FEATURE                 Location/Qualifiers
REGION                  1..227
                        note = GmBBX7 soybean B-box polypeptide
source                  1..227
                        mol_type = protein
                        organism = Glycine max
SEQUENCE: 448
MVNQLFDSCK SATATLYCRI DTTFLCGTCD SKVHAANKLV SRHPRVALCE VCKQASTHVT  60
CKAGAAALCL TCDSEIHSTN PLASRHERIP ITLFFEYVHS VKASSSINFH HCFFSDTDAD  120
VSTKEAEVAS WLLNNLKTYL NSSQYLFSEK FRHRRWRHSS VEQLQAVHLR APNIFLHSYF  180
SRSRTFGVIN YYILTGVRSN INDFSLNLQN QVKNIIKSKI ALNNFFQ                 227

SEQ ID NO: 449          moltype = DNA  length = 930
FEATURE                 Location/Qualifiers
misc_feature            1..930
                        note = GmBBX11
source                  1..930
                        mol_type = unassigned DNA
                        organism = Glycine max
SEQUENCE: 449
atggcttcca agctctgcga ctcatgcaaa tccgccactg ctaccttgta ctgccgccct  60
gacgccgcgt tcctctgcgg cgcctgcgat tctaaggtcc acgccgccaa caagctcgcg  120
tcgcgccacc cgcgcgtggc gctctgcgag gtgtgcgagc aggccccggc gcacgtaacc  180
tgcaaggctg atgccgccgc gctctgcctt gcctgcgacc gcgacatcca ctccgccaac  240
cccctcgcca gccgccacga gcgcatcccc gtctcaccgt tcttcgagtc cgtacactcc  300
gtcaaggcct cctcgccgat caacttccta gatgaccacc gcttcttctc cgacgccgat  360
gctgacgtca gcaccgagga ggccgaggcc gcctcctggc tgcttcctaa tccgaagaca  420
gatctaaatt cctctcagta cttgttctcc gaaaccgagc cggttcctta catagatctg  480
gattatgctg ccgtggatcc taaggcggag cagaaaagct ccgccaccgc cgacggcgtc  540
gttcccgtgc agagcaactt cgagccattc gcctacggtt acaagtacaa taccactctc  600
tcacagtctc agatgagcca gagtgtatcg tcgtcgtcga tggaggttgg agtcgtgccg  660
gacgggaaca caatgtcgga gacatcgaac tgcagctaca gcaaggtgcc tccggtgacg  720
gtgacggtga cggcgcagtt ctcggcggcg gatagggagg cgagagtgtt gaggtacagg  780
gagaagagga agaaccgtaa gttcgagaag acgattcgtt acgcatcgag aaaagcatat  840
gcggaggcga ggccaaggat caaagggagg tttgcgaaac gcactgaccc ggaccctctg  900
gctggatacg gcgtcgttcc gtcgtgttga                                  930

SEQ ID NO: 450          moltype = AA  length = 174
FEATURE                 Location/Qualifiers
REGION                  1..174
                        note = GmBBX11 soybean B-box polypeptide
source                  1..174
                        mol_type = protein
                        organism = Glycine max
SEQUENCE: 450
MASKLCDSCK SATATLYCRP DAAFLCGACD SKVHAANKLA SRHPRVALCE VCEQAPAHVT  60
CKADAAALCL ACDRDIHSAN PLASRHERIP VSPFFESVHS VKASSPINFL DDHRFFSDAD  120
ADVSTEEAEA ASWLLPNPKT DLNSSQYLFS ETEPVPYIDL DYAAVDPKAE QKSS        174

SEQ ID NO: 451          moltype = DNA  length = 933
FEATURE                 Location/Qualifiers
misc_feature            1..933
                        note = GmBBX12
source                  1..933
                        mol_type = unassigned DNA
                        organism = Glycine max
```

-continued

```
SEQUENCE: 451
atggcttcca agctctgcga ctcatgcaaa tcagccactg ctaccttgta ctgccgcccc  60
gacgcggcct tcctctgcgg cgcctgtgac tctaaggttc atgccgccaa caagctcgca  120
tcgcgccacc cgcgcgtcgt gctctgcgag gtgtgcgagc aggcgcccgc gcatgtgacc  180
tgtaaagccg acgccgccgc gctctgcctt gcctgcgatc gcgatatcca ctccgccaac  240
cccctcgcca gccgccacga gcgcatcccc gtcacgccgt tcttcgagtc cgtacattca  300
gtcaaggcct cctcgccgat caacttccac caccgcttct tctccgacgc cgacgctgat  360
gctgacgtca gcaccgagga ggccgaggcc gcgtcatggc tgctacctaa tccaaagaca  420
gatctaaatt cgtctcagta cttgttctcc gaaaccgaac cggttcctta catagatctg  480
gattacgcgg ccatggatcc gaagacggag cagaaaagtt ccgccaccgc cgacggcgtc  540
gttccggtgc agagcaactt cgagccgttc acctacggtt acaagtacaa cactactctc  600
tcacagtcac agtctcatat gagccagagt gtatcttctc cgtcgtcgat ggaagttgga  660
gttgtgccgg acgggaacac gatgtcggag atatcgaact gcagctacag caaagtggca  720
ccggtgacgg tgacggcgca gttctcggcg gcggataggg aggctagagt gttgaggtac  780
agggagaaga ggaagaaccg aaagttcgag aagaccattc gttacgcatc gagaaaagcg  840
tatgccgaaa cgaggccaag aatcaaagga aggttcgcga aacgcactga tgcggaccct  900
ctggctggat acggcgtcgt tccgtcgtgt tga                                933

SEQ ID NO: 452         moltype = AA  length = 310
FEATURE                Location/Qualifiers
REGION                 1..310
                       note = GmBBX12 soybean B-box polypeptide
source                 1..310
                       mol_type = protein
                       organism = Glycine max
SEQUENCE: 452
MASKLCDSCK SATATLYCRP DAAFLCGACD SKVHAANKLA SRHPRVVLCE VCEQAPAHVT  60
CKADAAALCL ACDRDIHSAN PLASRHERIP VTPFFESVHS VKASSPINFH HRFFSDADAD  120
ADVSTEEAEA ASWLLPNPKT DLNSSQYLFS ETEPVPYIDL DYAAMDPKTE QKSSATADGV  180
VPVQSNFEPF TYGYKYNTTL SQSQSHMSQS VSSPSSMEVG VVPDGNTMSE ISNCSYSKVA  240
PVTVTAQFSA ADREARVLRY REKRKNRKFE KTIRYASRKA YAETRPRIKG RFAKRTDADP  300
LAGYGVVPSC                                                          310

SEQ ID NO: 453         moltype = DNA  length = 1260
FEATURE                Location/Qualifiers
misc_feature           1..1260
                       note = GmBBX13
source                 1..1260
                       mol_type = unassigned DNA
                       organism = Glycine max
SEQUENCE: 453
atgagttcgg ctactaagaa cgcggcaaac gcggttgggg ccaaaacggc aagagcatgt  60
gacagctgca taaccaaacg tgcacgttgg tactgtgctg ccgatgatgc ttttctctgc  120
caggcctgcg actcttctgt tcactcggcg aatcctttgg ctcgaagaca cgaacgagtc  180
cgcttgaaaa cggcgtccta caagtccact gatgaacaac aacaacaaca acaacaacaa  240
cctcccacgt ggcacactaa gaaacctcga acgccgaggc acgggaaaca ttctcgtaac  300
aacaaccctt tccatttggt ccctgaagag ggttcggagg aggcgaattc ccatgatgag  360
aacgaggagc agcttcttta tagggtcccc atattcgacc cttttgttgc tgagctatgt  420
gggactaata gttctccttc tcctgttact tcaactgatc aaggagtagt tgctgctgct  480
gaggttgaat acaaagggtt tcaaagcaat ggtttttgta gcaatagcag tgagatggaa  540
aacttgcatg ggatgcttcc ttctgatgca gaacttgctg agttcgctgc tgatgtggag  600
agcttgttgg gtagggggct tgaaaacgag tgcgtgggga tggaagaatt gggactggtt  660
gatgcgaaag aggaggagtg ttcggtaggt agtgggaagg tgaagatgga agatcaggaa  720
gagagccctc tggtggagat ggagatggat atggtcgtgg gcagagatga tcaatcgttt  780
gagttgagct ttgattatga aacgtgtgaa gaggtgaagg tttgtgattt gggattgggg  840
aatgaattag gagcgaagaa agagaatgat gatgaggtga aaaagaacaa gatttcgttg  900
cagctagact atgaggcggt aatcatcgcc tgggctagcc aaaaatctcc gtggaccacc  960
gctgacaaac caaacttgga ccctgatgag tgctggaaac aatgcatggg aagttgcgaa  1020
acggcatatc atcatccttg cggtgaaatg ggtggatttg ggattcatcc agtgataata  1080
gacgggggca gagaggcgag ggtgtcaaga tacagagaga agcgccgaac gaggttgttc  1140
tcgaagaaaa taaggtacga agttaggaaa ttgaatgctg agaagagacc cagaatgaag  1200
gggaggtttg tcaagagggc ttcctttgca ccaccaacat ttcctttgct aaataaataa  1260

SEQ ID NO: 454         moltype = AA  length = 419
FEATURE                Location/Qualifiers
REGION                 1..419
                       note = GmBBX13 soybean B-box polypeptide
source                 1..419
                       mol_type = protein
                       organism = Glycine max
SEQUENCE: 454
MSSATKNAAN AVGAKTARAC DSCITKRARW YCAADDAFLC QACDSSVHSA NPLARRHERV  60
RLKTASYKST DEQQQQQQQQ PPTWHTKKPR TPRHGKHSRN NNPFHLVPEE GSEEANSHDE  120
NEEQLLYRVP IFDPFVAELC GTNSSPSPVT STDQGVVAAA EVEYKGFQSN GFCSNSSEME  180
NLHGMLPSDA ELAEFAADVE SLLGRGLENE CVGMEELGLV DAKEEECSVG SGKVKMEDQE  240
ESPLVEMEMD MVVGRDDQSF ELSFDYETCE EVKVCDLGLG NELGAKKEND DEVKKNKISL  300
QLDYEAVIIA WASQKSPWTT ADKPNLDPDE CWKQCMGSCE TAYHHPCGEM GGFGIHPVII  360
DGGREARVSR YREKRRTRLF SKKIRYEVRK LNAEKRPRMK GRFVKRASFA PPTFPLLNK   419
```

```
SEQ ID NO: 455          moltype = DNA  length = 1257
FEATURE                 Location/Qualifiers
misc_feature            1..1257
                        note = GmBBX14
source                  1..1257
                        mol_type = unassigned DNA
                        organism = Glycine max
SEQUENCE: 455
atgagttcgg ctactaagaa cgcagcaaac gcggttgggg gaaaaactgc aagagcatgt  60
gacggctgca taacgaaacg tgcacgttgg tactgtgctg ccgatgatgc ttttctctgc  120
caggcttgtg actcttcggt tcacttggcg aatcctttgg ctcgaagaca cgaacgagtc  180
cgcttgaaaa ccgcgtcgta caagtccacc gatgaacgac gacaacctcc cacgtggcac  240
accaagaaac ctcgaacgcc cagacatggg aaacattctc gtaacaacaa ccctttccac  300
ttggtccctg aagagggttc cgaagaggcg aattcccatg atgagaatga ggagcagctc  360
gtttataggg tccccatagt cgaccctttt gttgctgagc tatgtgggac taatagttct  420
ccttcttctg ttacttcaac tgatcaaggg gtagtagctg ctgctgctgc tgcttctgct  480
gaggttgaat acaaagggat tcaaagcaat gatttttgta gcaatagcaa tgagatcgaa  540
aacttgcatg ggatgcttcc ttcggatgca gaacttgctg agtttgctgc tgatgttgag  600
agctttttgg gtagggggct tgaaaacaag tgcgtgggga tggaagaatt gggactcgtt  660
gataccaaag aagaggagtg ttcggtgggt agtgggaagg tgaaggtgga agaggaagag  720
agccctctga tggagatgga tatgggaaga gatgatcaat catttgagtt gagctttgat  780
tatgagacgt gtgaagaggt aaaggagatg aaggttagtg atttggaatt ggggaatgag  840
ttaggagaga tgaaagagaa tgatgatgat gaggtgaaaa ggaagaaggt atcgttgcag  900
cttgattatg aggcgataat catcgcctgg gctagccaaa agtctccgtg gaccactgct  960
gacaaacaaa acttggaccc tgatgagtgc tggcaccaat gcatgggaag ttgcggaacg  1020
gcatttcatc acccttacgg tgaactgggt ggatttggga ttcattcagt gatagtagac  1080
gggggcagag aggcaagggt gtcaagatac agagagaagc gccgaactag gttgttctcg  1140
aagaaaataa ggtacgaggt taggaaattg aatgcagaga agagacccag aatgaagggg  1200
aggtttgtta agagggcttc ctttgcacca ccaacatttc ctttgctaaa taaataa     1257

SEQ ID NO: 456          moltype = AA  length = 88
FEATURE                 Location/Qualifiers
REGION                  1..88
                        note = GmBBX14 soybean B-box polypeptide
source                  1..88
                        mol_type = protein
                        organism = Glycine max
SEQUENCE: 456
MSSATKNAAN AVGGKTARAC DGCITKRARW YCAADDAFLC QACDSSVHLA NPLARRHERV  60
RLKTASYKST DERRQPPTWH TKKPRTPR                                    88

SEQ ID NO: 457          moltype = DNA  length = 1098
FEATURE                 Location/Qualifiers
misc_feature            1..1098
                        note = GmBBX15
source                  1..1098
                        mol_type = unassigned DNA
                        organism = Glycine max
SEQUENCE: 457
atgagagaca tgaaagacgc aggtgccttg ggaggcaaga cagcaagagc ctgcgacagc  60
tgcgtaagca gaagagcaag gtggttctgt gcagctgatg atgctttcct ctgccatggc  120
tgcgacactt tggttcattc cgcgaaccag ttagcaagca ggcacgaaag ggttcggctt  180
caaactgctt cctcaaaagt aaccaccacg cacgcatggc acagtggatt cacacgcaag  240
gcaagaaccc cgcgtcacaa cagcaagcac tttgcgctgc aacagcgtct caaagacgaa  300
gttctcttca acaacaccag tgttcttccc ctcgtgccgg agctcggagg ggaagaacaa  360
gaaccggtgg ttgtggataa cgatgagacg gaggagcaga tgctgtgtcg ggtgcccgtg  420
ttcgaccctt ttgatgtgag aaccgatgac ttggatagtt tttctgacat ggatttcgct  480
gagtttgctg ctgatgttga aagcctactt gataaagaag acgatgaaat aagtgcgtgt  540
gtgggagggg gagagggagt tcaaggtgca atggtgaagg ttaaggatga agaagaaatt  600
gatggtgatg tagcgtgtta tctggaatcg gtttttgatg atgcctttca ttggaataac  660
attgagtctg tgctgtcaga tgcacgggaa gagaaggagg gtgtggtggc gtgtgatgga  720
ggtgtcggtg atgaagaagg aggaacaaag agagacatat ttttgagact aaactatgat  780
gaggttatta ctgcttggtc tagccaaggt tcttctccat ggacaacttc aaacccacct  840
aagttcaact ctgattatga cttctccttg ggtttgagtg gtgtaggtgg ggaagtaaga  900
agcttaaggg ggcacctaga tggtggaaga gaagcaagag tgtcaaggta tagagagaag  960
agaaggactc gtttgtttgc aaagaagata agatatgaag taaggaagtt gaacgcagag  1020
aaaaggccta gaatgaaagg tcgttttgtg aagaggacat gctttgttgg agccaatgct  1080
tttcctgctt accactga                                              1098

SEQ ID NO: 458          moltype = AA  length = 365
FEATURE                 Location/Qualifiers
REGION                  1..365
                        note = GmBBX15 soybean B-box polypeptide
source                  1..365
                        mol_type = protein
                        organism = Glycine max
SEQUENCE: 458
MRDMKDAGAL GGKTARACDS CVSRRARWFC AADDAFLCHG CDTLVHSANQ LASRHERVRL  60
QTASSKVTTT HAWHSGFTRK ARTPRHNSKH FALQQRLKDE VLFNNTSVLP LVPELGGEEQ  120
```

-continued

```
EPVVVDNDET EEQMLCRVPV FDPFDVRTDD LDSFSDMDFA EFAADVESLL DKEDDEISAC  180
VGGGEGVQGA MVKVKDEEEI DGDVACYLES VFDDAFHWNN IESVLSDARE EKEGVVACDG  240
GVGDEEGGTK RDIFLRLNYD EVITAWSSQG SSPWTTSNPP KFNSDYDFSL GLSGVGGEVR  300
SLRGHLDGGR EARVSRYREK RRTRLFAKKI RYEVRKLNAE KRPRMKGRFV KRTCFVGANA  360
FPAYH                                                              365

SEQ ID NO: 459         moltype = DNA  length = 1116
FEATURE                Location/Qualifiers
misc_feature           1..1116
                       note = GmBBX16
source                 1..1116
                       mol_type = unassigned DNA
                       organism = Glycine max
SEQUENCE: 459
atgagagaca tgaaagacgc aggtgccctg ggaggcaaga cagcacgagc ctgcgatagc  60
tgcgtaagca gaagggcaag gtggttctgt gcagcagatg atgctttcct ctgccatgct  120
tgcgacactt tggttcattc cgcgaaccag ttagcaagca gacacgaaag ggttcggctt  180
caaactgcat cctctaaggc aaccacaacc actacgcacg catggcacag tggattcaca  240
cgcaaggcaa gaaccccgcg tcacaacaac agcaagcact ttgcgctgca acagcgtctc  300
aaacacgaag ttctcttcaa caacaccagt gttcttcccc tcgtgccgga gctcggaggg  360
gaagaacaag aaccggtggt tgtggacaac gatgaaacgg aggaacagat gctgtgtcgc  420
gtgcccgtgt tcgacccttt tgatgtgaga accgatgact tggatagctt ttctgacatg  480
gatttttctg aatttgctgc tgatgttgaa ggccggcttg acaaagaaga cgatgaaata  540
agtgcgtatg tgggaggagg agagggagtt caaggtgtat tggccaaggt taagggcgaa  600
gaagaaattg atggtgatgt agcgtgttat ctggagtcag tttttgacat gatcagtgat  660
gatgcctttc attggaataa tattgagtct gtggtgtcag atgcccggga agagaagggg  720
tgtgtggtgc catgtgatgg tggggttagt gaacaaggag gaataaagag agacatattt  780
ttgagactaa actatgatga ggttattact gcttggtcta gccaaggttc ttccccatgg  840
acaacttcaa acccacctaa gttcaactct gattatgact tctccttggg tttgagtggt  900
gtagatggag aaggaagaag cttaagggga cacctagatg gtggaagaga agcaagagtg  960
tcgaggtata gagagaagag aaggactcgt ttgtttgcaa agaagataag atatgaagta  1020
aggaagttga acgcagagaa aaggcctaga atgaaaggtc gttttgtgaa gaggacatgc  1080
tttgttggag ccaatgcttt tcctgcttac cactga                            1116

SEQ ID NO: 460         moltype = AA  length = 309
FEATURE                Location/Qualifiers
REGION                 1..309
                       note = GmBBX16 soybean B-box polypeptide
source                 1..309
                       mol_type = protein
                       organism = Glycine max
SEQUENCE: 460
ASSKATTTTT HAWHSGFTRK ARTPRHNNSK HFALQQRLKH EVLFNNTSVL PLVPELGGEE  60
QEPVVVDNDE TEEQMLCRVP VFDPFDVRTD DLDSFSDMDF SEFAADVEGR LDKEDDEISA  120
YVGGGEGVQG VLAKVKGEEE IDGDVACYLE SVFDMISDDA FHWNNIESVV SDAREEKGCV  180
VPCDGGVSEQ GGIKRDIFLR LNYDEVITAW SSQGSSPWTT SNPPKFNSDY DFSLGLSGVD  240
GEGRSLRGHL DGGREARVSR YREKRRTRLF AKKIRYEVRK LNAEKRPRMK GRFVKRTCFV  300
GANAFPAYH                                                          309

SEQ ID NO: 461         moltype = DNA  length = 1179
FEATURE                Location/Qualifiers
misc_feature           1..1179
                       note = GmBBX17
source                 1..1179
                       mol_type = unassigned DNA
                       organism = Glycine max
SEQUENCE: 461
atgaccaacg aaatgaaaga agcaagtgcc ttaggagcta gaacagcacg agcatgcgag  60
agctgcctaa aagtaagagc aaggtggtat tgtgcagctg atgatgcttt cctttgccat  120
ggctgtgaca acatggttca ctcagcaaac caattagcaa gcagacacga aagggtgaag  180
cttcaaactg catcctccaa ggtcaactac tcagtgaccc ctaaggtagc atggcacagt  240
ggattcacac gcaaggcaag aacccctcgc agcaacaaca agcactcatc gctgcaacaa  300
caacaacaaa aaccattaca tgaagaacaa ggagaagaag aagaacttgg aagtgaagag  360
ccattgctta atgatgagac cgaggagcaa ctcctgtgtc gcgtgcccgt atttgatgct  420
gagctttcct ttgacttgga aaacttttct tctgagtttc taccaacaga tatggatctt  480
gctgagtttt ctgctgatgt ggaaagctta cttggaaacg ggttgatga ggattcacct   540
gtgaagaaag gatcagaact agtgcttctt gattgcaaag aagaaggaga tgatgaaatg  600
gatgcatgtg ttaatggaat tggagccaac aaagatgcaa tggttaaggt caaagatgaa  660
gaagaacttg atgctgatga tgacacagct tgccatttgg attcgattct tgacatgaat  720
agcgaggcct ttaattggaa tattgctgag tcagagtcac ctgcacaggc acaagaagat  780
gaaaagtcat tactgcttgg gcaagtcaag gttctccatg gactacagga accccaccta  840
aacttggtaa cttctcttca accctctttg cttatgcagc agtatcttct tgaggaaggt  900
tgtgttgcgt cttcagtaac cgatgtaaaa ttcgtcgata tacctgaaat cattcgtagg  960
gcggagatgt gttatgcctt cgatggggga agagaagcaa gagtgtcaag gtaccgagag  1020
aagagaagaa cgcgtttatt tgcaaagaag ataaggtatg aagtgaggaa gttaaacgcg  1080
gagaaaagac ctagaatgaa aggtcgattt gtgaagagtg ttcctttgtt ggagccactg  1140
ctttgccagc ttaattatca atcatcacca ctgacatga                         1179

SEQ ID NO: 462         moltype = AA  length = 392
```

```
FEATURE               Location/Qualifiers
REGION                1..392
                      note = GmBBX17 soybean B-box polypeptide
source                1..392
                      mol_type = protein
                      organism = Glycine max
SEQUENCE: 462
MTNEMKEASA LGARTARACE SCLKVRARWY CAADDAFLCH GCDNMVHSAN QLASRHERVK  60
LQTASSKVNY SVTPKVAWHS GFTRKARTPR SNNKHSSLQQ QQQKPLHEEQ GEEEELGSEE  120
PLLNDETEEQ LLCRVPVFDA ELSFDLENFS SEFLPTDMDL AEFSADVESL LGNGVDEDSP  180
VKKGSELVLL DCKEEGDDEM DACVNGIGAN KDAMVKVKDE EELDADDDTA CHLDSILDMN  240
SEAFNWNIAE SESPAQAQED EKSLLLGQVK VLHGLQEPHL NLVTSLQPSL LMQQYLLEEG  300
CVASSVTDVK FVDIPEIIRR AEMCYAFDGG REARVSRYRE KRRTRLFAKK IRYEVRKLNA  360
EKRPRMKGRF VKSVPLLEPL LCQLNYQSSP LT                                392

SEQ ID NO: 463        moltype = DNA  length = 1284
FEATURE               Location/Qualifiers
misc_feature          1..1284
                      note = GmBBX18
source                1..1284
                      mol_type = unassigned DNA
                      organism = Glycine max
SEQUENCE: 463
atgaccaacg aaatgaaaga agcaagtgcc ttaggagcta gaacagcacg agcatgcgag  60
agctgcctaa aagtaagagc acggtggtat tgtgcagctg atgatgcatt cctttgccat  120
ggctgtgaca acatggttca ctcagcaaac caattagcaa gtagacacga aagggttaag  180
cttcaaactg catcctctaa ggtcaactac tcagtgaccc ctaaggtagc atggcacagt  240
ggattcacac gcaaggcaag aacgccacgc cacaacaaca acagacactc atcattgaaa  300
caacaacaac aaaaaaaacc attacatgaa gaacgaggag aggaagaagt gtttttcaat  360
aacactatta gtcttcttcc ccttgtgcct gagcttggaa gtgaagagcc attgcttaat  420
gatgagactg aggagcaact actgtgtcgc gtgccggtgt ttgatgctga gctgtgtagc  480
atatacaatg aagtgaagga cgaggttgta gctgctggtg aagaagcctt ggacttggaa  540
aactttcttt ccgagtttct tccatcagat acggaccttg ctgagtttac tgctgatgtg  600
aaaagctttc ttggaaacgg ggctgatgag gattcacctg atgatgatga gcacgtgaaa  660
gaatcagaac tactgattct tgattgcaaa gaagaagaag gagatgagga aatggatgaa  720
tgtattgatg gagtactaat tggagccaaa gatgcaatgg tgaaggtcaa agatgaagaa  780
gaacttgatg ctgatgatga cacagcttgc catttggatt cgattcttga tatgaacggc  840
gaggcattta attggaatat tgttgaatca gaatcacctg cacaggcaca agaagatgaa  900
gtgagtaaag tgggaactaa gaaggacata tttttgagat taaactatga agaagtcatt  960
actgcttggg caagtcaagg ttctccatgg actaatggga ccccacctaa gttcttcaac  1020
tctgatgatt gctggctaga cttcttgggt tcgaatggtg ggaatgttca atgctgttat  1080
ggggcagtgg gaagcttaag ggtgcatgca gatgggggaa gggaagcaag agtgtcaagg  1140
taccgagaga agagaagaac gcgtttattt gcaaagaaga taaggtatga agtgaggaag  1200
ttgaacgcgg agaaaaagacc tagaatgaaa ggtcgatttg tgaagaggac accctttgtt  1260
ggagccactg cgttgccagc ttaa                                         1284

SEQ ID NO: 464        moltype = AA  length = 171
FEATURE               Location/Qualifiers
REGION                1..171
                      note = GmBBX18 soybean B-box polypeptide
source                1..171
                      mol_type = protein
                      organism = Glycine max
SEQUENCE: 464
MTNEMKEASA LGARTARACE SCLKVRARWY CAADDAFLCH GCDNMVHSAN QLASRHERVK  60
LQTASSKVNY SVTPKVAWHS GFTRKARTPR HNNNRHSSLK QQQQKKPLHE ERGEEEVFFN  120
NTISLLPLVP ELGSEEPLLN DETEEQLLCR VPVFDAELCS IYNEVKDEVV A           171

SEQ ID NO: 465        moltype = DNA  length = 1230
FEATURE               Location/Qualifiers
misc_feature          1..1230
                      note = GmBBX19
source                1..1230
                      mol_type = unassigned DNA
                      organism = Glycine max
SEQUENCE: 465
atgggttata tatgtgattt ttgtggagac cagagatcca tggtgtactg ccgctctgac  60
gctgcatgct tatgtttgtc ttgtgatcgg aatgttcatt ctgctaatgc cctttctaag  120
cgtcattcac gcaccctttt atgcgagaga tgcaattcac aacctgcctt tgtaaggtgt  180
gttgaagaga agatttcact ttgtcagaat tgcgactggt tgggtcatgg cacctctaca  240
tcttcttcaa cacataagag acaagcaatc aattgctact ctggctgccc ttcagcggca  300
gaactgtctt cgatatggtc atttgtgtta gaaatcgctg ccataagtga gtctacatgt  360
gagcaagaac taggcttaat gagtattaat gagaacaagt gtgttggtgt tcctccggaa  420
gaccagaatg tgtctggttc agatgaagtt accgatctac ctgctttgaa caagtctttg  480
gttggtgcat ctttgatgcc tgaatcaagc tccgaacctt gtattctgga ccagccagct  540
ggacctacca atgaatgtct gccaaagtta tactgtcctg ctacaaaatg ccctgcctta  600
tctgaagatg ataatctgta tgatgatttc aacatggatg aagtggatct agatcttgag  660
aactatgaag aactttttgg tatggccctc agtcattctg aggagctttt tgaaaatggt  720
ggaattgata gcttgtttgg gacaaaaggc atgtctgctg gagattccaa ttgtcaggaa  780
```

```
gctattgctg ctgaggggtc gtcggttgga caggtcaatg caatgcaacc agcttgcagc  840
aatgcagcgt ctgcagattc cattttgagt actaaaactg aaccaattct ttgttttact  900
ggaaggcaaa ctcaatcaaa cctttctttt tctggtgtta ctggagagag tagtgctgga  960
gactatcaag actgtggggc ttcttcaatg cttctcatgg gagaacctcc ttggtttgct  1020
ccttgtccgg agaattccct acaatccgcc aaccgtagta atgctgtcat gcggtacaag  1080
gaaaagaaga agacacggat gtttgacaaa aaagttaggt atgcctctcg caaggcaagg  1140
gctgatgtca gaaggcgtgt gaaagggcgg tttgtcaaag ccggtgacgt ctatgattat  1200
gaccctttga gcacaaccag aagctgctga                                    1230

SEQ ID NO: 466          moltype = AA  length = 409
FEATURE                 Location/Qualifiers
REGION                  1..409
                        note = GmBBX19 soybean B-box polypeptide
source                  1..409
                        mol_type = protein
                        organism = Glycine max
SEQUENCE: 466
MGYICDFCGD QRSMVYCRSD AACLCLSCDR NVHSANALSK RHSRTLLCER CNSQPAFVRC  60
VEEKISLCQN CDWLGHGTST SSSTHKRQAI NCYSGCPSAA ELSSIWSFVL EIAAISESTC  120
EQELGLMSIN ENKCVGVPPE DQNVSGSDEV TDLPALNKSL VGASLMPESS SEPCILDQPA  180
GPTNECLPKL YCPATKCPAL SEDDNLYDDF NMDEVDLDLE NYEELFGMAL SHSEELFENG  240
GIDSLFGTKG MSAGDSNCQE AIAAEGSSVG QVNAMQPACS NAASADSILS TKTEPILCFT  300
GRQTQSNLSF SGVTGESSAG DYQDCGASSM LLMGEPPWFA PCPENSLQSA NRSNAVMRYK  360
EKKKTRMFDK KVRYASRKAR ADVRRRVKGR FVKAGDVYDY DPLSTTRSC               409

SEQ ID NO: 467          moltype = DNA  length = 1224
FEATURE                 Location/Qualifiers
misc_feature            1..1224
                        note = GmBBX20
source                  1..1224
                        mol_type = unassigned DNA
                        organism = Glycine max
SEQUENCE: 467
atgggctata tatgtgattt ctgtggagac cagagatcca tggtgtactg ccgctctgat  60
gctgcatgct tatgtttgtc ttgtgatcgg aatgttcatt ctgctaatgc cctttctaag  120
cgtcattcac gcaccctttt atgtgagaga tgcaattcac aacctgcctt tgtaaggtgt  180
gttgaagaga aaatttcact ttgtcagaat tgtgattggt tgggtcatgg cacctctaca  240
tcttcttcaa cacacaagag acaggcaatc aattgctact ctggctgccc ttcagcggct  300
gaactgtctt caatatggtc atttgtgtta gatatcgctg ccataagtga atctacatgt  360
gagcaagaac taggcttaat gagtattaat gagaacaaga gtgttggggt tcctccagag  420
ggccagaatg tgtctggttc agatgaagtt actgatcaac ctgctttgga caagtctttg  480
gttggtacat cttcaatgcc tgaatcaagc tccaaacctc gtattctgga ccagccagct  540
agacctgcca atgaatgtct ttcaaagtta tactgtcctg ctacaaaatt ccccgcatta  600
tgtgaaaatg ataatctgta tgatgatttc aacatggatg aagtggatct aaatcttgag  660
aactatgaag aactttttgg tatggccctc agtcattctg aagagctatt tgaaaatggt  720
ggaattgata gcttgtttgg gacaaaagac atgtctgctg gagatttcag ttgtgaggat  780
gctattgctg ctgaggcatc acaaattcca actatgttgg cacctcagcc tcacaatgca  840
gcatctgcag attccatttt gagtactaaa actgaaccaa ttctttgttt tacgggaagg  900
caagctcaat caaacctttc tttttctggc gttaccggag acagtagtgc tggagactat  960
caagactgtg gggcttcttc aatgcttctc atgggagaac ctccttggtt tgctccttgt  1020
cctgagaatt ccctacaatc agccaaccgt agtaatgctg tcatgcggta caaggaaaag  1080
aagaagacac ggatgtttga caaaaaagtg aggtatgcct ctcgcaaggc aagggctgat  1140
gtcagaaggc gcgtgaaagg ccggtttgtc aaagctggtg acgtctacga ttatgatcct  1200
ttgagcacaa ccagaagctt ctga                                          1224

SEQ ID NO: 468          moltype = AA  length = 407
FEATURE                 Location/Qualifiers
REGION                  1..407
                        note = GmBBX20 soybean B-box polypeptide
source                  1..407
                        mol_type = protein
                        organism = Glycine max
SEQUENCE: 468
MGYICDFCGD QRSMVYCRSD AACLCLSCDR NVHSANALSK RHSRTLLCER CNSQPAFVRC  60
VEEKISLCQN CDWLGHGTST SSSTHKRQAI NCYSGCPSAA ELSSIWSFVL DIAAISESTC  120
EQELGLMSIN ENKSVGVPPE GQNVSGSDEV TDQPALDKSL VGTSSMPESS SKPRILDQPA  180
RPANECLSKL YCPATKFPAL CENDNLYDDF NMDEVDLNLE NYEELFGMAL SHSEELFENG  240
GIDSLFGTKD MSAGDFSCED AIAAEASQIP TMLAPQPHNA ASADSILSTK TEPILCFTGR  300
QAQSNLSFSG VTGDSSAGDY QDCGASSMLL MGEPPWFAPC PENSLQSANR SNAVMRYKEK  360
KKTRMFDKKV RYASRKARAD VRRRVKGRFV KAGDVYDYDP LSTTRSF                 407

SEQ ID NO: 469          moltype = DNA  length = 1236
FEATURE                 Location/Qualifiers
misc_feature            1..1236
                        note = GmBBX21
source                  1..1236
                        mol_type = unassigned DNA
                        organism = Glycine max
SEQUENCE: 469
```

```
atgggttact tatgtgattt ttgtggagac cagaggtccc tggtgtactg ccgctctgat  60
gctgcgtgct tatgtttgtc gtgtgatcga aatgttcatt ctgctaatgc cctttctagg  120
cgtcattcga gaacccttgt atgcgagaga tgcaattcgc aacctgcatt tgtgaggtgt  180
gttgatgaga agatttcact ttgtcagaac tgtgattggt tgggtcatgg tacctcacca  240
tcttcttcga cacacaagag gcaatcaatc aattgctact ctggctgccc ttcagctgca  300
gaattttctt caatatggtc ctttttctta gacatccctt ctatgggtga agcatgtgag  360
caggaactag gtttgatgag cattaatgag aacagcaata agaatgcttg ggcttctcca  420
gaagggcaga atgtgtctgg ttcagctgaa gtgactgatc tacccagcaa gggtaaatct  480
tgggctggca catcttcagt acctgagtca agctcagaac ctcgtattct agaccagccg  540
cctggacctg ccaatgaatg tatgcccaag ttgtactgtc ctgggaagaa agtttctgga  600
atatatgaag atgatgatct atatgatgat ttcatcatgg atgaagtgga tctacaactt  660
gagaactacg aggaactttt tgggatggct ctcagtcact ctgaagagct tttgaaaat  720
ggtggaatta atagcttatt tgagacaaag gacatgtctg ctagtgctgg tgattcccat  780
tgtcagggtg ctgttgctgc tgagggatcg tctgctgagt tggtcaatgc tatccaacca  840
gcatgcagca atgcagcatc tgcagactca atgatgagta caaaaactga accaattgtt  900
tgttttacgg caaggcaatc tctatcaaac atttctttct ctggtgttac caaagatagt  960
gttggtgact atcaagattg tggtgcttct tcaatgcttc tcatgggaga gcctccctgg  1020
tgtcctcctt gccctgagag ttctctgcat tctgctaacc gcagcaatgc tgtcatgcgc  1080
tataaggaaa agaagaagac ccggaagttc gagaagaaag taaggtatgc ctctcgcaag  1140
gctagggctg atgtcagaaa gcgtgtgaag ggtcgatttg tcaaagccgg tgatgtctat  1200
gactatgacc ctttgaacca aaccagaagc tgctga                              1236
```

```
SEQ ID NO: 470          moltype = AA  length = 411
FEATURE                 Location/Qualifiers
REGION                  1..411
                        note = GmBBX21 soybean B-box polypeptide
source                  1..411
                        mol_type = protein
                        organism = Glycine max
SEQUENCE: 470
MGYLCDFCGD QRSLVYCRSD AACLCLSCDR NVHSANALSR RHSRTLVCER CNSQPAFVRC  60
VDEKISLCQN CDWLGHGTSP SSSTHKRQSI NCYSGCPSAA EFSSIWSFFL DIPSMGEACE  120
QELGLMSINE NSNKNAWASP EGQNVSGSAE VTDLPSKGKS WAGTSSVPES SSEPRILDQP  180
PGPANECMPK LYCPGKKVSG IYEDDDLYDD FIMDEVDLQL ENYEELFGMA LSHSEELFEN  240
GGINSLFETK DMSASAGDSH CQGAVAAEGS SAELVNAIQP ACSNAASADS MMSTKTEPIV  300
CFTARQSLSN ISFSGVTKDS VGDYQDCGAS SMLLMGEPPW CPPCPESSLH SANRSNAVMR  360
YKEKKKTRKF EKKVRYASRK ARADVRKRVK GRFVKAGDVY DYDPLNQTRS C           411
```

```
SEQ ID NO: 471          moltype = DNA  length = 1218
FEATURE                 Location/Qualifiers
misc_feature            1..1218
                        note = GmBBX22
source                  1..1218
                        mol_type = unassigned DNA
                        organism = Glycine max
SEQUENCE: 471
atgggttact tatgtgattt ttgtggagac cagaggtcct tggtgtactg ccgctctgat  60
tccgcgtgct tatgtttgtc atgcgatcga aatgttcatt ctgccaatgc actttctagg  120
cgtcattcga gaacccttgt atgcgagaga tgcaattcac aacctgcatt tgtgaggtct  180
gttgaagaga aaatttcact ttgtcagaac tgtgattggt tgggtcatgg tacctcaccg  240
tcttcttcga tgcacaagag gcaatcaatc aattgctact ctggctgccc ttcagcggca  300
gaattttctt caatatggtc ctttttctta gacatccctt ctttgggtga agcatgtgag  360
caggaactag gtttgatgag cattaatgag aacattcctc cagaagggca gaatgtgtct  420
ggttcaactg aagtgactga tctacccagc aagggtaaat cttgggctgg cacaccttca  480
atacctgagt caagctcaga acctcgtatt ctggaccagc cgcctggacc tgccaatgaa  540
tgtgtgccca agttgtactg tcctgggaag aaagcttctg gaatatgtga agatgatgat  600
ctatatgatg atttcatcat ggatgaagtt gatctagaac ttgagaacta tgaggaactt  660
tttgggatgg ctctcagtca ctctgaagag ctttttgaaa atggtggaat taatagctta  720
tttgaggcaa aggacatgtc tgctagtgct ggtgattccc attgtcaggg tgctgttgct  780
gctgagggat cgtctgctgg gttggtcaat cctatccaac cagcatgcag caatgcagca  840
tctgcagatt cagtgatgag tacaaaaact gaaccaattg tttgttttac ggcaaggcaa  900
tctcaatcaa acatttcctt ttctggtgtt accaaagata gtgctggtga ctatcaagac  960
tgtggtgctt cttcaatgct tctcatggga gaacctccct ggtgtcctcc ttgccctgag  1020
agttctctgc attctgctaa ccgaagcaat gctgtcatgc gctacaagga aaaaaagaag  1080
acccggaagt tcgagaagaa agtaagatat gcctctcgca aggctagggc tgatgtcaga  1140
aagcgtgtga agggccgatt tgtcaaagct ggtgatgtct atgactatga ccctttgaac  1200
caaaccagaa gctactga                                                  1218
```

```
SEQ ID NO: 472          moltype = AA  length = 405
FEATURE                 Location/Qualifiers
REGION                  1..405
                        note = GmBBX22 soybean B-box polypeptide
source                  1..405
                        mol_type = protein
                        organism = Glycine max
SEQUENCE: 472
MGYLCDFCGD QRSLVYCRSD SACLCLSCDR NVHSANALSR RHSRTLVCER CNSQPAFVRS  60
VEEKISLCQN CDWLGHGTSP SSSMHKRQSI NCYSGCPSAA EFSSIWSFFL DIPSLGEACE  120
QELGLMSINE NIPPEGQNVS GSTEVTDLPS KGKSWAGTPS IPESSSEPRI LDQPPGPANE  180
```

```
CVPKLYCPGK KASGICEDDD LYDDFIMDEV DLELENYEEL FGMALSHSEE LFENGGINSL  240
FEAKDMSASA GDSHCQGAVA AEGSSAGLVN PIQPACSNAA SADSVMSTKT EPIVCFTARQ  300
SQSNISFSGV TKDSAGDYQD CGASSMLLMG EPPWCPPCPE SSLHSANRSN AVMRYKEKKK  360
TRKFEKKVRY ASRKARADVR KRVKGRFVKA GDVYDYDPLN QTRSY                  405

SEQ ID NO: 473          moltype = DNA  length = 1155
FEATURE                 Location/Qualifiers
misc_feature            1..1155
                        note = GmBBX23
source                  1..1155
                        mol_type = unassigned DNA
                        organism = Glycine max
SEQUENCE: 473
atggatcctc tatgtgagtt ttgtggggtg gtgagagctg tggtttactg caagtcagat  60
tctgctcgtc tctgcttgca ttgcgatggc tgtgtacact ctgcaaattc tttgtctcgc  120
aggcattcgc gttccctcct ctgcgataag tgcaattccc agccggcaat gatccgctgc  180
atggatcata agttgtcatt gtgccaaggt tgtgactgga atccaaatga ctgttctgca  240
ttgggacata ggcgtgttgc attgaattgt tacactggtt gtccctcttt ggctgagttt  300
tccaggattt ggtcctttgt gtttgatgct aattcctcac ttggtggttg ggaatcggtt  360
ggtactttgc caaaaagtga gagctgcact agccagtgtt tggagcaaac tgatcataac  420
ggtggttcct ttggtttgtc tcaaatcatt ccatcaaatc caaattacac gccgttctgc  480
aaagacgaag catttttctt tcctcaagac tcaaaccagc caaaggaatg tcctaatcta  540
ggaattcatg atgggagtga actttgtgaa ggtttcaatg ttgataacct tcaattaaac  600
tttgaaagtg ctgatgaaat atttggctgt tcacaagatg ccacaagata ccaccttgaa  660
gatggaggaa tggactgttt attgatggat aaaaacatat cagtcacaga atctaattca  720
cttattgaga gtgccttgga ggcatcatca tctatccaac aagattgtgt ggcttttcaa  780
tcatccaggg cgggtgggtc agctagtgtg atgcaggtta tcaacagcaa tacaaattct  840
gcactaatga atcctagctg cactagaaac atcagtctgg gatttcctca gggtgttcat  900
tcaaagatgc cacttcaatt tcccaacatt gttggtgaaa ataattctac tgaatatcaa  960
gactgcaggt tttcgcaagt gtttctgccg ggtgaatccc cctgggaatc aaatttggag  1020
ggtacatgcc cacaagcaag ggataaagct aaaatgagat acaatgagaa aaagaaaact  1080
cgaatgtatg tacctttaat gctctcaata tattatggta aaatgaaatg gaaactgttc  1140
tttaaatttg tttaa                                                   1155

SEQ ID NO: 474          moltype = AA  length = 384
FEATURE                 Location/Qualifiers
REGION                  1..384
                        note = GmBBX23 soybean B-box polypeptide
source                  1..384
                        mol_type = protein
                        organism = Glycine max
SEQUENCE: 474
MDPLCEFCGV VRAVVYCKSD SARLCLHCDG CVHSANSLSR RHSRSLLCDK CNSQPAMIRC  60
MDHKLSLCQG CDWNPNDCSA LGHRRVALNC YTGCPSLAEF SRIWSFVFDA NSSLGGWESV  120
GTLPKSESCT SQCLEQTDHN GGSFGLSQII PSNPNYTPFC KDEAFFFPQD SNQPKECPNL  180
GIHDGSELCE GFNVDNLQLN FESADEIFGC SQDATRYHLE DGGMDCLLMD KNISVTESNS  240
LIESALEASS SIQQDCVAFQ SSRAGGSASV MQVINSNTNS ALMNPSCTRN ISLGFPQGVH  300
SKMPLQFPNI VGENNSTEYQ DCRFSQVFLP GESPWESNLE GTCPQARDKA KMRYNEKKKT  360
RMYVPLMLSI YYGKMKWKLF FKFV                                         384

SEQ ID NO: 475          moltype = DNA  length = 1272
FEATURE                 Location/Qualifiers
misc_feature            1..1272
                        note = GmBBX24
source                  1..1272
                        mol_type = unassigned DNA
                        organism = Glycine max
SEQUENCE: 475
atggatcctc tatgtgagtt ttgtcgggtg gtgagagctg tggtttactg taagtcagat  60
tctgctcgtc tctgcttgca ttgcgatggc tgtgtacact ctgcaaattc tttgtctcgc  120
aggcattcgc gttccctcct atgcgataag tgcaattccc agccggcaat gatccgctgc  180
atgaatcata agttgtcatt atgtcaaggt tgtgactgga atccaaatga ctgttctgca  240
ttgggacata ggcgccttgc attgaattgc tacactggtt gcccctcttt ggctgagttt  300
tctaggctct ggtcttttgt gtttgatgct aattcctcac ttggtggttg ggaatcggtt  360
ggtactttgc caaaaagtga gagctgcact agccagtgtt tggagcaaac tgatcataat  420
ggtggttatt ttggtttggt gagtgacaag ttggatgaaa ttgaatcttg tgtcagatat  480
caacctcgga tggatcagtc tcaaatcatt ccatcaaatc caaattacac accgtactgc  540
aaagacgaag catttttctt tcctcaagac tcaaaccagc caaagctgca ggaatgtcct  600
aatctaggaa ttcatgatgg gaatgaactt tgtgaaggtt tcaatgtgga taacgttcaa  660
ttaaactttg aaattgctga tgaaatattt tactgttcac aagttgccac aagataccac  720
cttgaagatg gaggaatgga ctgtttattg atggataaaa acatagcagt tacagaatct  780
agttcactta ttgagagtgc catggaggca tcatcatcta tccaacaaga ttgtgtggct  840
tttcaatcat cgagggctgg tgggtcagct agtgtgatgc aggttatcaa cagcaatacc  900
aattgtgcac ttatgaatcc tagctgcact aaaaacatca gtctgggatt tcctcagggc  960
ctagttcatt caaacatgcc acttcaattt cccaacatag ttggtgaaaa taattctact  1020
gaatatcaag actgcgggtt atcgcgagtg ggtgaatccc cctgggaatc aaatttggag  1080
ggtacatgcc cacaagcaag ggataaagct aaaatgagat acaatgagaa aaagaaaact  1140
cgaacctttg gtaagcaaat aagatatgct tctcgcaaag caagggccga tacaagaaaa  1200
cgtgtgaaag gtagatttgt taaagcaggt gaagcatatg attatgaccc tcttgggaca  1260
```

```
agggacatct aa                                                  1272

SEQ ID NO: 476         moltype = AA  length = 423
FEATURE                Location/Qualifiers
REGION                 1..423
                       note = GmBBX24 soybean B-box polypeptide
source                 1..423
                       mol_type = protein
                       organism = Glycine max
SEQUENCE: 476
MDPLCEFCRV VRAVVYCKSD SARLCLHCDG CVHSANSLSR RHSRSLLCDK CNSQPAMIRC  60
MNHKLSLCQG CDWNPNDCSA LGHRRLALNC YTGCPSLAEF SRLWSFVFDA NSSLGGWESV  120
GTLPKSESCT SQCLEQTDHN GGYFGLVSDK LDEIESCVRY QPRMDQSQII PSNPNYTPYC  180
KDEAFFFPQD SNQPKLQECP NLGIHDGNEL CEGFNVDNVQ LNFEIADEIF YCSQVATRYH  240
LEDGGMDCLL MDKNIAVTES SSLIESAMEA SSSIQQDCVA FQSSRAGGSA SVMQVINSNT  300
NCALMNPSCT KNISLGFPQG LVHSNMPLQF PNIVGENNST EYQDCGLSRV GESPWESNLE  360
GTCPQARDKA KMRYNEKKKT RTFGKQIRYA SRKARADTRK RVKGRFVKAG EAYDYDPLGT  420
RDI                                                            423

SEQ ID NO: 477         moltype = DNA  length = 1050
FEATURE                Location/Qualifiers
misc_feature           1..1050
                       note = GmBBX25
source                 1..1050
                       mol_type = unassigned DNA
                       organism = Glycine max
SEQUENCE: 477
atgagtggtg aagcgcgatc ctgtgactac tgtggccact ccacagcact tctttactgc  60
agagccgatt cagcaaaact ctgtttctcg tgcgatcgcg aggttcactc caccaaccag  120
ctcttctcga aacacacgcg cacgctgctc tgcgacgcat gcgatcattc ccctgccacc  180
atactctgtt ccaccgacac ctctgttctg tgccagaact gcgactggga gaagcacaac  240
cctgcgctct ccgattccct tcacgaacga aggcccctcg aaggcttcac tgggtgccct  300
tcagtctccg aactcttatc catcgtgggg ttttcggatt taagcaaaaa atctcttctt  360
tcttcgcctc agggaagtgg cgctgatggg atcttcggtg gagaaattga agggctttcg  420
gatttgtttg tgtgggattc tccttctttc gttacgcttg atgatttgat ttcttcttct  480
ccttcttctc atagctttca ggccatggag gttcctcctc tgcccaagaa tcggaaggct  540
gcttgtgggc aacacaaaga agagattctt agtcagcttc gggaattggc caagtctgag  600
ccattggacc ttgaaccata tgtgtcatcg gggaacttgt cctcgggttt tgaacgtgaa  660
ccagaggctg atatctttcc ttctcatgag tggcatagag aaagcagcga gcctatgtat  720
caggttgttc ctcctgaccc attaatgaga acttatacag aagaaattcc atttaaacat  780
tctacttctg ctgttgggga aactcaaacc tacggtgaca atggaggaaa accatccatt  840
tctcttaaat ctgaaaccct atcaactact cccaaagctg cagcatgtga gttaacaagc  900
caagaaagag attctgcatt attacggtac aagcagaaga agaaaactag gagatttgac  960
aaacacataa ggtatgaatc acgaaaagtt cgggcagaaa gcagggtaag agtcaagggt  1020
cgatttgcca agatggaaca tgaacattga                                1050

SEQ ID NO: 478         moltype = AA  length = 178
FEATURE                Location/Qualifiers
REGION                 1..178
                       note = GmBBX25 soybean B-box polypeptide
source                 1..178
                       mol_type = protein
                       organism = Glycine max
SEQUENCE: 478
MSGEARSCDY CGHSTALLYC RADSAKLCFS CDREVHSTNQ LFSKHTRTLL CDACDHSPAT  60
ILCSTDTSVL CQNCDWEKHN PALSDSLHER RPLEGFTGCP SVSELLSIVG FSDLSKKSLL  120
SSPQGSGADG IFGGEIEGLS DLFVWDSPSF VTLDDLISSS PSSHSFQAME VPPLPKNR   178

SEQ ID NO: 479         moltype = DNA  length = 1056
FEATURE                Location/Qualifiers
misc_feature           1..1056
                       note = GmBBX26
source                 1..1056
                       mol_type = unassigned DNA
                       organism = Glycine max
SEQUENCE: 479
atgagtggtg ctgaagcgcg accttgtgac tactgtggca actccacagc acttctctat  60
tgcagagccg attcagcaaa actctgtttc tcgtgcgatc gcgaagttca ctccaccaac  120
cagctcttct ccaagcacac gcgcacgctg ctctgcgacg catgcgatga ttcccctgcg  180
accatactct gttcaaccga cacctctgtt ctgtgccaga actgcgactg ggagaaccac  240
aaccctgcgc tctccgattc ccttcacgag cgaaggcccc tcgaaggctt cactgggtgc  300
ccttccgtct ccgaactctt gtccatcgtg ggttttcgg atatcagcaa aaatctctg   360
ctttttcgc ctcagggaag tgtcgctgat gggttcttcg gcgccagcga gattgaaggg  420
ctttcggata tgttcgtgtg ggatgcgcct tcttttgtta cgcttgatga tttgatttct  480
tcctctcctt cttctcatag ctttcaggcc atgaaggttc ctcctctgcc caagaatcga  540
aaggctgctt gtgggcaaca caaagaagag attcttagtc agcttcggga attggccaag  600
tctgagcctt tggaccttga accatatgtg caatcgggta acttgtcctt gggttttgaa  660
cgtgacccgg aggctgatat ctttccttct catgagtggc atagagaaag cagcgagcct  720
atgcatcaag ttgtgcctcc tgacccatca atgggaactt atactgaaga aattccagtt  780
```

```
aaacattcta cttctgctgt tggggaaaat cacacctatg gtgacaatga agggaaacca  840
tccatttctc tcaagtctga aaccctatca actactccca aagctgcagc atgtgagtta  900
acaagccaag aaagagattc tgcattatta cggtacaagc agaagaagaa aacaaggaga  960
tttgacaagc acataaggta tgaatcacga aaagttcggg ctgaaagcag ggtaagagtc  1020
aagggccgat ttgccaagat gggacatgaa cattga                            1056

SEQ ID NO: 480         moltype = AA  length = 351
FEATURE                Location/Qualifiers
REGION                 1..351
                       note = GmBBX26 soybean B-box polypeptide
source                 1..351
                       mol_type = protein
                       organism = Glycine max
SEQUENCE: 480
MSGAEARPCD YCGNSTALLY CRADSAKLCF SCDREVHSTN QLFSKHTRTL LCDACDDSPA  60
TILCSTDTSV LCQNCDWENH NPALSDSLHE RRPLEGFTGC PSVSELLSIV GFSDISKKSL  120
LFSPQGSVAD GFFGASEIEG LSDMFVWDAP SFVTLDDLIS SSPSSHSFQA MKVPPLPKNR  180
KAACGQHKEE ILSQLRELAK SEPLDLEPYV QSGNLSLGFE RDPEADIFPS HEWHRESSEP  240
MHQVVPPDPS MGTYTEEIPV KHSTSAVGEN HTYGDNEGKP SISLKSETLS TTPKAAACEL  300
TSQERDSALL RYKQKKKTRR FDKHIRYESR KVRAESRVRV KGRFAKMGHE H           351

SEQ ID NO: 481         moltype = DNA  length = 702
FEATURE                Location/Qualifiers
misc_feature           1..702
                       note = GmBBX27
source                 1..702
                       mol_type = unassigned DNA
                       organism = Glycine max
SEQUENCE: 481
atgatgaatg gttctccaaa ttcaaaacag agaacatgtg actattgcgg gagcttcacg  60
gctcttctgt actgcagagc cgattctgcg aagctttgtt tcttctgtga ccgtaaagtt  120
cacttcccaa accagctttt ctcgaagcac aagcgcgcgc agctctgtga tgcgtgtgga  180
gattcccctg cctcggtgct ctgttctgca gaaaactctg ttctgtgcca aaactgtgat  240
tgcggaaagc aaaaacattt ggtgtctgag gcgcaccaac ggaggccact cgaggggttc  300
tcggggtgcc cttctgtgac tgagttgtta acaattctgg gtctcagtga aaaatctctg  360
ctttcaaatg agggaacttc ccagattgat gatgaccttt cggatttgca cgtgtggagt  420
gctccttcta ttaatgggtt gaaacgtaag ggtgcgtgcg ggagacacaa agaagagatt  480
cttagtcaac tccgtgagct aataaagttg gagcccgact tgattcatgc tgaacgacaa  540
gggcaatttg gaaatttgcc tactgatttt gaacgagacg tggaggctaa tatatttcct  600
tcatatgagt gcacaaatgg gtccctaaaa cgaataattc aaatagatga aaggactata  660
gtagcctacg tttgtaatca atcatcaagg gctaaatgca ag                    702

SEQ ID NO: 482         moltype = AA  length = 177
FEATURE                Location/Qualifiers
REGION                 1..177
                       note = GmBBX27 soybean B-box polypeptide
source                 1..177
                       mol_type = protein
                       organism = Glycine max
SEQUENCE: 482
MMNGSPNSKQ RTCDYCGSFT ALLYCRADSA KLCFFCDRKV HFPNQLFSKH KRAQLCDACG  60
DSPASVLCSA ENSVLCQNCD CGKQKHLVSE AHQRRPLEGF SGCPSVTELL TILGLSEKSL  120
LSNEGTSQID DDLSDLHVWS APSINGLKRK GACGRHKEEI LSQLRELIKL EPDLIHA     177

SEQ ID NO: 483         moltype = DNA  length = 666
FEATURE                Location/Qualifiers
misc_feature           1..666
                       note = GmBBX28
source                 1..666
                       mol_type = unassigned DNA
                       organism = Glycine max
SEQUENCE: 483
atgatgagtg gttctccttc tccaaattca aaacagagaa catgcgacta ttgtggggac  60
ttcacggctc ttctgtattg cagtgccgat tctgcgaagc tatgtttctt ctgtgaccgc  120
aaagttcact ccccaaacca gcttttctcc aagcacacgc gagcgcagct ctgtgattcg  180
tgtggagatt cccctgcttc ggtgctctgt tctgcagaga actctgttct ttgccataac  240
tgtgactgcg aaaagcacaa acatttggcg tctgaagtgc accaacgaaa acccctcgag  300
gggttctcgg ggtgcccttc tgtgactgag ttgttaacga ttcttggtct ttctgaaaaa  360
tctctgcttt caaatgaggg gacttcccag attgattacg acctttcgga tttgcacgaa  420
tctctagcaa gtatattctc aggtgtgaac aatttcttta tttggttgat attgttattg  480
aatcagaatc gtaagagtgc gtttgggaga cacaaagaag agattcttag tcaactccgt  540
gagctaataa agttggagcc cgacttgatt catggagaag tagatgctga gcgacaaggg  600
caatttggaa atttgcctac tggctttgaa cgtgacgtgg aggctagtat gtttccttca  660
tatgag                                                            666

SEQ ID NO: 484         moltype = AA  length = 222
FEATURE                Location/Qualifiers
REGION                 1..222
                       note = GmBBX28 soybean B-box polypeptide
```

```
source                  1..222
                        mol_type = protein
                        organism = Glycine max
SEQUENCE: 484
MMSGSPSPNS KQRTCDYCGD FTALLYCSAD SAKLCFFCDR KVHSPNQLFS KHTRAQLCDS  60
CGDSPASVLC SAENSVLCHN CDCEKHKHLA SEVHQRKPLE GFSGCPSVTE LLTILGLSEK  120
SLLSNEGTSQ IDYDLSDLHE SLASIFSGVN NFFIWLILLL NQNRKSAFGR HKEEILSQLR  180
ELIKLEPDLI HGEVDAERQG QFGNLPTGFE RDVEASMFPS YE                    222

SEQ ID NO: 485          moltype = DNA  length = 1083
FEATURE                 Location/Qualifiers
misc_feature            1..1083
                        note = GmBBX29
source                  1..1083
                        mol_type = unassigned DNA
                        organism = Glycine max
SEQUENCE: 485
atgttgccat gcgactactg cgactccaaa cccgccttac tcttctgccg agctgattcc  60
gctaaactct gtttagtttg cgaccagcac gtgcacgccg ccaacgccct ctccctcaag  120
cacgtgcgct tccagatttg cgactcctgc aagtccgaca ccgccgtcct ccgctgctcc  180
acccacaacc tcgtcctctg tcacaactgc gacgtggacg cccacggtgc cgacgcttca  240
tccctccacc accaccacca ccaccaccgc cgccttcacg gcctctccgg ctgtccctcc  300
gtcccggaga tcgcctccgc gctgggcctt gatttccggg cccaggagcc cgtggtcccc  360
accgccgcct cccgcgatga ggtctatgag caggtgctgg aaattgcgcg ccagaggaac  420
aacggcctcg gcgccgaaca actcaagttc gacgactcac ccggaaacga cacgccgttc  480
acctccttgc ttatgttgca gaattctgaa tctgagtttg acgctagaaa aagtaacgat  540
aacaacggtt acggaaccga ggcatgggat cttcactgga attataataa ccccgcgtat  600
cagcctcctc aggtgtggga ttttcaatta caaaaatcaa cagattgcaa tgaaccaaga  660
gttgatgtgc acaacatgaa ttactcaaca attggtgatg atattgatat tctatcaaga  720
aataatcaat cggatcagtc atcatcaagc catgcaaaga ggaaagaaga gagcaacaaa  780
aaagctagag gtgggttatc atcagagtcc acattgtttg aatccatacc gtatagtggc  840
accaacaatg tcgttgtcat ggagcatctt gtgggtggga atgagaatgt tagcacctta  900
aaagccaggg ttagtttgca agagttggct aagaatagag gggatgccat gttacgctat  960
aaggagaaga agaaaacgcg aaggtacgac aagcacattc gctatgaatc aaggaaggcc  1020
agggctgata ctagaaaaag ggtgagaggg agatttgtga aggcaagtga tgttcaagca  1080
tga                                                               1083

SEQ ID NO: 486          moltype = AA  length = 360
FEATURE                 Location/Qualifiers
REGION                  1..360
                        note = GmBBX29 soybean B-box polypeptide
source                  1..360
                        mol_type = protein
                        organism = Glycine max
SEQUENCE: 486
MLPCDYCDSK PALLFCRADS AKLCLVCDQH VHAANALSLK HVRFQICDSC KSDTAVLRCS  60
THNLVLCHNC DVDAHGADAS SLHHHHHHHR RLHGLSGCPS VPEIASALGL DFRAQEPVVP  120
TAASRDEVYE QVLEIARQRN NGLGAEQLKF DDSPGNDTPF TSLLMLQNSE SEFDARKSND  180
NNGYGTEAWD LHWNYNNPAY QPPQVWDFQL QKSTDCNEPR VDVHNMNYST IGDDIDILSR  240
NNQSDQSSSS HAKRKEESNK KARGGLSSES TLFESIPYSG TNNVVVMEHL VGGNENVSTL  300
KARVSLQELA KNRGDAMLRY KEKKKTRRYD KHIRYESRKA RADTRKRVRG RFVKASDVQA  360

SEQ ID NO: 487          moltype = DNA  length = 1146
FEATURE                 Location/Qualifiers
misc_feature            1..1146
                        note = GmBBX30
source                  1..1146
                        mol_type = unassigned DNA
                        organism = Glycine max
SEQUENCE: 487
atgttgccat gcgattactg ccattccaaa cccgccatac tcttctgcag accagattcc  60
gctaaactat gcttgctatg cgaccagcac gtgcacgccg ccaacgccct ctccctcaag  120
cacgtgcgct tccagatttg cgactcctgc aagaccgaca ccgctgtcct ccgctgctcc  180
accgacaacc tcgtcctctg ccaccactgc gatgtggaaa cccacggtgc tgccgcttcc  240
tcccaccacc aacgtcaccg cctccacggc ctctccggct gcccctccgt cacggagatc  300
gtctccgcgc tgtgcctcga tttccgggcc caggatcccg tggtccccac cgccgcctcc  360
ggcggtcgcg atgaggtgta cgagcaggtg ctggaaatcg cgcggcagag gaacgacgac  420
ctcggcgccg aacaactcaa gttcgacgaa tcccccataa acgacgtcgt tgttgttgac  480
gagatgctga tgcagcaaac gccgttcacg tctttgctta tgttgccaaa ttccgaatct  540
gaattcgact cccgaaaaag taacgataac aacggttacg gaaccgaggc aggggatctt  600
ctctggaatt ataaccccgc gtatcagcct cctcaggtgt gggattttca gttacaaaaa  660
tcaagagatt gccatgaacc aagagttgta acatttgatg gtctagaagt tccaaaatta  720
tttcaggatg agcacaatat gaagtactca acaattggtg atgacattga tattctatca  780
agaaataatc aatcggatca gtcatcatca agccatgcaa agaagaaaga agagaacaac  840
aaaaaagcta aaggtgggtt atcatcagag tccaaactgt ttgaatccat accgtacaat  900
ggcaccaaca atgtcgtagt catggagcat cttgttggtg ggaatgaaaa tgttggcacc  960
ttaacagcca gggttagttt ggaagagttg gctaagaata gaggggatgc catgttgcgt  1020
tacaaggaga agaagaaaac tcgaaggtac gataagcaca ttcgctatga atcaaggaag  1080
gccagggctg atactagaaa aagggtgaga gggagatttg tgaaggcaag tgatgttcaa  1140
```

```
gcgtga                                                           1146

SEQ ID NO: 488          moltype = AA  length = 381
FEATURE                 Location/Qualifiers
REGION                  1..381
                        note = GmBBX30 soybean B-box polypeptide
source                  1..381
                        mol_type = protein
                        organism = Glycine max
SEQUENCE: 488
MLPCDYCHSK PAILFCRPDS AKLCLLCDQH VHAANALSLK HVRFQICDSC KTDTAVLRCS  60
TDNLVLCHHC DVETHGAAAS SHHQRHRLHG LSGCPSVTEI VSALCLDFRA QDPVVPTAAS  120
GGRDEVYEQV LEIARQRNDD LGAEQLKFDE SPINDVVVVD EMLMQQTPFT SLLMLPNSES  180
EFDSRKSNDN NGYGTEAGDL LWNYNPAYQP PQVWDFQLQK SRDCHEPRVV TFDGLEVPKL  240
FQDEHNMKYS TIGDDIDILS RNNQSDQSSS SHAKKKEENN KKAKGGLSSE SKLFESIPYN  300
GTNNVVVMEH LVGGNENVGT LTARVSLEEL AKNRGDAMLR YKEKKKTRRY DKHIRYESRK  360
ARADTRKRVR GRFVKASDVQ A                                          381

SEQ ID NO: 489          moltype = DNA  length = 570
FEATURE                 Location/Qualifiers
misc_feature            1..570
                        note = GmBBX31
source                  1..570
                        mol_type = unassigned DNA
                        organism = Glycine max
SEQUENCE: 489
atgcgaacgc tttgtgatgc ttgtgagagt gcggcggcta tagttttctg cgccgctgat  60
gaggctgcac tttgtcgtgc ctgtgatgag aaggttcaca tgtgcaataa gctagctagt  120
aggcatgtga gggttggtct tgcaagtcca agtgatgtgc cacggtgtga catatgtgag  180
aatgcaccag ctttcttcta ttgcgagaca gatggaagtt ccctttgttt gcagtgtgat  240
atgattgttc atgttggtgg taaaagaacg catggaagat atcttctgtt caggcaaaga  300
gttgagtttc caggagataa atctagtcat gctgaaaatc cggcttcaca agcattggaa  360
ccaggtgagg ctaaaagagg acaaaatcca cttcccaagc taaaaatggg agagaaacaa  420
caaaatcaca ggatgcctat ggttccaaca ccaggacctg atgctgatgg gcaaaccaag  480
atggaaacta aaatgattga tttgaacatg aagcctaata gaatacatga acaagcatca  540
aataaccagg ttagagttca tgggaagtaa                                 570

SEQ ID NO: 490          moltype = AA  length = 189
FEATURE                 Location/Qualifiers
REGION                  1..189
                        note = GmBBX31 soybean B-box polypeptide
source                  1..189
                        mol_type = protein
                        organism = Glycine max
SEQUENCE: 490
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQALE  120
PGEAKRGQNP LPKLKMGEKQ QNHRMPMVPT PGPDADGQTK METKMIDLNM KPNRIHEQAS  180
NNQVRVHGK                                                        189

SEQ ID NO: 491          moltype = DNA  length = 555
FEATURE                 Location/Qualifiers
misc_feature            1..555
                        note = GmBBX33
source                  1..555
                        mol_type = unassigned DNA
                        organism = Glycine max
SEQUENCE: 491
atgcgaacgc tttgtgatgc ttgtgagagc gccgcggcta tagttttctg cgccgctgat  60
gaggctgcac tttgtcgtgc ctgtgatgag aaggttcaca tgtgcaacaa gctagctagt  120
aggcatgtga gggttggtct tgctagtcca agtgatgtac cacggtgtga catatgtgag  180
aatgcacctg ctttcttcta ttgcgagaca gatggaagtt ccctttgttt gcagtgtgat  240
atgattgttc atgttggagg taaaagaacg catggaagat atcttctgtt caggcaaaga  300
gttgagtttc caggagataa atctagtcat gctgaaaatc cggcttcaca accattggaa  360
ccaggtgagg ctaaaagagg acaaaatcca cttcccaaac taaaaatggg agagaagcaa  420
caaaatcaca agatgcctat ggttccaacg ccaggacctg atgctgatgg gcatgccaag  480
atggaaagta aaatgattga tttgaacatg aagcctaata gaatacatga acaagcatca  540
aataatcagc cataa                                                 555

SEQ ID NO: 492          moltype = AA  length = 184
FEATURE                 Location/Qualifiers
REGION                  1..184
                        note = GmBBX33 soybean B-box polypeptide
source                  1..184
                        mol_type = protein
                        organism = Glycine max
SEQUENCE: 492
MRTLCDACES AAAIVFCAAD EAALCRACDE KVHMCNKLAS RHVRVGLASP SDVPRCDICE  60
NAPAFFYCET DGSSLCLQCD MIVHVGGKRT HGRYLLFRQR VEFPGDKSSH AENPASQPLE  120
```

-continued

```
PGEAKRGQNP LPKLKMGEKQ QNHKMPMVPT PGPDADGHAK MESKMIDLNM KPNRIHEQAS  180
NNQP                                                               184

SEQ ID NO: 493          moltype = DNA  length = 639
FEATURE                 Location/Qualifiers
misc_feature            1..639
                        note = GmBBX34
source                  1..639
                        mol_type = unassigned DNA
                        organism = Glycine max
SEQUENCE: 493
atgcgaaccc tttgcgacgt atgcgagagc gccgctgcca ttgtcttctg cgccgctgat  60
gaggctgctc tctgctccgc ttgtgaccac aagatccata tgtgtaacaa acttgctagt  120
agacacgttc gggttggcct tgctgacccc actgatgttc cacgctgtga catatgtgaa  180
aacgcacctg ctttctttta ctgtgagata gatggtagtt cgctgtgtct gcaatgtgat  240
atgattgtgc atgttggtgg taaaagaact catggaagat atcttctatt gaggcaaaga  300
gttcagtttc catgtgataa acctgcccaa atggaagaac tagggctgca acctatggat  360
caaaatgaat caaggaggga tgaaagtcag tcactcaagc taaaaataag agatagtcag  420
cagaatcaca gtgtctcacc tgttccaaga caagaaaata atattgatgg tcatggaaaa  480
atggataaaa agttaattga tcttaatacg aggccactgc ggttaaatgg agcagcacca  540
aacaaccagg aacgaggtat ggatatttta agaggcaata atcataaatc tgcgagtgtg  600
ccaccagtag aatccttcaa acaagagtct gagaagtaa                          639

SEQ ID NO: 494          moltype = AA  length = 90
FEATURE                 Location/Qualifiers
REGION                  1..90
                        note = GmBBX34 soybean B-box polypeptide
source                  1..90
                        mol_type = protein
                        organism = Glycine max
SEQUENCE: 494
MRTLCDVCES AAAIVFCAAD EAALCSACDH KIHMCNKLAS RHVRVGLADP TDVPRCDICE  60
NAPAFFYCEI DGSSLCLQCD MIVHVGGKRT                                   90

SEQ ID NO: 495          moltype = DNA  length = 639
FEATURE                 Location/Qualifiers
misc_feature            1..639
                        note = GmBBX35
source                  1..639
                        mol_type = unassigned DNA
                        organism = Glycine max
SEQUENCE: 495
atgcgaaccc tttgcgacgt atgcgagagc gccgctgcca ttctcttctg cgccgctgat  60
gaggccgctc tctgctccgc ttgtgaccac aagatccata tgtgtaacaa acttgctagt  120
aggcatgttc gagttggcct tgctgacccc actgatgttc cacgctgtga catatgtgaa  180
aatgcacctg ctttctttta ctgtgagata gatggtagtt cgctgtgtct gcaatgtgat  240
atgattgtgc atgttggtgg taaaagaacc catggaagat atcttctatt gaggcaaaga  300
gctcagtttc caggtgataa acctgcccaa atggaagaac tagagctgca acctatggat  360
caaaatgaat cgagaaggga tgaaagtcag tcactcaagc taaaaacaag agatagtcag  420
cagaatcaca gtgtctcacc ttttccaagg caagaaaata atattgatgg tcatggaaaa  480
atggataaaa agttaattga tcttaatacc aggccactgc ggttaaatgg atcagcacca  540
aacaaccagg aacaatgcat ggatatttta agaggcaata atcatgaatc tgccagtgtg  600
ccaccagtag aatccttcaa acaagagtct gagaagtaa                          639

SEQ ID NO: 496          moltype = AA  length = 212
FEATURE                 Location/Qualifiers
REGION                  1..212
                        note = GmBBX35 soybean B-box polypeptide
source                  1..212
                        mol_type = protein
                        organism = Glycine max
SEQUENCE: 496
MRTLCDVCES AAAILFCAAD EAALCSACDH KIHMCNKLAS RHVRVGLADP TDVPRCDICE  60
NAPAFFYCEI DGSSLCLQCD MIVHVGGKRT HGRYLLLRQR AQFPGDKPAQ MEELELQPMD  120
QNESRRDESQ SLKLKTRDSQ QNHSVSPFPR QENNIDGHGK MDKKLIDLNT RPLRLNGSAP  180
NNQEQCMDIL RGNNHESASV PPVESFKQES EK                                 212

SEQ ID NO: 497          moltype = DNA  length = 801
FEATURE                 Location/Qualifiers
misc_feature            1..801
                        note = GmBBX36
source                  1..801
                        mol_type = unassigned DNA
                        organism = Glycine max
SEQUENCE: 497
atgaagatcc actgcgacgt gtgtaacaag caccaggcct ctttcttctg caccgccgac  60
gaagctgccc tatgcgacgg ctgcgaccac cgcgtccacc acgccaacaa gctcgcctcc  120
aaacaccaac gcttctccct cacccacccc tctgcgaaac atttcccct ctgcgatgtt  180
tgccaggaga gaagagcctt cgtgttttgt cagcaagata gagcgattct gtgcaaagag  240
```

-continued

```
tgtgacgtgc ccattcattc tgccaacgac ctcaccaaga accatagcag gtttcttctc  300
actgggatta agttctctgc ttctgccacg ccttatgatt attcatcacc accaccacca  360
ccaccaccac caccacccaa gagaaaccct gttctcgatt ctccttcaac accgtcaccg  420
cctaagcctg gggaaactc gctaacaaac gaagaagaac ctggtttcac aggtagcagc  480
atttcagagt acttgataaa ctctatccca ggcatgaagt tcgaagattt cctcgattca  540
cattctcttc cctttgcttg ctccaagaat agtgatgaca tgttgtcgct gtttggtgag  600
ggaaacatgg tttctttctc acccggtggg ttctgggttc ctcaagcacc accatcttca  660
gtacaaatgg atcggcagag tgggtacaga gagacaaggg aaggtagcat tagatcaagt  720
tttggagatg ataatttcat agttccacag atgagtcctc ccagcaatgt gtctaataag  780
agatccaggc ttctctggta a                                            801
```

```
SEQ ID NO: 498         moltype = AA  length = 266
FEATURE                Location/Qualifiers
REGION                 1..266
                       note = GmBBX36 soybean B-box polypeptide
source                 1..266
                       mol_type = protein
                       organism = Glycine max
SEQUENCE: 498
MKIHCDVCNK HQASFFCTAD EAALCDGCDH RVHHANKLAS KHQRFSLTHP SAKHFPLCDV  60
CQERRAFVFC QQDRAILCKE CDVPIHSAND LTKNHSRFLL TGIKFSASAT PYDYSSPPPP  120
PPPPPPKRNP VLDSPSTPSP PKPGGNSLTN EEEPGFTGSS ISEYLINSIP GMKFEDFLDS  180
HSLPFACSKN SDDMLSLFGE GNMVSFSPGG FWVPQAPPSS VQMDRQSGYR ETREGSIRSS  240
FGDDNFIVPQ MSPPSNVSNK RSRLLW                                       266
```

```
SEQ ID NO: 499         moltype = DNA  length = 738
FEATURE                Location/Qualifiers
misc_feature           1..738
                       note = GmBBX37
source                 1..738
                       mol_type = unassigned DNA
                       organism = Glycine max
SEQUENCE: 499
atgaagatcc agtgcgacgt gtgtaacaaa cagcaggcat cgttgttctg caccgccgac  60
gaagccgccc tatgcgacgg ctgcgaccac cgcgtccacc acgccaacaa gctcgcctcc  120
aaacaccaac gcttctccct cagccacccc tctgcaaaac attttcctct ctgcgatgtt  180
tgccaggaga gaagagcctt tgtgttttgt cagcaagata gagcgattct gtgcaaagag  240
tgtgacgtgc ccgttcattc tgccaacgac ctcaccaaga accataacag gtttcttctc  300
actgggatta agttttctgc cctcgattct ccttcaacac ctcctaagcc tgcaggtgga  360
aactccctaa caaatcaaca accacaacaa caaactggtt tcacaggtag cagcatatca  420
gaatacttga taaacactat cccaggcatg gagttcgaag atttcctcga ttcacattct  480
cttccctttg cttgctccaa gaatagtgat gacatgatgt tgtcgatgtt tggtgaggga  540
aacatggttt cgttctcagc cggagggatc tgggttcctc aagcaccatc ttcagtacaa  600
atggatcagc agagtgggta caaagacaca tgggaaacta gcattagatc aagttttggg  660
gatgatagtt tattagttcc acagatgact cctcccagca atgtgtttaa taataagaga  720
tccaggcttc tatggtaa                                                738
```

```
SEQ ID NO: 500         moltype = AA  length = 245
FEATURE                Location/Qualifiers
REGION                 1..245
                       note = GmBBX37 soybean B-box polypeptide
source                 1..245
                       mol_type = protein
                       organism = Glycine max
SEQUENCE: 500
MKIQCDVCNK QQASLFCTAD EAALCDGCDH RVHHANKLAS KHQRFSLSHP SAKHFPLCDV  60
CQERRAFVFC QQDRAILCKE CDVPVHSAND LTKNHNRFLL TGIKFSALDS PSTPPKPAGG  120
NSLTNQQPQQ QTGFTGSSIS EYLINTIPGM EFEDFLDSHS LPFACSKNSD DMMLSMFGEG  180
NMVSFSAGGI WVPQAPSSVQ MDQQSGYKDT WETSIRSSFG DDSLLVPQMT PPSNVFNNKR  240
SRLLW                                                              245
```

```
SEQ ID NO: 501         moltype = DNA  length = 831
FEATURE                Location/Qualifiers
misc_feature           1..831
                       note = GmBBX38
source                 1..831
                       mol_type = unassigned DNA
                       organism = Glycine max
SEQUENCE: 501
atgaagatcc agtgcgacgt gtgcaacaaa cacgaggcct ccgtcttctg cacagccgac  60
gaagccgccc tctgcgacgg ctgcgaccac cgtgtccacc atgccaacaa actcgcctcc  120
aaacaccaac gcttctctct tctccgccct tctcataaac aacaccctct ctgcgatatt  180
tgccaggaga gaagagcctt cacgttctgt cagcaagaca gagcgattct ctgcaaagag  240
tgtgacgtgt caattcactc tgccaacgaa cacacccta agcacgatag gttccttctc  300
actggtgtta aactcgcagc ttctgccatg cttcgttcat cacaaactac ctctgattca  360
aactcaaccc cttctcttct taacgtttca catcaaacta ctccacttcc atcttccacc  420
accaccacca ccaccaacaa caacaacaac aaggttgctg ttgaaggaac tggttcaacg  480
agtgctagca gcatatcaga gtatttgata gagactcttc ctgggtggca agttgaggac  540
tttctcgatt catattttgt tccctttggt ttctgtaaga atgatgaagt gttgccacgg  600
```

```
ttggatgctg acgtggaggg gcatatgggt tcgttttcaa ccgagaacat ggggatctgg  660
gttcctcaag cgccaccacc tcttgtgtgt tcttcacaaa tggatcgggt gatagttcaa  720
agtgagacca acatcaaagg tagcagcata tcgaggttga aggatgatac tttcactgtt  780
ccacagatta gtcctccctc caattccaag agagccagat ttctatggta g           831

SEQ ID NO: 502          moltype = AA  length = 276
FEATURE                 Location/Qualifiers
REGION                  1..276
                        note = GmBBX38 soybean B-box polypeptide
source                  1..276
                        mol_type = protein
                        organism = Glycine max
SEQUENCE: 502
MKIQCDVCNK HEASVFCTAD EAALCDGCDH RVHHANKLAS KHQRFSLLRP SHKQHPLCDI  60
CQERRAFTFC QQDRAILCKE CDVSIHSANE HTLKHDRFLL TGVKLAASAM LRSSQTTSDS  120
NSTPSLLNVS HQTTPLPSST TTTTTNNNNN KVAVEGTGST SASSISEYLI ETLPGWQVED  180
FLDSYFVPFG FCKNDEVLPR LDADVEGHMG SFSTENMGIW VPQAPPPLVC SSQMDRVIVQ  240
SETNIKGSSI SRLKDDTFTV PQISPPSNSK RARFLW                           276

SEQ ID NO: 503          moltype = DNA  length = 837
FEATURE                 Location/Qualifiers
misc_feature            1..837
                        note = GmBBX39
source                  1..837
                        mol_type = unassigned DNA
                        organism = Glycine max
SEQUENCE: 503
atgaagatcc agtgcgacgt ttgcaacaaa cacgaggcct ccgtcttctg caccgccgat  60
gaagccgccc tctgcgacgg ctgcgaccac cgtgtccacc atgccaacaa actcgcctcc  120
aaacaccaac gcttctctct tctccgccct tctcctaaac aacaccctct ctgcgatatt  180
tgccaggaga gaagagcctt tacattctgt cagcaagaca gagcgattct ctgcaaagag  240
tgtgacgtgt caattcactc tgccaacgaa cacaccctta agcacgatag gttccttctc  300
accggtgtta aactttctgc ttctgctatg cttcgttcgt cagaaactac ctctgattca  360
aactcaaacc cttctcttct taacttttca caccaaacaa cattactacc tccatcttcc  420
accaccacca ccaccaccag caacaacaac aacaacaagg ttgctgttga aggaactggt  480
tcaactagtg ctagcagcat atcggagtat ttgatagaga ctcttcctgg gtggcaagtt  540
gaagactttc ttgattcata ttctgttccc tttggtttct gtaagaatga tgaagtgttg  600
ccacggtttg atggtgaaat ggaggggcat ctgagttctt tctcaaccga gaacatgggg  660
atctgggttc ctcaagcgcc accaactctt atgtgttctt cacaaatgga tcgggtgata  720
gttcacggtg agaccaatat caaaggtagc agcagatcaa ggttgaagga tgataatttc  780
actgttccac agattagtcc tccttccaat tccaagagag ccagatttct gtggtag     837

SEQ ID NO: 504          moltype = AA  length = 278
FEATURE                 Location/Qualifiers
REGION                  1..278
                        note = GmBBX39 soybean B-box polypeptide
source                  1..278
                        mol_type = protein
                        organism = Glycine max
SEQUENCE: 504
MKIQCDVCNK HEASVFCTAD EAALCDGCDH RVHHANKLAS KHQRFSLLRP SPKQHPLCDI  60
CQERRAFTFC QQDRAILCKE CDVSIHSANE HTLKHDRFLL TGVKLSASAM LRSSETTSDS  120
NSNPSLLNFS HQTTLLPPSS TTTTTTSNNN NNKVAVEGTG STSASSISEY LIETLPGWQV  180
EDFLDSYSVP FGFCKNDEVL PRFDGEMEGH LSSFSTENMG IWVPQAPPTL MCSSQMDRVI  240
VHGETNIKGS SRSRLKDDNF TVPQISPPSN SKRARFLW                         278

SEQ ID NO: 505          moltype = DNA  length = 960
FEATURE                 Location/Qualifiers
misc_feature            1..960
                        note = GmBBX40
source                  1..960
                        mol_type = unassigned DNA
                        organism = Glycine max
SEQUENCE: 505
atgaagatcc agtgtgctgt gtgtgacaaa gtggaagcct ccgtcttctg ctctgcagat  60
gaagctgctc tttgccatag ttgtgaccgc accattcacc acgccaacaa gcttgcaacc  120
aaacacccac gcttctctct ccattacccc acctcccaag acttccctct ttgtgatatt  180
tgccaagaga ggcgtgcata tctattttgc caagaagaca gggcattgct atgcagggag  240
tgtgacgttc ctatccacag ggcgaatgag catacccaga agcataacag gtttcttctc  300
accggagtga agctctctgg tacttctttg gatcctgctg cgtcctccac caattgcacc  360
catggctctg aaggaagaaa caacgctcga tctagaatga acagacccag atcatcagtt  420
tccaatgaag aaaatgcaag taattcttct tgcaaggttg aagacaacgt ggctagtgac  480
actggttcgg tttcaactag cagcatttct gagtacttga tcgaaacaat acccggttac  540
tgttttgaag accttcttga tgcttcattt gcacctaatg gtttctgtaa gaaccagaac  600
tatgatcgtc ataggcgttt caggaccaag atcttcaagt tattaggacg tgtttggttt  660
gagttaagga gattccaaaa tcttaacgct atcgatgatc aactgtttgt aaaaatctgt  720
tggaaaatat cttcttttgt ttttgttatt tgcatttctt tttgggctcc ctgctgcatt  780
ctttatgatt ttttttcat tctctattcc cgaccactgt ttcggcctct tattttagta  840
ttttttcaa ttttcattgg gttaattaat aatatttttt gggggggggt ccatgctttt  900
```

```
attgacatga acatgaattc attgaataac gcaactgaat attatgtgcc actttcttaa  960

SEQ ID NO: 506          moltype = AA  length = 319
FEATURE                 Location/Qualifiers
REGION                  1..319
                        note = GmBBX40 soybean B-box polypeptide
source                  1..319
                        mol_type = protein
                        organism = Glycine max
SEQUENCE: 506
MKIQCAVCDK VEASVFCSAD EAALCHSCDR TIHHANKLAT KHPRFSLHYP TSQDFPLCDI  60
CQERRAYLFC QEDRALLCRE CDVPIHRANE HTQKHNRFLL TGVKLSGTSL DPAASSTNCT  120
HGSEGRNNAR SRMNRPRSSV SNEENASNSS CKVEDNVASD TGSVSTSSIS EYLIETIPGY  180
CFEDLLDASF APNGFCKNQN YDRHRRFRTK IFKLLGRVWF ELRRFQNLNA IDDQLFVKIC  240
WKISSFVFVI CISFWAPCCI LYDFFFILYS RPLFRPLILV FFSIFIGLIN NIFWGGVHAF  300
IDMNMNSLNN ATEYYVPLS                                               319

SEQ ID NO: 507          moltype = DNA  length = 702
FEATURE                 Location/Qualifiers
misc_feature            1..702
                        note = GmBBX41
source                  1..702
                        mol_type = unassigned DNA
                        organism = Glycine max
SEQUENCE: 507
atgaagatcc agtgtgatgt gtgtgacaaa gtggaagcct ccgtcttctg tcctgcagat  60
gaagctgctc tttgccatag ctgtgatcgc accattcacc gcgccaacaa gcttgcaacc  120
aaacacgccc gtttctctct ccactacccc acctccaaag acttccctct ttgtgatata  180
tgccaagaga ggcgtgcata tctattttgc caagaagaca gggcgttgtt atgcagggaa  240
tgcgacgttc ctatccacag agccaatgag catacccaaa agcataacag gtttcttctc  300
acgggtgtga agctctctgg tacttgttta gatcctgctt cgtcctccac caattacacc  360
aataataata gagtcactgg ctctgaagga agaaacgacg ctcgatctag aatgaacaga  420
cccagatcat cagtttccaa tgaagaaaat gcaagtaatt cttcttgcaa ggttgaagac  480
aacgtggcta gtgacactgg ttcgatttca actagcagca tttctgagta cttgattgaa  540
acaatacccg gttactgttt tgaagacctc cttgatgctt cgtttgcacc taatggtttc  600
tgtaagaagc agaactttga tcatccctgg gcgtttcagg accaaaagcg aacaagtgga  660
gacactatgg ccgtgccgtt cctgaaacta gtcatccatt ga                      702

SEQ ID NO: 508          moltype = AA  length = 233
FEATURE                 Location/Qualifiers
REGION                  1..233
                        note = GmBBX41 soybean B-box polypeptide
source                  1..233
                        mol_type = protein
                        organism = Glycine max
SEQUENCE: 508
MKIQCDVCDK VEASVFCPAD EAALCHSCDR TIHRANKLAT KHARFSLHYP TSKDFPLCDI  60
CQERRAYLFC QEDRALLCRE CDVPIHRANE HTQKHNRFLL TGVKLSGTCL DPASSSTNYT  120
NNNRVTGSEG RNDARSRMNR PRSSVSNEEN ASNSSCKVED NVASDTGSIS TSSISEYLIE  180
TIPGYCFEDL LDASFAPNGF CKKQNFDHPW AFQDQKRTSG DTMAVPFLKL VIH         233

SEQ ID NO: 509          moltype = DNA  length = 648
FEATURE                 Location/Qualifiers
misc_feature            1..648
                        note = GmBBX42
source                  1..648
                        mol_type = unassigned DNA
                        organism = Glycine max
SEQUENCE: 509
atgaagatcc agtgtgatgt gtgccacaaa gaagtggcct ccttcttctg cccctcagat  60
gaagcctctc tctgccatgc ttgtgatcgc accatccacc atcccaacaa gctctcagaa  120
aaacacaaac gcttctctct tcaccacccc atttccacca aagactctcc tctttgtgat  180
atctgtcata atgctcaact cattattatt cctttccagg agaagcatat ggcttgtgac  240
aaggtttcgg tttcaacaag cagcatttct gagtacttga ttcagaccat tcccggttat  300
tgcatggaag atcttctaga tgcttcattc gcatccaata gtttatctaa ggattatgag  360
caccaatcag cgtttcagaa ccaagatgtt caagtcagca tgcgttcgtt cccactgcaa  420
acttgggtac cacaatctca aggtggatcc cctcaacgta gctttacttc gaatctttat  480
ccccagattg attctttagt tggagtgatg gaaatgccta aagccaaagc tggtgaagga  540
tactccaatt ggatatataa ttatgactac gcagcttaca aacttccttc aatttgtcct  600
ccattgatca aaaaaatgca aacgctctcg ttaatcaatt gtatgtga                648

SEQ ID NO: 510          moltype = AA  length = 215
FEATURE                 Location/Qualifiers
REGION                  1..215
                        note = GmBBX42 soybean B-box polypeptide
source                  1..215
                        mol_type = protein
                        organism = Glycine max
SEQUENCE: 510
```

```
MKIQCDVCHK EVASFFCPSD EASLCHACDR TIHHPNKLSE KHKRFSLHHP ISTKDSPLCD  60
ICHNAQLIII PFQEKHMACD KVSVSTSSIS EYLIQTIPGY CMEDLLDASF ASNSLSKDYE  120
HQSAFQNQDV QVSMRSFPLQ TWVPQSQGGS PQRSFTSNLY PQIDSLVGVM EMPKAKAGEG  180
YSNWIYNYDY AAYKLPSICP PLIKKMQTLS LINCM                             215

SEQ ID NO: 511          moltype = DNA  length = 867
FEATURE                 Location/Qualifiers
misc_feature            1..867
                        note = GmBBX43
source                  1..867
                        mol_type = unassigned DNA
                        organism = Glycine max
SEQUENCE: 511
atgaagatcc agtgtgatgt gtgtcacaat gaagttgctt ccttttctg cccctctgat  60
gaagcctctc tctgccatgc ttgtgatcgc accatccacc atgccaacaa gctcgcagac  120
aaacacaaac gcttctccct tcaccacccc acttccaaag actcccctct ttgtgatatc  180
tgtcatgaga ggcgtgcata tctttttgc aaagaggaca gagcaatact atgtagagaa  240
tgtgatcttt ctattcatgg ggtcaacgaa cataccaaga aacacaacag gtttcttctc  300
actggcgtaa agatcggtgc tgatgcttca gacccaacat cactttcctc aaatgacact  360
gccattgaag aaagaacaac ctctagttct aaaataaaca gaccaataag ttctttgtca  420
aatgagaata tcagttcttc tcccacggtt ggagacaaca tggcttgtga cacgggttcg  480
gtttcaacta gcagcatttc tgagtacttg attcagacca ttcccggtta ctgcatggaa  540
gatcttttag atgcttcatt tgcatctaat ggtttatcta aggattatga gcaccaatca  600
gcgtttcaga accaagatgt tcaagtcagc atgtgttcgt ttccactgca aagttgggta  660
ccacaatctc aagctggatc ccctcaacta attagcacta cctcgaatct tcatccccag  720
attaattctt tagttggagt aatggaaatg cctaaagcca aagctagtga aggatactcc  780
aattgcatat ataattatga ctactcagct tacaaagttc cttcaatttg tcctccattg  840
atcaaaaaat gtaaacgctc tcgttaa                                      867

SEQ ID NO: 512          moltype = AA  length = 288
FEATURE                 Location/Qualifiers
REGION                  1..288
                        note = GmBBX43 soybean B-box polypeptide
source                  1..288
                        mol_type = protein
                        organism = Glycine max
SEQUENCE: 512
MKIQCDVCHN EVASFFCPSD EASLCHACDR TIHHANKLAD KHKRFSLHHP TSKDSPLCDI  60
CHERRAYLFC KEDRAILCRE CDLSIHGVNE HTKKHNRFLL TGVKIGADAS DPTSLSSNDT  120
AIEERTTSSS KINRPISSLS NENISSSPTV GDNMACDTGS VSTSSISEYL IQTIPGYCME  180
DLLDASFASN GLSKDYEHQS AFQNQDVQVS MCSFPLQSWV PQSQAGSPQL ISTTSNLHPQ  240
INSLVGVMEM PKAKASEGYS NCIYNYDYSA YKVPSICPPL IKKCKRSR                288

SEQ ID NO: 513          moltype = DNA  length = 879
FEATURE                 Location/Qualifiers
misc_feature            1..879
                        note = GmBBX44
source                  1..879
                        mol_type = unassigned DNA
                        organism = Glycine max
SEQUENCE: 513
atgaagattc agtgcaacgt gtgcgaggcc gcggaggcca aggttctgtg ctgcgcggac  60
gaggcagcac tgtgctggga atgcgacgag aaggttcacg cagcaaacaa gctcgccagc  120
aagcaccaga gggtccctct ctctctctcc gcctctcaca tgcccaagtg tgacatatgc  180
caggaaatgg ttggttattt cttctgttta gaggatcgag ctttgctatg taggaattgt  240
gatgtatcta tacatacagc aaatgcctgt gtctctgatc atcaaaggtt tttgcttact  300
ggtgtgagag taggccttga agctactgag cgcggtgctt cctcgtcttc tgtgaagtca  360
cagtctgggg agaaaatgtc tgatgctaaa tcttcatcca tctccagaaa tgtttcctca  420
ctgccccagc catcaaatgc caatgaagtg ttacccctcc aaatgcaagg agttgaggag  480
tttccaccaa gcaatttctc aggttatact tctggaaacg tctcacaatg gcccattgaa  540
gaatttctcg gattaaatga actcagtcag tattataatt acatggatgg atcatctaag  600
gctgacagtg gtaaacttgg ggattctgat tcttctgttt tgaggtctgg tgaagaggat  660
atggatgatg acggcttctt gggacgtgtt ccagattcat cctggacagt tcctcagatc  720
ccttcccctc ctacagcttc gggtttatat tggccgaaag tccctcaata tacatctgac  780
agtgccatgt ctgttcctga catatgcttt tctcatgtgc gacagcccca ccatgcccag  840
cataattcta atgtttccaa aaggcgtagg caactataa                          879

SEQ ID NO: 514          moltype = AA  length = 292
FEATURE                 Location/Qualifiers
REGION                  1..292
                        note = GmBBX44 soybean B-box polypeptide
source                  1..292
                        mol_type = protein
                        organism = Glycine max
SEQUENCE: 514
MKIQCNVCEA AEAKVLCCAD EAALCWECDE KVHAANKLAS KHQRVPLSLS ASHMPKCDIC  60
QEMVGYFFCL EDRALLCRNC DVSIHTANAC VSDHQRFLLT GVRVGLEATE RGASSSSVKS  120
QSGEKMSDAK SSSISRNVSS LPQPSNANEV LPLQMQGVEE FPPSNFSGYT SGNVSQWPIE  180
EFLGLNELSQ YYNYMDGSSK ADSGKLGDSD SSVLRSGEED MDDDGFLGRV PDSSWTVPQI  240
```

-continued

```
PSPPTASGLY WPKVPQYTSD SAMSVPDICF SHVRQPHHAQ HNSNVSKRRR QL         292

SEQ ID NO: 515          moltype = DNA  length = 1125
FEATURE                 Location/Qualifiers
misc_feature            1..1125
                        note = GmBBX45
source                  1..1125
                        mol_type = unassigned DNA
                        organism = Glycine max
SEQUENCE: 515
atgaacctcg tggccgcaaa aaatatcctt catttttttc ttctttctct tctccgccac  60
ttcttaaacc ctgctcctct gcttcgtggt gccccaaacc tcttcttctc tttcttttcc  120
ctctctcaat tccaaacagt agatttagac accctttttgg aaaaggaagt gttttttgag  180
ggaaaggagg gaatttttttg tgtgggaggg tggaacccgg aattcggttt ggttggggta  240
gagaggatga agattcagtg taacgtgtgt gaggctgcgg aggccaaggt tctttgttgt  300
gctgatgagg ctgggctgtg ttgggagtgt gatgagaagg ttcatgcggc taacaagctt  360
gccagcaagc accagagagt gcctctttct acctcttcct ctcatatgcc taaatgtgac  420
atttgtcagg aagcattagg ctattttttc tgtctagaag atcgggctct gctctgcaga  480
aaatgtgatg tggcaataca cactgcaaat gcttatgtct ctggtcatca gaggtttctt  540
ctaactggtg taagagtagg ccttgaagct acagaccctg gtgcttcctc aacttctttg  600
aagtcagatt ctggggagaa agtttcagat tcttctgtct ctagaaaggt ttccacagcg  660
ccccagccat caaattataa tgaagtgtta cccgctgaag ttggaggagt tggggagttt  720
ccatcagcca aggtgtcctt tggtggtggt tccacagctg gaaatatctc acagtggact  780
attgatgaat ttattggctt aaacgagttc agtcagaatt atgattacat ggaaggatca  840
tcaagggctg acggtggtaa gcttggggat tctgattctc ctgttttaag atctggtgaa  900
gaggaaatgg aggaggagga tgactatttg gaacgcgttc cagattcgtc gtggacagtc  960
ccgcagatcc cttccccacc tacttcttct gggttatgct ggccaaaaga ccatactaat  1020
ctgtatggtt catctgatag tgttctgttt gttcctgaca taagcttctc tcacctgcaa  1080
caatctcaga ttagtatttt tttgagacgc cggaggcagc tttaa                 1125

SEQ ID NO: 516          moltype = AA  length = 374
FEATURE                 Location/Qualifiers
REGION                  1..374
                        note = GmBBX45 soybean B-box polypeptide
source                  1..374
                        mol_type = protein
                        organism = Glycine max
SEQUENCE: 516
MNLVAAKNIL HFFLLSLLRH FLNPAPLLRG APNLFFSFFS LSQFQTVDLD TLLEKEVFFE  60
GKEGIFCVGG WNPEFGLVGV ERMKIQCNVC EAAEAKVLCC ADEAGLCWEC DEKVHAANKL  120
ASKHQRVPLS TSSSHMPKCD ICQEALGYFF CLEDRALLCR KCDVAIHTAN AYVSGHQRFL  180
LTGVRVGLEA TDPGASSTSL KSDSGEKVSD SSVSRKVSTA PQPSNYNEVL PAEVGGVGEF  240
PSAKVSFGGG STAGNISQWT IDEFIGLNEF SQNYDYMEGS SRADGGKLGD SDSPVLRSGE  300
EEMEEEDDYL ERVPDSSWTV PQIPSPPTSS GLCWPKDHTN LYGSSDSVLF VPDISFSHLQ  360
QSQISIFLRR RRQL                                                   374

SEQ ID NO: 517          moltype = DNA  length = 717
FEATURE                 Location/Qualifiers
misc_feature            1..717
                        note = GmBBX46
source                  1..717
                        mol_type = unassigned DNA
                        organism = Glycine max
SEQUENCE: 517
atgaaaattc agtgcgatgt gtgtgagaaa gccccggcaa ccgtgatttg ctgcgcagat  60
gaggcagctt tgtgtgccaa atgtgacgtt gaagttcatg ctgcaaacaa gcttgcaagc  120
aagcaccaga ggcttctcct tcaatcttta tctaacaagc ttcccagatg tgacatatgt  180
caagataagc cagctttcat attttgtgtt gaggacagag cactcttctg taaagactgt  240
gatgaaccta ttcatttagc cagtagcctt tctgcaaacc accagcgctt ccttgctact  300
ggtatccggg tggctttggg ttctaattgc accaaaggca atgaaaaagg tcacgtggaa  360
ccatctaaac caaaagcaca agaagttcct gcgaaaattc cttctcagca agtgcctagc  420
ttcacatcct cttgggcagt tgatgacttg ttggaattaa cagactttga atcaccagac  480
aaagttcaga agcaatccct tgagtttgga gaacttgaat ggctagcaga tgtaggcctt  540
tttggtgaac agtttcctca tgaagcttta gcggcggctg aagttcctca gcttccaatg  600
actagcagtg ttggctcaca caaagccccc aaatccttgt tgtcttacaa aaagcctagg  660
attgaagtcc tagatgaaga tgatgatgag cacttcaccg taccagatct cggataa    717

SEQ ID NO: 518          moltype = AA  length = 238
FEATURE                 Location/Qualifiers
REGION                  1..238
                        note = GmBBX46 soybean B-box polypeptide
source                  1..238
                        mol_type = protein
                        organism = Glycine max
SEQUENCE: 518
MKIQCDVCEK APATVICCAD EAALCAKCDV EVHAANKLAS KHQRLLLQSL SNKLPRCDIC  60
QDKPAFIFCV EDRALFCKDC DEPIHLASSL SANHQRFLAT GIRVALGSNC TKGNEKGHVE  120
PSKPKAQEVP AKIPSQQVPS FTSSWAVDDL LELTDFESPD KVQKQSLEFG ELEWLADVGL  180
FGEQFPHEAL AAAEVPQLPM TSSVGSHKAP KSLLSYKKPR IEVLDEDDDE HFTVPDLG    238
```

```
SEQ ID NO: 519          moltype = DNA  length = 717
FEATURE                 Location/Qualifiers
misc_feature            1..717
                        note = GmBBX47
source                  1..717
                        mol_type = unassigned DNA
                        organism = Glycine max
SEQUENCE: 519
atgaagattc agtgtgatgt gtgtgagaaa gcccctgcaa ccgtgatttg ttgcgcagat  60
gaggcagctt tgtgtgccaa atgtgacgtt gaagttcatg ctgcaaacaa gcttgcaagc  120
aagcaccaga ggcttctcct tcaatgtcta tcaaacaagc ttcccagatg tgacatatgc  180
caagataagc cagctttcat attttgtgtt gaggacagag cactcttctg taaagactgt  240
gatgagccaa ttcatttagc cagtagcctt tctgcaaacc accagcgctt cctcgctact  300
ggtatcaggg tggctttggg ttctaattgc accaaaggcc atgaaaaagg taacatggaa  360
ccatctaatc caaatgcaca agaagttcct gtgaaaactc cttctcagca agtgcctagc  420
ttcacatcct cttgggcagt tgatgacttg ttggaattaa cagactttga atcgccagac  480
aaaaagcaat ccctggaatt tggagaactt gaatggctag cagatgcagg ccttttcagt  540
gaacagtttc ctcatgaagc tttagtcgca gctgaagttc ctcagcttcc agtgccacac  600
actagcagtg ttgcctcaca taaagccccc aaatccttgg tgtcttacaa aaagcctagg  660
attgaagtcc tggatgaaga tgatgatgaa cactgcactg tcccggatct cggataa     717

SEQ ID NO: 520          moltype = AA  length = 92
FEATURE                 Location/Qualifiers
REGION                  1..92
                        note = GmBBX47 soybean B-box polypeptide
source                  1..92
                        mol_type = protein
                        organism = Glycine max
SEQUENCE: 520
MKIQCDVCEK APATVICCAD EAALCAKCDV EVHAANKLAS KHQRLLLQCL SNKLPRCDIC  60
QDKPAFIFCV EDRALFCKDC DEPIHLASSL SA                                92

SEQ ID NO: 521          moltype = DNA  length = 720
FEATURE                 Location/Qualifiers
misc_feature            1..720
                        note = GmBBX48
source                  1..720
                        mol_type = unassigned DNA
                        organism = Glycine max
SEQUENCE: 521
atgaaaattc agtgtgatgt gtgtgagaga gctccggcaa cagtgatttg ttgtgcggat  60
gaggcagctt tgtgtgccaa atgtgacgtt gaagttcatg ctgcaaacaa gcttgcaagc  120
aagcaccaaa ggcttcttct tcaatgtcta tcaagcaagc ttccaagatg tgacatttgc  180
caagacaagc cagcattcat attttgtgtt gaagacagag cactcttctg tcaggattgt  240
gatgaaccaa ttcattcagc cggaagcctt tctgcgaacc accagcgctt ccttgctact  300
ggtatccgag tggcatcgag ttctaattgc accaaggaca atgaaaaaag tcacttggag  360
cctcctacta ggaatgcaca acaagtttct gcgaaaattc ctcctcagca agtgcctagc  420
ttcacttcct cttgggctgt tgatgactta ttggaactaa cagcctttga atcacctgag  480
aaaaaggaat ctctgcagtt tggagagctg gaatggctta cagatgtggg tatttttggt  540
gaacaatttg ctcaggaagc cttggctgca gctgaagtac ctcagcttcc agtaactcat  600
aacagtagca gtgttgcttc atacagaact tccaaatcct acatgtccca caaaaagcct  660
aggattgaag tcctaaatga tgatgatgat gagtatttta ctgtgcctga tcttggctaa  720

SEQ ID NO: 522          moltype = AA  length = 239
FEATURE                 Location/Qualifiers
REGION                  1..239
                        note = GmBBX48 soybean B-box polypeptide
source                  1..239
                        mol_type = protein
                        organism = Glycine max
SEQUENCE: 522
MKIQCDVCER APATVICCAD EAALCAKCDV EVHAANKLAS KHQRLLLQCL SSKLPRCDIC  60
QDKPAFIFCV EDRALFCQDC DEPIHSAGSL SANHQRFLAT GIRVASSSNC TKDNEKSHLE  120
PPTRNAQQVS AKIPPQQVPS FTSSWAVDDL LELTAFESPE KKESLQFGEL EWLTDVGIFG  180
EQFAQEALAA AEVPQLPVTH NSSSVASYRT SKSYMSHKKP RIEVLNDDDD EYFTVPDLG   239

SEQ ID NO: 523          moltype = DNA  length = 723
FEATURE                 Location/Qualifiers
misc_feature            1..723
                        note = GmBBX49
source                  1..723
                        mol_type = unassigned DNA
                        organism = Glycine max
SEQUENCE: 523
atgaaaattc agtgtgacgt gtgtgagaga gctccagcaa cagtgatttg ttgcgcggat  60
gaggctgctt tgtgtgccaa atgtgacgtt gaagttcatg ctgcaaacaa gcttgcaagc  120
aagcaccaaa gacttcttct tcaatgtcta tcaagcaagc ttcccacatg tgacatttgc  180
caagacaagc cagcattcat attttgtgtt gaagacagag cactcttctg tcaggattgt  240
```

```
gatgaaccaa ttcattcagc cggaagcctt tccgcgaacc accagcgctt ccttgctact  300
ggtatccgag tggcctcgag ttctaattgc accaaagaca atgaaaaaag tcactcggag  360
cctcctaata ggagtgcaca acaagtttct gcgaaaattc ctcctcagca agtgcctagc  420
ttcacatcct cttgggctgt tgatgactta ttggaactaa caggctttga atcacctgag  480
aaaaaggaat ctctgcagtt tggagagctg gaatggctta cagatgtggg tattttcggc  540
gaacaatttg ctcaggaagc cttggctgca gctgaagtac ctcagcttcc cgaaactcat  600
aacagtagca gtgttgcttc atacaaaacc tccaaatcct acatgtccca caaaaagcct  660
aggattgaag tcctaaatga tgatgatgat gatgagtatt ttactgtgcc cgatctcggc  720
taa                                                                723
```

```
SEQ ID NO: 524          moltype = AA  length = 92
FEATURE                 Location/Qualifiers
REGION                  1..92
                        note = GmBBX49 soybean B-box polypeptide
source                  1..92
                        mol_type = protein
                        organism = Glycine max
SEQUENCE: 524
MKIQCDVCER APATVICCAD EAALCAKCDV EVHAANKLAS KHQRLLLQCL SSKLPTCDIC  60
QDKPAFIFCV EDRALFCQDC DEPIHSAGSL SA                                92
```

```
SEQ ID NO: 525          moltype = DNA  length = 1317
FEATURE                 Location/Qualifiers
misc_feature            1..1317
                        note = GmBBX50
source                  1..1317
                        mol_type = unassigned DNA
                        organism = Glycine max
SEQUENCE: 525
atggagaagg tttgtgaatt ctgcacagct ttgaggccac ttgtttactg taaggctgat  60
gcagcatatc tttgtctttc ctgtgatgca aaggtgcatt tagcaaatgc agtgtccggc  120
cggcacctcc ggaacctcgt gtgtaactca tgcggatacc accttgctta tgttctgtgt  180
ttggaacaca aaatgttgat atgtcgtgac tgtgaccaaa agttgcacaa catttctttg  240
ccacataaga aacgagctat cagaagtttc atgggttgcc cttctgctaa agactttgca  300
gcactctggg ggtttgaatt gaatgagatt gaaaacagtg ccagtcagga tcagtttgat  360
tcagtttctt gtgtttctgc agatttaaat gttgcacaag tttcaggaaa gcctggcatt  420
caaactgagg tcccttcaat gctatctggg gccaaacttg atgggggagg atcaaccagt  480
caacaaggtc agatattgta tagtgatcaa aagcgtcaaa cgattctgca gcagattatt  540
gattttaaat ggcttcaaca aaatgaggag attgattatt ctgcaaagat caataggcta  600
caagaaaaag attcatctcc ttcagtatat cagactctta agaaattgga cgacaaattc  660
aatgagcaag cacaaaattc ccaagatctt gctactaatg ttctggaaaa agactgtccc  720
attatggagc tgaatcctga aactttgcct tctacgtttt ctcaacttga caatttatat  780
tcttcttcaa ctatcgatct tcccttgcat ggagaattgt tctggacatg caaaagtcca  840
cttcaaagta atcagttgtg gtcccaaaat attcaagacc ttgggatatg caaagaactt  900
gtttgtcaag atgattttaa catccctgat gttgacttaa ctttccaaaa ctatgaggaa  960
ctatttggag gagatcaaga tccaattaga atactgcttg atgatcaaga tgtctcctgc  1020
tcttctttag agaaggataa gtcagttgac aagtcagtta ttgacaatcc aagtgcaatg  1080
gaggaatctt ctgcagctgc gtccattact atctcccaat ctgatcttga caacaaggat  1140
atgaatcctc tcagccagta ctgtccaaga agcatggatc ctgctcatgc aattcgacca  1200
tttgattcaa ctataccatt ctctgttctg agattcaatg aggaaagcag ttgcacaaac  1260
catgatgaca gtgccctttc tccctacagt gaagggaggg cttattcagg tagttaa     1317
```

```
SEQ ID NO: 526          moltype = AA  length = 172
FEATURE                 Location/Qualifiers
REGION                  1..172
                        note = GmBBX50 soybean B-box polypeptide
source                  1..172
                        mol_type = protein
                        organism = Glycine max
SEQUENCE: 526
MEKVCEFCTA LRPLVYCKAD AAYLCLSCDA KVHLANAVSG RHLRNLVCNS CGYHLAYVLC  60
LEHKMLICRD CDQKLHNISL PHKKRAIRSF MGCPSAKDFA ALWGVELNEI ENSASQDQFD  120
SVSCVSADLN VAQVSGKPGI QTEVPSMLSG AKLDGGGSTS QQGQILYSDQ KR          172
```

```
SEQ ID NO: 527          moltype = DNA  length = 1317
FEATURE                 Location/Qualifiers
misc_feature            1..1317
                        note = GmBBX51
source                  1..1317
                        mol_type = unassigned DNA
                        organism = Glycine max
SEQUENCE: 527
atggagaagg tttgtgaatt ctgcacagct ttgaggccac ttgtttactg taaggctgat  60
gcagcatatc tttgtctatc ctgtgattca aaggtgcatt tagcaaatgc agtgtctggt  120
cggcacctcc ggaactttgt gtgccactca tgcggatacc atcttgctta tgttctgtgt  180
ttggaacata aaatgttgat ctgtcgtgac tgtgatcaaa agttgcataa catttcttta  240
ccacataaga aacgagctat cagaagtttc atgggctgcc cttctgctaa agactttgca  300
gcactctggg ggtttgaatc gaatgagatt gaaaacagtg ccactcagga tcagtttggt  360
tcagtttctt gtgtttctgc agatttgaat gttgcacaag tttcaggaaa gcctggcatt  420
```

```
caaactggga tcccctcaat gccatctgga gccaaatttg atgggggagg atcaaccagt  480
caacaaggtc agatattgta cagtgatcaa gagcgacaaa ctattctgca gcagattatt  540
gatttaaaaa tgcttcaaca aaatgaggac attgattatc ttgcaaagat caataggcta  600
caagaaaaag atttatctcc ttcagtatat cacactctta agaaattgga cgacaaattc  660
aatgagcaag cacaaaagtc ccaggatctt gctactaatg ttctggaaaa agactgtccc  720
actgtggagc tgaatcctga aactttgcct tctacgtttt ctcaatttga caatttatat  780
tcttcttcaa ttatcgatct tcccttgcat ggagagttgt tctggacatg ccgaagtcca  840
cttcaaagta atcagttgtg gtcccaaaat attcaagacc ttgggatatg caaagaactt  900
gtttgtcaag acgattttaa catccctgat gttgacttaa ctttccaaaa ctttgaggaa  960
ctatttggag gagatcaaga ttcaattaga atactgcttg atgatcaaga tgtctcctgc  1020
tcttctttag agaaggataa gtcagttggc aagtcagata ttgacaatcc aagtgcaatg  1080
gaggaatctt ctgcagctgc gtctattact atctcccaat ctgatcttga caataaggat  1140
atgaatcctc tcagccagta ccgtccaaga agcatggatc ccgcccttgc aattcgacca  1200
tttgattcaa ccataccatt ctccgttttg agattcaatg aggaaagcag ttgcactagc  1260
catgatgaca gtgccctttc tccctacagt gaaaggaagg cttattcagg tagttaa     1317

SEQ ID NO: 528         moltype = AA  length = 438
FEATURE                Location/Qualifiers
REGION                 1..438
                       note = GmBBX51 soybean B-box polypeptide
source                 1..438
                       mol_type = protein
                       organism = Glycine max
SEQUENCE: 528
MEKVCEFCTA LRPLVYCKAD AAYLCLSCDS KVHLANAVSG RHLRNFVCHS CGYHLAYVLC  60
LEHKMLICRD CDQKLHNISL PHKKRAIRSF MGCPSAKDFA ALWGFESNEI ENSATQDQFG  120
SVSCVSADLN VAQVSGKPGI QTGIPSMPSG AKFDGGGSTS QQGQILYSDQ ERQTILQQII  180
DLKMLQQNED IDYLAKINRL QEKDLSPSVY HTLKKLDDKF NEQAQKSQDL ATNVLEKDCP  240
TVELNPETLP STFSQFDNLY SSSIIDLPLH GELFWTCRSP LQSNQLWSQN IQDLGICKEL  300
VCQDDFNIPD VDLTFQNFEE LFGGDQDSIR ILLDDQDVSC SSLEKDKSVG KSDIDNPSAM  360
EESSAAASIT ISQSDLDNKD MNPLSQYRPR SMDPALAIRP FDSTIPFSVL RFNEESSCTS  420
HDDSALSPYS ERKAYSGS                                                438

SEQ ID NO: 529         moltype = DNA  length = 726
FEATURE                Location/Qualifiers
misc_feature           1..726
                       note = GmBBX52
source                 1..726
                       mol_type = unassigned DNA
                       organism = Glycine max
SEQUENCE: 529
atgaagggta agacttgcga gctttgtgat caacaagctt ctctctattg tccctccgat  60
tccgcatttc tctgctccga ctgcgacgcc gccgtgcacg ccgccaactt tctcgtagct  120
cgtcacctcc gccgcctcct ctgctccaaa tgcaaccgtt tcgccggatt tcacatctcc  180
tccggcgcta tatcccgcca cctctcgtcc acctgcagct cttgctcccc ggagaatcct  240
tccgctgact actccgattc tctcccttcc tcttctacct gcgtctccag ttccgagtct  300
tgctccacga agcagattaa ggtggagaag aagaggagtt ggtcgggttc ctccgtgacc  360
gacgacgcat ctccggcggc gaagaagcgg cagaggagtg gaggatcgga ggaggtgttt  420
gagaaatgga gcagagagat agggttaggg ttagggttag gggtaaacgg aaatcgcgtg  480
gcgtcgaacg ctctgagtgt gtgcctggga aagtggaggt ggcttccgtt cagggtggct  540
gctgcgacgt cgttttggtt ggggctgaga ttttgtgggg acagagggct ggcctcgtgt  600
cagaatctgg cgaggttgga ggcaatatcc ggagtgccag ttaagctgat tctggccgca  660
catggcgacc tggcacgtgt cttcacgcac cgccgcgaat tgcaggaagg atggggcgag  720
tcctag                                                             726

SEQ ID NO: 530         moltype = AA  length = 241
FEATURE                Location/Qualifiers
REGION                 1..241
                       note = GmBBX52 soybean B-box polypeptide
source                 1..241
                       mol_type = protein
                       organism = Glycine max
SEQUENCE: 530
MKGKTCELCD QQASLYCPSD SAFLCSDCDA AVHAANFLVA RHLRRLLCSK CNRFAGFHIS  60
SGAISRHLSS TCSSCSPENP SADYSDSLPS SSTCVSSSES CSTKQIKVEK KRSWSGSSVT  120
DDASPAAKKR QRSGGSEEVF EKWSREIGLG LGLGVNGNRV ASNALSVCLG KWRWLPFRVA  180
AATSFWLGLR FCGDRGLASC QNLARLEAIS GVPVKLILAA HGDLARVFTH RRELQEGWGE  240
S                                                                  241

SEQ ID NO: 531         moltype = DNA  length = 732
FEATURE                Location/Qualifiers
misc_feature           1..732
                       note = GmBBX53
source                 1..732
                       mol_type = unassigned DNA
                       organism = Glycine max
SEQUENCE: 531
atgaagccca agacttgcga gctttgtcat caactagctt ctctctattg tccctccgat  60
tccgcatttc tctgcttcca ctgcgacgcc gccgtccacg ccgccaactt cctcgtagct  120
```

```
cgccacctcc gccgcctcct ctgctccaaa tgcaaccgtt tcgccgcaat tcacatctcc  180
ggtgctatat cccgccacct ctcctccacc tgcacctctt gctccctgga gattccttcc  240
gccgactccg attctctccc ttcctcttct acctgcgtct ccagttccga gtcttgctct  300
acgaatcaga ttaaggcgga gaagaagagg aggaggagga ggaggagttt ctcgagttcc  360
tccgtgaccg acgacgcatc tccggcggcg aagaagcggc ggagaaatgg cggatcggtg  420
gcggaggtgt ttgagaaatg gagcagagag atagggttag ggttaggggt gaacggaaat  480
cgcgtggcgt cgaacgctct gagtgtgtgc ctcggaaagt ggaggtcgct tccgttcagg  540
gtggctgctg cgacgtcgtt ttggttgggg ctgagatttt gtggggacag aggcctcgcc  600
acgtgtcaga atctggcgag gttggaggca atatctggag tgccagcaaa gctgattctg  660
ggcgcacatg ccaacctcgc acgtgtcttc acgcaccgcc gcgaattgca ggaaggatgg  720
ggcgagtcct ag                                                      732

SEQ ID NO: 532         moltype = AA  length = 243
FEATURE                Location/Qualifiers
REGION                 1..243
                       note = GmBBX53 soybean B-box polypeptide
source                 1..243
                       mol_type = protein
                       organism = Glycine max
SEQUENCE: 532
MKPKTCELCH QLASLYCPSD SAFLCFHCDA AVHAANFLVA RHLRRLLCSK CNRFAAIHIS  60
GAISRHLSST CTSCSLEIPS ADSDSLPSSS TCVSSSESCS TNQIKAEKKR RRRRRSFSSS  120
SVTDDASPAA KKRRRNGGSV AEVFEKWSRE IGLGLGVNGN RVASNALSVC LGKWRSLPFR  180
VAAATSFWLG LRFCGDRGLA TCQNLARLEA ISGVPAKLIL GAHANLARVF THRRELQEGW  240
GES                                                                243

SEQ ID NO: 533         moltype = DNA  length = 375
FEATURE                Location/Qualifiers
misc_feature           1..375
                       note = GmBBX54
source                 1..375
                       mol_type = unassigned DNA
                       organism = Glycine max
SEQUENCE: 533
atgtgcaaag gtgcagaagg agaaaagcaa catggtttct gcagcagctt tctacataaa  60
gagagtgcaa ccagaagtgc tatatgttgt gagctatgtg ggttacaggc ttcattgtat  120
tgccaagctg atgatgccta cttgtgtaaa aaatgcgata aacgggttca tgaagctaat  180
tttttggccc ttaggcacat taggtgcttt ctgtgcaaca catgtcagaa ccttacgcga  240
agatatctca ttggagcatc actagaggtg gttcttccgg ccaatataaa ctggaccatt  300
agaaatctcc ttaacaacag aggaatctac agaaagtgtt caagaatgca taacagccct  360
tccctctttt tataa                                                   375

SEQ ID NO: 534         moltype = AA  length = 93
FEATURE                Location/Qualifiers
REGION                 1..93
                       note = GmBBX54 soybean B-box polypeptide
source                 1..93
                       mol_type = protein
                       organism = Glycine max
SEQUENCE: 534
MCKGAEGEKQ HGFCSSFLHK ESATRSAICC ELCGLQASLY CQADDAYLCK KCDKRVHEAN  60
FLALRHIRCF LCNTCQNLTR RYLIGASLEV VLP                               93

SEQ ID NO: 535         moltype = DNA  length = 375
FEATURE                Location/Qualifiers
misc_feature           1..375
                       note = GmBBX55
source                 1..375
                       mol_type = unassigned DNA
                       organism = Glycine max
SEQUENCE: 535
atgtgcaaag gtgcagaagg agaaaagcaa catggtttct gcagcagcta tctacataaa  60
gaatgtgcaa ccagaagtgc tacatgttgt gagctatgtg ggttacaggc ttcattgtat  120
tgtcaagctg atgatgcata cttgtgtaga aaatgtgata aaagggttca tgaagctaat  180
tttttggccc ttaggcacat taggtgcttt ctgtgcaaca catgtcaaaa ccttacgcga  240
agatatctca ttggagcatc aatagaggtg gttcttccag ccaacattaa ctggaccatt  300
ggaaatctcc ctagcaacag aggaatccac agaaagtgct caagaatgca taacaacctt  360
tccctcttgt tataa                                                   375

SEQ ID NO: 536         moltype = AA  length = 92
FEATURE                Location/Qualifiers
REGION                 1..92
                       note = GmBBX55 soybean B-box polypeptide
source                 1..92
                       mol_type = protein
                       organism = Glycine max
SEQUENCE: 536
MCKGAEGEKQ HGFCSSYLHK ECATRSATCC ELCGLQASLY CQADDAYLCR KCDKRVHEAN  60
FLALRHIRCF LCNTCQNLTR RYLIGASIEV VL                                92
```

```
SEQ ID NO: 537          moltype = DNA  length = 651
FEATURE                 Location/Qualifiers
misc_feature            1..651
                        note = GmBBX56
source                  1..651
                        mol_type = unassigned DNA
                        organism = Glycine max
SEQUENCE: 537
atggaggaat catcaacaac atgcgtgttg tgcgagaaga gggcaatgat gctctgcgac  60
tcggaccagg ctaagctatg ctgggaatgc gacgagaaag tccacagcgc caatttcttg  120
gtcgcgaaac attctagggt tcttttatgt cgtttgtgtc actccccgac tccgtggaag  180
gcttcgggga tgaaactcac gcccactgtg tcgttttgta accgctgcgt tgcggaacgg  240
aacgcgaggt ggaaccgatt ggtgaataat gaaaatgaac atcaacaaca gcaacaacaa  300
caacaacaga gtgattttgt ggtggatgat ggtagggaat atggttctga tcatgttttt  360
gatgatgacg atggtgatta tagtgatgat agtggtgaag aagaagaaga ggacgaggat  420
gatgaagagg agaatgagaa tcaagtggtt ccaatgtctt ctggttctgc cacgtcacca  480
cctaaggttg cctgtttagc gttgaagcga ttgagaaaca actctttttc tgtcgattct  540
tcacatgatg agacagcgtg ctcttcatct gagatgctta gttctacatt gcctagtggt  600
gatgaatcaa cctctttgag tagtgtatta aagaggcatc gggttgatta g          651

SEQ ID NO: 538          moltype = AA  length = 216
FEATURE                 Location/Qualifiers
REGION                  1..216
                        note = GmBBX56 soybean B-box polypeptide
source                  1..216
                        mol_type = protein
                        organism = Glycine max
SEQUENCE: 538
MEESSTTCVL CEKRAMMLCD SDQAKLCWEC DEKVHSANFL VAKHSRVLLC RLCHSPTPWK  60
ASGMKLTPTV SFCNRCVAER NARWNRLVNN ENEHQQQQQQ QQQSDFVVDD GREYGSDHVF  120
DDDDGDYSDD SGEEEEEDED DEEENENQVV PMSSGSATSP PKVACLALKR LRNNSFSVDS  180
SHDETACSSS EMLSSTLPSG DESTSLSSVL KRHRVD                            216

SEQ ID NO: 539          moltype = DNA  length = 465
FEATURE                 Location/Qualifiers
misc_feature            1..465
                        note = GmBBX57
source                  1..465
                        mol_type = unassigned DNA
                        organism = Glycine max
SEQUENCE: 539
atgaggaagt gtgagctctg taacagtccc gcgaagttgt tctgcgaatc agatcaagcc  60
agcctctgtt ggaaatgcga tgctaaggtt cacagtgcaa acttcctcgt caccaaacat  120
cccaggattc ttctctgcca tgtttgtcaa tcactaacag cgtggcacgg cacaggaccc  180
aagtttgtac ccaccatgtc agtttgcaac acttgtgtca acaacaatag tactgagacc  240
tgcagccaac agaatcatga agacgatgat gatgatggta cgggagagga tcatgcagaa  300
aacgacgatg gtggtgtggc tgaagatgat gatgatgatg atgatgaaga aaatcaagtg  360
gttccatgga catctacacc accaccccca gcttccactt cttcaaatag tgttacaact  420
agttctacca ggttctctga tgttgaagaa ggtggctccg attaa                  465

SEQ ID NO: 540          moltype = AA  length = 88
FEATURE                 Location/Qualifiers
REGION                  1..88
                        note = GmBBX57 soybean B-box polypeptide
source                  1..88
                        mol_type = protein
                        organism = Glycine max
SEQUENCE: 540
MRKCELCNSP AKLFCESDQA SLCWKCDAKV HSANFLVTKH PRILLCHVCQ SLTAWHGTGP  60
KFVPTMSVCN TCVNNNSTET CSQQNHED                                     88

SEQ ID NO: 541          moltype = DNA  length = 459
FEATURE                 Location/Qualifiers
misc_feature            1..459
                        note = GmBBX58
source                  1..459
                        mol_type = unassigned DNA
                        organism = Glycine max
SEQUENCE: 541
atgaggaagt gtgaactctg taatagtccc gcaaagttgt tctgtgaatc agatcaagcc  60
agcctctgtt gggaatgcga tgctaaggtt cacagtgcaa acttcctcgt caccaaacat  120
cccaggattc ttctctgcca tgtttgtcaa tcactaacgg cctggcacgg cacgggaccc  180
aagtttgtac ccaccatgtc cgtttgcaac acttgtgtca acaacaatag tgagacctgc  240
agccaacaga atcatgttga ggaccacgac gacaatcatg atgatggcac gggagaggat  300
catgtagaaa accatgatgg tggtgtgtct gaagatgatg aagaaaatca agttgttcca  360
tggacatcta caccaccacc cccagcttcc acttcttcaa atagtgttac aactagttct  420
accaggttct ctaatgttga agaaggtggc tccgattaa                         459
```

```
SEQ ID NO: 542          moltype = AA  length = 152
FEATURE                 Location/Qualifiers
REGION                  1..152
                        note = GmBBX58 soybean B-box polypeptide
source                  1..152
                        mol_type = protein
                        organism = Glycine max
SEQUENCE: 542
MRKCELCNSP AKLFCESDQA SLCWECDAKV HSANFLVTKH PRILLCHVCQ SLTAWHGTGP  60
KFVPTMSVCN TCVNNNSETC SQQNHVEDHD DNHDDGTGED HVENHDGGVS EDDEENQVVP  120
WTSTPPPPAS TSSNSVTTSS TRFSNVEEGG SD                              152

SEQ ID NO: 543          moltype = DNA  length = 534
FEATURE                 Location/Qualifiers
misc_feature            1..534
                        note = GmBBX59
source                  1..534
                        mol_type = unassigned DNA
                        organism = Glycine max
SEQUENCE: 543
atgaacaagt gcgaactgtg caaagttccg gcgaggatct tctgcgagtc ggaccaggcg  60
agcttatgct gggactgcga cgctaaggtt cacagcgcca acttcttggt cgcgagacac  120
gcgcgaacct tactctgccg cacgtgccgc tctcccacgc cgtggaaggc ctccggcgcc  180
tcactcgcca gcgccgtctc cgtctgcgac cgctgcgccg cctccgaaga accggaagag  240
agtgaagccg gcaatgacga cgaaccagac acggaggacg acgacaacga cgacgaggac  300
ggcgacaatc aggtcgtgcc gtggtcctcc tccccgccgc cgcctccgcc gtcgagctcc  360
tccggcagcg aatggtcgga gtgcaaaaac gacgacgctt ctatttccgc ctcggaacag  420
gaaacgacaa catgctcgtt gaaacgacag cgcgaggacg atgatgatgc ttcttccgat  480
cgtgatccca gggtgttgag aagggttggg cgtctcaacg gaggttgcgt gtga        534

SEQ ID NO: 544          moltype = AA  length = 177
FEATURE                 Location/Qualifiers
REGION                  1..177
                        note = GmBBX59 soybean B-box polypeptide
source                  1..177
                        mol_type = protein
                        organism = Glycine max
SEQUENCE: 544
MNKCELCKVP ARIFCESDQA SLCWDCDAKV HSANFLVARH ARTLLCRTCR SPTPWKASGA  60
SLASAVSVCD RCAASEEPEE SEAGNDDEPD TEDDDNDDED GDNQVVPWSS SPPPPPPSSS  120
SGSEWSECKN DDASISASEQ ETTTCSLKRQ REDDDDASSD RDPRVLRRVG RLNGGCV     177

SEQ ID NO: 545          moltype = DNA  length = 522
FEATURE                 Location/Qualifiers
misc_feature            1..522
                        note = GmBBX60
source                  1..522
                        mol_type = unassigned DNA
                        organism = Glycine max
SEQUENCE: 545
atgaagaagt gcgaactgtg taaagttccg gcgaggatct tctgcgagtc ggaccaggct  60
agcttatgct gggactgcga cgctaaggtt cacagcgcca acttcttggt cgcgaggcac  120
gtgcgaaccc tactctgccg cacgtgtcgt tctcccacgc cctggaaggc ctccggcgcc  180
tcactcgccc acgccgcctc cgtctgcgac cgctgcgccg ccgcggaaga gacggaagag  240
agcgaagccg gcaatgacga cgaaccagac accgaggacg acgacgatgt cgacaaccag  300
gtcgtgccgt ggtcctccac gccgccgccg ccgccgccgt cgagctcctc cggcagcgaa  360
tgctcggagt gcaaaaacaa cgttgcttct ttttccgcct cggaacagga aacgacaaca  420
tcctcgttga aacgacagcg cgaggacgac gacgatgctt cttccgatcc tgatcccagg  480
gtgttgagaa gggttgggcg tctcaacgga ggttgcgtgt ga                    522

SEQ ID NO: 546          moltype = AA  length = 89
FEATURE                 Location/Qualifiers
REGION                  1..89
                        note = GmBBX60 soybean B-box polypeptide
source                  1..89
                        mol_type = protein
                        organism = Glycine max
SEQUENCE: 546
MKKCELCKVP ARIFCESDQA SLCWDCDAKV HSANFLVARH VRTLLCRTCR SPTPWKASGA  60
SLAHAASVCD RCAAAEETEE SEAGNDDEP                                   89

SEQ ID NO: 547          moltype = DNA  length = 666
FEATURE                 Location/Qualifiers
misc_feature            1..666
                        note = GmBBX61
source                  1..666
                        mol_type = unassigned DNA
                        organism = Glycine max
SEQUENCE: 547
```

-continued

```
atgaagaact gcgagctatg caagcttcca gctaggacct tctgcgagtc ggaccaggct  60
agcttatgct gggactgcga cgccaaggtc cacggagcga acttcctcgt cgcgagacac  120
acgcgcacgc tcctctgcca cgcgtgccag tcactcacgc cgtggaaggc ctccggctct  180
gccctcggca acaccgtctc gctgtgccag agttgcgccg gcggaaccac cgaacagggc  240
ccagagagcc aaggagggaa tgacgacgac gacatagaca ccgacgatga ggatgactac  300
gatgacgatg gtgagagcga ggagaacgag gttgcagccg acgaggagga cggagacaac  360
caggttgtcc cttggtcctc cgagccgccg ccaccgtccc caagctcttc cagcagcgaa  420
gagtcgatta gccggtgcaa caacgtggac gaggtttcga ccacattgaa acgacgtcgc  480
gagaacgacg attttcaggg ttcgaattcg aataattgga aatgtgaacg gagcgaagtg  540
gacagaggat gttggttggc tcggttgcgg cggagaaccg ccgatgatgt ggcggttgag  600
cgacggaggg ctagagcggc gtttccgtac ggttgttgtg atgatagagc atctgaagac  660
gtttga                                                             666

SEQ ID NO: 548         moltype = AA  length = 221
FEATURE                Location/Qualifiers
REGION                 1..221
                       note = GmBBX61 soybean B-box polypeptide
source                 1..221
                       mol_type = protein
                       organism = Glycine max
SEQUENCE: 548
MKNCELCKLP ARTFCESDQA SLCWDCDAKV HGANFLVARH TRTLLCHACQ SLTPWKASGS  60
ALGNTVSLCQ SCAGGTTEQG PESQGGNDDD DIDTDDEDDY DDDGESEENE VAADEEDGDN  120
QVVPWSSEPP PPSPSSSSSE ESISRCNNVD EVSTTLKRRR ENDDFQGSNS NNWKCERSEV  180
DRGCWLARLR RRTADDVAVE RRRARAAFPY GCCDDRASED V                      221

SEQ ID NO: 549         moltype = DNA  length = 666
FEATURE                Location/Qualifiers
misc_feature           1..666
                       note = GmBBX62
source                 1..666
                       mol_type = unassigned DNA
                       organism = Glycine max
SEQUENCE: 549
atgaagaact gcgagttgtg caagcttccg gctcggactt tctgcgagtc ggaccaggct  60
agcttatgct gggactgcga cgccaaggtt catggagcca acttcctcgt ggaaagacac  120
acgcgcacgc tcctctgcca cgcgtgccag tcgcccacgc cgtggaaggc ctccggcgcc  180
gccctcggaa acaccgtctc gctgtgcgag agatgcgccg gcggaaccac cgaacaaggt  240
caagagagcc aaggaggcaa tgacgacgac atagacaccg acatagacac cgacgatgag  300
gatgactacg atgagagcga ggacgaggtt gccgccgacg aggaggacgg agacaaccag  360
gttgtccctt ggtcctccga gccgccgcca ccagccccga gctcttccag cagcgaagaa  420
tcggttagcc ggtgcaacaa cgtggacgag gtttcgacca cattgaaacg ccgtcgccag  480
gaggacaatg attttcaggg ttggaattcg aataattggg gatgtgaacg gagcgaagtg  540
gagagaggag gttggttggt tcggttgcgg cggagaaccg ccgatgatgt ggcggttgag  600
caacggagtg ctagagcggc gtctccagac ggttgctgtg gtgatagagc atctgaagac  660
gtttga                                                             666

SEQ ID NO: 550         moltype = AA  length = 88
FEATURE                Location/Qualifiers
REGION                 1..88
                       note = GmBBX62 soybean B-box polypeptide
source                 1..88
                       mol_type = protein
                       organism = Glycine max
SEQUENCE: 550
MKNCELCKLP ARTFCESDQA SLCWDCDAKV HGANFLVERH TRTLLCHACQ SPTPWKASGA  60
ALGNTVSLCE RCAGGTTEQG QESQGGND                                     88
```

MANIPULATING PLANT SENSITIVITY TO LIGHT

CROSS REFERENCE TO RELATED APPLICATION

This application is a continuation of U.S. patent application Ser. No. 17/404,842, filed Aug. 17, 2021, which is a continuation of U.S. application Ser. No. 15/802,397, filed Nov. 2, 2017, (abandoned), which application is a divisional of U.S. application Ser. No. 14/118,491, filed Jun. 20, 2014 (abandoned), which application incorporates by reference in its entirety, and is a National Phase of International Patent Application No. PCT/US2012/038719, filed on May 18, 2012 (expired), which claims the benefit of priority to U.S. Provisional Application Ser. No. 61/488,592 (filed on May 20, 2011), each of which is incorporated by reference herein in its entirety.

JOINT RESEARCH AGREEMENT

The claimed invention, in the field of functional genomics and characterization of plant genes for the improvement of plants, was made by or on behalf of Mendel Biotechnology, Inc. and Monsanto Company as a result of activities undertaken within the scope of a joint research agreement in effect on or before the date the claimed invention was made.

RELEVANT FIELD

The present disclosure relates to plant genomics and plant improvement.

BACKGROUND

A plant's traits, including its biochemical, developmental, or phenotypic characteristics that enhance yield or tolerance to various abiotic stresses, may be controlled through a number of cellular processes. One important way to manipulate that control is through transcriptional regulators-proteins that influence the expression of a particular gene or sets of genes. Transgenic plants that comprise cells having altered levels of at least one selected transcriptional regulator, for example, possess advantageous or desirable traits. Strategies for manipulating traits by altering a plant cell's transcriptional regulator content can therefore result in plants and crops with commercially valuable properties.

SUMMARY

The present disclosure identifies B-box genes that modify plant sensitivity to light. Manipulating light signaling processes through altering the expression/activities of these genes in plants will lead to enhanced agronomic characteristics, for example, increased crop yield and improved stress tolerance. Altering the expression/activity of the B-box genes of the present disclosure may also provide plants with altered levels of ureides, altered levels of hexose sugars, altered sucrose phosphate synthase (SPS) activity, altered levels of starch, and delayed senescence.

The present disclosure pertains to polynucleotide and polypeptide sequences provided herein and in the Sequence Listing. The present disclosure further pertains to nucleic acid constructs containing and/or expressing or suppressing the polynucleotide sequences provided herein and in the Sequence Listing, individually or in combination, either driven by a ubiquitously expressed, a stress- or a chemical-inducible, a tissue specific, a development specific or a diurnally-regulated promoter.

The present disclosure also pertains to transgenic plants with increased or decreased activities of one or more of the proteins provided herein and in the Sequence Listing, or encoded by the nucleic acid constructs containing and/or expressing or suppressing the polynucleotide sequences provided herein and in the Sequence Listing. The transgenic plants may exhibit changes in light sensitivity, resulting in improved vigor, improved yield and growth, and improved ability to cope with abiotic stresses compared to the wild type or other control plants. This approach can be combined with other growth-promoting factors to expand the benefits.

The present disclosure also provides methods for the selection and production of transgenic plants transformed with the disclosed B-box sequences or closely-related orthologs or paralogs. The selection may be made by identification in a plant (that is, a mature plant, a seed, a plant part, a seedling, plant tissue, plant cell, etc.) of the presence of a transgene or heterologous sequence that was transformed into the transgenic plant, or by an altered trait in the transgenic plant such as improved yield or increased tolerance to an abiotic stress, such as low nitrogen conditions, cold, water deprivation or drought, etc.

The present disclosure is also directed to transgenic seed produced by any of the transgenic plants of the present disclosure, including transgenic plants ectopically expressing or suppressing SEQ ID NO: 2N, where N=1-117, or 218-275, or ectopically expressing a polypeptide that regulates transcription and the polypeptide comprises a conserved domain of any of SEQ ID NO: 235-427, and to methods for selecting and/or making the disclosed transgenic plants and transgenic seeds.

BRIEF DESCRIPTION OF THE SEQUENCE LISTING AND DRAWINGS

The Sequence Listing provides exemplary polynucleotide and polypeptide sequences. The traits associated with the use of the sequences are included in the Examples.

Incorporation of the Sequence Listing. The file named "MDBT021USD1C2_ST26.xml" contains a computer readable form of the Sequence Listing and was created on Sep. 1, 2023. The file is 900,669 bytes (measured in MS-Windows®), was filed contemporaneously along with this application by electronic submission and is incorporated herein by reference in its entirety.

FIG. 1 shows light-responsiveness of *Arabidopsis* seedlings transformed with 35S::AtBBX28 (G1481):cMYC (AtBBX28 is provided as SEQ ID NO: 2). Several independently transformed lines were grown in red light and mean hypocotyl lengths of 20-30 seedlings of each line are plotted with the empty-vector control (pMEN 65) and seedlings overexpressing BBX32 (G1988 OE; SEQ ID NO: 430). The dotted line marks the hypocotyl length of the control (pMEN 65; SEQ ID NO: 428).

Figure 2:
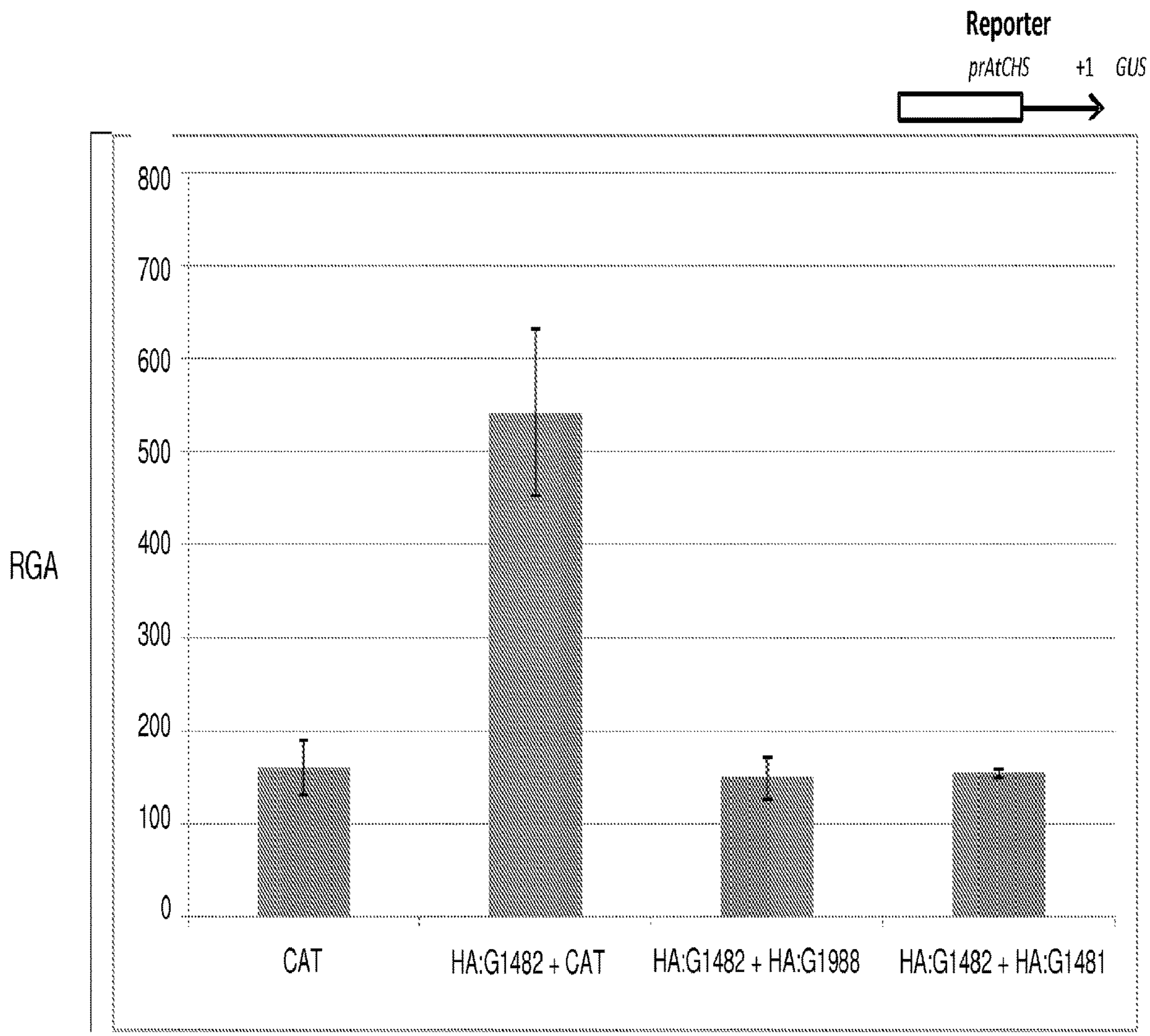

FIG. 2 shows AtBBX28 (G1481, SEQ ID NO: 2) suppressing transcriptional activity of AtBBX21 (G1482, SEQ ID NO: 56) in protoplast co-transfection assays. Protoplasts were co-transformed with prCHS::GUS reporter and either CAT (control) alone, or HA:AtBBX21 (G1482) with one CAT, HA: BBX32, or HA:AtBBX28 (G1481). Note that GUS is β-glucuronidase, CAT is chloramphenicol acetyltransferase, and HA is hemagglutinin protein-fusion tag (Niman et al., 1983).RGA=relative GUS activity.

Figure 3:
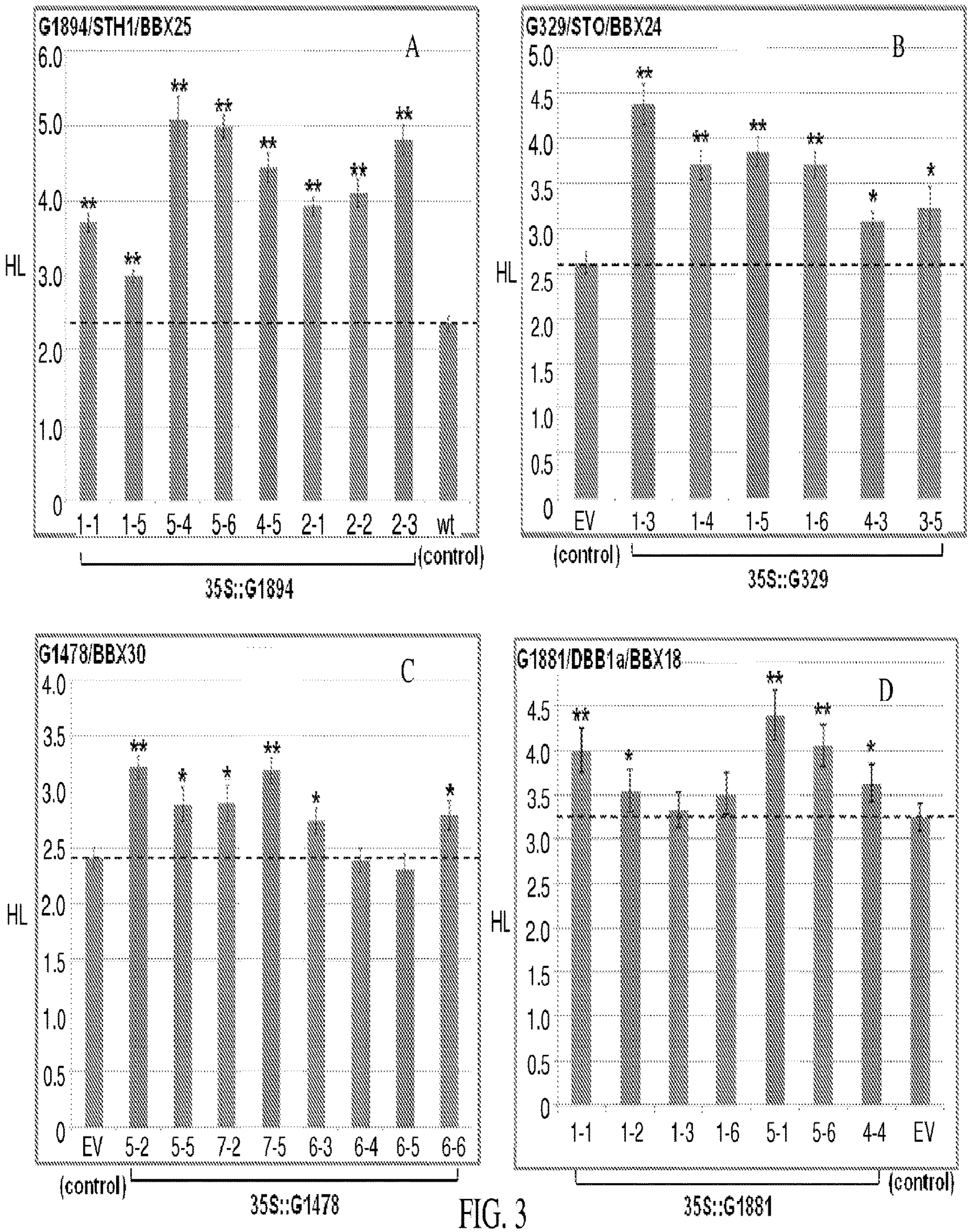
Figure 4:
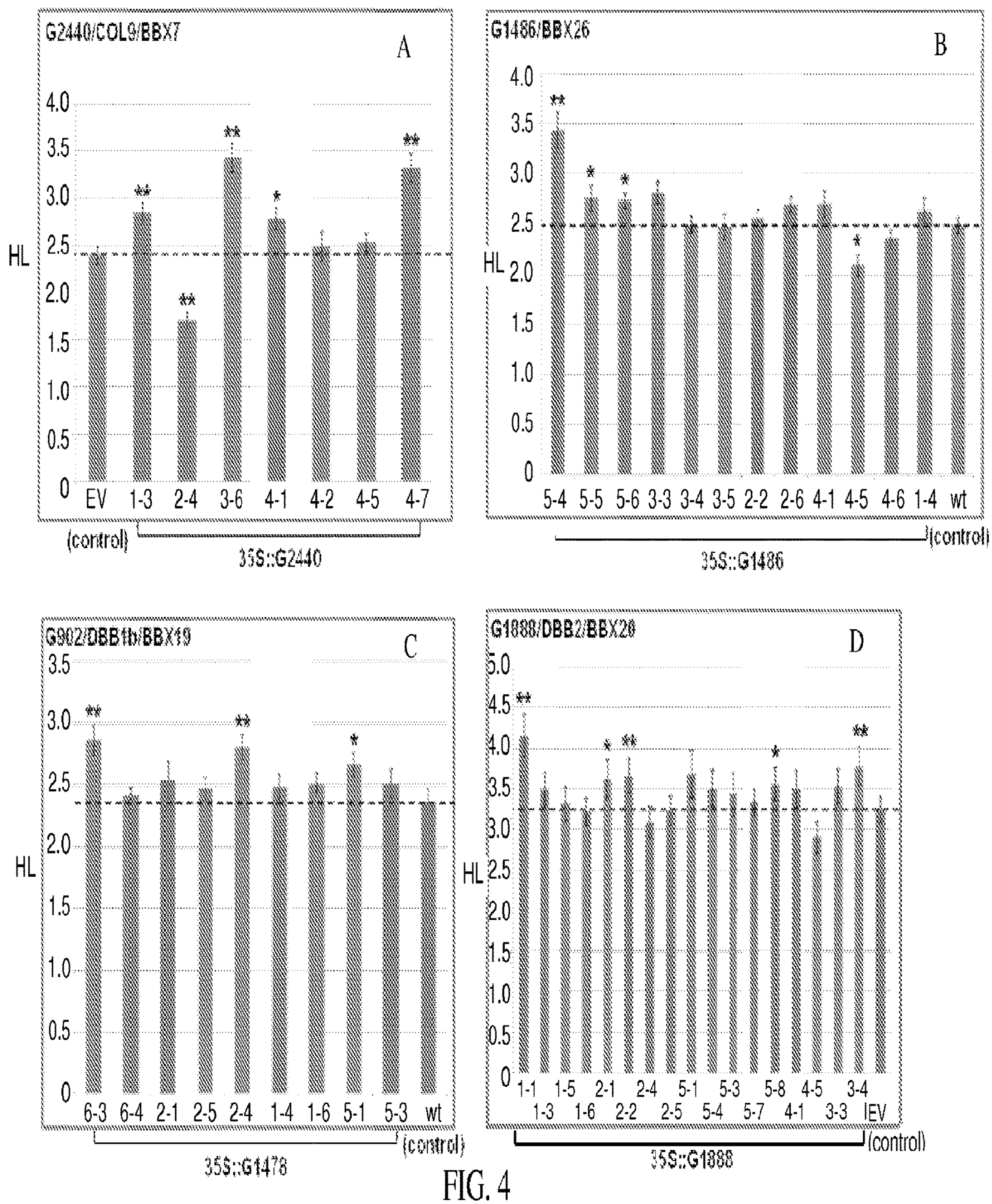

In FIGS. 3 and 4, the light-responsiveness of *Arabidopsis* seedlings of independently transformed lines is plotted as measures of hypocotyl length for the various plant lines. The dotted line marks the hypocotyl length of the control. Vertical axes are measured hypocotyl length (HL; in millimeters). An asterisk above the bars in FIGS. 3 and 4 indicates a p-value <0.05, and a double asterisk a p-value <0.01.

FIG. 3. *Arabidopsis* plant lines transformed with AtBBX25 (G1894, SEQ ID NO: 154; FIG. 3A), AtBBX24 (G329, SEQ ID NO: 152; FIG. 3B), AtBBX30 (G1478, SEQ ID NO: 40; FIG. 3C) and AtBBX18 (G1881, SEQ ID NO: 202; FIG. 3D) were grown in red light and mean hypocotyl lengths (HL) of 20-30 seedlings of each line are plotted with the control.

FIG. 4. *Arabidopsis* plant lines transformed with AtBBX7 (G2440, SEQ ID NO: 104; FIG. 4A), AtBBX26 (G1486, SEQ ID NO: 52; FIG. 4B), AtBBX19 (G902, SEQ ID NO: 200; FIG. 4C) and AtBBX20 (G1888, SEQ ID NO: 54; FIG. 4D) were grown in red light and mean hypocotyl lengths of 20-30 seedlings of each line are plotted with the control.

For FIGS. 5A-5E, FIGS. 6A-6D, FIG. 7, FIGS. 8A-8F, FIGS. 9A-9G and FIGS. 10A-10I, the SEQ ID NOs of the sequences appear in parentheses to the right of the sequence identifiers. In these Figures, an asterisk below any column indicates amino acid identity within the column. A colon indicates that the column is comprised of conservatively-related amino acid residues. A period indicates semi-conservatively-related amino acid residues.

FIGS. 5A-5E present an alignment of AtBBX25 (G1894, AT2G31380.1; SEQ ID NO: 154), AtBBX24 (G329, AT1G06040.1; SEQ ID NO: 152) and closely related sequences.

FIGS. 6A-6D represent an alignment of AtBBX19 (G902, AT4G38960.1; SEQ ID NO: 200), AtBBX18 (G1881, AT2G21320.1; SEQ ID NO: 202) and closely related sequences.

FIG. 7 shows an alignment of AtBBX30 (G1478, AT4G15248.1; SEQ ID NO: 40) and closely related sequences.

FIGS. 8A-8F present an alignment of AtBBX28 (G1481, AT4G27310.1; SEQ ID NO: 2) and AtBBX29 (G900, AT5G54470.1; SEQ ID NO: 4) and closely related sequences.

FIGS. 9A-9G displays an alignment of AtBBX20 (G1888, AT4G39070.1; SEQ ID NO: 54) and AtBBX21 (G1482, AT1G75540.1; SEQ ID NO: 56) and closely related sequences.

FIGS. 10A-10I show an alignment of AtBBX7 (G2440, AT3G07650.1, SEQ ID NO: 104), AtBBX8 (G1479, AT5G48250.1; SEQ ID NO: 106) and closely related sequences.

Figure 11:
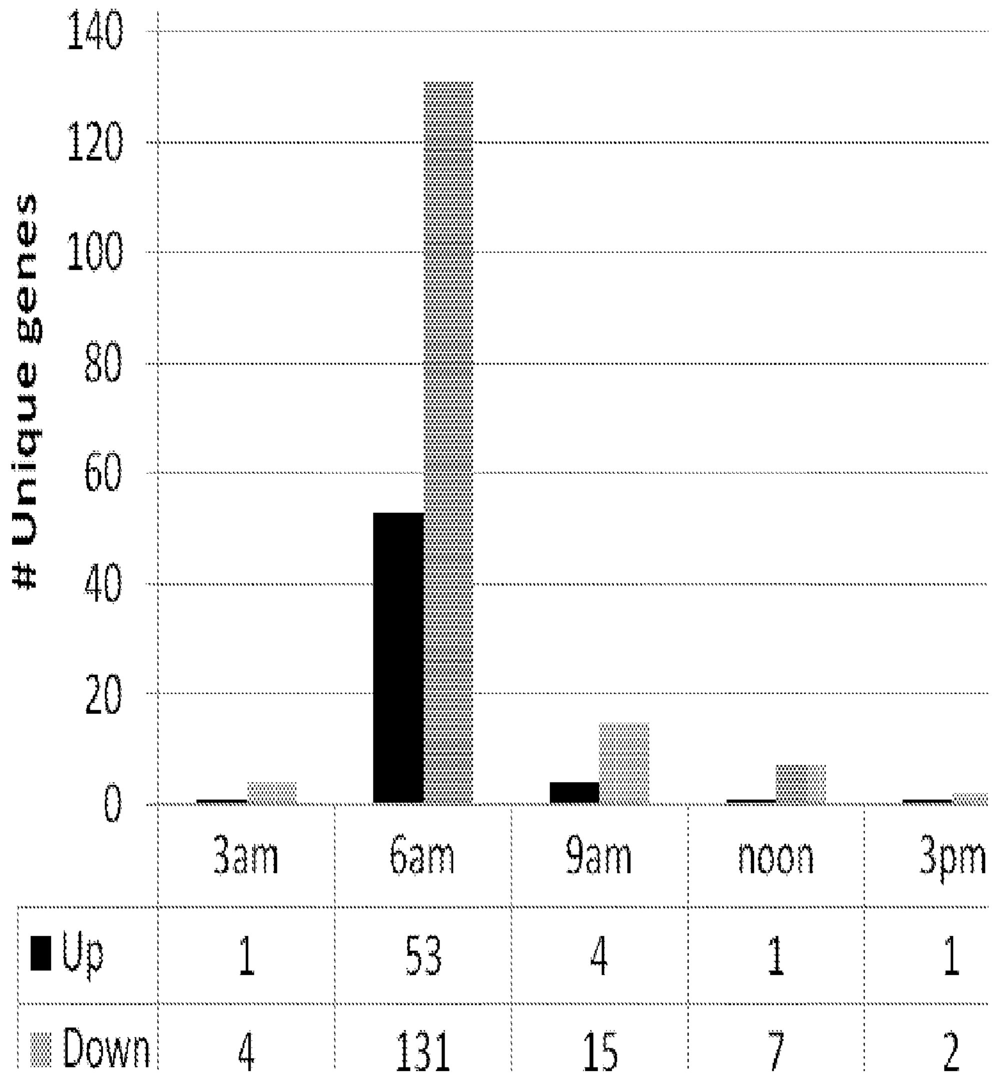
Figure 12A:
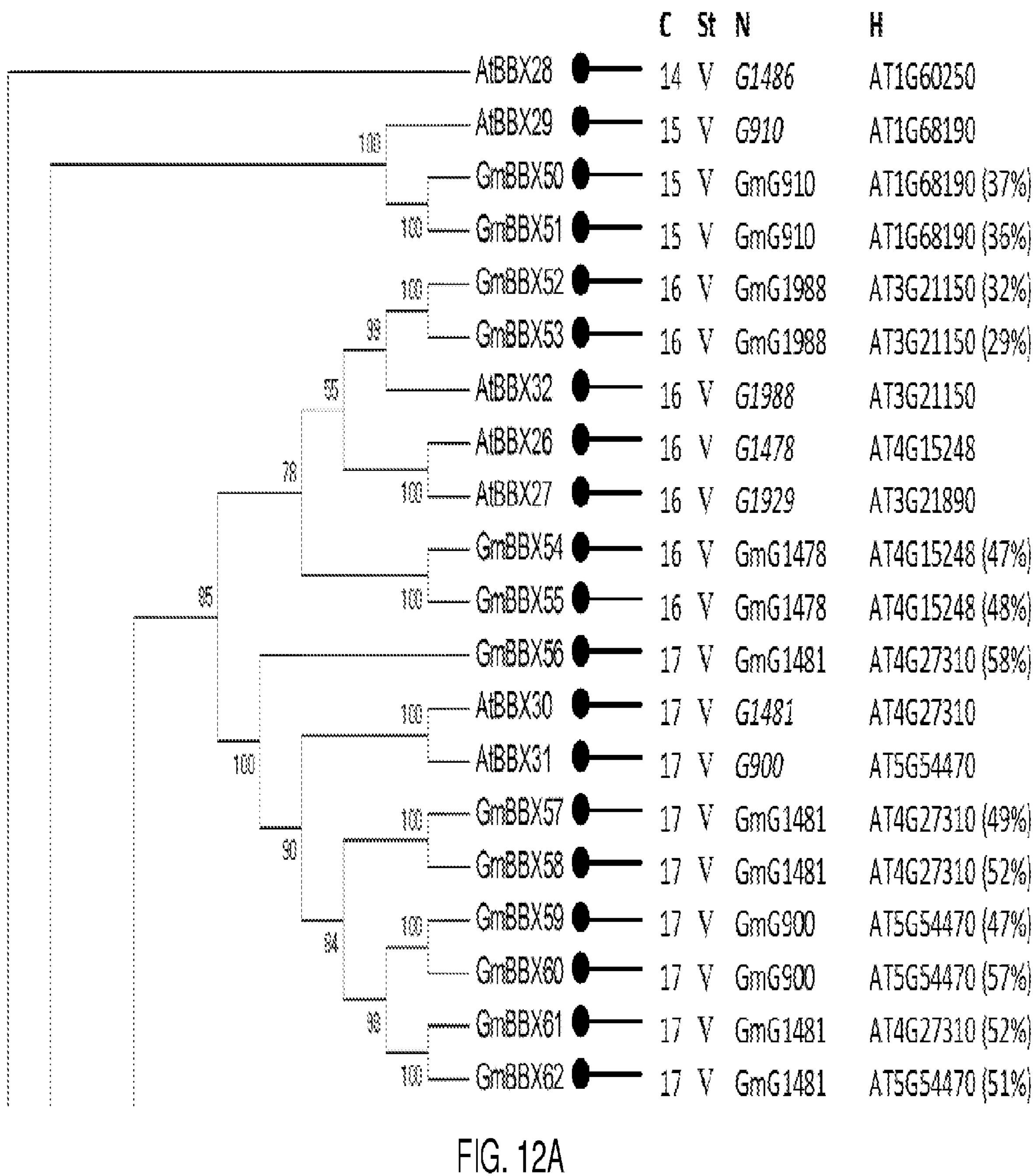
Figure 12B:
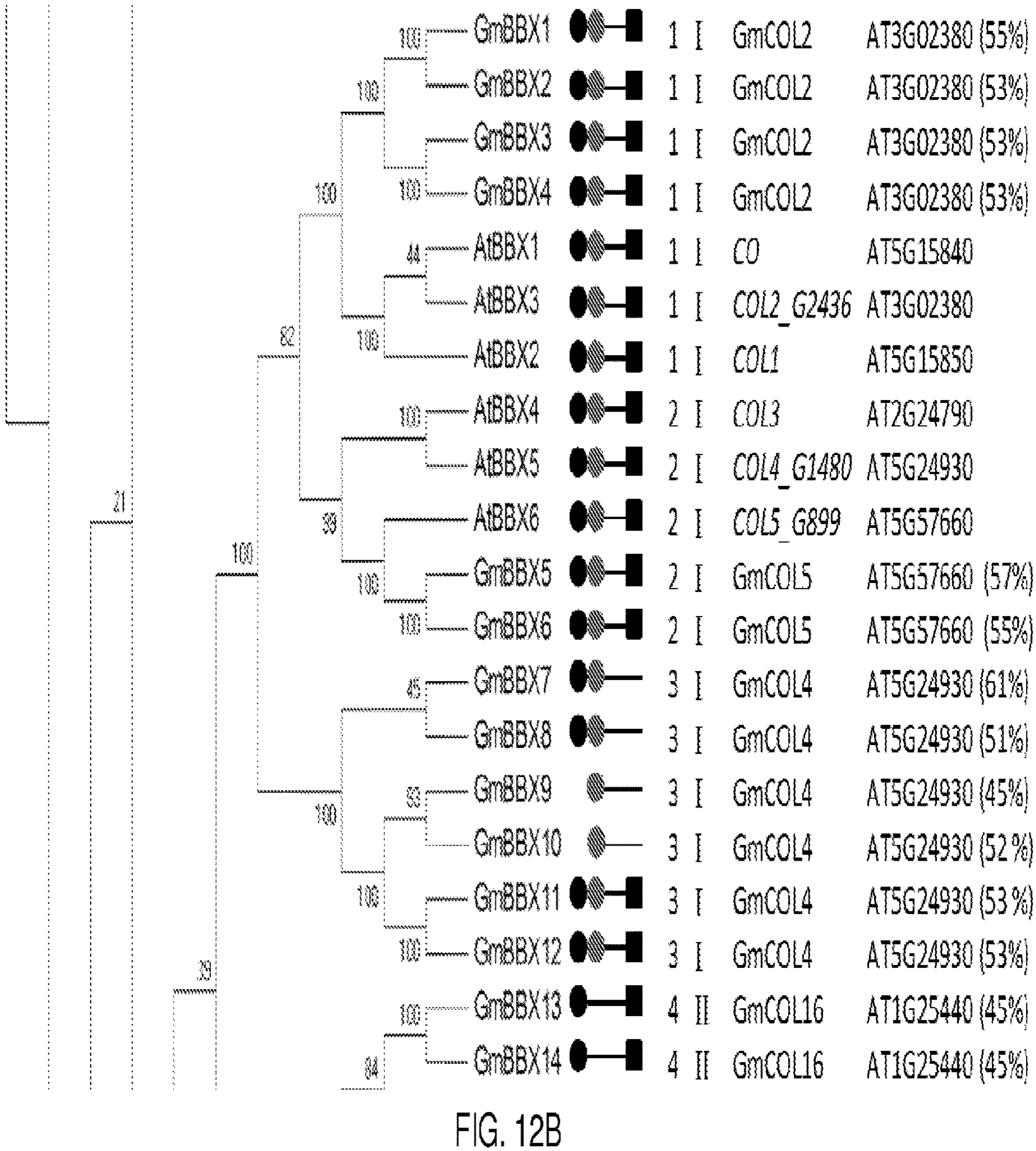
Figure 12C:
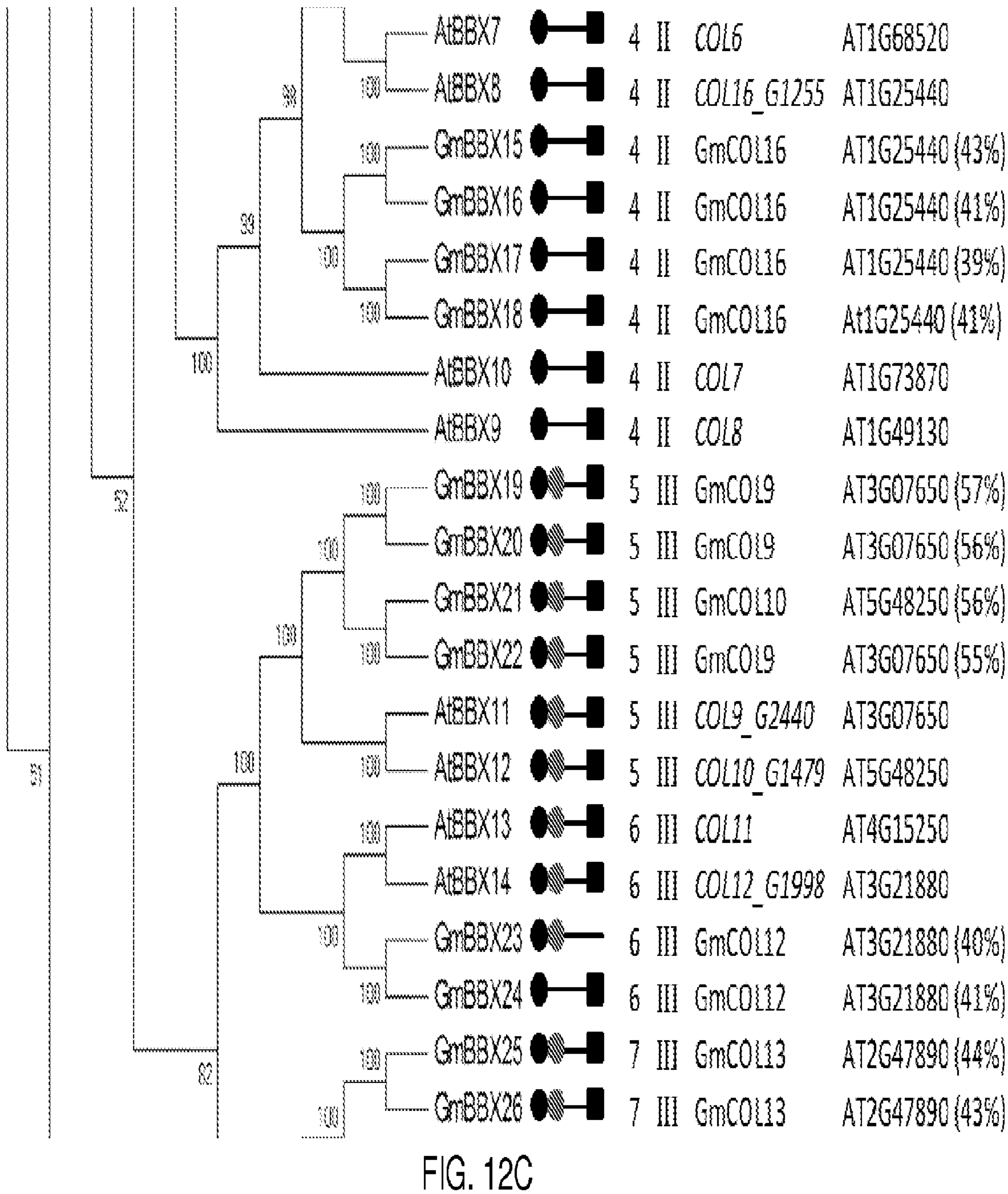
Figure 12D:
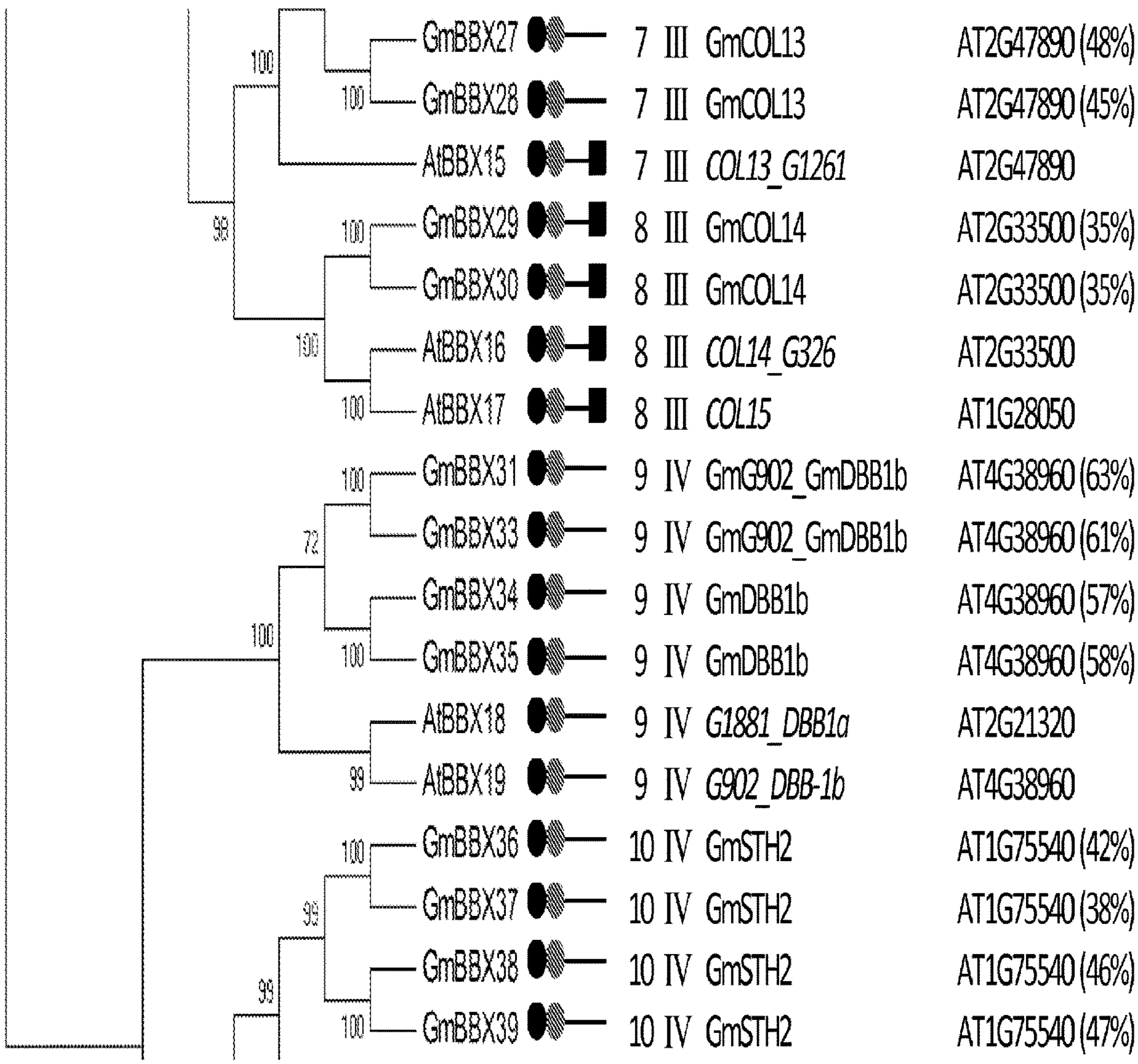
Figure 12E:
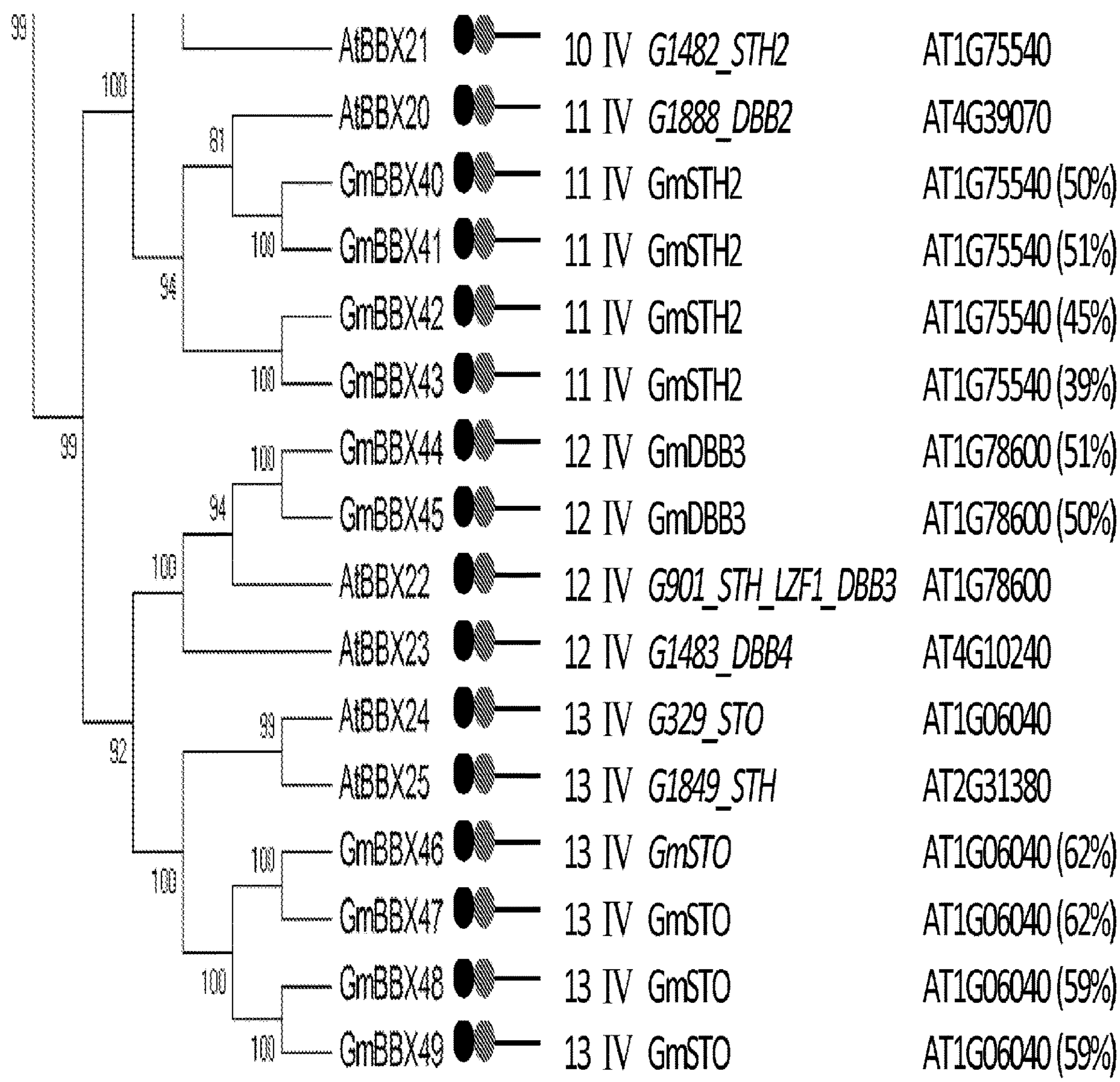
Figure 13A:
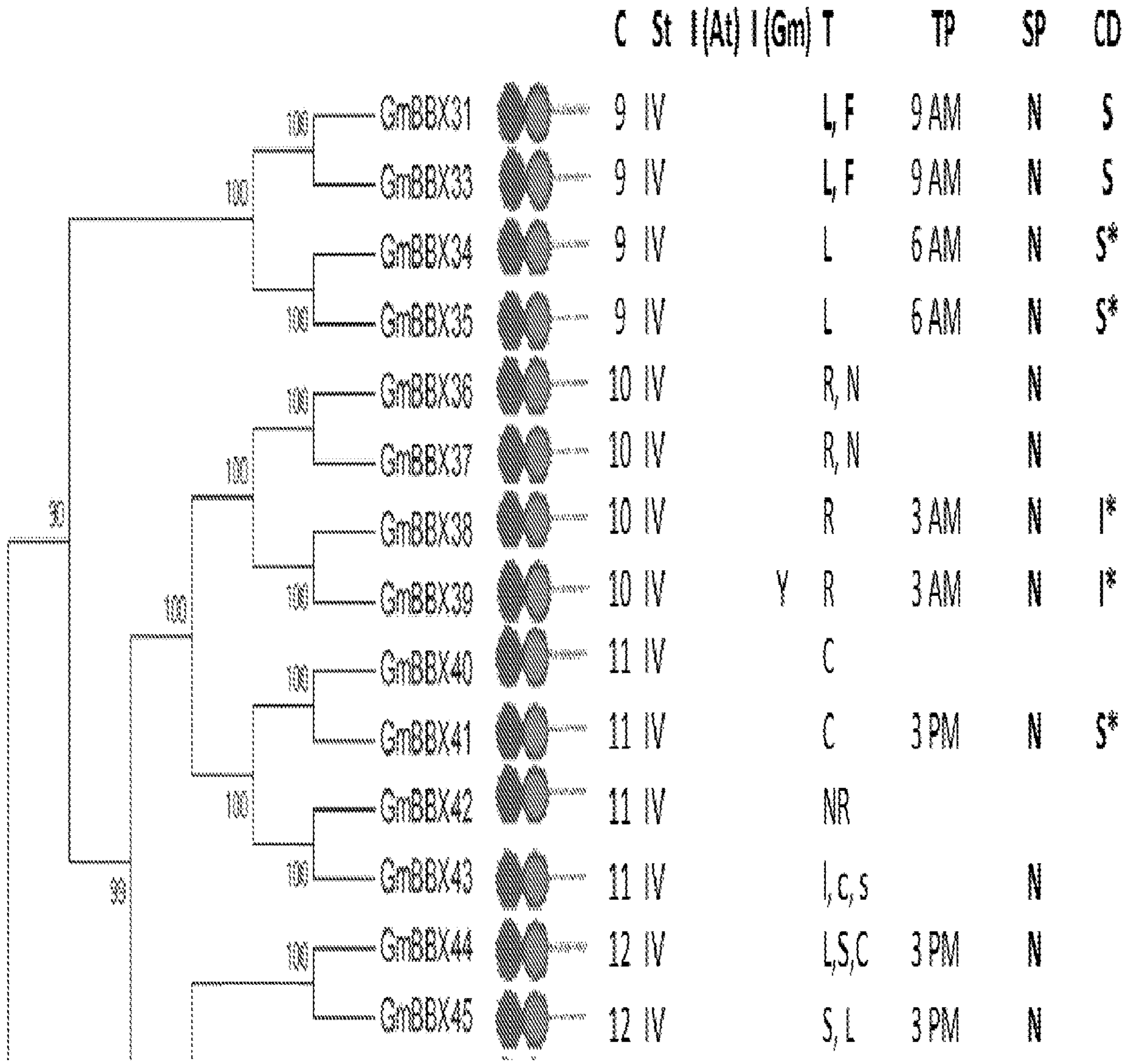
Figure 13B:
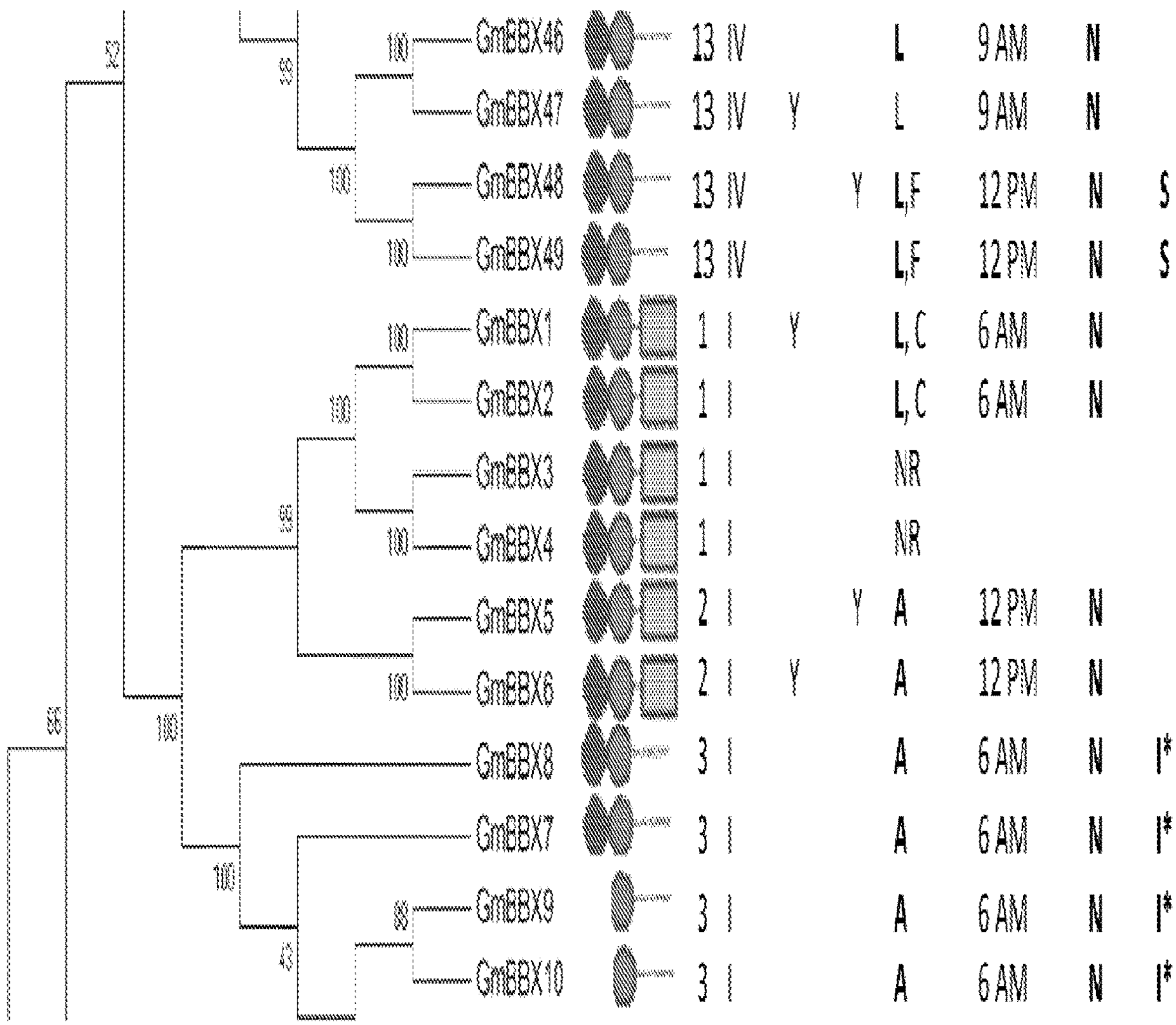
Figure 13C:
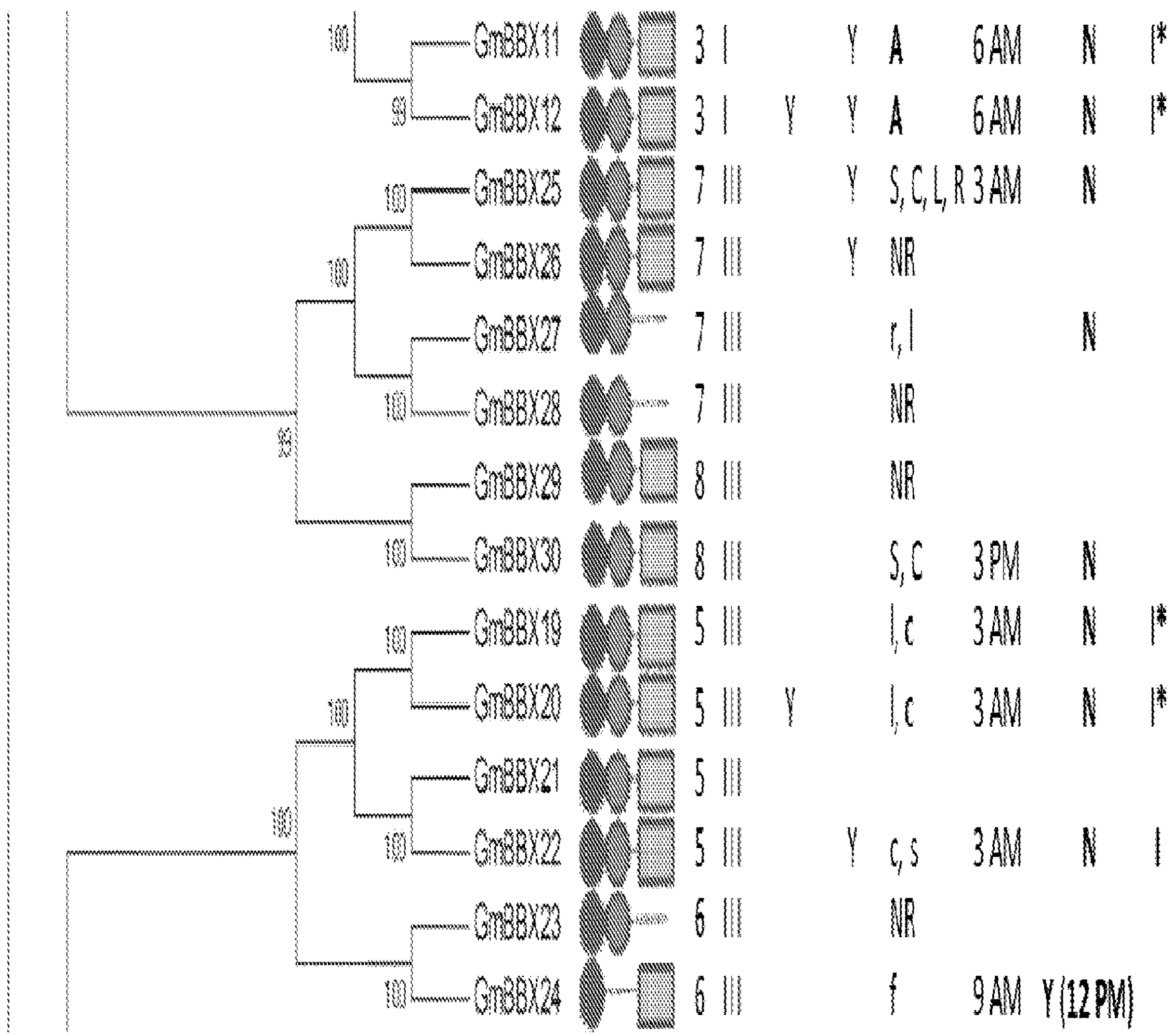
Figure 13D:
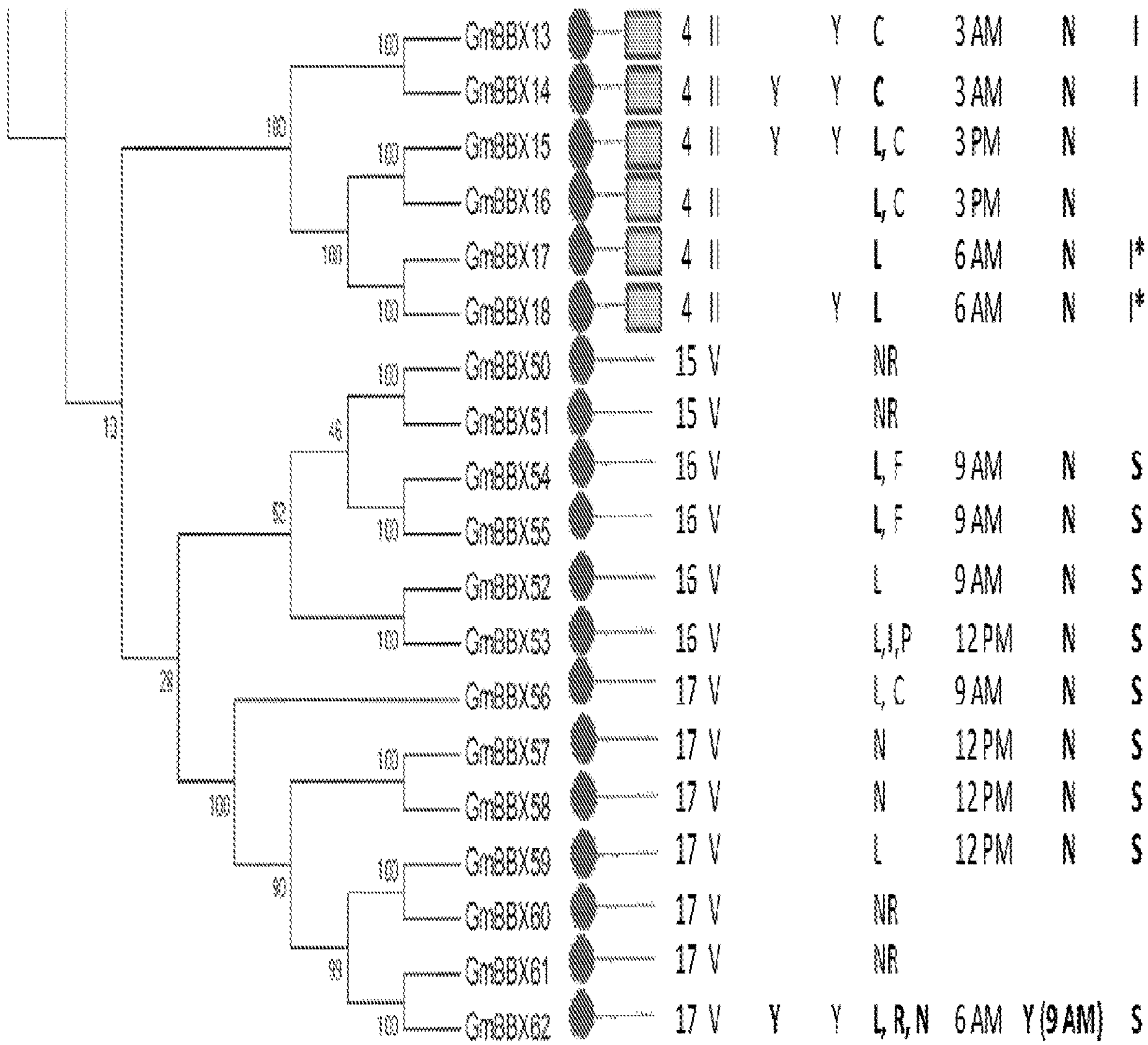

FIG. 11 shows microarray data from field grown soybean plants. Microarrays performed on tissues sampled throughout the day from the field demonstrated that 219 genes showed 2-fold or greater changes in abundance in transgenic events transformed with At. BBX32 relative to the control and that the majority of these changes occurred around dawn.

FIGS. 12A-12E shows a phylogenetic tree of the *Arabidopsis thaliana* and *Glycine max* B-box family, which contains 61 B-box sequences from soybean and 32 from *Arabidopsis*. Phylogenetic analysis of the B-box sequences shows that the sequences are clustered into structural groups (St) and clades (C).H refers to *Arabidopsis* homolog, N refers to other names.

FIGS. 13A-13D shows a phylogenetic tree for 61 B-box sequences from soybean. Phylogenetic analysis of the B-box sequences shows that these sequences are clustered into structural groups (St) and clades (C).A Y (yes) under I indicates a putative interactor of AtBBX32 (I (At)) or GmBBX52 (I (Gm)) based on Y2H analyses; T represents tissue of expression where L, 1=leaf; C, c=cotyledon; A, a=all tissues; S, s=seed; F, f=flowers; N, n=nodules; P, p=pod; R, r=root; NR=not represented in TxP, where bold upper-case letters represent high expression; upper-case letters represent moderate expression, and lower-case letters represent average expression. TP refers to time of peak expression. SP refers to whether or not a shift in peak expression was observed in transgenic soybean plants expressing BBX32 (Y for yes and N for no).CD refers to at least 1.5 fold(except where *~1.2-1.4 fold) change in expression at dawn in transgenic soybean plants expressing BBX32, where I=induced; S=suppressed. The first and second circles represent the first and the second B-box domain respectively; the rectangle represents the CCT domain.

Figure 14:
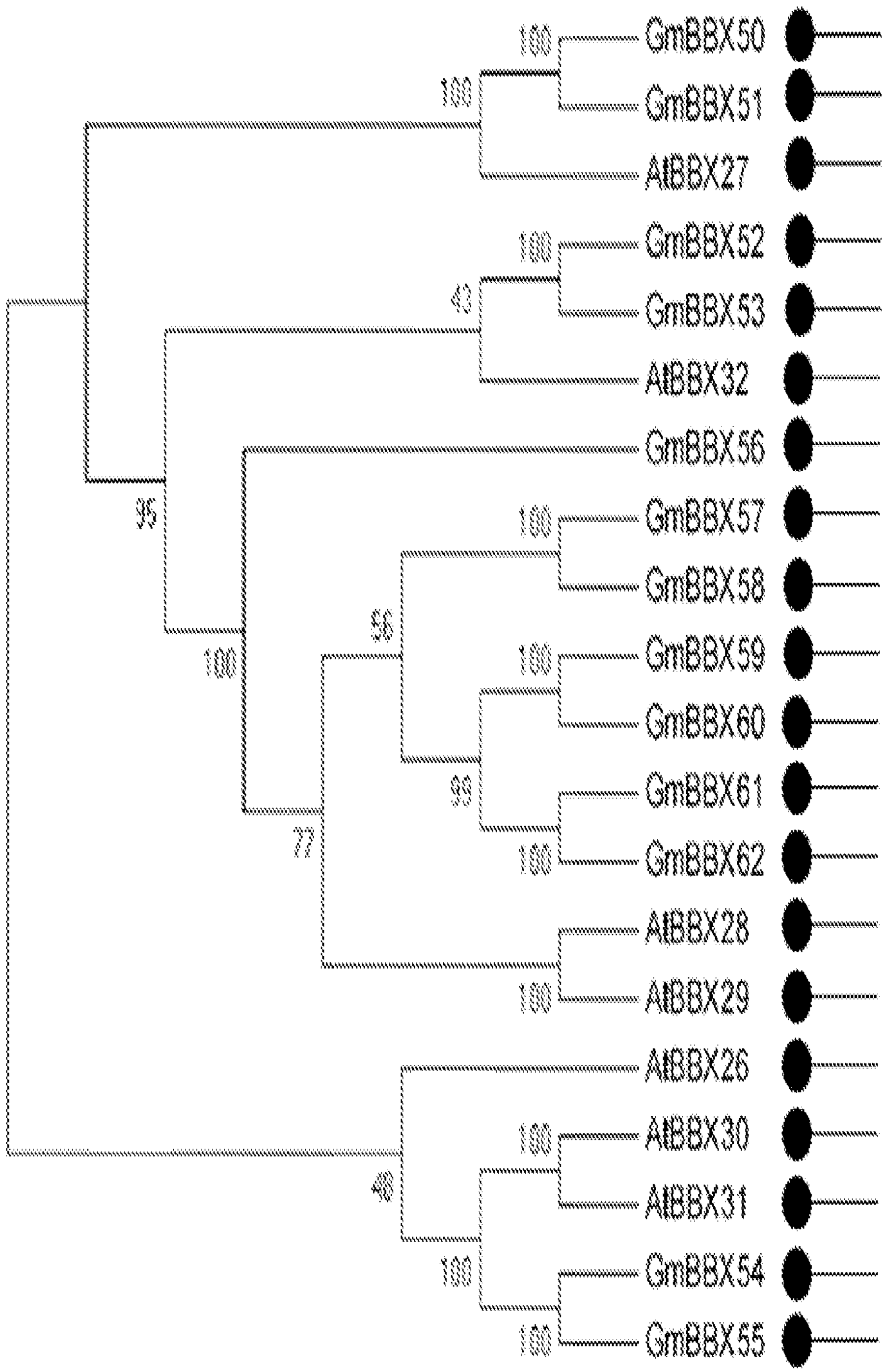

FIG. 14 represents the single B-box Glade in *Arabidopsis thaliana* and *Glycine max*. The *Arabidopsis thaliana* genome contains seven single B-box domain genes while the paleopolyploid *Glycine max* genome contains thirteen single B-box genes. Phylogenetic analysis indicates that GmBBX52 and GmBBX53 are orthologs of the *Arabidopsis thaliana* AtBBX32 gene.

Figure 15:
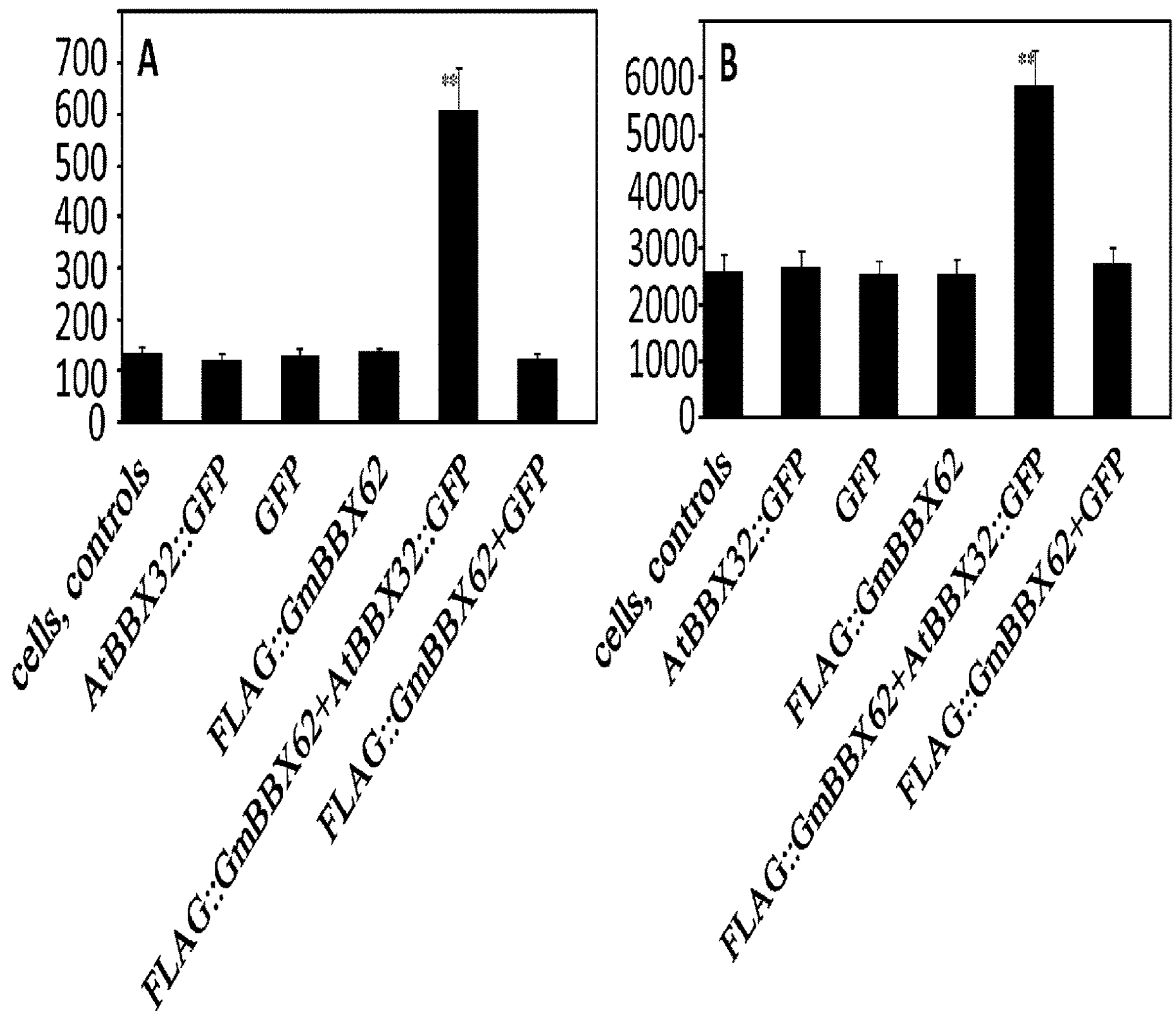

FIG. 15 shows AtBBX32 and GmBBX62 interaction in vivo in soybean cotyledon protoplasts. Luminex co-immunoprecipitation (co-IP) was performed using antibody against GFP (A). The reciprocal co-IP was conducted using antibody against Flag tag (B). Components within the co-precipitated protein complexes were probed with biotinylated anti-Flag (A) and anti-GFP (B) antibodies, and subsequently detected with a fluorescently labeled R-phycoerythrin. MFI stands for Median Fluorescence Intensity. ** Mean differs significantly from controls at p<0.05.

Figure 16:
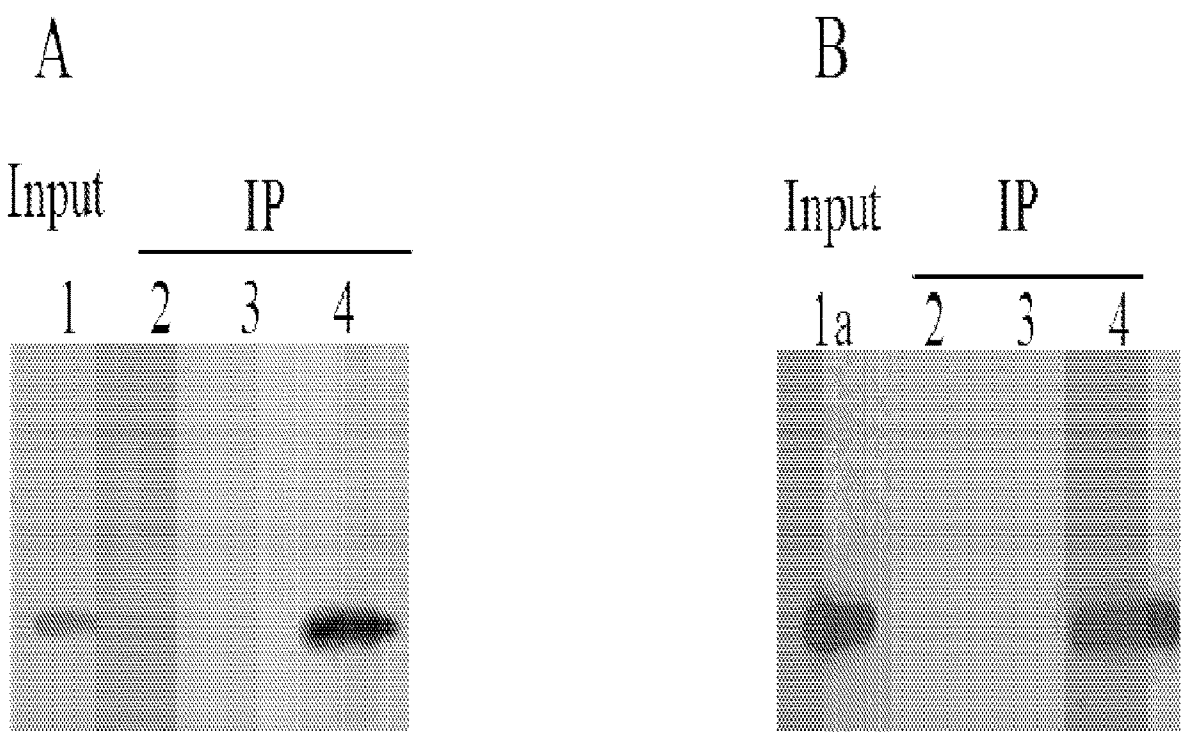

FIG. 16 demonstrates that AtBBX32 interacts directly with GmBBX62 via in vitro pull-down assay. Pull-down reactions were carried out using recombinant flag-GmBBX62 and soluble AtBBX32 extracts from wheat germ in vitro translation system. Protein bound to flag-GmBBX62 was washed, separated on SDS-PAGE and immunoblotted with anti-flag antibody (A) and anti-AtBBX32 antibody (B).Lane 1, flag-GmBBX62; la, AtBBX32 wheat germ extract; 2, anti-flag antibody bound beads only; 3, AtBBX32 only, no flag-GmBBX62; 4, flag-GmBBX62+AtBBX32.

Figure 17:
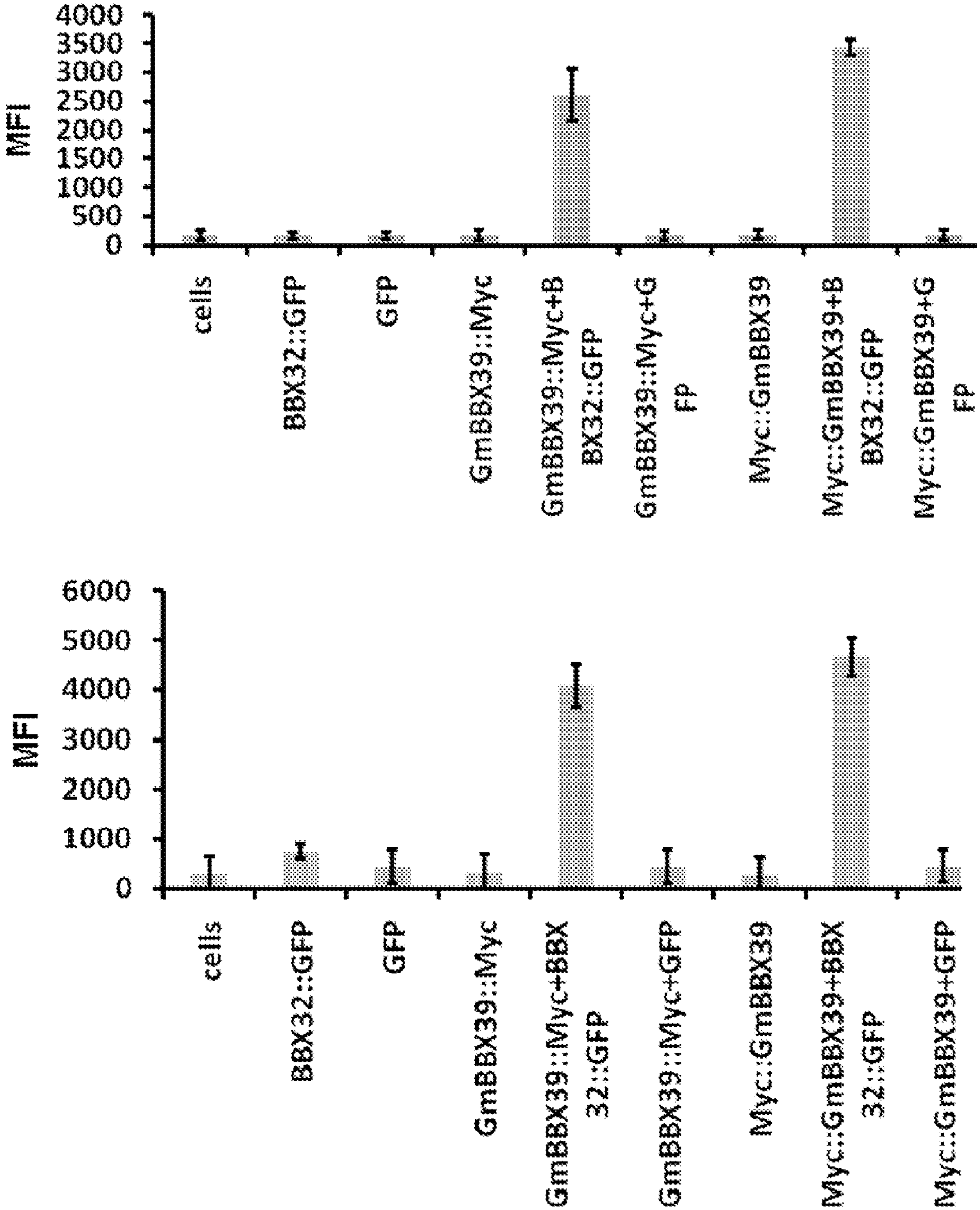

FIG. 17 shows AtBBX32 and GmBBX39 interaction in soybean protoplasts. Luminex co-IP assays were performed on extracts from soybean cotyledon protoplasts co-expressing AtBBX32 fused to GFP and GmBBX39 fused to the Myc epitope. A: IP with anti-GFP, detection with anti-Myc. B: IP with anti-Myc, detection with anti-GFP. MFI stands for Median Fluorescence Intensity. * denotes p<0.001.

DETAILED DESCRIPTION

The present disclosure relates to polynucleotides and polypeptides for modifying phenotypes of plants, particularly those associated with increased abiotic stress tolerance and increased yield with respect to a control plant (for example, a wild-type plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on, used to make and use the disclosed embodiments.

As used herein and in the appended claims, the singular forms "a", "an", and "the" include the plural reference unless the context clearly dictates otherwise. Thus, for example, a reference to "a plant cell" includes a plurality of such plant cells, and a reference to "a stress" is a reference to one or more stresses and equivalents thereof known to those skilled in the art, and so forth.

Definitions

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like.

The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcriptional regulator gene encodes a transcriptional regulator polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcriptional regulator or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, or non-naturally occurring amino acid residues.

"Protein" refers to an amino acid sequence, oligopeptide, peptide, polypeptide or portions thereof whether naturally occurring or synthetic.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be any-where from 0-100% similar, or any integer value between 0-100%. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A-4F may be used to identify conserved domains and relatedness within these domains. An alignment may suitably be determined by means of computer programs known in the art, such as MACVECTOR software, 1999 (Accelrys, Inc., San Diego, CA).

A "conserved domain" or "conserved region" as used herein refers to a region in heterologous polynucleotide or polypeptide sequences where there is a relatively high degree of sequence identity between the distinct sequences. A "B-box zinc finger" domain, such as is found in a polypeptide member of B-box zinc finger family, is an example of a conserved domain. With respect to polynucleotides encoding presently disclosed polypeptides, a conserved domain is preferably at least nine base pairs (bp) in length. A conserved domain with respect to presently disclosed polypeptides refers to a domain within a polypeptide family that exhibits a higher degree of sequence homology, such as at least about 56%, 57%. 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% sequence identity to a conserved domain of a disclosed polypeptide (e.g., SEQ ID NOs: 235-427). Sequences that possess or encode for conserved domains that meet these criteria of percentage identity, and that have comparable biological activity to the present polypeptide sequences, thus being members of the BBX32 Glade polypeptides, are encompassed by the present disclosure. A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcriptional regulator class, family or sub-family, or the exact amino acids of a particular transcriptional regulator consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Thus, by using alignment methods well known in the art, the conserved domains of the plant polypeptides, for example, for the B-box zinc finger proteins (Putterill et al., 1995), may be determined.

The conserved domains for many of the disclosed polypeptide sequences are listed in Table 1. Also, the polypeptides of Table 1 have conserved domains specifically indicated by amino acid coordinate start and stop sites. A comparison of the regions of these polypeptides allows one of skill in the art (see, for example, Reeves and Nissen, 1990, 1995) to identify domains or conserved domains for any of the polypeptides listed or referred to in this disclosure. "Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the disclosed, orthologous or paralogous polynucleotides may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985; Sambrook et al., 1989; and by Haymes et al., 1985; which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcriptional regulators having 56% or greater identity with the conserved domain of disclosed sequences.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the disclosed compositions and methods is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in functionally equivalent polypeptides. Thus, it will be readily appreciated by those of skill in the art, that any of a variety of polynucleotide sequences is capable of encoding the disclosed polypeptides and homolog polypeptides. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes a conserved domain of a polypeptide. Exemplary fragments also include fragments that comprise a conserved domain of a polypeptide. Exemplary fragments include fragments that comprise a conserved domain of a polypeptide, for example, any of SEQ ID NOs 235-427.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the disclosed methods is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, FIG. 2, adapted from Ku et al., 2000; and see also Tudge, 2000).

A "control plant" as used in the present disclosure refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present disclosure that is expressed in the transgenic or genetically modified plant being evaluated. A control plant may in other cases be a progeny of a hemizygous transgenic plant line that does not contain the recombinant DNA, known as a negative segregant or negative isoline. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding or polypeptide-suppressing sequence operably linked to (i.e., under regulatory control of) appropriate inducible, tissue-enhanced, tissue-specific, diurnally regulated or constitutive regulatory sequences that allow for the controlled expression of the polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

A constitutive promoter is active under most environmental conditions and in most plant parts.

Tissue-enhanced (also referred to as tissue-preferred), tissue-specific, cell type-specific, and inducible promoters constitute non-constitutive promoters. Promoters under developmental control include promoters that preferentially initiate transcription in certain tissues, such as xylem, leaves, roots, or seeds. Such promoters are examples of tissue-enhanced or tissue-preferred promoters (see U.S. Pat. No. 7,365,186). Tissue-enhanced promoters can be found upstream and operatively linked to DNA sequences normally transcribed in higher levels in certain plant tissues or specifically in certain plant tissues, respectively. "Cell-enhanced", "tissue-enhanced", or "tissue-specific" regulation thus refer to the control of gene or protein expression, for example, by a promoter, which drives expression that is not necessarily totally restricted to a single type of cell or tissue, but where expression is elevated in particular cells or tissues to a greater extent than in other cells or tissues within the organism, and in the case of tissue-specific regulation, in a manner that is primarily elevated in a specific tissue. Tissue-enhanced or preferred promoters have been described in, for example, U.S. Pat. No. 7,365,186, or U.S. Pat. No. 7,619,133.

A "condition-enhanced" promoter refers to a promoter that activates a gene in response to a particular environmental stimulus, for example, an abiotic stress, infection caused by a pathogen, light treatment, chemical stimulus, etc., and that drives expression in a unique pattern which may include expression in specific cell and/or tissue types within the organism (as opposed to a constitutive expression pattern in all cell types of an organism at all times).

A "diurnal promoter" is useful for regulating changes in the timing of gene expression to a specific time of day. Usually genes that are diurnally-regulated peak at the same time in the day/night cycle. Genes that are under the regulation of diurnal promoters exhibit altered expression profiles under the control of a circadian oscillator mostly during the switch time of light to dark but also with diurnal oscillations that persist within a period close to 24 hour day/night cycle. Diurnal regulation is subject to environmental inputs such as light and temperature and the coordination by the circadian clock.

"Wild type" or "wild-type", as used herein, refers to a plant cell, seed, plant component, plant part, plant tissue, plant organ or whole plant that has not been genetically modified or treated in an experimental sense. Wild-type cells, seeds, components, parts, tissues, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

"Trait modification", "modified trait" or "altered trait" refers to a detectable difference in a characteristic in a plant ectopically expressing a polynucleotide or polypeptide of the present disclosure relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be natural variations in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, leaf color, stem diameter, leaf size, leaf dimension, leaf density, internode distance or length, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the expression level of a set of genes in a cell in which a particular polypeptide is overexpressed or suppressed can be compared to the expression level of the same set of genes in a cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" or "suppression" refers to a plant, plant cell, or plant tissue having a disruption in at least one gene, where the disruption results in a reduced or abolished expression or activity of the polypeptide encoded by that gene compared to a control plant, cell, or tissue. A knockout or suppression can occur in different ways, including but not limited to: decreasing levels of a protein; suppressing a mutation that has resulted in decreased activity of a protein; suppressing the production of an inhibitory agent; elevating, reducing or eliminating the level of substrate that an enzyme requires for activity; producing a new protein; and activating a normally silent gene, to accumulate a product that does not normally increase under natural conditions. The suppressor can be another mutation on a different gene, a suppressor mutation on the same gene but located some distance from the first mutation, or a suppressor in the cytoplasm that has generated due to a change in non-chromosomal DNA. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene. To knockout or suppress a gene, a recombinant expression cassette can be made. For example, the recombinant cassette can comprise a promoter that is functional in a plant cell and that is operably-linked to a polynucleotide that when expressed in a plant cell is transcribed into a polynucleotide molecule that suppresses the level of an endogenous protein in the plant cell relative to a control. The polynucleotide molecule can be, for example, a dsRNA that is processed into siRNAs that targets a messenger RNA encoding the protein; a miRNA that targets a messenger RNA encoding the protein; a trans-acting small interfering RNA (ta-siRNA) that is processed into siRNAs and that targets a messenger RNA encoding the protein; and a cleavage blocker of a miRNA or a miRNA decoy of a miRNA, which both lead to decreased activity of a miRNA. Examples of such RNAi-mediated gene suppression approaches are disclosed in US Patent Application Publication 2009/61288019, which is incorporated herein by reference.

"Ectopic expression or altered expression" in reference to a polynucleotide indicates that the pattern of expression in, e.g., a transgenic plant or plant tissue, is different from the expression pattern in a wild-type plant or plant tissue or a reference plant or plant tissue of the same species. For example, a polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also be under the control of a heterologous promoter, or an inducible or tissue specific promoter. Thus, overexpression may occur throughout a plant, in specific tissues of the plant, or in the presence or absence of particular environmental signals, depending on the promoter used. Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates the expression of one or more genes in a plant with a transcriptional regulator having one or more specific binding domains that binds to a DNA regulatory sequence. Transcriptional regulators possess a conserved domain. The transcriptional regulators also comprise an amino acid subsequence that forms a transcription activation domain that regulates expression of one or more abiotic stress tolerance genes in a plant when the transcriptional regulator binds to the regulating region.

"Increased yield" or "improved yield" or "increased plant yield" refers to increased plant growth, increased crop growth, increased biomass, increased grain yield, and/or increased plant product production, and is dependent to some extent on temperature, plant size, organ size, planting density, light, water and nutrient availability, and how the plant copes with various stresses, such as through temperature acclimation and water or nutrient use efficiency.

"Planting density" refers to the number of plants that can be grown per acre. For crop species, planting or population density varies from crop to crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and even more preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al., 2003, in U.S. Patent Application No. 20030101479). A desirable higher population density for each of these examples, as well as other valuable species of plants, would be at least 10% higher than the average prevailing density or yield.

Description of the Specific Embodiments

Transcriptional Regulators Modify Expression of Endogenous Genes

A transcriptional regulator may include, but is not limited to, any polypeptide that can activate or repress transcription of a single gene or a number of genes. As one of ordinary skill in the art recognizes, transcriptional regulators can be identified by the presence of a region or domain of structural similarity or identity to a specific consensus sequence or the presence of a specific consensus DNA-binding motif (see, for example, Riechmann et al., 2000a). The plant transcriptional regulators of the present disclosure belong to the B-box zinc finger family (Putterill et al., 1995) and are putative transcriptional regulators.

Generally, transcriptional regulators are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The disclosed sequences may also be used to transform a plant and introduce desirable traits not found in the wild-type cultivar or strain. Plants may then be selected for those that produce the most desirable degree of over- or under-expression of target genes of interest and coincident trait improvement.

The sequences of the present disclosure and closely related orthologous or paralogous sequences may be from any species, particularly plant species, in a naturally occurring form or from any source whether natural, synthetic, semi-synthetic or recombinant. The disclosed sequences may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more of the disclosed polynucleotides and polypeptides, the disclosed polynucleotides and polypeptides have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcriptional regulators. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations. Expression of genes that encode polypeptides that modify expression of endogenous genes, polynucleotides, and proteins are well known in the art. In addition, transgenic plants comprising isolated polynucleotides encoding transcriptional regulators may also modify expression of endogenous genes, polynucleotides, and proteins. Examples include Peng et al., 1997, and Peng et al., 1999). In addition, many others have demonstrated that an *Arabidopsis* transcriptional regulator expressed in an exogenous plant species elicits the same or very similar phenotypic response. See, for example, Fu et al., 2001; Nandi et al., 2000; Coupland, 1995; and Weigel and Nilsson, 1995).

In another example, Mandel et al., 1992b, and Suzuki et al., 2001, teach that a transcriptional regulator expressed in another plant species elicits the same or very similar phenotypic response of the endogenous sequence, as often predicted in earlier studies of *Arabidopsis* transcriptional regulators in *Arabidopsis* (see Mandel et al., 1992a; Suzuki et al., 2001). Other examples include Muller et al., 2001; Kim et al., 2001; Kyozuka and Shimamoto, 2002; Boss and Thomas, 2002; He et al., 2000; and Robson et al., 2001).

In yet another example, Gilmour et al., 1998, teach an *Arabidopsis* AP2 transcriptional regulator, CBF1, which, when overexpressed in transgenic plants, increased plant freezing tolerance. Jaglo et al., 2001) further identified sequences in *Brassica napus* which encode CBF-like genes and showed that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis, B. napus*, wheat, rye, and tomato revealed the presence of conserved consecutive amino acid residues which bracket the AP2/EREBP DNA binding domains of the proteins and distinguish them from other members of the AP2/EREBP protein family (Jaglo et al., 2001).

Transcriptional regulators mediate cellular responses and control traits through altered expression of genes containing cis-acting nucleotide sequences that are targets of the introduced transcriptional regulator. It is well appreciated in the art that the effect of a transcriptional regulator on cellular responses or a cellular trait is determined by the particular genes whose expression is either directly or indirectly (e.g., by a cascade of transcriptional regulator binding events and transcriptional changes) altered by transcriptional regulator binding. In a global analysis of transcription comparing a standard condition with one in which a transcriptional regulator is overexpressed, the resulting transcript profile associated with transcriptional regulator overexpression is related to the trait or cellular process controlled by that transcriptional regulator. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Consequently, it is evident to one skilled in the art that similarity of transcript profile upon overexpression of different transcriptional regulators would indicate similarity of transcriptional regulator function.

The Disclosed Polypeptides and Polynucleotides

The present disclosure includes putative transcriptional regulators, and isolated or recombinant polynucleotides encoding the polypeptides, or novel sequence variant polypeptides or polynucleotides encoding novel variants of polypeptides derived from the specific sequences provided in the Sequence Listing; the disclosed recombinant polynucleotides may be incorporated in expression vectors for the purpose of producing transformed plants. Also provided are methods for modifying yield from a plant by modifying the mass, size or number of plant organs or seed of a plant by controlling a number of cellular processes, and for increasing a plant's resistance to abiotic stresses. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased yield or abiotic stress tolerance in diverse plant species.

Exemplary polynucleotides encoding the polypeptides provided in Table 1 and Table 2 were identified in the *Arabidopsis thaliana* GenBank database using publicly available sequence analysis programs and parameters, and an in-house proprietary database. Sequences initially identified were then further characterized to identify sequences comprising specified sequence strings corresponding to sequence motifs present in families of known polypeptides. Additional disclosed polynucleotides were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the sequence listing.

Many of the sequences in the Sequence Listing, derived from diverse plant species, have been ectopically expressed in overexpressor plants. The changes in the characteristic(s) or trait(s) of the plants were then observed and found to confer increased yield and/or increased abiotic stress tolerance. Therefore, the polynucleotides and polypeptides can be used to improve desirable characteristics of plants.

The disclosed polynucleotides were also ectopically expressed in overexpressor plant cells and the changes in the expression levels of a number of genes, polynucleotides, and/or proteins of the plant cells observed. Therefore, the polynucleotides and polypeptides can be used to change expression levels of genes, polynucleotides, and/or proteins of plants or plant cells.

General Considerations Related to Improving Plant Yield

The instant disclosure provides a novel method involving new gene technologies to improve plant yield. It is expected that either individually or in a combination with other genes or promoters, these novel methods will provide significantly higher improvements compared to previous methods.

Plants have evolved to sense the direction, color, intensity and duration of the incumbent light signals. Plants use this information to redirect their growth and developmental processes to optimize light absorption by promoting elongation growth under low light. Several genes have been implicated in playing roles in light signaling mechanisms regulating plant growth and development. Here, light responsiveness of young seedlings overexpressing some of the individual B-box genes to determine their roles in light signaling was examined. There is precedent that suppressing light signaling leads to crop improvement (U.S. Pat. No. 7,692,067).

The instant disclosure identifies several *Arabidopsis thaliana* B-box genes which can function negatively in light signaling and it is expected that either independently or in combination with other genes (such as with AtBBX32, GmBBX52 or GmBBX53) or specific promoters, these polynucleotides and their encoded polypeptides will provide significantly improved yield benefits and resistance to abiotic stress. It is also expected that these polynucleotides and their encoded polypeptides will provide plants with altered levels of ureides, altered levels of hexose sugars, altered SPS activity, altered levels of starch, and delayed senescence (International Application No. PCT/US2012/029885),It is further expected that the functionally similar orthologs or paralogs of these polynucleotides and their encoded polypeptides, either expressed individually or in combination with other polynucleotides and their encoded polypeptides, will lead to plants with higher yield advantages, improved stress tolerance, altered levels of ureides, altered levels of hexose sugars, altered SPS activity, altered levels of starch, and delayed senescence.

The instant disclosure also identifies several *Glycine max* B-box genes. Some of the encoded polypeptides of these *Glycine max* genes may interact with AtBBX32, or may be overexpressed or suppressed, in transgenic soybean plants overexpressing AtBBX32. Some of the encoded polypeptides of these *Glycine max* genes may interact with GmBBX52 in transgenic soybean plants overexpressing GmBBX52. Since expression of AtBBX32 and its soybean homologs, GmBBX52 and GmBBX53, modulates a variety of traits including yield, it is expected that either independently or in combination with other genes (such as with AtBBX32, GmBBX52 or GmBBX53) or specific promoters, altering the levels of these polynucleotides and their encoded polypeptides will provide plants with significantly improved yield benefits, resistance to abiotic stress, altered levels of ureides, altered levels of hexose sugars, altered SPS activity, altered levels of starch, and delayed senescence. It is also expected that the functionally similar orthologs or paralogs of these polynucleotides and their encoded polypeptides, either expressed individually or in combination with other polynucleotides and their encoded polypeptides, will lead to plants with higher yield advantages, improved stress tolerance, altered levels of ureides, altered levels of hexose sugars, altered SPS activity, altered levels of starch, and delayed senescence.

Background Information for BBX32, the BBX32 Clade, and Related Sequences

BBX32 is a B-box zinc finger protein with homology to the CONSTANS family of transcriptional regulators. BBX32 is expressed in many tissues and may be diurnally regulated.

As disclosed below in the Examples, constitutive expression of BBX32 in *Arabidopsis* modulates plant growth processes, including elongation of hypocotyls, extended petioles and upheld leaves, early flowering; enhanced root and/or shoot growth in phosphate-limited media; more secondary roots on control media, enhanced growth and reduced anthocyanin in low nitrogen/high sucrose media supplemented with glutamine, enhanced root growth on salt-containing media, and enhanced root growth on polyethylene glycol-containing media, as compared to control plants. BBX32 overexpression in soybean plants has been shown to result in a statistically significant increase in yield in field trials (see U.S. Pat. No. 7,692,067) as compared to controls that do not contain the BBX32 polynucleotide.

As noted in the Examples presented below, overexpression of BBX32 in *Arabidopsis* produced several phenotypes consistent with a role of this gene in light regulated development and possibly diurnal or circadian regulated processes. Light exerts a major influence in the initiation and maintenance (re-setting) of the plant circadian processes. Early seedling development is light dependent (de-etiolation) and is marked by inhibition of hypocotyl cell elongation along with cotyledon expansion and greening. Light controls morphological changes throughout the life of the plant, either directly or by regulating circadian gene expression. Some of these changes include petiole development, control of growth rate and flowering. It is likely that the ectopic expression of BBX32 product affects light signaling and/or circadian processes. Based upon the observations described above, it is clear that BBX32 is involved in photomorphogenesis and regulating plant growth and development. Hence, its overexpression may improve plant vigor, thus explaining the yield enhancements seen in 35S::BBX32 soybean plants.

TABLE 1

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| | | AtBBX28 (G1481)clade (clade identifier G1481): | | | | |
| 2 | At/G1481 | 100.0% to G1481 | 5-41 | CDLCNGVARMYCESD QASLCWDCDGKVHGA NFLVAKH | 235 | 100% (37/37) |
| 4 | At/G900 | 48.4% to G1481 | 6-42 | CELCCGVARMYCESD QASLCWDCDGKVHGA NFLVAKH | 236 | 95% (37/37) |
| 6 | Zm/ACN33981.1 | 35.3% to G1481 | 28-64 | CELCGAAARVYCGAD EATLCWGCDAQVHGA NFLVARH | 237 | 65% (24/37) |
| 8 | Pt/Pt_568988 | 37.1% to G1481 | 89-125 | CELCGSSARMYCESD QASLCWDCDEKVHTA NFLVAKH | 238 | 84% (31/37) |
| 10 | Pt/Pt_571834 | 26.5% to G1481 | 4-40 | CELCKNPARTYCESD EANLCWNCDTKVHGA NFLVARH | 239 | 73% (27/37) |
| 12 | Pt/Pt_582065 | 35.4% to G1481 | 4-40 | CELCGSSARMFCESD QASLCWDCDEKVHSA NFLVAKH | 240 | 81% (30/37) |
| 14 | Pt/Pt_758524 | 28.3% to G1481 | 4-40 | CELCDSFAQMHCESD QAILCSACDAYVHSA NFLAAKH | 241 | 65% (24/37) |
| 16 | Os/Os08g08120.1 | 34.8% to G1481 | 24-60 | CELCGAAARVYCGAD EATLCWGCDAQVHGA NFLVARH | 242 | 65% (24/37) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 18 | Os/Os08g08120.2 | 36.0% to G1481 | 24-60 | CELCGAAARVYCGAD EATLCWGCDAQVHGA NFLVARH | 243 | 65% (24/37) |
| 20 | Os/Os08g08120.3 | 36.3% to G1481 | 24-60 | CELCGAAARVYCGAD EATLCWGCDAQVHGA VFLVARH | 244 | 65% (24/37) |
| 22 | Gm/Glyma06g39810.1 | 41.0% to G1481 | 8-44 | CVLCEKRAMMLCDSD QAKLCWECDEKVHSA NFLVAKH | 245 | 70% (26/37) |
| 24 | Gm/Glyma06g45620.1 | 38.9% to G1481 | 4-40 | CELCKVPARIFCESD QASLCWDCDAKVHSA NFLVARH | 246 | 76% (27/37) |
| 26 | Gm/G4015 | 23.7% to G1481 | 6-42 | CELCHQLASLYCPSD SAFLCFHCDAAVHAA NFLVARH | 247 | 59% (22/37) |
| 28 | Gm/Glyma09g35960.1 | 21.0% to G1481 | 6-42 | CALCKKRAMMLCDSD QAKLCWECDEKVHSA NFLVAKH | 248 | 70% (26/37) |
| 30 | Gm/Glyma12g11230.1 | 37.1% to G1481 | 4-40 | CELCKVPARIFCESD QASLCWDCDAKVHSA NFLVARH | 249 | 76% (28/37) |
| 32 | Gm/Glyma12g32470.1 | 41.5% to G1481 | 4-40 | CELCKLPARTFCESD QASLCWDCDAKVHGA NFLVARH | 250 | 78% (29/37) |
| 34 | Gm/G4014 | 38.1% to G1481 | 4-40 | CELCNSPAKLFCESD QASLCWKCDAKVHSA NFLVTKH | 251 | 73% (27/37) |
| 36 | Gm/G4016 | 39.6% to G1481 | 4-40 | CELCKLPARTFCESD QASLCWDCDAKVHGA NFLVERH | 252 | 76% (28/37) |
| 38 | Gm/Glyma15g07140.1 | 37.2% to G1481 | 4-40 | CELCNSPAKLFCESD QASLCWECDAKVHSA NFLVTKH | 253 | 73% (27/37) |
| AtBBX25 (G1894) clade (clade identifier G1894): | | | | | | |
| 152 | At/G329 | 69.2% to G1894 | 5-42[a] | CDVCEKAPATVICCA DEAALCPQCDIEIHA ANKLASKH | 254 | 87% (33/38) |
| 152 | At/G329 | 69.2% to G1894 | 57-94[b] | CDICQEKAAFIFCVE DRALLCRDCDESIHV ANSRSANH | 255 | 84% (32/38) |
| 154 | At/G1894 | 100.0% to G1894 | 5-42[a] | CDVCEKAPATLICCA DEAALCAKCDVEVHA ANKLASKH | 256 | 100% (38/38) |
| 154 | At/G1894 | 100.0% to G1894 | 57-94[b] | CDICLEKAAFIFCVE DRALLCRDCDEATHA PNTRSANH | 257 | 100% (38/38) |
| 156 | Zm/ACF84591.1 | 50.0% to G1894 | 5-42[a] | CDACEGAAATVVCCA DEAALCARCDVEIHA ANKLASKH | 258 | 82% (31/38) |
| 156 | Zm/ACF84591.1 | 50.0% to G1894 | 57-94[b] | CDVCQEKAAFIFCVE DRALFCQDCDEPIHV PGTLSGNH | 259 | 74% (28/38) |
| 158 | Zm/ACF86823.1 | 50.4% to G1894 | 5-42[a] | CDACEGAAATVVCCA DEAALCARCDVEIHA ANKLASKH | 260 | 82% (31/38) |
| 158 | Zm/ACF86823.1 | 50.4% to G1894 | 57-94[b] | CDVCQEKAAFIFCVE DRALFCRDCDEPIHV PGTLSGNH | 261 | 76% (29/38) |
| 162 | Zm/CAW36812.1 | 50.4% to G1894 | 5-42[a] | CDACEGAAATVVCCA DEAALCARCDVEIHA ANKLASKH | 262 | 82% (31/38) |
| 162 | Zm/CAW36812.1 | 50.4% to G1894 | 57-94[b] | CDVCQEKAAFIFCVE DRALFCRDCDEPIHV PGTLSGNH | 263 | 76% (29/38) |
| 176 | Pt/Pt_216458 | 45.4% to G1894 | 5-42[a] | CDVCEKAPATVICCA DEAALCEKCDIEVII AANKLASKH | 264 | 92% (35/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 176 | Pt/Pt_216458 | 45.4% to G1894 | 57-94[b] | CDICQEKAAFIFCVE DRALFCRDCDEPIHS AGSLSANH | 265 | 76% (29/38) |
| 178 | Pt/Pt_827145 | 62.7% to G1894 | 5-42[a] | CDVCEKAPATVICCA DEAALCAKCDIEVHA ANKLASKH | 266 | 95% (36/38) |
| 178 | Pt/Pt_827145 | 62.7% to G1894 | 57-94[b] | CDICQEKAAFIFCVE DRALFCRDCDEPIHS AGSLSANH | 267 | 76% (29/38) |
| 180 | Os/Os02g39360.1 | 49.6% to G1894 | 5-42[a] | CDACESAAAAVVCCA DEAALCAACDVEVHA ANKLAGKH | 268 | 79% (30/38) |
| 180 | Os/Os02g39360.1 | 49.6% to G1894 | 57-94[b] | CDVCQEKAAFIFCVE DRALFCRDCDEPIHV PGTLSGNH | 269 | 76% (29/38) |
| 182 | Os/Os04g41560.2 | 48.1% to G1894 | 5-42[a] | CDACEAAAATVVCCA DEAALCARCDVEIHA ANKLASKH | 270 | 82% (31/38) |
| 182 | Os/Os04g41560.2 | 48.1% to G1894 | 58-95[b] | CDVCQEKAAFIFCVE DRALFCRDCDEPIHV PGTLSGNH | 271 | 76% (29/38) |
| 184 | Os/Os04g41560.4 | 41.8% to G1894 | 5-42[a] | CEACEAAAATVVCCA DEAALCARCDVEIHA ANKLASKH | 272 | 82% (31/38) |
| 184 | Os/Os04g41560.4 | 41.8% to G1894 | 58-95[b] | CDVCQEKAAFIFCVE DRALFCRDCDEPIHV PGTLSGNH | 273 | 76% (29/38) |
| 186 | Gm/Glyma11g13570 | 58.9% to G1894 | 5-42[a] | CDVCEKAPATVICCA DEAALCAKCDVEVHA ANKLASKH | 274 | 97% (37/38) |
| 186 | Gm/Glyma11g13570.1 | 58.9% to G1894 | 57-94[b] | CDICQDKPAFIFCVE DRALFCKDCDEPIHL ASSLSANH | 275 | 68% (26/38) |
| 188 | Gm/Glyma12g05570.1 | 58.7% to G1894 | 5-42[a] | CDVCEKAPATVICCA DEAALCAKCDVEVHA ANKLASKH | 276 | 97% (37/38) |
| 188 | Gm/Glyma12g05570.1 | 58.7% to G1894 | 57-94[b] | CDICQDKPAFIFCVE DRALFCKDCDEPIHL ASSLSANH | 277 | 68% (26/38) |
| 190 | Gm/Glyma13g41980.1 | 58.1% to G1894 | 5-42[a] | CDVCERAPATVICCA DEAALCAKCDVEVHA ANKLASKH | 278 | 95% (36/38) |
| 190 | Gm/Glyma13g41980.1 | 58.1% to G1894 | 57-94[b] | CDICQDKPAFIFCVE DRALFCQDCDEPIHS AGSLSANH | 279 | 68% (26/38) |
| 192 | Gm/Glyma13g41908.2 | 39.1% to G1894 | 24-57[a] | QDKPAFIFCVEDRAL FCQDCDEPIHSAGSL SANH | 280 | 35% (12/34) |
| 192 | Gm/Glyma13g41908.2 | 39.1% to G1894 | 25-57[b] | DKPAFIFCVEDRALF CQDCDEPIHSAGSLS ANH | 281 | 67% (22/33) |
| 194 | Gm/Glyma13g41980.3 | 39.1% to G1894 | 24-57[a] | QDKPAFIFCVEDRAL FCQDCDEPIHSAGSL SANH | 282 | 35% (12/34) |
| 194 | Gm/Glyma13g41980.3 | 39.1% to G1894 | 25-57[b] | DKPAFIFCVEDRALF CQDCDEPIHSAGSLS ANH | 283 | 67% (22/33) |
| 196 | Gm/Glyma15g03400.1 | 57.9% to G1894 | 5-42[a] | CDVCERAPATVICCA DEAALCAKCDVEVHA ANKLASKII | 284 | 95% (36/38) |
| 196 | Gm/Glyma15g03400.1 | 57.9% to G1894 | 57-94[b] | CDICQDKPAFIFCVE DRALFCQDCDEPIHS AGSLSANH | 285 | 68% (26/38) |
| 198 | Sl/AAS67368 | 58.2% to G1894 | 5-42[a] | CDVCEKAQATVICCA DEAALCAKCDIEVHA ANKLASKH | 286 | 92% (35/38) |
| 198 | Sl/AAS67368 | 58.2% to G1894 | 57-94[b] | CDICQDKAAFIFCVE DRALFCKDCDEAIHS ASSLAKNH | 287 | 68% (26/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| AtBBX20 (G1888) clade (clade identifier G1888): | | | | | | |
| 54 | At/G1888 | 100.0% to G1888 | 5-42[a] | CAVCDKEEASVFCCA DEAALCNGCDRHVHF ANKLAGKH | 288 | 100% (38/38) |
| 54 | At/G1888 | 100.0% to G1888 | 58-95[b] | CDICGERRALLFCQE DRAILCRECDIPIHQ ANEHTKKH | 289 | 100% (38/38) |
| 56 | At/G1482 | 37.4% to G1888 | 5-42[a] | CDVCDKEEASVFCTA DEASLCGGCDHQVHH ANKLASKH | 290 | 79% (30/38) |
| 56 | At/G1482 | 37.4% to G1888 | 60-97[b] | CDICQDKKALLFCQQ DRAILCKDCDSSIHA ANEHTKKH | 291 | 74% (28/38) |
| 58 | Zm/ACG44133.1 | 40.7% to G1888 | 5-42[a] | CDVCAAEAASVFCCA DEAALCDACDDRVHR ANKLAGKH | 292 | 76% (29/38) |
| 58 | Zm/ACG44133.1 | 40.7% to G1888 | 61-98[b] | CDICQERRGFLFCKE DRAILCRECDAPVHS ANDMTRRH | 293 | 71% (27/38) |
| 60 | Zm/CAW36814.1 | 44.4% to G1888 | 5-42[a] | CDVCAAEAASVFCCA DEAALCDACDDRVHR ANKLAGKH | 294 | 76% (29/38) |
| 60 | Zm/CAW36814.1 | 44.4% to G1888 | 61-98[b] | CDICQERRGFLFCKE DRAILCRECDAPVHS ANDMTRRH | 295 | 71% (27/38) |
| 68 | Pt/Pt_195637 | 51.0% to G1888 | 5-42[a] | CDVCDNVEATVFCCA DEAALCDGCDHRVHH ANKLASKH | 296 | 76% (29/38) |
| 68 | Pt/Pt_195637 | 51.0% to G1888 | 58-95[b] | CDICQERRALLFCQE DRAILCRECDLPIHK ANEHTQKH | 297 | 89% (34/38) |
| 70 | Pt/Pt_550941 | 39.5% to G1888 | 5-42[a] | CDVCNKEEASVFCTA DEAALCDTCDHRVHH ANKLASKH | 298 | 76% (29/38) |
| 70 | Pt/Pt_550941 | 39.5% to G1888 | 58-95[b] | CDICQEKRAFLFCQQ DRAILCRECDGPIHT ANEHTQKH | 299 | 82% (31/38) |
| 72 | Pt/Pt_801530 | 38.2% to G1888 | 5-42[a] | CDVCSKEEASVFCTA DEAALCDTCDHRVHH ANKLASKH | 300 | 76% (29/38) |
| 72 | Pt/Pt_801530 | 38.2% to G1888 | 58-95[b] | CDICQDKRAFLFCQQ DRAILCRDCDGPIHT ANEHTQKH | 301 | 76% (29/38) |
| 74 | Pt/Pt_804174 | 54.5% to G1888 | 5-42[a] | CDVCDKCRATVFCCA DEAALCDGCDHRVHH ANTLASKH | 302 | 76% (29/38) |
| 74 | Pt/Pt_804174 | 54.5% to G1888 | 58-95[b] | CDICQERRAVLFCQE DRAILCRECDLPIHK VNEHTQKH | 303 | 84% (32/38) |
| 76 | Os/Os02g43170.1 | 37.5% to G1888 | 5-42[a] | CDVCAAEAASVFCCA DEAALCDACDIIRVI IRANKLAGKH | 304 | 76% (29/38) |
| 76 | Os/Os02g43170.1 | 37.5% to G1888 | 65-102[b] | CDICQEKRGFLFCKE DRAILCRECDVPVHT ASELTMRH | 305 | 68% (26/38) |
| 78 | Os/Os02g43170.2 | 43.4% to G1888 | 5-42[a] | CDVCAAEAASVFCCA DEAALCDACDHRVHR ANKLAGKH | 306 | 76% (29/38) |
| 78 | Os/Os02g43170.2 | 43.4% to G1888 | 65-102[b] | CDICQEKRGFLFCKE DRAILCRECDVPVHT ASELTMRH | 307 | 68% (26/38) |
| 80 | Os/Os04g45690.1 | 37.7% to G1888 | 5-42[a] | CDVCAAEAASVFCCA DEAALCDACDRRVHS ANKLAGKH | 308 | 79% (30/38) |
| 80 | Os/Os04g45690.1 | 37.7% to G1888 | 63-100[b] | CDICQEKRGFLFCKE DRAILCRECDVTVHT TSRLTRRH | 309 | 63% (24/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 82 | Os/G5159 | 37.7% to G1888 | 5-42[a] | CDVCAAEAASVFCCA DEAALCDACDRRVHS ANKLAGKH | 310 | 79% (30/38) |
| 82 | Os/G5159 | 37.7% to G1888 | 63-100[b] | CDICQEKRGFLFCKE DRAILCRECDVTVHT TSELTRRH | 311 | 63% (24/38) |
| 84 | Os/Os06g49880.1 | 31.8% to G1888 | 5-42[a] | CDVCAAEPAAVLCCA DEAALCSACDRRVHR ANRLASKH | 312 | 68% (26/38) |
| 84 | Os/Os06g49880.1 | 31.8% to G1888 | 66-103[b] | CDVCREKRGLVFCVE DRAILCADCDEPIHS ANDLTAKH | 313 | 66% (25/38) |
| 86 | Os/Os06g49880.2 | 31.9% to G1888 | 5-42[a] | CDVCAAEPAAVLCCA DEAALCSACDRRVHR ANRLASKH | 314 | 68% (26/38) |
| 86 | Os/Os06g49880.2 | 31.9% to G1888 | 66-103[b] | CDVCREKRGLVFCVE DRAILCADCDEPIHS ANDLTAKH | 315 | 66% (25/38) |
| 88 | G/mGlyma04g01120.1 | 40.1% to G1888 | 5-42[a] | CAVCDKVEASVFCSA DEAALCHSCDRTIHH ANKLATKH | 316 | 79% (30/38) |
| 88 | G/mGlyma04g01120.1 | 40.1% to G1888 | 58-95[b] | CDICQERRAYLFCQE DRALLCRECDVPIHR ANEHTQKH | 317 | 84% (32/38) |
| 90 | Gm/G5365 | 39.4% to G1888 | 5-42[a] | CDVCNKQASFFCTAD EAALCDGCDHRVHHA NKLASKH | 318 | 71% (27/38) |
| 90 | Gm/G5365 | | 58-95[b] | CDVCQERRAFVFCQQ DRAILCKECDVPIHS ANDLTKNH | 319 | |
| 92 | Gm/Glyma04g02960.2 | 41.7% to G1888 | 5-42[a] | CDVCNKHQASFFCTA DEAALCDGCDHRVHH ANKLASKH | 320 | 71% (27/38) |
| 92 | Gm/Glyma04g02960.2 | 41.7% to G1888 | 58-95[b] | CDVCQERRAFVFCQQ DRAILCKECDVPIHS ANDLTKNH | 321 | 71% (27/38) |
| 94 | Gm/Glyma06g01140.1 | 49.4% to G1888 | 5-42[a] | CDVCDKVEASVFCPA DEAALCHSCDRTIHR ANKLATKH | 322 | 76% (29/38) |
| 94 | Gm/Glyma06g01140.1 | 49.4% to G1888 | 58-95[b] | CDICQERRAYLFCQE DRALLCRECDVPIHR ANEHTQKH | 323 | 84% (32/38) |
| 96 | Gm/G5367 | 39.1% to G1888 | 5-42[a] | CDVCNKQQASLFCTA DEAALCDGCDHRVHH ANKLASKH | 324 | 71% (27/38) |
| 96 | Gm/G5367 | 39.1% to G1888 | 58-95[b] | CDVCQERRAFVFCQQ DRAILCKECDVPVHS ANDLTKNH | 325 | 68% (26/38) |
| 98 | Gm/Glyma11g12060.1 | 40.8% to G1888 | 5-42[a] | CDVCHNEVASFFCPS DEASLCHACDRTIHH ANKLADKH | 326 | 63% (24/38) |
| 98 | Gm/Glyma11g12060.1 | 40.8% to G1888 | 58-95[b] | CDICHERRAYLFCKE DRAILCRECDLSIHG VNEHTKKH | 327 | 82% (31/38) |
| 100 | Gm/G5396 | 43.0% to G1888 | 5-42[a] | CDVCNKHEASVFCTA DEAALCDGCDHRVHH ANKLASKH | 328 | 76% (29/38) |
| 100 | Gm/G5396 | 43.0% to G1888 | 58-95[b] | CDICQERRAFTFCQQ DRAILCKECDVSIHS ANEHTLKH | 329 | 76% (29/38) |
| 102 | Gm/G5400 | 43.0% to G1888 | 5-42[a] | CDVCNKHEASVFCTA DEAALCDGCDHRVHH ANKLASKH | 330 | 76% (29/38) |
| 102 | Gm/G5400 | 43.0% to G1888 | 58-95[b] | CDICQERRAFTFCQQ DRAILCKECDVSIHS ANEHTLKH | 331 | 76% (29/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| AtBBX26 (G1486) clade (clade identifier G1486): | | | | | | |
| 52 | At/G1486 | 100.0% to G1486 | 5-41 | CHTCRHVTAVIHCVT EALNFCLTCDNLRHH NNIHAEH | 332 | 100% (37/37) |
| AtBBX30 (G1478) or AtBBX31 (G1929) clade (clade identifier G1478): | | | | | | |
| 40 | At/G1478 | 100.0% to G1478 | 32-68 | CELCGENATVYCEAD AAFLCRKCDRWVHSA NFLARRH | 333 | 100% (37/37) |
| 42 | At/G1929 | 62.3% to G1478 | 31-67 | CELCDGDASVFCEAD SAFLCRKCDRWVHGA NFLAWRII | 334 | 78% (29/37) |
| 44 | Pt/Pt_562313 | 43.2% to G1478 | 32-68 | CELCGSRASLYCQAD DAFLCQKCDKWVHGA NFLAQRH | 335 | 73% (27/37) |
| 46 | Pt/Pt_594447 | 44.1% to G1478 | 31-67 | CELCGSRATLYCQAD HAFLCQKCDGWVHGA NFLALRH | 336 | 76% (28/37) |
| 48 | Gm/Glyma12g32230.1 | 43.8% to G1478 | 30-66 | CELCGLQASLYCQAD DAYLCKKCDKRVHEA NFLALRH | 337 | 68% (25/37) |
| 50 | Gm/G4019 | 40.6% to G1478 | 30-66 | CELCGLQASLYCQAD DAYLCRKCDKRVHEA NFLALRH | 338 | 70% (26/37) |
| AtBBX7 (G2440) or AtBBX8 (G1479) clade (clade identifier G2440): | | | | | | |
| 104 | At/G2440 | 100.0% to G2440 | 5-42[a] | CDFCGEQRSMVYCRS DAACLCLSCDRSVHS ANALSKRH | 339 | 100% (38/38) |
| 104 | At/G2440 | 100.0% to G2440 | 48-94[b] | CERCNAQPATVRCVE ERVSLCQNCDWSGHN NSNNNNSSSSTSTQQ H | 340 | 96% (45/47) |
| 104 | At/G2440 | 100.0% to G2440 | 315-356[c] | RNNAVMRYKEKKKAR KFDKRVRYASRKARA DVRRRVKGRFVK | 341 | 100% (42/42) |
| 106 | At/G1479 | 70.1% to G2440 | 5-42[a] | CDFCGEQRSMVYCRS DAACLCLSCDRNVHS ANALSKRH | 342 | 97% (37/38) |
| 106 | At/G1479 | 70.1% to G2440 | 48-87[b] | CERCNAQPASVRCSD ERVSLCQNCDWSGHD GKNSTTTSHH | 343 | 80% (32/40) |
| 106 | At/G1479 | 70.1% to G2440 | 316-357[c] | RNNAVMRYKEKKKAR KFDKRVRYVSRKERA DVRRRVKGRFVK | 344 | 95% (40/42) |
| 108 | Zm/ACF80403.1 | 49.6% to G2440 | 5-42[a] | CGFCGKQRSMIYCRS DAASLCLSCDRSVHS ANALSRRH | 345 | 87% (33/38) |
| 108 | Zm/ACF80403.1 | 49.6% to G2440 | 48-85[b] | CDRCGLQPASVRCLE DNTSLCQNCDWNGHD AASGASGH | 346 | 55% (21/38) |
| 108 | Zm/ACF80403.1 | 49.6% to G2440 | 349-390[c] | RDSALTRYKEKKKKR MFDKKIRYASRKARA DVRKRVKGRFIK | 347 | 76% (32/42) |
| 110 | Zm/ACG34885.1 | 50.4% to G2440 | 5-42[a] | CDFCGEQRSMVYCRS DAASLCLSCDRNVHS ANALSRRH | 348 | 92% (35/38) |
| 110 | Zm/ACG34885.1 | 50.4% to G2440 | 48-85[b] | CERCASQPAMVRCLA ENASLCQNCDWNGHI AGSSSAGH | 349 | 58% (22/38) |
| 110 | Zm/ACG34885.1 | 50.4% to G2440 | 350-391[c] | RDSALTRYKEKKMRR KFDKKIRYASRKARA DVRKRVKGRFVK | 350 | 79% (33/42) |
| 114 | Zm/ACN25813.1 | 47.1% to G2440 | 5-42[a] | CDFCGKQRSMIYCRS DAASLCLSCDRNVHS ANALSRRH | 351 | 87% (33/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 114 | Zm/ACN25813.1 | 47.1% to G2440 | 48-85[b] | CDRCGSQPASVRCLE DNASLCQNCDWNGHD AESGASGH | 352 | 55% (21/38) |
| 114 | Zm/ACN25813.1 | 47.1% to G2440 | 372-391[c] | YASRKARADVRKRVK GRFIK | 353 | 90% (18/20) |
| 120 | Pt/Pt_247140 | 59.7% to G2440 | 5-42[a] | CDFCGEQRSMVYCRS DAASLCLSCDRNVHS ANALSKRH | 354 | 95% (36/38) |
| 120 | Pt/Pt_247140 | 59.7% to G2440 | 48-85[b] | CERCNSQPALVRCAE ERISLCQNCDWIGHG TSTSASTH | 355 | 74% (28/38) |
| 120 | Pt/Pt_247140 | 59.7% to G2440 | 322-363[c] | RSDAVMRYKEKKKTR MFEKKVRYASRKARA DVRRRVKGRFVK | 356 | 86% (36/42) |
| 122 | Pt/Pt_409151 | 59.9% to G2440 | 5-42[a] | CDFCGEQRSMVYCRS DAACLCLSCDQIVHS ANALSKRH | 357 | 95% (36/38) |
| 122 | Pt/Pt_409151 | 59.9% to G2440 | 48-85[b] | CERCNSQPALVRRVE ERISLCQNCDWMGYG SSTSASTH | 358 | 71% (27/38) |
| 122 | Pt/Pt_409151 | 59.9% to G2440 | 372-391[c] | RSDAVKRYMEKKKTR KFEKKVRYASRKARA DVRRRVKGRFVK | 359 | 83% (35/42) |
| 124 | Os/Os02g49230.1 | 51.7% to G2440 | 5-42[a] | CDFCREQRSMVYCRS DAASLCLSCDRNVHS ANALSRRH | 360 | 89% (34/38) |
| 124 | Os/Os02g49230.1 | 51.7% to G2440 | 48-85[b] | CDRCVGQPAAVRCLE ENTSLCQNCDWNGHG AASSAAGH | 361 | 61% (23/38) |
| 124 | Os/Os02g49230.1 | 51.7% to G2440 | 350-391[c] | RDNALTRYKEKKKRR KFDKKIRYASRKARA DVRKRVKGRFVK | 362 | 83% (35/42) |
| 126 | Os/Os02g49230.2 | 44.2% to G2440 | 78-115[a] | CDFCREQRSMVYCRS DAASLCLSCDRNVHS ANALSRRH | 363 | 89% (34/38) |
| 126 | Os/Os02g49230.2 | 44.2% to G2440 | 121-158[b] | CDRCVGQPAAVRCLE ENTSLCQNCDWNGHG AASSAAGH | 364 | 61% (23/38) |
| 126 | Os/Os02g49230.2 | 44.2% to G2440 | 423-464[c] | RDNALTRYKEKKKRR KFDKKIRYASRKARA DVRKRVKGRFVK | 365 | 83% (35/42) |
| 128 | Os/Os02g49230.3 | 51.7% to G2440 | 5-42[a] | CDFCREQRSMVYCRS DAASLCLSCDRNVHS ANALSRRH | 366 | 89% (34/38) |
| 128 | Os/Os02g49230.3 | 51.7% to G2440 | 48-85[b] | CDRCVGQPAAVRCLE ENTSLCQNCDWNGHG AASSAAGH | 367 | 61% (23/38) |
| 128 | Os/Os02g49230.3 | 51.7% to G2440 | 350-391[c] | RDNALTRYKEKKKRR KFDKKIRYASRKARA DVRKRVKGRFVK | 368 | 83% (35/42) |
| 130 | Os/Os02g49230.4 | 51.7% to G2440 | 5-42[a] | CDFCREQRSMVYCRS DAASLCLSCDRNVHS ANALSRRH | 369 | 89% (34/38) |
| 130 | Os/Os02g49230.4 | 51.7% to G2440 | 48-85[b] | CDRCVGQPAAVRCLE ENTSLCQNCDWNGHG AASSAAGH | 370 | 61% (23/38) |
| 130 | Os/Os02g49230.4 | 51.7% to G2440 | 350-391[c] | RDNALTRYKEKKKRR KFDKKIRYASRKARA DVRKRVKGRFVK | 371 | 83% (35/42) |
| 132 | Os/Os02g49230.5 | 51.8% to G2440 | 5-42[a] | CDFCREQRSMVYCRS DAASLCLSCDRNVHS ANALSRRH | 372 | 89% (34/38) |
| 132 | Os/Os02g49230.5 | 51.8% to G2440 | 48-85[b] | CDRCVGQPAAVRCLE ENTSLCQNCDWNGHG AASSAAGH | 373 | 61% (23/38) |
| 132 | Os/Os02g49230.5 | 51.8% to G2440 | 349-390[c] | RDNALTRYKEKKKRR KFDKKIRYASRKARA DVRKRVKGRFVK | 374 | 83% (35/42) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 134 | Os/Os02g49230.6 | 51.7% to G2440 | 5-42[a] | CDFCREQRSMVYCRS DAASLCLSCDRNVHS ANALSRRH | 375 | 89% (34/38) |
| 134 | Os/Os02g49230.6 | 51.7% to G2440 | 48-85[b] | CDRCVGQPAAVRCLE ENTSLCQNCDWNGHG AASSAAGH | 376 | 61% (23/38) |
| 134 | Os/Os02g49230.6 | 51.7% to G2440 | 350-391[c] | RDNALTRYKEKKKRR KFDKKIRYASRKARA DVRKRVKGRFVK | 377 | 83% (35/42) |
| 136 | Os/Os06g19444.1 | 51.7% to G2440 | 5-42[a] | CDFCGEQRSMVYCRS DAASLCLSCDRNVHS ANALSRRH | 378 | 92% (35/38) |
| 136 | Os/Os06g19444.1 | 51.7% to G2440 | 48-85[b] | CDRCASQPAMVRCLV ENASLCQNCDWNGHS AGSSAAGH | 379 | 58% (22/38) |
| 136 | Os/Os06g19444.1 | 51.7% to G2440 | 373-392[c] | YASRKARADVRKRVK GRFVK | 380 | 95% (19/20) |
| 138 | Os/Os06g19444.2 | 51.8% to G2440 | 5-42[a] | CDFCGEQRSMVYCRS DAASLCLSCDRNVHS ANALSRRH | 381 | 92% (35/38) |
| 138 | Os/Os06g19444.2 | 51.8% to G2440 | 48-85[b] | CDRCASQPAMVRCLV ENASLCQNCDWNGHS AGSSAAGH | 382 | 58% (22/38) |
| 138 | Os/Os06g19444.2 | 51.8% to G2440 | 372-391[c] | YASRKARADVRKRVK GRFVK | 383 | 95% (19/20) |
| 140 | Gm/Glyma02g38870.1 | 56.3% to G2440 | 5-42[a] | CDFCGDQRSLVYCRS DSACLCLSCDRNVHS ANALSRRH | 384 | 87% (33/38) |
| 140 | Gm/Glyma02g38870.1 | 56.3% to G2440 | 48-85[b] | CERCNSQPAFVRSVE EKISLCQNCDWLGHG TSPSSSMH | 385 | 68% (26/38) |
| 140 | Gm/Glyma02g38870.1 | 56.3% to G2440 | 348-389[c] | RSNAVMRYKEKKKTR KFEKKVRYASRKARA DVRKRVKGRFVK | 386 | 88% (37/42) |
| 142 | Gm/Glyma13g1590.1 | 36.6% to G2440 | | | | |
| 142 | Gm/Glyma13g1590.1 | 36.6% to G2440 | | | | |
| 142 | Gm/Glyma13g1590.1 | 36.6% to G2440 | 224-365[c] | RSNAVMRYKEKKKTR KFDKKVRYASRKARA DVRRRVKGRFVK | 387 | 90% (38/42) |
| 144 | Gm/Glyma14g36930.1 | 55.3% to G2440 | 5-42[a] | CDFCGDQRSLVYCRS DAACLCLSCDRNVHS ANALSRRH | 388 | 89% (34/38) |
| 144 | Gm/Glyma14g36930.1 | 55.3% to G2440 | 48-85[b] | CERCNSQPAFVRCVD EKISLCQNCDWLGHG TSPSSSTH | 389 | 68% (26/38) |
| 144 | Gm/Glyma14g36930.1 | 55.3% to G2440 | 354-395[c] | RSNAVMRYKEKKKTR KFEKKVRYASRKARA DVRKRVKGRFVK | 390 | 88% (37/42) |
| 146 | Gm/Glyma14g36930.2 | 55.3% to G2440 | 5-42[a] | CDFCGDQRSLVYCRS DAACLCLSCDRNVHS ANALSRRH | 391 | 89% (34/38) |
| 146 | Gm/Glyma14g36930.2 | 55.3% to G2440 | 48-85[b] | CERCNSQPAFVRCVD EKISLCQNCDWLGHG TSPSSSTH | 392 | 68% (26/38) |
| 146 | Gm/Glyma14g36930.2 | 55.3% to G2440 | 354-395[c] | RSNAVMRYKEKKKTR KFEKKVRYASRKARA KVRKRVKGRFVK | 393 | 88% (37/42) |
| 148 | Gm/Glyma20g07050.1 | 37.4% to G2440 | | | | |
| 148 | Gm/Glyma20g07050.1 | 37.4% to G2440 | | | | |
| 148 | Gm/Glyma20g07050.1 | 37.4% to G2440 | 226-267[c] | RSNAVMRYKEKKKTR MFDKKVRYASRKARA DVRRRVKGRFVK | 394 | 90% (38/42) |
| 150 | Gm/Glyma20g07050.2 | 37.4% to G2440 | | | | |
| 150 | Gm/Glyma20g07050.2 | 37.4% to G2440 | | | | |

TABLE 1-continued

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| Conserved domains and potentially valuable morphological traits of B-box sequences | | | | | | |
| 150 | Gm/Glyma20g07050.2 | 37.4% to G2440 | 226-267[c] | RSNAVMRYKEKKKTR MFDKKVRYASRKARA DVRRRVKGRFVK | 395 | 90% (38/42) |
| AtBBX19 (G902) or AtBBX18 (G1881) clade (clade identifier G902): | | | | | | |
| 200 | At/G902 | 100.0% to G902 | 5-42[a] | CDACENAAAHFCAAD EAALCRPCDEKVHMC NKLASRH | 396 | 100% (38/38) |
| 200 | At/G902 | 100.0% to G902 | 56-91[b] | CDICENAPAFFYCEI DGSSLCLQCDMVVHV GGKRTH | 397 | 100% (36/36) |
| 202 | At/G1881 | 70.1% to G902 | 5-42[a] | CDACESAAAIVFCAA DEAALCCSCDEKVHK CNKLASRH | 398 | 87% (33/38) |
| 202 | At/G1881 | 70.1% to G902 | 56-91[b] | CDICENAPAFFYCEI DGSSLCLQCDMVVHV GGKRTH | 399 | 100% (36/36) |
| 204 | Zm/ACF85933.1 | 57.5% to G902 | 5-42[a] | CDVCESAPAVLFCAA DEAALCRPCDEKVHM CNKLASRH | 400 | 87% (33/38) |
| 204 | Zm/ACF85933.1 | 57.5% to G902 | 56-91[b] | CDICENSPAFFYCEI DGTSLCLSCDMTVHV GGKRTH | 401 | 89% (32/36) |
| 208 | Zm/ACL52378.1 | 57.8% to G902 | 5-42[a] | CDVCESAPAVLFCAA DEAALCRPCDEKVHM CNKLASRH | 402 | 87% (33/38) |
| 208 | Zm/ACL52378.1 | 57.8% to G902 | 56-91[b] | CDICENSPAFFYCEI DGTSLCLSCDMTVHV GGKRTH | 403 | 89% (32/36) |
| 212 | Pt/Pt_648693 | 61.4% to G902 | 5-42[a] | CDVCESAAAILFCAA DEAALCRSCDEKVHM CNKLASRH | 404 | 89% (34/38) |
| 212 | Pt/Pt_648693 | 61.4% to G902 | 56-91[b] | CDICEKAPAFFYCEI DGSSLCLQCDMIVHV GGKRTH | 405 | 94% (34/36) |
| 214 | Pt/Pt_721866 | 61.0% to G902 | 5-42[a] | CDVCESAAAILFCAA DEAALCRSCDEKVHL CNKLASRH | 406 | 87% (33/38) |
| 214 | Pt/Pt_721866 | 61.0% to G902 | 56-91[b] | CDICENAPAFFYCEI DGSSLCLQCDMIVHV GGKRTH | 407 | 97% (35/36) |
| 216 | Pt/Pt_741179 | 54.5% to G902 | 5-42[a] | CDACESAFAIVFCAA DEAALCLACDKKVHM CNKLASRH | 408 | 84% (32/38) |
| 216 | Pt/Pt_741179 | 54.5% to G902 | 56-91[b] | CDICENAPAFFYCET DGSSLCLQCDMTVHV GGKRTH | 409 | 94% (34/36) |
| 218 | Pt/Pt_820080 | 56.2% to G902 | 5-42[a] | CDACESAAAIVFCAA DEAALCLACDEKVHM CMKLASRH | 410 | 89% (34/38) |
| 218 | Pt/Pt_820080 | 56.2% to G902 | 56-91[b] | CDICENAPAFFYCET DGSSLCLQCDMTVHV GGKRTH | 411 | 94% (34/36) |
| 220 | Os/Os09g35880.1 | 57.1% to G902 | 5-42[a] | CDVCESAPAVLFCVA DEAALCRSCDEKVHM CNKLARRH | 412 | 79% (30/38) |
| 220 | Os/Os09g35880.1 | 57.1% to G902 | 56-91[b] | CDICENAPAFFYCEI DGTSLCLSCDMTVHV GGKRTH | 413 | 92% (33/36) |
| 222 | Gm/Glyma01g37370.1 | 55.2% to G902 | 5-42[a] | CDACESAAAIVFCAA DEAALCRACDEKVHM CNKLASRH | 414 | 92% (35/38) |
| 222 | Gm/Glyma01g37370.1 | 55.2% to G902 | 56-91[b] | CDICENAPAFFYCET DGSSLCLQCDMIVHV GGKRTH | 415 | 94% (34/36) |
| 224 | Gm/Glyma11g07930.1 | 56.7% to G902 | 5-42[a] | CDACESAAAIVFCAA DEAALCRACDEKVHM CNKLASRH | 416 | 92% (35/38) |

TABLE 1-continued

Conserved domains and potentially valuable morphological traits of B-box sequences

| Column 1 Poly-peptide SEQ ID NO: | Column 2 Species/GID No. | Column 3 Percent identity of polypeptide to clade identifier | Column 4 Amino acid coordinates of domain | Column 5 Domain sequence | Column 6 SEQ ID NO: of domain | Column 7 Percent identity of domain in column 5 (no. identical residues) |
|---|---|---|---|---|---|---|
| 224 | Gm/Glyma11g07930.1 | 56.7% to G902 | 56-91[b] | CDICENAPAFFYCET DGSSLCLQCDMIVHV GGKRTH | 417 | 94% (34/36) |
| 226 | Gm/Glyma11g07930.2 | 55.7% to G902 | 5-42[a] | CDACESAAAIVFCAA DEAALCRACDEKVHM CNKLASRH | 418 | 92% (35/38) |
| 226 | Gm/Glyma11g07930.2 | 55.7% to G902 | 56-91[b] | CDICENAPAFFYCET DGSSLCLQCDMIVHV GGKRTH | 419 | 94% (34/36) |
| 228 | Gm/Glyma11g07930.3 | 55.7% to G902 | 5-42[a] | CDACESAAAIVFCAA DEAALCRACDEKVHM CNKLASRH | 420 | 92% (35/38) |
| 228 | Gm/Glyma11g07930.3 | 55.7% to G902 | 56-91[b] | CDICENAPAFFYCET DGSSLCLQCDMIVHV GGKRTH | 421 | 94% (34/36) |
| 230 | Gm/Glyma11g07930.4 | 56.2% to G902 | 5-42[a] | CDACESAAAIVFCAA DEAALCRACDEKVHM CMKLASRH | 422 | 92% (35/38) |
| 230 | Gm/Glyma11g07930.4 | 56.2% to G902 | 56-91[b] | CDICENAPAFFYCET DGSSLCLQCDMIVHV GGKRTH | 423 | 94% (34/36) |
| 232 | Gm/Glyma11g11850.1 | 58.0% to G902 | 5-42[a] | CDVCESAAAILFCAA DEAALCSACDHKIHM CNKLASRH | 424 | 82% (31/38) |
| 232 | Gm/Glyma11g11850.1 | 58.0% to G902 | 56-91[b] | CDICENAPAFFYCEI DGSSLCLQCDMIVHV GGKRTH | 425 | 97% (35/36) |
| 234 | Gm/Glyma12g04130.1 | 62.2% to G902 | 5-42[a] | CDVCESAAAIVFCAA DEAALCSACDHKIHM CNKLASRH | 426 | 82% (31/38) |
| 234 | Gm/Glyma12g04130.1 | 62.2% to G902 | 56-91[b] | CDICENAPAFFYCEI DGSSLCLQCDMIVHV GGKRTH | 427 | 97% (35/36) |

Species abbreviations for Table 1: At—*Arabidopsis thaliana*; Gm—*Glycine max*; Os—*Oryza sativa*; Pt—*Populus trichocarpa*; Sl—*Solanum lycopersicum*; Zm—*Zea mays*.
[a]first B-box type ZF domain
[b]second B-box type ZF domain
[c]putative CCT nuclear localization domain Exemplary polynucleotides encoding the polypeptides of soybean B-box proteins (GmBBX) as represented in Table 2 were identified from yeast two hybrid screens and from phylogenetic analysis.

TABLE 2

*Glycine max* B-box polynucleotide and polypeptide sequences (GmBBX).

| Column 1 Polynucleotide SEQ ID NO: | Column 2 Polypeptide SEQ ID NO: | Column 3 Gene Name | Column 4 Domains |
|---|---|---|---|
| 435 | 436 | GmBBX1 | zf-B_box[2]::CCT |
| 437 | 438 | GmBBX2 | zf-B_box[2]::CCT |
| 439 | 440 | GmBBX3 | zf-B_box[2]::CCT |
| 441 | 442 | GmBBX4 | zf-B_box[2]::CCT |
| 443 | 444 | GmBBX5 | zf-B_box[2]::CCT |
| 445 | 446 | GmBBX6 | zf-B_box[2]::CCT |
| 447 | 448 | GmBBX7 | zf-B_box[2] |
| 449 | 450 | GmBBX11 | zf-B_box[2]::CCT |
| 451 | 452 | GmBBX12 | zf-B_box[2]::CCT |
| 453 | 454 | GmBBX13 | zf-B_box[1]::CCT |
| 455 | 456 | GmBBX14 | zf-B_box[1]::CCT |
| 457 | 458 | GmBBX15 | zf-B_box[1]::CCT |
| 459 | 460 | GmBBX16 | zf-B_box[1]::CCT |
| 461 | 462 | GmBBX17 | zf-B_box[1]::CCT |
| 463 | 464 | GmBBX18 | zf-B_box[1]::CCT |

TABLE 2-continued

*Glycine max* B-box polynucleotide and polypeptide sequences (GmBBX).

| Column 1 Polynucleotide SEQ ID NO: | Column 2 Polypeptide SEQ ID NO: | Column 3 Gene Name | Column 4 Domains |
|---|---|---|---|
| 465 | 466 | GmBBX19 | zf-B_box[2]::CCT |
| 467 | 468 | GmBBX20 | zf-B_box[2]::CCT |
| 469 | 470 | GmBBX21 | zf-B_box[2]::CCT |
| 471 | 472 | GmBBX22 | zf-B_box[2]::CCT |
| 473 | 474 | GmBBX23 | zf-B_box[2] |
| 475 | 476 | GmBBX24 | zf-B_box[1]::CCT |
| 477 | 478 | GmBBX25 | zf-B_box[2]::CCT |
| 479 | 480 | GmBBX26 | zf-B_box[2]::CCT |
| 481 | 482 | GmBBX27 | zf-B_box[2] |
| 483 | 484 | GmBBX28 | zf-B_box[2] |
| 485 | 486 | GmBBX29 | zf-B_box[2]::CCT |
| 487 | 488 | GmBBX30 | zf-B_box[2]::CCT |
| 489 | 490 | GmBBX31 | zf-B_box[2] |
| 491 | 492 | GmBBX33 | zf-B_box[2] |
| 493 | 494 | GmBBX34 | zf-B_box[2] |
| 495 | 496 | GmBBX35 | zf-B_box[2] |
| 497 | 498 | GmBBX36 | zf-B_box[2] |
| 499 | 500 | GmBBX37 | zf-B_box[2] |
| 501 | 502 | GmBBX38 | zf-B_box[2] |
| 503 | 504 | GmBBX39 | zf-B_box[2] |
| 505 | 506 | GmBBX40 | zf-B_box[2] |

TABLE 2-continued

*Glycine max* B-box polynucleotide and polypeptide sequences (GmBBX).

| Column 1 Polynucleotide SEQ ID NO: | Column 2 Polypeptide SEQ ID NO: | Column 3 Gene Name | Column 4 Domains |
|---|---|---|---|
| 507 | 508 | GmBBX41 | zf-B_box[2] |
| 509 | 510 | GmBBX42 | zf-B_box[2] |
| 511 | 512 | GmBBX43 | zf-B_box[2] |
| 513 | 514 | GmBBX44 | zf-B_box[2] |
| 515 | 516 | GmBBX45 | zf-B_box[2] |
| 517 | 518 | GmBBX46 | zf-B_box[2] |
| 519 | 520 | GmBBX47 | zf-B_box[2] |
| 521 | 522 | GmBBX48 | zf-B_box[2] |
| 523 | 524 | GmBBX49 | zf-B_box[2] |
| 525 | 526 | GmBBX50 | zf-B_box[1] |
| 527 | 528 | GmBBX51 | zf-B_box[1] |
| 529 | 530 | GmBBX52 | zf-B_box[1] |
| 531 | 532 | GmBBX53 | zf-B_box[1] |
| 533 | 534 | GmBBX54 | zf-B_box[1] |
| 535 | 536 | GmBBX55 | zf-B_box[1] |
| 537 | 538 | GmBBX56 | zf-B_box[1] |
| 539 | 540 | GmBBX57 | zf-B_box[1] |
| 541 | 542 | GmBBX58 | zf-B_box[1] |
| 543 | 544 | GmBBX59 | zf-B_box[1] |
| 545 | 546 | GmBBX60 | zf-B_box[1] |
| 547 | 548 | GmBBX61 | zf-B_box[1] |
| 549 | 550 | GmBBX62 | zf-B_box[1] |

Abbreviations for Table 2
zf-B_box[1]: first B-box type zinc finger domain
zf-B_box[2]: second B-box type zinc finger domain
CCT: nuclear localization domain
Gm: Glycine max Orthologs and Paralogs Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen, 1998, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al., 1994; Higgins et al., 1996). Groups of similar genes can also be identified with pair-wise BLAST analysis (Feng and Doolittle, 1987). For example, a Glade of very similar MADS domain transcriptional regulators from *Arabidopsis* all share a common function in flowering time (Ratcliffe et al., 2001), and a group of very similar AP2 domain transcriptional regulators from *Arabidopsis* are involved in tolerance of plants to freezing (Gilmour et al., 1998). Analysis of groups of similar genes with similar function that fall within one Glade can yield sub-sequences that are particular to the Glade. These sub-sequences, known as consensus sequences, can not only be used to define the sequences within each Glade, but define the functions of these genes; genes within a Glade may contain paralogous sequences, or orthologous sequences that share the same function (see also, for example, Mount, 2001).

Transcriptional regulator gene sequences are conserved across diverse eukaryotic species lines (Goodrich et al., 1993; Lin et al., 1991; Sadowski et al., 1988). Plants are no exception to this observation; diverse plant species possess transcriptional regulators that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994; Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcriptional regulators, including:

(i) AP2 family *Arabidopsis* G47 (found in U.S. Pat. No. 7,135,616), a phylogenetically-related sequence from soybean, and two phylogenetically-related homologs from rice all can confer greater tolerance to drought, hyperosmotic stress, or delayed flowering as compared to control plants;

(ii) CAAT family *Arabidopsis* G481 (found in PCT patent publication WO2004076638), and numerous phylogenetically-related sequences from dicots and monocots can confer greater tolerance to drought-related stress as compared to control plants;

(iii) Myb-related *Arabidopsis* G682 (found in PCT patent publication WO2004076638) and numerous phylogenetically-related sequences from dicots and monocots can confer greater tolerance to heat, drought-related stress, cold, and salt as compared to control plants;

(iv) WRKY family *Arabidopsis* G1274 (found in U.S. Pat. No. 7,196,245) and numerous closely-related sequences from dicots and monocots have been shown to confer increased water deprivation tolerance, and (v) AT-hook family soy sequence G3456 (found in US Patent publication US20040128712A1) and numerous phylogenetically-related sequences from dicots and monocots, increased biomass compared to control plants when these sequences are overexpressed in plants.

The polypeptides sequences belong to distinct clades of polypeptides that include members from diverse species. In each case, most or all of the Glade member sequences derived from both dicots and monocots have been shown to confer increased yield or tolerance to one or more abiotic stresses when the sequences were overexpressed. These studies each demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

As shown in Table 1 and Table 2, polypeptides that are phylogenetically related to disclosed polypeptides, including SEQ ID NOs: 2n, where n=1 to 117 or 218 to 275, may have conserved domains that share at least 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity to the listed sequences, for example, SEQ ID NOs: 235-427, and have similar functions in that the disclosed and closely related polypeptides may, when overexpressed, confer at least one trait selected from the group consisting of decreased sensitivity to light, increased yield, greater height, greater stem diameter, greater resistance to lodging, increased secondary rooting, greater cold tolerance, greater tolerance to water deprivation, reduced stomatal conductance, altered C/N sensing, increased low nitrogen tolerance, greater late season growth and vigor, greater number of primary nodes, greater late season canopy coverage, increased tolerance to hyperosmotic stress, altered levels of ureides, altered levels of hexose sugars, altered SPS activity, altered levels of starch, and delayed senescence, as compared to a control plant.

At the nucleotide level, sequences that are closely related to the disclosed polynucleotide sequences will typically share at least about 30% or at least 40%, at least 41%, at least 42%, at least 43%, at least 44%, at least 45%, at least 46%, at least 47%, at least 48%, or at least 49% nucleotide sequence identity, preferably at least about 50%, at least 51%, at least 52%, at least 53%, at least 54%, at least 55%, at least 56%, at least 57%, at least 58%, or at least 59% nucleotide sequence identity, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or about 100% sequence identity to one or more of the listed full-length polynucleotide sequences, or to a polynucleotide sequence encoding a conserved domain of a listed polypeptide sequence. The degeneracy of the genetic code enables major variations in the nucleotide sequence of a polynucleotide while maintaining the amino acid sequence of the encoded protein. Polynucleotides that encode polypeptides that are closely-related, that is, orthologous or paralogous, to the disclosed polypeptide sequences will be identifiable by having at least any of the percentage identities provided in this paragraph.

At the polypeptide level, sequences that are closely related to the disclosed polypeptide sequences will typically share at least about 30% or at least 40%, at least 41%, at least 42%, at least 43%, at least 44%, at least 45%, at least 46%, at least 47%, at least 48%, or at least 49% amino acid sequence identity, preferably at least about 50%, at least 51%, at least 52%, at least 53%, at least 54%, at least 55%, at least 56%, at least 57%, at least 58%, or at least 59% nucleotide sequence identity, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or about 100% sequence identity to one or more of the listed full-length polypeptide sequences, or to conserved domain of a listed full length sequence, or to a listed conserved domain, or to a listed polypeptide sequence but excluding or outside of the region(s) encoding a known consensus sequence or consensus DNA-binding site, or outside of the region(s) encoding one or all conserved domains. Polypeptides, or their domains, that are closely-related, that is, orthologous or paralogous, to the disclosed polypeptide sequences, or their domains, will be identifiable by having at least any of the percentage identities provided in this paragraph.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp, 1988). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, WI), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990; Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Unless otherwise indicated for comparisons of predicted polynucleotides, "sequence identity" refers to the % sequence identity generated from a tBlastx using the NCBI version of the algorithm at the default settings using gapped alignments with the filter "off" (see, for example, internet website at www.ncbi.nlm.nih.govf).

Other techniques for alignment are described by Doolittle, 1996. Preferably, an alignment program that permits gaps in the sequence is utilized to align the sequences. The Smith-Waterman is one type of algorithm that permits gaps in sequence alignments (see Shpaer, 1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein, 1990). Identity between sequences can also be determined by other methods known in the art, e.g., by varying hybridization conditions (see US Patent Application No. 20010010913).

Thus, the present disclosure provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhammer et al., 1997), and the like, can be used to manipulate and analyze polynucleotide and polypeptide sequences encoded by polynucleotides. These databases, algorithms and other methods are well known in the art and are described in Ausubel et al., 1997, and in Meyers, 1995.

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow, 2002, have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and B-box zinc finger domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present disclosure according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in Tables 1 and 2 and in the Sequence Listing. In addition to the sequences in Table 1, Table 2, and the Sequence Listing, the present disclosure encompasses isolated nucleotide sequences that are phylogenetically and structurally similar to sequences listed in the Sequence Listing and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions.

Polynucleotides that encode polypeptides that are closely-related, that is, orthologous or paralogous, to the disclosed polypeptide sequences may be identifiable by their ability to hybridize to the disclosed polynucleotides under high stringency conditions, including the high stringency conditions provided herein.

Single stranded polynucleotides hybridize when they associate based on a variety of well characterized physical-chemical forces, such as hydrogen bonding, solvent exclusion, base stacking and the like. The stringency of hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the present disclosure are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger, 1987, pages 467-469; and Anderson and Young, 1985).

Stability of DNA duplexes is affected by such factors as base composition, length, and degree of base pair mismatch. Hybridization conditions may be adjusted to allow DNAs of different sequence relatedness to hybridize. The melting temperature (T m) is defined as the temperature when 50% of the duplex molecules have dissociated into their constituent single strands. The melting temperature of a perfectly matched duplex, where the hybridization buffer contains formamide as a denaturing agent, may be estimated by the following equations:

$$T_m(°\ C.)=81.5+16.6(\log[Na+])+0.41(\%\ G+C)-0.62(\%\ \text{formamide})-500/L \quad \text{(I) DNA-DNA:}$$

$$T_m(°\ C.)=79.8+18.5(\log[Na+])+0.58(\%\ G+C)+0.12(\%\ G+C)2-0.5(\%\ \text{formamide})-820/L \quad \text{(II) DNA-RNA:}$$

$$T_m(°\ C.)=79.8+18.5(\log[Na+])+0.58(\%\ G+C)+0.12(\%\ G+C)2-0.35(\%\ \text{formamide})-820/L \quad \text{(III) RNA-RNA:}$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex>150 base pairs. Hybridization may be performed at low to moderate stringency (25-50° C. below T m), followed by post-hybridization washes at increasing stringencies. Maximum rates of hybridization in solution are determined empirically to occur at $T_m$-25° C. for DNA-DNA duplex and $T_m$-15° C. for RNA- DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC at 65° C.;

50% formamide, 4×SSC at 42° C.; or 0.5×SSC, 0.1% SDS at 65° C.;

with, for example, two wash steps of 10-30 minutes each. Useful variations on these conditions will be readily apparent to those skilled in the art.

A person of skill in the art would not expect substantial variation among polynucleotide species encompassed within the scope of the present disclosure because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C. −68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the present disclosure are polynucleotide sequences that are capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

Sequence Variations

It will readily be appreciated by those of skill in the art that the instant disclosure includes any of a variety of polynucleotide sequences provided in the Sequence Listing or capable of encoding polypeptides that function similarly to those provided in the Sequence Listing. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (that is, peptides having some degree of equivalent or similar biological activity) but differ in sequence from the sequence shown in the sequence listing due to degeneracy in the genetic code, are also within the scope of the instant disclosure and claims.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, for example, site-directed mutagenesis, available in the art. Accordingly, any and all such variations of a sequence selected from the above tables are a feature of the disclosure.

In addition to silent variations, other conservative variations that alter one, or a few amino acids in the encoded polypeptide, can be made without altering the function of the polypeptide. For example, substitutions, deletions and insertions introduced into the sequences provided in the Sequence Listing are also envisioned. Such sequence modifications can be engineered into a sequence by site-directed mutagenesis (for example, Olson et al., Smith et al., Zhao et al., and other articles in Wu, 1993), or the other methods known in the art or noted herein Amino acid substitutions are typically of single residues; insertions usually will be on the order of about from 1 to 10 amino acid residues; and deletions will range about from 1 to 30 residues. In preferred embodiments, deletions or insertions are made in adjacent pairs, for example, a deletion of two residues or insertion of two residues. Substitutions, deletions, insertions or any combination thereof can be combined to arrive at a sequence. The mutations that are made in the polynucleotide encoding the transcriptional regulator should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 3 when it is desired to maintain the activity of the protein. Table 3 shows amino acids which can be substituted for an amino acid in a protein and which are typically regarded as conservative substitutions.

TABLE 3

Possible conservative amino acid substitutions

| Amino Acid Residue | Conservative substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

The polypeptides provided in the Sequence Listing have a novel activity, such as, for example, regulatory activity. Although all conservative amino acid substitutions (for example, one basic amino acid substituted for another basic amino acid) in a polypeptide will not necessarily result in the polypeptide retaining its activity, it is expected that many of these conservative mutations would result in the polypeptide retaining its activity. Most mutations, conservative or non-conservative, made to a protein but outside of a conserved domain required for function and protein activity will not affect the activity of the protein to any great extent.

EXAMPLES

It is to be understood that the present disclosure is not limited to the particular devices, machines, materials and methods described. Although particular embodiments are described, equivalent embodiments may be used to produce the instant compositions and practice the instant methods.

The disclosure, now being generally described, will be more readily understood by reference to the following examples, which are included merely for purposes of illustration of certain aspects and embodiments of the present disclosure and are not intended to limit claims to the instant compositions or methods. It will be recognized by one of skill in the art that a polypeptide that is associated with a particular first trait may also be associated with at least one other, unrelated and inherent second trait which was not predicted by the first trait.

Example I. Vector and Cloning Information for *Arabidopsis*

A number of constructs were used to modulate the activity of the disclosed sequences. An individual project was defined as the analysis of lines for a particular construct (for example, this might include any of the disclosed lines that constitutively overexpress a disclosed B-box polypeptide sequence). In the present study, a full-length wild-type version of a gene was directly fused to a promoter that drove its expression in transgenic plants. Such a promoter could be the native promoter of that gene, or the CaMV 35S promoter. Alternatively, a promoter that drives tissue specific or conditional expression could be used in similar studies.

In the present study, expression of a given polynucleotide from a particular promoter was achieved by either a direct-promoter fusion construct in which that sequence was cloned directly behind the promoter of interest, or by a two-component expression system. A direct fusion approach has the advantage of allowing for simple genetic analysis if a given promoter-polynucleotide line is to be crossed into different genetic backgrounds at a later date. The two-component method, on the other hand, potentially allows for greater versatility in the creation of various promoter-gene combinations, and has the potential for generating stronger expression to be obtained via an amplification of transcription.

A list of constructs (PIDs) used to transform plants, indicating the promoter fragment that was used to drive the transgene and the cloning vector backbone, is provided in Table 4. Compilations of the sequences of promoter fragments and the expressed transgene sequences within the PIDs are provided in the Sequence Listing. The list of constructs presented in Table 4 is not intended to limit the instant description; other constructs that may be used to transform plants, and which may comprise useful promoter-gene combinations that are active in various tissues or in response to various or particular environmental conditions may also be envisioned.

Example II. Transformation

Gruber et al., 1993, described several expression vectors and culture methods that may be used for cell or tissue transformation and subsequent regeneration.

Dicot and monocot expression vectors Transformation of plants and plant parts by *Agrobacterium*-mediated transformation can be practiced using a recombinant DNA construct, vector or cassette with the genetic elements as shown in Table 5 for dicots and Table 6 for monocots. The disclosed recombinant polynucleotides in the Sequence Listing "MBI_0120 PCT_ST25" may be incorporated in such recombinant DNA constructs. The elements in a recombinant DNA construct provided in Tables 5 and 6 are only examples of different elements that can be used for the purpose of producing transgenic plants that have incorporated the polynucleotides. Other elements can be used as well in combination with the polynucleotides of the present disclosure to achieve trait modification.

A base recombinant DNA construct specifically useful for inserting a recombinant expression cassette into a chromosome in a nucleus in a dicot plant by *Agrobacterium*-mediated transformation is provided in Table 5. In Table 5, column 1 describes the function of the segment of the vector, column 2 provides a short name of a discrete genetic element and column 3 provides a more detailed description of the element.

TABLE 4

Sequences of promoter fragments and the expressed transgene sequences

| Gene Identifier | SEQ ID NO: of Gene Identifier | Plant from which sequence derived | Construct (PID) | Promoter:: Leader | Expression construct(s) |
|---|---|---|---|---|---|
| AT4G27310; or AtBBX28 (G1481) | 1 | *Arabidopsis* | pMON125158 | 35S::Hsp70L | Direct promoter-fusion |
| AT2G31380; or AtBBX25 (G1894) | 153 | *Arabidopsis* | pMON125664 | 35S::Hsp70L | Direct promoter-fusion |
| AT1G06040 or AtBBX24 (G329) | 151 | *Arabidopsis* | pMON125195 | 35S::Hsp70L | Direct promoter-fusion |
| AT4G15248; or AtBBX30 (G1478) | 39 | *Arabidopsis* | pMON125199 | 35S::Hsp70L | Direct promoter-fusion |
| At2G21320; or AtBBX18 (G1881) | 201 | *Arabidopsis* | pMON125196 | 35S::Hsp70L | Direct promoter-fusion |
| AT3G07650 or AtBBX7 (G2440) | 103 | *Arabidopsis* | pMON125230 | 35S::Hsp70L | Direct promoter-fusion |
| AT1G60250 or AtBBX26 (G1486) | 51 | *Arabidopsis* | pMON125732 | 35S::Hsp70L | Direct promoter-fusion |
| At4G38960 or AtBBX19 (G9902) | 199 | *Arabidopsis* | pMON125730 | 35S::Hsp70L | Direct promoter-fusion |
| AT4G39070 or AtBBX20 (G1888) | 53 | *Arabidopsis* | pMON125197 | 35S::Hsp70L | Direct promoter-fusion |

TABLE 5

Example of an expression vector useful for transformation of dicot plants and plant parts.

| Function | Name | Element Description |
|---|---|---|
| *Agrobacterium* T-DNA transfer | B-AGRtu.left border | Agro left border sequence, essential for transfer of T-DNA. |
| Plant selectable marker expression cassette | P-At.Act7 | Promoter from the *Arabidopsis* actin 7 gene |
| | L-At.Act7 | 5'UTR of *Arabidopsis* Act7 gene |
| | I-At.Act7 | Intron from the *Arabidopsis* actin7 gene |
| | TS-At.ShkG-CTP2 | Transit peptide region of *Arabidopsis* EPSPS |
| | CR-AGRtu.aroA-CP4.nno_At | Codon modified CP4 coding region |
| | T-AGRtu.nos | A 3' non-translated region of the nopaline synthase gene of *Agrobacterium tumefaciens* Ti plasmid which functions to direct polyadenylation of the mRNA. |
| Gene of interest expression cassette | P-CaMV.35S-cnh | Promoter for 35S RNA from CaMV containg a duplication of the −90 to −350 region. |
| | GOI | A polynucleodtide or polypeptide-coding sequence in Tables 1 or 2 |
| | T-Gb.E6-3b | 3' untranslated region from the fiber protein E6 gene of sea-island cotton. |
| *Agrobacterium* T-DNA transfer | B-AGRtu.right border | Agro right border sequence, essential for transfer of T-DNA. |
| Maintenance in *E. coli* | OR-Ec.oriV-RK2 | The vegetative origin of replication from plasmid RK2. |
| | CR-Ec.rop | Coding region for repressor of primer from the ColE1 plasmid. Expression of this gene product interferes with primer binding at the origin of replication, keeping plasmid copy number low. |
| | OR-Ec.ori-ColE1 | The minimal origin of replication from the *E. coli* plasmid ColE1. |
| | P-Ec.aadA-SPC/STR | Promoter for Tn7 adenylytransferase (AAD (3")) |
| | CR-Ec.aadA-SPC/STR | Coding region for Tn7 adenylyltransferase (AAD (3")) conferring spectinomycin and streptomycin resistance. |
| | T-Ec.aadA-SPC/STR | 3' UTR from the Tn7 adenylyltransferase (AAD (3")) gene of *E. coli*. |

An example of an expression vector that may be used to transform a monocot plant by *Agrobacterium*-mediated transformation is provided in Table 6. In Table 6, column 1 describes the function of the segment of the vector, column 2 provides a short name of the discrete genetic elements and column 3 provides a more detailed description of the elements.

TABLE 6

Example of an expression vector useful for transformation of monocot plants and plant parts.

| Function | Name | Element Description |
|---|---|---|
| *Agrobacterium* T-DNA trasfer | B-AGRtu.right border | *Agrobacterium* right border sequence essential for transfer of T-DNA. |
| Gene of interest expression cassette | E-Os.Act1 | Upstream promoter region of the rice actin 1 gene |
| | E-CaMV.35S.2xA1-B3 | Duplicated35S A1-B3 domain without TATA box |
| | P-Os.Act1 | Promoter region of the rice actin 1 gene |
| | L-Ta.Lhcb1 | 5' untranslated leader of wheat major chlorophyll a/b binding protein |
| | I-Os.Act1 | First intron and flanking UTR exon sequences from the rice actin 1 gene |
| | GOI | A polynucleotide or polypeptide-coding sequence in Table 1 and Table 2 |
| | T-St.Pis4 | 3' non-translated region of the potato proteinase inhibitor II gene which functions to direct polyadenylation of the mRNA |
| Plant selectable marker expression cassette | P-Os.Act1 | Promoter from the rice actin 1 gene |
| | L-Os.Act1 | First exon of the rice actin 1 gene |
| | I-Os.Act1 | First intron and flanking UTR exon sequences from the rice actin 1 gene |
| | TS-At.ShkG-CTP2 | Transit peptide region of *Arabidopsis* EPSPS |
| | CR-AGRtu.aroA-CP4.nat | Coding region for bacterial strain CP4 native aroA gene. |
| | T-AGRtu.nos | A 3' non-trranslated region of the nopaline synthase gene of *Argrobacterium tumefaciens* Ti plasmid which functions to direct polyadenylation of the mRNA. |
| *Agrobacterium* T-DNA transfer | B-AGRtu.left border | Agro left border sequence, essential for transger of T-DNA. |

TABLE 6-continued

Example of an expression vector useful for transformation of monocot plants and plant parts.

| Function | Name | Element Description |
|---|---|---|
| Maintenance in *E. coli* | OR-Ec.oriV-RK2 | The vegetative origin of replication from plasmid RK2. |
| | CR-Ec.rop | Coding region for repressor of primer from the ColE1 plasmid. Expression of this gene product interferes with primer binding at the origin of replication, keeping plasmid copy number low. |
| | OR-Ec.ori-ColE1 | The minimal origin of replication from the *E. coli* plasmid ColE1. |
| | P.Ec.aadA-SPC/STR | Promoter for Tn7 adenylyltransferase (AAD (3")) |
| | CR-Ec.aadA-SPC/STR | Coding region for Tn7 adenylyltransferase (AAD (3")) conferring spectinomycin and streptomycin resistance. |
| | T-Ec.aadA-SPC/STR | 3' UTR from the Tn7 adenylyltransferase (AAD (3")) gene of *E. coli*. |

To construct expression vectors for expressing a protein identified in Table 1 and Table 2, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the intron element and the polyadenylation element (Table 5 or Table 6, depending on whether the plant to be transformed is a dicot or monocot, respectively).

To construct expression vectors for suppressing a protein identified in Tables 1 and 2, the amplified protein coding nucleotides may be assembled in a sense and antisense arrangement and inserted into the base expression vector at the insertion site in the gene of interest expression cassette (Table 5 or Table 6, depending on whether the plant to be transformed is a dicot or monocot, respectively) to provide transcribed RNA that will form a double-stranded RNA for RNA interference suppression of the protein. Expression vectors for suppressing a protein identified in Tables 1 and 2 may also be designed to insert an expression cassette that expresses (a) a miRNA that targets the gene for suppression, (b) a messenger RNA that is translated to the target protein and has a synthetic miRNA recognition site that would result in down-modulation of the target protein, (c) an RNA that forms a dsRNA and that is processed into siRNAs that effect down regulation of the target protein, (d) a ssRNA that forms a ta-siRNA which results in the production of siRNAs that effect down-modulation of the target protein.

Transformation of Dicots or Eudicots to Produce Increased Yield and/or Abiotic Stress Tolerance Crop species that overexpress or suppress the disclosed and closely related polypeptides may produce plants with increased water deprivation or drought tolerance, cold and/or nutrient tolerance and/or yield in both stressed and non-stressed conditions. Thus, polynucleotide sequences listed in the Sequence Listing recombined into, for example, one of the disclosed expression vector, or another suitable expression vector such as one comprising a sequence that is closely related to the instantly disclosed sequences, may be transformed into a plant for the purpose of modifying plant traits such as improved yield and/or quality. The expression vector may contain a constitutive promoter, an inducible promoter, a diurnally-regulated promoter, a tissue-enhanced promoter, a tissue-preferred promoter, or a tissue-specific promoter operably linked to the polynucleotide.

The expression vector may be introduced into a variety of plants by means well known in the art such as, for example, direct DNA transfer or *Agrobacterium tumefaciens*-mediated transformation. It is now a routine to produce transgenic plants from most dicot plants (see Weissbach and Weissbach, 1989; Gelvin et al., 1990; Herrera-Estrella et al., 1983; Bevan, 1984; and Klee, 1985). Methods for analysis of traits are routine in the art and examples are disclosed above. There are a substantial number of alternatives to *Agrobacterium*-mediated transformation protocols. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 (Christou et al, issued May 14, 1991); and U.S. Pat. No. 5,322,783 (Tomes et al., issued Jun. 21, 1994)). Alternatively, sonication methods (see, for example, Zhang et al., 1991); direct uptake of DNA into protoplasts using $CaCl_2$) precipitation, polyvinyl alcohol or poly-L-ornithine (see, for example, Hain et al., 1985; Draper et al., 1982); liposome or spheroplast fusion (see, for example, Deshayes et al., 1985; Christou et al., 1987); and electroporation of protoplasts and whole cells and tissues (see, for example, Donn et al., 1990; D'Halluin et al., 1992; and Spencer et al., 1994) have been used to introduce foreign DNA and expression vectors into plants.

Transformation of *Arabidopsis*

Transformation of *Arabidopsis* was performed by an *Agrobacterium*-mediated protocol based on the method of Bechtold and Pelletier, 1998. Unless otherwise specified, all experimental work was done using the Columbia ecotype.

Plant preparation. *Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. *Agrobacterium* stocks were inoculated from single colony plates or from glycerol stocks and grown with the appropriate antibiotics until saturation. On the morning of transformation, the saturated cultures were centrifuged and bacterial pellets were re-suspended in Infiltration Media (0.5×MS, 1×B5 Vitamins, 5% sucrose, 1 mg/ml benzylaminopurine riboside, 200 μl/L Silwet L77) until an A600 reading of 0.8 was reached.

Transformation and seed harvest. The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This seed was deemed TO seed, since it was obtained from the TO generation, and was later plated on selection plates (with either kanamycin or sulfonamide, see Example VI). Resistant plants that were identified on such selection plates comprised the T1 generation.

Several independently transformed lines with each gene were grown on MS-agar plates without sucrose. After stratification, a 3 h white light treatment was used to synchronize germination, followed by 21 h of dark treatment, before transferring the plates to continuous red light (30-40 μmoles/m 2/s). Hypocotyl lengths were measured from digital images of 20-30 seedlings per line and compared to appropriate controls. Mean values of hypocotyl length were plotted with standard errors to determine whether increased expression of each of the B-box genes resulted in elongated hypocotyls, suggesting a negative role in light signaling.

Transformation of Tomato Plants

Transformation of tomato plants may be conducted using the protocols of Koornneef et al, 1986, and in U.S. Pat. No. 6,613,962. The latter method is described briefly here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 nM α-naphthalene acetic acid and 4.4 nM 6-benzylaminopurine. The explants are then infected with a diluted overnight culture of *Agrobacterium tumefaciens* containing an expression vector comprising a disclosed or orthologous or paralogous polynucleotide for 5-10 minutes, blotted dry on sterile filter paper and cocultured for 48 hours on the original feeder layer plates. Overnight cultures of *Agrobacterium tumefaciens* are diluted in liquid MS medium with 2% (w/v) sucrose, pH 5.7) to an $OD_{600}$ of 0.8.

Following cocultivation, the cotyledon explants are transferred to Petri dishes with selective medium comprising MS medium with 4.56 nM zeatin, 67.3 nM vancomycin, 418.9 nM cefotaxime and 171.6 nM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of Soybean Plants

Transformation of soybean plants may be conducted using the methods found in, for example, Mild et al., 1993, and U.S. Pat. Nos. 5,914,451, 5,824,877 and 6,384,301.

For *Agrobacterium* mediated transformation, soybean seeds are imbibed overnight and the meristem explants excised. Soybean explants are mixed with induced *Agrobacterium* cells from a strain containing plasmid DNA with the gene of interest cassette and a plant selectable marker cassette no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

Transformation of Cotton Plants

Transformation of cotton plants may be performed as generally described in WO0036911, U.S. Pat. Nos. 5,846,797, 7,790,460 and 7,947,869.

Transformation of Canola Plants

Transformation of rapeseed/canola plants may be performed as described in U.S. Patent Publication No. 2010/0218271. Alternatively, transformation of cotyledonary petioles and hypocotyls of 5-6 day old young canola seedlings are used as explants for tissue culture and transformed according to Babic et al., 1998.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterizations are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant.

Obtaining and Screening Events

The above process is repeated to produce multiple events of transgenic soybean, cotton and canola plant cells that are transformed with recombinant DNA of the present disclosure. Progeny transgenic plants and seed of the transformed plant cells are screened for decreased sensitivity to light, increased yield, greater height, greater stem diameter, greater resistance to lodging, increased secondary rooting, greater cold tolerance, greater tolerance to water deprivation or drought, reduced stomatal conductance, altered C/N sensing, increased tolerance to nitrogen limited conditions, greater late season growth and vigor, greater number of primary nodes, greater late season canopy coverage, increased tolerance to hyperosmotic stress, altered levels of ureides, altered levels of hexose sugars, altered SPS activity, altered levels starch, and delayed senescence.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and their conferred traits may be moved into distinct lines of plants using traditional backcrossing techniques well known in the art.

Transformation of Monocots to Produce Increased Yield or Abiotic Stress Tolerance Cereal plants such as, but not limited to, corn, wheat, rice, sorghum, sugarcane, or barley, may be transformed with the present polynucleotide sequences, including monocot or dicot-derived sequences such as those presented in the present Tables, cloned into an expression vector such as the one described in Table 6 or pGA643 containing a kanamycin-resistance marker or a herbicide-tolerance marker such as a glyphosate-tolerance marker, and expressed constitutively under, for example, the CaMV 35S or COR15 promoters, or with tissue-specific, tissue-enhanced, tissue preferred, diurnally-regulated or inducible promoters. The expression vectors may be one found in the Sequence Listing (for example, pMEN65, SEQ ID NO: 428), or any other suitable expression vector may be similarly used.

The expression vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting the dedifferentiating tissue with the *Agrobacterium* containing the expression vector.

The sample tissues are immersed in a suspension of $3\times10^{-9}$ cells of *Agrobacterium* containing the expression vector for 3-10 minutes. The callus material is cultured on solid medium at 25° C. in the dark for several days. The calli grown on this medium are transferred to fresh Regeneration medium at 2-3 week intervals(2 or 3 times) until shoots develop. Shoots are then transferred to Shoot-Elongation medium every 2-3 weeks. Healthy-looking shoots are transferred to rooting medium and after roots have developed, the plants are placed into moist potting soil.

For *Agrobacterium*-mediated transformation of corn embryo cells, corn plants of a readily transformable line are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing a selective agent and subcultured at about two week intervals. Transformed plant cells are recovered 6 to 8 weeks after initiation of selection. To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

The transformed plants are analyzed for the presence of the NPTII or other marker protein by ELISA, using the ELISA NPTII kit from 5Prime-3Prime Inc. (Boulder, CO), or for the presence of the transgene by PCR.

Examples of wheat transformation are illustrated in U.S. Pat. No. 6,153,812 (microprojectile bombardment method) and U.S. Pat. No. 7,026,528 (*Agrobacterium*-mediated method).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1990), wheat (Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). After microprojectile bombardment the tissues are selected on selection medium to identify the transgenic embryogenic cells (Gordon-Kamm et al., 1990). Transgenic plants are regenerated by standard corn regeneration techniques (Fromm et al., 1990; Gordon-Kamm et al., 1990).

Example III. Stacking of the Disclosed Polynucleotides with Other Sequences of Interest Including Other Disclosed Polynucleotides It is envisioned that one or more of the polynucleotides in the instant sequence listing can be introduced into a plant in combination with other disclosed polynucleotide sequences, or with other polynucleotide sequences of interest (that is, the polynucleotides may be "stacked" within the plant) for the purpose of producing plants with enhanced or multiple useful traits. A single plant may thus comprise and ectopically express, overexpress, or suppress one or more of the disclosed polynucleotide sequences and/or their encoded polypeptides. For example, since it was shown that AtBBX32 was physically associated with GmBBX62 in vivo (Example V), introduction and co-expression of both AtBBX32 and GmBBX62 in a transgenic plant may provide the transgenic plant with enhanced traits. Therefore, stacking of the disclosed polynucleotide sequences may be used to create one or more transgenic plants with at least one useful trait, said traits including, for example (but not limited to), decreased sensitivity to light, increased yield, greater height, greater stem diameter, greater resistance to lodging, increased secondary rooting, greater cold tolerance, greater tolerance to water deprivation or drought, reduced stomatal conductance, altered C/N sensing, increased tolerance to nitrogen limiting conditions, improved late season growth and vigor, greater number of nodes, greater late season canopy coverage, increased tolerance to hyperosmotic stress, altered levels of ureides, altered levels of hexose sugars, altered SPS activity, altered levels of starch, and delayed senescence, as compared to a control plant that does not ectopically express or overexpress the disclosed polynucleotide sequences.

The combinations of polynucleotides introduced into target plants may also include multiple copies of any one of the disclosed polynucleotides. The disclosed polynucleotides may also be stacked with any other polynucleotide or combination of polynucleotide to produce transgenic plants with one or more useful trait combinations, including, for example (but not limited to), one or more of the traits listed in the previous paragraph, and possibly herbicide resistance (e.g., glyphosate resistance), disease resistance or tolerance, increased tolerance to heat, increased tolerance to oxidative stress, increased oil content, male sterility, lodging resistance, early flowering and/or development, delayed flowering and/or development, extended flowering and/or development time, traits desirable for chemical processing, and/or improved digestibility.

The combinations of polynucleotides within an individual plant can be introduced through a variety of means. This may include, for example, transforming a target plant with two or more nucleic acid sequences of interest at the same time or at different times, or introducing the two or more nucleic acid sequences of interest by different means such as a combination of transformation and breeding, where the nucleic acid sequences may be integrated into one or more loci. The two sequence cassettes can be contained in separate expression vectors (trans), where one of the expression vectors comprises a trans-acting element. A trans-acting element is a DNA sequence that controls transcriptional activity of a target gene through a diffusible gene product such as a protein, microRNA, or other diffusible repressor or activator. The regulated target gene may include a polynucleotide of the instant Sequence Listing. Alternatively, the two sequence cassettes can be contained in the same expression vector (cis). Introducing the sequences at the same time into a plant may be referred to as co-transformation, simultaneous transformation, or parallel transformation. Combinations of recombinant polynucleotides can also be introduced into a plant through subsequent, serial or super-transformation or re-transformation, that is, by providing a transgenic plant previously transformed with one polynucleotide of interest, and transforming the same plant with one or more distinct recombinant polynucleotides. In this method, a transgenic plant exhibiting one or more desired traits can be used as a target plant to introduce additional traits by super-transformation.

Thus, if the polynucleotide sequences (including one or more of the disclosed polynucleotide sequences) are introduced into plants by genetic transformation, the polynucleotide sequences can be transformed into the plant at any time and in any order.

Another method of stacking genes in a plant combines transformation with breeding methods. A plant that has been transformed with at least one polynucleotide sequence of interest (including one or more of the disclosed polynucleotide sequences) may be cross-bred with a transgenic or non-transformed plant in order to stack more than one gene in the plant.

Expression of the polynucleotide sequences can be regulated by the same promoter or by different promoters.

It may also be desirable to introduce an expression vector or cassette that will suppress the expression of a polynucleotide of interest. This may be combined with any combination of other suppression vectors or cassettes or overexpression vectors or cassettes to generate a desirable combination of traits in the plant, including traits disclosed in this Example.

Example IV. Expression and Analysis of Increased Yield and/or Abiotic Stress Tolerance in non-*Arabidopsis* Species or Crop Plants It has been shown that overexpression of a B-box polypeptide, BBX32 (At.BBX32; SEQ ID NO: 430), decreases light sensitivity of plants when the polypeptide is overexpressed in the plants, including in plants other than *Arabidopsis* (e.g., crop plants). BBX32 has been shown to improve crop performance and acts to repress the transcriptional activity of another B-box protein, AtBBX21 (G1482, SEQ ID NO: 56) on its native target promoter (prCHS) sequences (unpublished data). The instantly disclosed results provide evidence that HA:AtBBX28 (G1481) inhibited the transcriptional activity of HA:AtBBX21 to levels similar to the repression by HA:BBX32 (FIG. 2), suggesting that AtBBX28 is able to act as a repressor like BBX32. AtBBX28 may have common targets with BBX32 (FIG. 2) or it may act on specific targets independently of BBX32.

In fact, a number of the disclosed polypeptide sequences, including those found in the Sequence Listing, including SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234,436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548 or 550 or orthologous sequences (as defined or claimed herein) that function in the same manner, may alter light sensitivity of plants when the sequences are overexpressed in the plants. It is expected that structurally similar orthologs and paralogs of the disclosed polypeptide sequences, which may be derived from diverse plant species, will also alter light sensitivity of plants when these orthologous and paralogous sequences are overexpressed. Furthermore, it is expected that the disclosed B-box polypeptide sequences, and structurally similar orthologs and paralogs of the disclosed B-box polypeptide sequences, can, at least in part and as a result of their altering light sensitivity, confer increased yield or increased tolerance to a number of abiotic stresses, including water deprivation or drought, cold, and nitrogen-limiting conditions, altered levels of ureides, altered levels of hexose sugars, altered SPS activity, altered levels of starch, and delayed senescence, relative to control plants, and thus may increase yield of crop or other commercially important plant species.

Relationships between the disclosed sequences in the present disclosure may be recognized by comparing structural similarity, for example, determined by a disclosed percentage identity to full length protein or their conserved domains, or by hybridization to a disclosed polynucleotide sequence.

Northern blot analysis, RT-PCR or microarray analysis of the regenerated, transformed plants may be used to show expression of a polypeptide of the present disclosure, or related orthologous or paralogous sequences that are capable of inducing increased yield or increased tolerance to abiotic stresses, including water deprivation, cold, and low nitrogen conditions.

After a eudicot plant, dicot plant, monocot plant or plant cell has been transformed (and the latter regenerated into a plant) and shown to have increased tolerance to abiotic stresses, including water deprivation or drought, cold, and nitrogen-limiting conditions, that is, able to tolerate greater planting density with a coincident increase in yield, or tolerance to abiotic stress, or produce greater yield relative to a control plant in the absence of stress conditions or under stress conditions, the transformed plant may be crossed with itself or a plant from the same line, a non-transformed or wild-type plant, or another transformed plant from a different transgenic line of plants.

The functions of specific polypeptides, including closely-related orthologs, may be analyzed and may be further characterized and incorporated into crop plants. The ectopic overexpression of these sequences may be regulated using constitutive, inducible, or tissue specific regulatory elements. Genes that have been examined and have been shown to modify plant traits (including altered light sensitivity with predicted increased yield and/or abiotic stress tolerance)

encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group from which the sequence is derived.

As an example of a first step to determine water deprivation-related tolerance, seeds of these transgenic plants may be subjected to germination assays to measure sucrose sensing, severe desiccation or drought. Methods that may be used to measure relative sucrose sensing, severe desiccation tolerance or drought tolerance in genetically altered (for example, over-expressing) and control plants are as follows. For sucrose sensing, germination assays may be conducted in growth media containing 9.4% sucrose with *Arabidopsis* overexpressors of BBX32 and closely-related sequences. Growing the plants under controlled temperature and humidity on sterile medium produces uniform plant material that has not been exposed to additional stresses (such as water stress) which could cause variability in the results obtained. Where possible, assay conditions are originally tested in a blind experiment with controls that have phenotypes related to the condition tested.

Prior to plating, seed for all experiments are surface sterilized in the following manner: (1) 5 minute incubation with mixing in 70% ethanol, (2) 20 minute incubation with mixing in 30% bleach, 0.01% triton-X 100, (3) 5×rinses with sterile water, (4) Seeds are re-suspended in 0.1% sterile agarose and stratified at 4° C. for 3-4 days. Germination assays follow modifications of the same basic protocol. Sterile seeds are sown on the conditional media that has a basal composition of 80% MS+Vitamins Plates are incubated at 22° C. under 24-hour light (120-130 $\mu E\ m^{-2}S^{-1}$) in a growth chamber. Evaluation of germination and seedling vigor is performed five days after planting.

For severe desiccation (plate-based water deprivation) assays, seedlings are grown for 14 days on MS+Vitamins+1% Sucrose at 22° C. Plates are opened in a sterile hood for 3 hr for hardening and then seedlings are removed from the media and dried for two hours in the sterile hood. After this time the plants are transferred back to plates and incubated at 22° C. for recovery. The plants are then evaluated after five days.

The soil drought assay (performed in clay pots) is based on that described by Haake et al., 2002.

Previously, we have performed clay-pot assays on segregating T2 populations, sown directly to soil. However, in the current procedure, seedlings are first germinated on selection plates containing either kanamycin or sulfonamide.

Seeds are sterilized by a 2 minute ethanol treatment followed by 20 minutes in 30% bleach/0.01% Tween and five washes in distilled water. Seeds were sown to MS agar in 0.1% agarose and stratified for three days at 4° C., before transfer to growth cabinets with a temperature of 22° C. After seven days of growth on selection plates, seedlings are transplanted to 3.5 inch diameter clay pots containing 80 g of a 50:50 mix of vermiculite:perlite topped with 80 g of ProMix. Typically, each pot contains 14 seedlings, and plants of the transgenic line being tested are in separate pots to the wild-type controls. Pots containing the transgenic line versus control pots are interspersed in the growth room, maintained under 24-hour light conditions (18-23° C., and 90-100 $\mu E\ m^{-2}S^{-1}$) and watered for a period of 14 days. Water is then withheld and pots are placed on absorbent paper for a period of 8-10 days in to apply a drought treatment. After this period, a visual qualitative “drought score” from 0-6 is assigned to record the extent of visible drought stress symptoms. A score of “6” corresponds to no visible symptoms whereas a score of “0” corresponds to extreme wilting and the leaves having a “crispy” texture. At the end of the drought period, pots are re-watered and scored after 5-6 days; the number of surviving plants in each pot is counted, and the proportion of the total plants in the pot that survived is calculated.

In a given experiment, six or more pots of a transgenic line are compared with six or more pots of the appropriate control. The mean drought score and mean proportion of plants surviving (survival rate) are calculated for both the transgenic line and the wild-type pots. In each case a p-value* is calculated, which indicates the significance of the difference between the two mean values. The results for each transgenic line across each planting for a particular project are then presented in a results table.

Calculation of p-values. For the assays where control and experimental plants were in separate pots, survival is analyzed with a logistic regression to account for the fact that the random variable is a proportion between 0 and 1. The reported p-value is the significance of the experimental proportion contrasted to the control, based upon regressing the logit-transformed data.

Drought score, being an ordered factor with no real numeric meaning, is analyzed with a non-parametric test between the experimental and control groups. The p-value is calculated with a Mann-Whitney rank-sum test.

Plants overexpressing the disclosed, orthologous or paralogous sequences may be found to be more tolerant to high sucrose by having better germination, longer radicles, and more cotyledon expansion.

Disclosed or orthologous or paralogous sequences, or other sequences closely related to the disclosed B-box polynucleotides and B-box polypeptides, may also be used to generate transgenic plants that are more tolerant to nitrogen-limiting conditions or cold than control plants.

All of these abiotic stress tolerances conferred by disclosed B-box polynucleotides and B-box polypeptides may contribute to increased yield of commercially available plants. BBX32 overexpressors have been shown to increase yield of plants in the apparent absence of significantly obvious abiotic stress, as evidenced by including increased height, increased early season vigor and estimated stand count, and increased late season canopy coverage observed in soy plants overexpressing BBX32. Thus, it is expected that disclosed B-box polynucleotides and B-box polypeptides, and closely related orthologs and paralogs, will also improve yield in plants relative to control plants, including in leguminous species, even in the absence of overt abiotic stresses.

It is expected that the disclosed methods may be applied to identify other useful and valuable sequences of the present polypeptide clades, and the sequences may be derived from a diverse range of plant species. These sequences and/or the sequences provided in the Sequence Listing may be introduced into plants other than *Arabidopsis* (e.g., crop plants), and by expressing said sequences may thus be made more tolerant than controls to water deprivation assays, nitrogen-limiting conditions or cold, and/or produce greater yield. It is expected that said plants under these conditions are greener, more vigorous, will have better survival rates than controls, or will recover better from these treatments than control plants.

Example V. Results

The data presented herein present the results obtained in experiments with polynucleotides and polypeptides that may be expressed in plants in order to obtain advantageous traits in said plants including improved yield under non-stressed or low stress conditions, or for reduced yield losses under biotic and abiotic stress conditions.

We have previously demonstrated that under a variety of conditions, including unstressed, nutrient stress, or osmotic stress conditions, *Arabidopsis* seedlings ectopically expressing AtBBX32 showed increased hypocotyl growth rates and altered transcription of genes associated with light regulated signal transduction and photosynthesis. Soybean plants ectopically expressing AtBBX32 were taller, tended to have more nodes, pods, and flowers, greater late season canopy coverage, improved late season vigor, in some cases had thicker stems, and ultimately had significantly higher broad acre yield than wild-type soybean plants did (e.g., see Creelman et al., U.S. Pat. No. 7,692,067). Based on a phylogenetic analysis of the soybean B-box family, G4004 (also referred to as *Glycine max* BBX53 or GmBBX53, and listed as SEQ ID NO: 432 or 532), GmBBX52 variant (SEQ ID NO: 434) and GmBBX52 (SEQ ID NO: 530) were identified as the soybean orthologs of the *Arabidopsis* AtBBX32 gene. Like AtBBX32, both soybean genes contain a single N-terminus B-box domain. Both soybean genes had diurnal oscillations in transcript abundance. *Arabidopsis* plants overexpressing either GmBBX52 or GmBBX53 displayed increased hypocotyl growth rates and altered transcription of genes associated with light regulated signal transduction and photosynthesis, similar to plant lines over-expressing AtBBX32. In order to better understand the biological role of GmBBX52 and GmBBX53 genes on soybean yield, we generated constructs that would constitutively express either GmBBX52 or GmBBX53 or knock-down both GmBBX52 and GmBBX53 transcript levels. Eight independently generated plants from both the GmBBX52 constitutive over-expression construct and the GmBBX52/GmBBX53-miRNA constructs and four independent events from the GmBBX53 over-expression construct were tested in broad acre yield trials. Lines ectopically over-expressing GmBBX52 yielded, on average, 6.1% more bushels per acre than did wild-type control plants, while the top performing line yielded 9.0% more bushels per acre. Lines ectopically over-expressing GmBBX53 yielded 4.1% higher than the wild-type control, while the top event improved yield by 6.7% over the wild-type control. In contrast, miRNA mediated suppression of GmBBX52 and GmBBX53 transcript levels led to a significant decrease in GmBBX52 RNA levels and decreased yield. GmBBX52/GmBBX53-miRNA lines yielded, on average, 5.5% fewer bushels per acre than control lines while the lowest yielding line across the eight produced 11.8% fewer bushels per acre relative to controls. These data demonstrate that the ectopic expression of the soybean homologs of AtBBX32, GmBBX52 and GmBBX53, led to yield improvements similar to that of soybean plants expressing the *Arabidopsis* gene.

We then examined several independently transformed *Arabidopsis* lines overexpressing other disclosed B-box polynucleotides. The level of gene expression is expected to vary in each line, which is likely to result in a range of hypocotyl lengths. Lines with hypocotyl lengths similar to the controls are likely to lack any significant expression from the transgene. On the other hand, an increase in hypocotyl length may be attributed to the transgene, either through an indirect effect or directly through overexpression of the specific B-box transgene. Increased hypocotyl lengths of multiple independent transformants of the same gene can be used to correlate the reduced light responsiveness to increased gene expression. Using this method, a number of independent *Arabidopsis* transgenic lines carrying 35S::AtBBX28:cMYC were found to have longer hypocotyls than control lines transformed with an empty vector control (pMEN 65), and some of the 35S::AtBBX28:cMYC lines had hypocotyl lengths similar to BBX32-over-expressing seedlings (FIG. 1). These data suggest that seedlings over-expressing AtBBX28 are hyposensitive to red light implying that AtBBX28 functions negatively in light signal transduction.

BBX32 improves crop performance and is thought to repress the transcriptional activity of another B-box protein, AtBBX21 (SEQ ID NO: 56) on its native target promoter (prCHS) sequences (unpublished data). To test whether AtBBX28 (SEQ ID NO: 2) can also repress gene expression, we co-transformed prCHS::GUS reporter constructs with HA:AtBBX21 or in combination with HA:AtBBX28, HA:BBX32 or CAT (used as control) in *Arabidopsis*. Our results show that HA:AtBBX28 inhibited the transcriptional activity of HA:AtBBX21 to levels similar to the repression by HA: BBX32 (FIG. 2). These data suggest that AtBBX28 is able to act as a repressor like BBX32. AtBBX28 may have common targets with BBX32 (FIG. 2) or it may act on specific targets independently of BBX32. Other B-box proteins were analyzed for their potential roles in light signaling. Seedlings of several independently transformed *Arabidopsis* lines transformed with B-box genes were grown under red light to examine the effects on hypocotyl length. As seen in FIGS. 3 and 4, we identified 8 additional B-box genes which, when constitutively expressed, produced longer hypocotyls in light. The levels of expression of these genes in the transgenic lines are not yet known, but as expected the magnitude of the hypocotyl length phenotype varied greatly between independent transformants of the same gene. These results indicate that AtBBX25 (G1894, SEQ ID NO: 154), AtBBX26 (G1486, SEQ ID NO: 52), AtBBX30 (G1478, SEQ ID NO: 40), AtBBX7 (G2440, SEQ ID NO: 104), AtBBX24 (G329, SEQ ID NO: 152), AtBBX20 (G1888, SEQ ID NO: 54), AtBBX19 (G902, SEQ ID NO: 200), and AtBBX18 (G1881, SEQ ID NO: 202) function to suppress light signaling. One or more of these genes can be used to alter light sensitivity leading to increased crop yield and stress tolerance.

AtBBX32 Modulates Expression of Soybean BBX Proteins

A microarray analysis was performed to examine the expression of AtBBX32 on the modulation of gene expression in field grown soybean sampled at five time points: 3:00 am, 6:00 am (dawn), 9:00 am, noon, and 3:00 pm. The expression of AtBBX32 in soybean affected the abundance of specific gene transcripts with the majority of these changes in gene expression occurring at dawn as shown in FIG. 11.

Phylogenetic analyses of the *Arabidopsis thaliana* and *Glycine max* B-box gene families were conducted for the purpose of identifying functional similarities of proteins in the B-box family (FIGS. 12, 13 and 14). The phyogenetic trees were generated using an in-house proprietary database and clustalW analysis clusters to group sequences based on the domain structure of the proteins. The genomes of both species contain large families of B-box domain genes; the *Arabidopsis* genome contains 32 predicted B-box domain proteins, while the paleopolyploid soybean genome contains 61 B-box containing genes. The phylogenetic analysis conducted using 32 B-box sequences from *Arabidopsis thaliana* and 61 B-box sequences from *Glycine max* grouped the *Arabidopsis* and soybean sequences into five structural groups and seventeen clades (FIG. 12). A phylogenetic tree specific for the 61 B-box sequences from soybean is shown in FIG. 13. Two of the soybean B-box sequences showed a shift in the time of peak expression. Three sequences were induced significantly at dawn and thirteen were down-regulated in the At.BBX32 transgenic soybean plants (FIG. 13). A single B-box Glade is further represented in FIG. 14 for *Arabidopsis thaliana* and *Glycine max* sequences. Within the phylogenetic grouping of AtBBX32-like single B-box domain containing genes, thirteen B-box genes from *Glycine max* grouped with seven *Arabidopsis* single B-box genes. Phylogenetic analysis indicates that GmBBX52 and GmBBX53 are orthologs of the *Arabidopsis thaliana* AtBBX32 gene.

Utilities of B-Box Polynucleotides, Polypeptides and Phylogenetically-Related Sequences Based on the data obtained in the instantly disclosed Examples, a total of nine *Arabidopsis* B-box genes and several GmBBX genes that function negatively in light signaling have been identified, and it is expected that either independently or in combination with other genes or specific promoters (for example, heterologous promoters, or constitutive, inducible, diurnally-regulated, tissue-enhanced, tissue-preferred, or tissue-specific promoters), these genes will provide significantly improved yield benefits and resistance to abiotic stress.

Sequences that are orthologous, i.e., full length sequences or modified sequences that share significant sequence identity or similarity, to those provided in the Sequence Listing, may be derived from any of a wide variety of plants, including but not limited to, the plant families Myrtaceae, Pinaceae, Salicaceae, Leguminosae, Umbelliferae, Cruciferae, Curcurbitaceae, Solanaceae, Brassicaceae, or from the plants *Arabidopsis thaliana*, soybean, potato, cotton, rape, oilseed rape (including canola), sunflower, alfalfa, clover; or fruits and vegetables, such as banana, blackberry, blueberry, strawberry, and raspberry, cantaloupe, carrot, cauliflower, coffee, cucumber, eggplant, mint, grapes, honeydew, lettuce, mango, melon, onion, papaya, peas, beans, peppers, pineapple, pumpkin, spinach, squash, tobacco, tomato, tomatillo, watermelon, rosaceous fruits (such as apple, peach, pear, cherry and plum), vegetable brassicas (such as broccoli, cabbage, cauliflower, Brussels sprouts, and kohlrabi), barley; rye; millet; sorghum; currant; avocado; citrus fruits such as oranges, lemons, grapefruit and tangerines, artichoke, cherries; nuts such as the walnut and peanut; endive; leek; roots such as arrowroot, beet, cassava, turnip, radish, yam, sweet potato, wheat, corn or sweet corn (maize), rice, wild rice, sugarcane, bamboo, oats, turfgrass, brome-grass, *Miscanthus*, pampas grass, or switchgrass (*Panicum*). In addition, homologous sequences may be derived from plants that are evolutionarily-related to crop plants, but which may not have yet been used as crop plants. Examples include deadly nightshade (*Atropa belladona*), related to tomato; jimson weed (*Datura strommium*), related to peyote; and teosinte (*Zea* species), related to corn (maize).

Transgenic plants (or plant cells, or plant explants, or plant tissues) incorporating the disclosed polynucleotides and expressing the disclosed polypeptides or orthologs of the disclosed polypeptides can be produced by a variety of well-established techniques as described in the Examples. After construction of a nucleic acid vector, including an expression vector or cassette, including one or more polynucleotides encoding one or more B-box transcriptional regulators or B-box transcriptional regulator orthologs, standard techniques can be used to introduce the vector into a plant, a plant cell, a plant explant or a plant tissue of interest. Optionally, the plant cell, explant or tissue can be regenerated to produce a transgenic plant.

The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Poaceae (formerly Gramineae, including wheat, corn, rice, barley, millet, etc.), Solanaceae (potato, tomato, tobacco, peppers, etc.), and various other crops. See protocols described in Ammirato et al., 1984; Shimamoto et al. 1989; Fromm et al., 1990; and Vasil et al., 1990).

Identification of interacting partners with AtBBX32

Genetic and biochemical approaches were employed to identify proteins that may interact with AtBBX32 in transgenic soybean plants. Engineering of crop plants with polynucleotides that encode or suppress such proteins may improve yield and other agronomic traits.

Yeast 2-Hybrid Screen

In order to identify BBX32 binding partners that may be involved in the regulation of AtBBX32 in overexpressing transgenic soybean, a yeast 2-hybrid (Y2H) screen was carried out using full length and truncatedAtBBX32 and the soy orthologGmBBX52 as baits in a total of 6 screens against a soybean cDNA library (Table 7). The six BBX32 baits from Table 7 were subcloned into pUC vectors and then recloned as LexA fusion constructs for use in Y2H screens. Most bait constructs were prepared in the pB27 background, which placed the LexA gene at the N terminus of the bait sequence. Other vector backbones include pB29 for C terminal LexA fusions and pB6 for N terminal Gal4 fusions. Two control screens were also performed using GmCOP1-like protein and GmPABP-like (Poly A binding protein) protein as baits (data not shown).

A random primed library was made from total RNA isolated from wild-type non-transgenic V5 soy leaves harvested at 4 hr intervals during a 14 hr diurnal cycle as well as from dark germinated soy seedlings. The two uppermost leaf tri-foliates, shoot, and meristem tissues were harvested from V5 stage soy plants at 3 am, 7 am, 11 am, 3 pm, 7 pm, and 11 pm. Whole seedlings were collected at a single time point. All tissues were harvested from plants grown in the growth chamber where lights were turned on at 5 am and off at 7 pm. RNA was isolated from all tissues for preparation of a cDNA library in the appropriate prey vector. The two-hybrid screens were performed by Hybrigenics Services.

Interacting clones were isolated and sequenced. Combining all six screens, approximately 471 interacting contigs were identified. Contigs are defined as an interacting fragment of a particular sequence. Separate contigs may represent overlapping portions of the same mRNA. Furthermore, some contigs identified in separate screens may be identical, thus reducing the total number of contigs identified. Translated BLAST searches against the public database revealed approximately 45 groups of contigs and 57 single contigs (including 333 different contigs) with similarity to *Arabidopsis* genes. An additional three contig groups did not show significant homology to publicly available gene sequences. Six contig groups did not show significant homology to genes within the *Arabidopsis* genome nor to the map to known soy genes. Of the remaining single contigs that map to soy gene sequences, approximately 107 showed no matches to known plant genes.

TABLE 7

Bait insert sequences tested against the soy DNA library described above. Italicized sequence in N and C terminal baits contained overlap regions pesent in both bait constructs.

| Bait | Sequence | Nucleotides |
|---|---|---|
| N-terminal At.BBX32 | MVSFCELCGAEADLHCAADSAFLCRSCDAKFHASNFLFARHFRRVICPNC KSL*TQNFVSGPLLPWPPRTTCCSE* | 1-222 |
| C-terminal At.BBX32 | *TQNFVSGPLLPWPPRTTCCSE*SSSSCCSSLDCVSSSELSSTTRDVNRARG RENRVNAKAVAVTVADGIFVNWCGKLGLNRDLTNAVVSYASLALAVETRP RATKRVFLAAAFWFGVKNTTTWQNLKKVEDVTGVSAGMIRAVESKLARAM TQQLRRWRVDSEEGWAENDNV | 160-678 |
| Full length At.BBX32 | MVSFCELCGAEADLHCAASSAFLCRSCDAKFHASNFLFARHFRRVICPNC KSLTQNFVSGPLLPWPPRTTCCSESSSSSCCSSLDCVSSSELSSTTRDVN RARGRENRVNAKAVAVTVADGIFVNWCGKLGLNRDLTNAVVSYASLALAV ETRPRATKRVFLAAAFWFGVKNTTTWQNLKKVEDVTGVSAGMIRAVESKL ARAMTQQLRRWRVDSEEGWAENDNV | 1-678 |
| N-terminal Gm.BBX52 | MKPKTCELCHQLASLYCPSDSAFLCFHCDAAVHAANFLVARHLRRLLCSK CNRF*AAIHISGAISRHLSSTCTSCSL* | 1-228 |
| C-terminal Gm.BBX52 | *AAIHISGAISRHLSSTCTSCSL*EIPSADSDSLPSSSTCVSSSESCSTNQI KAEKKRRRRRRSFSSSSVTDDASPAAKKRRRNGGSVAEVFEKWSREIGLG LGVNGNRVASNALSVCLGKWRSLPFRVAAATSFWLGLRFCGDRGLATCQN LARLEAISGVPAKLILGAHANLARVFTHRRELQEGWGES | 163-732 |
| Full length Gm.BBX52 | MKPKTCELCHQLASLYCPSDSAFLCFHCDAAVHAANFLVARHLRRLLCSK CNRFAAIHISGAISRHLSSTCTSCSLEIPSADSDSLPSSSTCVSSSESCS TNQIKAEKKRRRRRRSFSSSSVTDDASPAAKKRRRNGGSVAEVFEKWSRE IGLGLGVNGNRVASNALSVCLGKWRSLPFRVAAATSFWLGLRFCGDRGLA TCQNLARLEAISGVPAKLILGAHANLARVFTHRRELQEGWGES | 1-732 |

Analysis of the Y2H prey identified in each screen revealed several consistent patterns of potential interaction. In general, the N-terminal, B-Box containing region of both the AtBBX32 and Gm BBX32 proteins showed potential interaction with other B-Box proteins. Many of the potentially interacting proteins are expressed during a timeframe in which AtBBX32 overexpression has been shown to influence expression of the most mRNAs in growth chamber experiments (2 hr predawn and dawn). At a molecular level, AtBBX32 overexpression resulted in marked changes in mRNA expression for a number of nuclear genes, suggesting that AtBBX32 plays a role in transcriptional regulation (FIG. 11). As a putative component of the transcriptional network, it is likely that BBX32 functions through interactions with other proteins. Taken together, these data indicate that, like BBX32, these genes may modulate a variety of traits, including yield, when overexpressed or suppressed in plants.

AtBBX32 putative interacting proteins from the yeast 2 hybrid screens were identified and are further described in the phylogenetic tree in FIGS. 12 and 13. Several possible interacting proteins of GmBBX52 were also identified from yeast 2 hybrid screens. For example, GmG1481 (GmBBX62) was identified and is proposed to function in protein-protein stabilization and could facilitate light signaling in leaves, roots and nodules. The interaction of BBX32 with B-box proteins may also help in stabilizing the nuclear complex. Together such a complex could lead to altered gene expression of key regulatory and metabolic genes resulting in enhanced vigor, growth and yield.

AtBBX32 and GmBBX62 are Physically Associated In Vivo

To confirm the interaction between AtBBX32 and GmBBX62 identified through Y2H screening: the ability of AtBBX32 to associate with GmBBX62 in vivo was tested. AtBBX32::GFP and Flag::GmBBX62 fusion proteins were transiently co-expressed in soybean protoplasts. Soybean protoplasts were isolated from 4-6 mm cotyledons and transformed as described by Abel and Theologis, 1994. Approximately $1\times10^6$ protoplasts were transformed in 15 mL Falcon conical tubes with 90 ng of Qiagen prepped plasmid DNA. Protoplasts were then incubated at 22° C. for 18 to 24 hours, and harvested at 150×g for 3 minutes and lysed with lysis buffer (50 mM Tris pH 7.8, 150 mM NaCl, 1% Triton-X 100 and Complete Protease Inhibitor (Roche) for 1 hr on ice with vortex mixing every 15 min. The lysate was centrifuged for 5 mM at 3000×g and soluble fractions were retained for use in Luminex-based co-immunoprecipitation assays.

Luminex co-immunoprecipitation (co-IP) assay was carried out using the miniaturized sandwich immunoassay and co-IP method with modifications, Poetz et al., 2009. This combination of co-IP and sandwich immunoassay allows the relative quantification of components of the complex. Briefly, antibodies for GFP (MBL International, D153-3) and FLAG (Bethyl Laboratories, A190-101A) were covalently coupled to carboxylated fluorescent microspheres (Luminex) according to the manufacturer's protocol. Fifty n1 of protoplast cell lysate (above) was aliquoted to three different wells in a 96 well clear flat-bottom plate (Bio-Rad) for Luminex assays. To each sample, 50 n1 of conjugated beads was added to each appropriate well and incubated for 30 minutes with shaking. Forward and reverse co-IPs were performed with anti-GFP conjugated beads and anti-FLAG conjugated beads. Beads were captured for 2 minutes and washed three times with PBST (137 mM NaCl, 8.1 mM Na2HPO4, 2.68 mM KCl, 1.47 mM $KH_2PO_4$, and 0.05% Tween-20). Biotinylated GFP (ab6658, 1:1000; Abcam) and FLAG (A190-101B, 1:1000; Bethyl) antibodies were added to appropriate wells. The plate was incubated on a shaker for 30 minutes. After washing, 100 n1 of reporter NeutrAvidin R-phycoerythrin at a 1:1000 dilution was added to each well and incubated for 30 minutes with subsequent washing. Each well was resuspended in 100 n1 of PBST buffer before plates were analyzed using FLEX MAP 3D system (Luminex Corp, Austin, TX). Approximately 100 beads were measured per sample to determine the median fluorescence intensity (MFI).

A co-immunoprecipitation (co-IP) experiment was performed with the co-expressed soybean protoplast extracts using an antibody against GFP. The protein complex was captured via the immobilized GFP antibody and the associated components within the complex were detected via anti-FLAG antibody and visualized using phycoerythrin-conjugated reporter molecules. As shown in FIG. 15A, the median fluorescence intensity (MFI) from cell extracts co-expressing AtBBX32::GFP and Flag::GmBBX62 is significantly higher (6-fold) than the control samples, including non-transfected cells and cell extracts lacking either AtBBX32::GFP or FLAG::GmBBX62. As expected, low fluorescence signals for the single gene construct samples did not show a significant difference from non-transfected cell extract, suggesting that these signals represent non-specific binding. A reciprocal co-IP experiment with anti-FLAG antibody-immobilized beads was also performed. The presence of AtBBX32::GFP within the complex was detected by anti-GFP antibody. Similarly, the fluorescence intensity for the co-expressed cell extract exhibited a 5-fold increase compared to the controls (FIG. 15B). The results indicate that AtBBX32 and GmBBX62 physically interact in soybean cells, further demonstrating the biological relevance of GmBBX62 as a partner of AtBBX32.

AtBBX32 Binds GmBBX62 In Vitro

In vitro pull-down and ELISA-based protein-protein interaction assays were also conducted to confirm the binding of AtBBX32 with GmBBX62. Purified FLAG::GmBBX62 was bound to anti-FLAG M2 agarose resin and incubated with soluble protein extracts from wheat germ lysate expressing AtBBX32. The beads were pelleted and washed, and the bound protein complexes were eluted using SDS-PAGE loading buffer. The eluted protein complexes were identified by western blotting analysis. As expected, FLAG::GmBBX62 was detected with anti-Flag antibody from FLAG-GmBBX62-bound beads (FIG. 16A), confirming the presence of the GmBBX62 protein in reactions. AtBBX32 within the protein complex was detected with anti-AtBBX32 antibody from FLAG::GmBBX62 beads but not from the negative controls (FIG. 16B), demonstrating that FLAG::GmBBX62 can bind to AtBBX32 in vitro.

Co-Immunoprecipitation of AtBBX32 with GmBBX39 and Bead-Based Fluorescence Detection Bead-based co-IP assays with Luminex on-bead detection method was used to confirm the interaction between the AtBBX32 and GmBBX39 proteins. Pairs of potential interacting proteins were co-expressed in soybean cotyledon protoplasts as described above.

Capture antibodies for GFP (MBL International, D153-3),Myc (Bethyl Laboratories cat #A190-104A)and FLAG (Bethyl Laboratories, A190-101A) were covalently coupled to carboxylated fluorescent microspheres (Luminex) according to the manufacturer's protocol Luminex two-step Carbodimide coupling protocol was modified as follows: 3.5×$10^6$ beads were conjugated to 1514 of antibody and resuspended in coupling buffer containing 100 mM MES pH 6. Biotinylated antibodies for GFP (Abcam, ab6658), Myc (Bethyl Laboratories cat #A190-104B)and FLAG (Bethyl laboratories, A190-101B) were used for detection of interacting proteins in the miniaturized sandwich immunoassay. NeutrAvidin R-phycoerythrin was used as the reporter assay reagent (Invitrogen, A2660).

Protein input for BBX32::GFP and interactions were detected using the miniaturized sandwich immunoassay and co-IP method (Poetz, et al., 2009).Protein complexes were captured from extracts on antibody-conjugated beads, and the bound partner proteins were detected with biotinylated antibodies. NeutrAvidin R-phycoerythrin provided a fluorescence read-out for the quantity of bound detection antibody. Interacting proteins were defined as pairs of potential interacting proteins that yielded a greater median fluorescence intensity (MFI) than any of the controls (single protein expressed or untransformed cells) with a p-value <0.001 and a change in MFI that was 4-fold or greater when compared to each of the controls.

To assess the potential interaction between AtBBX32 and GmBBX39, two experiments were conducted consisting of a total of three repetitions (exp. 1, n=1; exp. 2, n=2). BBX32::GFP was co-expressed with FLAG::GmBBX39 in soybean cotyledon protoplasts. Expression analyses on one replicate of each treatment using either Luminex (BBX32::GFP) or Western blot (FLAG::BBX39) detection confirmed that each protein was expressed at detectable levels (data not shown). When co-expressed in protoplasts, BBX32::GFP and FLAG::BBX39 co-precipitated with either anti-GFP or anti-FLAG beads (FIG. 17). BBX32::GFP did not co-IP with anti-FLAG beads in the absence of FLAG::BBX39 and FLAG::BBX39 did not co-IP with anti-GFP beads in the absence of BBX32::GFP. These results demonstrate that AtBBX32 and GmBBX39 physically interact in soybean protoplasts. Similar experiments also demonstrated physical interactions between GmBBX39 and GmBBX62, between GmBBX52 and GmBBX39, and between GmBBX52 and GmBBX62 (data not shown).

REFERENCES CITED

Abel and Theologis (1994) *Plant J.* 5: 421-427

Aldemita and Hodges (1996) *Planta* 199: 612-617

Altschul (1990) *J. Mol. Biol.* 215: 403-410

Altschul (1993) *J. Mol. Evol.* 36: 290-300

Ammirato et al., eds. (1984), Handbook of Plant Cell Culture —Crop Species, Macmillan Publ. Co., New York, NY Anderson and Young (1985) "Quantitative Filter Hybridisation", In: Hames and Higgins, ed., Nucleic Acid Hybridisation, A Practical Approach. Oxford, IRL Press, 73-111

Ausubel et al. (1997) Short Protocols in Molecular Biology, John Wiley & Sons, New York, NY, unit 7.7

Babic et al. (1998) *Plant Cell Reports* 17: 183-188

Bairoch et al. (1997) *Nucleic Acids Res.* 25: 217-221

Bechtold and Pelletier (1998) *Methods Mol. Biol.* 82: 259-266

Berger and Kimmel (1987), "Guide to Molecular Cloning Techniques", in Methods in Enzymology, vol. 152, Academic Press, Inc., San Diego, CA Bevan (1984) *Nucleic Acids Res.* 12: 8711-8721

Borevitz et al. (2000) *Plant Cell* 12: 2383-2393
Boss and Thomas (2002) *Nature*, 416: 847-850
Bruce et al. (2000) *Plant Cell* 12: 65-79
Cassas et al. (1993) *Proc. Natl. Acad. Sci. USA* 90: 11212-11216
Cheikh et al. (2003) U.S. Patent Application No. US20030101479
Christou et al. (1987) *Proc. Natl. Acad. Sci. USA* 84: 3962-3966
Christou (1991) *Bio/Technol.* 9:957-962
Christou et al. (1992) *Plant. J.* 2: 275-281
D'Halluin et al. (1992) *Plant Cell* 4: 1495-1505
Daly et al. (2001) *Plant Physiol.* 127: 1328-1333
Deshayes et al. (1985) *EMBO J.*, 4: 2731-2737
Donn et al.(1990) in Abstracts of VIIth International Congress on Plant Cell and Tissue Culture IAPTC, A2-38: 53
Doolittle, ed. (1996) *Methods in Enzymology, vol.* 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Str. Biol.* 6: 361-365
Eisen (1998) *Genome Res.* 8: 163-167
Feng and Doolittle (1987) *J. Mol. Evol.* 25: 351-360
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gelvin et al. (1990) *Plant Molecular Biology Manual*, Kluwer Academic Publishers
Gilmour et al. (1998) *Plant J.* 16: 433-442
Goodrich et al. (1993) *Cell* 75: 519-530
Gordon-Kamm et al. (1990) *Plant Cell* 2: 603-618
Gruber et al., in Glick and Thompson (1993) *Methods in Plant Molecular Biology and Biotechnology*. eds., CRC Press, Inc., Boca Raton
Haake et al. (2002) *Plant Physiol.* 130: 639-648
Hain et al. (1985) *Mol. Gen. Genet.* 199: 161-168
Haymes et al. (1985) *Nucleic Acid Hybridization: A Practical Approach*, IRL Press, Washington, D.C.
He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) Nucleic Acids Res. 19: 6565-6572
Herrera-Estrella et al. (1983) *Nature* 303: 209
Hiei et al. (1994) *Plant J.* 6:271-282
Hiei et al. (1997) *Plant Mol. Biol.* 35:205-218
Higgins and Sharp (1988) Gene 73: 237-244
Higgins et al. (1996) *Methods Enzymol.* 266: 383-402
Ishida (1990) *Nature Biotechnol.* 14:745-750
Jaglo et al. (2001) *Plant Physiol.* 127: 910-917
Kashima et al. (1985) *Nature* 313: 402-404
Khanna et al. (2006) *Plant Cell* 18, 2157-2171
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Koornneef et al (1986) In *Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Lin et al. (1991) Nature 353: 569-571
Mandel (1992a) Nature 360: 273-277
Mandel et al. (1992b) *Cell* 71-133-143
Meyers (1995) Molecular Biology and Biotechnology, Wiley VCH, New York, NY, p 856-853
Mild et al. (1993) in Methods in Plant Molecular Biology and Biotechnology, p. 67-88, Glick and Thompson, eds., CRC Press, Inc., Boca Raton
Mount (2001), in Bioinformatics: Sequence and Genome Analysis, Cold Spring Harbor Laboratory Press, Cold Spring Harbor, New York, p. 543
Miller et al. (2001) *Plant J.* 28: 169-179
Nandi et al. (2000) *Curr. Biol.* 10: 215-218
Niman et al. (1983). *Proc. Natl. Acad. Sci. U.S.A.* 80: 4949-4953
Peng et al. (1997) *Genes Development* 11: 3194-3205
Peng et al. (1999) *Nature* 400: 256-261
Poetz, O., K. Luckert, et al. (2009) *Anal. Biochem.* 395:244-248
Putterill et al. (1995) Cell 80: 847-857
Ratcliffe et al. (2001) *Plant Physiol.* 126: 122-132
Reeves and Nissen (1990) *J. Biol. Chem.* 265, 8573-8582
Reeves and Nissen (1995). *Prog. Cell Cycle Res.* 1: 339-349
Riechmann et al. (2000a) *Science* 290, 2105-2110
Riechmann and Ratcliffe (2000b) *Curr. Opin. Plant Biol.* 3, 423-434
Rieger et al. (1976) Glossary of Genetics and Cytogenetics: Classical and Molecular, 4th ed., Springer Verlag, Berlin
Robson et al. (2001) *Plant J.* 28: 619-631
Sadowski et al. (1988) *Nature* 335: 563-564
Sambrook et al. (1989) Molecular Cloning: A Laboratory Manual, 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shimamoto et al. 1989*; Nature* 338: 274-276
Shpaer(1997) Methods Mol. Biol. 70: 173-187
Smith et al. (1992) *Protein Engineering* 5: 35-51
Sonnhammer et al. (1997) *Proteins* 28: 405-420
Spencer et al. (1994) *Plant Mol. Biol.* 24: 51-61
Suzuki et al. (2001) *Plant J.* 28: 409-418
Thompson et al. (1994) *Nucleic Acids Res.* 22: 4673-4680
Tudge (2000) in *The Variety of Life*, Oxford University Press, New York, NY pp. 547-606
Vasil et al. (1990) *Bio/Technol.* 8: 429-434
Vasil et al. (1992) *Bio/Technol.* 10:667-674
Vasil et al. (1993) *Bio/Technol.* 11:1553-1558
Vasil (1994) *Plant Mol. Biol.* 25: 925-937
Wahl and Berger (1987) Methods Enzymol. 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) Methods for Plant Molecular Biology, Academic Press
Wu (ed.) *Meth. Enzymol.* (1993) vol. 217, Academic Press
Zhang et al. (1991) *Bio/Technology* 9: 996-997

All publications and patent applications mentioned in this specification are herein incorporated by reference to the same extent as if each individual publication or patent application was specifically and individually indicated to be incorporated by reference.

The present disclosure is not limited by the specific embodiments described herein. The disclosure now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

What is claimed is:

1. A method for increasing yield in a plant, the method comprising the steps of:

introducing into a target plant at least one recombinant polynucleotide comprising at least one nucleotide sequence that encodes a polypeptide thereby producing a transgenic plant, wherein the nucleotide sequence is operably linked to a heterologous promoter, wherein the polypeptide comprises an amino acid sequence that has a 95% percentage identity to the amino acid sequence of SEQ ID NO:530;

overexpressing the polypeptide in the transgenic plant; and selecting the transgenic plant that overexpresses the polypeptide having at least 95% percentage identity to the amino acid sequence of SEQ ID NO:530 for having an increased yield of at least 6.1% as compared to a control plant.

2. The method of claim 1, wherein the target plant comprises a second recombinant polynucleotide comprising a trans-acting element that controls expression of the polypeptide;

wherein the target plant expresses a protein encoded by a nucleic acid selected from the group consisting of: SEQ ID NO: 429, SEQ ID NO: 431, and SEQ ID NO: 433; or wherein the target plant is stably transformed with the at least one recombinant polynucleotide.

3. The method of claim 1, wherein the promoter is a constitutive, inducible, tissue-specific, tissue-enhanced, light-regulated, stress-inducible, diurnally-regulated, chemically-inducible, or cell-specific promoter.

4. The method of claim 1, the method steps further comprising: crossing the transgenic plant with itself, a second plant from the same line as the target plant, a non-transgenic plant, a wild-type plant, or a transgenic plant from a different line of plants, to produce a transgenic seed.

5. The method of claim 1, wherein the selecting step comprises selecting the transgenic plant for having increased yield of at least 9% as compared to the control plant.

6. The method of claim 1, wherein the polypeptide comprises the amino acid sequence of SEQ ID NO:530.

7. The method of claim 1, wherein the nucleotide sequence comprises the polynucleotide nucleotide sequence set forth as SEQ ID NO:529.

* * * * *